(12) United States Patent
Strittmatter et al.

(10) Patent No.: US 7,173,118 B2
(45) Date of Patent: Feb. 6, 2007

(54) NOGO RECEPTOR HOMOLOGS

(75) Inventors: Stephen M. Strittmatter, Clinton, CT (US); Richard L. Cate, Cohasset, MA (US); Dinah W. Y. Sah, Boston, MA (US)

(73) Assignees: Biogen Idec MA Inc., Cambridge, MA (US); Yale University, New Haven, CT (US)

( * ) Notice: Subject to any disclaimer, the term of this patent is extended or adjusted under 35 U.S.C. 154(b) by 21 days.

(21) Appl. No.: 10/735,256

(22) Filed: Dec. 12, 2003

(65) Prior Publication Data
US 2005/0048520 A1 Mar. 3, 2005

Related U.S. Application Data

(63) Continuation of application No. 09/972,546, filed on Oct. 6, 2001, now abandoned.

(60) Provisional application No. 60/238,361, filed on Oct. 6, 2000.

(51) Int. Cl.
| | | |
|---|---|---|
| C07H 21/04 | (2006.01) | |
| C12N 5/00 | (2006.01) | |
| C12N 15/11 | (2006.01) | |
| C12N 5/10 | (2006.01) | |
| C12N 5/16 | (2006.01) | |
| C12N 5/06 | (2006.01) | |
| C12N 5/02 | (2006.01) | |
| C07H 21/02 | (2006.01) | |
| C07H 21/00 | (2006.01) | |

(52) U.S. Cl. .................. 536/23.1; 435/320.1; 435/325; 435/252.3

(58) Field of Classification Search ..................... None
See application file for complete search history.

(56) References Cited

U.S. PATENT DOCUMENTS

| 5,250,414 A | 10/1993 | Schwab et al. ............ 435/7.72 |
| 5,684,133 A | 11/1997 | Schwab et al. ............. 530/350 |
| 5,858,708 A | 1/1999 | Bandman et al. .......... 435/69.1 |
| 6,025,333 A | 2/2000 | Schwab et al. ............... 514/18 |
| 2002/0025554 A1 | 2/2002 | Khodadoust ............... 435/69.1 |
| 2003/0012704 A1 | 7/2003 | Strittmatter et al. |
| 2005/0221420 A1 | 10/2005 | Barske et al. |
| 2005/0271655 A1 | 12/2005 | Lee et al. |

FOREIGN PATENT DOCUMENTS

| WO | WO 98/06841 | 2/1998 |
| WO | WO 99/46281 | 9/1999 |
| WO | WO 99/66041 | 12/1999 |
| WO | WO 00/05364 | 2/2000 |
| WO | WO 00/31235 | 6/2000 |
| WO | WO 00/32221 | 6/2000 |
| WO | WO 00/37638 | 6/2000 |
| WO | WO 00/53756 | 9/2000 |
| WO | WO 00/53758 | 9/2000 |
| WO | WO 00/58473 | 10/2000 |
| WO | WO 00/70050 | 11/2000 |
| WO | WO 00/73452 | 12/2000 |
| WO | WO 01/09162 | 2/2001 |
| WO | WO 01/51520 | 7/2001 |
| WO | WO 03/018631 | 3/2003 |

OTHER PUBLICATIONS

Gustafsson, J. A.. New insights in oestrogen receptor (ER) research-the ERb. Eur J Cancer. Sep. 2000;36 Suppl 4:S16.*
Nykjaer et al. p75NTR—live or let die. Curr Opin Neurobiol. Feb. 2005; 15:49-57.*
C.E. Bandtlow, et al., "NI-35/250/Nogo-A: A Neurite Growth Inhibitor Restricting Structural Plasticity and Regeneration of Nerve Fibers in the Adult Vertebrate CNS," *Glia*, 29(2), pp. 175-181 (2000).
M.S. Chen, et al., "Nogo-A is a Myelin-Associated Neurite Outgrowth Inhibitor and an Antigen for Monoclonal Antibody IN-1," *Nature*, 403(6768), pp. 434-439 (2000).
A.E. Fournier, et al., "Identification of a Receptor Mediating Nogo-66 Inhibition of Axonal Regeneration," *Nature*, 409(6818), pp. 341-346 (2001).
T. GrandPre, et al., "Identification of the Nogo Inhibitor of Axon Regeneration as a Reticulon Protein," *Nature*, 403(6768), pp. 439-444 (2000).
P. Hu, et al., "Homo Sapiens Chromosome 22q11 PAC Clone p215k21 Distal to DGCR Region," *EMBL Database Entry AC006549*, Accession No. AC006549 (1999).
A.B. Huber, et al., "Nogo-A, a Potent Inhibitor of Neurite Outgrowth and Regeneration," *Biol. Chem.*, 381(5-6), pp. 407-419 (2000).
D. Merkler, et al., "Locomotor Recovery in Spinal Cord-Injured Rats Treated with an Antibody Neutralizing the Myelin-Associated Neurite Growth Inhibitor Nogo-A," *J. Neurosci.*, 21(10), pp. 3665-3673 (2001).
M. Oudega, et al., "Neutralizing Antibodies Against Neurite Growth Inhibitor NI-35/250 Do Not Promote Regeneration of Sensory Axons in the Adult Rat Spinal Cord," *Neuroscience*, 100(4), pp. 873-883 (2000).
R. Prinjha, et al., "Inhibitor of Neurite Outgrowth in Humans," *Nature*, 403(6768), pp. 383-384 (2000).

(Continued)

*Primary Examiner*—Janet L. Andres
*Assistant Examiner*—Chang-Yu Wang
(74) *Attorney, Agent, or Firm*—Sterne, Kessler, Goldstein & Fox, P.L.L.C.

(57) ABSTRACT

The invention relates generally to genes that encode proteins that inhibit axonal growth. The invention relates specifically to genes encoding NgR protein homologs in humans and mice. The invention also includes compositions and methods for modulating the expression and activity of Nogo and the NgR proteins. Specifically, the invention includes peptides, proteins and antibodies that block Nogo-mediated inhibition of axonal extension. The compositions and methods of the invention are useful in the treatment of cranial or cerebral trauma, spinal cord injury, stroke or a demyelinating disease.

36 Claims, 6 Drawing Sheets

OTHER PUBLICATIONS

O. Raineteau, et al., "Sprouting and Regeneration After Pyramidotomy and Blockade of the Myelin-Associated Neurite Growth Inhibitors N1 35/250 in Adult Rats," *Eur. J. Neurosci.*, 11(4), pp. 1486-1490 (1999).

O. Raineteau, et al., "Functional Switch Between Motor Tracts in the Presence of the mAB IN-1 in the Adult Rat," *Proc. Natl. Acad. Sci. U.S.A.*, 98(12), pp. 6929-6934 (2001).

A.A. Spillmann, et al., "Identification and Characterization of a Bovine Neurite Growth Inhibitor (bNI-220)," *J. Biol. Chem.*, 273(30), pp. 19283-19293 (1998).

M. Tatagiba, et al., "Regeneration of Injured Axons in the Adult Mammalian Central Nervous System," *Neurosurgery*, 40(3), pp. 541-547 (1997).

M. Thallmair, et al., "Neurite Growth Inhibitors Restrict Plasticity and Functional Recovery Following Corticospinal Tract Lesions," *Nat. Neurosci.*, 1(2), pp. 124-131(1998).

W.J. Z'Graggen, et al., "Functional Recovery and Enhanced Corticofugal Plasticity After Unilateral Pyramidal Tract Lesion and Blockade of Myelin-Associated Neurite Growth Inhibitors in Adult Rats," *J. Neurosci.*, 18(12), pp. 4744-4757 (1998).

Pignot et al. "Characterization of two novel proteins, NgRH1 and NgRH2, structurally and biochemically homologous to the Nogo-66 receptor," *J. Biochem.* 85(3): 717-728 (2003).

Kobe and Kajava "The leucine-rich repeat as a protein recognition motif," *Curr. Opin. Structural Biol.* 11(6):725-32 (2001).

Andrade et al. "Protein Repeats: Structures, Functions, and Evolution," *J. Structural Biol.* 134: 117-131 (2001).

Skolnick et al. "From genes to protein structure and function: novel applications of computational approaches in the genomic era, " *Trends Biotech.* 18:34-39 (2000).

Bork "Powers and Pitfalls in Sequence Analysis: The 70% Hurdle," *Genome Research* 10: 398-400 (2000).

Doerks et al. "Protein annotation: detective work for function prediction," *Trends Genet.* 14: 248-250 (1998).

Smith et al. "The challenges of genome sequence annotation or 'The devil is in the details,'" *Nature Biotech.* 15: 1222-1223 (1997).

Brenner "Errors in genome annotation," *Trends Genet.* 15: 132-133 (1999).

Bork et al. "Go hunting in sequence databases but watch out for the traps," *Trends Genet.* 12: 425-427 (1996).

Li et al. "The Genetic Defect in Two Well-Studied Cases of Bernard-Soulier Syndrome: A Point Mutation in the Fifth Leucine-Rich Repeat of Platelet Glycoprotein Ibα," *Blood* 86(10): 3805-3814 (1995).

Wang et al. "Localization of Nogo-A and Nogo-66 Receptor Proteins at Sites of Zxon-Myelin and Synpatic Contact." *J. Neurosci.* 22 (13): 5505-5515 (2002).

Hunt et al. "Nogo Receptor mRNA Expression in Intact and Regenerating CNS Neurons," *Molec. Cellular Neurosci.* 20(4): 537-552 (2002).

Wells "Additivity of Mutational Effects in Proteins," *Biochemistry* 29:8509-8517 (1990).

Ngo et al. "Computational Complexity, Protein Structure Prediction, and the Levinthal Paradox," in *The Protein Folding Problem and Tertiary Structure Prediction*, pp. 492-495 (1994).

Database EMBL, Accession No. AC013606, Birren, B., et al., 39 pages (Nov. 1999).

Database EMBL, Accession No. AC021768, Birren, B., et al., 74 pages (Jan. 2000).

Copy of Communication pursuant to Article 96(2) EPC for European Application No. 01 979 595.4, mailed May 17, 2005, European Patent Office, The Netherlands.

Domeniconi, M., et al., "Myelin-Associated Glycoprotein Interacts with the Nogo66 Receptor to Inhibit Neurite Outgrowth," *Neuron* 35:283-290, Cell Press (Jul. 2002).

GrandPré, T., et al., "Nogo-66 receptor antagonist peptide promotes axonal regeneration," *Nature* 417:547-551, Nature Publishing Group (May 2002).

International Search Report for International Application No. PCT/US2005/002535, European Patent Office, Netherlands, mailed Oct. 24, 2005.

Li, M., et al., "Effect of soluble Nogo reeceptor treatment on functional and histological outcome after spinal cord injury in the rat," Biosis Database, Accession No. PREV200400194121, Abstract No. 80.22, *Presented at the 33rd Annual Meeting of the Society of Neuroscience*, New Orleans, LA (Nov. 8-12, 2003).

Li, W., et al., "A Neutralizing Anti-Nogo66 Receptor Monoclonal Antibody Reverses Inhibition of Neurite Outgrowth by Central Nervous System Myelin," *J. Biol. Chem.* 42:43780-43788, The American Society for Biochemistry and Molecular Biology, Inc. (Oct. 2004).

Li, W., et al., "Neutralization of NGR1 May Be Sufficient to Promote Rat DRG Neurite Outgrowth in the Presence of CNS Myeline," SFN 2003 Abstract Viewer & Itinerary Planner, Program No. 678.3, *Presented at the 33rd Annual Meeting of the Society of Neuroscience*, New Orleans, LA (Nov. 8-12, 2003).

Oertle, T., et al., "Nogo-A Inhibits Neurite Outgrowth and Cell Spreading with Three Discrete Regions," *J. Neurosci.* 23:5393-5406, Society for Neuroscience (Jul. 2003).

\* cited by examiner

FIG. 1A

```
              1                                                        50
NOGO-R2       ------MLPC LRRLLQAPAS AC..LLLML LA..LPLAAP SCPMLCTCYS
NOGO-R3       MSWQSGTTVT QSPVQAAQVS GCCVELLLLL LAGELPLGG. GCPRDCVCYP
NOGO-R1       ---------- ----MKRAS AGGSRLLAWV LWLQAWQVAA PCPGACVCYN
Consensus     ---------- ---------S --------LL L--------- -CP--C-CY- 51                                                       100
NOGO-R2       SP.PTVSCQA NNFSSVPLSL PPSTQRLFLQ NNLIRTLRPG TFGS..NLLT
NOGO-R3       AP.MTVSCQA HNFAAIPEGI PEDSERIFLQ NNRITFLQQG HFSP.AMVT
NOGO-R1       EPKVTTSCPQ QGLQAVPVGI PAASQRIFLH GNRISHVPAA SFRACRNLTI
Consensus     -P--T-SC-- ---------- P-------R-FL -N-I------ -F--------

101                                                      150
NOGO-R2       LWLFSNNLST IYPGTFRHLQ ALEELDLGDN RHLRSLEPDT FQGLERLQSL
NOGO-R3       LWIYSNNITF IAPNTFEGFV HLEELDLGDN RQLRTLAPET FQGLVKLHAL
NOGO-R1       LWLHSNVLAR IDAAAFTGLA LLEQLDLSDN AQLRSVDPAT FHGLGRLHTL
Consensus     LW--SN---- I------F--- --LE-LDL-DN --LR----P-T F-GL--L--L 151                                                      200
NOGO-R2       HLYRCQLSSL PCNIFRGLVS LQYLYLQENS LLHLQDDLFA DLANLSHLFL
NOGO-R3       YLYKCGLSAL PAGIFGGLHS LQYLYLQDNH IEYLQDDIFV DLVNLSHLFL
NOGO-R1       HLDRCGLQEL GPGLFRGLAA LQYLYLQDNA LQALPDDTFR DLGNLTHLFL
Consensus     -L--C-L--L ----F-GL-- LQYLYLQ-N- ---L-DD-F- DL-NL-HLFL 201                                                      250
NOGO-R2       HGNRLRLLTE HVFRGLGSLD RLLLHGNRLQ GVHRAAFRGL SRLTILYLFN
NOGO-R3       HGNKLWSLGQ GIFRGLVNLD RLLLHENQLQ WVHHKAFHDL HRLTTLFLFN
NOGO-R1       HGNRISSVPE RAFRGLHSLD RLLLHQNRVA HVHPHAFRDL GRLMTLYLFA
Consensus     HGN------- --FRGL--LD RLLLH-N--- -VH--AF--L -RL--L-LF-
```

Fig. 1B

```
              251
NOGO-R2       NSLASLPGEA LADLPSLEFL RLNANPWACD CRARPLWAWF QRARVSSSDV
NOGO-R3       NSLTELQGDC LAPLVALEFL RLNGNAWDCG CRARSLWEWL RRFRGSSSAV
NOGO-R1       NNLSALPTEA LAPLRALQYL RLNDNPWVCD CRARPLWAWL QKFRGSSSEV      300
Consensus     N-L--L---- LA-L--L--L RLN-N-W-C- CRAR-LW-W- ---R-SSS-V 301
NOGO-R2       TCATPPERQC RDLRALREAD FQAC....P.P AAPTRPGSRA ..........
NOGO-R3       PCATPELRQG QDLKLLRVED FRNC....TGP VSPHQIKSHT ..........
NOGO-R1       PCSLPQRLAG RDLKRLAAND LQGCAVATGP YHPIWTGRAT DEEPLGLPKC      350
Consensus     -C--P----G -DL--L----D ----C----P ----P----- ----------

351
NOGO-R2       .......RGN ..SSSNH.LY G.VAE..... AGAPPADPS. .TLYRDLPA
NOGO-R3       ..LTTSDRAA ..RKEHHPSH G.ASRDKGHP HCHPPGSRSG YKKAGKNCTS
NOGO-R1       CQPDAADKAS VLEPGRPASA GNALKGRVPP GDSPPGNGSG PRHI.NDSPF      400
Consensus     ---------- ---------- G--------- ---PP---S- ----------

401
NOGO-R2       EDSRGR.... QGGDAPTE.D DYWGGY.... ..........  GGED QRGEQMCPGA
NOGO-R3       HRNRNQISKV SSGKELTELQ DYAPDYQHKF SFDIMPTARP KRKGKCARRT
NOGO-R1       GTLPGSAEPP LTAVRPEGSE P..PGFPTSG PRRRPGCSRK NRTRSHCRLG      450
Consensus     ---------- ---------- ---------- ---------- -R--------

451                                                       491
NOGO-R2       ACQAPPDSRG PALSAGLPSP LLCLLLLVPH HL~~~~~~~~ ~
NOGO-R3       PIRAPSGVQQ ASSGTALGAP LLAWILGLAV TLR~~~~~~~ ~
NOGO-R1       QAGSGGGGTG DSEGSGALPS LTCSLTPLGL ALVLWTVLGP C
Consensus     ---------- ---------- L--------- -L-------- ~
```

FIG. 3

```
                                                                              50
Human NOGO-R1    ----------  ----------  ----------  ----MKRASA  GGSRLLAWVL  WLQAWQVAAP  CPGACVCYNE
Murine NOGO-R1   ----------  ----------  ----------  -----MKRASS GGSRLLAWVL  WLQAWRVATP  CPGACVCYNE
Murine NOGO-R3   MSWQSGTTVT  QSPVQAAQVS  GCCVELLLLL  LAGELPLGGG  CPRDCVCYPA
Human NOGO-R3    ----------  ----------  ----------  ----------  ----------
Human NOGO-R2    ----------  ----------  MLPGLRRLLQ  APASACLLLM  LLALPLAAPS  CPMLCTCYSS
Consensus        ----------  ----------  ----------  ----------  ----------  CP---C--CY--

LRR NT                                      LRR 1                                     100
 51 Human NOGO-R1    PKVTTSCPQQ  GLQAVPVGIP  AASQRIFLHG  NRISHVPAAS  FRACRNLTIL
    Murine NOGO-R1   PKVTTSCPQQ  GLQAVPTGIP  ASSQRIFLHG  NRISHVPAAS  FQSCRNLTIL
    Murine NOGO-R3   P.MTVSCQAH  NFAAIPEGIP  EDSERIFLQN  NRITFLQQGH  FSP..AMVTL
    Human NOGO-R3    ----------  ----EGIP    VDSERVFLQN  NRIGLLQPGH  FSP..AMVTL
    Human NOGO-R2    P.PTVSCQAN  NFSSVPLSLP  PSTQRLFLQN  NLIRTLRPGT  FGS..NLLTL
    Consensus        P--T-SC---  -------P--  ----R-FL--  N--I------  -F--------L LRR 2                                      LRR 3                                     150
101 Human NOGO-R1    WLHSNVLARI  DAAAFTGLAL  LEQLDLSDNA  QLRSVDPATF  HGLGRLHTLH
    Murine NOGO-R1   WLHSNALARI  DAAAFTGLTL  LEQLDLSDNA  QLHVVDPTTF  HGLGHLHTLH
    Murine NOGO-R3   WIYSNNITFI  APNTFEGFVH  LEELDLGDNR  QLRTLAPETF  QGLVKLHALY
    Human NOGO-R3    WIYSNNITYI  HPSTFEGFVH  LEELDLGDNR  QLRTLAPETF  QGLVKLHALY
    Human NOGO-R2    WLFSNNLSTI  YPGTFRHLQA  LEEIDLGDNR  HLRSLEPDTF  QGLERLQSLH
    Consensus        W--SN-----I ------F----  LE-LDL-DN-  -L----P-TF -GL-L-----L LRR 4                                      LRR 5                                     200
151 Human NOGO-R1    LDRCGLQELG  PGLFRGLAAL  QYLYLQDNAL  QALPDDTFRD  LGNLTHLFLH
    Murine NOGO-R1   LDRCGLRELG  PGLFRGLAAL  QYLYLQDNNL  QALPDNTFRD  LGNLTHLFLH
    Murine NOGO-R3   LYKCGLSALP  AGIFGGLHSL  QYLYLQDNHI  EYLQDDIFVD  LVNLSHLFLH
    Human NOGO-R3    LYKCGLSALP  AGVFGGLHSL  QYLYLQDNHI  EYLQDDIFVD  LVNLSHLFLH
    Human NOGO-R2    LYRCQLSSLP  GNIFRGLVSL  QYLYLQENSL  LHLQDDLFAD  LANLSHLFLH
    Consensus        L--C-L--L-  ---F-GL----L QYLYLQ-N--  --L-D--F-D  L--NL-HLFLH
```

FIG. 3, cont.

```
                 201       LRR 6                      LRR 7                        250
Human NOGO-R1    GNRISSVPER AFRGLHSLDR LLLHQNRVAH VHPHAFRDLG RLMTLYLFAN
Murine NOGO-R1   GNRIPSVPEH AFRGLHSLDR LLLHQNHVAR VHPHAFRDLG RLMTLYLFAN
Murine NOGO-R3   GNKLWSLGQG IFRGLVNLDR LLLHENQLQW VHHKAFHDLH RLTTLFLFNN
Human NOGO-R3    GNKLWSLGPG TFRGLVNLDR LLLHENQLQW VHHKAFHDLR RLTTLFLFNN
Human NOGO-R2    GNRLRLLTEH VFRGLGSLDR LLLHGNRLQG VHRAAFRGLS RLTILYLFNN
Consensus        GN-------- -FRGL--LDR LLLH--N--- VH--AF--L- RL--L-LF-N 251       LRR 8                                 LRR CT     300
Human NOGO-R1    NLSALPTEAL APLRALQYLR LNDNPWVCDC RARPLWAWLQ KFRGSSSEVP
Murine NOGO-R1   NLSMLPAEVL MPLRSLQYLR LNDNPWVCDC RARPLWAWLQ KFRGSSSEVP
Murine NOGO-R3   SLTELQGDCL APLVALEFLR LNGNAWDCGC RARSLWEWLR RFRGSSSAVP
Human NOGO-R3    SLSELQGECL APLGALEFLR LNGNPWDCGC RARSLWEWLQ RFRGSSSAVP
Human NOGO-R2    SLASLPGEAL ADLPSLEFLR LNANPWACDC RARPLWAWFQ RARVSSSDVT
Consensus        -L-L-----L --L--L--LR LN-N-W-C-C RAR-LW-W-- --R-SSS-V-

301                                                        350
Human NOGO-R1    CSLPQRLAGR DLKRLAANDL QGCAVATGPY HPIWTGRATD EEPLGLPKCC
Murine NOGO-R1   CNLPQRLADR DLKRLAASDL EGCAVASGPF RPIQTSQLTD EELLSLPKCC
Murine NOGO-R3   CATPELRQGQ DLKLLRVEDF RNCTGPVSP. HQIKSHTLTT SDRAARKEHH
Human NOGO-R3    CVSPGLRHGQ DLKLLRAEDF RNCTGPASP. HQIKSHTLTT TDRAARKEHH
Human NOGO-R2    CATPPERQGR DLRALREADF QACP.PAAP. TRPGSRA... ..RGNSSSNH
Consensus        C--P------ DL-L---D-- --C------- --------P- ----------

351                                                        400
Human NOGO-R1    QPDAADKASV LEPGRPASAG NALKGRVPPG DSPPGNGSGP RHINDSPFGT
Murine NOGO-R1   QPDAADKASV LEPGRPASAG NALKGRVPPG DTPPGNGSGP RHINDSPFGT
Murine NOGO-R3   PSHGASRDKG HPHGHPPGSR SGYK...... .KAGKNCTSH RNRNQISKVS
Human NOGO-R3    SPHGPTRSKG HPH...GPR  PGHR...... .KPGKNCTNP RNRNQISKAG
Human NOGO-R2    .LYGVA.EAG AP...PADPS TLYR...... .DLPA..... ....EDSRGR
Consensus        ---------- ---------- ---------- ---------- ----------
```

FIG. 3, cont.

```
                401                                                            450
Human NOGO-R1   LPGSAEPPLT AVRPEGSEPP GF...PTSGP RRRPGCSRKN RTRSHCRLGQ
Murine NOGO-R1  LPSSAEPPLT ALRPGGSEPP GL...PTTGP RRRPGCSRKN RTRSHCRLGQ
Murine NOGO-R3  .SGKELTELQ DYAPDYQHKF SFDIMPTARP KRKGKCARRT PIRAPSGVQQ
Human NOGO-R3   .AGKQAPELP DYAPDYQHKF SFDIMPTARP KRKGKCARRT PIRAPSGVQQ
Human NOGO-R2   .QGGDAPTED DYWGGY.... ......GGED QRGEQMCPGA ACQAPPD...
Consensus       ---------- ---------- ---------- -----R---- ----------

451                    Putative GPI Signals                   490
Human NOGO-R1   AGSGGGGTGD SEGSGALPSL TCSLTPLGLA LVLWTVLGPC
Murine NOGO-R1  AGSGASGTGD AEGSGALPAL ACSLAPLGLA LVLWTVLGPC
Murine NOGO-R3  .......... ..ASSGTALG APLLAWILGL AVTLR~~~~~
Human NOGO-R3   .......... ..ASSASSLG ASLLAWTLGL AVTLR~~~~~
Human NOGO-R2   .......... ..SRGPALSA GLPS PLLCL LLLVPHHL~~
Consensus       ---------- ---------- ---------- ----------
```

NOGO RECEPTOR HOMOLOGS

This application is a continuation of U.S. application Ser. No. 09/972,546, filed Oct. 6, 2001, now abandoned, which claims benefit of U.S. Patent Application No. 60/238,361, filed Oct. 6, 2000, both of which are incorporated by reference herein in their entirety.

FIELD OF THE INVENTION

The invention relates to neurology and molecular biology. More particularly, the invention relates to CNS neurons and axonal growth

BACKGROUND

Among the mechanisms through which the cells of an organism communicate with each other and obtain information and stimuli from their environment is through cell membrane receptor molecules expressed on the cell surface. Many such receptors have been identified, characterized, and sometimes classified into major receptor superfamilies based on structural motifs and signal transduction features. The receptors are a first essential link for translating an extracellular signal into a cellular physiological response.

Receptors on neurons are particularly important in the development of the nervous system during embryogenesis. The neurons form connections with target cells during development through axonal extension of the neurons toward the target cells in a receptor-mediated process. Axons and dendrites have a specialized region of their distal tips known as the growth cone. Growth cones enable the neuron to sense the local environment through a receptor-mediated process and direct the movement of the axon or dendrite of the neuron toward the neuron's target cell. This process is known as elongation. Growth cones can be sensitive to several guidance cues, for example, surface adhesiveness, growth factors, neurotransmitters and electric fields. The guidance of growth at the cone depends on various classes of adhesion molecules, intercellular signals, as well as factors that stimulate and inhibit growth cones.

Interestingly, damaged neurons do not elongate in the central nervous system (CNS) following injury due to trauma or disease, whereas axons in the peripheral nervous system (PNS) regenerate readily. The fact that damaged CNS neurons fail to elongate is not due to an intrinsic property of CNS axons, but rather due to the CNS environment that is not permissive for axonal elongation. Classical grafting experiments by Aguayo and colleagues (e.g., Richardson et al., (1980) *Nature* 284, 264–265) demonstrated that CNS axons can in fact elongate over substantial distances within peripheral nerve grafts, and that CNS myelin inhibits CNS axon elongation. Therefore, given the appropriate environment, CNS axons can regenerate, implying that CNS axonal injury can potentially be addressed by appropriate manipulation of the CNS environment.

The absence of axon regeneration following injury can be attributed to the presence of axon growth inhibitors. These inhibitors are predominantly associated with myelin and constitute an important barrier to regeneration. Axon growth inhibitors are present in CNS-derived myelin and the plasma membrane of oligodendrocytes that synthesize myelin in the CNS (Schwab et al., (1993) *Annu. Rev. Neurosci.* 16, 565–595). Myelin-associated inhibitors appear to be a primary contributor to the failure of CNS axon regeneration in vivo after an interruption of axonal continuity, whereas other non-myelin associated axon growth inhibitors in the CNS may play a lesser role. These inhibitors block axonal regeneration following neuronal injury due to trauma, stroke or viral infection.

Numerous myelin-derived axon growth inhibitors have been characterized (see, for review, David et al., (1999) WO995394547; Bandman et al., (1999) U.S. Pat. No. 5,858,708; Schwab, (1996) *Neurochem. Res.* 21, 755–761). Several components of CNS white matter, NI35, NI250 (Nogo) and Myelin-associated glycoprotein (MAG), which have inhibitory activity for axonal extension, have been described as well (Schwab et al., (1990) WO9005191; Schwab et al., (1997) U.S. Pat. No. 5,684,133). In particular, Nogo is a 250 kDa myelin-associated axon growth inhibitor that was originally characterized based on the effects of the purified protein in vitro and monoclonal antibodies that neutralize the protein's activity (Schwab (1990) *Exp. Neurol.* 109, 2–5). The Nogo cDNA was first identified through random analysis of brain cDNA and had no suggested function (Nagase et al., (1998) *DNA Res.* 5, 355–364). The identification of this Nogo cDNA as the cDNA encoding the 250 kDa myelin-associated axon growth inhibitor was discovered only recently (GrandPre et al., (2000) *Nature* 403, 439–444; Chen et al., (2000) *Nature* 403, 434–439; Prinjha at al., (2000) *Nature* 403, 383–384).

Importantly, Nogo has been shown to be the primary component of CNS myelin responsible for inhibiting axonal elongation and regeneration. Nogo's selective expression by oligodendrocytes and not by Schwann cells (the cells that myelinate P.S. axons) is consistent with the inhibitory effects of CNS myelin, in contrast to P.S. Myelin (GrandPre et al., (2000) *Nature* 403, 434–439). In culture, Nogo inhibits axonal elongation and causes growth cone collapse (Spillmann et al., (1998) *J. Biol. Chem.* 272, 19283–19293). Antibodies (e.g., IN-1) against Nogo have been shown to block most of the inhibitory action of CNS myelin on neurite growth in vitro (Spillmann et al., (1998) *J. Biol. Chem.* 272:19283–19293). These experiments indicate that Nogo is the main component of CNS myelin responsible for inhibition of axonal elongation in culture. Furthermore, in vivo, the IN-1 antibody has been shown to enhance axonal regeneration after spinal cord injury, resulting in recovery of behaviors such as contact placing and stride length (Schnell and Schwab (1990) *Nature* 343, 269–272; Bregman et al., (1995) *Nature* 378, 498–501). Thus, there is substantial evidence that Nogo is a disease-relevant molecular target. Agents that interfere with the binding of Nogo to its receptor would be expected to improve axonal regeneration in clinical states in which axons have been damaged, and improve patient outcome.

Modulation of Nogo has been described as a means for treatment of regeneration for neurons damaged by trauma, infarction and degenerative disorders of the CNS (Schwab et al., (1994) WO9417831: Tatagiba et al., (1997) *Neurosurgery* 40, 541–546) as well as malignant tumors in the CNS such as glioblastoma (Schwab et al., (1993) U.S. Pat. No. 5,250,414); Schwab et al., (2000) U.S. Pat. No. 6,025,333).

Antibodies which recognize Nogo have been suggested to be useful in the diagnosis and treatment of nerve damage resulting from trauma, infarction and degenerative disorders of the CNS (Schnell & Schwab, (1990) *Nature* 343, 269–272; Schwab et al., (1997) U.S. Pat. No. 5,684,133). For CNS axons, there is a correlation between the presence of myelin and the inhibition of axon regeneration over long distances (Savio and Schwab (1990) *Proc. Natl. Acad. Sci.* 87, 4130–4133; Keirstead et al., (1992) *Proc. Natl. Acad Sci.* 89, 11664–11668). After Nogo is blocked by antibodies, neurons can again extend across lesions caused by nerve damage (Schnell and Schwab (1990) *Nature* 343, 269–272).

SUMMARY OF THE INVENTION

Genes encoding homologs (NgR2 and NgR3) of a Nogo receptor (NgR1) in mice and humans have been discovered. Various domains in the polypeptide encoded by the NgR2 and NgR3 genes have been identified and compared to domains in mouse and human NgR1 polypeptides. This comparison has led to identification of a consensus sequence (NgR consensus sequence) that characterizes a family of proteins (NgR family). Based on these and other discoveries, the invention features molecules and methods for modulating axonal growth in CNS neurons.

The invention provides a polypeptide that contains a polypeptide containing a tryptophan rich LRRCT domain consisting of the amino acid sequence:

N $X_1$ W $X_2$ C $X_3$ C R A R $X_4$ L W $X_5$ W $X_6$ $X_7$ $X_8$ $X_9$ R $X_{10}$ S S S $X_{11}$ V    [SEQ ID NO: 19]

$X_{12}$ C $X_{13}$ $X_{14}$ P $X_{15}$ $X_{16}$ $X_{17}$ $X_{18}$ $X_{19}$ $X_{20}$ D L $X_{21}$ $X_{22}$ L $X_{23}$ $X_{24}$ $X_{25}$ D $X_{26}$ $X_{27}$ $X_{28}$ C wherein X is any protein amino acid or a gap, and the polypeptide does not include amino acid sequence from residue 260 to 309 of SEQ ID NO: 5 (human NgR1) or SEQ ID NO: 17 (mouse NgR1).

Preferably, X17 and X23 are (independently) arginine or lysine. In some embodiments, the amino acid sequence of the LRRCT domain is residues 261–310 of SEQ ID NO:2, or residues 261–310 of SEQ ID NO: 2 with up to 10 conservative amino acid substitutions. In some embodiments, the polypeptide contains the following NTLRRCT amino acid sequence:

ID NO: 14 (human NgR3). In some embodiments, the polypeptide contains: (a) a NTLRRCT domain, and (b) less than a complete CTS domain, provided that a partial CTS domain, if present, consists of no more than the first 39 amino acids of the CTS domain. While the polypeptide may contain a functional GPI domain, a functional GPI domain may be absent, e.g., when a soluble polypeptide is desired. A polypeptide of the invention optionally includes an amino acid sequence of a heterologous polypeptide, e.g., an Fc portion of an antibody.

The invention also provides a nucleic acid encoding an above-described polypeptide; a vector containing the nucleic acid, which nucleic acid may be operably linked to an expression control sequence; and a transformed host cell containing the vector. A method of producing a polypeptide of the invention is also provided. The method includes introducing a nucleic acid encoding the above-described polypeptide into a host cell, culturing the cell under conditions suitable for expression of the polypeptide, and recovering the polypeptide.

The invention also provides an antisense molecule whose nucleotide sequence is complementary to a nucleotide sequence encoding a polypeptide selected from the group consisting of: a polypeptide consisting of residues 311–395 of SEQ ID NO: 2, a polypeptide consisting of residues 256–396 of SEQ ID NO:14 and a polypeptide consisting of residues 321–438 of SEQ ID NO: 4, wherein the nucleic acid is from 8 to 100 nucleotides in length, e.g., about 20, 30, C P $X_1$ $X_2$ C $X_3$ C Y $X_4$ $X_5$ P $X_6$ $X_7$ T $X_8$ S C $X_9$ $X_{10}$ $X_{11}$ $X_{12}$ $X_{13}$ $X_{14}$ $X_{15}$ $X_{16}$ P    [SEQ ID NO: 18]

$X_{17}$ $X_{18}$ $X_{19}$ P $X_{20}$ $X_{21}$ $X_{22}$ $X_{23}$ R $X_{24}$ F L $X_{25}$ $X_{26}$ N $X_{27}$ I $X_{28}$ $X_{29}$ $X_{30}$ $X_{31}$ $X_{32}$ $X_{33}$ $X_{34}$ F $X_{35}$ $X_{36}$ $X_{37}$ $X_{38}$ $X_{39}$ $X_{40}$ $X_{41}$ $X_{42}$ L W $X_{43}$ $X_{44}$ S N $X_{45}$ $X_{46}$ $X_{47}$ $X_{48}$ I $X_{49}$ $X_{50}$ $X_{51}$ $X_{52}$ F $X_{53}$ $X_{54}$ $X_{55}$ $X_{56}$ $X_{57}$ L E $X_{58}$ L D L $X_{59}$ D N $X_{60}$ $X_{61}$ L $X_{62}$ $X_{63}$ $X_{64}$ $X_{65}$ P $X_{66}$ T F $X_{67}$ G L $X_{68}$ $X_{69}$ L $X_{70}$ $X_{71}$ L $X_{72}$ L $X_{73}$ $X_{74}$ C $X_{75}$ L $X_{76}$ $X_{77}$ L $X_{78}$ $X_{79}$ $X_{80}$ $X_{81}$ F $X_{82}$ G L $X_{83}$ $X_{84}$ L Q Y L Y L Q $X_{85}$ N $X_{86}$ $X_{87}$ $X_{88}$ $X_{89}$ L $X_{90}$ D $X_{91}$ $X_{92}$ F $X_{93}$ D L $X_{94}$ N L $X_{95}$ H L F L H G N $X_{96}$ $X_{97}$ $X_{98}$ $X_{99}$ $X_{100}$ $X_{101}$ $X_{102}$ $X_{103}$ $X_{104}$ F R G L $X_{105}$ $X_{106}$ L D R L L L H $X_{107}$ N $X_{108}$ $X_{109}$ $X_{110}$ $X_{111}$ V H $X_{112}$ $X_{113}$ A F $X_{114}$ $X_{115}$ L $X_{116}$ R L $X_{117}$ $X_{118}$ L $X_{119}$ L F $X_{120}$ N $X_{121}$ L $X_{122}$ $X_{123}$ L $X_{124}$ $X_{125}$ $X_{126}$ $X_{127}$ L $X_{128}$ $X_{129}$ L $X_{130}$ $X_{131}$ L $X_{132}$ $X_{133}$ L R L N $X_{134}$ N $X_{135}$ W $X_{136}$ C $X_{137}$ C R $X_{138}$ R $X_{139}$ L W $X_{140}$ W $X_{141}$ $X_{142}$ $X_{143}$ $X_{144}$ R $X_{145}$ S S S $X_{146}$

V $X_{147}$ C $X_{148}$ $X_{149}$ P $X_{150}$ $X_{151}$ $X_{152}$ $X_{153}$ $X_{154}$ $X_{155}$ D L $X_{156}$ $X_{157}$ L $X_{158}$ $X_{159}$ $X_{160}$

D $X_{161}$ $X_{162}$ $X_{163}$ C wherein X is any amino acid residue or a gap and wherein the polypeptide is not the polypeptide of SEQ ID NO: 5 (human NgR1) or SEQ ID NO: 17 (mouse NgR1). For example, $X_6$, $X_{37}$ and $X_{38}$ may represent a gap. Specific examples of polypeptides of the invention are SEQ ID NO: 2 (human NgR2), SEQ ID NO: 4 (mouse NgR3), and SEQ 40, 50, 60, 70, 80 or 90 nucleotides. The invention also provides a nucleic acid encoding such an antisense molecule.

The invention also provides an antibody that binds to an above-described polypeptide. Polypeptides or antibodies of the invention can be formulated into pharmaceutical compositions containing the polypeptide or antibody and a pharmaceutically acceptable carrier.

The invention also provides a method for decreasing inhibition of axonal growth of a CNS neuron. The method includes the step of contacting the neuron with an effective amount of a polypeptide or antibody of the invention. The invention also provides a method for treating a central nervous system disease, disorder or injury. The method includes administering to a mammal, e.g., a human, an effective amount of a polypeptide or antibody of the invention. Exemplary diseases, disorders and injuries that may be treated using molecules and methods of the invention include, but are not limited to, cerebral injury, spinal cord injury, stroke, demyelinating diseases, e.g., multiple sclerosis, monophasic demyelination, encephalomyelitis, multifocal leukoencephalopathy, panencephalitis, Marchiafava-Bignami disease, Spongy degeneration, Alexander's disease, Canavan's disease, metachromatic leukodystrophy and Krabbe's disease.

The invention also provides a method for identifying a molecule that binds a polypeptide of the invention. The method includes the steps of: (a) providing a polypeptide of the invention; (b) contacting the polypeptide with the candidate molecule; and (c) detecting binding of the candidate molecule to the polypeptide.

Unless otherwise defined, all technical and scientific terms used herein have the same meaning as commonly understood by one of ordinary skill in the art to which the invention belongs. In case of conflict, the present application, including definitions, will control. All publications, patent and other references mentioned herein are incorporated by reference.

The materials, methods and examples presented below are illustrative only, and not intended to be limiting. Other features and advantages of the invention will be apparent from the detail description and from the claims.

BRIEF DESCRIPTION OF THE FIGURES

FIG. 1A–1B shows an alignment of NgR2 (SEQ ID NO:2) and NgR3 (SEQ ID NO:4) with the known NgR, NgR1 (SEQ ID NO:5) and the Consensus Sequence (SEQ ID NO:6).

FIG. 3. An alignment of the amino acid sequences of human NgR1, murine NgR1, murine NgR3, human NgR3 and human NgR2. Numbering begins with amino acid #1 of murine NgR3. The consensus sequence is listed below. The LRR NT domain is indicated by a shaded box; domains LLR 1, LLR 3, LLR 5, and LLR 7 are indicated by open boxes; LLR 2, LLR 4, LLR 6 and LLR 8 are indicated by shaded boxes; and the LLR CT domain is indicated by a shaded box. Amino acids in bold in LLR 8 indicate a conserved glycosylation sites. A dot indicates conserved cystine residue in LRR4. Box at C terminus indicates putative GPI signals.

DETAILED DESCRIPTION OF THE INVENTION

Figure 2:
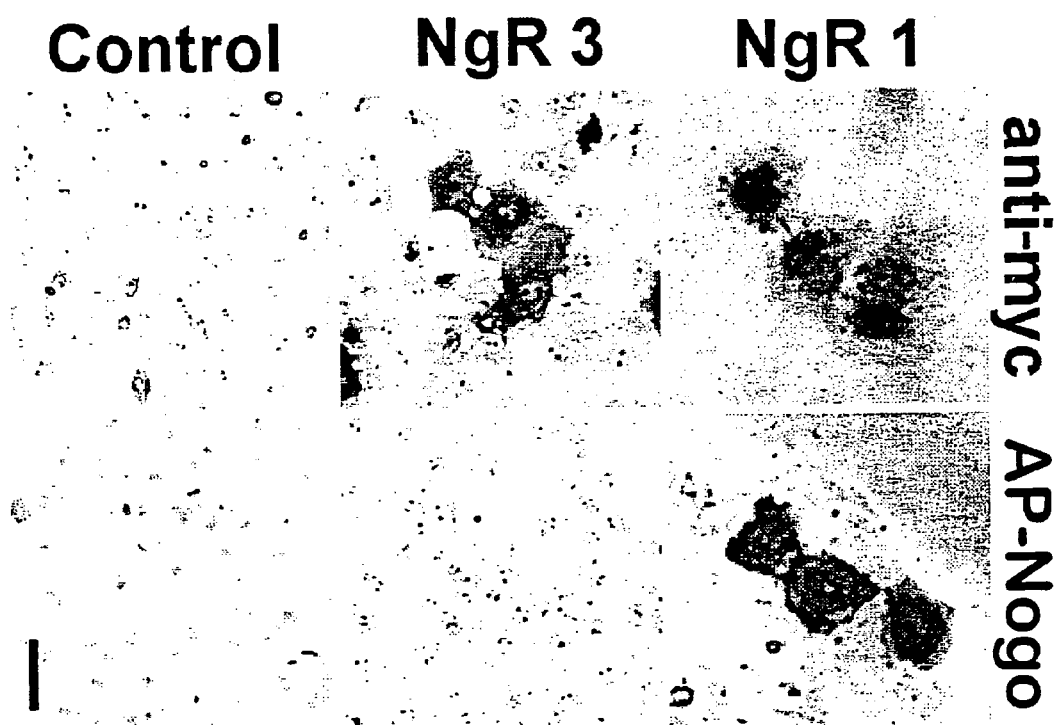
FIG. 2. mNgR3 does not bind hNogoA(1055–1120). COS-7 cells were transfected with vectors encoding myc-NgR1 or myc-NgR3, fixed, and stained with anti-myc antibodies or AP-hNogoA(1055–1120).

The present invention provides purified and isolated polynucleotides (e.g., DNA sequences and RNA transcripts, both sense and complementary antisense strands, both single- and double-stranded, including splice variants thereof) encoding NgR homologs, referred to herein as NgR. Unless indicated otherwise, as used herein, the abbreviation in lower case (NgR) refers to a gene, cDNA, RNA or nucleic acid sequence, whereas the upper case version (NgR) refers to a protein, polypeptide, peptide, oligopeptide, or amino acid sequence. Specific proteins are designated by number, e.g., "NgR2" is a human NgR homolog, "NgR3" is a murine-derived NgR homolog, and "NgR1" is the known NgR identified by Dr. Stephen Strittmatter. Known NgRs are herein referred to as "NgRs." DNA polynucleotides of the invention include genomic DNA, cDNA and DNA that has been chemically synthesized in whole or in part.

Standard reference works setting forth the general principles of recombinant DNA technology known to those of skill in the art include Ausubel et al., CURRENT PROTOCOLS IN MOLECULAR BIOLOGY, John Wiley & Sons, New York (1998); Sambrook et al., MOLECULAR CLONING: A LABORATORY MANUAL, 2d Ed., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

As used herein, the term "axon" refers to a long cellular protrusion from a neuron, whereby action potentials are conducted, either to or from the cell body.

As used herein, the term "axonal growth" refers to an extension of the long process or axon, originating at the cell body and proceeded by the growth cone.

As used herein, the term "central nervous system disorder" refers to any pathological state associated with abnormal function of the central nervous system (CNS). The term includes, but is not limited to, altered CNS function resulting from physical trauma to cerebral tissue, viral infection, autoimmune machanisms and genetic mutation.

As used herein, the term "demyelinating disease" refers to a pathological disorder characterized by the degradation of the myelin sheath of the oligodendrocyte cell membrane.

As used herein, the term "growth cone" refers to a specialized region at the tip of a growing neurite that is responsible for sensing the local environment and moving the axon toward its appropriate synaptic target cell.

As used herein, the term "growth cone movement" refers to the extension or collapse of the growth cone toward a neuron's target cell.

As used herein, the term "neurite" refers to a process growing out of a neuron. As it is sometimes difficult to distinguish a dendrite from in axon in culture, the term "neurite" is used for both.

As used herein, the term "oligodendrocyte" refers to a neuroglial cell of the CNS whose function is to myelinate CNS axons.

"Synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. By the term "region" is meant a physically contiguous portion of the primary structure of a biomolecule. In the case of proteins, a region is defined by a contiguous portion of the amino acid sequence of that protein. The term "domain" is herein defined as referring to a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region. Examples of NgR protein domains include, but are not limited to, the signal peptide, extracellular (i.e., N-terminal) domain, and leucine-rich repeat domains.

As used herein, the term "activity" refers to a variety of measurable indicia suggesting or revealing binding, either direct or indirect; affecting a response, i.e., having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event. Such activities may be measured by assays such as competitive inhibition of NgR1 binding to Nogo assays wherein, for example, unlabeled, soluble NgR2 is added to an assay system in increasing concentrations to inhibit the binding of Nogo to NgR1 expressed on the surface of CHO cells. As another example, one may assess the ability of neurons to extend across lesions caused by nerve damage (as in Schnell and Schwab (1990) *Nature* 343, 269–272) following inhibition of Nogo by various forms of NgR2 and/or NgR3 as a biological indicator of NgR function.

As used herein, the term "antibody" is meant to refer to complete, intact antibodies, and Fab, Fab', F(ab)2, and other fragments thereof. Complete, intact antibodies include monoclonal antibodies such as murine monoclonal antibodies, chimeric antibodies, anti-idiotypic antibodies, anti-anti-idiotypic antibodies, and humanized antibodies.

As used herein, the term "binding" means the physical or chemical interaction between two proteins or compounds or associated proteins or compounds or combinations thereof. Binding includes ionic, non-ionic, hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to, small molecules, peptides, proteins, sugars, nucleotides or nucleic acids, and such compound can be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule, or polypeptide encoding the NgR or fragment thereof.

As used herein, the phrase "homologous nucleotide sequence," or "homologous amino acid sequence," or variations thereof, refers to sequences characterized by an identity at the nucleotide level, or a homology at the amino acid level, of at least the specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding NgR1. Homologous amino acid sequences include those amino acid sequences which contain conservative amino acid substitutions and which polypeptides have the same binding and/or activity. A homologous amino acid sequence does not, however, include the amino acid sequence encoding other known NgRs. Percent homology can be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Adv. Appl. Math., 1981, 2, 482–489, which is incorporated herein by reference in its entirety).

As used herein, the term "isolated" nucleic acid molecule refers to a nucleic acid molecule (DNA or RNA) that is substantially free of nucleic acids encoding other proteins with which it is associated in nature, i.e., a nucleic acid that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated NgR nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

As used herein, the term "heterologous" refers to a nucleotide or amino acid sequence that is a different, or non-corresponding sequence, or a sequence derived from a different species. For example, a mouse NgR nucleotide or amino acid sequence is heterologous to a human NgR nucleotide or amino acid sequence, and a human NgR nucleic or amino acid sequence is heterologous to a human immunoglobulin nucleotide or amino acid sequence.

As used herein, a "soluble NgR polypeptide" is a NgR polypeptide that does not anchor itself in a membrane. Such soluble polypeptides include, for example, NgR2 and NgR3 polypeptides that lack a sufficient portion of their GPI anchor signal to anchor the polypeptide or are modified such that the GPI anchor signal is not adequate to result in replacement of the peptide with a GPI anchor. In preferred embodiments, up to 5, 10, 20 or 25 amino acids are removed from the C-terminus of NgR2 or NgR3 to make the respective proteins soluble. As used herein soluble NgR polypeptides include full-length or truncated (e.g., with internal deletions) NgR.

Soluble NgR polypeptides may include the entire NgR protein up to the putative GPI signal sequence (e.g., amino acid 1 to about amino acid 395 of NgR2, and from amino acid 1 to about amino acid 438 of NgR3). In other embodiments, the signal peptide of the proteins may be removed or truncated (e.g., all or part of the signal sequence of NgR2, which spans amino acid 1 to about amino acid 30 of SEQ ID NO:2, may be removed; all or part of the signal sequence of NgR3, which spans amino acid 1 to about amino acid 40 of SEQ ID NO:4, may be removed). In some embodiments, the mature NgR2 (SEQ ID NO:8) and the mature NgR3 (SEQ ID NO:9) are used.

Soluble NgR polypeptides include at least one of the putative ligand-binding portions of NgR, including the first cysteine-rich region (SEQ ID NO:10, the leucine repeat region (SEQ ID NO:12) and the second cysteine-rich region (SEQ ID NO:11). In some embodiments, soluble NgR polypeptides consist of amino acid 1 through about amino acid 395 of SEQ ID NO:2, or amino acid 1 through about amino acid 438 of SEQ ID NO:4.

In other embodiments, the soluble NgR polypeptides are fusion proteins that contain amino acids 30 through about amino acid 395 of mature NgR2 or amino acid 40 through about amino acid 438 of NgR3, the C-terminal 10 amino acids of a human IgG1 hinge region containing the two cysteine residues thought to participate in interchain disulfide bonding, and the CH2 and CH3 regions of a human IgG1 heavy chain constant domain. This type of recombinant protein is designed to modulate inhibition of axonal elongation through inhibition of the Nogo ligand binding to NgR1, or by inhibiting the ligand of the NgR from interacting with cell surface NgR. The NgR portion of the fusion binds to the Nogo ligand and the IgG1 portion binds to the FcγRI (macrophage) and FcγIII (NK cells and neutrophils) receptors.

The production of the soluble polypeptides useful in this invention may be achieved by a variety of methods known in the art. For example, the polypeptides may be derived from intact transmembrane NgR molecules by proteolysis using specific endopeptidases in combination with exopeptidases, Edman degradation, or both. The intact NgR molecle, in turn, may be purified from its natural source using conventional methods. Alternatively, the intact NgR may be produced by known recombinant DNA techniques using cDNAs, expression vectors and well-known techniques for recombinant gene expression.

Preferably, the soluble polypeptides useful in the present invention are produced directly, thus eliminating the need for an entire NgR as a starting material. This may be achieved by conventional chemical synthesis techniques or by well-known recombinant DNA techniques wherein only those DNA sequences which encode the desired peptides are expressed in transformed hosts. For example, a gene which encodes the desired soluble NgR polypeptide may be synthesized by chemical means using an oligonucleotide synthesizer. Such oligonucleotides are designed based on the amino acid sequence of the desired soluble NgR polypeptide. Specific DNA sequences coding for the desired peptide also can be derived from the full-length DNA sequence by isolation of specific restriction endonuclease fragments or by PCR synthesis of the specified region from cDNA.

A nucleic acid molecule of the present invention, e.g., a nucleic acid molecule having the nucleotide sequence of SEQ ID NOs:1, 3 or a complement of either of these nucleotide sequences, can be isolated using standard molecular biology techniques and the sequence information provided herein. Using all or a portion of the nucleic acid sequences of SEQ ID NOs:1 or 3 as a hybridization probe, NgR nucleic acid sequences can be isolated using standard hybridization and cloning techniques (e.g., as described in Sambrook et al., eds., MOLECULAR CLONING: A LABORATORY MANUAL 2$^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993).

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NgR nucleotide sequences can be prepared by standard synthetic techniques, e.g., using an automated DNA synthesizer.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" refers to the inhibition or activation factors causing or contributing to the abnormal condition. A therapeutic effect relieves to some extent one or more of the symptoms of the abnormal condition. In reference to the treatment of abnormal conditions, a therapeutic effect can refer to one or more of the following: (a) an increase in the proliferation, growth, and/or differentiation of cells; (b) inhibition (i.e., slowing or stopping) of cell death; (c) inhibition of degeneration; (d) relieving to some extent one or more of the symptoms associated with the abnormal condition; and (e) enhancing the function of the affected population of cells. Compounds demonstrating efficacy against abnormal conditions can be identified as described herein.

The term "abnormal condition" refers to a function in the cells or tissues of an organism that deviates from their normal functions in that organism. An abnormal condition can relate to cell proliferation, cell differentiation, cell signaling, or cell survival. An abnormal condition may also include obesity, diabetic complications such as retinal degeneration, and irregularities in glucose uptake and metabolism, and fatty acid uptake and metabolism.

Abnormal cell proliferative conditions, for example, include cancers such as fibrotic and mesangial disorders, abnormal angiogenesis and vasculogenesis, wound healing, psoriasis, diabetes mellitus and inflammation.

Abnormal differentiation conditions include, for example, neurodegenerative disorders, slow wound healing rates and slow tissue grafting healing rates.

Abnormal cell signaling conditions include, for example, psychiatric disorders involving excess neurotransmitter activity.

Abnormal cell survival conditions may also relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques.

The abnormal condition can also be prevented or treated by administering a compound to a group of cells having an aberration in a signal transduction pathway to an organism. The effect of administering a compound on organism function can then be monitored. The organism is preferably a mouse, rat, rabbit, guinea pig or goat, more preferably a monkey or ape, and most preferably a human.

By "amplification" it is meant increased numbers of DNA or RNA in a cell compared with normal cells. "Amplification" as it refers to RNA can be the detectable presence of RNA in cells, since in some normal cells there is no basal expression of RNA. In other normal cells, a basal level of expression exists, therefore in these cases amplification is the detection of at least 1–2-fold, and preferably more, compared to the basal level.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission or (for amino acids) by three letters code.

Nucleic Acids

Genomic DNA of the invention comprises the protein-coding region for a polypeptide of the invention and is also intended to include allelic variants thereof It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode a NgR polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification-resulting from recombination during chromosomal segregation or exposure to conditions which give rise to genetic mutation. Allelic variants, like wild-type genes, are naturally occurring sequences (as opposed to non-naturally occurring variants arising from in vitro manipulation).

The invention also comprehends cDNA that is obtained through reverse transcription of an RNA polynucleotide encoding NgR (conventionally followed by second-strand synthesis of a complementary strand to provide a double-stranded DNA).

Preferred DNA sequences encoding a human NgR polypeptide is set out in SEQ ID NOs:1 and 13. A preferred DNA of the invention comprises a double stranded molecule comprising the coding molecule (i.e., the "coding strand") along with the complementary molecule (the "non-coding strand" or "complement") having a sequence unambiguously deducible from the coding strand according to Watson-Crick base-pairing rules for DNA. Also preferred are other polynucleotides encoding NgR polypeptides, as shown in SEQ ID NO:3, which comprises murine NgR homolog, NgR3.

Also preferred are nucleotide sequences that encode at least a portion of a NgR polypeptide that has at least one biological function of a NgR. More preferred are nucleotide sequences that encode a portion of NgR that encodes at least the mature NgR without the hydrophobic C-terminal GPI signal. Also preferred are nucleotide sequences that encode the portion of NgR that encodes at least the ligand-binding region of NgR.

The invention further embraces other species, preferably mammalian, homologs of the human NgR DNA. Species homologs, sometimes referred to as "orthologs," in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with human DNA of the invention. Generally, percent sequence "homology" with respect to polynucleotides of the invention may be calculated as the percentage of nucleotide bases in the candidate sequence that are identical to nucleotides in the NgR sequences set forth in SEQ ID NOs:1, 3 or 13, after aligning the sequences and introducing gaps, if necessary, to achieve the maximum percent sequence identity.

The polynucleotide sequence information provided by the invention makes possible large-scale expression of the encoded polypeptide by techniques well known and routinely practiced in the art. Polynucleotides of the invention also permit identification and isolation of polynucleotides encoding related NgR polypeptides, such as human allelic variants and species homologs, by well-known techniques including Southern and/or Northern hybridization, and polymerase chain reaction (PCR). Examples of related polynucleotides include human and non-human genomic sequences, including allelic variants, as well as polynucleotides encoding polypeptides homologous to NgR and structurally related polypeptides sharing one or more biological, immunological, and/or physical properties of NgR. Non-human species genes encoding proteins homologous to NgR can also be identified by Southern and/or PCR analysis and are useful in animal models for NgR disorders. Knowledge of the sequence of a human NgR DNA also makes possible through use of Southern hybridization or polymerase chain reaction (PCR) the identification of genomic DNA sequences encoding NgR expression control regulatory sequences such as promoters, operators, enhancers, repressors, and the like. Polynucleotides of the invention are also useful in hybridization assays to detect the capacity of cells to express NgR. Polynucleotides of the invention may also provide a basis for diagnostic methods useful for identifying a genetic alteration(s) in a NgR locus that underlies a disease state or states, which information is useful both for diagnosis and for selection of therapeutic strategies.

The disclosure herein of a full-length polynucleotide encoding a NgR polypeptide makes readily available to the worker of ordinary skill in the art every possible fragment of the full-length polynucleotide. The invention, therefore, provides fragments of NgR-encoding polynucleotides comprising at least 6, and preferably at least 14, 16, 18, 20, 25, 50, or 75 consecutive nucleotides of a polynucleotide encoding NgR. Preferably, fragments of polynucleotides of the invention comprise sequences unique to the NgR-encoding polynucleotide sequence, and therefore hybridize under highly stringent or moderately stringent conditions only (i.e., "specifically") to polynucleotides encoding NgR (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent and enzymatic labeling.

Fragments of polynucleotides are particularly useful as probes for detection of full-length or fragment of NgR polynucleotides. One or more polynucleotides can be included in kits that are used to detect the presence of a polynucleotide encoding NgR, or used to detect variations in a polynucleotide sequence encoding NgR.

The invention also embraces DNAs encoding NgR polypeptides that hybridize under moderately stringent or high stringency conditions to the noncoding strand, or complement, of the polynucleotide in any of SEQ ID NOs:1 or 3.

Stringent conditions are known to those skilled in the art and can be found in CURRENT PROTOCOLS IN MOLECULAR BIOLOGY, John Wiley & Sons, N.Y. (1989), 6.3.1?6.3.6. Preferably, the conditions are such that sequences at least about 65%, 70%, 75%, 85%, 90%, 95%, 98% or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NOs:1 or 3 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). As used herein, "stringent hybridization conditions" means: 42° C. in a hybridization solution comprising 50% formamide, 1% SDS, 1 M NaCl, 10% (wt/vol) dextran sulfate, and washing twice for 30 minutes at 60° C. in a wash solution comprising 0.1×SSC and 1% SDS.

Vectors

Another aspect of the present invention is directed to vectors, or recombinant expression vectors, comprising any of the nucleic acid molecules described above. Vectors are used herein either to amplify DNA or RNA encoding NgR and/or to express DNA which encodes NgR. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), that serve equivalent functions.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67, 31–40), pMAL (New England Biolabs, Beverly, Mass.) and pRIT5 (Pharmacia, Piscataway, N.J.) that fuse glutathione-S-transferase (GST), maltose E binding protein, or protein A, respectively, to the target recombinant protein.

Examples of suitable inducible non-fusion *E. coli* expression vectors include pTrc (Amrann et al., (1988) *Gene* 69, 301–315) and pET11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20, 2111–2118). Such alteration of nucleic acid sequences of the invention can be carried out by standard DNA synthesis techniques.

In another embodiment, the NgR expression vector is a yeast expression vector. Examples of vectors for expression in yeast *S. cerevisiae* include pYepSecl (Baldari, et al, (1987) *EMBO J.* 6, 229–234), pMFa (Kurjan and Herskowitz (1982) *Cell* 30, 933–943), pJRY88 (Schultz et al., (1987) *Gene* 54, 113–123), pYES2 (Invitrogen Corporation, San Diego, Calif., and picZ (InVitrogen Corp, San Diego, Calif.).

Alternatively, NgR can be expressed in insect cells using baculovirus expression vectors. Baculovirus vectors available for expression of proteins in cultured insect cells (e.g., SF9 cells) include the pAc series (Smith et al, (1983) *Mol. Cell. Biol.* 3, 2156–2165) and the pVL series (Lucklow and Summers (1989) *Virology* 170, 31–39).

In yet another embodiment, a nucleic acid of the invention is expressed in mammalian cells using a mammalian expression vector. Examples of mammalian expression vectors include pCDM8 (Seed (1987) *Nature* 329, 840) and pMT2PC (Kaufman et al. (1987) *EMBO J.* 6, 187–195). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells. See, e.g., Chapters 16 and 17 of Sambrook et al., (Eds.) MOLECULAR CLONING: A LABORATORY MANUAL. $2^{nd}$ Ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1, 268–277), lymphoid-specific promoters (Calame and Eaton (1988) *Adv. Immunol.* 43, 235–275), in particular promoters of T cell receptors (Winoto and Baltimore (1989) *EMBO J.* 8, 729–733) and immunoglobulins (Banerji et al. (1983) *Cell* 33, 729–740; Queen and Baltimore (1983) *Cell* 33, 741–748), neuron-specific promoters (e.g., the neurofilament promoter; Byrne and Ruddle (1989) *Proc. Natl. Acad Sci. USA* 86, 5473–5477), pancreas-specific promoters (Edlund et al. (1985) *Science* 230, 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss (1990) *Science* 249, 374–379) and the α-fetoprotein promoter (Campes and Tilghman (1989) *Genes Dev.* 3, 537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense NgR mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue-specific or cell-type-specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., *Antisense RNA as a molecular tool for genetic analysis*, REVIEWS—TRENDS IN GENECS, Vol. 1(1) 1986.

Preferred vectors include, but are not limited to, plasmids, phages, cosmids, episomes, viral particles or viruses and integratable DNA fragments (i.e., fragments integratable into the host genome by homologous recombination). Preferred viral particles include, but are not limited to, adenoviruses, baculoviruses, parvoviruses, herpesviruses, poxviuses, adeno-associated viruses, Semliki Forest viruses, vaccinia viruses and retroviruses. Preferred expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescrip™ vectors (Stratagene), pQE™ vectors (Qiagen), pSE420™ (Invitrogen) and pYES2™ (Invitrogen).

Preferred expression vectors are replicable DNA constructs in which a DNA sequence encoding NgR is operably linked or connected to suitable control sequences capable of effecting the expression of the NgR in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include, but are not limited to a transcriptional promoter, enhancers, an optional operator sequence to control transcription, polyadenylation signals, a sequence encoding suitable mRNA ribosomal binding and sequences which control the termination of transcription and translation. Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NgR proteins, mutant forms of NgR, fusion proteins, etc.).

Preferred vectors preferably contain a promoter that is recognized by the host organism. The promoter sequences of the present invention may be prokaryotic, eukaryotic or viral. Examples of suitable prokaryotic sequences include the PR and PL promoters of bacteriophage lambda (THE BACTERIOPHAGE LAMBDA, Hershey, A. D. (Ed.), Cold Spring Harbor Laboratory Press, Cold Spring Harbor, N.Y. (1973), which is incorporated herein by reference in its entirety; LAMBDA II, Hendrix, R. W. (Ed.), Cold Spring Harbor Laboratory Press, Cold Spring Harbor, N.Y. (1980), which is incorporated herein by reference in its entirety); the trp, recA, heat shock, and lacZ promoters of *E. coli* and the SV40 early promoter (Benoist et al., (1981) *Nature* 290, 304–310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine and human metallothionein.

Additional regulatory sequences can also be included in preferred vectors. Preferred examples of suitable regulatory sequences are represented by the Shine-Dalgarno sequence of the replicase gene of the phage MS-2 and of the gene cII of bacteriophage lambda. The Shine-Dalgarno sequence may be directly followed by DNA encoding NgR and result in the expression of the mature NgR protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and NgR DNA. An example of a suitable marker is dihydrofolate reductase (DHFR) or thymidine kinase (see, U.S. Pat. No. 4,399,216).

Nucleotide sequences encoding NgR may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining and ligation with appropriate ligases. Techniques for such manipulation are disclosed by Sambrook et al., supra and are well known in the art. Methods for construction of mammalian expression vectors are disclosed in, for example, Okayama et al., (1983) *Mol. Cell. Biol.* 3:280, Cosman et al. (1986) *Mol. Immunol.* 23:935, Cosman et al, (1984) *Nature* 312:768, EP-A-0367566, and WO 91/18982, each of which is incorporated herein by reference in its entirety.

Host Cells and Transformed Host Cells

According to another aspect of the invention, host cells are provided, including prokaryotic and eukaryotic cells, comprising a polynucleotide of the invention (or vector of the invention) in a manner that permits expression of the encoded NgR polypeptide. Preferably, the cell produces little or no endogenous NgR polypeptide. Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, or fusion with carriers such as liposomes, micelles, ghost cells and protoplasts. Expression systems of the invention include bacterial, yeast, fungal, plant, insect, invertebrate, vertebrate and mammalian cells systems.

Host cells of the invention are a valuable source of immunogen for development of antibodies specifically immunoreactive with NgR. Host cells of the invention are also useful in methods for the large-scale production of NgR polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of NgR DNA sequences allows for modification of cells to permit, or increase, expression of endogenous NgR. Cells can be modified (e.g., by homologous recombination) to provide increased expression by replacing, in whole or in part, the naturally occurring NgR promoter with all or part of a heterologous promoter so that the cells express NgR at higher levels. The heterologous promoter is inserted in such a manner that it is operatively linked to endogenous NgR encoding sequences. (See, for example, PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the NgR coding sequence, amplification of the marker DNA by standard selection methods results in co-amplification of the NgR coding sequences in the cells.

The DNA sequence information provided by the present invention also makes possible the development (e.g., by homologous recombination or "knock-out" strategies; see Capecchi, *Science* 244:1288–1292 (1989)) of animals that fail to express functional NgR or that express a variant of NgR. Such animals (especially small laboratory animals such as rats, rabbits and mice) are useful as models for studying the in vivo activities of NgR and modulators of NgR.

Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces* and *Staphylococcus*.

If a eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, Eds. (1973), which is incorporated herein by reference in its entirety).

In addition, a yeast cell may be employed as a host cell. Preferred yeast cells include, but are not limited to, the genera *Saccharomyces, Pichia* and *Kluveromyces*. Preferred yeast hosts are *S. cerevisiae* and *P. pastoris*. Preferred yeast vectors can contain an origin of replication sequence from a 2T yeast plasmid, an autonomously replication sequence (ARS), a promoter region, sequences for polyadenylation, sequences for transcription termination and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology*, 1988, 6, 47; BACULOVIRUS EXPRESSION VECTORS: A LABORATORY MANUAL, O'Rielly et al. (Eds.), W.H. Freeman and Company, New York, 1992; and U.S. Pat. No. 4,879,236, each of which is incorporated herein by reference in its entirety). In addition, the MAX-BAC™ complete baculovirus expression system (Invitrogen) can, for example, be used for production in insect cells.

Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, dihydrofolate reductase (DHFR) and methotrexate. Nucleic acid encoding a selectable marker can be introduced into a host cell on the same vector as that encoding NgR or can be introduced on a separate vector. Cells stably transfected with the introduced nucleic acid can be identified by drug selection (e.g., cells that have incorporated the selectable marker gene will survive, while the other cells die).

In a preferred embodiment, the polypeptides of the invention, including forms of NgR2 and NgR3, soluble forms of NgR, chimeric NgR polypeptides, NgR/Ig fusions and fragments and variations of each of the above are expressed in Chinese Hamster Ovary (CHO) cells.

In order to introduce the DNA fragment coding for the NgR protein or polypeptide into the CHO cell to express the recombinant NgR protein or polypeptide, it is necessary to construct the expression vector.

The vectors for CHO expression include, but are not limited to, pA1–11, pXT1, pRc/CMV, pRc/RSV and pcDNAINeo. The promoter is not specifically limited provided it effectively promotes expression in CHO cells. Examples of suitable promoters are: SRα, SV40, LTR, CMV, and HSV-TK. Of these, CMV and Srα promoters are preferred.

In addition to the above-mentioned promoters, the expression vectors may contain enhancers, splicing signals, polyadenylation signals, selectable markers and an SV40 replication origin. Suitable selectable markers include, but are not limited to the dihydrofolate reductase (DHFR) gene which provides resistance to methotrexate (MTX), the ampicillin resistance gene, and the neomycin resistance gene.

Examples of the expression vectors each containing the DNA coding for NgR, portions, fragments and soluble constructs thereof, include the vector (such as one described above), into which the promoter is operably linked (preferably upstream) to the nucleotide sequence encoding the desired NgR construct; a polyadenylation signal downstream from the nucleotide sequence encoding the NgR construct; and, preferably, the vector includes an operable DHFR gene. Preferably, the ampicillin resistant gene is also operably contained in the vector.

CHO cell lacking the DHFR gene (Urlaub, G. et al., (1980) *Proc. Natl. Acad. Sci. USA* 77, 4216–4220) and CHO-K1 (*Proc. Natl. Acad. Sci. USA* 60, 1275 (1968)) are suitable for use.

The NgR expression vectors prepared as above are introduced into CHO cells by any known method, including, but not limited to the calcium phosphate method (Graham and van der Eb (1973) *Virol.* 52, 456–467) and electroporation (Nuemann et al., (1982) *EMBO J.* 1, 841–845).

Transformants carrying the expression vectors are selected based on the above-mentioned selectable markers. Repeated clonal selection of the transformants using the selectable markers allows selection of stable cell lines having high expression of the NgR constructs. Increased MTX concentrations in the selection medium allows gene amplification and greater expression of the desired protein. The CHO cell containing the recombinant NgR can be produced by cultivating the CHO cells containing the NR expression vectors constitutively expressing the NgR constructs.

Media used in cultivating CHO cells includes DMEM medium supplemented with about 0.5 to 20% fetal calf serum, DMEM medium and RPMI1640 medium. The pH of the medium is preferably about 6 to 8. Cultivation is preferably at about 30 to 40° C. for about 15 to 72 hours with aeration.

A host cell of the invention, such as a prokaryotic or eukaryotic host cell in culture, can be used to produce (i.e., express) NgR protein. Accordingly, the invention further provides methods for producing NgR protein using the host cells of the invention. In one embodiment, the method comprises culturing the host cell of invention (into which a recombinant expression vector encoding NgR has been introduced) in a suitable medium such that NgR protein is produced. In another embodiment, the method further comprises isolating NgR from the medium or the host cell.

In situations where the NgR polypeptide will be found primarily intracellularly, intracellular material (including inclusion bodies for Gram-negative bacteria) can be extracted from the host cell using any standard technique known to one of ordinary skill in the art. Such methods would encompass, by way of example and not by way of limitation, lysing the host cells to release the contents of the periplasm/cytoplasm by French press, homogenization and/or sonication followed by centrifugation.

If the NgR polypeptide has formed inclusion bodies in the cytosol, such inclusion bodies may frequently bind to the inner and/or outer cellular membranes. Upon centrifugation, the inclusion bodies will be found primarily in the pellet material. The pellet material can then be treated at pH extremes or with one or more chaotropic agents such as a detergent, guanidine, guanidine derivatives, urea, or urea derivatives in the presence of a reducing agent such as dithiothreitol at alkaline pH or tris-carboxyethyl phosphine at acid pH to release, break apart and solubilize the inclusion bodies. Once solubilized, NgR polypeptide can be analyzed using gel electrophoresis, immunoprecipitation or the like. Various methods of isolating the NgR polypeptide would be apparent to one of ordinary skill in the art, for example, isolation may be accomplished using standard methods such as those set forth below and in Marston et al (1990) *Meth. Enzymol.* 182, 264–275 (incorporated by reference herein in its entirety).

If isolated NgR polypeptide is not biologically active following the isolation procedure employed, various methods for "refolding" or converting the polypeptide to its tertiary structure and generating disulfide linkages, can be used to restore biological activity. Methods known to one of ordinary skill in the art include adjusting the pH of the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. It may be required to employ a reducing agent or the reducing agent plus its oxidized form in a specific ratio, to generate a particular redox potential allowing for disulfide shuffling to occur in the formation of the protein's cysteine bridge(s). Some of the commonly used redox couples include cysteine/cysteine, glutathione (GSH)/dithiobis GSH, cupric chloride, dithiothreitol (DTT)/dithiane DTT, 2-mercaptoethanol (bME)/dithio-b(ME). To increase the efficiency of the refolding, it may be necessary to employ a cosolvent, such as glycerol, polyethylene glycol of various molecular weights and arginine.

Transgenic Animals

The host cells of the invention can also be used to produce non-human transgenic animals. For example, in one embodiment, a host cell of the invention is a fertilized oocyte or an embryonic stem cell into which NgR-coding sequences have been introduced. Such host cells can then be used to create non-human transgenic animals in which exogenous NgR sequences have been introduced into their genome or homologous recombinant animals in which endogenous NgR sequences have been altered. Such animals are useful for studying the function and/or activity of NgR and for identifying and/or evaluating modulators of NgR activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NgR gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NgR-encoding nucleic acid into the male pronuclei of a fertilized oocyte, e.g., by microinjection, retroviral infection, and allowing the oocyte to develop in a pseudopregnant female foster animal. The human NgR DNA sequence of SEQ ID NOs:1 or 3 can be introduced as a transgene into the genome of a non-human animal. Alternatively, a nonhuman homolog of the human NgR gene, such as a mouse NgR gene, can be isolated based on hybridization to the human NgR cDNA (described further above) and used as a transgene. Intronic sequences and polyadenylation signals can also be included in the transgene to increase the efficiency of expression of the transgene. A tissue-specific regulatory sequence(s) can be operably linked to the NgR transgene to direct expression of NgR protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, in MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NgR transgene in its genome and/or expression of NgR mRNA in tissues or cells of the animals. A transgenic founder animal can then be used to breed additional animals carrying the transgene. Moreover, transgenic animals carrying a transgene encoding NgR can further be bred to other transgenic animals carrying other transgenes.

To create a homologous recombinant animal, a vector is prepared which contains at least a portion of a NgR gene into which a deletion, addition or substitution has been introduced to thereby alter, e.g., functionally disrupt, the NgR gene. The NgR gene can be a human gene (e.g., SEQ ID NOs:1 or 13), but more preferably, is a non-human homolog of a human NgR gene. For example, a mouse homolog of human NgR gene of SEQ ID NOs:1 or 13 can be used to construct a homologous recombination vector suitable for altering an endogenous NgR gene in the mouse genome. In one embodiment, the vector is designed such that, upon homologous recombination, the endogenous NgR gene is functionally disrupted (i.e., no longer encodes a functional protein; also referred to as a "knock out" vector).

Alternatively, the vector can be designed such that, upon homologous recombination, the endogenous NgR gene is mutated or otherwise altered but still encodes functional protein (e.g., the upstream regulatory region can be altered to thereby alter the expression of the endogenous NgR protein). In the homologous recombination vector, the altered portion of the NgR gene is flanked at its 5' and 3' ends by additional nucleic acid of the NgR gene to allow for homologous recombination to occur between the exogenous NgR gene carried by the vector and an endogenous NgR gene in an embryonic stem cell. The additional flanking NgR nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced NgR gene has homologously recombined with the endogenous NgR gene are selected (see e.g., Li et al. (1992) *Cell* 69:915).

The selected cells are then injected into a blastocyst of an animal (e.g., a mouse) to form aggregation chimeras. See e.g., Bradley 1987, In: TERATOCARCINOMAS AND EMBRYONIC STEM CELLS: A Practical Approach, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr. Opin. Biotechnol.* 2:823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Antisense

Also provided by the invention are antisense polynucleotides that recognize and hybridize to NgR polynucleotides. Full-length and fragment antisense polynucleotides are provided. Fragment antisense molecules of the invention include (i) those that specifically recognize and hybridize to NgR RNA (as determined by sequence comparison of DNA encoding NgR to DNA encoding other known molecules). Identification of sequences unique to NgR encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Antisense polynucleotides are particularly relevant to regulating expression of NgR by those cells expressing NgR mRNA.

Antisense oligonucleotides, or fragments of a nucleotide sequence set forth in SEQ ID NO:1, 3, 13 or sequences complementary or homologous thereto, derived from the nucleotide sequences of the present invention encoding NgR are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. In specific aspects, antisense nucleic acid molecules are provided that comprise a sequence complementary to at least about 10, 25, 50, 100, 250 or 500 nucleotides or an entire NgR coding strand, or to only a portion thereof Nucleic acid molecules encoding fragments, homologs, derivatives and analogs of a NgR protein of SEQ ID NO:2, 4 or 14 or antisense nucleic acids complementary to a NgR nucleic acid sequence of SEQ ID NOs:1, 3 or 13 are additionally provided.

In one embodiment, an antisense nucleic acid molecule is antisense to a "coding region" of the coding strand of a nucleotide sequence encoding NgR. The term "coding region" refers to the region of the nucleotide sequence comprising codons which are translated into amino acid residues (e.g., the protein coding region of human NgR corresponds to the coding region SEQ ID NO:1, 3 or 13). In another embodiment, the antisense nucleic acid molecule is antisense to a "noncoding region" of the coding strand of a nucleotide sequence encoding NgR. The term "noncoding region" refers to 5' and 3' sequences which flank the coding region that are not translated into amino acids (i.e., also referred to as 5' and 3' untranslated regions).

Antisense oligonucleotides are preferably directed to regulatory regions of a nucleotide sequence of SEQ ID NO:1, 3, 13 or mRNA corresponding thereto, including, but not limited to, the initiation codon, TATA box, enhancer sequences, and the like. Given the coding strand sequences encoding NgR disclosed herein (e.g., SEQ ID NO:1, 3 or 13), antisense nucleic acids of the invention can be designed according to the rules of Watson and Crick or Hoogsteen base pairing. The antisense nucleic acid molecule can be complementary to the entire coding region of NgR mRNA, but more preferably is an oligonucleotide that is antisense to only a portion of the coding or noncoding region of NgR mRNA. For example, the antisense oligonucleotide can be complementary to the region surrounding the translation start site of NgR mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopenienyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention (preferably oligonucleotides of 10 to 20 nucleotides in length) are typically administered to a subject or generated in situ such that they hybridize with or bind to cellular mRNA and/or genomic DNA encoding a NgR protein to thereby inhibit expression of the protein, e.g., by inhibiting transcription and/or translation. Suppression of NgR expression at either the transcriptional or translational level is useful to generate cellular or animal models for diseases/conditions characterized by aberrant NgR expression. The hybridization can be by conventional nucleotide complementarity to form a stable duplex, or, for example, in the case of an antisense nucleic acid molecule that binds to DNA duplexes, through specific interactions in the major groove of the double helix.

Phosphorothioate and methylphosphonate antisense oligonucleotides are specifically contemplated for therapeutic use by the invention. The antisense oligonucleotides may be further modified by adding poly-L-lysine, transferrin polylysine or cholesterol moieties at their 5' end.

An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., (1987) *Nucleic Acids Res*. 15, 6625–6641). The antisense nucleic acid molecule can also comprise a 2'-o-methylribonucleotide (Inoue et al., (1987) *Nucleic Acids Res*. 15, 6131–6148) or a chimeric RNA-DNA analogue (Inoue et al., (1987) *FEBS Lett*. 215, 327–330).

The NgR sequences taught in the present invention facilitate the design of novel transcription factors for modulating NgR expression in native cells and animals, and cells transformed or transfected with NgR polynucleotides. For example, the $Cys_2$-$His_2$ zinc finger proteins, which bind DNA via their zinc finger domains, have been shown to be amenable to structural changes that lead to the recognition of different target sequences. These artificial zinc finger proteins recognize specific target sites with high affinity and low dissociation constants, and are able to act as gene switches to modulate gene expression. Knowledge of the particular NgR target sequence of the present invention facilitates the engineering of zinc finger proteins specific for the target sequence using known methods such as a combination of structure-based modeling and screening of phage display libraries (Segal et al., (1999) *Proc. Natl. Acad Sci. USA* 96, 2758–2763; Liu et al., (1997) *Proc. Natl. Acad. Sci. USA* 94, 5525–5530; Greisman et al. (1997) *Science* 275, 657–661; Choo et al., (1997) *J. Mol. Biol*. 273, 525–532). Each zinc finger domain usually recognizes three or more base pairs. Since a recognition sequence of 18 base pairs is generally sufficient in length to render it unique in any known genome, a zinc finger protein consisting of 6 tandem repeats of zinc fingers would be expected to ensure specificity for a particular sequence (Segal et al, (1999), above). The artificial zinc finger repeats, designed based on the promoter of NgR sequences, are fused to activation or repression domains to promote or suppress NgR expression (Liu et al., (1997), above). The promoter of NgR may be obtained by standard methods known to one of ordinary skill in the art with the disclosure contained herein and knowledge of the NgR sequence. Alternatively, the zinc finger domains can be fused to the TATA box-binding factor (TBP) with varying lengths of linker region between the zinc finger peptide and the TBP to create either transcriptional activators or repressors (Kim et al., (1997) *Proc. Natl. Acad Sci. USA* 94, 3616–3620. Such proteins and polynucleotides that encode them, have utility for modulating NgR expression in vivo in both native cells, animals and humans; and/or cells transfected with NgR-encoding sequences. The novel transcription factor can be delivered to the target cells by transfecting constructs that express the transcription factor (gene therapy), or by introducing the protein. Engineered zinc finger proteins can also be designed to bind RNA sequences for use in therapeutics as alternatives to antisense or catalytic RNA methods (McColl et al., (1997) *Proc. Natl. Acad. Sci. USA* 96, 9521–9526); Wu et al., (1995) *Proc. Natl. Acad. Sci. USA* 92, 344–348). The present invention contemplates methods of designing such transcription factors based on the gene sequence of the invention, as well as customized zinc finger proteins, that are useful to modulate NgR expression in cells (native or transformed) whose genetic complement includes these sequences.

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes, described in Haselhoff and Gerlach (1988) Nature 334, 585–591) can be used to catalytically cleave NgR mRNA transcripts to thereby inhibit translation of NgR mRNA. A ribozyme having specificity for a NgR-encoding nucleic acid can be designed based upon the nucleotide sequence of a NgR DNA disclosed herein (i.e., SEQ ID NOs:1, 3 or 13). For example, a derivative of a Tetrahymena L-19 IVS RNA can be constructed in which the nucleotide sequence of the active site is complementary to the nucleotide sequence to be cleaved in a NgR-encoding mRNA. See, e.g., Cech et al U.S. Pat. No. 4,987,071; and Cech et al. U.S. Pat. No. 5,116,742. Alternatively, NgR mRNA can be used to select a catalytic RNA having a specific ribonuclease activity from a pool of RNA molecules. See, e.g., Bartel et al., (1993) Science 261, 1411–1418.

Alternatively, NgR gene expression can be inhibited by targeting nucleotide sequences complementary to the regulatory region of the NgR (e.g., the NgR promoter and/or enhancers) to form triple helical structures that prevent transcription of the NgR gene in target cells. See generally, Helene (1991) Anticancer Drug Des. 6: 569–584; Helene. et al., (1992) Ann. N.Y. Acad. Sci. 660:27–36; and Maher (1992) BioEssays 14, 807–815.

In various embodiments, the nucleic acids of NgR can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., (1996) Bioorg. Med. Chem. Lett. 4, 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., (1996) above; Perry-O'Keefe et al., (1996) Proc. Natl. Acad. Sci. USA 93,14670–14675.

PNAs of NgR can be used in therapeutic and diagnostic applications. For example, PNAs can be used as antisense or antigene agents for sequence-specific modulation of gene expression by, e.g., inducing transcription or translation arrest or inhibiting replication. PNAs of NgR can also be used, e.g., in the analysis of single base pair mutations in a gene by, e.g., PNA directed PCR clamping; as artificial restriction enzymes when used in combination with other enzymes, e.g., S1 nucleases (Hyrup (1996), above); or as probes or primers for DNA sequence and hybridization (Hyrup et al., (1996), above; Perry-O'Keefe (1996), above).

In another embodiment, PNAs of NgR can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NgR can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), above). The synthesis of PNA-DNA chimeras can be performed as described in Hyrup (1996), above and Finn et al. (1996) Nucleic Acids Res. 24, 3357–3363. For example, a DNA chain can be synthesized on a solid support using standard phosphoramidite coupling chemistry, and modified nucleoside analogs, e.g., 5'-(4-methoxytrityl) amino-5'-deoxy-thymidine phosphoramidite, can be used between the PNA and the 5' end of DNA (Mag et al. (1989) Nucleic Acids Res. 17, 973–988). PNA monomers are then coupled in a stepwise manner to produce a chimeric molecule with a 5' PNA segment and a 3' DNA segment (Finn et al. (1996), above). Alternatively, chimeric molecules can be synthesized with a 5' DNA segment and a 3' PNA segment. See, Petersen et al. (1975) Bioorg. Med Chem. Lett. 5:1119–1124.

In other embodiments, the oligonucleotide may include other appended groups such as peptides (e.g., for targeting host cell receptors in vivo), or agents facilitating transport across the cell membrane (see Letsinger et al., (1989) Proc. Natl. Acad. Sci. USA 86, 6553–6556; Lemaitre et al., (1987) Proc. Natl. Acad Sci. USA 84, 648–652; PCT Publication No. WO 88/09810) or the blood-brain barrier (see, e.g., PCT Publication No. WO 89/10134). In addition, oligonucleotides can be modified with hybridization triggered cleavage agents (see, e.g., Krol et al., (1988) Biotechniques 6, 958–976) or intercalating agents (see, e.g., Zon (1988) Pharm. Res. 5, 539–549). To this end, the oligonucleotide may be conjugated to another molecule, e.g., a peptide, a hybridization triggered cross-linking agent, a transport agent, a hybridization-triggered cleavage agent, etc.

Automated sequencing methods can be used to obtain or verify the nucleotide sequence of NgR. The NgR nucleotide sequences of the present invention are believed to be 100% accurate. However, as is known in the art, nucleotide sequence obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

Polypeptides

The invention also provides purified and isolated mammalian NgR polypeptides encoded by a polynucleotide of the invention. Presently preferred is a human NgR polypeptide comprising the amino acid sequence set forth in SEQ ID NO:2 or SEQ ID NO:14. Another preferred embodiment is a mouse NgR polypeptide comprising the amino acid sequence of NgR3, as set forth in SEQ ID NO:4.

One aspect of the invention pertains to isolated NgR proteins, and biologically active portions thereof, or derivatives, fragments, analogs or homologs thereof. Also provided are polypeptide fragments suitable for use as immunogens to raise anti-NgR antibodies. Preferably, fragments of NgR proteins comprise at least one biological activity of NgR. In one embodiment, native NgR proteins can be isolated from cells or tissue sources by an appropriate purification scheme using standard protein purification techniques. In another embodiment, NgR proteins are produced by recombinant DNA techniques. Alternative to recombinant expression, a NgR protein or polypeptide can be synthesized chemically using standard peptide synthesis techniques.

The invention also embraces polypeptides that have at least 99%, at least 95%, at least 90%, at least 85%, at least 80%, at least 75%, at least 70%, at least 65%, at least 60%, at least 55%, at least 50% or at least 45% identity and/or homology to the preferred polypeptide of the invention. In addition, the invention embraces polypeptides having the consensus sequence shown in SEQ ID NO:6, shown in Table 5) excluding the previously characterized NgR ("NgR1"), and polypeptides comprising at least about 90% of the consensus sequence.

The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

In one aspect, percent homology is calculated as the percentage of amino acid residues in the smaller of two sequences which align with identical amino acid residue in the sequence being compared, when four gaps in a length of 100 amino acids may be introduced to maximize alignment (Dayhoff, in ATLAS OF PROTEIN SEQUENCE AND STRUCTURE, Vol. 5, p. 124, National Biochemical Research Foundation, Washington, D.C. (1972), incorporated herein by reference).

A determination of homology or identity is typically made by a computer homology program known in the art. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (*Adv. Appl. Math.*, 1981, 2, 482–489, which in incorporated herein by reference in its entirety). Employing the GAP software provided in the GCG program package, (see Needleman and Wunsch (1970) *J. Mol. Biol.* 48, 443–453) the following settings for nucleic acid sequence comparison may be used: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOs:1, 3 or 13. BestFit was originally written for Version 1.0 by Paul Haeberli from a careful reading of the papers by Needleman and Wunsch (1970), above, and Smith and Waterman (1981), above. The following Bestfit settings for nucleic acid sequence comparison may be used: GAP creation penalty of 8.0 and GAP extension penalty of 2, the coding region of the analogous nucleic acid sequences referred to above exhibits a degree of identity preferably of at least 70%, 75%, 80%, 85%, 90%, 95%, 98% or 99%, with the CDS (encoding) part of the amino acid sequence shown in SEQ ID NOs:2, 4 or 14.

Alternatively, homology may be determined by hybridization analysis wherein a nucleic acid sequence is hybridized to the complement of a sequence encoding the aforementioned proteins under stringent, moderately stringent, or low stringent conditions. See e.g. Ausubel, et al., (Eds.) CURRENT PROTOCOLS IN MOLECULAR BIOLOGY, John Wiley & Sons, New York, N.Y., 1993, and below.

Polypeptides of the invention may be isolated from natural cell sources or may be chemically synthesized, but are preferably produced by recombinant procedures involving host cells of the invention.

An "isolated" or "purified" protein or biologically active portion thereof is substantially free of cellular material or other contaminating proteins from the cell or tissue source from which the NgR protein is derived, or substantially free from chemical precursors or other chemicals when chemically synthesized. The language "substantially free of cellular material" includes preparations of NgR protein in which the protein is separated from cellular components of the cells from which it is isolated or recombinantly produced. In one embodiment, the language "substantially free of cellular material" includes preparations of NgR protein having less than about 30% (by dry weight) of non-NgR protein (also referred to herein as a "contaminating protein"), more preferably less than about 20% of non-NgR protein, still more preferably less than about 10% of non-NgR protein, and most preferably less than about 5% non-NgR protein. When the NgR protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of NgR protein in which the protein is separated from chemical precursors or other chemicals that are involved in the synthesis of the protein. In one embodiment, the language "substantially free of chemical precursors or other chemicals" includes preparations of NgR protein having less than about 30% (by dry weight) of chemical precursors or non-NgR chemicals, more preferably less than about 20% chemical precursors or non-NgR chemicals, still more preferably less than about 10% chemical precursors or non-NgR chemicals, and most preferably less than about 5% chemical precursors or non-NgR chemicals.

Biologically active portions of a NgR protein include peptides comprising amino acid sequences sufficiently homologous to or derived from the amino acid sequence of the NgR protein, e.g., the amino acid sequence shown in SEQ ID NO:2, 4 or 14 that include fewer amino acids than the full length NgR proteins, and exhibit at least one activity of a NgR protein. Typically, biologically active portions comprise a domain or motif with at least one activity of the NgR protein. A biologically active portion of a NgR protein can be a polypeptide which is, for example, 10, 25, 50, 100 or more amino acids in length.

A biologically active portion of a NgR protein of the present invention may contain at least one of the features that is conserved between the NgR proteins (e.g., a conserved cysteine as the N-terminus of the mature protein, four conserved cysteines in the N-terminus before a leucine-rich region, four conserved cysteines C-terminal with respect to a leucine repeat region, eight leucine-rich repeats, and a hydrophobic C-terminus), An alternative biologically active portion of a NgR protein may contain at least two of the above-identified domains. Another biologically active portion of a NgR protein may contain at least three of the above-identified domains. Yet another biologically active portion of a NgR protein of the present invention may contain at least four of the above-identified domains.

Moreover, other biologically active portions, in which other regions of the protein are deleted, can be prepared by recombinant techniques and evaluated for one or more of the functional activities of a native NgR protein.

In an embodiment, the NgR protein has an amino acid sequence shown in SEQ ID NO:2, 4 or 14. In other embodiments, the NgR protein is substantially homologous to SEQ ID NO:2, 4 or 14 and retains the functional activity of the protein of SEQ ID NO:2, 4 or 14, yet differs in amino acid sequence due to natural allelic variation or mutagenesis, as described in detail below.

Accordingly, in another embodiment, the NgR protein is a protein that comprises an amino acid sequence at least about 45% homologous to the amino acid sequence of SEQ ID NO:2 or SEQ ID NO:4 or SEQ ID NO:14 and retains the functional activity of the NgR proteins of SEQ ID NO:2, 4 or 14.

Use of mammalian host cells is expected to provide for such post-translational modifications (e.g., glycosylation, truncation, lipidation and phosphorylation) as may be needed to confer optimal biological activity on recombinant expression products of the invention. Glycosylated and non-glycosylated forms of NgR polypeptides are embraced by the invention.

The invention also embraces variant (or analog) NgR polypeptides. In one example, insertion variants are provided wherein one or more amino acid residues supplement a NgR amino acid sequence. Insertions may be located at either or both termini of the protein, or may be positioned within internal regions of the NgR amino acid sequence. Insertional variants with additional residues at either or both termini can include, for example, fusion proteins and proteins including amino acid tags or labels.

Insertion variants include NgR polypeptides wherein one or more amino acid residues are added to a NgR acid sequence or to a biologically active fragment thereof.

Variant products of the invention also include mature NgR products, i.e., NgR products wherein leader or signal sequences are removed, with additional amino terminal residues. The additional amino terminal residues may be derived from another protein, or may include one or more residues that are not identifiable as being derived from specific proteins. NgR products with an additional methionine residue at position -1 (Met$^{-1}$-NgR) are contemplated, as are variants with additional methionine and lysine residues at positions -2 and -1 (Met$^{-2}$-Lys$^{-1}$-NgR). Variants of NgR with additional Met, Met-Lys, Lys residues (or one or more basic residues in general) are particularly useful for enhanced recombinant protein production in bacterial host cells.

Polypeptide Variants

The invention also embraces NgR variants having additional amino acid residues which result from use of specific expression systems.

As used herein, a NgR "chimeric protein" or "fusion protein" comprises a NgR polypeptide operatively linked to a non-NgR polypeptide. A "NgR polypeptide" refers to a polypeptide having an amino acid sequence corresponding to NgR, whereas a "non-NgR polypeptide" refers to a polypeptide having an amino acid sequence corresponding to a protein that is not homologous to the NgR protein, e.g., a protein that is different from the NgR protein and that is derived from the same or a different organism. Within a NgR fusion protein the NgR polypeptide can correspond to all or a portion of a NgR protein. In one embodiment, a NgR fusion protein comprises at least one biologically active portion of a NgR protein. In another embodiment, a NgR fusion protein comprises at least two biologically active portions of a NgR protein. In yet another embodiment, a NgR fusion protein comprises at least three biologically active portions of a NgR protein. Within the fusion protein, the term "operatively linked" is intended to indicate that the NgR polypeptide and the non-NgR polypeptide are fused in-frame to each other. The non-NgR polypeptide can be fused to the N-terminus or C-terminus of the NgR polypeptide.

For example, in one embodiment a NgR fusion protein comprises a NgR domain operably linked to the extracellular domain of a second protein. Such fusion proteins can be further utilized in screening assays for compounds which modulate NgR activity (such assays are described in detail below).

For example, use of commercially available vectors that express a desired polypeptide as part of a glutathione-S-transferase (GST) fusion product provides the desired polypeptide having an additional glycine residue at position -1 after cleavage of the GST component from the desired polypeptide.

In another embodiment, the fusion protein is a NgR protein containing a heterologous signal sequence at its N-terminus. For example, the native NgR signal sequence (i.e., amino acids 1–30 of SEQ ID NO:2 and amino acids 1–40 of SEQ ID NO:4) can be removed and replaced with a signal sequence from another protein. In certain host cells (e.g., mammalian host cells), expression and/or secretion NgR can be increased through use of a heterologous signal sequence.

In yet another embodiment, the fusion protein is a NgR-immunoglobulin fusion protein in which the NgR sequences comprising one or more domains are fused to sequences derived from a member of the immunoglobulin protein family. The NgR-immunoglobulin fusion proteins of the invention can be incorporated into pharmaceutical compositions and administered to a subject to inhibit an interaction between NgR ligand and a NgR protein on the surface of a cell, to thereby suppress NgR-mediated signal transduction in vivo. NgR-immunoglobulin fusion proteins can be used to affect the bioavailability of a NgR cognate ligand. Inhibition of the NgR ligand/NgR interaction may be useful therapeutically for both the treatment of proliferative and differentiative disorders, as well as modulating (e.g., promoting or inhibiting) cell survival. Moreover, the NgR-immunoglobulin fusion proteins of the invention can be used as immunogens to produce anti-NgR antibodies in a subject, to purify NgR ligands, and in screening assays to identify molecules that inhibit the interaction of NgR with NgR ligand.

A NgR chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (Eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A NgR-encoding nucleic acid can be cloned into such an expression vector such that the fusion moiety is linked in-frame to the NgR protein.

Variants resulting from expression in other vector systems are also contemplated.

Insertional variants also include fusion proteins wherein the amino terminus and/or the carboxy terminus of NgR is/are fused to another polypeptide.

In another aspect, the invention provides deletion variants wherein one or more amino acid residues in a NgR polypeptide are removed. Deletions can be effected at one or both termini of the NgR polypeptide, or with removal of one or more non-terminal amino acid residues of NgR. Deletion variants, therefore, include all fragments of a NgR polypeptide.

The invention also embraces polypeptide fragments of the sequence set forth in SEQ ID NO:2, 4 or 14 wherein the fragments maintain biological (e.g., ligand binding and/or intracellular signaling) immunological properties of a NgR polypeptide. Fragments comprising at least 4, 5, 10, 15, 20, 25, 30, 35, or 40 consecutive amino acids of SEQ ID NO:2, 4 or 14 are contemplated by the invention. Preferred polypeptide fragments display antigenic properties unique to, or specific for, human NgR and its allelic and species homologs. Fragments of the invention having the desired biological and immunological properties can be prepared by any of the methods well known and routinely practiced in the art.

In still another aspect, the invention provides substitution variants of NgR polypeptides. Substitution variants include those polypeptides wherein one or more amino acid residues of a NgR polypeptide are removed and replaced with alternative residues. In one aspect, the substitutions are conservative in nature; however, the invention embraces substitutions that are also non-conservative. Conservative substitutions for this purpose may be defined as set out in Tables 2, 3, or 4 below.

TABLE 1

| $X_{aa}$# (based on a NTLRRCT domain) | Column I (R1, R2, R3) | Column II (R2 + R3 only) |
|---|---|---|
| $X_1$ | G, R, M | |
| $X_2$ | A, D, C | |
| $X_3$ | V, T | |
| $X_4$ | N, P, S | |
| $X_5$ | E, A, S | |
| $X_6$ | nothing, K | nothing |
| $X_7$ | V, M, P | |
| $X_8$ | T, V | V |
| $X_9$ | Q, P | Q |
| $X_{10}$ | Q, A | Q |
| $X_{11}$ | Q, H, N | |
| $X_{12}$ | G, N | N |
| $X_{13}$ | L, F | F |
| $X_{14}$ | Q, A, S | |
| $X_{15}$ | A, S | |
| $X_{16}$ | V, I | |
| $X_{17}$ | V, T, E, L | |
| $X_{18}$ | S, G | |
| $X_{19}$ | L, I | |
| $X_{20}$ | A, E, V, P | |
| $X_{21}$ | A, S, D | |
| $X_{22}$ | S, T | |

TABLE 1-continued

| $X_{aa}$# (based on a NTLRRCT domain) | Column I (R1, R2, R3) | Column II (R2 + R3 only) |
|---|---|---|
| $X_{23}$ | Q, E | |
| $X_{24}$ | I V L | |
| $X_{25}$ | Q, H | Q |
| $X_{26}$ | N, G | N |
| $X_{27}$ | R, L | |
| $X_{28}$ | T, G, R, S | |
| $X_{29}$ | F, L, T, H | |
| $X_{30}$ | L, V | L |
| $X_{31}$ | Q, R, P | |
| $X_{32}$ | Q, P, A | P |
| $X_{33}$ | G, A | G |
| $X_{34}$ | H, T, S | |
| $X_{35}$ | S, G, R | |
| $X_{36}$ | P, S, A | |
| $X_{37}$ | C, nothing | nothing |
| $X_{38}$ | R, nothing | nothing |
| $X_{39}$ | A, N | |
| $X_{40}$ | M, L | |
| $X_{41}$ | V, L, T | |
| $X_{42}$ | T, I | T |
| $X_{43}$ | L, I | |
| $X_{44}$ | Y, F, H | |
| $X_{45}$ | N, V | N |
| $X_{46}$ | I, L | |
| $X_{47}$ | T, S, A | |
| $X_{48}$ | F, Y, T, R | |
| $X_{49}$ | A, H, Y, D | |
| $X_{50}$ | P, A | P |
| $X_{51}$ | N, S, G, A | |
| $X_{52}$ | T, A | T |
| $X_{53}$ | E, R, T | |
| $X_{54}$ | G, H | |
| $X_{55}$ | F, L | |
| $X_{56}$ | V, Q, H | |
| $X_{57}$ | H, A, L | |
| $X_{58}$ | E, Q | E |
| $X_{59}$ | G, S | G |
| $X_{60}$ | R, A | R |
| $X_{61}$ | Q, H | Q |
| $X_{62}$ | R, H | H |
| $X_{63}$ | T, S | |
| $X_{64}$ | L, V | L |
| $X_{65}$ | A, E, D | |
| $X_{66}$ | E, D, A | |
| $X_{67}$ | Q, H | Q |
| $X_{68}$ | V, E, G | |
| $X_{69}$ | K, R | |
| $X_{70}$ | H, Q | |
| $X_{71}$ | A, S, T | |
| $X_{72}$ | Y, H | |
| $X_{73}$ | Y, D | Y |
| $X_{74}$ | K, R | |
| $X_{75}$ | G, Q | |
| $X_{76}$ | S, Q | S |
| $X_{77}$ | A, S, E | |
| $X_{78}$ | P, G | P |
| $X_{79}$ | A, G, P | |
| $X_{80}$ | G, N | |
| $X_{81}$ | I, V, L | |
| $X_{82}$ | G, R | |
| $X_{83}$ | H, V, A | |
| $X_{84}$ | S, A | S |
| $X_{85}$ | D, E | |
| $X_{86}$ | H, S, A | |
| $X_{87}$ | I, L | |
| $X_{88}$ | E, L, Q | |
| $X_{89}$ | Y, H, A | |
| $X_{90}$ | Q, P | Q |
| $X_{91}$ | D, N | |
| $X_{92}$ | I, L, T | |
| $X_{93}$ | V, A, R | |
| $X_{94}$ | V, A, G | |
| $X_{95}$ | S, T | S |
| $X_{96}$ | K, R | |
| $X_{97}$ | L, I | L |

TABLE 1-continued

| $X_{aa}\#$ (based on a NTLRRCT domain) | Column I (R1, R2, R3) | Column II (R2 + R3 only) |
|---|---|---|
| $X_{98}$ | W, R, S | |
| $X_{99}$ | S, L | |
| $X_{100}$ | L, V | L |
| $X_{101}$ | G, T, P | |
| $X_{102}$ | Q, P, E | |
| $X_{103}$ | G, H, R | |
| $X_{104}$ | I, T, V, A | |
| $X_{105}$ | V, G, H | |
| $X_{106}$ | N, S | |
| $X_{107}$ | E, G, Q | |
| $X_{108}$ | Q, R | |
| $X_{109}$ | L, V | |
| $X_{110}$ | Q, A | |
| $X_{111}$ | W, G, H | |
| $X_{112}$ | H, R, P | |
| $X_{113}$ | K, A, H | |
| $X_{114}$ | H, R | |
| $X_{115}$ | D, G | |
| $X_{116}$ | H, R, S, G | |
| $X_{117}$ | T, M | |
| $X_{118}$ | T, I | |
| $X_{119}$ | F, Y | |
| $X_{120}$ | N, A | |
| $X_{121}$ | S, N | |
| $X_{122}$ | T, A, S | |
| $X_{123}$ | E, S, A | |
| $X_{124}$ | Q, P | |
| $X_{125}$ | G, T | |
| $X_{126}$ | D, E | D |
| $X_{127}$ | C, A | |
| $X_{128}$ | P, D | |
| $X_{129}$ | V, G, P, R | |
| $X_{130}$ | A, S | |
| $X_{131}$ | E, Q | Q |
| $X_{132}$ | F, Y | F |
| $X_{133}$ | G, A, D | |
| $X_{134}$ | A, P | |
| $X_{135}$ | D, A, V | |
| $X_{136}$ | G, D | |
| $X_{137}$ | A, E | |
| $X_{138}$ | S, P | |
| $X_{139}$ | E, A | |
| $X_{140}$ | L, F | |
| $X_{141}$ | R, Q | |
| $X_{142}$ | R, K | R |
| $X_{143}$ | R, K | R |
| $X_{144}$ | F, A | |
| $X_{145}$ | G, V | |
| $X_{146}$ | A, D, E | |
| $X_{147}$ | T, P | |
| $X_{148}$ | A, V, S | |
| $X_{149}$ | T, S, L | |
| $X_{150}$ | E, G, P, Q | |
| $X_{151}$ | L, E, R | |
| $X_{152}$ | R, L | R |
| $X_{153}$ | G, D | |
| $X_{154}$ | Q, H, A | |
| $X_{155}$ | Q, R | |
| $X_{156}$ | K, R | |
| $X_{157}$ | L, A, R | |
| $X_{158}$ | R, A | R |
| $X_{159}$ | V, A, E | |
| $X_{160}$ | E, A, N | |
| $X_{161}$ | F, L | F |
| $X_{162}$ | R, Q | |
| $X_{163}$ | N, A, G | |

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 2 (from WO 97/09433, page 10, published Mar. 13, 1997 (PCT/GB96/02197, filed Sep. 6, 1996), immediately below.

TABLE 2

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, [BIOCHEMISTRY, Second Edition; Worth Publishers, Inc. NY, N.Y. (1975), pp. 71–77] as set out in Table 3, immediately below.

TABLE 3

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Boderline: | G |
| Uncharged-polar | |
| A. Hydroxyl: | S T Y |
| B. Amides: | N Q |
| C. Sylfhydryl: | C |
| D. Boderline: | G |
| Positively Charged (Basic): | K R H |
| Negatively Charged (Acidic): | D E |

As still another alternative, exemplary conservative substitutions are set out in Table 4, below.

TABLE 4

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

In addition, amino acid residues that are conserved among family members of the NgR proteins of the present invention, as indicated by the alignment presented herein, are also predicted to be particularly unamenable to alteration. For example, NgR proteins of the present invention can contain at least one domain that is a typically conserved region in NgRs. Examples of these conserved domains include, e.g., leucine-rich repeat domain. Amino acid residues that are not conserved or are only semi-conserved among members of the NgR proteins may be readily amenable to alteration.

Full-length NgRs have an LRR region characterized by the amino acid consensus sequence shown in SEQ ID NO: 19. At least some full-length NgRs also include a CT signaling (CTS) domain and a GPI domain.

The NgR domain designations used herein are defined as follows:

| Domain | hNgR1 SEQ ID: 5 | mNgR1 SEQ ID NO: 17 | hNgR2 SEQ ID: 2 | hNgR3 SEQ ID: 14 | mNgR3 SEQ ID: 4 |
|---|---|---|---|---|---|
| Signal Seq. | 1–26 | 1–26 | 1–30 | — | 1–40 |
| LRRNT | 27–56 | 27–56 | 31–59 | — | 41–69 |
| LRR1 | 57–81 | 57–81 | 60–82 | 5–27 | 70–92 |
| LRR2 | 82–105 | 82–105 | 83–106 | 28–51 | 93–106 |
| LRR3 | 106–130 | 106–130 | 107–131 | 52–76 | 106–141 |
| LRR4 | 131–154 | 131–154 | 132–155 | 77–100 | 142–165 |
| LRR5 | 155–178 | 155–178 | 156–179 | 101–124 | 166–189 |
| LRR6 | 179–202 | 179–202 | 180–203 | 125–148 | 190–213 |
| LRR7 | 203–226 | 203–226 | 204–227 | 149–172 | 214–237 |
| LRR8 | 227–250 | 227–250 | 228–251 | 173–196 | 238–261 |
| LRRCT | 260–309 | 260–309 | 261–310 | 206–255 | 271–320 |
| CTS (CT Signaling) | 310–445 | 310–445 | 311–395 | 256–396 | 321–438 |
| GPI | 446–473 | 456–473 | 396–420 | 370–392 | 439–462 |

In some embodiments of the invention, the above domains are modified. Modification can be in a manner that preserves domain functionality. Modification can include addition, deletion or substitution of certain amino acids. Exemplary modifications include conservative amino acid substitutions. Preferably such substitutions number 20 or fewer per 100 residues. More preferably, such substitutions number 10 or fewer per 100 residues. Further exemplary modifications include addition of flanking sequences of up to five amino acids at the N terminus and/or C terminus of one or more of the domains.

In some embodiments, the isolated nucleic acid molecule encodes a polypeptide at least about 70%, 80%, 90%, 95%, 98%, and most preferably at least about 99% homologous to SEQ ID NO:2, 4 or 14.

Mutations can be introduced into SEQ ID NOS:1, 3 or 13 by standard techniques, e.g., site-directed mutagenesis and PCR-mediated mutagenesis. Conservative amino acid substitutions can be made at one or more amino acid residues predicted to be non-essential. Alternatively, mutations can be introduced randomly along a NgR coding sequence. This can be accomplished, e.g., by saturation mutagenesis. The resulting mutants can be screened for NgR biological activity. Biological activities of NgR may include but are not limited to: (1) protein:protein interactions, e.g., with other NgRs or other cell-surface proteins involved in Nogo-related signaling; (2) complex formation with a NgR ligand; (3) binding to an anti-NgR antibody.

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs. Similarly, the invention further embraces NgR polypeptides that have been covalently modified to include one or more water-soluble polymer attachments such as polyethylene glycol, polyoxyethylene glycol or polypropylene glycol. Variants that display ligand binding properties of native NgR and are expressed at higher levels, as well as variants that provide for constitutively active receptors, are particularly useful in assays of the invention; the variants are also useful in providing cellular, tissue and animal models of diseases/conditions characterized by aberrant NgR activity.

Chemically modified NgR polypeptide compositions in which the NgR polypeptide is linked to a polymer are included within the scope of the present invention. The polymer may be water soluble to prevent precipitation of the protein in an aqueous environment, such as a physiological environment. Suitable water-soluble polymers may be selected from the group consisting of, for example, polyethylene glycol (PEG), monomethoxypolyethylene glycol, dextran, cellulose, or other carbohydrate based polymers, poly-(N-vinyl pyrrolidone) polyethylene glycol, polypropylene glycol homopolymers, a polypropylene oxide/ethylene oxide copolymer polyoxyethylated polyols (e.g. glycerol) and polyvinyl alcohol. The selected polymer is usually modified to have a single reactive group, such as an active ester for acylation or an aldehyde for alkylation, so that the degree of polymerization may be controlled. Polymers may be of any molecular weight, and may be branched or unbranched, and mixtures of such polymers may also be used. When the chemically modified NgR polymer is destined for therapeutic use, pharmaceutically acceptable polymers will be selected for use.

When the polymer is to be modified by an acylation reaction, the polymer should have a single reactive ester group. Alternatively, if the polymer is to be modified by reductive alkylation, the polymer should have a single reactive aldehyde group. A preferred reactive aldehyde is polyethylene glycol propionaldehyde, which is water stable, or mono C1—C10 alkoxy or aryloxy derivatives thereof (see U.S. Pat. No. 5,252,714, incorporated by reference herein in its entirety).

Pegylation of NgR polypeptides may be carried out by any of the pegylation reactions known in the art, as described, for example, in the following references: *Focus on Growth Factors* 3, 4–10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of polypeptides such as NgR is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Chemical derivatization of NgR polypeptides may be performed under any suitable conditions used to react a biologically active substance with an activated polymer molecule. Methods for preparing pegylated NgR polypeptides will generally comprise the steps of (a) reacting the polypeptide with polyethylene glycol, such as a reactive ester or aldehyde derivative of PEG, under conditions whereby NgR polypeptide becomes attached to one or more PEG groups, and (b) obtaining the reaction products. It will be apparent to one of ordinary skill in the art to select the optimal reaction conditions or the acylation reactions based on known parameters and the desired result.

Pegylated and other polymer:NgR polypeptides may generally be used to treat conditions that may be alleviated or modulated by administration of the NgR polypeptides described herein. However, the chemically-derivatized polymer:NgR polypeptide molecules disclosed herein may have additional activities, enhanced or reduced biological activity, or other characteristics, such as increased or decreased half-life, as compared to the nonderivatized molecules. The NgR polypeptides, fragments thereof, variants and derivatives, may be employed alone, together, or in combination with other pharmaceutical compositions. The cytokines, growth factors, antibiotics, antiinflammatories and/or chemotherapeutic agents as is appropriate for the indication being treated.

The present invention provides compositions comprising purified polypeptides of the invention. Preferred compositions comprise, in addition to the polypeptide of the invention, a pharmaceuitically acceptable (i.e., sterile and non-toxic) liquid, semisolid, or solid diluent that serves as a pharmaceutical vehicle, excipient or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil and cocoa butter.

Variants that display ligand binding properties of native NgR and are expressed at higher levels, as well as variants that provide for constitutively active receptors, are particularly useful in assays of the invention; the variants are also useful in assays of the invention and in providing cellular, tissue and animal models of diseases/conditions characterized by aberrant NgR activity.

With the knowledge of the nucleotide sequence information disclosed in the present invention, one skilled in the art can identify and obtain nucleotide sequences which encode NgR from different sources (i.e., different tissues or different organisms) through a variety of means well known to the skilled artisan and as disclosed by, for example, Sambrook et al., MOLECULAR CLONING: A LABORATORY MANUAL, Second Edition, Cold Spring Harbor Press, Cold Spring Harbor, N.Y. (1989), which is incorporated herein by reference in its entirety.

For example, DNA that encodes NgR may be obtained by screening of mRNA, cDNA, or genomic DNA with oligonucleotide probes generated from the NgR gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al. (1989) above.

A nucleic acid molecule comprising any of the NgR nucleotide sequences described above can alternatively be synthesized by use of the polymerase chain reaction (PCR) procedure, with the PCR oligonucleotide primers produced from the nucleotide sequences provided herein. See U.S. Pat. No. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase-mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, METHODS IN ENZYMOLOGY 152 Academic Press, San Diego, Calif., which is incorporated herein by reference in its entirety.

The nucleic acid molecules of the present invention, and fragments derived therefrom, are useful for screening for restriction fragment length polymorphism (RFLP) associated with certain disorders, as well as for genetic mapping.

Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for NgR or fragments thereof. Preferred antibodies of the invention are human antibodies which are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind NgR polypeptides exclusively (i.e., are able to distinguish NgR polypeptides from other known NgR polypeptides by virtue of measurable differences in binding affinity, despite the possible existence of localized sequence identity, homology, or similarity between NgR and such polypeptides).

The antigenic peptide of NgR comprises at least 8 amino acid residues of the amino acid sequence shown in SEQ ID NO:2, 4 or 14 and encompasses an epitope of NgR such that an antibody raised against the peptide forms a specific immune complex with NgR. Preferably, the antigenic peptide comprises at least 10 anino acid residues, more preferably at least 15 amino acid residues, even more preferably at least 20 amino acid residues, and most preferably at least 30 amino acid residues. Preferred epitopes encompassed by the antigenic peptide are regions of NgR that are located on the surface of the protein, e.g., hydrophilic regions.

It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. in ANTIBODIES: A LABORATORY MANUAL, Cold Spring Harbor Laboratory Press; Cold Spring Harbor, N.Y. (1988), Chapter 6. Antibodies that recognize and bind fragments of the NgR polypeptides of the invention are also contemplated, provided that the antibodies are specific for NgR polypeptides. Antibodies of the invention can be produced using any method well known and routinely practiced in the art.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed NgR protein or a chemically synthesized NgR polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum* or similar immunostimulatory agents. If desired, the antibody molecules directed against NgR can be isolated from the mammal (e.g., from the blood) and further purified by well known techniques, such as protein A chromatography to obtain the IgG fraction.

The term "monoclonal antibody" or "monoclonal antibody composition," as used herein, refers to a population of antibody molecules that contain only one species of an antigen binding site capable of immunoreacting with a particular epitope of NgR. A monoclonal antibody composition thus typically displays a single binding affinity for a particular NgR protein with which it immunoreacts. For preparation of monoclonal antibodies directed towards a particular NgR protein, or derivatives, fragments, analogs or homologs thereof, any technique that provides for the production of antibody molecules by continuous cell line culture may be utilized. Such techniques include, but are not limited to, the hybridoma technique (see Kohler and Milstein (1975) *Nature* 256, 495–497); the trioma technique; the human B-cell hybridoma technique (see Kozbor et al., (1983) *Immunol. Today* 4, 72) and the EBV hybridoma technique to produce human monoclonal antibodies (see Cole et al., (1985) in MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote et al., (1983) *Proc. Natl. Acad Sci. USA* 80, 2026–2030) or by transforming human B-cells with Epstein Barr Virus in vitro (see Cole et al., (1985), above).

According to the invention, techniques can be adapted for the production of single-chain antibodies specific to a NgR protein (see e.g., U.S. Pat. No. 4,946,778). In addition, methods can be adapted for the construction of Fab expression libraries (see e.g., Huse et al., (1989) *Science* 246, 1275–1281) to allow rapid and effective identification of monoclonal F$_{ab}$ fragments with the desired specificity for a NgR protein or derivatives, fragments, analogs or homologs thereof. Non-human antibodies can be "humanized" by techniques well known in the art. See e.g., U.S. Pat. No. 5,225,539. In one method, the non-human CDRs are inserted into a human antibody or consensus antibody framework sequence. Further changes can then be introduced into the antibody framework to modulate affinity or immunogenicity. Antibody fragments that contain the idiotypes to a NgR protein may be produced by techniques known in the art including, but not limited to: (i) an F(ab')$_2$ fragment produced by pepsin digestion of an antibody molecule; (ii) an Fab fragment generated by reducing the disulfide bridges of an F(ab')$_2$ fragment; (iii) an Fab fragment generated by the treatment of the antibody molecule with papain and a reducing agent and (iv) F$_v$ fragments.

Additionally, recombinant anti-NgR antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., (1988) *Science* 240, 1041–1043; Liu et al., (1987) *Proc. Natl. Acad. Sci. USA* 84, 3439–3443; Liu et al., (1987) *J. Immunol.* 139, 3521–3526; Sun et al., (1987) *Proc. Natl. Acad. Sci. USA* 84, 214–218; Nishimura et al., (1987) *Cancer Res.* 47, 999–1005; Wood et al., (1985) *Nature* 314, 446–449; Shaw et al,. (1988) *J.*

*Natl. Cancer Inst.* 80, 1553–1559); Morrison (1985) *Science* 229, 1202–1207; Oi et al., (1986) *BioTechniques* 4, 214; U.S. Pat. No. 5,225,539; Jones et al., (1986) *Nature* 321, 552–525; Verhoeyan et al., (1988) *Science* 239, 1534; and Beidler et al., (1988) *J. Immunol.* 141, 4053–4060.

In a preferred embodiment of the invention a portion of a NgR is joined to an Fc portion of an antibody to form a NgR/Fc fusion protein. Preferably, the Ig fusion protein is soluble. The NgR/Fc fusion protein may be formed by recombinant techniques as described above. In one embodiment, a portion of a NgR including the entire amino acid sequence of NgR except the C-terminal hydrophobic region is fused to an Fc portion of an antibody. In preferred embodiments, the NgR is a human NgR and the Fc is also human. More preferably, the human Fc portion is derived from an IgG antibody. In other embodiments, the N-terminal signal sequence is omitted. Such antibodies are useful in binding Nogo to prevent Nogo signaling through the NgR.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a NgR protein is facilitated by generation of hybridomas that bind to the fragment of a NgR protein possessing such a domain. Antibodies that are specific for one or more domains within a NgR protein, e.g., domains spanning the above-identified conserved regions of NgRs, or derivatives, fragments analogs or homologs thereof, are also provided herein.

Anti-NgR antibodies may be used in methods known within the art relating to the localization and/or quantitation of a NgR protein (e.g., for use in measuring levels of the NgR protein within appropriate physiological samples, for use in diagnostic methods, for use in imaging the protein, and the like). In a given embodiment, antibodies for NgR proteins, or derivatives, fragments analogs or homologs thereof, that contain the antibody derived binding domain, are utilized as pharmacologically-active compounds [hereinafter "Therapeutics"].

An anti-NgR antibody (e.g., monoclonal antibody) can be used to isolate NgR by standard techniques, such as affinity chromatography or immunoprecipitation. An anti-NgR antibody can facilitate the purification of natural NgR from cells and of recombinantly produced NgR expressed in host cells. Moreover, an anti-NgR antibody can be used to detect NgR protein (e.g., in a cellular lysate or cell supernatant) in order to evaluate the abundance and pattern of expression of the NgR protein. Anti-NgR antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin and aequorin, and examples of suitable radioactive material include $^{125}$I, $^{131}$I, $^{35}$S or $^3$H.

Another aspect of the present invention is directed to methods of inducing an immune response in a mammal against a polypeptide of the invention by administering to the mammal an amount of the polypeptide sufficient to induce an immune response. The amount will be dependent on the animal species, size of the animal, and the like but can be determined by those skilled in the art.

Another aspect of the invention is directed to anti-idiotypic antibodies and anti-anti-idiotypic antibodies. An anti-idiotypic antibody is an antibody that recognizes determinants of another antibody (a target antibody). Generally, the anti-idiotypic antibody recognizes determinants of the antigen-binding site of the target antibody. Typically, the target antibody is a monoclonal antibody. An anti-idiotypic antibody is generally prepared by immunizing an animal (particularly, mice) of the same species and genetic type as the source of the target monoclonal antibody, with the target monoclonal antibody. The immunized animal mounts an immune response to the idiotypic determinants of the target monoclonal antibody and produces antibodies against the idiotypic determinants of the target monoclonal antibody. Antibody-producing cells, such as splenic cells, of the immunized animal may be used to generate anti-idiotypic monoclonal antibodies. Furthermore, an anti-idiotypic antibody may also be used to immunize animals to produce anti-anti-idiotypic antibodies. These immunized animals may be used to generate anti-anti-idiotypic monoclonal antibodies using standard techniques. The anti-anti-idiotypic antibodies may bind to the same epitope as the original, target monoclonal antibody used to prepare the anti-idiotypic antibody. The anti-anti-idiotypic antibodies represent other monoclonal antibodies with the same antigen specificity as the original target monoclonal antibody.

If the binding of the anti-idiotypic antibody with the target antibody is inhibited by the relevant antigen of the target antibody, and if the anti-idiotypic antibody induces an antibody response with the same specificity as the target antibody, it mimics the antigen of the target antibody. Such an anti-idiotypic antibody is an "internal image anti-idiotype" and is capable of inducing an antibody response as if it were the original antigen. (Bona and Kohler (1984) ANTI-IDIOTYPIC ANTIBODIES AND INTERNAL IMAGE, IN MONOCLONAL AND ANTI-IDIOTYPIC ANTIBODIES: PROBES FOR RECEPTOR STRUCTURE AND FUNCTION, Venter J. C. et al. (Eds), Alan R. Liss, New York, N.Y., pp 141–149, 1984). Vaccines incorporating internal image anti-idiotype antibodies have been shown to induce protective responses against viruses, bacteria, and parasites (Kennedy et al., (1986) 232, 220–223; 1047; McNamara et al., (1985) *Science* 226, 1325–1326). Internal image anti-idiotypic antibodies have also been shown to induce immunity to tumor related antigens (Raychauhuri et al., (1986) *J. Immunol.* 137, 1743–1749; Raychauhuri et al., (1987) *J. Immunol.* 139, 3902–3910; Bhattacharya-Chatterjee et al., (1987) *J. Immunol.* 139, 1354–1360; Bhattacharya-Chatterjee et al., (1988) *J. Immunol.* 141, 1398–1403; Herlyn. et al. (1989) *Intern. Rev. Immunol.* 4, 347–357; Chen et al. (1990) *Cell Imm. Immunother. Cancer* 351–359; Herlyn et al., (1991) in vivo 5, 615–624; Furuya et al. (1992) *AntiCancer Res.* 12, 27–32; Mittelman, A. et al. (1992) *Proc. Natl. Acad. Sci., USA* 89, 466470; Durrant. et al., (1994) *Cancer Res.* 54, 4837–4840; Mittelman. et al. (1994) *Cancer Res.* 54, 415–421; Schmitt. et al. (1994) *Hybridoma* 13, 389–396; Chakrobarty. et al. (1995) *J. Immunother.* 18, 95–103; Chakrobarty. et al. (1995) *Cancer*

*Res.* 55, 1525–1530; Foon, K. A. et al. (1995) *Clin. Cancer Res.* 1, 1205–1294; Herlyn et al. (1995) *Hybridoma* 14, 159–166; Sclebusch et al (1995) *Hybridoma* 14, 167–174; Herlyn. et al. (1996) *Cancer Immunol Immunother.* 43, 65–76).

Anti-idiotypic antibodies for NgR may be prepared, for example, by immunizing an animal, such as a mouse, with a immunogenic amount of a composition comprising NgR2 (SEQ ID NO:2), NgR3 (SEQ ID NOs:4 or 14), or immunogenic portion thereof, containing at least one antigenic epitope of NgR. The composition may also contain a suitable adjuvant, and any carrier necessary to provide immunogenicity. Monoclonal antibodies recognizing NgR may be prepared from the cells of the immunized animal as described above. A monoclonal antibody recognizing an epitope of NgR is then selected and used to prepare a composition comprising an immunogenic amount of the anti-NgR monoclonal antibody. Typically, a 25 to 200 µg dose of purified anti-NgR monoclonal would be sufficient in a suitable adjuvant.

Animals may be immunized 2–6 times at 14 to 30 day intervals between doses. Typically, animals are immunized by any suitable route of administration, such as intraperitoneal, subcutaneous, intravenous or a combination of these. Anti-idiotypic antibody production may be monitored during the immunization period using standard immunoassay methods. Animals with suitable titers of antibodies reactive with the target monoclonal antibodies may be reimmunized with the monoclonal antibody used as the immunogen three days before harvesting the antibody producing cells. Preferably, spleen cells are used, although other antibody producing cells may be selected. Antibody-producing cells are harvested and fused with myeloma cells to produce *Hybridomas*, as described above, and suitable anti-idiotypic antibody-producing cells are selected.

Anti-anti-idiotypic antibodies are produced by another round of immunization and *Hybridoma* production by using the anti-idiotypic monoclonal antibody as the immunogen.

Antibodies of the invention are useful for, e.g., therapeutic purposes (by modulating activity of NgR), diagnostic purposes to detect or quantitate NgR, and purification of NgR. Therefore, kits comprising an antibody of the invention for any of the purposes described herein ate also comprehended.

Kits

The present invention is also directed to kits, including pharmaceutical kits. The kits can comprise any of the nucleic acid molecules described above, any of the polypeptides described above, or any antibody which binds to a polypeptide of the invention as described above, as well appropriate controls, such as positive and/or negative controls. The kit preferably comprises additional components, such as, for example, instructions, solid support, reagents helpful for quantification, and the like. For example, the kit can comprise: a labeled compound or agent capable of detecting NgR protein or mRNA in a biological sample; means for determining the amount of NgR in the sample; and means for comparing the amount of NgR in the sample with a standard. The compound or agent can be packaged in a suitable container.

Screening Assays

The DNA and amino acid sequence information provided by the present invention also makes possible identification of binding partner compounds with which a NgR polypeptide or polynucleotide will interact. Methods to identify binding partner compounds include solution assays, in vitro assays wherein NgR polypeptides are immobilized and cell-based assays. Identification of binding partner compounds of NgR polypeptides provides candidates for therapeutic or prophylactic intervention in pathologies associated with NgR normal and aberrant biological activity.

The invention also provides a method (also referred to herein as a "screening assay") for identifying modulators, i.e., candidate or test compounds or agents (e.g., peptides, peptidomimetics, small molecules (e.g., molecules of less than 1,000 Daltons) or other drugs) that bind to NgR proteins or have a stimulatory or inhibitory effect on, for example, NgR expression or NgR activity.

In one embodiment, the invention provides assays for screening candidate or test compounds which bind to or modulate the activity of a NgR protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12, 145).

Examples of methods for the synthesis of molecular libraries can be found in the art, for example in: DeWitt et al., (1993) *Proc. Natl. Acad. Sci. USA* 90, 6909; Erb et al., (1994) *Proc. Natl. Acad. Sci. USA* 91,11422; Zuckermann et al. (1994) *J. Med. Chem* 37, 2678; Cho et al., (1993) *Science* 261, 1303; Carrell et al., (1994) *Angew Chem. Int. Ed. Engl.* 33, 2059; Carell et al., (1994) *Angew Chem. Int. Ed. Engl.* 33, 2061; and Gallop et al., (1994) *J. Med. Chem* 37, 1233.

Libraries of compounds may be presented in solution (e.g., Houghten (1992) *BioTechniques* 13, 412–421), or on beads (Lam (1991) *Nature* 354, 82–84), on chips (Fodor (1993) *Nature* 364, 555–556), bacteria (Ladner, U.S. Pat. No. 5,223,409), spores (Ladner, above), plasmids (Cull et al. (1992) *Proc. Natl. Acad. Sci. USA* 89, 1865–1869) or on phage (Scott and Smith (1990) *Science* 249, 386–390; Devlin (1990) *Science* 249, 404–406; Cwirla et al. (1990) *Proc. Natl. Acad. Sci. USA* 87, 6378–6382; Felici (1991) *J. Mol. Biol.* 222, 301–310; Ladner, above).

1. Cell-based Assays

The invention also provides cell-based assays to identify binding partner compounds of a NgR polypeptide. In one embodiment, the invention provides a method comprising the steps of contacting a NgR polypeptide expressed on the surface of a cell with a candidate binding partner compound and detecting binding of the candidate binding partner compound to the NgR polypeptide. In another embodiment, an assay is a cell-based assay comprising contacting a cell expressing a membrane-bound form of NgR protein, or a biologically active portion thereof, on the cell surface with a test compound and determining the ability of the test compound to modulate (e.g., stimulate or inhibit) the activity of the NgR protein or biologically active portion thereof.

In one embodiment, an assay is a cell-based assay in which a cell which expresses a membrane-bound form of NgR protein, or a biologically active portion thereof, on the cell surface is contacted with a test compound and the ability of the test compound to bind to a NgR protein determined. The cell, for example, can be of mammalian origin or a yeast cell. Determining the ability of the test compound to bind to the NgR protein can be accomplished, for example, by coupling the test compound with a radioisotope or enzymatic label such that binding of the test compound to the NgR protein or biologically active portion thereof can be determined by detecting the labeled compound in a complex. For example, test compounds can be labeled with $^{125}$I, $^{35}$S, $^{14}$C, or $^3$H, either directly or indirectly, and the radioisotope detected by direct counting of radioemission or by scintillation counting. Alternatively, test compounds can be enzymatically labeled with, for example, horseradish peroxidase, alkaline phosphatase or luciferase, and the enzymatic label detected by determination of conversion of an appropriate substrate to product. In one embodiment, the assay comprises contacting a cell which expresses a membrane-bound form of NgR protein or a biologically active portion thereof, on the cell surface with a known compound which binds NgR to form an assay mixture, contacting the assay mixture with a test compound, and determining the ability of the test compound to interact with a NgR protein, wherein determining the ability of the test compound to interact with a NgR protein comprises determining the ability of the test compound to preferentially bind to NgR or a biologically active portion thereof as compared to the known compound.

Determining the ability of the test compound to modulate the activity of NgR or a biologically active portion thereof can be accomplished, for example, by determining the ability of the NgR protein to bind to or interact with a NgR target molecule. As used herein, a "target molecule" is a molecule with which a NgR protein binds or interacts in nature, for example, a molecule on the surface of a cell which expresses a NgR protein, a molecule on the surface of a second cell, a molecule in the extracellular milieu, a molecule associated with the internal surface of a cell membrane or a cytoplasmic molecule. A NgR target molecule can be a non-NgR molecule or a NgR protein or polypeptide of the present invention. In one embodiment, a NgR target molecule is a component of a signal transduction pathway that facilitates transduction of an extracellular signal (e.g., a signal generated by binding of a compound to a membrane-bound NgR molecule) through the cell membrane and into the cell. The target, for example, can be a second intercellular protein that has catalytic activity or a protein that facilitates the association of downstream signaling molecules with NgR. In a preferred embodiment, the detection comprises detecting a calcium flux or other physiological event in the cell caused by the binding of the molecule.

Specific binding molecules, including natural ligands and synthetic compounds, can be identified or developed using isolated or recombinant NgR products, NgR variants, or preferably, cells expressing such products. Binding partners are useful for purifying NgR products and detection or quantification of NgR products in fluid and tissue samples using known immunological procedures. Binding molecules are also manifestly useful in modulating (i.e., blocking, inhibiting or stimulating) biological activities of NgR, especially those activities involved in signal transduction.

2. Cell-free Assays (a) Direct Binding:

The invention includes several assay systems for identifying NgR binding partners. In solution assays, methods of the invention comprise the steps of (a) contacting a NgR polypeptide with one or more candidate binding partner compounds and (b) identifying the compounds that bind to the NgR polypeptide. Identification of the compounds that bind the NgR polypeptide can be achieved by isolating the NgR polypeptide/binding partner complex and separating the binding partner compound from the NgR polypeptide. An additional step of characterizing the physical, biological and/or biochemical properties of the binding partner compound is also comprehended in another embodiment of the invention. In one aspect, the NgR polypeptide/binding partner complex is isolated using an antibody immunospecific for either the NgR polypeptide or the candidate binding partner compound.

In still other embodiments, either the NgR polypeptide or the candidate binding partner compound comprises a label or tag that facilitates its isolation, and methods of the invention to identify binding partner compounds include a step of isolating the NgR polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAGE® tag (Eastman Kodak, Rochester, N.Y.), well known and routinely used in the art, are embraced by the invention.

(b) Immobilized NgR

In one variation of an in vitro assay, the invention provides a method comprising the steps of (a) contacting an immobilized NgR polypeptide, or a biologically active fragment thereof with a candidate binding partner compound and (b) detecting binding of the candidate compound to the NgR polypeptide. In an alternative embodiment, the candidate binding partner compound is immobilized and binding of NgR is detected. Immobilization is accomplished using any of the methods well known in the art, including covalent bonding to a support, a bead or a chromatographic resin, as well as non-covalent, high affinity interactions such as antibody binding, or use of streptavidin/biotin binding wherein the immobilized compound includes a biotin moiety. Binding of a test compound to NgR, or interaction of NgR with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, and not by way of limitation, GST-NgR fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NgR protein, and the mixture is incubated under conditions conducive to complex formation (e.g., at physiological conditions for salt and pH). Following incubation, the beads or microtiter plate wells are washed to remove any unbound components, the matrix immobilized in the case of beads, and the complexes determined either directly or indirectly, for example, as described above. Alternatively, the complexes can be dissociated from the matrix, and the level of NgR binding or activity determined using standard techniques.

Other techniques for immobilizing proteins on matrices can also be used in the screening assays of the invention. For example, either NgR or its target molecule can be immobilized utilizing conjugation of biotin and streptavidin. Biotinylated NgR or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with NgR or target molecules, but which do not interfere with binding of the NgR protein to its target molecule, can be derivatized to the wells of the plate, and unbound target or NgR trapped in the wells by antibody conjugation. Methods for detecting such complexes, in addition to those described above for the GST-immobilized complexes, include immunodetection of complexes using antibodies reactive with the NgR or target molecule, as well as enzyme-linked assays that rely on detecting an enzymatic activity associated with the NgR or target molecule.

Detection of binding can be accomplished (i) using a radioactive label on the compound that is not immobilized, (ii) using of a fluorescent label on the non-immobilized compound, (iii) using an antibody immunospecific for the non-immobilized compound, (iv) using a label on the non-immobilized compound that excites a fluorescent support to which the immobilized compound is attached, (v) determining the activity of the NgR, as well as other techniques well known and routinely practiced in the art.

Determining the activity of the target molecule, for example, may be accomplished by detecting induction of a cellular second messenger of the target (i.e. intracellular $Ca^{2+}$, diacylglycerol $IP_3$, etc.), detecting catalytic/enzymatic activity of the target an appropriate substrate, detecting the induction of a reporter gene (comprising a NgR-responsive regulatory element operatively linked to a nucleic acid encoding a detectable marker, e.g., luciferase), or detecting a cellular response, for example, cell survival, cellular differentiation, or cell proliferation.

(c) Competition Experiments

In yet another embodiment, the assay comprises contacting the NgR protein or biologically active portion thereof with a known compound which binds NgR to form an assay mixture, contacting the assay mixture with a test compound, and determining the ability of the test compound to interact with a NgR protein, wherein determining the ability of the test compound to interact with a NgR protein comprises determining the ability of the test compound to preferentially bind to NgR or biologically active portion thereof as compared to the known compound.

In yet another embodiment, the cell-free assay comprises contacting the NgR protein or biologically active portion thereof with a known compound which binds NgR to form an assay mixture, contacting the assay mixture with a test compound, and determining the ability of the test compound to interact with a NgR protein, wherein determining the ability of the test compound to interact with a NgR protein comprises determining the ability of the NgR protein to modulate the activity of a NgR target molecule.

The cell-free assays of the present invention are amenable to use of both the soluble form or the membrane-bound form of NgR. In the case of cell-free assays comprising the membrane-bound form of NgR, it may be desirable to utilize a solubilizing agent such that the membrane-bound form of NgR is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-(3-cholamidopropyl)dimethylamminiol-1-propane sulfonate (CHAPS), 3-(3-cholamidopropyl)dimethylamminiol-2-hydroxy-1-propane sulfonate (CHAPSO), or N-dodecyl-N,N-dimethyl-3-ammonio-1-propane sulfonate.

Modulators

Agents that modulate (i.e., increase, decrease, or block) NgR activity or expression may be identified by incubating a putative modulator with a cell containing a NgR polypeptide or polynucleotide and determining the effect of the putative modulator on NgR activity or expression. The selectivity of a compound that modulates the activity of NgR can be evaluated by comparing its effects on NgR to its effect on other NgR compounds. Selective modulators may include, for example, antibodies and other proteins, peptides or organic molecules which specifically bind to a NgR polypeptide or a NgR-encoding nucleic acid. Modulators of NgR activity will be therapeutically useful in treatment of diseases and physiological conditions in which normal or aberrant NgR activity is involved. NgR polynucleotides, polypeptides and modulators may be used in the treatment of such diseases and conditions associated with demyelination. NgR polynucleotides and polypeptides, as well as NgR modulators, may also be used in diagnostic assays for such diseases or conditions.

Methods of the invention to identify modulators include variations on any of the methods described above to identify binding partner compounds, the variations including techniques wherein a binding partner compound has been identified and the binding assay is carried out in the presence and absence of a candidate modulator. A modulator is identified in those instances where binding between the NgR polypeptide and the binding partner compound changes in the presence of the candidate modulator compared to binding in the absence of the candidate modulator compound. A modulator that increases binding between the NgR polypeptide and the binding partner compound is described as an enhancer or activator, and a modulator that decreases binding between the NgR polypeptide and the binding partner compound is described as an inhibitor.

In another embodiment, modulators of NgR expression may be identified in a method wherein a cell is contacted with a candidate compound and the expression of NgR mRNA or protein in the cell is determined. The level of expression of NgR mRNA or protein in the presence of the candidate compound is compared to the level of expression of NgR mRNA or protein in the absence of the candidate compound. The candidate compound can then be identified as a modulator of NgR expression based on this comparison. For example, when expression of NgR mRNA or protein is greater (statistically significantly greater) in the presence of the candidate compound than in its absence, the candidate compound is identified as a stimulator of NgR mRNA or protein expression. Alternatively, when expression of NgR mRNA or protein is less (statistically significantly less) in the presence of the candidate compound than in its absence, the candidate compound is identified as an inhibitor of NgR mRNA or protein expression. The level of NgR mRNA or protein expression in the cells can be determined by methods described herein for detecting NgR mRNA or protein.

High Throughput Screening

The invention also comprehends high-throughput screening (HTS) assays to identify compounds that interact with or inhibit biological activity (i.e., affect enzymatic activity, binding activity, etc.) of a NgR polypeptide. HTS assays permit screening of large numbers of compounds in an efficient manner. Cell-based HTS systems are contemplated to investigate NgR receptor-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the NgR polypeptide.

Another aspect of the present invention is directed to methods of identifying compounds that bind to either NgR or nucleic acid molecules encoding NgR, comprising contacting NgR, or a nucleic acid molecule encoding the same, with a compound, and determining whether the compound binds NgR or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, Ausubel et al. (Eds.), CURRENT PROTOCOLS IN MOLECULAR BIOLOGY, 1999, John Wiley & Sons, NY, which is incorporated herein by reference in its entirety. The NgR proteins, for example, can be used as "bait proteins" in a two-hybrid assay or three hybrid assay (see, e.g., U.S. Pat. No. 5,283,317; Zervos et al., (1993) Cell 72, 223–232; Madura et al., (1993) J. Biol. Chem. 268, 12046–12054; Bartel et al., (1993) BioTechniques 14, 920–924; Iwabuchi et al., (1993) Oncogene 8, 1693–1696; and Brent WO 94/10300), to identify other proteins that bind to or interact with NgR ("NgR-binding proteins" or "NgR-bp") and modulate NgR activity. Such NgR-binding proteins are also likely to be involved in the propagation of signals by the NgR proteins as, for example, upstream or downstream elements of the NgR pathway.

Other assays may be used to identify specific ligands of a NgR receptor, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., (1989) Nature 340, 245–246, and Fields et al., (1994) Trends Genet. 10, 286–292, both of which are incorporated herein by reference. The two-hybrid system is a genetic assay based on the modular nature of most transcription factors used for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a NgR gene product, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal. The compounds to be screened include (which may include compounds that are suspected to bind NgR, or a nucleic acid molecule encoding the same), but are not limited to, extracellular, intracellular, biological or chemical origin.

The function of the NgR gene product is unclear and no ligands have yet been found which bind the gene product. The yeast two-hybrid assay is useful to identify proteins that bind to the gene product. In an assay to identify proteins that bind to a NgR receptor, or fragment thereof, a fusion polynucleotide encoding both a NgR receptor (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not even necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al. (1997) Anal. Chem. 69:1683–1691, incorporated herein by reference. This technique screens combinatorial libraries of 20–30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

The methods of the invention also embrace ligands, especially neuropeptides, that are attached to a label, such as a radiolabel (e.g., $^{125}I$, $^{35}S$, $^{32}P$, $^{33}P$, $^{3}H$), a fluorescence label, a chemiluminescent label, an enzymic label and an immunogenic label. Modulators falling within the scope of the invention include, but are not limited to, non-peptide molecules such as non-peptide mimetics, non-peptide allosteric effectors, and peptides. The NgR polypeptide or polynucleotide employed in such a test may either be free in solution, attached to a solid support, borne on a cell surface or located intracellularly or associated with a portion of a cell. One skilled in the art can, for example, measure the formation of complexes between NgR and the compound being tested. Alternatively, one skilled in the art can examine the diminution in complex formation between NgR and its substrate caused by the compound being tested.

Another aspect of the present invention is directed to methods of identifying compounds which modulate (i.e., increase or decrease) activity of NgR comprising contacting NgR with a compound, and determining whether the compound modifies activity of NgR. The activity in the presence of the test compared is measured to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The present invention is particularly useful for screening compounds by using NgR in any of a variety of drug screening techniques. The compounds to be screened include (which may include compounds which are suspected to modulate NgR activity), but are not limited to, extracellular, intracellular, biologic or chemical origin. The NgR polypeptide employed in such a test may be in any form, preferably, free in solution, attached to a solid support, borne on a cell surface or located intracellularly. One skilled in the art can, for example, measure the formation of complexes between NgR and the compound being tested. Alternatively, one skilled in the art can examine the diminution in complex formation between Nogo-R and its substrate caused by the compound being tested.

The activity of NgR polypeptides of the invention can be determined by, for example, examining the ability to bind or be activated by chemically synthesized peptide ligands. Alternatively, the activity of the NgR can be assayed by examining their ability to bind calcium ions, hormones, chemokines, neuropeptides, neurotransmitters, nucleotides, lipids, odorants and photons. Alternatively, the activity of the NgR can be determined by examining the activity of effector molecules including, but not limited to, adenylate cyclase, phospholipases and ion channels. Thus, modulators of NgR activity may alter a NgR receptor function, such as a binding property of a receptor or an activity. In various embodiments of the method, the assay may take the form of an ion flux assay, a yeast growth assay, a non-hydrolyzable GTP assay such as a [$^{35}$S]-GTP S assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay (e.g., using [$^3$H]-arachidonic acid) and an assay for extracellular acidification rates, as well as other binding or function-based assays of NgR activity that are generally known in the art. NgR activity can be determined by methodologies that are used to assay for FaRP activity, which is well known to those skilled in the art. Biological activities of NgR receptors according to the invention include, but are not limited to, the binding of a natural or an unnatural ligand, as well as any one of the functional artivities of NgRs known in the art.

Non-limiting examples of NgR activities include transmembrane signaling of various forms, which may involve phosphatidylinositol (PI) association and/or the exertion of an influence over PI; another exemplary activity of NgRs is the binding of accessory proteins or polypeptides that differ from known GPI proteins.

The modulators of the invention exhibit a variety of chemical structures, which can be generally grouped into non-peptide mimetics of natural NgR receptor ligands, peptide and non-peptide allosteric effectors of NgR receptors, and peptides that may function as activators or inhibitors (competitive, uncompetitive and non-competitive) (e.g., antibody products) of NgR receptors. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries.

Other assays can be used to examine enzymatic activity including, but not limited to, photometric, radiometric, HPLC, electrochemical, and the like, which are described in, for example, ENZYME ASSAYS: A PRACTICAL APPROACH, Eisenthal and Danson (Eds.), 1992, Oxford University Press, which is incorporated herein by reference in its entirety.

The use of cDNAs in drug discovery programs is well-known; assays capable of testing thousands of unknown compounds per day in high-throughput screens (HTSs) are thoroughly documented. The literature is replete with examples of the use of radiolabelled ligands in HTS binding assays for drug discovery (see Williams (1991) *Med Res. Rev.*, 11, 147–184; Sweetnam et al., (1993) *J. Nat. Prod.* 56, 441–455 for review). Recombinant receptors are preferred for binding assay HTS because they allow for better specificity (higher relative purity), provide the ability to generate large amounts of receptor material, and can be used in a broad variety of formats (see Hodgson (1992) *Bio/Technology* 10, 973–980; each of which is incorporated herein by reference in its entirety).

A variety of heterologous systems is available for functional expression of recombinant receptors that are well known to those skilled in the art. Such systems include bacteria (Strosbeg et al. (1992) *Trends Pharmacol. Sci.* 13, 95–98), yeast (Pausch (1997) *Trends Biotechnol.* 15, 487–494), several kinds of insect cells (Vanden Broeck (1996) *Int. Rev. Cytol.* 164, 189–268), amphibian cells (Jayawickreme et al. (1997) *Curr. Opin. Biotechnol.* 8, 629–634) and several mammalian cell lines (CHO, HEK293, COS, etc.; see Gerhardt et al. (1997) *Eur. J. Pharmacol.* 334, 1–23). These examples do not preclude the use of other possible cell expression systems, including cell lines obtained from nematodes (PCT application WO 98/37177).

In preferred embodiments of the invention, methods of screening for compounds which modulate NgR activity comprise contacting test compounds with NgR and assaying for the presence of a complex between the compound and NgR. In such assays, the ligand is typically labeled. After suitable incubation, free ligand is separated from that present in bound form, and the amount of free or uncomplexed label is a measure of the ability of the particular compound to bind to NgR.

In another embodiment of the invention, high throughput screening for compounds having suitable binding affinity to NgR is employed. Briefly, large numbers of different small peptide test compounds are synthesized on a solid substrate. The peptide test compounds are contacted with NgR and washed. Bound NgR is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed NgR can be used for HTS binding assays in conjunction with its defined ligand. The identified peptide is labeled with a suitable radioisotope, including, but not limited to, $^{125}$I, $^{3}$H, $^{35}$S or $^{32}$P, by methods that are well known to those skilled in the art. Alternatively, the peptides may be labeled by well-known methods with a suitable fluorescent derivative (Baindur et al. (1994) Drug Dev. Res. 33, 373–398; Rogers (1997) Drug Discov. Today 2, 156–160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams (1991) Med. Res. Rev. 11, 147–184; Sweetnam et al. (1993) J. Nat. Prod. 56, 441–455). Alternative methods include a scintillation proximity assay (SPA) or a FlashPlate format in which such separation is unnecessary (Nakayama (1998) Curr. Opin. Drug Disc. Dev. 1, 85–91 Bossé et al. (1998) J. Biomol. Screening 3, 285–292). Binding of fluorescent ligands can be detected in various ways, including fluorescence energy transfer (FRET), direct spectrophotofluorometric analysis of bound ligand, or fluorescence polarization (Rogers.(1997) Drug Discov. Today 2, 156–160; Hill (1998) Curr. Opin. Drug Disc. Dev. 1, 92–97).

Examples of such biological responses include, but are not limited to, the following: the ability to survive in the absence of a limiting nutrient in specifically engineered yeast cells (Pausch (1997) Trends in Biotechnol. 15, 487–494); changes in intracellular $Ca^{2+}$ concentration as measured by fluorescent dyes (Murphy et al. (1998) Cur. Opin. Drug Disc. Dev. 1, 192–199). Fluorescence changes can also be used to monitor ligand-induced changes in membrane potential or intracellular pH; an automated system suitable for HTS has been described for these purposes (Schroeder et al. (1996) J. Biomol. Screening 1, 75–80). Melanophores prepared from Xenopus laevis show a ligand-dependent change in pigment organization in response to heterologous NgR activation; this response is adaptable to HTS formats (Jayawickreme et al. (1997) Curr. Opin. Biotechnol. 8, 629–634). Assays are also available for the measurement of common second messengers, including cAMP, phosphoinositides and arachidonic acid, but these are not generally preferred for HTS.

Preferred methods of HTS employing these receptors include permanently transfected CHO cells, in which agonists and antagonists can be identified by the ability to transduce the signal for the binding of Nogo in membranes prepared from these cells through the putative GPI anchor. In another embodiment of the invention, permanently transfected CHO cells could be used for the preparation of membranes which contain significant amounts of the recombinant receptor proteins; these membrane preparations would then be used in receptor binding assays, employing the radiolabelled ligand specific for the particular receptor. Alternatively, a functional assay, such as fluorescent monitoring of ligand-induced changes in internal $Ca^{2+}$ concentration or membrane potential in permanently transfected CHO cells containing each of these receptors individually or in combination would be preferred for HTS. Equally preferred would be an alternative type of mammalian cell, such as HEK293 or COS cells, in similar formats. More preferred would be permanently transfected insect cell lines, such as Drosophila S2 cells. Even more preferred would be recombinant yeast cells expressing the Drosophila melanogaster receptors in HTS formats well known to those skilled in the art (e.g., Pausch (1997), above).

The invention contemplates a multitude of assays to screen and identify inhibitors of ligand binding to NgR receptors. In one example, the NgR receptor is immobilized and interaction with a binding partner is assessed in the presence and absence of a candidate modulator such as an inhibitor compound. In another example, interaction between the NgR receptor and its binding partner is assessed in a solution assay, both in the presence and absence of a candidate inhibitor compound. In either assay, an inhibitor is identified as a compound that decreases binding between the NgR receptor and its binding partner. Another contemplated assay involves a variation of the di-hybrid assay wherein an inhibitor of protein/protein interactions is identified by detection of a positive signal in a transformed or transfected host cell, as described in PCT publication number WO 95/20652, published Aug. 3, 1995.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof For a review, see Cane et al., Science (1998) 282, 63–68. Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers (1997) Curr. Opin. Biotechnol. 8, 701–707. Identification of modulators through use of the various libraries described herein permits modification of the candidate "hit" (or "lead") to optimize the capacity of the "hit" to modulate activity.

Still other candidate inhibitors contemplated by the invention can be designed and include soluble forms of binding partners, as well as such binding partners as chimeric, or fusion, proteins. A "binding partner" as used herein broadly encompasses non-peptide modulators, as well as such peptide modulators as neuropeptides other than natural ligands, antibodies, antibody fragments, and modified compounds comprising antibody domains that are immunospecific for the expression product of the identified NgR gene.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with NgR. Radiolabeled competitive binding studies are described in Lin et al., (1997) *Antimicrob. Agents Chemother.* 41, 2127–2131, the disclosure of which is incorporated herein by reference in its entirety.

In other embodiments of the invention, the polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to remove unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to the ligand for the NgR of the invention, but which are smaller and exhibit a longer half time than the endogenous ligand in a human or animal body. When an organic compound is designed, a molecule according to the invention is used as a "lead" compound. The design of mimetics to known pharmaceutically active compounds is a well-known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the DNAs of the present invention are useful to design new drugs, more specific and therefore with a higher pharmacological potency.

Comparison of the protein sequence of the present invention with the sequences present in all the available databases showed a significant homology with the transmembrane portion of G protein coupled receptors. Accordingly, computer modeling can be used to develop a putative tertiary structure of the proteins of the invention based on the available information of the transmembrane domain of other proteins. Thus, novel ligands based on the predicted structure of NgR can be designed.

This invention further pertains to novel agents identified by the above-described screening assays and uses thereof for treatments as described herein.

Compositions and Pharmaceutical Compositions

In a particular embodiment, the novel molecules identified by the screening methods according to the invention are low molecular weight organic molecules, in which case a composition or pharmaceutical composition can be prepared thereof for oral or parenteral administration. The compositions, or pharmaceutical compositions, comprising the nucleic acid molecules, vectors, polypeptides, antibodies and compounds identified by the screening methods described herein, typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The nature of the carrier or other ingredients will depend on the specific route of administration and particular embodiment of the invention to be administered. Examples of techniques and protocols that are useful in this context are, inter alia, found in Remington's PHARMACEUTICAL SCIENCES, 16th ed., (1980) Osol, A (Ed.), which is incorporated herein by reference in its entirety. Preferred examples of such carriers or diluents include, but are not limited to, water, saline, Ringer's solution, dextrose solution and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral and parenteral (e.g., intravenous, intradermal, subcutaneous, inhalation, transdermal (topical), transmucosal and rectal administration). Solutions or suspensions used for parenteral, intradermal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NgR protein or anti-NgR antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compounds are delivered in the form of an aerosol spray from pressured container or dispenser which contains a suitable propellant, e.g., a gas such as carbon dioxide or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811. It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) *Proc. Natl. Acad. Sci. USA* 91, 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack or dispenser together with instructions for administration.

The dosage of these low molecular weight compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

Another aspect of the present invention is the use of the NgR nucleotide sequences disclosed herein for identifying homologs of the Nogo-R, in other animals, including but not limited to humans and other mammals and invertebrates. Any of the nucleotide sequences disclosed herein, or any portion thereof, can be used, for example, as probes to screen databases or nucleic acid libraries, such as, for example, genomic or cDNA libraries, to identify homologs using screening procedures well known to those skilled in the art. Accordingly, homologs having at least 50%, more preferably at least 60%, more preferably at least 70%, more preferably at least 80%, more preferably at least 90%, more preferably at least 95%, and most preferably at least 100% homology with NgR sequences can be identified.

The present compounds and methods, including nucleic acid molecules, polypeptides, antibodies, compounds identified by the screening methods described herein, have a variety of pharmaceutical applications and may be used, for example, to treat or prevent unregulated cellular growth, such as cancer cell and tumor growth. In a particular embodiment, the present molecules are used in gene therapy. For a review of gene therapy procedures, see e.g. Anderson *Science* (1992) 256, 808–813, which is incorporated herein by reference in its entirety.

The present invention also encompasses a method of agonizing (stimulating) or antagonizing a NgR natural binding partner associated activity in a mammal comprising administering to said mammal an agonist or antagonist to one of the above disclosed polypeptides in an amount sufficient to effect said agonism or antagonism. One embodiment of the present invention, then, is a method of treating diseases in a mammal with an agonist or antagonist of the protein of the present invention comprising administering the agonist or antagonist to a mammal in an amount sufficient to agonize or antagonize NgR-associated functions.

Methods of determining the dosages of compounds to be administered to a patient and modes of administering compounds to an organism are disclosed in U.S. application Ser. No. 08/702,282, filed Aug. 23, 1996, and International patent publication number WO 96/22976, published Aug. 1, 1996, both of which are incorporated herein by reference in their entirety, including any drawings, figures or tables. Those skilled in the art will appreciate that such descriptions are applicable to the present invention and can be easily adapted to it.

The proper dosage depends on various factors such as the type of disease being treated, the particular composition being used and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors and major organs can also be determined to facilitate the selection of drugs most appropriate to inhibit a disorder. Such measurements can be carried out. For example, BPLC analysis can be performed on the plasma of animals treated with the drug and the location of radiolabeled compounds can be determined using detection methods such as X-ray, CAT scan and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: (1) the compound is administered to mice (an untreated control mouse should also be used); (2) blood samples are periodically obtained via the tail vein from one mouse in each treatment group; and (3) the samples are analyzed for red and white blood cell counts, blood cell composition and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, (1993) *J. Am. Vet. Med. Assoc.* 202;229–249). Representative animals from each treatment group can then be examined by gross necropsy for immediate evidence of metastasis, unusual illness or toxicity. Gross abnormalities in tissue are noted and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness. Plasma levels should reflect the potency of the drug. Generally, the more potent the compound the lower the plasma levels necessary to achieve efficacy.

NgR mRNA transcripts have been found in the brain and heart. SEQ ID NOs: 1 and/or, 3 will, as detailed above, enable screening the endogenous neurotransmitters/hormones/ligands which activate, agonize, or antagonize NgR and for compounds with potential utility in treating disorders including CNS disorders (e.g., stroke) and degenerative disorders such as those associated with demyelination.

For example, NgR receptor activation may mediate the prevention of neurite outgrowth. Inhibition would be beneficial in both chronic and acute brain injury. See, e.g., Donovan et al., (1997) *J. Neurosci.* 17, 5316–5326; Turgeon et al., (1998) *J. Neurosci.* 18, 6882–6891; Smith-Swintosky et al., (1997) *J. Neurochem.* 69, 1890–1896; Gill et al., (1998) *Brain Res.* 797, 321–327; Suidan et al., (1996) *Semin. Thromb. Hemost.* 22, 125–133.

Pharmacogenomics

Agents, or modulators that have a stimulatory or inhibitory effect on NgR activity (e.g NgR gene expression), as identified by a screening assay described herein can be administered to individuals to treat (prophylactically or therapeutically) disorders (e.g., a disease condition such as a demyelination disorder) associated with aberrant NgR activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NgR protein, expression of NgR nucleic acid or mutation content of NgR genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum (1996) *Clin. Exp. Pharmacol. Physiol.* 23, 983–985 and Linder (1997) *Clin. Chem.* 43, 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NgR protein, expression of NgR nucleic acid, or mutation content of NgR genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NgR modulator, such as a modulator identified by one of the exemplary screening assays described herein.

Monitoring Clinical Efficacy

Monitoring the influence of agents (e.g., drugs, compounds) on the expression or activity of NgR (e.g., the ability to modulate aberrant cell proliferation and/or differentiation) can be applied not only in basic drug screening, but also in clinical trials. For example, the effectiveness of an agent determined by a screening assay as described herein to increase NgR gene expression, protein levels or upregulate NgR activity, can be monitored in clinical trials of subjects exhibiting decreased NgR gene expression, protein levels, or downregulated NgR activity. Alternatively, the effectiveness of an agent determined by a screening assay to decrease NgR gene expression, protein levels, or downregulate NgR activity can be monitored in clinical trials of subjects exhibiting increased NgR gene expression, protein levels, or upregulated NgR activity. In such clinical trials, the expression or activity of NgR and, preferably, other genes that have been implicated in, for example, a disease or disorder, can be used as a "read out" or markers of the immune responsiveness of a particular cell.

For example, genes, including NgR, that are modulated in cells by treatment with an agent (e.g., compound, drug or small molecule) that modulates NgR activity (e.g., identified in a screening assay as described herein) can be identified. Thus, to study the effect of agents on demyelination disorders, for example, in a clinical trial, cells can be isolated and RNA prepared and analyzed for the levels of expression of NgR and other genes implicated in the disorder. The levels of gene expression (i.e., a gene expression pattern) can be quantified by Northern blot analysis or RT-PCR, as described herein, or alternatively by measuring the amount of protein produced by one of the methods as described herein or by measuring the levels of activity of NgR or other genes. In this way, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a NgR protein, mRNA, or genomic DNA in the preadministration sample; (iii) obtaining one or more post-administration samples from the subject; (iv) detecting the level of expression or activity of the NgR protein, mRNA, or genomic DNA in the post-administration samples; (v) comparing the level of expression or activity of the NgR protein, mRNA or genomic DNA in the pre-administration sample with the NgR protein, mRNA or genomic DNA in the post administration sample or samples; and (vi) altering the administration of the agent to the subject accordingly. For example, increased administration of the agent may be desirable to increase the expression or activity of NgR to higher levels than detected, i.e., to increase the effectiveness of the agent. Alternatively, decreased administration of the agent may be desirable to decrease expression or activity of NgR to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant NgR expression or activity.

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) a NgR polypeptide, or analogs, derivatives, fragments or homologs thereof, (ii) antibodies to a NgR peptide; (iii) nucleic acids encoding a NgR peptide; (iv) administration of antisense nucleic acid and nucleic acids that are "dysfunctional" (i.e., due to a heterologous insertion within the coding sequences of coding sequences to a NgR peptide) are utilized to "knockout" endogenous function of a NgR peptide by homologous recombination (see, e.g., Capecchi (1989) *Science* 244, 1288–1292); or (v) modulators (i.e., inhibitors, agonists and antagonists, including additional peptide mimetic of the invention or antibodies specific to a peptide of the invention) that alter the interaction between a NgR peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, a NgR peptide, or analogs, derivatives, fragments or homologs thereof, or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a NgR peptide). Methods that are well-known within the art include, but are not limited to, immunoassays (e.g. by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with an aberrant NgR expression or activity, by administering to the subject an agent that modulates NgR expression or at least one NgR activity. Subjects at risk for a disease that is caused or contributed to by aberrant NgR expression or activity can be identified by, for example, any or a combination of diagnostic or prognostic assays as described herein. Administration of a prophylactic agent can occur prior to the manifestation of symptoms characteristic of the NgR aberrancy, such that a disease or disorder is prevented or, alternatively, delayed in its progression. Depending on the type of NgR aberrancy, for example, a NgR agonist or NgR antagonist agent can be used for treating the subject. The appropriate agent can be determined based on screening assays described herein.

Another aspect of the invention pertains to methods of modulating NgR expression or activity for therapeutic purposes. The modulatory method of the invention involves contacting a cell with an agent that modulates one or more of the activities of NgR protein activity associated with the cell. An agent that modulates NgR protein activity can be an agent as described herein, such as a nucleic acid or a protein, a naturally-occurring cognate ligand of a NgR protein, a peptide, a NgR peptidomimetic, or other small molecule. In one embodiment, the agent stimulates one or more NgR protein activity. Examples of such stimulatory agents include active NgR protein and a nucleic acid molecule encoding NgR that has been introduced into the cell. In another embodiment, the agent inhibits one or more NgR protein activity. Examples of such inhibitory agents include antisense NgR nucleic acid molecules and anti-NgR antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NgR protein or nucleic acid molecule. In one embodiment, the method involves administering an agent (e.g., an agent identified by a screening assay described herein), or combination of agents that modulates (e.g., upregulates or downregulates) NgR expression or activity. In another embodiment, the method involves administering a NgR protein or nucleic acid molecule as therapy to compensate for reduced or aberrant NgR expression or activity.

Gene Therapy

Mutations in the NgR gene that result in loss of normal function of the NgR gene product underlie NgR human disease states. The invention comprehends gene therapy to restore NgR activity to treat those disease states. Delivery of a functional NgR gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson (1998) *Nature*, supplement to 392(6679):25–20. For additional reviews of gene therapy technology see Friedmann (1989) *Science* 244, 1275–1281; Verma (1990) *Sci. Am.* 68–84; and Miller (1992) *Nature* 357, 455–460. Alternatively, it is contemplated that in other human disease states, preventing the expression of, or inhibiting the activity of, NgR will be useful in treating disease states. It is contemplated that antisense therapy or gene therapy could be applied to negatively regulate the expression of NgR.

The present invention provides for both prophylactic and therapeutic methods of treating a subject at risk of (or susceptible to) a disorder or having a disorder associated with aberrant NgR expression or activity.

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) a NgR polypeptide, or analogs, derivatives, fragments or homologs thereof; (ii) antibodies to a NgR peptide; (iii) nucleic acids encoding a NgR peptide; (iv) administration of antisense nucleic acid and nucleic acids that are "dysfunctional" (i.e., due to a heterologous insertion within the coding sequences of coding sequences to a NgR peptide) are utilized to "knockout" endogenous function of a NgR peptide by homologous recombination (see, e.g., Capecchi (1989), above); or (v) modulators (i.e., inhibitors, agonists and antagonists, including additional peptide mimetic of the invention or antibodies specific to a peptide of the invention) that alter the interaction between a NgR peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, a NgR peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a NgR peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with an aberrant NgR expression or activity, by administering to the subject an agent that modulates NgR expression or at least one NgR activity. Subjects at risk for a disease that is caused or contributed to by aberrant NgR expression or activity can be identified by, for example, any or a combination of diagnostic or prognostic assays as described herein. Administration of a prophylactic agent can occur prior to the manifestation of symptoms characteristic of the NgR aberrancy, such that a disease or disorder is prevented or, alternatively, delayed in its progression. Depending on the type of NgR aberrancy, for example, a NgR agonist or NgR antagonist agent can be used for treating the subject. The appropriate agent can be determined based on screening assays described herein.

Another aspect of the invention pertains to methods of modulating NgR expression or activity for therapeutic purposes. The modulatory method of the invention involves contacting a cell with an agent that modulates one or more of the activities of NgR protein activity associated with the cell. An agent that modulates NgR protein activity can be an agent as described herein, such as a nucleic acid or a protein, a naturally-occurring cognate ligand of a NgR protein, a peptide, a NgR peptidomimetic, or other small molecule. In one embodiment, the agent stimulates one or more NgR protein activity. Examples of such stimulatory agents include active NgR protein and a nucleic acid molecule encoding NgR that has been introduced into the cell. In another embodiment, the agent inhibits one or more NgR protein activity. Examples of such inhibitory agents include antisense NgR nucleic acid molecules and anti-NgR antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NgR protein or nucleic acid molecule. In one embodiment, the method involves administering an agent (e.g., an agent identified by a screening assay described herein), or combination of agents that modulates (e.g., upregulates or downregulates) NgR expression or activity. In another embodiment, the method involves administering a NgR protein or nucleic acid molecule as therapy to compensate for reduced or aberrant NgR expression or activity.

The present invention is not to be limited in scope by the specific embodiments described herein. Indeed, various modifications of the invention in addition to those described herein will become apparent to those skilled in the art from the foregoing description and accompanying figure. Such modifications are intended to fall within the scope of the appended claims.

The following Table 5 contains the sequences of exemplary polynucleotides and polypeptides of the invention.

TABLE 5

The following DNA sequence NgR2 <SEQ ID NO. 1> was identified in humans:

ATGCTGCCCGGGCTCAGGCGCCTGCTGCAAGCTCCCGCCTCGGCCTGCCTCCTGCTGATG

CTCCTGGCCCTGCCCCTGGCGGCCCCCAGCTGCCCCATGCTCTGCACCTGCTACTCATCC

CCGCCCACCGTGAGCTGCCAGGCCAACAACTTCTCCTCTGTGCCGCTGTCCCTGCCACCC

AGCACTCAGCGACTCTTCCTGCAGAACAACCTCATCCGCACGCTGCGGCCAGGCACCTTT

GGGTCCAACCTGCTCACCCTGTGGCTCTTCTCCAACAACCTCTCCACCATCTACCCGGGC

ACTTTCCGCCACTTGCAAGCCCTGGAGGAGCTGGACCTCGGTGACAACCGGCACCTGCGC

TCGCTGGAGCCCGACACCTTCCAGGGCCTGGAGCGGCTGCAGTCGCTGCATTTGTACCGC

TGCCAGCTCAGCAGCCTGCCCGGCAACATCTTCCGAGGCCTGGTCAGCCTGCAGTACCTC

TACCTCCAGGAGAACAGCCTGCTCCACCTACAGGATGACTTGTTCGCGGACCTGGCCAAC

CTGAGCCACCTCTTCCTCCACGGGAACCGCCTGCGGCTGCTCACAGAGCACGTGTTTCGC

GGCCTGGGCAGCCTGGACCGGCTGCTGCTGCACGGGAACCGGCTGCAGGGCGTGCACCGC

GCGGCCTTCCGCGGCCTCAGCCGCCTCACCATCCTCTACCTGTTCAACAACAGCCTGGCC

TCGCTGCCCGGCGAGGCGCTCGCCGACCTGCCCTCGCTCGAGTTCCTGCGGCTCAACGCT

AACCCCTGGGCGTGCGACTGCCGCGCGCGGCCGCTCTGGGCCTGGTTCCAGCGCGCGCGC

GTGTCCAGCTCCGACGTGACCTGCGCCACCCCCCGGAGCGCCAGGGCCGAGACCTGCGC

GCGCTCCGCGAGGCCGACTTCCAGGCGTGTCCGCCCGCGGCACCCACGCGGCCGGGCAGC

CGCGCCCGCGGCAACAGCTCCTCCAACCACCTGTACGGGGTGGCCGAGGCCGGGCGCCC

CCAGCCGATCCCTCCACCCTCTACCGAGATCTGCCTGCCGAAGACTCGCGGGGGCGCCAG

GGCGGGGACGCGCCTACTGAGGACGACTACTGGGGGGGCTACGGGGGTGAGGACCAGCGA

GGGGAGCAGATGTGCCCCGGCGCTGCCTGCCAGGCGCCCCCGGACTCCCGAGGCCCTGCG

TABLE 5-continued

CTCTCGGCCGGGCTCCCCAGCCCTCTGCTTTGCCTCCTGCTCCTGGTGCCCCACCACCTC

The following amino acid sequence <SEQ ID NO. 2> is the predicted amino acid sequence derived from the DNA sequence of SEQ ID NO. 1:

M L P G L R R L L Q A P A S A C L L L M L L A L P L A A P S C

P M L C T C Y S S P P T V S C Q A N N F S S V P L S L P P S T

Q R L F L Q N N L I R T L R P G T F G S N L L T L W L F S N N

L S T I Y P G T F R H L Q A L E E L D L G D N R H L R S L E P

D T F Q G L E R L Q S L H L Y R C Q L S S L P G N I F R G L V

S L Q Y L Y L Q E N S L L H L Q D D L F A D L A N L S H L F L

H G N R L R L L T E H V F R G L G S L D R L L L H G N R L Q G

V H R A A F R G L S R L T I L Y L F N N S L A S L P G E A L A

D L P S L E F L R L N A N P W A C D C R A R P L W A W F Q R A

R V S S S D V T C A T P P E R Q G R D L R A L R E A D F Q A C

P P A A P T R P G S R A R G N S S S N H L Y G V A E A G A P P

A D P S T L Y R D L P A E D S R G R Q G G D A P T E D D Y W G

G Y G G E D Q R G E Q M C P G A A C Q A P P D S R G P A L S A

G L P S P L L C L L L L V P H H L

The following DNA sequence NgR3 <SEQ ID NO. 3> was identified in mouse:

ATGTCTTGGCAGTCTGGAACCACAGTGACACAATCTCCCGTGCAGGCTGCTCAGGTCTCA

GGGTGCTGTGTGGAATTGCTGCTGTTGCTGCTCGCTGGAGAGCTACCTCTGGGTGGTGGT

TGTCCTCGAGACTGTGTGTGCTACCCTGCGCCCATGACTGTCAGCTGCCAGGCACACAAC

TTTGCTGCCATCCCGGAGGGCATCCCAGAGGACAGTGAGCGCATCTTCCTGCAGAACAAT

CGCATCACCTTCCTCCAGCAGGGCCACTTCAGCCCCGCCATGGTCACCCTCTGGATCTAC

TCCAACAACATCACTTTCATTGCTCCCAACACCTTCGAGGGCTTTGTGCATCTGGAGGAG

CTAGACCTTGGAGACAACCGACAGCTGCGAACGCTGGCACCCGAGACCTTCCAAGGCCTG

GTGAAGCTTCACGCCCTCTACCTCTATAAGTGTGGACTGAGCGCCCTGCCCGCAGGCATC

TTTGGTGGCCTGCACAGCCTGCAGTATCTCTACTTGCAGGACAACCATATCGAGTACCTC

CAAGATGACATCTTTGTGGACCTGGTCAATCTCAGTCACTTGTTTCTCCATGGTAACAAG

CTATGGAGCCTGGGCCAAGGCATCTTCCGGGGCCTGGTGAACCTGGACCGGTTGCTGCTG

CATGAGAACCAGCTACAGTGGGTTCACCACAAGGCTTTCCATGACCTCCACAGGCTAACC

ACCCTCTTTCTCTTCAACAACAGCCTCACTGAGCTGCAGGGTGACTGTCTGGCCCCCCTG

GTGGCCTTGGAGTTCCTTCGCCTCAATGGGAATGCTTGGGACTGTGGCTGCGGGCACGT

TCCCTGTGGGAATGGCTGCGAAGGTTCCGTGGCTCTAGCTCTGCTGTCCCCTGCGCGACC

CCCGAGCTGCGGCAAGGCCAGGATCTGAAGCTGCTGAGGGTGGAGGACTTCCGGAACTGC

ACAGGACCAGTGTCCTCACCAGATCAAGTCTCACACGCTTACCACCTCTGACAGGGCT

GCCCGCAAGGAGCACCATCCGTCCCATGGGGCCTCCAGGGACAAAGGCCACCCACATGGC

CATCCGCCTGGCTCCAGGTCAGGTTACAAGAAGGCAGGCAAGAACTGCACCAGCCACAGG

AACCGGAACCAGATCTCTAAGGTGAGCTCTGGGAAAGAGCTTACCGAACTGCAGGACTAT

GCCCCCGACTATCAGCACAAGTTCAGCTTTGACATCATGCCCACCGCACGACCCAAGAGG

AAGGGCAAGTGTGCTCGCAGGACCCCCATCCGTGCCCCCAGTGGGGTGCAGCAGGCATCC

TABLE 5-continued

TCAGGCACGGCCCTTGGGGCCCCACTCCTGGCCTGGATACTGGGGCTGGCAGTCACTCTC

CGC

The following protein sequence <SEQ ID NO. 4> is deduced protein of SEQ ID NO: 3:

M S W Q S G T T V T Q S P V Q A A Q V S G C C V E L L L L L L

A G E L P L G G G C P R D C V C Y P A P M T V S C Q A H N F A

A I P E G I P E D S E R I F L Q N N R I T F L Q Q G H F S P A

M V T L W I Y S N N I T F I A P N T F E G F V H L E E L D L G

D N R Q L R T L A P E T F Q G L V K L H A L Y L Y K C G L S A

L P A G I F G G L H S L Q Y L Y L Q D N H I E Y L Q D D I F V

D L V N L S H L F L H G N K L W S L G Q G I F R G L V N L D R

L L L H E N Q L Q W V H H K A F H D L H R L T T L F L F N N S

L T E L Q G D C L A P L V A L E F L R L N G N A W D C G C R A

R S L W E W L R R F R G S S S A V P C A T P E L R Q G Q D L K

L L R V E D F R N C T G P V S P H Q I K S H T L T T S D R A A

R K E H H P S H G A S R D K G H P H G H P P G S R S G Y K K A

G K N C T S H R N R N Q I S K V S S G K E L T E L Q D Y A P D

Y Q H K F S F D I M P T A R P K R K G K C A R R T P I R A P S

G V Q Q A S S G T A L G A P L L A W I L G L A V T L R

The following protein sequence <SEQ ID NO. 5> is NgR1 from humans:

M K R A S A G G S R L L A W V L W L Q A W Q V A A P C P G A

C

C Y N E P K V T T S C P Q Q G L Q A V P V G I P A A S Q R I

F L H G N R I S H V P A A S F R A C R N L T I L W L H S N V L

A R I D A A A F T G L A L L E Q L D L S D N A Q L R S V D P A

T F H G L G R L H T L H L D R C G L Q E L G P G L F R G L A A

L Q Y L Y L Q D N A L Q A L P D D T F R D L G N L T H L F L H

G N R I S S V P E R A F R G L H S L D R L L H Q N R V A H V

H P H A F R D L G R L M T L Y L F A N N L S A L P T E A L A P

L R A L Q Y L R L N D N P W V C D C R A R P L W A W L Q K F R

G S S S E V P C S L P Q R L A G R D L K R L A A N D L Q G C A

V A T G P Y H P I W T G R A T D E E P L G L P K C C Q P D A A

D K A S V L E P G R P A S A G N A L K G R V P P G D S P P G N

G S G P R H I N D S P F G T L P G S A E P P L T A V R P E G S

E P P G F P T S G P R R R P G C S R K N R T R S H C R L G Q A

G S G G G G T G D S E G S G A L P S L T C S L T P L G L A L V

L W T V L G P C

The following amino acid sequence <SEQ ID NO: 6> is a Consensus Sequence of NgR based on homology with NgR1

TABLE 5-continued

C P X X C X C Y X X P X X T X S C X X X X X X X P X
X X P X X X X R X F L X X N X I X X X X X X X F X X X X X X X X L W X
X S N X X X X I X X X X F X X X X X L E X L D L X D N X X L R
X X X P X T F X G L X X L X L X L X X C L X X L X X X X F X
G L X X L Q Y L Y L Q X N X X X X L X D D X F X D L X N L X H
L F L H G N X X X X X X X X X F R G L X X D R L L L H X N X
X X X V H X X A F X X L X R L X X L X L F X N X L X X L X X X
X L A X L X X L X X L R L N X N X W X C X C R A R X L W X W X
X X X R X S S S X V X C X X P X X X X G X D L X X L X X X D X
X X C X X X X X P X X P X X X X X X X X X X X X X X X X X X X
X X X X X X X X X X X X X X X G X X X X X X X X X X X X
P P X X X S X X X X X X X X X X X X X X X X X X X X X X X
X X X X X X X X X X X X X X X X X X X X X X X X X R X X X
X X X X X X X X X X X X X X X X X X X X X X X X L X X X X X
X X X X L

The following protein sequence <SEQ ID NO: 7> is the 66 amino acid active domain of Nogo:

R I Y K G V I Q A I Q K S D E G H P F R A Y L E S E V A I S E
E L V Q K Y S N S A L G H V N C T I K E L R R L F L V D D L V
D S L K

The following protein sequence <SEQ ID NO: 8> is the amino acid sequence of the mature NgR2:

C P M L C T C Y S S P P T V S C Q A N N F S S V P L S L P P S

T Q R L F L Q N N L I R T L R P G T F G S N L L T L W L F S N

N L S T I Y P G T F R H L Q A L E E L D L G D N R H L R S L E

P D T F Q G L E R L Q S L H L Y R C Q L S S L P G N I F R G L

V S L Q Y L Y L Q E N S L L H L Q D D L F A D L A N L S H L F

L H G N R L R L L T E H V F R G L G S L D R L L L H G N R L Q

G V H R A A F R G L S R L T I L Y L F N N S L A S L P G E A L

A D L P S L E F L R L N A N P W A C D C R A R P L W A W F Q R

A R V S S S D V T C A T P P E R Q G R D L R A L R E A D F Q A

C P P A A P T R P G S R A R G N S S S N H L Y G V A E A G A P

P A D P S T L Y R D L P A E D S R G R Q G G D A P T E D D Y W

G G Y G G E D Q R G E Q M C P G A A C Q A P P D S R G P A L S

A G L P S P L L C L L L L V P H H L

The following protein sequence <SEQ ID NO: 9> is the amino acid sequence of the mature NgR3:

C P R D C V C Y P A P M T V S C Q A H N F A A I P E G I P E D

S E R I F L Q N N R I T F L Q Q G H F S P A M V T L W I Y S N

N I T F I A P N T F E G F V H L E E L D L G D N R Q L R T L A

TABLE 5-continued

P E T F Q G L V K L H A L Y L Y K C G L S A L P A G I F G G L

H S L Q Y L Y L Q D N H I E Y L Q D D I F V D L V N L S H L F

L H G N K L W S L G Q G I F R G L V N L D R L L L H E N Q L Q

W V H H K A F H D L H R L T T L F L F N N S L T E L Q G D C L

A P L V A L E F L R L N G N A W D C G C R A R S L W E W L R R

F R G S S S A V P C A T P E L R Q G Q D L K L L R V E D F R N

C T G P V S P H Q I K S H T L T T S D R A A R K E H H P S H G

A S R D K G H P H G H P P G S R S G Y K K A G K N C T S H R N

R N Q I S K V S S G K E L T E L Q D Y A P D Y Q H K F S F D I

M P T A R P K R K G K C A R R T P I R A P S G V Q Q A S S G T

A L G A P L L A W I L G L A V T L R

The following amino acid sequence <SEQ ID NO: 10> is a conserved cysteine motif (Cysteine domain 1) of the NgR and homologs based on the Consensus Sequence:

C P X X C X C Y X X P X X T X S C

The following amino acid sequence <SEQ ID NO: 11> is a conserved cysteine motif (Cysteine domain 2) of the NgR and homologs based on the Consensus Sequence:

N X W X C X C R A R X L W X W X X X X R X S S S X V X C X X P

X X X X G X D L X X L X X X D X X X C

The following amino acid sequence <SEQ ID NO: 12> is a conserved Leucine-rich domain of the NgR and homologs based on the Consensus Sequence:

R X F L X X N X I X X X X X X X F X X X X X X X X L W X X S N

X X X X I X X X X F X X X X X L E X L D L X D N X X L R X X X

P X T F X G L X X L X L X L X X C X L X X L X X X X F X G L X

X L Q Y L Y L Q X N X X X X L X D D X F X D L X N L X H L F L

H G N X X X X X X X X X F R G L X X L D R L L L H X N X X X X

V H X X A F X X L X R L X X L X L F X N X L X X L X X X X L A

X L X X L X X L R L

Unless otherwise indicated, X is any amino acid. For example, X where indicated may be no amino acid. Additional features of the invention will be apparent from the following Examples. Examples 1–5 are actual, while the remaining Examples are prophetic.

As shown by the following Examples, a gene encoding novel NgRs have been identified by computational analysis of DNA sequence data. The proteins encoded by NgR2 and NgR3 have a putative signal sequence, eight leucine-rich repeat domains in a conserved leucine-rich region (SEQ ID NO:12), a conserved cysteine-rich region (SEQ ID NO:10) N-terminal to the leucine-rich region, a second cysteine-rich domain (SEQ ID NO:11) C-terminal to the leucine-rich region, and a putative glycophosphatidylinositol-linkage (GPI-linkage) site. NgR2 and NgR3 differ from the previously identified NgR sequence. The NgR homologs, when compared to known NgRs, show a consensus sequence (SEQ ID NOs:6). The putative mature NgR2 and NgR3 are shown in Table 5 as SEQ ID NOs: 8 and 9, respectively.

EXAMPLE 1

Tblastn Query of the HTG Database

The protein sequence for the human NgR (NgR1) (SEQ ID NO:5) was used to query the high throughput genomic (HTG) database the use of which is familiar to those skilled in the art. The HTG database is a part of GenBank, a comprehensive NIH genetic sequence database, which includes an annotated collection of all publicly available DNA sequences (*Nucleic Acids Res.* (2000) 28, 15–8). The HTG database includes sequences obtained from genomic DNA. Within genomic DNA, genes are typically encoded by multiple segments of DNA called exons. Thus when one aligns a cDNA sequence (or a protein sequence encoded by a cDNA sequence) to a genomic sequence, the sequence will be broken up into segments depending on the number of exons in the gene.

The BLAST algorithm, which stands for Basic Local Alignment Search Tool is suitable for determining sequence similarity (Altschul et al., (1990) *J. Mol. Biol.* 215, 403–410, which is incorporated herein by reference in its entirety). Software for performing BLAST analyses is publicly available through the National Center for Biotechnology Information (http://www.ncbi.nlm.nih.gov/). The basic BLAST algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., (1992) *Proc. Natl. Acad. Sci. USA* 89, 10915–10919, which is incorporated herein by reference in its entirety) alignments (B) of 50, expectation (E) of 10, M=5, N=4, and a comparison of both strands.

The BLAST algorithm (Karlin et al., (1993) *Proc. Natl. Acad. Sci. USA* 90, 5873–5787, which is incorporated herein by reference) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a NgR gene or cDNA if the smallest sum probability in comparison of the test nucleic acid to a NgR nucleic acid is less than about 1, preferably less than about 0.1, more preferably less than about 0.01, and most preferably less than about 0.001.

To query the HTG database with the NgR protein sequence, we used a variation of the BLAST algorithm known as the tblastn program, which compares a protein query sequence against a nucleotide sequence database dynamically translated in all reading frames (*J. Mol. Biol.* (1990) 215, 403–410; *Nucleic Acids Res.* (1997) 25, 3389–3402). The results of the tblastn search indicated the presence of genes in the database with a significant identity to the NgR. In addition to finding hits to genomic clones which contain the human and mouse NgR genes, we found hits to clones where the identity was not as high, but still very significant. Three human clones were found (Accession numbers: AC068514, AC016869, AC013606) with an e-value of 4e-43 and one mouse clone was found (Accession No. AC021768) with an e-value of 1e-78. The three human clones all appeared to encode the same gene, so further analysis was confined to AC013606.

EXAMPLE 2

Prediction of the Human NgR2 Protein Sequence (AC013606)

The human NgR protein sequence aligned with two regions of translated sequence from nucleotide sequence AC013606, indicating that the new gene was encoded by at least two exons. In order to define the complete gene, we used the computer program GENSCAN™ (*J. Mol. Biol.* (1997) 268, 78–94) which can identify complete exon/intron structures of genes in genomic DNA. The gene prediction by GENESCAN™ contained seven exons. By comparing these predicted exons to the NgR, it was concluded that the new human gene contains two of these exons and a part of another (containing the initiating methionine). The predicted cDNA (mRNA) encoded by these three exons was assembled from AC013606 (HTG11; deposited March 2000; length=143899; GenBank release 118.0; SEQ ID NO: 15) by combining nucleotides from the three exons whose coordinates are: 123292–123322 (exon 1); 130035–130516 (exon 2); and 138589–139335 (exon 3). The sequence for this cDNA sequence is SEQ ID NO:1 (nucleotide sequence of human NgR2; AC013606). The translation of this cDNA provides the protein sequence of human NgR2 (SEQ ID NO:2).

We used the protein sequence of human NgR2 as a query sequence against the human EST database. A number of hits of high significance were found indicating that the NgR2 mRNA is expressed in a number of tissues including fetal brain. Furthermore, two of these ESTs provided support for the exon structure that we deduced. One EST (Accession No: GB_EST19:AI346757) contains 565 nucleotides corresponding to amino acids 84–271 of the human NgR2 (SEQ ID No:4). This spans the second intron located between amino acids 171 and 172, and provides positive evidence for the splicing of exons 2 and 3 at the mRNA level. Another EST (GB_EST26:AI929019) contains 545 nucleotides, part of which corresponds to amino acids 1–75 of the human NgR2 (SEQ ID NO:2). This spans the first intron located between amino acids 10 and 11, and provides positive evidence for the splicing of exons 1 and 2 at the mRNA level.

EXAMPLE 3

Prediction of the Mouse NgR3 Protein Sequence (AC021768)

The human NgR protein sequence aligned with only one region of translated sequence from nucleotide sequence AC021768, indicating that most of the new mouse gene was encoded by one large exon. However, upon inspection, the protein encoded by this exon was missing an initiating methionine. In order to define the complete gene, we used the computer program GENSCAN as described above. The gene prediction by GENSCAN contained two exons; the large one found by visual inspection and a short one at the 5' end which provided an initiating methionine. The predicted cDNA (mRNA) encoded by these two exons was assembled from AC021768 (HTG14; deposited March 2000; length=215980; GenBank release 118.0; SEQ ID NO: 16) by combining nucleotides from the two exons whose coordinates are: the complement of 164265–164325 (exon 1); and the complement of 155671–156992 (exon 2). The sequence for this cDNA sequence is SEQ ID NO:3 (nucleotide sequence of mouse NgR3; AC021768). The translation of this cDNA provides the protein sequence of mouse NgR3 (SEQ ID NO:4).

We used the protein sequence of mouse NgR3 as a query sequence against the mouse EST database. One hit of high significance was found indicating that the NgR2 mRNA is expressed in the heart. This EST (GB_EST20: AI428334) contains 463 nucleotides, part of which correspond to amino acids 45–193 of mouse NgR3 (SEQ ID NO:4).

EXAMPLE 4

Similarity Between the NgRs

An alignment between NgR1 and the two new receptors is shown in FIG. 1A–1B. The similarities between these proteins include:

(1) The SignalP program, which locates the signal sequence cleavage position, predicts a cleavage before the first conserved cysteine in all the proteins. Thus the mature protein in all cases will have a cysteine at the N-terminus.

(2) All proteins contain eight Leucine Rich Repeats (LRR). LRRs are short sequence motifs present in a number of proteins with diverse functions and cellular locations. These repeats are usually involved in protein-protein interactions. Each LRR is composed of a beta-alpha unit.

(3) All three proteins contain a leucine rich repeat N-terminal domain (LRRNT), in which four cysteines are conserved. LRRs are often flanked by cysteine rich domains at both their N and C termini.

(4) All three proteins contain a LRR C-terminal domain (LRRCT). The LRRCTs of the three NgR proteins can be distinguished from those of other LRR containing proteins, by the pattern of typtophans and cysteines which are completely conserved in this domain.

(5) All three proteins contain a conserved cysteine in the fourth LRR domain.

(6) All three proteins contain a conserved potential glycosylation site in the eighth LRR domain.

(7) NgR2 and NgR3 have a hydrophobic C-terminus, as does NgR1, an indication that they probably also undergo a modification similar to NgR1, where a GPI moiety is covalently linked to a C-terminal amino acid. This allows the protein to remain tethered to the cell.

EXAMPLE 5

Preparation of Nogo Proteins

A Nogo binding assay was developed which utilizes a method widely used in examining semaphorin and ephrin axonal guidance function (Flanagan & Vanderhaeghen (1998) *Annu. Rev. Neurosci.* 21,309–345, Takahashi et al., (1999) *Cell* 99, 59–69). It involves fusing a secreted placental alkaline phosphatase (AP) moiety to the ligand in question to provide a biologically active receptor binding agent which can be detected with an extremely sensitive calorimetric assay. For Nogo, an expression vector is created encoding a signal peptide, a His6 tag for purification, AP, and the 66 amino acid active domain of Nogo. The fusion protein can be purified from the conditioned medium of transfected cells in milligram amounts. This protein is biologically active as a growth cone collapsing agent with an $EC_{50}$ of 1 nM.

Alternatively, a glutathione-S-transferase Nogo (GST-Nogo) fusion protein may be prepared. For GST-Nogo, an expression vector (e.g., a pGEX vector) is created encoding a signal peptide, GST, and the 66 amino acid active domain of Nogo. GST-Nogo may be purified from the culture medium and used as a GST fusion protein, or GST may be cleaved from the Nogo portion of the fusion protein with an enzyme that recognizes the specific amino acid cleavage sit engineered between the GST portion and the Nogo portion of the fusion protein. Such sites are part of the commercially available GST vectors. The specific cleavage sites and enzymes may be used in accordance with the Manufacturer's specifications.

It has been found that AP-Nogo is actually slightly more potent than GST-Nogo, perhaps because the protein is synthesized in a eukaryotic rather than a prokaryotic cell.

Binding of Nogo to immobilized NgR homologs may be performed in an ELISA-type assay in which AP-Nogo is allowed to react with an immobilized receptor homolog. Specificity of binding may be demonstrated in a competitive binding assay using increasing amounts of GST-Nogo in the type of assay to show a decreasing amount of binding of AP-Nogo (as judged in the colorimetric assay).

EXAMPLE 6

Transfected COS Cell Binding Assays

The homologs of the present invention may be used in transfection studies in COS cells to demonstrate binding of Nogo. Specifically, nucleotide sequences encoding NgR2 and NgR3 may be transfected into COS cells using a suitable vector. Non-transfected COS-7 cells do not bind AP-Nogo. However, transfection of COS cells with nucleic acid sequences encoding NgRs will make them capable of binding Nogo. AP alone does not bind with any stable affinity to these transfected cells, indicating that any affinity of Nogo for NgR2 or NgR3 would be due to the 66 amino acids derived from Nogo. Furthemore, specific affinity of Nogo for the NgR2 or NgR3 proteins may be tested in displacement of AP-Nogo assays using GST-Nogo. NgR2 and/or NgR3 may also bind homologs of Nogo, which may also be tested using this assay.

EXAMPLE 7

Expression of NgR in Human Cell Lines Using Northern Blot and a Random-Primed Probe A Northern blot is purchased from a commercial source, or RNA samples from cells of interest are run on an agarose gel and blotted to a membrane using any of the well known techniques for Northern blotting. The blot is probed with a fragment of NgR2 (SEQ ID NO:1) or NgR3 (SEQ ID NO:3). The probe is prepared from 50 ng of cDNA labeled by a random-primed method (Feinberg and Vogelstein (1983) *Anal. Biochem.* 132, 6–13). Hybridization is carried out at 68° C. for 1 hour in ExpressHyb™ solution (Clontech, Cat. No. 8015–1) followed by washing with 2×SSC/0.05% SDS at room temperature and two washes with 0.1×SSC/0.1% SDS at 50° C. Expression of NgR2 and/or NgR3 can be assessed by the presence of an appropriately sized band on the blot.

EXAMPLE 8

Cloning of cDNA Corresponding to NgRs

To obtain the full-length clone corresponding to NgR2 from a cDNA library, the following method may be used. A cDNA library is generated using standard methods from a tissue known to contain NgR2. Such a tissue was identified in Example 2. 1×10⁶ plaque forming units from the cDNA library may be screened in duplicate on OPTITRAN™ filters. The filters are hybridized with $^{32}$P-labeled oligonucleotides that are generated from the ESTs corresponding to portions of NgR2. The hybridization reaction may consist of 400 mls plaque screen buffer (50 mM Tris pH 7.5, 1M NaCl, 0.1% Sodium pyrophosphate, 0.2% Polyvinylpryolidine and 0.2% Ficoll) containing 10% Dextran sulfate and 100 µg/ml tRNA and 80 pmol each $^{32}$P-labeled oligonucleotide at 65° C. overnight. The filters are washed twice with 2×SSC/1% SDS and twice with 1×SSC/1% SDS and exposed to film. Duplicate positives are purified. DNA from each of these clones is analyzed by restriction enzyme digest followed by agarose gel electrophoresis and Southern blotting. The filters are hybridized to the $^{32}$P-labeled oligonucleotides used for the original hybridization to confirm that inserts hybridize to the probe. The insert is then sequenced to confirm that it represents the cDNA for NgR2. Similar methods may be used to generate a full-length clone corresponding to NgR3.

Alternatively, a full-length clone of NgR2 or NgR3 can be obtained by a person of ordinary skill in the art employing conventional PCR techniques.

EXAMPLE 9

Hybridization Analysis to Demonstrate NgR Expression in the Brain

The expression of NgR in mammals, such as the rat, may be investigated by in situ hybridization histochemistry. To investigate expression in the brain, for example, coronal and sagittal rat brain cryosections (20 µm thick) are prepared using a Reichert-Jung cryostat. Individual sections are thaw-mounted onto silanized, nuclease-free slides (CELL Associates, Inc., Houston, Tex.), and stored at −80° C. Sections are processed starting with post-fixation in cold 4% paraformaldehyde, rinsed in cold phosphate-buffered saline (PBS), acetylated using acetic anhydride in triethanolamine buffer, and dehydrated through a series of alcohol washes in 70%, 95%, and 100% alcohol at room temperature. Subsequently, sections are delipidated in chloroform, followed by rehydration through successive exposure to 100% and 95% alcohol at room temperature. Microscope slides containing processed cryosections are allowed to air dry prior to hybridization. Other tissues may be assayed in a similar fashion.

A NgR-specific probe may be generated using PCR. Following PCR amplification, the fragment is digested with restriction enzymes and cloned into pBluescript II cleaved with the same enzymes. For production of a probe specific for the sense strand of NgR, a cloned NgR fragment cloned in pBluescript II may be linearized with a suitable restriction enzyme, which provides a substrate for labeled run-off transcripts (i.e., cRNA riboprobes) using the vector-borne T7 promoter and commercially available T7 RNA polymerase. A probe specific for the antisense strand of NgR may also be readily prepared using the NgR clone in pBluescript II by cleaving the recombinant plasmid with a suitable restriction enzyme to generate a linearized substrate for the production of labeled run-off cRNA transcripts using the T3 promoter and cognate polymerase. The riboprobes may be labeled with [$^{35}$S]-UTP to yield a specific activity of about 0.40×10⁶ cpm/pmol for antisense riboprobes and about 0.65×10⁶ cpm/pmol for sense-strand riboprobes. Each riboprobe may be subsequently denatured and added (2 pmol/ml) to hybridization buffer which contains 50% formamide, 10% dextran, 0.3 M NaCl, 10 mM Tris (pH 8.0), 1 mM EDTA, 1×Denhardt's Solution, and 10 mM dithiothreitol. Microscope slides containing sequential brain cryosections may be independently exposed to 45 µl of hybridization solution per slide and silanized cover slips may be placed over the sections being exposed to hybridization solution. Sections are incubated overnight (15–18 hours) at 52° C. to allow hybridization to occur. Equivalent series of cryosections are then exposed to sense or antisense NgR-specific cRNA riboprobes.

Following the hybridization period, coverslips are washed off the slides in 1×SSC, followed by RNase A treatment involving the exposure of slides to 20 µg/ml RNase A in a buffer containing 10 mM Tris-HCl (pH 7.4), 0.5 M EDTA, and 0.5 M NaCl for 45 minutes at 37° C. The cryosections are then subjected to three high-stringency washes in 0.1× SSC at 52° C. for 20 minutes each. Following the series of washes, cryosections are dehydrated by consecutive exposure to 70%, 95%, and 100% ammonium acetate in alcohol, followed by air drying and exposure to Kodak BioMax™ MR-1 film. After 13 days of exposure, the film is developed, and any significant hybridization signal is detected. Based on these results, slides containing tissue that hybridized, as shown by film autoradiograms, are coated with Kodak NTB-2 nuclear track emulsion and the slides are stored in the dark for 32 days. The slides are then developed and counterstained with hematoxylin. Emulsion-coated sections are analyzed microscopically to determine the specificity of labeling. The signal is determined to be specific if autoradiographic grains (generated by antisense probe hybridization) are clearly associated with cresyl violate-stained cell bodies. Autoradiographic grains found between cell bodies indicate non-specific binding of the probe.

In some cases, such as using a probe to detect a NgR homolog in a heterologous species, in order to achieve optimal hybridization, it may be necessary to decrease the stringency conditions. Such conditions are well known to those of ordinary skill in the art and examples are provided above.

Expression of NgR in the brain provides an indication that modulators of NgR activity have utility for treating neurological disorders. Some other diseases for which modulators of NgR may have utility include depression, anxiety, bipolar disease, epilepsy, neuritis, neurasthenia, neuropathy, neuroses, and the like. Use of NgR modulators, including NgR ligands and anti-NgR antibodies, to treat individuals having such disease states is intended as an aspect of the invention.

EXAMPLE 10

Northern Blot Analysis of NgR-RNA with a PCR-generated Probe

Northern blot hybridizations may be performed to examine the expression of NgR mRNA. A clone containing at least a portion of the sequence of SEQ ID NO:1 may be used as a probe. Vector-specific primers are used in PCR to generate a hybridization probe fragment for $^{32}$P-labeling. The PCR is performed as follows:

Mix:  1 µl  NgR-containing plasmid
      2 µl  fwd primer (10–50 pM)
      2 µl  rev primer (10–50 pM)
     10 µl  10xPCR buffer (such as that provided with the enzyme, Amersham Pharmacia Biotech)

-continued

| | |
|---|---|
| 1 µl | 10 mM dNTP (such as #1 969 064 from Boehringer Mannheim) |
| 0.5 µl | Taq polymerase (such as #27-0799-62, Amersham Pharmacia Biotech) |
| 83.5 µl | water |

PCR is performed in a Thermocycler using the following program:

| | | |
|---|---|---|
| 94° C. | 5 min | |
| 94° C. | 1 min | |
| 55° C. | 1 min | 30 cycles |
| 72° C. | 1 min | |
| 72° C. | 10 min | |

The PCR product may be purified using QIAquick PCR Purification Kit (#28104) from Qiagen, and radictively labeled with $^{32}$P-dCTP (#AA0005/250, Amersham Pharmacia Biotech)) may be done by random priming using "Ready-to-go DNA Labeling Beads" (#27-9240-01) from Amersham Pharmacia Biotech. Hybridization is carried out on Human Multiple Tissue Northern Blot from Clontech as described in manufacturer's protocol, or on a Northern Blot prepared by running RNA samples from cells of interest on an agarose gel and blotting to a membrane using any of the known Northern blotting protocols. After exposure overnight on Molecular Dynamics Phosphor Imager screen (#MD146-814) bands of an appropriate size are visualized.

EXAMPLE 11

Recombinant Expression of NgR in Eukaryotic Host Cells

A. Expression of NgR in Mammalian Cells

To produce NgR protein, a NgR-encoding polynucleotide is expressed in a suitable host cell using a suitable expression vector and standard genetic engineering techniques. For example, a NgR-encoding sequence described in Table 4 is subcloned into the commercial expression vector pzeoSV2 (Invitrogen, San Diego, Calif.) and transfected into Chinese Hamster Ovary (CHO) cells using the transfection reagent FuGENE6™ (Boehringer-Mannheim) and the transfection protocol provided in the product insert. Other eukaryotic cell lines, including human embryonic kidney (HEK 293) and COS cells, are suitable as well. Cells stably expressing NgR are selected by growth in the presence of 100 µg/ml zeocin (Stratagene, LaJolla, Calif.). As an alternative to FuGENE6™, the expression vector may carry the gene for dihydrofolate reductase (dhfr) and selection of clones with methotrexate (MTX) drug pressure allows for stable transformation of CHO cells. Optionally, NgR may be purified from the cells using standard chromatographic techniques. To facilitate purification, antisera is raised against one or more synthetic peptide sequences that correspond to portions of the NgR amino acid sequence, and the antisera is used to affinity purify Nogo-R. The NgR also may be expressed in-frame with a tag sequence (e.g., polyhistidine, hemaglutinin, FLAG) to facilitate purification. Moreover, it will be appreciated that many of the uses for NgR polypeptides, such as assays described below, do not require purification of NgR from the host cell.

B. Expression of NgR in CHO Cells

For expression of NgR in Chinese hamster ovary.(CHO) cells, a plasmid bearing the relevant NgR coding sequence is prepared, using a vector which also bears the selectable marker dihydrofolate reductase (DHFR). The plasmid is transfected into CHO cells. Selection under MTX drug pressure allows for preparation of stable transformants of a NgR (NgR2 or NgR3) in an expression plasmid carrying a selectable marker such as DHFR.

C. Expression of NgR in 293 Cells

For expression of NgR in mammalian cells 293 (transformed human, primary embryonic kidney cells), a plasmid bearing the relevant NgR coding sequence is prepared, using vector pSecTag2A (Invitrogen). Vector pSecTag2A contains the murine IgK chain leader sequence for secretion, the c-myc epitope for detection of the recombinant protein with the anti-myc antibody, a C-terminal polyhistidine for purification with nickel chelate chromatography, and a Zeocin resistant gene for selection of stable transfectants. The forward primer for amplification of this NgR cDNA is determined by routine procedures and preferably contains a 5' extension of nucleotides to introduce the HindIII cloning site and nucleotides matching the NgR sequence. The reverse primer is also determined by routine procedures and preferably contains a 5' extension of nucleotides to introduce an XhoI restriction site for cloning and nucleotides corresponding to the reverse complement of the NgR sequence. The PCR conditions are 55° C. as the annealing temperature. The PCR product is gel purified and cloned into the HindIII-XhoI sites of the vector.

The DNA is purified using Qiagen chromatography columns and transfected into 293 cells using DOTAP™ transfection media (Boehringer Mannheim, Indianapolis, Ind.). Transiently transfected cells are tested for expression after 24 hours of transfection, using western blots probed with anti-His and anti-NgR peptide antibodies. Permanently transfected cells are selected with Zeocin and propagated. Production of the recombinant protein is detected from both cells and media by Western blots probed with anti-His, anti-Myc or anti-NgR peptide antibodies.

D. Transient Expression of Nogo-R in COS Cells

For expression of the NgR in COS7 cells, a polynucleotide molecule having a nucleotide sequence of SEQ ID NO:1, for example, can be cloned into vector p3-CI. This vector is a pUC18-derived plasmid that contains the HCMV (human cytomegalovirus) promoter-intron located upstream from the bGH (bovine growth hormone) polyadenylation sequence and a multiple cloning site.

The forward primer is determined by routine procedures and preferably contains a 5' extension which introduces an XbaI restriction site for cloning, followed by nucleotides which correspond to a nucleotide sequence of SEQ ID NO:1. The reverse primer is also determined by routine procedures and preferably contains 5'-extension of nucleotides which introduces a SalI cloning site followed by nucleotides which correspond to the reverse complement of a nucleotide sequence of SEQ ID NO:1.

The PCR consists of an initial denaturation step of 5 min at 95° C., 30 cycles of 30 sec denaturation at 95° C., 30 sec annealing at 58° C. and 30 sec extension at 72° C., followed by 5 min extension at 72° C. The PCR product is gel purified and ligated into the XbaI and SalI sites of vector p3-CI. This construct is transformed into E. coli cells for amplification and DNA purification. The DNA is purified with Qiagen chromatography columns and transfected into COS 7 cells using Lipofectamine™ reagent from BRL, following the manufacturer's protocols. Forty-eight and 72 hours after transfection, the media and the cells are tested for recombinant protein expression.

NgR expressed from a COS cell culture can be purified by concentrating the cell-growth media to about 10 mg of protein/ml, and purifying the protein by, for example, chromatography. Purified NgR is concentrated to 0.5 mg/ml in an Amicon concentrator fitted with a YM-10 membrane and stored at −80° C. NgR3 may also be expressed using this method and the nucleotide sequence of SEQ ID NO:3 or SEQ ID NO:13.

E. Expression of NgR in Insect Cells

For expression of NgR in a baculovirus system, a polynucleotide molecule having a nucleotide sequence of SEQ ID NO:1, 3 or 13 can be amplified by PCR. The forward primer is determined by routine procedures and preferably contains a 5' extension which adds the NdeI cloning site, followed by nucleotides which correspond to a nucleotide sequence of SEQ ID NO:1 (or SEQ ID NO:3 or SEQ ID NO:13, respectively). The reverse primer is also determined by routine procedures and preferably contains a 5' extension which introduces the KpnI cloning site, followed by nucleotides which correspond to the reverse complement of a nucleotide sequence of SEQ ID NO:1 (or SEQ ID NO:3 or SEQ ID NO:13, respectively).

The PCR product is gel purified, digested with NdeI and KpnI, and cloned into the corresponding sites of vector pACHTL-A (Pharmingen, San Diego, Calif.). The pAcHTL expression vector contains the strong polyhedrin promoter of the Autographa californica nuclear polyhedrosis virus (AcMNPV), and a 6×His tag upstream from the multiple cloning site. A protein kinase site for phosphorylation and a thrombin site for excision of the recombinant protein precede the multiple cloning site is also present. Of course, many other baculovirus vectors could be used in place of pAcHTL-A, such as pAc373, pVL94 1 and pAcIM1. Other suitable vectors for the expression of NgR polypeptides can be used, provided that the vector construct includes appropriately located signals for transcription, translation, and trafficking, such as an in-frame AUG and a signal peptide, as required. Such vectors are described in Luckow et al., Virology 170:31–39, among others.

The virus is grown and isolated using standard baculovirus expression methods, such as those described in Summers et al. (1987) A MANUAL OF METHODS FOR BACULOVIRUS VECTORS AND INSECT CELL CULTURE PROCEDURES, Texas Agricultural Experimental Station Bulletin No. 1555.

In a preferred embodiment, pAcHLT-A containing NgR gene is introduced into baculovirus using the "BaculoGold™" transfection kit (Pharmingen, San Diego, Calif.) using methods established by the manufacturer. Individual virus isolates are analyzed for protein production by radiolabeling infected cells with $^{35}$S-methionine at 24 hours post infection. Infected cells are harvested at 48 hours post infection, and the labeled proteins are visualized by SDS-PAGE. Viruses exhibiting high expression levels can be isolated and used for scaled up expression.

For expression of a NgR polypeptide in a Sf9 cells, a polynucleotide molecule having the nucleotide sequence of SEQ ID NO:1 (or SEQ ID NO:3 or SEQ ID NO:13) can be amplified by PCR using the primers and methods described above for baculovirus expression. The NgR cDNA is cloned into vector pAcHLT-A (Pharmingen) for expression in Sf9 insect. The insert is cloned into the NdeI and KpnI sites, after elimination of an internal NdeI site (using the same primers described above for expression in baculovirus). DNA is purified with Qiagen chromatography columns and expressed in Sf9 cells. Preliminary Western blot experiments from non-purified plaques are tested for the presence of the recombinant protein of the expected size which reacted with the NgR-specific antibody. These results are confirmed after further purification and expression optimization in HiG5 cells.

F. Expression of Soluble Forms of NgR2 and NgR3 as NgR-Ig Fusion Proteins

To generate a NgR2-Ig fusion protein, standard methods may be used as described in the literature (e.g. Sanicola et al. (1997) Proc. Natl. Acad Sci. USA. 94, 6238–6243). For example, a DNA fragment encoding NgR2 without the sequence encoding the hydrophobic C-terminus (GPI anchor signal) may be ligated to a DNA fragment encoding the Fc domain of IgG1 (which may be human IgG1), and the chimeric fragment may be cloned into an expression vector to generate a plasmid. The plasmid may then be transfected into Chinese hamster ovary cells to generate a stable cell line producing the fusion protein. The fusion protein is then purified from conditioned media using standard methods. For example, clarified conditioned media from the cell line may be loaded by gravity directly onto Protein A Sepharose. The column may then be washed with five column volumes each of PBS, PBS containing 0.5 M NaCl, and 25 mM sodium phosphate, 100 mM NaCl (pH 5.0). The bound protein may then be eluted with 25 mM $NaH_2PO_4$, 100 mM NaCl (pH 2.8) and immediately neutraized with $\frac{1}{10}$ fraction volume of 0.5 M $Na_2HPO_4$ (pH 8.6).

Similar methods may be used to generate a NgR3-Ig fusion protein.

EXAMPLE 12

Interaction Trap/Two-Hybrid System

In order to assay for NgR-interacting proteins, the interaction trap/two-hybrid library screening method can be used. This assay was first described in Fields et al. (1989) Nature 340, 245, which is incorporated herein by reference in its entirety. A protocol is published in CURRENT PROTOCOLS IN MOLECULAR BIOLOGY 1999, John Wiley & Sons, NY and Ausubel, F. M. et al. 1992, SHORT PROTOCOLS IN MOLECULAR BIOLOGY, fourth edition, Greene and Wiley-interscience, NY, which is incorporated herein by reference in its entirety. Kits are available from Clontech, Palo Alto, Calif. (Matchmaker Two-Hybrid System 3).

A fusion of the nucleotide sequences encoding all or partial NgR and the yeast transcription factor GAL4 DNA-binding domain (DNA-BD) is constructed in an appropriate plasmid (i.e., pGBKT7) using standard subcloning techniques. Similarly, a GAL4 active domain (AD) fusion library is constructed in a second plasmid (i.e., pGADT7) from cDNA of potential NgR-binding proteins (for protocols on forming cDNA libraries, see Sambrook et al. 1989, MOLECULAR CLONING: A LABORATORY MANUAL, second edition, Cold Spring Harbor Laboratory Press, Cold Spring Harbor, N.Y.), which is incorporated herein by reference in its entirety. The DNA-BD/NgR fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity. Yeast cells are transformed (ca. 105 transformants/mg DNA) with both the NgR and library fusion plasmids according to standard procedure (Ausubel, et al., 1992, SHORT PROTOCOLS IN MOLECULAR BIOLOGY, fourth edition, Greene and Wiley-interscience, NY, which is incorporated herein by reference in its entirety). In vivo binding of DNA-BD/NgR with AD/library proteins results in transcription of specific yeast plasmid reporter genes (i.e., lacZ, HIS3, ADE2, LEU2). Yeast cells are plated on nutrient-deficient media to screen for expression of reporter genes. Colonies are dually assayed for β-galactosidase activity upon growth in Xgal (5-bromo-4-chloro-3-indolyl-b-D-galactoside) supplemented media (filter assay for b-galactosidase activity is described in Breeden et al., (1985) *Cold Spring Harb. Symp. Quant. Biol.*, 50, 643, which is incorporated herein by reference in its entirety). Positive AD-library plasmids are rescued from transformants and reintroduced into the original yeast strain as well as other strains containing unrelated DNA-BD fusion proteins to confirm specific NgR/library protein interactions. Insert DNA is sequenced to verify the presence of an open reading frame fused to GAL4 AD and to determine the identity of the NgR-binding protein.

EXAMPLE 13

Antibodies to Nogo-R

Standard techniques are employed to generate polyclonal or monoclonal antibodies to the NgR receptor, and to generate useful antigen-binding fragments thereof or variants thereof, including "humanized" variants. Such protocols can be found, for example, in Sambrook et al. (1989), above, and Harlow et al. (Eds.), ANTIBODIES A LABORATORY MANUAL; Cold Spring Harbor Laboratory Press, Cold Spring Harbor, N.Y. (1988). In one embodiment, recombinant NgR polypeptides (or cells or cell membranes containing such polypeptides) are used as antigen to generate the antibodies. In another embodiment, one or more peptides having amino acid sequences corresponding to an immunogenic portion of NgR (e.g., 6, 7, 8, 9, 10, 11, 12, 13, 14, 15, 16, 17, 18, 19, 20, or more amino acids) are used as antigen. Peptides corresponding to extracellular portions of Nogo-R, especially hydrophilic extracellular portions, are preferred. The antigen may be mixed with an adjuvant or linked to a hapten to increase antibody production.

A. Polyclonal or Monoclonal Antibodies

As one exemplary protocol, recombinant NgR or a synthetic fragment thereof is used to immunize a mouse for generation of monoclonal antibodies (or larger mammal, such as a rabbit, for polyclonal antibodies). To increase antigenicity, peptides are conjugated to Keyhole Limpet Hemocyanin (Pierce), according to the manufacturer's recommendations. For an initial injection, the antigen is emulsified with Freund's Complete Adjuvant and injected subcutaneously. At intervals of two to three weeks, additional aliquots of NgR antigen are emulsified with Freund's Incomplete Adjuvant and injected subcutaneously. Prior to the final booster injection, a serum sample is taken from the immunized mice and assayed by western blot to confirm the presence of antibodies that immunoreact with NgR. Serum from the immunized animals may be used as polyclonal antisera or used to isolate polyclonal antibodies that recognize NgR. Alternatively, the mice are sacrificed and their spleen removed for generation of monoclonal antibodies.

To generate monoclonal antibodies, the spleens are placed in 10 ml serum-free RPMI 1640, and single cell suspensions are formed by grinding the spleens in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer-Mannheim) is stirred into the pellet, followed by the addition of serum-free RPMI. Thereafter, the cells are centrifuged, resuspended in RPMI containing 15% FBS, 100 µM sodium hypoxanthine, 0.4 µM aminopterin, 16 µM thymidine (HAT) (Gibco), 25 units/ml IL-6 (Boehringer-Mannheim) and $1.5 \times 10^6$ thymocytes/ml, and plated into 10 Corning flat-bottom 96-well tissue culture plates (Corning, Corning, N.Y.).

On days 2, 4, and 6 after the fusion, 100 µl of medium is removed from the wells of the fusion plates and replaced with fresh medium. On day 8, the fusions are screened by ELISA, testing for the presence of mouse IgG that binds to NgR. Selected fusion wells are further cloned by dilution until monoclonal cultures producing anti-NgR antibodies are obtained.

B. Humanization of Anti-NgR Monoclonal Antibodies

The expression pattern of NgR as reported herein and the potential of NgRs as targets for therapeutic intervention suggest therapeutic indications for NgR inhibitors (antagonists). NgR-neutralizing antibodies comprise one class of therapeutics useful as NgR antagonists. Following are protocols to improve the utility of anti-NgR monoclonal antibodies as therapeutics in humans by "humanizing" the monoclonal antibodies to improve their serum half-life and render them less immunogenic in human hosts (i.e., to prevent human antibody response to non-human anti-NgR antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest with the constant domains of human antibody molecules. (See, e.g., Morrison et al., (1989) *Adv. Immunol.*, 44, 65–92). The variable domains of NgR-neutralizing anti-NgR antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. (See, e.g., Jones et al., (1986) *Nature* 321, 522–525; Riechmann et al., (1988) *Nature* 332, 323–327; Verhoeyen et al., (1988) *Science* 239, 1534–1536; and Tempest et al., (1991) *Bio/Technology* 9, 266–271). If necessary, the β-sheet framework of the human antibody surrounding the CDR3 regions also is modified to more closely mirror the three dimensional structure of the antigen-binding domain of the original monoclonal antibody. (See Kettleborough et al., (1991) *Protein Engin.* 4, 773–783; and Foote et al., (1992) *J. Mol. Biol.* 224, 487–499).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan (1991) *Mol. Immunol.* 28, 489–498.

The foregoing approaches are employed using NgR-neutralizing anti-NgR monoclonal antibodies and the hybridomas that produce them to generate humanized NgR-neutralizing antibodies useful as therapeutics to treat or palliate conditions wherein NgR expression or ligand-mediated NgR signaling is detrimental.

C. Human NgR-Neutralizing Antibodies from Phage Display

Human NgR-neutralizing antibodies are generated by phage display techniques such as those described in Aujame et al. (1997) *Human Antibodies* 8, 155–168; Hoogenboom (1997) *TIBTECH* 15, 62–70; and Rader et al. (1997), *Curr. Opin. Biotechnol.* 8, 503–508, all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is screened for NgR-specific phage-antibodies using labeled or immobilized NgR as antigen-probe.

D. Human NgR-neutralizing Antibodies from Transgenic Mice

Human NgR-neutralizing antibodies are generated in transgenic mice essentially as described in Bruggemann et al. (1996) *Immunol. Today* 17, 391–397 and Bruggemann et al. (1997) *Curr. Opin. Biotechnol.* 8, 455–458. Transgenic mice carrying human V-gene segments in germline configuration and that express these transgenes in their lymphoid tissue are immunized with a NgR composition using conventional immunization protocols hybridomas are generated using B cells from the immunized mice using conventional protocols and screened to identify hybridomas secreting anti-NgR human antibodies (e.g., as described above).

EXAMPLE 14

Assays to Identify Modulators of NgR Activity

Set forth below are several nonlimiting assays for identifying modulators (agonists and antagonists) of NgR activity. Among the modulators that can be identified by these assays are natural ligand compounds of the receptor; synthetic analogs and derivatives of natural ligands; antibodies, antibody fragments, and/or antibody-like compounds derived from natural antibodies or from antibody-like combinatorial libraries; and/or synthetic compounds identified by high-throughput screening of libraries; and the like. All modulators that bind NgR are useful for identifying NgR in tissue samples (e.g., for diagnostic purposes, pathological purposes, and the like). Agonist and antagonist modulators are useful for up-regulating and down-regulating NgR activity, respectively, to treat disease states characterized by abnormal levels of NgR activity. The assays may be performed using single putative modulators, and/or may be performed using a known agonist in combination with candidate antagonists (or visa versa).

A. cAMP Assays

In one type of assay, levels of cyclic adenosine monophosphate (cAMP) are measured in NgR-transfected cells that have been exposed to candidate modulator compounds. Protocols for cAMP assays have been described in the literature. (See, e.g., Sutherland et al., (1968) *Circulation* 37, 279; Frandsen et al., (1976) *Life Sciences* 18, 529–541; Dooley et al., (1997) *J. Pharmacol. Exp. Therap.* 283, 735–41; and George et al., (1997) *J. Biomol. Screening* 2, 235–40). An exemplary protocol for such an assay, using an Adenylyl Cyclase Activation FlashPlate® Assay from NEN™ Life Science Products, is set forth below.

Briefly, the NgR coding sequence (e.g., a cDNA or intronless genomic DNA) is subcloned into a commercial expression vector, such as pzeoSV2 (Invitrogen), and transiently transfected into Chinese Hamster Ovary (CHO) cells using known methods, such as the transfection protocol provided by Boehringer-Mannheim when supplying the FuGENE 6 transfection reagent. Transfected CHO cells are seeded into 96-well microplates from the FlashPlate® assay kit, which are coated with solid scintillant to which antisera to cAMP has been bound. For a control, some wells are seeded with wild type (untransfected) CHO cells. Other wells in the plate receive various amounts of a cAMP standard solution for use in creating a standard curve.

One or more test compound (i.e., candidate modulators) are added to the cells in each well, with water and/or compound-free medium/diluent serving as a control or controls. After treatment, cAMP is allowed to accumulate in the cells for exactly 15 minutes at room temperature. The assay is terminated by the addition of lysis buffer containing [$^{125}$I]-labeled cAMP, and the plate is counted using a Packard Topcount™ 96-well microplate scintillation counter. Unlabeled cAMP from the lysed cells (or from standards) and fixed amounts of [125I]-cAMP compete for antibody bound to the plate. A standard curve is constructed, and cAMP values for the unknowns are obtained by interpolation. Changes in intracellular cAMP levels of cells in response to exposure to a test compound are indicative of NgR modulating activity. Modulators that act as agonists of receptors which couple to the $G_s$ subtype of G proteins will stimulate production of cAMP, leading to a measurable 3–10 fold increase in cAMP levels. Agonists of receptors which couple to the $G_{i/o}$ subtype of G proteins will inhibit forskolin-stimulated cAMP production, leading to a measurable decrease in cAMP levels of 50–100%. Modulators that act as inverse agonists will reverse these effects at receptors that are either constitutively active or activated by known agonists.

B. Aequorin Assays

In another assay, cells (e.g., CHO cells) are transiently co-transfected with both a NgR expression construct and a construct that encodes the photoprotein apoaquorin. In the presence of the cofactor coelenterazine, apoaquorin will emit a measurable luminescence that is proportional to the amount of intracellular (cytoplasmic) free calcium. (See generally, Cobbold, et al. "Aequorin measurements of cytoplasmic free calcium," In: McCormack J. G. and Cobbold P. H., eds., CELLULAR CALCIUM: A PRACTICAL APPROACH. Oxford: IRL Press (1991); Stables et al., (1997) *Anal. Biochem.* 252, 115–26; and Haugland, HANDBOOK OF FLUORESCENT PROBES AND RESEARCH CHEMICALS. Sixth edition. Molecular Probes, Eugene, Oreg. (1996)).

In one exemplary assay, NgR is subcloned into the commercial expression vector pzeoSV2 (Invitrogen) and transiently co-transfected along with a construct that encodes the photoprotein apoaquorin (Molecular Probes, Eugene, Oreg.) into CHO cells using the transfection reagent FuGENE 6 (Boehringer-Mannheim) and the transfection protocol provided in the product insert.

The cells are cultured for 24 hours at 37° C. in MEM (Gibco/BRL, Gaithersburg, Md.) supplemented with 10% fetal bovine serum, 2 mM glutamine, 10 U/ml penicillin and 10 µg/ml streptomycin, at which time the medium is changed to serum-free MEM containing 5 µM coelenterazine (Molecular Probes, Eugene, Oreg.). Culturing is then continued for two additional hours at 37° C. Subsequently, cells are detached from the plate using VERSEN (Gibco/BRL), washed, and resuspended at 200,000 cells/ml in serum-free MEM.

Dilutions of candidate NgR modulator compounds are prepared in serum-free MEM and dispensed into wells of an opaque 96-well assay plate at 50 µl/well. Plates are then loaded onto an MLX microtiter plate luminometer (Dynex Technologies, Inc., Chantilly, Va.). The instrument is programmed to dispense 50 µl cell suspensions into each well, one well at a time, and immediately read luminescence for 15 seconds. Dose-response curves for the candidate modulators are constructed using the area under the curve for each light signal peak. Data are analyzed with SlideWrite, using the equation for a one-site ligand, And $EC_{50}$ values are obtained. Changes in luminescence caused by the compounds are considered indicative of modulatory activity. Modulators that act as agonists at receptors which couple to the $G_q$ subtype of G proteins give an increase in luminescence of up to 100 fold Modulators that act as inverse agonists will reverse this effect at receptors that are either constitutively active or activated by known agonists.

C. Luciferase Reporter Gene Assay

The photoprotein luciferase provides another useful tool for assaying for modulators of NgR activity. Cells (e.g., CHO cells or COS 7 cells) are transiently co-transfected with both a NgR expression construct (e.g., NgR in pzeoSV2) and a reporter construct which includes a gene for the luciferase protein downstream from a transcription factor binding site, such as the cAMP-response element (CRE), AP-1, or NF-kappa B. Expression levels of luciferase reflect the activation status of the signaling events. (See generally, George et al. (1997) *J. Biomol. Screening* 2, 235–240; and Stratowa et al. (1995) *Curr. Opin. Biotechnol.* 6, 574–5 81). Luciferase activity may be quantitatively measured using, e.g., luciferase assay reagents that are commercially available from Promega (Madison, Wis.).

In one exemplary assay, CHO cells are plated in 24-well culture dishes at a density of 100,000 cells/well one day prior to transfection-and cultured at 37° C. in MEM (Gibco/BRL) supplemented with 10% fetal bovine serum, 2 mM glutamine, 10 U/ml penicillin and 10 µg/ml streptomycin. Cells are transiently co-transfected with both a NgR expression construct and a reporter construct containing the luciferase gene. The reporter plasmids CRE-luciferase, AP-1-luciferase and NF-kappaB-luciferase may be purchased from Stratagene (Legally, Calif.). Transfections are performed using the FuGENE 6 transfection reagent (Boehringer-Mannheim) according to the supplier's instructions. Cells transfected with the reporter construct alone are used as a control. Twenty-four hours after transfection, cells are washed once with PBS pre-warmed to 37° C. Serum-free MEM is then added to the cells either alone (control) or with one or more candidate modulators and the cells are incubated at 37° C. for five hours. Thereafter, cells are washed once with ice-cold PBS and lysed by the addition of 100 µl of lysis buffer per well from the luciferase assay kit supplied by Promega. After incubation for 15 minutes at room temperature, 15 µl of the lysate is mixed with 50 µl of substrate solution (Promega) in an opaque-white, 96-well plate, and the luminescence is read immediately on a Wallace model 1450 MicroBeta scintillation and luminescence counter (Wallace Instruments, Gaithersburg, Md.).

Differences in luminescence in the presence versus the absence of a candidate modulator compound are indicative of modulatory activity. Receptors that are either constitutively active or activated by agonists typically give a 3–20-fold stimulation of luminescence compared to cells transfected with the reporter gene alone. Modulators that act as inverse agonists will reverse this effect.

D. Intracellular Calcium Measurement Using FLIPR

Changes in intracellular calcium levels are another recognized indicator of receptor activity, and such assays can be employed to screen for modulators of NgR activity. For example, CHO cells stably transfected with a NgR expression vector are plated at a density of $4 \times 10^4$ cells/well in Packard black-walled, 96-well plates specially designed to discriminate fluorescence signals emanating from the various wells on the plate. The cells are incubated for 60 minutes at 37° C. in modified Dulbecco's PBS (D-PBS) containing 36 mg/L pyruvate and 1 g/L glucose with the addition of 1% fetal bovine serum and one of four calcium indicator dyes (Fluo-3™ AM, Fluo-4™ AM, Calcium Green™-1 AM, or Oregon Green™ 488 BAPTA-1 AM), each at a concentration of 4 µM. Plates are washed once with modified D-PBS without 1% fetal bovine serum and incubated for 10 minutes at 37° C. to remove residual dye from the cellular membrane. In addition, a series of washes with modified D-PBS without 1% fetal bovine serum is performed immediately prior to activation of the calcium response.

A calcium response is initiated by the addition of one or more candidate receptor agonist compounds, calcium ionophore A23187 (10 µM; positive control), or ATP (4 µM; positive control). Fluorescence is measured by Molecular Device's FLIPR with an argon laser (excitation at 488 nm). (See, e.g., Kuntzweiler et al. (1998) *Drug Dev. Res.* 44, 14–20). The F-stop for the detector camera is set at 2.5 and the length of exposure is 0.4 milliseconds. Basal fluorescence of cells is measured for 20 seconds prior to addition of candidate agonist, ATP, or A23187, and the basal fluorescence level is subtracted from the response signal. The calcium signal is measured for approximately 200 seconds, taking readings every two seconds. Calcium ionophore A23187 and ATP increase the calcium signal 200% above baseline levels. In general, activated NgRs increase the calcium signal at least about 10–15% above baseline signal.

E. [$^{35}$S]GTPγS Binding Assay

It is also possible to evaluate whether NgR signals through a G protein-mediated pathway. Because G protein-coupled receptors signal through intracellular G proteins whose activity involves GTP binding and hydrolysis to yield bound GDP, measurement of binding of the non-hydrolyzable GTP analog [$^{35}$S]-GTPγS in the presence and absence of candidate modulators provides another assay for modulator activity. (See, e.g., Kowal et al., (1998) Neuropharmacology 37, 179–187.).

In one exemplary assay, cells stably transfected with a NgR expression vector are grown in 10 cm tissue culture dishes to subconfluence, rinsed once with 5 ml of ice-cold $Ca^{2+}/Mg^{2+}$-free phosphate-buffered saline, and scraped into 5 ml of the same buffer. Cells are pelleted by centrifugation (500×g, 5 minutes), resuspended in TEE buffer (25 mM Tris, pH 7.5, 5 mM EDTA, 5 mM EGTA), and frozen in liquid nitrogen. After thawing, the cells are homogenized using a Dounce homogenizer (1 ml TEE per plate of cells), and centrifuged at 1,000×g for 5 minutes to remove nuclei and unbroken cells.

The homogenate supernatant is centrifuged at 20,000×g for 20 minutes to isolate the membrane fraction, and the membrane pellet is washed once with TEE and resuspended in binding buffer (20 mM HEPES, pH 7.5, 150 mM NaCl, 10 mM $MgCl_2$, 1 mM EDTA). The resuspended membranes can be frozen in liquid nitrogen and stored at −70° C. until use.

Aliquots of cell membranes prepared as described above and stored at −70° C. are thawed, homogenized, and diluted into buffer containing 20 mM HEPES, 10 mM $MgCl_2$, 1 mM EDTA, 120 mM NaCl, 10 μM GDP, and 0.2 mM ascorbate, at a concentration of 10–50 μg/ml. In a final volume of 90 μl, homogenates are incubated with varying concentrations of candidate modulator compounds or 100 μM GTP for 30 minutes at 30° C. and then placed on ice. To each sample, 10 μl guanosine 5'-O-(3[$^{35}$S]thio) triphosphate (NEN, 1200 Ci/mmol; [$^{35}$S]-GTPγS), was added to a final concentration of 100–200 pM. Samples are incubated at 30° C. for an additional 30 minutes, 1 ml of 10 mM HEPES, pH 7.4, 10 mM $MgCl_2$, at 4° C. is added and the reaction is stopped by filtration.

Samples are filtered over Whatman GF/B filters and the filters are washed with 20 ml ice-cold 10 mM HEPES, pH 7.4, 10 mM $MgCl_2$. Filters are counted by liquid scintillation spectroscopy. Nonspecific binding of [$^{35}$S]-GTPγS is measured in the presence of 100 μM GTP and subtracted from the total. Compounds are selected that modulate the amount of [$^{35}$S]-GTPγS binding in the cells, compared to untransfected control cells. Activation of receptors by agonists gives up to a five-fold increase in [$^{35}$S]-GTPγS binding. This response is blocked by antagonists.

F. [$^3$H]Arachidonic Acid Release

The activation of NgRs may also potentiate arachidonic acid release in cells, providing yet another useful assay for modulators of NgR activity. (See, e.g., Kanterman et al., (1991) *Mol. Pharmacol.* 39, 364–369.) For example, CHO cells that are stably transfected with a NgR expression vector are plated in 24-well plates at a density of 15,000 cells/well and grown in MEM medium supplemented with 10% fetal bovine serum, 2 mM glutamine, 10 U/ml penicillin and 10 μg/ml streptomycin for 48 hours at 37° C. before use. Cells of each well are labeled by incubation with [$^3$H]-arachidonic acid (Amersham Corp., 210 Ci/mmol) at 0.5 μCi/ml in 1 ml MEM supplemented with 10 nM HEPES, pH 7.5, and 0.5% fatty-acid-free bovine serum albumin for 2 hours at 37° C. The cells are then washed twice with 1 ml of the same buffer.

Candidate modulator compounds are added in 1 ml of the same buffer, either alone or with 10 μM ATP and the cells are incubated at 37° C. for 30 minutes. Buffer alone and mock-transfected cells are used as controls. Samples (0.5 ml) from each well are counted by liquid scintillation spectroscopy. Agonists which activate the receptor will lead to potentiation of the ATP-stimulated release of [$^3$H]-arachidonic acid. This potentiation is blocked by antagonists.

G. Extracellular Acidification Rate

In yet another assay, the effects of candidate modulators of NgR activity are assayed by monitoring extracellular changes in pH induced by the test compounds (see, e.g., Dunlop et al. (1998) *J. Pharmacol. Toxicol. Meth.* 40, 47–55). In one embodiment, CHO cells transfected with a NgR expression vector are seeded into 12 mm capsule cups (Molecular Devices Corp.) at 4×10$^5$ cells/cup in MEM supplemented with 10% fetal bovine serum, 2 mM L-glutamine, 10 U/ml penicillin, and 10 μg/ml streptomycin. The cells are incubated in this medium at 37° C. in 5% $CO_2$ for 24 hours.

Extracellular acidification rates are measured using a Cytosensor microphysiometer (Molecular Devices Corp.). The capsule cups are loaded into the sensor chambers of the microphysiometer and the chambers are perfused with running buffer (bicarbonate-free MEM supplemented with 4 mM L-glutamine, 10 units/ml penicillin, 10 μg/ml streptomycin, 26 mM NaCl) at a flow rate of 100 μl/minute. Candidate agonists or other agents are diluted into the running buffer and perfused through a second fluid path. During each 60-second pump cycle, the pump is run for 38 seconds and is off for the remaining 22 seconds. The pH of the running buffer in the sensor chamber is recorded during the cycle from 43–58 seconds, and the pump is re-started at 60 seconds to start the next cycle. The rate of acidification of the running buffer during the recording time is calculated by the Cytosoft program. Changes in the rate of acidification are calculated by subtracting the baseline value (the average of 4 rate measurements immediately before addition of a modulator candidate) from the highest rate measurement obtained after addition of a modulator candidate. The selected instrument detects 61 mV/pH unit. Modulators that act as agonists of the receptor result in an increase in the rate of extracellular acidification compared to the rate in the absence of agonist. This response is blocked by modulators which act as antagonists of the receptor.

EXAMPLE 15 mNgR3 Does Not Bind hNogo-A(1055–1120)

To functionally test the mouse NgR3 (hereinafter, mNgR3) for its ability to bind hNogo-A(1055–1120), a cDNA expression vector for a myc epitope-tagged mNgR3protein was created. The mouse NgR3 cDNA was amplified by PCR from mouse adult brain cDNA, from the signal sequence to the stop codon, and ligated into the pSecTag2 vector such that the vector encodes a signal sequence followed by a myc tag followed by the mature mNgR3 sequence. This plasmid was transfected into COS07cells, and expression of a myc-tagged protein of the predicted size was verified by immunoblot analysis. Alkaline phosphatase-hNogo-A(1055–1120) binding studies and myc immunohistology were conducted as described (Fournier et al., supra).

The cells expressing mNgR3 express the myc-tagged protein but binding to AP-hNogo-A(1055–1120) was not observed under the conditions employed (FIG. 8).

EXAMPLE 16

Identification of Partial Human NgR3 cDNA and Protein Sequences

The tblastn program was used to search for the human homolog of mouse NgR3. The mouse NgR3 protein sequence (SEQ ID NO:4) was used to query a proprietary human expressed sequence tag (EST) database from Incyte yielding one highly significant hit: Incyte Template ID 190989.1. This sequence (937 nucleotides) contains an open reading frame of 312 amino acids in the second reverse frame that exhibits 88% identity with residues 66 to 381 of mouse NgR3 (SEQ ID NO:4), strongly indicating that it is part of the human NgR3 homolog.

A query of SEQ ID NO:4 against the public human EST database in Genbank also produced a hit with a 465-bp EST (Accession number: R35699; Version number: R35699.1; GI: 792600). There are a number of single nucleotide deletions and insertions within this sequence which cause frame shift errors. All of the reliable sequence contained in this public EST is present in the Incyte EST (Template ID 190989.1).

To obtain more nucleotide sequence that would extend the amino acid sequence at that carboxy terminal end, the I.M.A.G.E. Consortium clone No. 38319, which corresponds to Genbank accession No. R35699, was purchased from Incyte Genomics Inc. and subjected to further DNA sequence analysis. This clone consists of a NotI/HinD III fragment containing the sequence of interest, cloned into the NotI/HinD III sites of the vector Lafmid BA (http://image.llnl.gov/image/html/libs/lafmidBA.shtml). The clone was received as an agar stab, which was streaked out on LB agar plates containing 50 ug/ml ampicillin to isolate individual colonies. Six colonies were grown in LB medium with antibiotic, and plasmid DNA was prepared using the Promega Wizard Plus Miniprep DNA Purification System (Promega #A7500). These DNAs were subsequently digested with NotI and HinD III restriction enzymes to confirm that the clones contained an insert. The insert of one isolate was sequenced using a combination of vector specific and gene specific primers yielding a partial nucleotide sequence of human NgR3 of 1176 nucleotides (SEQ ID NO:13). A translation of this sequence provides a partial sequence for human NgR3 of 392 amino acids (SEQ ID NO:14).

The nucleotide sequence of SEQ ID NO:13 differs from the Incyte EST sequence at three positions. Nucleotide positions 12–13 in SEQ ID NO:13 are CG, whereas the corresponding nucleotides in the Incyte Template ID 190989.1 are GT (i.e., positions 12–13 of the complement of Incyte Template ID 190989.1). In addition, position 641 in SEQ ID NO:13 is a C, whereas the corresponding nucleotide in the Incyte Template ID 190989.1 sequence is an A (i.e., position 641 of the complement of Incyte Template ID 190989.1). This results in two changes in amino acids when comparing SEQ ID NO:14 to the ORF encoded by. Incyte Template 190989.1: SEQ ID NO:14 contains a valine at position 5, whereas the ORF encoded by Incyte Template ID 190989.1 contains a leucine; SEQ ID NO:14 contains an alanine at position 214, whereas the ORF encoded by Incyte Template ID 190989.1 contains a glutamic acid.

The nucleotide sequence of SEQ ID NO:13 differs from the public EST (Accession number: R35699; Version number: R35699.1; GI: 792600) sequence at two positions (within the first 200 nucleotides of reliable sequence). Nucleotide positions 12–13 in SEQ ID NO:13 are CG, whereas the corresponding nucleotides in the public EST are GT (i.e., positions 12–13 of the public EST; Accession no: R35699; Version no: R35699.1; GI: 792600) This leads to a single amino acid change when comparing SEQ ID NO: 14 to the ORF encoded by the public EST: SEQ ID NO:14 contains a valine at position 5, while the ORF encoded by the public EST contains a leucine.

A Bestfit analysis of the partial human amino acid sequence with the full-length mouse amino acid sequence indicates that the human NgR3 amino acid sequence is complete at the carboxy terminal end and that they share 89.54% identity. An alignment of all the NgR proteins is shown in FIG. 9. Although the human NgR3 amino acid sequence is missing the first 25 amino acids, it can be determined that the human NgR3 protein contains the following features in common with the other NgR sequences: (1) eight Leucine Rich Repeat (LRR) domains; (2) an LRR carboxy-terminal (LRR-CT) domain; (3) a conserved cysteine in the fourth LRR domain; (4) a conserved potential glycosylation site in the eighth LRR domain; and (5) a hydrophobic carboxyl terminus.

As those skilled in the art will appreciate, numerous changes and modifications may be made to the preferred embodiments of the invention without departing from the spirit of the invention. It is intended that all such variations fall within the scope of the invention.

The entire disclosure of each publication cited herein is hereby incorporated by reference. This application claims benefit from U.S. provisional application 60/238,361, filed Oct. 6, 2000, which is incorporated by reference herein in its entirety.

KEY FOR SEQUENCE LISTING

| | |
|---|---|
| SEQ ID NO: 1 | human NgR2 cDNA sequence derived from genomic sequence AC013606 |
| SEQ ID NO: 2 | human NgR2 amino acid sequence |
| SEQ ID NO: 3 | mouse NgR3 cDNA sequence derived from AC021768 |
| SEQ ID NO: 4 | a mouse NgR3 amino acid sequence |
| SEQ ID NO: 5 | a human NgR1 amino acid sequence |
| SEQ ID NO: 6 | a consensus amino acid sequence for NgRs |
| SEQ ID NO: 7 | #1055–1120 amino acid residues of hNogoA (Nogo-66) |
| SEQ ID NO: 8 | a mature human NgR2 amino acid sequence |
| SEQ ID NO: 9 | a mature mouse NgR3 amino acid sequence |
| SEQ ID NO: 10 | a consensus NgR LLRNT amino acid sequence |
| SEQ ID NO: 11 | a consensus NgR LRRCT domain amino acid sequence |
| SEQ ID NO: 12 | a consensus NgR LRR domain amino acid sequence |
| SEQ ID NO: 13 | a partial human NgR3 nucleotide sequence |
| SEQ ID NO: 14 | a partial human NgR3 amino acid sequence |
| SEQ ID NO: 15 | a genomic sequence encoding a human NgR2 sequence. |
| SEQ ID NO: 16 | a genomic sequence (complementary strand) encoding a mouse NgR3 |
| SEQ ID NO: 17 | a mouse NgR1 amino acid sequence |
| SEQ ID NO: 18 | a consensus sequence for the NTLRRCT domain of NgR |
| SEQ ID NO: 19 | an consensus NgR LRRCT domain amino acid sequence |

What is claimed is:

1. An isolated polynucleotide comprising a first nucleic acid which encodes a polypeptide at least 80% identical to a polypeptide comprising amino acids 1 to 310 of SEQ ID NO:2, wherein said polypeptide decreases inhibition of axonal elongation.

2. The polynucleotide of claim 1, wherein said polypeptide is at least 90% identical to amino acids 1 to 310 of SEQ ID NO:2.

3. The polynucleotide of claim 2, wherein said polypeptide is at least 95% identical to amino acids 1 to 310 of SEQ ID NO:2.

4. The polynucleotide of claim 3 wherein said polypeptide comprises amino acids 1 to 310 of SEQ ID NO:2.

5. The polynucleotide of claim 1, further comprising a second nucleic acid.

6. The polynucleotide of claim 5, wherein said second nucleic acid encodes a heterologous polypeptide.

7. The polynucleotide of claim 6, wherein said heterologous polypeptide forms a fusion protein with the polypeptide encoded by said first nucleic acid.

8. The polynucleotide of claim 7, wherein said heterologous polypeptide is Fc.

9. The polynucleotide of claim 7, wherein said heterologous polypeptide is selected from the group consisting of Glutathione S-transferase (GST), a Histidine tag (His tag), and alkaline phosphatase (AP).

10. A vector comprising the polynucleotide of claim 1.

11. The vector of claim 10, wherein said polynucleotide is operably linked to one or more expression control elements.

12. An isolated host cell comprising the polynucleotide of claim 1.

13. The host cell of claim 12, wherein said polynucleotide is operably linked to one or more expression control elements.

14. An isolated polynucleotide comprising a first nucleic acid which encodes a polypeptide at least 80% identical to a polypeptide comprising amino acids 31 to 310 of SEQ ID NO:2, wherein said polypeptide decreases inhibition of axonal elongation.

15. The polynucleotide of claim 14, wherein said polypeptide is at least 90% identical to amino acids 31 to 310 of SEQ ID NO:2.

16. The polynucleotide of claim 15, wherein said polypeptide is at least 95% identical to amino acids 31 to 310 of SEQ ID NO:2.

17. The polynucleotide of claim 16, wherein said polypeptide comprises amino acids 31 to 310 of SEQ ID NO:2.

18. The polynucleotide of claim 14, further comprising a second nucleic acid.

19. The polynucleotide of claim 18, wherein said second nucleic acid encodes a heterologous polypeptide.

20. The polynucleotide of claim 19, wherein said heterologous polypeptide forms a fusion protein with the polypeptide encoded by said first nucleic acid.

21. The polynucleotide of claim 20, wherein said heterologous polypeptide is Fc.

22. The polynucleotide of claim 20, wherein said heterologous polypeptide is selected from the group consisting of Glutathione S-transferase (GST), a Histidine tag (His tag), and alkaline phosphatase (AP).

23. A vector comprising the polynucleotide of claim 14.

24. The vector of claim 23, wherein said polynucleotide is operably linked to one or more expression control elements.

25. An isolated host cell comprising the polynucleotide of claim 14.

26. The host cell of claim 25, wherein said polynucleotide is operably linked to one or more expression control elements.

27. An isolated polynucleotide comprising a first nucleic acid which encodes, except for 1 to 10 conservative amino acid substitutions, a polypeptide selected from the group consisting of amino acids 1–310 of SEQ ID NO:2 and amino acids 31–310 of SEQ ID NO:2; wherein said polypeptide decreases inhibition of axonal elongation.

28. The polynucleotide of claim 27, further comprising a second nucleic acid.

29. The polynucleotide of claim 28, wherein said second nucleic acid encodes a heterologous polypeptide.

30. The polynucleotide of claim 29, wherein said heterologous polypeptide forms a fusion protein with the polypeptide encoded by said first nucleic acid.

31. The polynucleotide of claim 30, wherein said heterologous polypeptide is Fc.

32. The polynucleotide of claim 30, wherein said heterologous polypeptide is selected from the group consisting of Glutathione S-transferase (GST), a Histidine tag (His tag), and alkaline phosphatase (AP).

33. A vector comprising the polynucleotide of claim 27.

34. The vector of claim 33, wherein said polynucleotide is operably linked to one or more expression control elements.

35. An isolated host cell comprising the polynucleotide of claim 27.

36. The host cell of claim 35, wherein said polynucleotide is operably linked to one or more expression control elements.

* * * * *

UNITED STATES PATENT AND TRADEMARK OFFICE
CERTIFICATE OF CORRECTION

PATENT NO. : 7,173,118 B2  Page 1 of 1
APPLICATION NO. : 10/735256
DATED : February 6, 2007
INVENTOR(S) : Strittmatter et al.

It is certified that error appears in the above-identified patent and that said Letters Patent is hereby corrected as shown below:

In column 1, above "FIELD OF THE INVENTION" at line 9, please insert the following:

--GOVERNMENT LICENSE RIGHTS

This invention was made with Government support under NS033020 awarded by National Institute of Health. The Government has certain rights in the invention.--

Signed and Sealed this
Thirtieth Day of October, 2012

David J. Kappos
*Director of the United States Patent and Trademark Office*

SEQUENCE LISTING

<160> NUMBER OF SEQ ID NOS: 19

<210> SEQ ID NO 1
<211> LENGTH: 1260
<212> TYPE: DNA

<213> ORGANISM: Homo sapiens

<400> SEQUENCE: 1

```
atgctgcccg ggctcaggcg cctgctgcaa gctcccgcct cggcctgcct cctgctgatg    60
ctcctggccc tgcccctggc ggcccccagc tgccccatgc tctgcacctg ctactcatcc   120
ccgcccaccg tgagctgcca ggccaacaac ttctcctctg tgccgctgtc cctgccaccc   180
agcactcagc gactcttcct gcagaacaac ctcatccgca cgctgcggcc aggcaccttt   240
gggtccaacc tgctcaccct gtggctcttc tccaacaacc tctccaccat ctacccgggc   300
actttccgcc acttgcaagc cctggaggag ctggacctcg gtgacaaccg cacctgcgc    360
tcgctggagc ccgacacctt ccagggcctg gagcggctgc agtcgctgca tttgtaccgc   420
tgccagctca gcagcctgcc cggcaacatc ttccgaggcc tggtcagcct gcagtacctc   480
tacctccagg agaacagcct gctccaccta caggatgact tgttcgcgga cctggccaac   540
ctgagccacc tcttcctcca cgggaaccgc tgcggctgc tcacagagca cgtgtttcgc    600
ggcctgggca gcctggaccg gctgctgctg cacgggaacc ggctgcaggg cgtgcaccgc   660
gcggccttcc gcggcctcag ccgcctcacc atcctctacc tgttcaacaa cagcctggcc   720
tcgctgcccg gcgaggcgct cgccgacctg ccctcgctcg agttcctgcg gctcaacgct   780
aaccctgggg cgtgcgactg ccgcgcgcgg ccgctctggg cctggttcca gcgcgcgcgc   840
gtgtccagct ccgacgtgac ctgcgccacc ccccggagc gccagggccg agacctgcgc   900
gcgctccgcg aggccgactt ccaggcgtgt ccgcccgcgg cacccacgcg gccgggcagc   960
cgcgcccgcg gcaacagctc ctccaaccac ctgtacgggg tggccgaggc cggggcgccc  1020
ccagccgatc cctccaccct ctaccgagat ctgcctgccg aagactcgcg ggggcgccag  1080
ggcggggacg cgcctactga ggacgactac tggggggct acggggtga ggaccagcga    1140
ggggagcaga tgtgccccgg cgctgcctgc caggcgcccc cggactcccg aggccctgcg  1200
ctctcggccg ggctccccag ccctctgctt tgcctcctgc tcctggtgcc ccaccacctc  1260
```

<210> SEQ ID NO 2
<211> LENGTH: 420
<212> TYPE: PRT
<213> ORGANISM: Homo sapiens

<400> SEQUENCE: 2

```
Met Leu Pro Gly Leu Arg Arg Leu Leu Gln Ala Pro Ala Ser Ala Cys
 1               5                  10                  15

Leu Leu Leu Met Leu Leu Ala Leu Pro Leu Ala Ala Pro Ser Cys Pro
            20                  25                  30

Met Leu Cys Thr Cys Tyr Ser Ser Pro Thr Val Ser Cys Gln Ala
        35                  40                  45

Asn Asn Phe Ser Ser Val Pro Leu Ser Leu Pro Pro Ser Thr Gln Arg
    50                  55                  60

Leu Phe Leu Gln Asn Asn Leu Ile Arg Thr Leu Arg Pro Gly Thr Phe
65                  70                  75                  80

Gly Ser Asn Leu Leu Thr Leu Trp Leu Phe Ser Asn Asn Leu Ser Thr
                85                  90                  95

Ile Tyr Pro Gly Thr Phe Arg His Leu Gln Ala Leu Glu Glu Leu Asp
            100                 105                 110

Leu Gly Asp Asn Arg His Leu Arg Ser Leu Glu Pro Asp Thr Phe Gln
        115                 120                 125

Gly Leu Glu Arg Leu Gln Ser Leu His Leu Tyr Arg Cys Gln Leu Ser
```

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |
| Ser | Leu | Pro | Gly | Asn | Ile | Phe | Arg | Gly | Leu | Val | Ser | Leu | Gln | Tyr | Leu |
| 145 |     |     |     |     | 150 |     |     |     |     | 155 |     |     |     |     | 160 |
| Tyr | Leu | Gln | Glu | Asn | Ser | Leu | Leu | His | Leu | Gln | Asp | Asp | Leu | Phe | Ala |
|     |     |     |     | 165 |     |     |     |     | 170 |     |     |     |     | 175 |     |
| Asp | Leu | Ala | Asn | Leu | Ser | His | Leu | Phe | Leu | His | Gly | Asn | Arg | Leu | Arg |
|     |     |     | 180 |     |     |     |     | 185 |     |     |     |     | 190 |     |     |
| Leu | Leu | Thr | Glu | His | Val | Phe | Arg | Gly | Leu | Gly | Ser | Leu | Asp | Arg | Leu |
|     |     | 195 |     |     |     |     | 200 |     |     |     |     | 205 |     |     |     |
| Leu | Leu | His | Gly | Asn | Arg | Leu | Gln | Gly | Val | His | Arg | Ala | Ala | Phe | Arg |
| 210 |     |     |     |     | 215 |     |     |     |     | 220 |     |     |     |     |     |
| Gly | Leu | Ser | Arg | Leu | Thr | Ile | Leu | Tyr | Leu | Phe | Asn | Asn | Ser | Leu | Ala |
| 225 |     |     |     |     | 230 |     |     |     |     | 235 |     |     |     |     | 240 |
| Ser | Leu | Pro | Gly | Glu | Ala | Leu | Ala | Asp | Leu | Pro | Ser | Leu | Glu | Phe | Leu |
|     |     |     |     | 245 |     |     |     |     | 250 |     |     |     |     | 255 |     |
| Arg | Leu | Asn | Ala | Asn | Pro | Trp | Ala | Cys | Asp | Cys | Arg | Ala | Arg | Pro | Leu |
|     |     |     | 260 |     |     |     |     | 265 |     |     |     |     | 270 |     |     |
| Trp | Ala | Trp | Phe | Gln | Arg | Ala | Arg | Val | Ser | Ser | Ser | Asp | Val | Thr | Cys |
|     |     | 275 |     |     |     |     | 280 |     |     |     |     | 285 |     |     |     |
| Ala | Thr | Pro | Pro | Glu | Arg | Gln | Gly | Arg | Asp | Leu | Arg | Ala | Leu | Arg | Glu |
| 290 |     |     |     |     | 295 |     |     |     |     | 300 |     |     |     |     |     |
| Ala | Asp | Phe | Gln | Ala | Cys | Pro | Pro | Ala | Ala | Pro | Thr | Arg | Pro | Gly | Ser |
| 305 |     |     |     |     | 310 |     |     |     |     | 315 |     |     |     |     | 320 |
| Arg | Ala | Arg | Gly | Asn | Ser | Ser | Asn | His | Leu | Tyr | Gly | Val | Ala | Glu |     |
|     |     |     |     | 325 |     |     |     |     | 330 |     |     |     |     | 335 |     |
| Ala | Gly | Ala | Pro | Pro | Ala | Asp | Pro | Ser | Thr | Leu | Tyr | Arg | Asp | Leu | Pro |
|     |     |     | 340 |     |     |     |     | 345 |     |     |     |     | 350 |     |     |
| Ala | Glu | Asp | Ser | Arg | Gly | Arg | Gln | Gly | Gly | Asp | Ala | Pro | Thr | Glu | Asp |
|     |     |     | 355 |     |     |     |     | 360 |     |     |     |     | 365 |     |     |
| Asp | Tyr | Trp | Gly | Gly | Tyr | Gly | Gly | Glu | Asp | Gln | Arg | Gly | Glu | Gln | Met |
|     | 370 |     |     |     |     | 375 |     |     |     |     | 380 |     |     |     |     |
| Cys | Pro | Gly | Ala | Ala | Cys | Gln | Ala | Pro | Pro | Asp | Ser | Arg | Gly | Pro | Ala |
| 385 |     |     |     |     | 390 |     |     |     |     | 395 |     |     |     |     | 400 |
| Leu | Ser | Ala | Gly | Leu | Pro | Ser | Pro | Leu | Leu | Cys | Leu | Leu | Leu | Val |     |
|     |     |     |     | 405 |     |     |     |     | 410 |     |     |     |     | 415 |     |
| Pro | His | His | Leu |     |     |     |     |     |     |     |     |     |     |     |     |
|     |     |     | 420 |     |     |     |     |     |     |     |     |     |     |     |     |

<210> SEQ ID NO 3
<211> LENGTH: 1383
<212> TYPE: DNA
<213> ORGANISM: Mus sp.

<400> SEQUENCE: 3

```
atgtcttggc agtctggaac cacagtgaca caatctcccg tgcaggctgc tcaggtctca      60
gggtgctgtg tggaattgct gctgttgctg ctcgctggag agctacctct gggtggtggt     120
tgtcctcgag actgtgtgtg ctaccctgcg cccatgactg tcagctgcca ggcacacaac     180
tttgctgcca tcccggaggg catcccagag acagtgagc gcatcttcct gcagaacaat     240
cgcatcacct tcctccagca gggccacttc agccccgcca tggtcaccct ctggatctac     300
tccaacaaca tcactttcat tgctcccaac accttcgagg ctttgtgca tctggaggag     360
ctagaccttg agacaaccg acagctgcga acgctggcac ccgagacctt ccaaggcctg     420
gtgaagcttc acgccctcta cctctataag tgtggactga gcgccctgcc cgcaggcatc     480
```

-continued

```
tttggtggcc tgcacagcct gcagtatctc tacttgcagg acaaccatat cgagtacctc      540
caagatgaca tctttgtgga cctggtcaat ctcagtcact tgtttctcca tggtaacaag      600
ctatggagcc tgggccaagg catcttccgg ggcctggtga acctggaccg gttgctgctg      660
catgagaacc agctacagtg ggttcaccac aaggctttcc atgacctcca caggctaacc      720
accctctttc tcttcaacaa cagcctcact gagctgcagg gtgactgtct ggccccctg       780 gtggccttgg agttccttcg cctcaatggg aatgcttggg actgtggctg ccgggcacgt     840
tccctgtggg aatggctgcg aaggttccgt ggctctagct ctgctgtccc ctgcgcgacc      900
cccgagctgc ggcaaggcca ggatctgaag ctgctgaggg tggaggactt ccggaactgc      960
acaggaccag tgtctcctca ccagatcaag tctcacacgc ttaccacctc tgacagggct     1020
gcccgcaagg agcaccatcc gtcccatggg gcctccaggg acaaaggcca cccacatggc     1080
catccgcctg ctccaggtc aggttacaag aaggcaggca agaactgcac cagccacagg      1140
aaccggaacc agatctctaa ggtgagctct gggaaagagc ttaccgaact gcaggactat     1200
gcccccgact atcagcacaa gttcagcttt gacatcatgc ccaccgcacg acccaagagg     1260
aagggcaagt gtgctcgcag gacccccatc cgtgccccca gtggggtgca gcaggcatcc     1320
tcaggcacgg cccttggggc cccactcctg gcctggatac tggggctggc agtcactctc     1380
cgc                                                                   1383
```

<210> SEQ ID NO 4
<211> LENGTH: 461
<212> TYPE: PRT
<213> ORGANISM: Mus sp.

<400> SEQUENCE: 4

```
Met Ser Trp Gln Ser Gly Thr Thr Val Thr Gln Ser Pro Val Gln Ala
  1               5                  10                  15

Ala Gln Val Ser Gly Cys Cys Val Glu Leu Leu Leu Leu Leu Leu Ala
             20                  25                  30

Gly Glu Leu Pro Leu Gly Gly Gly Cys Pro Arg Asp Cys Val Cys Tyr
         35                  40                  45

Pro Ala Pro Met Thr Val Ser Cys Gln Ala His Asn Phe Ala Ala Ile
     50                  55                  60

Pro Glu Gly Ile Pro Glu Asp Ser Glu Arg Ile Phe Leu Gln Asn Asn
 65                  70                  75                  80

Arg Ile Thr Phe Leu Gln Gln Gly His Phe Ser Pro Ala Met Val Thr
                 85                  90                  95

Leu Trp Ile Tyr Ser Asn Asn Ile Thr Phe Ile Ala Pro Asn Thr Phe
            100                 105                 110

Glu Gly Phe Val His Leu Glu Glu Leu Asp Leu Gly Asp Asn Arg Gln
        115                 120                 125

Leu Arg Thr Leu Ala Pro Glu Thr Phe Gln Gly Leu Val Lys Leu His
    130                 135                 140

Ala Leu Tyr Leu Tyr Lys Cys Gly Leu Ser Ala Leu Pro Ala Gly Ile
145                 150                 155                 160

Phe Gly Gly Leu His Ser Leu Gln Tyr Leu Tyr Leu Gln Asp Asn His
                165                 170                 175

Ile Glu Tyr Leu Gln Asp Asp Ile Phe Val Asp Leu Val Asn Leu Ser
            180                 185                 190

His Leu Phe Leu His Gly Asn Lys Leu Trp Ser Leu Gly Gln Gly Ile
        195                 200                 205
```

-continued

```
Phe Arg Gly Leu Val Asn Leu Asp Arg Leu Leu His Glu Asn Gln
    210                 215                 220

Leu Gln Trp Val His His Lys Ala Phe His Asp Leu His Arg Leu Thr
225                 230                 235                 240

Thr Leu Phe Leu Phe Asn Asn Ser Leu Thr Glu Leu Gln Gly Asp Cys
                245                 250                 255

Leu Ala Pro Leu Val Ala Leu Glu Phe Leu Arg Leu Asn Gly Asn Ala
                260                 265                 270

Trp Asp Cys Gly Cys Arg Ala Arg Ser Leu Trp Glu Trp Leu Arg Arg
                275                 280                 285

Phe Arg Gly Ser Ser Ala Val Pro Cys Ala Thr Pro Glu Leu Arg
    290                 295                 300

Gln Gly Gln Asp Leu Lys Leu Arg Val Glu Asp Phe Arg Asn Cys
305                 310                 315                 320

Thr Gly Pro Val Ser Pro His Gln Ile Lys Ser His Thr Leu Thr Thr
                325                 330                 335

Ser Asp Arg Ala Ala Arg Lys Glu His His Pro Ser His Gly Ala Ser
                340                 345                 350

Arg Asp Lys Gly His Pro His Gly His Pro Pro Gly Ser Arg Ser Gly
                355                 360                 365

Tyr Lys Lys Ala Gly Lys Asn Cys Thr Ser His Arg Asn Arg Asn Gln
    370                 375                 380

Ile Ser Lys Val Ser Ser Gly Lys Glu Leu Thr Glu Leu Gln Asp Tyr
385                 390                 395                 400

Ala Pro Asp Tyr Gln His Lys Phe Ser Phe Asp Ile Met Pro Thr Ala
                405                 410                 415

Arg Pro Lys Arg Lys Gly Lys Cys Ala Arg Arg Thr Pro Ile Arg Ala
                420                 425                 430

Pro Ser Gly Val Gln Gln Ala Ser Ser Gly Thr Ala Leu Gly Ala Pro
                435                 440                 445

Leu Leu Ala Trp Ile Leu Gly Leu Ala Val Thr Leu Arg
    450                 455                 460
```

<210> SEQ ID NO 5
<211> LENGTH: 473
<212> TYPE: PRT
<213> ORGANISM: Homo sapiens

<400> SEQUENCE: 5

```
Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
                20                  25                  30

Cys Tyr Asn Glu Pro Lys Val Thr Thr Ser Cys Pro Gln Gln Gly Leu
            35                  40                  45

Gln Ala Val Pro Val Gly Ile Pro Ala Ala Ser Gln Arg Ile Phe Leu
        50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
                100                 105                 110

Ser Asp Asn Ala Gln Leu Arg Ser Val Asp Pro Ala Thr Phe His Gly
```

```
                115                 120                 125
Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
                180                 185                 190

Val Pro Glu Arg Ala Phe Arg Gly Leu His Ser Leu Asp Arg Leu Leu
            195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
    275                 280                 285

Leu Pro Gln Arg Leu Ala Gly Arg Asp Leu Lys Arg Leu Ala Ala Asn
290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
    355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
                420                 425                 430

Gln Ala Gly Ser Gly Gly Gly Thr Gly Asp Ser Glu Gly Ser Gly
    435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470

<210> SEQ ID NO 6
<211> LENGTH: 440
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (3)..(4)
```

```
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid
<220> FEATURE:
<221> NAME/KEY: MOD_RES
<222> LOCATION: (15)
<223> OTHER INFORMATION: Variable amino acid
<220> FEATURE:
<221> NAME/KEY: MOD_RES
<222> LOCATION: (18)..(25)
<223> OTHER INFORMATION: Variable amino acid
<220> FEATURE:
<221> NAME/KEY: MOD_RES
<222> LOCATION: (27)..(29)
<223> OTHER INFORMATION: Variable amino acid
<220> FEATURE:
<221> NAME/KEY: MOD_RES
<222> LOCATION: (31)..(34)
<223> OTHER INFORMATION: Variable amino acid
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (39)..(40)
<223> OTHER INFORMATION: Variable amino acid
<220> FEATURE:
<221> NAME/KEY: MOD_RES
<222> LOCATION: (42)
<223> OTHER INFORMATION: Variable amino acid
<220> FEATURE:
<221> NAME/KEY: MOD_RES
<222> LOCATION: (44)..(50)
<223> OTHER INFORMATION: Variable amino acid
<220> FEATURE:
<221> NAME/KEY: MOD_RES
<222> LOCATION: (52)..(59)
<223> OTHER INFORMATION: Variable amino acid
<220> FEATURE:
<221> NAME/KEY: MOD_RES
<222> LOCATION: (62)..(63)
<223> OTHER INFORMATION: Variable amino acid
<220> FEATURE:
<221> NAME/KEY: MOD_RES
<222> LOCATION: (66)..(69)
<223> OTHER INFORMATION: Variable amino acid
<220> FEATURE:
<221> NAME/KEY: MOD_RES
<222> LOCATION: (71)..(74)
<223> OTHER INFORMATION: Variable amino acid
<220> FEATURE:
<221> NAME/KEY: MOD_RES
<222> LOCATION: (76)..(80)
<223> OTHER INFORMATION: Variable amino acid
<220> FEATURE:
<221> NAME/KEY: MOD_RES
<222> LOCATION: (83)
<223> OTHER INFORMATION: Variable amino acid
<220> FEATURE:
<221> NAME/KEY: MOD_RES
<222> LOCATION: (87)
<223> OTHER INFORMATION: Variable amino acid
<220> FEATURE:
<221> NAME/KEY: MOD_RES
<222> LOCATION: (90)..(91)
<223> OTHER INFORMATION: Variable amino acid
<220> FEATURE:
<221> NAME/KEY: MOD_RES
```

```
-continued

<222> LOCATION: (94)..(96)
<223> OTHER INFORMATION: Variable amino acid
<220> FEATURE:
<221> NAME/KEY: MOD_RES
<222> LOCATION: (98)
<223> OTHER INFORMATION: Variable amino acid
<220> FEATURE:
<221> NAME/KEY: MOD_RES
<222> LOCATION: (101)
<223> OTHER INFORMATION: Variable amino acid
<220> FEATURE:
<221> NAME/KEY: MOD_RES
<222> LOCATION: (104)..(105)
<223> OTHER INFORMATION: Variable amino acid
<220> FEATURE:
<221> NAME/KEY: MOD_RES
<222> LOCATION: (107)
<223> OTHER INFORMATION: Variable amino acid
<220> FEATURE:
<221> NAME/KEY: MOD_RES
<222> LOCATION: (109)
<223> OTHER INFORMATION: Variable amino acid
<220> FEATURE:
<221> NAME/KEY: MOD_RES
<222> LOCATION: (111)..(112)
<223> OTHER INFORMATION: Variable amino acid
<220> FEATURE:
<221> NAME/KEY: MOD_RES
<222> LOCATION: (114)
<223> OTHER INFORMATION: Variable amino acid
<220> FEATURE:
<221> NAME/KEY: MOD_RES
<222> LOCATION: (116)..(117)
<223> OTHER INFORMATION: Variable amino acid
<220> FEATURE:
<221> NAME/KEY: MOD_RES
<222> LOCATION: (119)..(122)
<223> OTHER INFORMATION: Variable amino acid
<220> FEATURE:
<221> NAME/KEY: MOD_RES
<222> LOCATION: (124)
<223> OTHER INFORMATION: Variable amino acid
<220> FEATURE:
<221> NAME/KEY: MOD_RES
<222> LOCATION: (127)..(128)
<223> OTHER INFORMATION: Variable amino acid
<220> FEATURE:
<221> NAME/KEY: MOD_RES
<222> LOCATION: (136)
<223> OTHER INFORMATION: Variable amino acid
<220> FEATURE:
<221> NAME/KEY: MOD_RES
<222> LOCATION: (138)..(141)
<223> OTHER INFORMATION: Variable amino acid
<220> FEATURE:
<221> NAME/KEY: MOD_RES
<222> LOCATION: (143)
<223> OTHER INFORMATION: Variable amino acid
<220> FEATURE:
<221> NAME/KEY: MOD_RES
<222> LOCATION: (146)
<223> OTHER INFORMATION: Variable amino acid
<220> FEATURE:
<221> NAME/KEY: MOD_RES
<222> LOCATION: (148)
<223> OTHER INFORMATION: Variable amino acid
<220> FEATURE:
<221> NAME/KEY: MOD_RES
<222> LOCATION: (151)
<223> OTHER INFORMATION: Variable amino acid
<220> FEATURE:
<221> NAME/KEY: MOD_RES
<222> LOCATION: (154)
<223> OTHER INFORMATION: Variable amino acid
<220> FEATURE:
<221> NAME/KEY: MOD_RES
<222> LOCATION: (162)..(170)
<223> OTHER INFORMATION: Variable amino acid
<220> FEATURE:
```

-continued

```
<221> NAME/KEY: MOD_RES
<222> LOCATION: (175)..(176)
<223> OTHER INFORMATION: Variable amino acid
<220> FEATURE:
<221> NAME/KEY: MOD_RES
<222> LOCATION: (184)
<223> OTHER INFORMATION: Variable amino acid
<220> FEATURE:
<221> NAME/KEY: MOD_RES
<222> LOCATION: (186)..(189)
<223> OTHER INFORMATION: Variable amino acid
<220> FEATURE:
<221> NAME/KEY: MOD_RES
<222> LOCATION: (192)..(193)
<223> OTHER INFORMATION: Variable amino acid
<220> FEATURE:
<221> NAME/KEY: MOD_RES
<222> LOCATION: (196)..(197)
<223> OTHER INFORMATION: Variable amino acid
<220> FEATURE:
<221> NAME/KEY: MOD_RES
<222> LOCATION: (199)
<223> OTHER INFORMATION: Variable amino acid
<220> FEATURE:
<221> NAME/KEY: MOD_RES
<222> LOCATION: (202)..(203)
<223> OTHER INFORMATION: Variable amino acid
<220> FEATURE:
<221> NAME/KEY: MOD_RES
<222> LOCATION: (205)
<223> OTHER INFORMATION: Variable amino acid
<220> FEATURE:
<221> NAME/KEY: MOD_RES
<222> LOCATION: (208)
<223> OTHER INFORMATION: Variable amino acid
<220> FEATURE:
<221> NAME/KEY: MOD_RES
<222> LOCATION: (210)
<223> OTHER INFORMATION: Variable amino acid
<220> FEATURE:
<221> NAME/KEY: MOD_RES
<222> LOCATION: (212)..(213)
<223> OTHER INFORMATION: Variable amino acid
<220> FEATURE:
<221> NAME/KEY: MOD_RES
<222> LOCATION: (215)..(218)
<223> OTHER INFORMATION: Variable amino acid
<220> FEATURE:
<221> NAME/KEY: MOD_RES
<222> LOCATION: (221)
<223> OTHER INFORMATION: Variable amino acid
<220> FEATURE:
<221> NAME/KEY: MOD_RES
<222> LOCATION: (223)..(224)
<223> OTHER INFORMATION: Variable amino acid
<220> FEATURE:
<221> NAME/KEY: MOD_RES
<222> LOCATION: (226)..(227)
<223> OTHER INFORMATION: Variable amino acid
<220> FEATURE:
<221> NAME/KEY: MOD_RES
<222> LOCATION: (232)
<223> OTHER INFORMATION: Variable amino acid
<220> FEATURE:
<221> NAME/KEY: MOD_RES
<222> LOCATION: (234)
<223> OTHER INFORMATION: Variable amino acid
<220> FEATURE:
<221> NAME/KEY: MOD_RES
<222> LOCATION: (236)
<223> OTHER INFORMATION: Variable amino acid
<220> FEATURE:
<221> NAME/KEY: MOD_RES
<222> LOCATION: (238)
<223> OTHER INFORMATION: Variable amino acid
<220> FEATURE:
<221> NAME/KEY: MOD_RES
<222> LOCATION: (243)
<223> OTHER INFORMATION: Variable amino acid
```

```
<220> FEATURE:
<221> NAME/KEY: MOD_RES
<222> LOCATION: (246)
<223> OTHER INFORMATION: Variable amino acid
<220> FEATURE:
<221> NAME/KEY: MOD_RES
<222> LOCATION: (248)..(251)
<223> OTHER INFORMATION: Variable amino acid
<220> FEATURE:
<221> NAME/KEY: MOD_RES
<222> LOCATION: (253)
<223> OTHER INFORMATION: Variable amino acid
<220> FEATURE:
<221> NAME/KEY: MOD_RES
<222> LOCATION: (257)
<223> OTHER INFORMATION: Variable amino acid
<220> FEATURE:
<221> NAME/KEY: MOD_RES
<222> LOCATION: (259)
<223> OTHER INFORMATION: Variable amino acid
<220> FEATURE:
<221> NAME/KEY: MOD_RES
<222> LOCATION: (261)..(262)
<223> OTHER INFORMATION: Variable amino acid
<220> FEATURE:
<221> NAME/KEY: MOD_RES
<222> LOCATION: (264)..(267)
<223> OTHER INFORMATION: Variable amino acid
<220> FEATURE:
<221> NAME/KEY: MOD_RES
<222> LOCATION: (269)
<223> OTHER INFORMATION: Variable amino acid
<220> FEATURE:
<221> NAME/KEY: MOD_RES
<222> LOCATION: (272)..(273)
<223> OTHER INFORMATION: Variable amino acid
<220> FEATURE:
<221> NAME/KEY: MOD_RES
<222> LOCATION: (275)..(277)
<223> OTHER INFORMATION: Variable amino acid
<220> FEATURE:
<221> NAME/KEY: MOD_RES
<222> LOCATION: (279)..(281)
<223> OTHER INFORMATION: Variable amino acid
<220> FEATURE:
<221> NAME/KEY: MOD_RES
<222> LOCATION: (283)..(287)
<223> OTHER INFORMATION: Variable amino acid
<220> FEATURE:
<221> NAME/KEY: MOD_RES
<222> LOCATION: (289)..(290)
<223> OTHER INFORMATION: Variable amino acid
<220> FEATURE:
<221> NAME/KEY: MOD_RES
<222> LOCATION: (292)..(328)
<223> OTHER INFORMATION: Variable amino acid
<220> FEATURE:
<221> NAME/KEY: MOD_RES
<222> LOCATION: (330)..(341)
<223> OTHER INFORMATION: Variable amino acid
<220> FEATURE:
<221> NAME/KEY: MOD_RES
<222> LOCATION: (344)..(346)
<223> OTHER INFORMATION: Variable amino acid
<220> FEATURE:
<221> NAME/KEY: MOD_RES
<222> LOCATION: (348)..(399)
<223> OTHER INFORMATION: Variable amino acid
<220> FEATURE:
<221> NAME/KEY: MOD_RES
<222> LOCATION: (401)..(428)
<223> OTHER INFORMATION: Variable amino acid
<220> FEATURE:
<221> NAME/KEY: MOD_RES
<222> LOCATION: (431)..(439)
<223> OTHER INFORMATION: Variable amino acid

<400> SEQUENCE: 6
```

-continued

```
Cys Pro Xaa Xaa Cys Xaa Cys Tyr Xaa Xaa Pro Xaa Xaa Thr Xaa Ser
  1               5                  10                 15

Cys Xaa Xaa Xaa Xaa Xaa Xaa Xaa Pro Xaa Xaa Xaa Pro Xaa Xaa
             20                  25                  30

Xaa Xaa Arg Xaa Phe Leu Xaa Xaa Asn Xaa Ile Xaa Xaa Xaa Xaa Xaa
         35                  40                  45

Xaa Xaa Phe Xaa Xaa Xaa Xaa Xaa Xaa Xaa Leu Trp Xaa Xaa Ser
     50                  55                  60

Asn Xaa Xaa Xaa Xaa Ile Xaa Xaa Xaa Phe Xaa Xaa Xaa Xaa
 65              70                  75                  80

Leu Glu Xaa Leu Asp Leu Xaa Asp Asn Xaa Xaa Leu Arg Xaa Xaa Xaa
                 85                  90                  95

Pro Xaa Thr Phe Xaa Gly Leu Xaa Xaa Leu Xaa Leu Xaa Leu Xaa Xaa
             100                 105                 110

Cys Xaa Leu Xaa Xaa Leu Xaa Xaa Xaa Xaa Phe Xaa Gly Leu Xaa Xaa
         115                 120                 125

Leu Gln Tyr Leu Tyr Leu Gln Xaa Asn Xaa Xaa Xaa Xaa Leu Xaa Asp
    130                 135                 140

Asp Xaa Phe Xaa Asp Leu Xaa Asn Leu Xaa His Leu Phe Leu His Gly
145             150                 155                 160

Asn Xaa Xaa Xaa Xaa Xaa Xaa Xaa Xaa Phe Arg Gly Leu Xaa Xaa
             165                 170                 175

Leu Asp Arg Leu Leu Leu His Xaa Asn Xaa Xaa Xaa Xaa Val His Xaa
         180                 185                 190

Xaa Ala Phe Xaa Xaa Leu Xaa Arg Leu Xaa Xaa Leu Xaa Leu Phe Xaa
         195                 200                 205

Asn Xaa Leu Xaa Xaa Leu Xaa Xaa Xaa Xaa Leu Ala Xaa Leu Xaa Xaa
210                 215                 220

Leu Xaa Xaa Leu Arg Leu Asn Xaa Asn Xaa Trp Xaa Cys Xaa Cys Arg
225                 230                 235                 240

Ala Arg Xaa Leu Trp Xaa Trp Xaa Xaa Xaa Xaa Arg Xaa Ser Ser Ser
             245                 250                 255

Xaa Val Xaa Cys Xaa Xaa Pro Xaa Xaa Xaa Xaa Gly Xaa Asp Leu Xaa
         260                 265                 270

Xaa Leu Xaa Xaa Xaa Asp Xaa Xaa Xaa Cys Xaa Xaa Xaa Xaa Xaa Pro
    275                 280                 285

Xaa Xaa Pro Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Gly Xaa Xaa Xaa Xaa Xaa Xaa
             325                 330                 335

Xaa Xaa Xaa Xaa Xaa Pro Pro Xaa Xaa Ser Xaa Xaa Xaa Xaa
             340                 345                 350

Xaa Xaa Xaa Xaa Xaa Xaa Xaa Xaa Xaa Xaa Xaa Xaa Xaa Xaa
             355                 360                 365

Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Arg
385                 390                 395                 400

Xaa Xaa Xaa Xaa Xaa Xaa Xaa Xaa Xaa Xaa Xaa Xaa Xaa Xaa
             405                 410                 415

Xaa Xaa Xaa Xaa Xaa Xaa Xaa Xaa Xaa Xaa Xaa Xaa Leu Xaa Xaa Xaa
```

```
                420              425              430
Xaa Xaa Xaa Xaa Xaa Xaa Xaa Leu
        435              440

<210> SEQ ID NO 7
<211> LENGTH: 66
<212> TYPE: PRT
<213> ORGANISM: Homo sapiens

<400> SEQUENCE: 7

Arg Ile Tyr Lys Gly Val Ile Gln Ala Ile Gln Lys Ser Asp Glu Gly
 1               5                  10                  15

His Pro Phe Arg Ala Tyr Leu Glu Ser Glu Val Ala Ile Ser Glu Glu
            20                  25                  30

Leu Val Gln Lys Tyr Ser Asn Ser Ala Leu Gly His Val Asn Cys Thr
        35                  40                  45

Ile Lys Glu Leu Arg Arg Leu Phe Leu Val Asp Asp Leu Val Asp Ser
    50                  55                  60

Leu Lys
 65

<210> SEQ ID NO 8
<211> LENGTH: 390
<212> TYPE: PRT
<213> ORGANISM: Homo sapeins

<400> SEQUENCE: 8

Cys Pro Met Leu Cys Thr Cys Tyr Ser Ser Pro Thr Val Ser Cys
 1               5                  10                  15

Gln Ala Asn Asn Phe Ser Ser Val Pro Leu Ser Leu Pro Pro Ser Thr
            20                  25                  30

Gln Arg Leu Phe Leu Gln Asn Asn Leu Ile Arg Thr Leu Arg Pro Gly
        35                  40                  45

Thr Phe Gly Ser Asn Leu Leu Thr Leu Trp Leu Phe Ser Asn Asn Leu
    50                  55                  60

Ser Thr Ile Tyr Pro Gly Thr Phe Arg His Leu Gln Ala Leu Glu Glu
 65                  70                  75                  80

Leu Asp Leu Gly Asp Asn Arg His Leu Arg Ser Leu Glu Pro Asp Thr
            85                  90                  95

Phe Gln Gly Leu Glu Arg Leu Gln Ser Leu His Leu Tyr Arg Cys Gln
        100                 105                 110

Leu Ser Ser Leu Pro Gly Asn Ile Phe Arg Gly Leu Val Ser Leu Gln
        115                 120                 125

Tyr Leu Tyr Leu Gln Glu Asn Ser Leu Leu His Leu Gln Asp Asp Leu
        130                 135                 140

Phe Ala Asp Leu Ala Asn Leu Ser His Leu Phe Leu His Gly Asn Arg
145                 150                 155                 160

Leu Arg Leu Leu Thr Glu His Val Phe Arg Gly Leu Gly Ser Leu Asp
                165                 170                 175

Arg Leu Leu Leu His Gly Asn Arg Leu Gln Gly Val His Arg Ala Ala
            180                 185                 190

Phe Arg Gly Leu Ser Arg Leu Thr Ile Leu Tyr Leu Phe Asn Asn Ser
        195                 200                 205

Leu Ala Ser Leu Pro Gly Glu Ala Leu Ala Asp Leu Pro Ser Leu Glu
        210                 215                 220

Phe Leu Arg Leu Asn Ala Asn Pro Trp Ala Cys Asp Cys Arg Ala Arg
```

```
                225                 230                 235                 240
Pro Leu Trp Ala Trp Phe Gln Arg Ala Arg Val Ser Ser Ser Asp Val
                245                 250                 255
Thr Cys Ala Thr Pro Glu Arg Gln Gly Arg Asp Leu Arg Ala Leu
            260                 265                 270
Arg Glu Ala Asp Phe Gln Ala Cys Pro Pro Ala Ala Pro Thr Arg Pro
            275                 280                 285
Gly Ser Arg Ala Arg Gly Asn Ser Ser Asn His Leu Tyr Gly Val
            290                 295                 300
Ala Glu Ala Gly Ala Pro Pro Ala Asp Pro Ser Thr Leu Tyr Arg Asp
305                 310                 315                 320
Leu Pro Ala Glu Asp Ser Arg Gly Arg Gln Gly Gly Asp Ala Pro Thr
                325                 330                 335
Glu Asp Asp Tyr Trp Gly Gly Tyr Gly Glu Asp Gln Arg Gly Glu
                340                 345                 350
Gln Met Cys Pro Gly Ala Ala Cys Gln Ala Pro Pro Asp Ser Arg Gly
            355                 360                 365
Pro Ala Leu Ser Ala Gly Leu Pro Ser Pro Leu Leu Cys Leu Leu Leu
370                 375                 380
Leu Val Pro His His Leu
385                 390

<210> SEQ ID NO 9
<211> LENGTH: 421
<212> TYPE: PRT
<213> ORGANISM: Mus sp.

<400> SEQUENCE: 9

Cys Pro Arg Asp Cys Val Cys Tyr Pro Ala Pro Met Thr Val Ser Cys
  1                 5                  10                  15
Gln Ala His Asn Phe Ala Ala Ile Pro Glu Gly Ile Pro Glu Asp Ser
                20                  25                  30
Glu Arg Ile Phe Leu Gln Asn Asn Arg Ile Thr Phe Leu Gln Gln Gly
            35                  40                  45
His Phe Ser Pro Ala Met Val Thr Leu Trp Ile Tyr Ser Asn Asn Ile
    50                  55                  60
Thr Phe Ile Ala Pro Asn Thr Phe Glu Gly Phe Val His Leu Glu Glu
65                  70                  75                  80
Leu Asp Leu Gly Asp Asn Arg Gln Leu Arg Thr Leu Ala Pro Glu Thr
                85                  90                  95
Phe Gln Gly Leu Val Lys Leu His Ala Leu Tyr Leu Tyr Lys Cys Gly
            100                 105                 110
Leu Ser Ala Leu Pro Ala Gly Ile Phe Gly Gly Leu His Ser Leu Gln
        115                 120                 125
Tyr Leu Tyr Leu Gln Asp Asn His Ile Glu Tyr Leu Gln Asp Asp Ile
    130                 135                 140
Phe Val Asp Leu Val Asn Leu Ser His Leu Phe Leu His Gly Asn Lys
145                 150                 155                 160
Leu Trp Ser Leu Gly Gln Gly Ile Phe Arg Gly Leu Val Asn Leu Asp
                165                 170                 175
Arg Leu Leu Leu His Glu Asn Gln Leu Gln Trp Val His Lys Ala
            180                 185                 190
Phe His Asp Leu His Arg Leu Thr Thr Leu Phe Leu Phe Asn Asn Ser
        195                 200                 205
```

```
Leu Thr Glu Leu Gln Gly Asp Cys Leu Ala Pro Val Ala Leu Glu
    210                 215                 220

Phe Leu Arg Leu Asn Gly Asn Ala Trp Asp Cys Gly Cys Arg Ala Arg
225                 230                 235                 240

Ser Leu Trp Glu Trp Leu Arg Arg Phe Arg Gly Ser Ser Ala Val
            245                 250                 255

Pro Cys Ala Thr Pro Glu Leu Arg Gln Gly Gln Asp Leu Lys Leu Leu
                260                 265                 270

Arg Val Glu Asp Phe Arg Asn Cys Thr Gly Pro Val Ser Pro His Gln
            275                 280                 285

Ile Lys Ser His Thr Leu Thr Thr Ser Asp Arg Ala Ala Arg Lys Glu
    290                 295                 300

His His Pro Ser His Gly Ala Ser Arg Asp Lys Gly His Pro His Gly
305                 310                 315                 320

His Pro Pro Gly Ser Arg Ser Gly Tyr Lys Lys Ala Gly Lys Asn Cys
                325                 330                 335

Thr Ser His Arg Asn Arg Asn Gln Ile Ser Lys Val Ser Ser Gly Lys
            340                 345                 350

Glu Leu Thr Glu Leu Gln Asp Tyr Ala Pro Asp Tyr Gln His Lys Phe
            355                 360                 365

Ser Phe Asp Ile Met Pro Thr Ala Arg Pro Lys Arg Lys Gly Lys Cys
370                 375                 380

Ala Arg Arg Thr Pro Ile Arg Ala Pro Ser Gly Val Gln Gln Ala Ser
385                 390                 395                 400

Ser Gly Thr Ala Leu Gly Ala Pro Leu Leu Ala Trp Ile Leu Gly Leu
                405                 410                 415

Ala Val Thr Leu Arg
            420

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid
<220> FEATURE:
<221> NAME/KEY: MOD_RES
<222> LOCATION: (15)
<223> OTHER INFORMATION: Variable amino acid

<400> SEQUENCE: 10

Cys Pro Xaa Xaa Cys Xaa Cys Tyr Xaa Xaa Pro Xaa Xaa Thr Xaa Ser
  1               5                   10                  15

Cys
```

```
<210> SEQ ID NO 11
<211> LENGTH: 50
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (14)
<223> OTHER INFORMATION: Variable amino acid
<220> FEATURE:
<221> NAME/KEY: MOD_RES
<222> LOCATION: (16)..(19)
<223> OTHER INFORMATION: Variable amino acid
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (25)
<223> OTHER INFORMATION: Variable amino acid
<220> FEATURE:
<221> NAME/KEY: MOD_RES
<222> LOCATION: (27)
<223> OTHER INFORMATION: Variable amino acid
<220> FEATURE:
<221> NAME/KEY: MOD_RES
<222> LOCATION: (29)..(30)
<223> OTHER INFORMATION: Variable amino acid
<220> FEATURE:
<221> NAME/KEY: MOD_RES
<222> LOCATION: (32)..(35)
<223> OTHER INFORMATION: Variable amino acid
<220> FEATURE:
<221> NAME/KEY: MOD_RES
<222> LOCATION: (37)
<223> OTHER INFORMATION: Variable amino acid
<220> FEATURE:
<221> NAME/KEY: MOD_RES
<222> LOCATION: (40)..(41)
<223> OTHER INFORMATION: Variable amino acid
<220> FEATURE:
<221> NAME/KEY: MOD_RES
<222> LOCATION: (43)..(45)
<223> OTHER INFORMATION: Variable amino acid
<220> FEATURE:
<221> NAME/KEY: MOD_RES
<222> LOCATION: (47)..(49)
<223> OTHER INFORMATION: Variable amino acid

<400> SEQUENCE: 11

Asn Xaa Trp Xaa Cys Xaa Cys Arg Ala Arg Xaa Leu Trp Xaa Trp Xaa
 1               5                  10                  15

Xaa Xaa Xaa Arg Xaa Ser Ser Ser Xaa Val Xaa Cys Xaa Xaa Pro Xaa
            20                  25                  30

Xaa Xaa Xaa Gly Xaa Asp Leu Xaa Xaa Leu Xaa Xaa Xaa Asp Xaa Xaa
        35                  40                  45
```

```
Xaa Cys
    50

<210> SEQ ID NO 12
<211> LENGTH: 196
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (10)..(16)
<223> OTHER INFORMATION: Variable amino acid
<220> FEATURE:
<221> NAME/KEY: MOD_RES
<222> LOCATION: (18)..(25)
<223> OTHER INFORMATION: Variable amino acid
<220> FEATURE:
<221> NAME/KEY: MOD_RES
<222> LOCATION: (28)..(29)
<223> OTHER INFORMATION: Variable amino acid
<220> FEATURE:
<221> NAME/KEY: MOD_RES
<222> LOCATION: (32)..(35)
<223> OTHER INFORMATION: Variable amino acid
<220> FEATURE:
<221> NAME/KEY: MOD_RES
<222> LOCATION: (37)..(40)
<223> OTHER INFORMATION: Variable amino acid
<220> FEATURE:
<221> NAME/KEY: MOD_RES
<222> LOCATION: (42)..(46)
<223> OTHER INFORMATION: Variable amino acid
<220> FEATURE:
<221> NAME/KEY: MOD_RES
<222> LOCATION: (49)
<223> OTHER INFORMATION: Variable amino acid
<220> FEATURE:
<221> NAME/KEY: MOD_RES
<222> LOCATION: (53)
<223> OTHER INFORMATION: Variable amino acid
<220> FEATURE:
<221> NAME/KEY: MOD_RES
<222> LOCATION: (56)..(57)
<223> OTHER INFORMATION: Variable amino acid
<220> FEATURE:
<221> NAME/KEY: MOD_RES
<222> LOCATION: (60)..(62)
<223> OTHER INFORMATION: Variable amino acid
<220> FEATURE:
<221> NAME/KEY: MOD_RES
<222> LOCATION: (64)
<223> OTHER INFORMATION: Variable amino acid
<220> FEATURE:
<221> NAME/KEY: MOD_RES
<222> LOCATION: (67)
<223> OTHER INFORMATION: Variable amino acid
<220> FEATURE:
<221> NAME/KEY: MOD_RES
<222> LOCATION: (70)..(71)
<223> OTHER INFORMATION: Variable amino acid
<220> FEATURE:
<221> NAME/KEY: MOD_RES
<222> LOCATION: (73)
<223> OTHER INFORMATION: Variable amino acid
```

```
<220> FEATURE:
<221> NAME/KEY: MOD_RES
<222> LOCATION: (75)
<223> OTHER INFORMATION: Variable amino acid
<220> FEATURE:
<221> NAME/KEY: MOD_RES
<222> LOCATION: (77)..(78)
<223> OTHER INFORMATION: Variable amino acid
<220> FEATURE:
<221> NAME/KEY: MOD_RES
<222> LOCATION: (80)
<223> OTHER INFORMATION: Variable amino acid
<220> FEATURE:
<221> NAME/KEY: MOD_RES
<222> LOCATION: (82)..(83)
<223> OTHER INFORMATION: Variable amino acid
<220> FEATURE:
<221> NAME/KEY: MOD_RES
<222> LOCATION: (85)..(88)
<223> OTHER INFORMATION: Variable amino acid
<220> FEATURE:
<221> NAME/KEY: MOD_RES
<222> LOCATION: (90)
<223> OTHER INFORMATION: Variable amino acid
<220> FEATURE:
<221> NAME/KEY: MOD_RES
<222> LOCATION: (93)..(94)
<223> OTHER INFORMATION: Variable amino acid
<220> FEATURE:
<221> NAME/KEY: MOD_RES
<222> LOCATION: (102)
<223> OTHER INFORMATION: Variable amino acid
<220> FEATURE:
<221> NAME/KEY: MOD_RES
<222> LOCATION: (104)..(107)
<223> OTHER INFORMATION: Variable amino acid
<220> FEATURE:
<221> NAME/KEY: MOD_RES
<222> LOCATION: (109)
<223> OTHER INFORMATION: Variable amino acid
<220> FEATURE:
<221> NAME/KEY: MOD_RES
<222> LOCATION: (112)
<223> OTHER INFORMATION: Variable amino acid
<220> FEATURE:
<221> NAME/KEY: MOD_RES
<222> LOCATION: (114)
<223> OTHER INFORMATION: Variable amino acid
<220> FEATURE:
<221> NAME/KEY: MOD_RES
<222> LOCATION: (117)
<223> OTHER INFORMATION: Variable amino acid
<220> FEATURE:
<221> NAME/KEY: MOD_RES
<222> LOCATION: (120)
<223> OTHER INFORMATION: Variable amino acid
<220> FEATURE:
<221> NAME/KEY: MOD_RES
<222> LOCATION: (128)..(136)
<223> OTHER INFORMATION: Variable amino acid
<220> FEATURE:
<221> NAME/KEY: MOD_RES
<222> LOCATION: (141)..(142)
<223> OTHER INFORMATION: Variable amino acid
<220> FEATURE:
<221> NAME/KEY: MOD_RES
<222> LOCATION: (150)
<223> OTHER INFORMATION: Variable amino acid
<220> FEATURE:
<221> NAME/KEY: MOD_RES
<222> LOCATION: (152)..(155)
<223> OTHER INFORMATION: Variable amino acid
<220> FEATURE:
<221> NAME/KEY: MOD_RES
<222> LOCATION: (158)..(159)
<223> OTHER INFORMATION: Variable amino acid
<220> FEATURE:
<221> NAME/KEY: MOD_RES
<222> LOCATION: (162)..(163)
```

<223> OTHER INFORMATION: Variable amino acid
<220> FEATURE:
<221> NAME/KEY: MOD_RES
<222> LOCATION: (165)
<223> OTHER INFORMATION: Variable amino acid
<220> FEATURE:
<221> NAME/KEY: MOD_RES
<222> LOCATION: (168)..(169)
<223> OTHER INFORMATION: Variable amino acid
<220> FEATURE:
<221> NAME/KEY: MOD_RES
<222> LOCATION: (171)
<223> OTHER INFORMATION: Variable amino acid
<220> FEATURE:
<221> NAME/KEY: MOD_RES
<222> LOCATION: (174)
<223> OTHER INFORMATION: Variable amino acid
<220> FEATURE:
<221> NAME/KEY: MOD_RES
<222> LOCATION: (176)
<223> OTHER INFORMATION: Variable amino acid
<220> FEATURE:
<221> NAME/KEY: MOD_RES
<222> LOCATION: (178)..(179)
<223> OTHER INFORMATION: Variable amino acid
<220> FEATURE:
<221> NAME/KEY: MOD_RES
<222> LOCATION: (181)..(184)
<223> OTHER INFORMATION: Variable amino acid
<220> FEATURE:
<221> NAME/KEY: MOD_RES
<222> LOCATION: (187)
<223> OTHER INFORMATION: Variable amino acid
<220> FEATURE:
<221> NAME/KEY: MOD_RES
<222> LOCATION: (189)..(190)
<223> OTHER INFORMATION: Variable amino acid
<220> FEATURE:
<221> NAME/KEY: MOD_RES
<222> LOCATION: (192)..(193)
<223> OTHER INFORMATION: Variable amino acid

<400> SEQUENCE: 12

Arg Xaa Phe Leu Xaa Xaa Asn Xaa Ile Xaa Xaa Xaa Xaa Xaa Xaa
 1               5                  10                  15

Phe Xaa Xaa Xaa Xaa Xaa Xaa Xaa Xaa Leu Trp Xaa Xaa Ser Asn Xaa
                20                  25                  30

Xaa Xaa Xaa Ile Xaa Xaa Xaa Xaa Phe Xaa Xaa Xaa Xaa Xaa Leu Glu
            35                  40                  45

Xaa Leu Asp Leu Xaa Asp Asn Xaa Xaa Leu Arg Xaa Xaa Xaa Pro Xaa
     50                  55                  60

Thr Phe Xaa Gly Leu Xaa Xaa Leu Xaa Leu Xaa Leu Xaa Xaa Cys Xaa
 65                  70                  75                  80

Leu Xaa Xaa Leu Xaa Xaa Xaa Xaa Phe Xaa Gly Leu Xaa Xaa Leu Gln
                85                  90                  95

Tyr Leu Tyr Leu Gln Xaa Asn Xaa Xaa Xaa Xaa Leu Xaa Asp Asp Xaa
                100                 105                 110

Phe Xaa Asp Leu Xaa Asn Leu Xaa His Leu Phe Leu His Gly Asn Xaa
                115                 120                 125

Xaa Xaa Xaa Xaa Xaa Xaa Xaa Xaa Phe Arg Gly Leu Xaa Xaa Leu Asp
130                 135                 140

Arg Leu Leu Leu His Xaa Asn Xaa Xaa Xaa Xaa Val His Xaa Xaa Ala
145                 150                 155                 160

Phe Xaa Xaa Leu Xaa Arg Leu Xaa Xaa Leu Xaa Leu Phe Xaa Asn Xaa
                165                 170                 175

Leu Xaa Xaa Leu Xaa Xaa Xaa Xaa Leu Ala Xaa Leu Xaa Xaa Leu Xaa
                180                 185                 190

Xaa Leu Arg Leu
    195

<210> SEQ ID NO 13
<211> LENGTH: 1176
<212> TYPE: DNA
<213> ORGANISM: Homo sapiens

<400> SEQUENCE: 13

```
gagggcatcc ccgtggacag cgagcgcgtc ttcctgcaga acaaccgcat cggcctcctc      60
cagcccggcc acttcagccc cgccatggtc accctgtgga tctactcgaa caacatcacc     120
tacatccacc ccagcacctt cgagggcttc gtgcacctgg aggagctgga cctcggcgac     180
aaccggcagc tgcggacgct ggcacccgag accttccagg gcctggtgaa gcttcacgcc     240
ctctacctct acaagtgtgg gctcagcgcc ttgccggccg gcgtctttgg cggcctgcac     300
agcctgcagt acctctacct gcaggacaac cacatcgagt acctccagga cgacatcttc     360
gtggacctgg tcaacctcag ccacctgttt ctccacggca acaagctgtg gagtctgggc     420
ccgggcacct tccggggcct ggtgaacctg accgtctttt gctgcacga gaaccagctg     480
cagtgggtcc accacaaggc attccacgac ctccgcaggc tgaccaccct cttcctcttc     540
aacaacagcc tctcggagct gcagggtgag tgcctggccc cgctgggggc cctggagttc     600
ctccgcctca acggcaaccc ctgggactgt ggttgtcgcg cgcgctccct gtgggaatgg     660
ctgcagaggt tccggggctc cagctccgct gtcccctgtg tgtcccctgg ctgcggcac      720
ggccaggacc tgaagctgct gagggccgag gacttccgga actgcacggg accagcgtcc     780
ccgcaccaga tcaagtcaca cacgctcacc accaccgaca gggccgcccg caaggaacac     840
cactcacccc acggccccac caggagcaag ggccaccccg acggccccg gcccggccac     900
aggaagccgg ggaagaactg caccaacccc aggaaccgca atcagatctc taaggcgggc     960
gccgggaaac aggcccccga gctgccagac tatgccccag actaccagca caagttcagt    1020
tttgacatca tgcctacggc ccggcccaag aggaagggca agtgtgcccg caggacccc     1080
atccgtgccc ccagcggggt gcagcaggcc tcctcggcca gttccctggg ggcctccctc    1140
ctggcctgga cactgggct ggcggtcact ctccgc                               1176
```

<210> SEQ ID NO 14
<211> LENGTH: 392
<212> TYPE: PRT
<213> ORGANISM: Homo sapiens

<400> SEQUENCE: 14

Glu Gly Ile Pro Val Asp Ser Glu Arg Val Phe Leu Gln Asn Asn Arg
  1               5                  10                  15

Ile Gly Leu Leu Gln Pro Gly His Phe Ser Pro Ala Met Val Thr Leu
             20                  25                  30

Trp Ile Tyr Ser Asn Asn Ile Thr Tyr Ile His Pro Ser Thr Phe Glu
         35                  40                  45

Gly Phe Val His Leu Glu Glu Leu Asp Leu Gly Asp Asn Arg Gln Leu
     50                  55                  60

Arg Thr Leu Ala Pro Glu Thr Phe Gln Gly Leu Val Lys Leu His Ala
 65                  70                  75                  80

Leu Tyr Leu Tyr Lys Cys Gly Leu Ser Ala Leu Pro Ala Gly Val Phe
                 85                  90                  95

Gly Gly Leu His Ser Leu Gln Tyr Leu Tyr Leu Gln Asp Asn His Ile

```
                100                 105                 110
Glu Tyr Leu Gln Asp Asp Ile Phe Val Asp Leu Val Asn Leu Ser His
            115                 120                 125
Leu Phe Leu His Gly Asn Lys Leu Trp Ser Leu Gly Pro Gly Thr Phe
    130                 135                 140
Arg Gly Leu Val Asn Leu Asp Arg Leu Leu His Glu Asn Gln Leu
145                 150                 155                 160
Gln Trp Val His His Lys Ala Phe His Asp Leu Arg Leu Thr Thr
            165                 170                 175
Leu Phe Leu Phe Asn Asn Ser Leu Ser Glu Leu Gln Gly Glu Cys Leu
    180                 185                 190
Ala Pro Leu Gly Ala Leu Glu Phe Leu Arg Leu Asn Gly Asn Pro Trp
            195                 200                 205
Asp Cys Gly Cys Arg Ala Arg Ser Leu Trp Glu Trp Leu Gln Arg Phe
    210                 215                 220
Arg Gly Ser Ser Ala Val Pro Cys Val Ser Pro Gly Leu Arg His
225                 230                 235                 240
Gly Gln Asp Leu Lys Leu Leu Arg Ala Glu Asp Phe Arg Asn Cys Thr
            245                 250                 255
Gly Pro Ala Ser Pro His Gln Ile Lys Ser His Thr Leu Thr Thr Thr
    260                 265                 270
Asp Arg Ala Ala Arg Lys Glu His His Ser Pro His Gly Pro Thr Arg
            275                 280                 285
Ser Lys Gly His Pro His Gly Pro Arg Pro Gly His Arg Lys Pro Gly
290                 295                 300
Lys Asn Cys Thr Asn Pro Arg Asn Arg Asn Gln Ile Ser Lys Ala Gly
305                 310                 315                 320
Ala Gly Lys Gln Ala Pro Glu Leu Pro Asp Tyr Ala Pro Asp Tyr Gln
            325                 330                 335
His Lys Phe Ser Phe Asp Ile Met Pro Thr Ala Arg Pro Lys Arg Lys
            340                 345                 350
Gly Lys Cys Ala Arg Arg Thr Pro Ile Arg Ala Pro Ser Gly Val Gln
            355                 360                 365
Gln Ala Ser Ser Ala Ser Ser Leu Gly Ala Ser Leu Leu Ala Trp Thr
    370                 375                 380
Leu Gly Leu Ala Val Thr Leu Arg
385                 390
```

```
<210> SEQ ID NO 15
<211> LENGTH: 143899
<212> TYPE: DNA
<213> ORGANISM: Homo sapiens
<220> FEATURE:
<221> NAME/KEY: modified_base
<222> LOCATION: (2044)..(2144)
<223> OTHER INFORMATION: a, t, c, g, other or unknown
<220> FEATURE:
<221> NAME/KEY: modified_base
<222> LOCATION: (6609)
<223> OTHER INFORMATION: a, t, c, g, other or unknown
<220> FEATURE:
<221> NAME/KEY: modified_base
<222> LOCATION: (6625)..(6724)
<223> OTHER INFORMATION: a, t, c, g, other or unknown
<220> FEATURE:
<221> NAME/KEY: modified_base
<222> LOCATION: (14153)..(14252)
<223> OTHER INFORMATION: a, t, c, g, other or unknown
<220> FEATURE:
<221> NAME/KEY: modified_base
```

```
<222> LOCATION: (19512)..(19611)
<223> OTHER INFORMATION: a, t, c, g, other or unknown
<220> FEATURE:
<221> NAME/KEY: modified_base
<222> LOCATION: (22595)..(22694)
<223> OTHER INFORMATION: a, t, c, g, other or unknown
<220> FEATURE:
<221> NAME/KEY: modified_base
<222> LOCATION: (27825)..(27924)
<223> OTHER INFORMATION: a, t, c, g, other or unknown
<220> FEATURE:
<221> NAME/KEY: modified_base
<222> LOCATION: (34953)..(35052)
<223> OTHER INFORMATION: a, t, c, g, other or unknown
<220> FEATURE:
<221> NAME/KEY: modified_base
<222> LOCATION: (40783)..(40882)
<223> OTHER INFORMATION: a, t, c, g, other or unknown
<220> FEATURE:
<221> NAME/KEY: modified_base
<222> LOCATION: (49000)..(49099)
<223> OTHER INFORMATION: a, t, c, g, other or unknown
<220> FEATURE:
<221> NAME/KEY: modified_base
<222> LOCATION: (62884)..(62983)
<223> OTHER INFORMATION: a, t, c, g, other or unknown
<220> FEATURE:
<221> NAME/KEY: modified_base
<222> LOCATION: (75528)..(75627)
<223> OTHER INFORMATION: a, t, c, g, other or unknown
<220> FEATURE:
<221> NAME/KEY: modified_base
<222> LOCATION: (87944)..(88043)
<223> OTHER INFORMATION: a, t, c, g, other or unknown
<220> FEATURE:
<221> NAME/KEY: modified_base
<222> LOCATION: (111030)..(111129)
<223> OTHER INFORMATION: a, t, c, g, other or unknown

<400> SEQUENCE: 15
aagcacatac aggtgacatt acagaactga cagttatgcc aggcactgta cttagcccct      60
ataccatcct caaacagctg tatgatgtag attgggtatt aacccccatta ataacaaaag    120
tacagggaac aaagtgactt tccaaaggtc atgccattca aggagggtg aatcttaggt     180
tggacgcagg ctgtctgact ctggagtctg aggtgttaat gctgcctcct ccatgggaac    240
agcccaagtg aaaaacagct gatccactct tcatttactt ggcatctgtg ctaagctggt    300
ccctgagcca agtctgagc aacagaaaca gaagctctgc attaggagct tgtgagcatg     360
tcaatgccgg gtaaaggagt gctggaaacc gctgggatgg ccgccgagca ctaggccgtt    420
gaaggtgggc tctgtgtgac tggttcctct cactctggc ctggctgcct gcaggaagaa     480
gatcaagctg agtgggctgg ccctggacca aaggtgaca ggtgacctct tctacaccca     540
tgtgaccacc atgggccaga ggctcagcca gaaggcccc agcctggagg acggttcgga     600
tgccttcatg tcacccagg atgttcgggg cacctcagaa aaccttcctg agagtgagtg     660
tctggtcaag gtgccggcct tgggggatag tgatggtggg tcctcatatt cagtgagcac    720
tcatggttga gtatttattc gcacccctct tcagtcctta caacacccca tgatgtaggt    780
ggggcatgct cctcatttac agatgggcac atcaaagctc agctaacgct gggaagttca    840
gattcagggt taccctgctg gattcctggg attggggagg gaggagcttc caaaatgggg    900
acaaggtctc tgggcctgtc gggtagctgg tttcctcagg gccccttgca acctctgagc    960
ttattgcatc aggtgcagcc aggcccgtga gcctcctggc aggggtcctc cacacctggc   1020
tgtcttttgc cccctgctgg tcacaggagg agctgcagca cctgcctggg ctgcttctca   1080
ggagggtaca tgaagatccc aggaccgcca gctccatgat aagtggaagg agctccttgg   1140
```

```
agtcaggagc gggagttgag gagtttgagt cctgctctcc agttataggc tatgtgactt    1200
gtgtagatca cctaaccttg ctcttgattt ccttacctct taaactagca ctaaaagcac    1260
cccacaaact gtaaagttag ttgtgatgat tgaatgacac catgggtgtg aagctctttt    1320
gtaaagtgca aaacggtgtg cagtttgagg gtggttaccc ccagtgccga ttctcagagg    1380
gcaacatggc taagggcacg agctggagtt aggctgacct gctgcttcca gccctgtgag    1440
cttgagcaag tcatttaact tcctgagctg cagtttcctc atcagtaaaa tgtgataagg    1500 ataggggttgt tgtaagattt tattaaatgg ggtaataaat gtcaagtatg tagcccatag    1560
tgagtgcttc agagttttttt tcttttgttt ctttcccccc cgccccgaga tggagcctta    1620
ctctgttgcc caggctggag tgcagtggca tgatcttggc tcactgcaac ctccgcctcc    1680
cgggttcaag caattctcct gcctcagcct cccaaatagc tgggactaca ggcgtgcacc    1740
accatgctcg gctaattttt gtatctttag tagagacggg gtttcaccat gttggccagg    1800
ctggtctcga actcctgacc tcatgatgct cctgcctcag cccccgaaag ttttgggatt    1860
acaagtgtga gccccgtgc cctgccaggt tttttttttt tttttttttt tgtaaaacac    1920
ccacagggta ttgctgttgc ctgggctgga gtgcggtagt gcaatcatag ttcactgcag    1980
ccttgacctc ctgggctcaa gtgatcctcc tgcctcagcc tcctgagtag ctgggaatac    2040
aggnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnttttgta ttttaagtag    2160
agacagggtt ttcccaatgt tggccaaggc tggtctaaaa ctcccaacct caggtgatcc    2220
acccacctca gcctcccaaa gtactgggat tacaggcgtg agacaccgtg cccagccagg    2280
aggcttattt tcttgataaa ttacccagtc tcaggtattt ctctacagcg atgcaagaac    2340
agcctaatac atccaggctc agcatcagtg gacccaggtg ggagagctta agatgtcaag    2400
gtctgaatgc cgcttccaca cacctttggg acctagggac tccctctctt tttcttttt    2460 cagtagaaga tgttatcttc tccttttctct gaccagtagt tggtgatggt ttcagagata    2520 gttttttcagt caagatatat ttcagtggct tcactgagcc caagttccct cgcctctcta    2580
ggactttatt tccttgtttc tagaagaggg ataacacata ttttctaagg tggttgtgag    2640
attaagggag ctggtaccgg gtggtgcata aggacaggat agagcaatgg tgagaccact    2700
caaaaagcga aaagttgacc tcgagggtg acacttatca aatcagcaca cagtgggagt    2760
ggaaggaatg tccctcatca gttacaatat ttggagagtg caagttatag aaaacccagc    2820
cctggccggg cgcggtgggt catgcctata atcccagcac tttgggaggc tgaggcaggt    2880
ggatcacgag gtcaggagtt caagaccagc ctgaccaacg tggtgaaacc ccacctctac    2940
taaaaataca aaattagctg ggcgtggtgg tgtgtgcctg taatctgagc tactcaggag    3000
gctgaggcac gagaatcact tgaaaccggg aggtggagtt tgcagtgagc cgagatcgca    3060
ccactgcact ccagcctggg caacagagcg agactccatc tcaaacgaaa aaaaaaaag    3120 aaagaaaacc cagctctaac tggcttaaac agtaagaaga tctattatat tatccatctc    3180
aggcagcagc aagcccagag gtagggact ccaaggttgg ttgatccagg gcttaacgat    3240
gtcatcaaag acccaggttc tttctgtctc ggcacctctg tctgcagggc cagcttcatc    3300
ctaagccaga ttgttcttgt cttgattaca agttggctgc tgggccagca gacgctgcct    3360
gcctccctgt tcatcttcag aagtagaaag tggccttcc ccagtcatgg aatgaaagag    3420
tttcctttct gtctgggatt gcttaggtcc acccacctga agccaatgac tgtcaccagg    3480
aaggtaatat acactgattg tcttaagtca gggttcctga gccagtcttg ggcaaggagt    3540
```

-continued

```
gtgatactgt catgattgtc ttgggctcat cagggcagct ctgcagatga gatcaaactc    3600
caagctacat tattctgaac agtgggaagt aggaaagaga cattttggga gatacaaaac    3660
acaatgtcta tcccatatcc ctaggtccag gtcacagtgt cttggttgga catcaaatgt    3720
agaaaaagaa agactgtcca tccatttatc tacctattca tctggttttt gattttttt    3780
aaattttatt ttaagacatt ctcactctgt cacccagact ggagtgcagt ggtttgatca    3840
tggctcatgg cagcctcaac ctcccaggct caagtgaccc tcccatgctc aagtgatcct    3900
cctacctcag cctcccaagt agctagaact aaaggtgcat gccaccacgc tcagttaatt    3960
tttgcattttt ttgtagagat ggggtttcgt catgatgccc atgctagtct ggaattcctg    4020
aactcaagca atatgcctgc ctttgcctcc caaaatgctg ggattgtagg catgagccac    4080
tgctcctggc tcatctgttt aataatttat gaaacaacta ctgggtgctg agcacggggc    4140
cagggctggg agatctagca gggaccaggc agatctctgc caagtcgttg gtttcttaaa    4200
ggttttgctc ataattcccc ttttcttttc tctttcgttt ttttcttttt ctttctttct    4260
ttctttcttt tttttttttt gagacagagt ctcactctgt tacccaggct ggagtgcagt    4320
ggtgcgatct cagctcactg caacctctgc ctcctgggtt caagcgattc tcctgcctca    4380
gcctcccgag tagctgggac tacaggcgcc tgccaccatg cccggctaat tttttgtgttt    4440
ttagtagaga ctgggtttca ccatattggc caggctggtc ttgaactcct gaccttgtga    4500
tccgcccgct tcggcctccc acagtgctgg gattacaggc gtgagccacg gcgcccagcc    4560
agtttcccctt tcaatgaggg cctccctgac ctccatactc tactcctcca cctgcccac    4620
tcagctctac tttttcttcc ccatagcact caagacctcc taacatacta cgtaagttat    4680
ttatttacta ggcttactgt gtattgtctg tcttcctcta ctagaatgta aactccatga    4740
gaatagaaat ttttgccttt ttatttagtg tggtgtctgc agcccctggc ttagtccctg    4800
gcatacaaca gtcactccac ccacagttgc tgaataagtg actaaaggtc cctgccctca    4860
tattgttatg agggagtgtg catgttgtta gagaaaaatc tgaggcacaa taaaattta    4920
tagagtttaa gttttctttt ttaagcaatc cacgaattgg ggtagtttca gaggtagttt    4980
ttcagtcatg acgtatttca atggcttcac tgagcccaag ttctttcacc tctctaggac    5040
tttatttcct tatttctaga acggggataa cacatagttc ataaggcagt tatgagagta    5100
agggagctgg tatggggtga tgcataagga caggatagag cagtggtgag accgctcaga    5160
tgacaaagcg tcagagacca gtatttacga cggaaatgtg gaagcatgat aaagaaatta    5220
tttgggctgg gcacaatgac tcacaactaa taaaactttg ggaggccaag gtgggaggat    5280
cacttgactt gcagaaggtc aaggctgcag tgagctgtga ttttgccact gcactccagc    5340
ctggtcaaca gagtgagacc ctggctcgaa acgttatttg attggttaca gttatacagt    5400
tgccttattt ggtctattcc atttgaaagt tcctagttct ataattttaa gtttgttggc    5460
tgtttctgat tggttaagct taagttttgt tttcctttaa tacagttaag tgccccataa    5520
tgacattttg gtcaaggaca gaccacatat acagtggtgg tcccataaga ttataatgga    5580
gctgaaacat tcctattgtc tatggcgtag tggtcctgat gttgtagcgc aatgcattag    5640
ttatatgttt gtggcaatgc tggtgtaaac acacctactg cactgccagt gatataaaag    5700
aatagcacat acagttatat atagtacata atatctgata atgataatac ataactatat    5760
tactggttta tatatttact atattattta tctttatttt attttttgaga cagagtctca    5820
ttctgtcacc caggctggag tgcagtggcg cgatcttggc tcaccgcaac ctccgcttcc    5880
```

```
tgggttcaag tgattctcct gcctcagtct cctgagtagc tgggattaca ggtgtgcacc    5940
atgacaccct gctaatatgt tttgtatttt tagtagagat ggggtttcac catgttggcc    6000
aggctggtct tgaactactg acctcaagtg atcaccccgc ctcggcttcc caaagtgctg    6060
ggattacagg cgtgagccac cacgcatggc ctatttataa ttattttaga gtgtacgcct    6120
tatacttata aaaaaaagct aactgtcaaa cagcctcggg caggtccttc aacagatatt    6180
ccagaagaca ttgttatcat aggagatgac agctccgtgc atattattgt ccctgaaaac    6240
cttctagtgt ggaagtggaa acagtgata ttgatgatag gacccagtgt aggcctaggc    6300
taatgtgtgt gtttgtgtct ttgcttttaa caagaaagtt taaaaagtta aaataaaata    6360
caaaaatttt taaatagaaa aaagctgccc aggaacaatg gctcacacct gtaatcccac    6420
cattcgggga ggccaaggtg ggtggattgc ttgagctcag gagttcaaga ccagcctggg    6480
caacatggtg aaaccccatc tctacaaaaa atacaaaaat tagccgggtg tggtggcatg    6540
cggctatagt tccagctaat cgaggggctg aggtgggagg atcactgggg gggaggtggt    6600
tgaggctgna gtgagctgtg attgnnnnnn nnnnnnnnnn nnnnnnnnnn nnnnnnnnnn    6660
nnnnnnnnnn nnnnnnnnnn nnnnnnnnnn nnnnnnnnnn nnnnnnnnnn nnnnnnnnnn    6720
nnnnatattc ttaaaaaaat tttttttttat ttttgagaca gaatttctct cttgttgccc    6780
aggctggagt gcaatggcgc tatctcagct caggcaacc tccacctcct gggttcaagc    6840
gattctcctg ccttagcctc ccaggtacag gcgcccgcca ccatgctcgg ctaatttttg    6900
tatttttagt agagatgggg tttcaccatg ttgtccaggc tggtcttgaa atcctgcctc    6960
aggtgatcca ccccctcgg cctcccaaag tgctggaatt tacaggcgtg agccactgtg    7020
cctggcctcc tttacatttt tttaaattta atttttaattt tttaattttt aatttctcat    7080
atatatatat ttttaagact agccaagtga agcagtggga gtggaaaagg aactggtttt    7140
gatcaatagg tgtaaacacc actgcactgg gaccagccta ttttacattc ctgttagcag    7200
tgatgagggt tcactttctt tgtagcctca acaatatgtg tcgttgccca tctttttttt    7260
tttttttttt tttttttttg agatggagtc tcactctgtt gcctaggctg gaatgcaatg    7320
gcatgatctc agctcactgc aacctccgcc tcccaggttc aagtgattct tgtgtctcag    7380
cctcctgagt agatgggatt acaggcgtcc accaccacgc ccggctaatt ttttgtattt    7440
tcagtagaga tggggtttca ccatgttggc caggttggtt tcgaactcct gacctcaagt    7500
gatccgccca cctcggcctc ccaaagtgct gggattacag gcatgagcca ccgcgcccgg    7560
cctgcccatc ttttttttgt tatagccatc ctagtggatg taaagttttt ttgtgatttt    7620
gatttgtgtt tccctactga tcaatgatgt tgagcatctt ttcctgtgct tattggcttt    7680
tggtatatct ttggagaaag gtctattcag gtcctttgcc cactttaaaa ttaggttatc    7740
tttctattac tgagatgtaa gagttctttta tgttctagat ataagtctcc tacatatgat    7800
ttgtaaaaat tttccttcca ttattgggtt gtctttcact ttcttttggt gtcctttagt    7860
gcacaacagt ttttaatatt gaagtccaat tttctatttt tctcttttgc cacttgtatc    7920
ttggtgtcat gtttaaggaa ctattgccta atctcaggtc acaaagattt acacctgtgt    7980
ttccttctt cccttccttcc ttccttcctt ccttctttcc ctccctccct ctctccctcc    8040
ctccctctct ccctccctcc ctccttccct tcctccctcc ctccctcctt ccttccttcc    8100
ttccttcctt ccttccttcc ttccttcctt ccttcctttg tccttctgac ggaatcttgc    8160
tctgtcaccc aggctggagt gtagtggcac gatcttggct cactgcaacc tctgcctcct    8220
gggttcaagc aattctcctg cctcagcctc ctgagtagct gggactacag gcacacacca    8280
```

```
ccatgcccag ctaattttg tattttagt agagacgggg tttcaccaca ttggccagga    8340
tggtttcgat ctcctgacct cgtgatccac cgccttggc ctcccaaagt gctgggattg    8400
caggtgtgag ccaccatgcc cggcctgtgt tttcttagag ttttgtagtt ttagctctta    8460
tagttagatc cttgatccat tttgagttga ttttgtatat agtgtgagat atccacctgg    8520
tgttgtaaat tgcccagaag tgggtatgct tctaaatctg gctgttaggg attactagag    8580
gtgaccaaag tgattttttt ctttgtttct ttttttttt ggagacagag tctccgtcac    8640
ccaggctgga gtgcaatggc ttcatcttgg ctcagtgcaa cctctgcctt ctggtttcaa    8700
gcagttctcc tgcctcagac tcctgagtag ctggtattac aggcgtgtac caccatgctt    8760
ggctaatttt tgtatttta gtaaagatgc agtttcacct gttggccagg cttttctgga    8820
actcccggcc tcaagtgatc catctgcctc tacctcccaa agtgctggga ttacaggtgg    8880
gagccaccgt gcccagtcct tttctcagaa tttatttgtt ttttttgtt ttgtttcatt    8940
tttgagatag ggtctcactc tgtcagctag gcaggagttc agtggtgtga tcattgctgc    9000
agccttgaac ttctggactc acgtgatctt cccacctcag cctcctgagt agctaggatt    9060
acaggcatgt gcttccacac ctggctaatt tttaatttt ctaggactta tttgtccatt    9120
cttgcaaagc agggtacaac atgcctatct ctacctacct ctcttccctt caagggactc    9180
cagccaaaat ccttgaggct ctcgggctga ctgtgggtgc tgttgcctga tctgcctcag    9240
tcatgctgca tgatcaaaag tgtccgtttt ctgcttcttg aactttatt cactttgggt    9300
gtcagtcttc ctctgcagtg tcccaagaac acagaattag accaggaatc tgtgttgcca    9360
tagtgtgtgg aaagaggcag acttccaact ccgctatgtg ctgttgggtg attgaagctt    9420
aattttcttt ctatctttct ttctttctt tcttttttt tttttggag atggaatctc    9480
gctctgttgc ccaggctgga gtgcagtggt gcgatctcac ctcactgcaa cctccgcctc    9540
ccaggttcaa gcgattctcc tgcctcagcc tcctgagtag ctgggattac aggtgcatgc    9600
caccatgccc ggctaatttg tgtaatttta gtagaaacag tgtttcacca tattggtcag    9660
gctggtctcg acctcctcac ctcaggtgat ccacccgcct tggcctccca agtgtcggg    9720
attacaggcg tgagccaccg tgcctggcac ttaatttct taatacctca attacccat    9780
atggtaaaat gggactagta atccataccct tatagcgctg ttgtgaaaat gaatgaggg    9840
taagcagata aaatttcaga ctacggatgg gattgttact acattctgaa cctggctttg    9900
ctgttatttg ctatgtgacc ttatcttctc tggatctcca ttctttccaa gtctataaaa    9960
caaagtggac aattgtcaac ctttcttcca agagcaatg atttaaggat caaatgatgt    10020
catttaacaa aaatatgaag agctcaacaa atgaggaact cattattatt attacaatta    10080
ttattatttt agaaataggg tcttgttctc ttgcctaggc tggagtccag tggtataaac    10140
acagctcaat gcatcttcag cctcctggat acaagtgatc ctcatgtctc atcccctaa    10200
gtagctggga ccacaggcat gtaccaccac gcacggctaa ttttttattt tttatttta    10260
ttttttgaga cagtctttgc ttgtcgccca gactggagtg cagcagcgca atcaccgctc    10320
actgcaacct ccgcctcctg ggttcaagtg attctgctgc ctcaacctcc caagtagctg    10380
ggattacagg cctgtgccac catgcccggc taattttt gtattttgg taaagacggg    10440
gtttcaccat gttgcccagg ctgatctaga acccctggcc tcaagtgatc ccctttctt    10500
ggcctcctaa agtgctagga ttacaggcgt gagcctctgc acctggcctc ggctaatttt    10560
ttatttttg tagagacagg ttctcactat gttgccaggg ctggtcttga actcctgggc    10620
```

-continued

```
tcaagtgatc ttcccacctc agcctcccaa agtgctgaga ttacagatgt gagccactgt   10680
gcctggcctg gaactcatta ttgaagcatt cactagtatc aactttgggg ttacctggcc   10740
acatcctctg acctacctat aagggtatca cagctaacgg agcctctgtt tctcagaatt   10800
taggcagaag cagttcaatt tatcacaaac tactctatat ccagcataag tgcccaaata   10860
aaacaattgc taaagttctt taggcattta ctgtttgtta gttagatatt tagtcctcac   10920
tacaaatctg tgatacaggt attattttta ttaaccccat tttatagaag agaaacctga   10980
agctcagaga tgctaagtaa cttgtgcaag gtcacacagc tagtaaataa agggcagagt   11040
aaagatttag tttcacattg gactccagaa cctttctact gggactcatg ggaatagtgt   11100
ggatgtccct gaccttcagt ggcccagggc tctcctgggg gaatccagcc atagacaaga   11160
caccagcgag agcccaatcc taagattttg tttgtttgtt tttgagacaa ggtctcactc   11220
tgtcaccaga ctggagtgca gtggcatgat caatgctcac tgcaaccttg atctcccagg   11280
ctcaagcaat cctcccacct cagcctcctg agtagcttgg actacaggtg cacaccacca   11340
cacctgacta attttaaaat tttatttaat taattactta ctattatttt ttgagacagg   11400
gtatcacttt gtcacccaag ctggactgca atggtgtggt ctcagctcat tgcgtcctcc   11460
acctcccagg ttcaagtgat cctcccacct cagcctctgg agttgcaggg actgcaggtg   11520
tgcgccacta tgctcagcta atgtttttat tttttgtata gatggggtct cactatgttg   11580
ccagggctag tctcaaactc ttggactcaa gcgatcctcc tgtcttggcc tcccaaagtg   11640
ccgggattac aggcataaac caccacaccc aaccctaag gtgttttgc tgaatgtgac   11700
catgtcagag gcaggaaagg gaagcatcat ggggttagga aaggaacact gagcagggag   11760
acaaagaaaa tgggatcatt ttgtgagtgt tcgctgtgtg tgtatgtgtg acaattctca   11820
gagccagcct ctcaggtggt tgagaccaca gtccccattt cccagatgag ataatggagc   11880
ctcagagagt ttctgcagca cagctagtgg aattagaatt tgaacccggc tcttccagac   11940
tccaggtgct tcacaaccat cccaaaccta gtcatttgca gtttaccttc atgattttac   12000
catttccctt tgccatagct agtgttattt acttaataat cccttttgaa tcagtctgct   12060
taaaaaaaaa tagcttcatt ctaaagtgta atattcttgg aatatcgggt ttgctgttac   12120
ccacccccac acgttataca tatacatgta tgtttctaat acatatatat gtacgtatat   12180
acgtgtatcg tttttttgtta ttttttttgt tgttgttagt ttttttaga tggagtctct   12240
ctctgtagcc caggctggag tgcagtggtg tgatttcggc tcactggaac ctctgcctcc   12300
tgggttcaag cgattctcct gcctcagcct ctggagtagc tgggattaca ggcacccacc   12360
actacacccg gctaatgttt gtattttag tagagacagg gtttcaccat gttggccagg   12420
tgggtcttga actcctgatc tcaagtgatc cacctgcttt ggcttcccaa agtgctggga   12480
ttataggtgc gagctactgc ggctggccaa tgtatgtttt taatacacat tcaaataacg   12540
aataactatg aaacctgaaa aactgctcca tgttacttcc tgaacccatc ttgagtgctc   12600
acatgctgtg cataccacat attgggaaac actgctttcc ctggcttcca gcccagctt   12660
aatcactgtc ccatcctatg cttcgcttta tttgtctata aatgttgggg ttgggggttg   12720
atgccaaaga ccttttctgt tgtcattaac atggacacag ctctaagagg tcttggcatc   12780
ttgggctggc tctcctttta gttcagaatt tggattttta tccaactact cagagtgatc   12840
aagccttcct tatgaatgaa ctcgttggtc aaactcataa aaggctgatc gataaaacag   12900
gaatgaatgt atgaattgac actaagtcat tagcatttca cgggaatgga ttctccgtta   12960
gtggaagagc acatgtcctt tctggcactg atgtgtgctt gggaaactta ctgagctaac   13020
```

```
tggcccatgt aacacagagg cccttttggtg cagtggaaaa ctgttgactt tggagattat    13080
cttgagtttg aatctgagcc tgcctgtaag aagctggcta actgaattgc tttgcttctt    13140
ggacccttac catttataaa atggggacca ttgtactcac cctttagggt tattgcatgg    13200
attaaatggg attctctata gaaatatttg gcacaaagta ggtgtaaatt tgcacgctag    13260
tgggattgtt tgtgagggaa attgtcattt gattatcaaa gacttaggag caggaacagt    13320
gtctaattca gggactgcaa atggaaatgc cagctgaggc caggcatttg ctaataattg    13380
ggtaaagcag gcaggtgta gaatagcaat gtctgggaat taaaagagag gtgaggacgt    13440
gtatgacctt gagaaggcaa gccctggcaa aaggggatgg cctccactca gctacagtca    13500
tgcctagatc ttctaacttt ttatttttat tttattttt tgagacgag tcttgctctg    13560 tcacccaggc tggagtgcag tggcgcgatc tcggctcact gcaagctccg cctcccgggt    13620
tcacgccatt ctcctgcctc agcctcccaa gtagctggga ctacgggcgc caccaccat    13680 gcccggctaa ttttttttt gtattttag tagagatggg gtttcaccgt gttagccagg    13740
atggtctcga tctcctgact ttgtgattta ccctccttgg cctcccaaag tgctgggatt    13800
acaggcttga gccaccgcac ctggccgatc ttctaacttt ttaaagagaa gcaagacatc    13860 tggatttta tgtgataact cctgattta aactggcacc caattataat ttacaacact    13920
ataagggtca acattgccag cagagcaaaa catggtgggg ggcaactgct ggtcaccggt    13980
gtgcagcctc tggtctaaaa tcatcttgt atttcttctt gctttacgca ttgtcccagc    14040
acagtgctgt tgtatagtaa atatccagta agtgggtgta gaatgaataa accaatgcag    14100 ataacctgt agagaggccg ggcacagttg ctcatgtctg taatctcagc acnnnnnnn    14160 nnnnnnnnn nnnnnnnnn nnnnnnnnn nnnnnnnnnn nnnnnnnnnn nnnnnnnnn    14220 nnnnnnnnn nnnnnnnnn nnnnnnnn nntagtccca gcactttggg aggccaaggt    14280
gggtagatca cctgaggtca ggagttcaag accagcctgg ccaatatagt gaaaccccgt    14340
ctctacaaaa ataaaaaaat tatctgggca tgattgcagg tgcctctaat cccagctact    14400
cgggaggctg aggccggaga attgcttgaa cctgggaggc ggaggttgta gtgagccgag    14460
atcatgccat tgcactccag cctaggtgac ggagcaagat tctgtctcaa aaaaaaaaa    14520 aaaaaaaag aaaaagaaa agaaaagaa acaatgaatg agtgtgaggc tcatggtagt    14580
attggttcct gagagtagcc aaccttattg gtcatcccag ccacgaagtg aaatggtacc    14640
cctggcttgg gccaatgaat gaggaagaat aatggcaaat gggggtctat gcctccaccc    14700
tccaccacta gggaggtctc aagcttgaaa tccagtgacc aggtttttag gtcctggacc    14760
tggccagtcc tcctacagtc aagtagataa gtggagggtt tggtccgttg ggctacggag    14820
atagtgatca aggccgttac tctgcaatca gactcagaaa tggcctctca gttacttctc    14880
catttgtggg tcttttggaa gagcagagaa gaggaaggaa tttaggtctt ctcaccctct    14940
gggctgcctg tccctgctcc ctgagccatg gagggctggg gtggaatatg gggaataaat    15000
ctgtactttt tttttttttt tttttgaga cagagtctcg ctccgtcgcc caggctggag    15060
tgccgtggcg tgatctctgc tcacagcagc atctgcctcc cgggttcaag ttattcttcc    15120
acctcagtct cctgagtagc tgggattaca ggtgccacc accacgcccg gctaattttt    15180
gtatttttag tagagacagg gtttcactgt gttgggcagg ctggtctcaa ataccctgacc    15240 tcaggtgatc cacccgcaca tgcctcccaa agtgctggaa ttacaggcat gagccaccgt    15300
gcccggtcct accaatctgc acattttaat tgacaagggt caccctccac tcatgtgcca    15360
```

```
ggcatagttc tgagaagcat cccacaagga tgcctctgag ttcaccctga caagtccact    15420
agctcttggc agagacatct ggcaaattca aggcttgaga catgctggcc tctctttaaa    15480
gtgcagcaaa ttttgtctag agcttggtca gttaaaattt tgatgttttg ttttgcatta    15540
atttcaattt ttaagaaatg ttgcattaaa atgttattta tcttgaatag taaatttctt    15600
agtgtcccct taatttctta gtgtgtctga gttgagagcc tcccctgcct gattctagtc    15660
cagaccctgg ggtgacagaa gactggtggg agatgggagg tgaggagggg agtgttggtt    15720
ggagaggatg atctacagag tgctggagag actctgtatg gagcttttca tgctgcctgt    15780
ttgccagccc tgaagctatg ccttgaggtt gggcaaggtg gcatatccta gatcagagat    15840
cctcaactgg ggccattttt ctccccagag gacatttgga aacatgtgga gacattttg     15900 atcatctgcg ggggtgggga gagggctac tgacatctgg tgagtagaga ccagagggac      15960
cattaaactt tctacaacgc ccaggacagc ccctccacaa taaagagtta tttgacctca    16020
catattaata gcacaaagtt gaggaacctt gatctagatc cacagcacag aagaaaggat    16080
gtagattttt cacacattaa agatgagaaa gcttgtgcct gtaatccctg tgactcagga    16140
ggctgtggca ggaggattac ttgagcccag gaattcaggg ttacagtgaa ctatcatcgc    16200
agcactgcac tccagcctgg gtgacagagc aagattttgt ctcttaaaaa aaaaaagat    16260 gaggacaggc acagtggctc atgcctgtaa tcccagcatt tgggaggcc gaagtgggtg      16320 gatcacgagg tcaggagttc aagaccagcc tggccagcat agtgaaaccc catctctact    16380
aaaaatacaa aaaattagcc agctacttgg gaggctgagg caggagaagc gcttgaaccc    16440
gggaggtgga gcttgcagtg agccaaaatc ttgccattgc actccagcct gggcgacaga    16500
gcaagactcc gtctcaaaaa gaaaaaaaaa aagatgaga aagaggaagg gagagaaaaa      16560
agagagagag gaaagaaaga gagaaggttt tggagtcaaa aagacttaga aattccagtt    16620
cttccacttc ccatggaacc ttggcaagtt gccttctctc tttctctgaa tctcacattt    16680
tgcctctgtg aagtagggggt ggtacctggt ggagatgatg cggagatgag ggtgaggggt    16740
gtgttgcaca ctatgcccct aggatgggtg agagcttggg agcactgaac ctcccttcc      16800 cctcttgttt cttccccca ttgtctccca ccagctccct gggatctcca cttcactctc      16860
tgggattcca ccagcaggag gctactcctg gagttaaggc gtgttgttca gactggggca    16920 ttttagggg cataaataat aattatgcct ggacaatgga cataacatct agggccttct      16980
gaagcaaacc agggtgtggg gtacccaaac aaggcagtag gccccaggag gcaggtccct    17040
gcagtcccag cagagagcag ggcacagggt tgagaagact gagcaaactt cattatcagc    17100
tcctttgtcc cccactctgt cctggagcaa tcattctggc ctcttcccac ttccccaaaa    17160
acccagtata aaggctgctt ctggcccctg aagccagagg cactgagagt ggaggtctca    17220
gactcttgga aggtgagttc ttttctggct gcccaggcag gaccagtgta ggccctggga    17280
agaagcagca cctcataggg caaacacgta ggaggcctgt ccttaggaac atcatagcta    17340
agcagacctg tccccgcagg ggcaggagtc tgggctaagg gtgatactgg agagcagcaa    17400
cggagactga aagacaaatg aaatttggta cctgagttat ccctcccacc attccttttc    17460
tagactctcc agctcagggt ctgttcatgg caagaggaga aagcaatctt gtttgctctt    17520
taatcaaaca attaaacaaa tattccctct atactatgtg ccaggggcta tactagacac    17580
acaaagacag ccccaagaag gacggtggag tagtgtcctc gctaaaagac agtagatatg    17640
caatgcctct tgctcctgcc ctttctcctg ctgggaacag tttctgctct tcatctgggt    17700
aagtctctcc cttccctcct catgcgtctt tccctttttt ccttttttcct acactcccct    17760
```

```
cccccccgctt ttatttgcac tcatgaggcc aggaccacag ccttccctct ttagctgata    17820
cagctcatct ccggtaagat atcacttgga ctcagaactg taacctggaa cttctcttt     17880 tttgtttgat tttttttgt tgttgttgtt tttgttttt tttttgttg tttttgttt        17940 tgttttgaga cggagtctcg ctctgttgcc caggctggag tgcagtggcg cgatctcggc    18000
tcaccacaaa ctccgcctcc cgggttcaag caattcttct gcctcagcct cctgagtagc    18060
tgggactaca ggcacatgcc accacgcctg gctaatcttt gtattttag tagagatggg     18120 gtttcaccat atttgccagg ctggtctcaa actcctaacc ttgtgattcg cccgccccgg    18180
cctcccaaag tgctgggatt acaggcgtga gccaccgcac ccggcaaact gtaacctgaa    18240 cttcagaag gaaaaccac ccacctgtta agatgaaggg ctggtgactg ccccaggctt      18300
ctcacacgtg ctttctccca ccttcaaaac acacactcgt ggtgtcggcc agaagtcagg    18360
ttcttgtcca tttgtgggtg tgacccgaga gatctctcct tacctaacac caaggaaatc    18420
ctccagtctt gtcttcaggt ggaattccta ggaaagctcg agcgacgttg ctggagctgt    18480
ccacggtgct ggaactagga agctcttgac ctgatggcag gttacctctt cttcccagag    18540
aatgatgccc cccatctgga gagcctagag acacaggcag acctaggcca ggatctggat    18600
agttcaaagg agcaggagag agacttggct ctgacggagg aggtgattca ggcagaggga    18660
gaggaggtca aggcttctgc ctgtcaagac aactttgagg atgaggaagc catggagtcg    18720
gacccagctg ccttagacaa ggacttccag tgccccaggg aagaagacat tgttgaagtg    18780
cagggaagtc caaggtgcaa gatctgccgc tacctattgg tgcggactcc taaaactttt    18840
gcagaagctc agtaagtag tagggaggct actgcggagg acctggggga aaagagagta    18900
cattcagtct tctgttccct attcattag gctagtggtt ctcaaagcct cgcatgcatc     18960
agaatcacct ggagttgttg ttaaaacaca gctttctggg cctcacctgc acgacttctg    19020
atttaggagg gctgaggtga agcctgagaa tttgcattta caacaaatcc ccaggtgatg    19080
atgatattgt tggtctgggg agaaccaccg atttaaacaa aaggctttgg tgttagaaac    19140
gcctgtgtta aattctggtt ctgccttta ttagctgtgt tacctgggca agttgctttg     19200
cctttcaaag ctttagcacc ttcatttgta aaacgaagat atatagcacc aacttcttag    19260
agttgtggtg agcattaaat gagataatac atgaaaagtg tttggaatag tcactgggct    19320
gtaataaact ctcaataagc ggtggttata attattatga gtattatcat ttcctgtagg    19380
attgtcctga cagctaatta agaagcaaaa gataggatta agggaggcaa gtaggtttat    19440
ttttaacctg aaaagggatg ccgggctctt gcctggagac tcagaaactt gaaataaatg    19500
agagggaatt cnnnnnnnn nnnnnnnnn nnnnnnnnn nnnnnnnnn nnnnnnnnn         19560 nnnnnnnnn nnnnnnnnn nnnnnnnnn nnnnnnnnn nnnnnnnnn ngaattctct         19620 gttagcacat agccagaaca tctagaaggg gtggtaggag tggggattag aggttccagc    19680
tggaggcaat ggcacttgca aaggctttgt tgaagtggcg taagtgtgga ggtggagcat    19740
tcaggaaagg agagcttcag cttcagtgtg gctggagtgc tgggtgtgaa gagaggtgaa    19800
gatgaggctt ggaggctggg cagattttgc tccaaaagag cttggtgaac tgtgataagg    19860
agtttggatt ttctcctact aaggacaaca gcaaactatt gaagagttta aatcgttcag    19920
tgacaatgac acgtttgcgt tttggtggct cactcgagct gccagccagg tagacagtgg    19980
cagaagatgg aagataaagc actaaagggt gatgaggcag gaagccagtg aggagagaaa    20040
ggggacgatg tgagtgacag taaatcattt gttgggttgc tattgtgtgc taagctctgt    20100
```

```
gctaaattct tcacgtgtat tatttcagct aatccatcta acaactctgt aaggcaggta    20160
caatcgttcc cagctgaaga agctgaggct ctcaaaagct agtaacttgc ctaagttcat    20220
gcagcatgca agttgtccag ccaggattct aacttagaca ccagaggcca cttttaacca    20280
ctgctctagg actgggggaa atggtcccta gtgagatatg tgtcgagttt catatttcat    20340
tcaacaatat tgttggcctg ctacatgtga agagctgtgg aaagcgccca aagtgagtta    20400
gatccctatg agcaagtggg atggggtgg agtggacagt aggagggctg aacacacat     20460 aaaagggtat aagaaataac aattaggccg gccaggggtg gtggctcacg cttttaatcc    20520
cagcactttg ggaggccgag gagggtggat cacttgaggc caggagtttg agaccagccc    20580
ggccaacatg gtaaaacccc atctctacta aaaatgcaaa aattagctgg gctggtggtg    20640
cacgcctgta atcccagcta cttgggaggc tgaggcacga gaatcacttg aacccaggag    20700
gcagaggtta cagtgaactg agattgcacc actctactcc agcctgggag acagagtgtg    20760
accctgtctc aaaaaaagaa aacaaaacaa gtaggtactt tctgccatag ggaggattca    20820
taaactgcta gtcctcaggt gcattttgc ttatcagttt taaaaatcag agaatgtctc      20880
aaagaattag gatgtcagct tcttttgaaa atttgggcca gaagcggtgg ctcacgcctg    20940
taatcccagc actttgggag gctgaggtgg gtagatcacc cgaggtcagg agttggagac    21000
cagcctgacc aacatggcga aaccccgtat ctactaaaaa tacaaaaatt agctgggctg    21060
gtggtgcatg cctttagttc cagctactca ggatgctgag gcatgagaat cacttgaacc    21120
cgggaggcag gggttacagt gaaatgagat tgcaccactg cactctagcc tgggagacag    21180
agcaagaccc tgcctcgaaa aaaagaaaaa gaaaatttgg aagatctgac aacagttgac    21240
ctgcattcct gctcggcaac agcctgatgg tggatgggca gaggctcagt tgtctgccaa    21300
acctcccatc actgatgtct tccctcgctg tcatcatctg cttgacatgt aggcatttgg    21360
tgtgtgcctt ctgctctggg tgcccagatg aattggatgc tatatgagaa acattctgt     21420 aaatgtcttg tggtaggcaa cctcaaagat cactgggcc tccaatgatc cctccttcct     21480
ggtattcatg cctgtgtata atcctctccc ttgagtgtgt actacacctg gatacttgct    21540
tctaataaac agaacacagc aagggtaatg ggatgctact tctaaggtta aattacaaga    21600
gtgtaaagtc tgtcttgttt gtttccctct cttgatcttc ctctcattct ctctctctcc    21660
ctctctctca ctttcttact gtcttgtcct tcccttttgtt tactctgatg aagcaagcta   21720
gcaagcatcc atgttgtgag ctgacctatg aagaggccca tgtggtggta aggaactgag    21780
ggcagcctct acccagcaag gaactgagtc actcatcata tgggtgagct tggagacaaa    21840
tccttcccca cttgagcttt cagatgacgg cagccctggc tgatgctttg caggcttgtg    21900
agagaccctg agacagaaca ctcagctaag ctataccta tctcctgaga tagagtataa      21960
tacatgtagt tttaagctac tatgttttgg gataatttgt tactcagcaa tagataacca    22020
atacatatac catgtacata actgtttcag ttgtctgaga ctatatttag tcattttaca    22080
cctacatcaa gaatgtgtca ggcaccattc caggtacttg gaatacatca attaacagaa    22140
taggtaaaga ggccaggcat agggctcaca tctataatcc cagcactttg ggaggcccag    22200
gtgggaggac tgcttgagcc caggagttga gaccagcctg ggtaaaatag tgagacactg    22260
tctcaactaa aaaaaaaaaa aattagttgg gcacagtggc acatgcctgt ggtgccagct    22320
gctcaggagg ctgaggtggg aagatcgctt gagcccagga gtttgaagct ccagtgagcc    22380
acggtcacaa aactgcactc tagcctgagc aacagaaaaa gacccctgtctc caattaaaaa  22440 aaaaaaaaaa aaaggaaag aaagaaaaaa ataggtaaag atccttgatt cttgccctct      22500
```

```
tggaacttct attctagagg gggatggttt ttcacagtag aagtctgtgt tgacagcgct    22560
gtttaaagct ccttcagcat ctggggaaaa ggttnnnnnn nnnnnnnnnn nnnnnnnnnn    22620
nnnnnnnnnn nnnnnnnnnn nnnnnnnnnn nnnnnnnnnn nnnnnnnnnn nnnnnnnnnn    22680
nnnnnnnnnn nnnnatttt tagagatagg gtcttgctat gttgcccacc aggctggtct    22740
tgaactcctg ggctcaagca atcctcctgc ctcagcctcc tgagtagctg ggaatacagg    22800
tgtgcaccac catgcctggc ttatttcata tatatatatt tttatatata tgtatattta    22860
tatatataaa tatatatata atttctgtat ataaataaat aaatatatat atatatatat    22920
ttttagagat agggtcttgc tatgttgacc accaggtctt gaactcctgg gctcaagtga    22980
tcctcctacc tctgcctttc aaagtgttgg gattacaggc gtgagccatg gcacctaact    23040
gagttatttt taccacacga agcataggac atacatccaa aaatgttctg agctgagcaa    23100
gagcctggag gcaagtgaat ctgaactttc ccgtctttga agaaaccagt ctctctccaa    23160
agtcacatag ttagtgtcac tcccccaag aactgcatga gctgggacaa tcagagggca    23220
gtggaaggtc tggggctcag gggcgccccc tgctgtctcc ccagggtctg tcccttacg     23280
caagagcctc tgctccccca ctttcctgtg gagcctcctc accatgggca tgacccagct    23340
gcggatcatc ttctacatgg ctgctgtgaa caagatgctg gagtaccttg tgactggtgg    23400
ccaggagcat ggtgaggcac cgctgaggcc cctgggggtt gggggcacag gcgggtcacc    23460
ctggctgagc tcccctcacc atacgttccc ctacccacag agacaaatga acagcaacaa    23520
aaggtggcag agacaggtag ggctatgaaa gcagggccct ggctcacgcc caccccactg    23580
caacccgctt ctcaggggc gggactcctc taggcctggg cccacccagg taacccttt      23640
gtgggatgta agagtctggg ttcagaggaa ggctattttg gtgctctctg gcctccgctg    23700
gaagggggtga tagtgtccac tgagtgccag ttcctgaccc cactgccctt cccatcctgc   23760
ccagttgggt tctactcctc cgtcttcggg gccatgcagc tgttgtgcct tctcacctgc    23820
cccctcattg gctacatcat ggactggcgg atcaaggact gcgtggacgc cccaactcag    23880
ggcactgtcc tcggagatgc caggtgacct gcctgtacag ggatggtgac agcaagtggt    23940
caggcagtgc ttttcatttt ctctgtgcgt ttacatccag cagcttgttg ctttctccca    24000
agaaccctag gagatcaggg gtacctcccc attttacaga tgaggaaact gaggctagga    24060
agggacctgg cttgcttaat aataagaata gctaatgcag agtgctgact gtgcacttgg    24120
caccttgcct tgtttagtcc tacaacacct ctttgaggta gatgcgttaa tatcttcatt    24180
ttgcagttga ggaaaccgag gtacagggtt gcacagttag gtcattcacc caagatcaca    24240
cagctttcag tggcagcctc cagaacctgt gttataaggg tacacgctaa agtcttgtta    24300
gggctagaat aggtagagtt ggtatattag atatttattg ctgtataaca aatcacccca    24360
aggcttggca tttaaaaaca acaaacactt ctcatctcat acagtttctg acagtcagaa    24420
atcagggaga gactcagccg gctgattctg agtcacagtc tctcatgaag acatagtcag    24480
gctgtcagcc agggctgcag tcatctgaag ggctgactgg ggttggagaa tctatgtcag    24540
ttcaattacc cccatggcct ctccataggg ctgctcagga cacagcacct gctttccctt    24600
gagcaagagg gctaagcgac agagaccccg tatcttctct cacataatct cagacgtagc    24660
ataccatcac ttctgttacg ttctattata ggcacagagc aaccctgata tactgtggaa    24720
ggagactgga caaagcaggg gaataccagg aggcaggatc cttgagggct gtcttgttgg    24780
ctggagacca ccattgaggg tttttttttt tttttttatt gagacagtct tgctctgtcg    24840
```

```
cccaggctgg agtgcagtgg cacgatctca gctcactgca acctctgcct cccaggttca    24900
agcgattctc ctgcctcagc ctcccgagta gctgggattc accatggagt cttgaaccca    24960
gattctgtga ctgcttttgc tcttttttgtg ttcatccaaa cagtccctgt ttatcctaag    25020
aggatgggag aaagagactg ggagagaagg aaatccagtg gcctccctcc ctgctagcag    25080
agcctggccc tggcactgag ccttcctcct ctaccctctg ctcctaatgg tgagggtccc    25140
ctagcagggc ccttctgtcc aggacacatg gccgcctgt cctcacccca gcctactgac     25200
ctctctcctg ggctggcctc agtgcccttg attgtgccgg agagaggaag cgctggacag    25260
tcaggccaag ctgctgtccc caggagggca tctgcttatg tctagggcag ggacaccttc    25320
ctgaggactt ctgatgagag acggtgtgag agcttcccac ttcccacctt ccttcccatc    25380
cttggttctc aaaccttcaa gtgtgcatga gaatcactta gtgggggata tttgtccaaa    25440
tgcagatttg cagatatccc cgctgagatt ctgagggccg agatgaggcc tgtgaatctg    25500
catgttaaga aagcacccgc tttgatgcgt gtgtcattgg gtaggggagc aacactttga    25560
gaaacatgga gctagagaac gtgggtttct atgggtttcc catagaaaca tggatttctg    25620
tgttttctgc tgccctgaca tcgaaggcac atctgaaggg ggaggggcca ggccaagaac    25680
cagggagtcc tgggaacgta gaggcagcag ccagtgactt cccgtactcc tcagggacgg    25740
ggttgctacc aaatccatca gaccacgcta ctgcaagatc caaaagctca ccaatgccat    25800
cagtgccttc accctgacca acctgctgct tgtgggtttt ggcatcacct gtctcatcaa    25860
caacttacac ctccaggtac ccaccttcat ccttcccctc tccctgcctc ccgaggctcc    25920
tccaaaggga tggtccatcc agcacctgcc ttccaggaag cgcagttctg gtcttctgat    25980
ctggatctat tttccgggtt ctccaggaag tgtttctagt agattgggtt ggcgaggggg    26040
tgggaattga ggcccagttg gcctcttcgc cctacccctc cttcctccag cctccacaca    26100
ctctcctaac ctcttcactc tctctttttg gttttagttt gtgaccttg tcctgcacac     26160
cattgttcga ggtttcttcc actcagcctg tgggagtctc tatgctgcag tgtgagtctg    26220
ttgggctgaa atgccttcct gagctttgca accgtgatca gagaaccca gggaagggtt     26280
gggagggccc caggcatccc ctaatgcacc tctctctgag acctctgat ggcagggagc     26340
tcacttcctt aaaggcagcc tatcctgctg taattgactc ccctgttgg agtcttccct     26400
tagaggaagc tgaaatacct ggcttgatga cactttggtt ctatgtctgc tgtttgaaac    26460
ggcccccaga atggcctccc ctccatgccc accctgaaga aatttcccaa gggcagccat    26520
ttgccttata attttcctct tcatgttgga cagtccccac ttgcatctct ctcctggttt    26580
cccctgctgg gcgctgctga gggactctcc cctgtgtatg tgatggagta acaggacatt    26640
acaataatga tgacaaaatg acaaccatta tcaagtgctc cgttggtgca ggcagcaggc    26700
aggatccttg accatcactc cctgagttca gcctcactgc agcggtctcg gcagagggca    26760
gctctctttc cttcatctgc tcaagccaga accctggagt ttccttgatg tttctctccc    26820
tcacactcca tgttcactcc atcctcagta cagccagcag cagcttctac acaccccaaa    26880
tctgaccctt cttgtcacct ccactgctgc ctctccagtc ctagccacca acatctctag    26940
cctggattat tgtggcagcc tttagtctcc cacatctgcc ctggcccgc tgtctcagtc     27000
tatttttaac acagggctg cagtcacctg tcaggacata agtctcttca catcactctg     27060
tggtgtcctg tctcatctgt ctcagagtaa aagccaaagg ctttactatg gcctaaaaag    27120
ccctgcaagc tctggcccca gcacttcact ccctctagc tccccctcct ccattgttca     27180
ctctgccaca gccacagtgc ttcctagtgc tccggaagtc tcaagtgtgt tccctgcttg    27240
```

-continued

```
gcatctttgc atgtactagt ccctgtttct agaacattct tctccagata tctgcaaggt    27300
gcccaatctt accttctctc cttcttcagg tctttccctg actgtcctct tctcagtgag    27360
gcctcccttg gctgtcccat gtacaattgc aacctcccta ctgcccgctt ctctgcttgg    27420
tttttctcag cgtttatcac taacactctg cctatctctt gcttattgtc tgaccgccac    27480
ctgctccatg ggaatgccac ctcctcgatg caggaatct gttgacttgc ttgatcgtgg     27540
tatctccagc acctagagca gtgcctggca catagtaggt tctcagctaa atgtttgttg    27600
acagaataca gtggacagtc ctgcgaggtc aatgccatcc ctgttattag tggaggaagt    27660
ggggctcagg gagtttgagc cacttgccaa tatcacacat acaggaggtg tgagaaccca    27720
gctcagtggc cctgaagttg gagcatttgc cctcaaggct ggggaccaaa gagcccatgc    27780
aaagagcccg aacgcttaag caccaccctg cctggccagc ggggnnnnnn nnnnnnnnnn    27840
nnnnnnnnnn nnnnnnnnnn nnnnnnnnnn nnnnnnnnnn nnnnnnnnnn nnnnnnnnnn    27900
nnnnnnnnnn nnnnnnnnnn nnncccact gcgcctggcc cattactttt aatggcaaaa    27960
accacaatta cttttgcacc cacataaata gttaccatgg gctgagcatg gtggctcagg    28020
cctgcaatcc cagcactttg ggaggctgag ccaggcggat cacttgaggc caggagttca    28080
agaccagcct ggccaacatg gtgaaacccc gtctccacta aaaatacaa aaattagctg      28140
ggtgtggtgg cgcgtgcctg taatcccagc tattcaggag gcagaggttg cagttcactg    28200
aaatcatgcc actgcactcc agcctgggcg acagaatgag actctgtctc aaaaataat     28260
aaataaataa ataaatattt accatgtttt gaccacctgt tatgtgccaa ctgtattact    28320
taaaaacacc catgggaggc tgggcacagt ggctcacgcc tgtaatcgga cactttggaa    28380
gggcaagcgg ggaggatccc ttaaggccag gagttcaaaa ccagcctagg taacacagta    28440
agccctgtct ctacaaaaaa taaaaaaatt aactgggcat ggtggtgtgt gcctgtaacc    28500
ccagctcctc gggaggcaga gggagaggtt cgcttgagcc cagcagtttt aggttgcagt    28560
gagccaggac caagacacta cactccagcc tgagtgacag agcaagacac tgcctctaaa    28620
caaacaaaca aacaaaagcg acctgtgggt aggtaggaac aggctcatag tacagatgag    28680
aaagcagagc ttgagggct caagcgatt gccaagcaga ggtccaagcc gaggtctctc      28740
tgaatccaaa gttaattccg tctatcatat caccacagcc ctctctgccc agggagagt     28800
ctctgcccac tccagccact cacgtgtaat tgacttcctc aggggcagga aaggcttcga    28860
tgggccagtt gagggtgcag ttcagaaaga taaggcaggc caggcagac caggtgaaca     28920
tgatgaccac gaaggccaca ccggcatcgt agatcagctg tgagaggagg gggcaggccc    28980
gtgggggaga ctgcctggcc ccagacccca ccaaggtaga tcccaggcct cagaggcctt    29040
aaagaagttc tcttctcccc ttgtccttgt gcccaatttg cagatgagga aaccaagacc    29100
agaagtttag agtcagactc agaagaccca tcattccttt ttcttttca cttgaggccc     29160
cctagagagc tatgaaatag tctccacaaa gcctgaagtt gctggccact ggctcaaaat    29220
atctctgaaa tttccattat cttaaaaaaa tacatacatt tttgcctatg actccacaaa    29280
cattcatgtt catgttcgca caaaaatgtc catttcatag tacgtacaaa ggaaacttag    29340
tgctctaggt ttaccgggcc taatcgtgtt tatcctgccc cttcctggca cattccccag    29400
gggaaaaggc aaacccagac tgctcatgct cagccttttc tcacctttcc caggtcctcc    29460
cacgtgcaac aactgggggg gttggggaga gggaggtgca agtgctctgc ccaagggctc    29520
tcaaccccag ggcaggtaag ttctcaattg aatgagattc tgtgcaaatg tgtcagccct    29580
```

```
tcttatggaa gaagctgatg caccatctgt cctcttgtcc tccccatacc atctgaccag   29640
gataattaat gtctgctctc ccctcaggct cctgctcaaa cctttttctc tgcagtcttg   29700
gaccttggtg cctttcctc cctaggggca ggacagagct tcaaagggcc acaccccaa    29760 atgtgtggag gtaagatctg gctcttcaaa cactacttca gttgaaaaga agggagaact   29820
gcccaccctc catgcctgcc caccagaaca actgatggcc cccccaccca tgcgctctct   29880
caaactcctt tggagacact gagcaaaagt accttcttta gtactctttg taaagtgcaa   29940
aacggtatgc agtttggtac tgcccaccgt ggaggttgag gagcatggca tggctcaaag   30000
ggtcctttga tatttgacag aggaaattga ggccccatc ttgcactgag ctaaaacttt    30060
ggtcccctgg cttcgaggta caccaggttg acctgtccag gatccagcct ggcataaact   30120
cactttgtga ccttggacca aaccacccat cctctctgga aggtgtggaa aaatgtggcc   30180
ccaaaggctg aataaagcca gagagtcagg gaccttgaac gcatgtgaag gggctggact   30240
tgattctgta ggtgaagcta aaccactgaa ggttttcag cagtgtgtga gccagttccc    30300
catctgagat ctttctggaa gtcacgtgag tgacagagta cagagaaaaa gaatcagagg   30360
cagggagacc agctgagaaa gcttgctgtg gcccaggaga gaggggaag gcctgcattg     30420 ggatgatgac agagaaagga gagcggagaa gtcagacccg tgggtcagca ctagctgctg   30480
ctcactcggc cccacccggt tcttgtgtca agacaaaaag aaaacccagg tggcctcata   30540
ccttgattcc tgggaacgta atggcagaag aggcgtaaga gccaatcatg agggccatta   30600
acgtggagcg caggttccca aacatgttgg gcagctgagg agggaaagca gcacccatga   30660
ggtggggaca ccgtgaccct tgcccagcat tcccagccct gctccataca atagctccag   30720
gagacgcagc agaaaagccc caaggtaaaa caaacagaaa aatcaatgtg ggaaactgta   30780
ctctgccccc tgcctacaca gtcacagtgc cctttagctt caaaaaggct cccagacacc   30840
cctcagagag acattttgtt aattttgttt aattccaggt ttcccaagtt tgttacgtaa   30900
cacctctgaa aaacacatgg aataggtgct taagaaacac tgatcttggc tgggcgcagt   30960
ggctcatgcc tgtaatccca gcactttggg aagccgaagc tggtgggaag cttgaggtca   31020
ggagttcaag accagcctgg acaacatggt gaaaccccat ctccaccaaa aatacaaaaa   31080
ttagctaggc atggtggcat gcgcctgtaa tcccacctac tccagaggct gaggcaggag   31140
aatcgcttga acctgggagg tggaggttgc agtgagccga gatcgcacca ctgcacttta   31200
gcctgggtga cagagcgaga ctatgtcccc accccccaaa aaaaaagaaa agaaaagaaa   31260
gaaacagtga tcttgtccaa cccatttgag atgagacaat tgagacccag ggaggaaaag   31320
tgtactcaag ttcacagagc acattaatgg cttctccc attgtcgttg tcccagccct      31380
aacccaaggc tgtgaccatg gctgtgtccc ggtaataggc agtgcctctt aaccctctcg   31440
gttgacgtcc cagcccagtt tctgcctaat caggacaaat cacatcctgg gaggtgaggg   31500
tggaaataag ggagggaact gagccagggc agacagtctc cagaggaggt ggctctgacg   31560
cagagcaggg tcagaaccca caccaggaga gaatttaatt gatcatgtgt tccactcacc   31620
tgcctcagcc aagccctcag ggcaggggaa ggcaaagtca ggatgcccctt cgcacacacc   31680 ctcctctggc cccaccatcc tccccaagtc actagatccc acagctgaga aggaccttag   31740
gatccgtaca aagcctaaac acactccaca gaggggggaaa ctgagactct gaagggaggc  31800
ctcaacagct ctggtaaaaa aggcgtttag gccgggcgca gtggctcaca cctgtaatcc   31860
cagcactttg ggaggccgag gcgggtggat tgcctgagct caggagttcg cgaccagcct   31920
gagcaacacg gtgaaacccc gtctccacta aaatacgaaa aaattagccg ggcgtggagg   31980
```

```
cgtgcacctg tagtcccagc tactcgggag gctgaggcag gagaattgct tgaacctagg    32040
aggcagaggt tgcagtgagc cgagatcgcg ccactgcact ccagcctggg cgacactgcg    32100
agactccgtc tcaacaacaa aaaaaaaaaa atggtgttta aacacatata actaaattat    32160
ccttccccct tcccctgaag tggctggctc aggaaaaacc tctacccact caggcagagg    32220
ttttcctgca ccctgcatcc gtgaggcacc actgccaagg acgccaggga aggctgccag    32280
gcctggagag gggcagggcc cctcccctc caagggcca caaacgctgt ctgcgcccag    32340
taccgtgggt aaggcgaggc cggccggcta accccgggct ggcggccttg cagcgtgcgt    32400
ggcaacagca gctgggcccg caagactcag cacgggacgt cctcgtccaa gtctgggcca    32460
agagcagcgg cccaggggc ggggccggcc agagggagcg gggagaggct gagggcggt    32520
gccagcgccg gaccctgcca ttggctggag attacaggag gcgggacat agcagggagg    32580
agccgctgga caagccccac ccggccgcca gggagggtct gaggtcaaga gccgagaga    32640
agggatttag ggccctgggc caagttgcac agcagggaga aggggctgcg cagaggggcg    32700
gggagaaagg gatccgcttc cttccttttag agctgtgaaa tgtccccggt tggaattaaa    32760
ggcggctgct ggggagaggt gaaattcagc caaaaccacc cagtcaggca gcccttctca    32820
gagataaaca gtccgagcca gcccggccag gaaccttccc ctccaacctc cctaagcctt    32880
taacactcct aagcctttaa cgcgtttaca cactcacata aataaacaca ctttgagcaa    32940
cacacataca ccactcacca catgtaatag gtcaagccat gtgcacgacg aggtgtcgac    33000
aatttcatat ggttcaacct agtacactca caaacacacc taccaactca tggctttcac    33060
agggacgggg tcacacaccc actctcccac gacatggcaa gcgtgcacac gctatctcaa    33120
gctgctccct ccccctcaag atcatgttac ccagttttat tttcttccca gcacctatga    33180
cgactgacat aatttattag tttacttgtt tattgggtta tctgtgcccc tcacccccaa    33240
aatgtaacct ccagcaggga ggatgactcg gtcagtcctg attgtgctgt agtccaggac    33300
ctagaacaga gctccatgga cattcatggg ctctgtacac acaaacacac acattaacat    33360
acaccccgac acacagcctc atccacacac acacagcctc acacctgctc tttgcagcca    33420
cctgcacagt ttctcacaca ctcacttgat ctagtgatct gcgtccacag gcccctcccc    33480
cagcccactc atactgccct caccccactc actctgccct caccccactc gggggaactc    33540
tgctgccagg ccaggcctgt gacactcacc gtgagtgaag tgaacgttag gcagatgcca    33600
ccaaagccat tcaggacag cgccaggaat atcaacggag acagagctgg aaagggaaa    33660
gcagcagatg agggcatttg gggagctgtg ggaagccaag ggcgggagct ggggtaaaca    33720
tccgccttca tcccacctat tcttttcttg tggggccaca agaggacaga caactcacct    33780
tccacgtccc gggaggccag ggccatgagg gtgcaggacg cagtgaagca ggcactgtgg    33840
agacacaggg aagggcgagg ggttggcctg tgagcacccc ccctcccctc ccctgcagc    33900
acggtccctg tcctcccgtt ccccatagcc cagccacctc acctgccaac cagccgcacg    33960
ggtcgggggc caaagcggtc catgaggatc cccagtggca gggtggtggc gctgagcacg    34020
aaggaaccaa tggtgaagcc caggttgagc atctcgtcct gctggtcaca gcctggccac    34080
ctgcgctgct catcctgggt ggtgttggtg ctgctctcag ctgaggaggg ggaagggagg    34140
gctcagcaca tgacaccagg aacagctggg cacaggagag agcagcccac agtcaggcgg    34200
cctgctttca aatcccatgc caagtgcctt tgggggtacc ctagagtcac atctcctctg    34260
atggggctgc tccagaaatg gcagccatta gtacctgacc ctgggagagt cttgtgcaca    34320
```

```
cacagcctga ggcttcaact agctcaaatg aaatactgga cataaaagta tttactaagt    34380
tgtaatatgc actcagtgtc caagcttagg gggttgtgga cccccaacaa gaagtgcccc    34440
catatctaga ggcaaaggca aaggcagtga gtggtactct aatggctata acaagaattc    34500
attaaaatgg cccggcgtgg tagttcatgc ctgtaatccc accactgtgg gaggctgaga    34560
caggcagatc gcttaagcct acaagtttga gaccagcctg gcaacatgg taaaacccca     34620 tctctaaata aaaaaagaa atttagaaag aacactaaaa cttagaggaa gctttcccga     34680
taaatgatag tctgataaaa taatagctaa tacttattga gcacttaact atgctccagg    34740
cactgttata agtcagttaa taaagtatcc cgttccctag gtgatgaagc tgaggcacag    34800
aatgagaacc aggcactgcc ctccagtccc ctctagaagt ccacttggag gacttgtcct    34860
taacggtaaa ctgccaactt ggagttgtga caagttaagg agaaaagcta gtgataggag    34920
acaaagggct gcttcgcttt actcaatgct cannnnnnnn nnnnnnnnnn nnnnnnnnnn    34980
nnnnnnnnnn nnnnnnnnnn nnnnnnnnnn nnnnnnnnnn nnnnnnnnnn nnnnnnnnnn    35040
nnnnnnnnnn nntccctccc tccctccctc cctcccttcc ttccttcctt ccttccttcc    35100
ttccttcctt ccctccatct tctccacacc tggtatcatc atacagaagc agagaggact    35160
gcacttggtg aaagtttcaa ttctcctgtg tggagaggtg agcactgagg aagggtggg     35220 ggctgtcaaa ggagacttac ccaatctttc cagcccacca atcccttgcc cagtgtttct    35280
ataaaataag ggccttttgc atctgattta agtaggaagc tgattcctga gcccctcaga    35340
tctgctgaat cagatagcta agggggccct ggaatctgca ttttagcaag cggaggtggg    35400
ttatgaagca ctccaaagtt tgagacacgc ctcaaaggtg gagtggttct gtgggggca     35460 gaaaggaaaa tgcaaagggg gaaggggtca cacttgggga aggtttcaga caataccgag    35520
tggaaagggt gatgccaggt gtggggagta acagatagag gaggcaaagt gagtggagac    35580
caagccagac cggggaggag ggggccacag ccaaggtgag acaggtcagc agccagaaac    35640
cgaagcagac acttgcaggg tgcaccccgc cctctcttcg tggcaatctg agaccgagga    35700
cgtggagacc ctggagagcc cccaaccttg tttctggggg gtgggtcaga gaggaagcct    35760
ctcatccccg ggcaccagcg gccttcccgg gaggctcaac acgcagatac ctggataggc    35820
gtccatcact cccccggcca gagcccacca acgctcctcg aggtccgacc ttgtccctcc    35880
ttctacccca cagtccccag tcctagctca tctgcataaa gctccaatta acatgttttt    35940
cctttgctat ttgcgatccc agaactcgtt ccccacccg agcccgtttc ccgccgcttc     36000
ctcgcccctg ggagggcggc cccattaacc ctcgcgaccc gggccgctcc tggcggtcct    36060
gaccccgcca cccgtcccg cggcgggggt ctggggtga ggggcgcgcc ctggggcaga      36120
ggattgcgcg gcagggtctg ccacagggca gaggccaggg ctctccggga aaaggcagg    36180 cgcatatatg ccccccttttc tgggaaaaga cggggagggg ggcttctcct gggagactcc    36240
aggcttcgaa attcctcgtt ccctatcctc cggcccccgc accctcctc ctccccgcca    36300 cgcaccctct ccctccccca gccatctgtt ccactccgca gcgccgcgac aaacacggct    36360
ccagctcgct tccgccctg cccagccccc tccccaagcc ccgggagtg ggggagtgag     36420 cagacgccct tctcctagga ggccggaatt tctgcctcca tctcccaccg gggtccggct    36480
ggccagaggc aagcttcgag acccccacc aaccaccacc accgttgcga gggccggtga    36540
ggctgcagat aacgcttgca aggacgggag tcggggaggg tgtagggcga gtttaaagga    36600
cgggcagagc aagcccggg aagaggcagg ggttttccct cccgggtcgc cgccccccgc    36660
accctcggag ccagccgcag ccacgcagcg ccgcctgccg ggcacaccaa ggacctggcg    36720
```

```
cgcacgtggc gcttaccccc accccgggt ccgctcctgg ctcgcgctca gcctcccag    36780 actattcgca aattgaggat cccggacaca gagtgcagag accccggcaa gcctactgaa   36840
agccagccga acccgctggt gggtgctagc caattctgat tttgtacttt acaaaaacaa   36900
aaaaagtcag tgttggaagt cgggagtctg ggctcagagc agcagggatc tgcgatgtga   36960 cttttgccaag tctccagacc cctgaggaca ggttttccta tctgaaaacg gaggggacag   37020
tctctcttat taacttctca agagaaacaa agacaaaggg agggaaaatg cttagctgg    37080 aatgctgtct tacagagcca acctttggag gtgggggaga tggccaaggc ctctgaggtc   37140
actcttggcc ccaggagcag ctgagaaccg gaaagaagct tgggacctcc tttctgcaga   37200
gctatccttt ccacagactg ccgaggttcc aaattgagct ccaccaccta acactgtgtg   37260 ccccttgggtg tgtgccttaa cctctctggg cttgtttcct acagcgacaa gaaagaatga   37320
caacaccaac ctcttaggct atagtttgga taaaatgaga tagctgtgta gaacagacag   37380
atcctaaacc aatgttagtt ttcccttcat ttggggactt gctctaaccct ccagggctta   37440 tgtcccagag gcacaagcag gtgcagggct ggataaataa ggtatgtctt tctgcaggat   37500
ctcttgtcct cactgatggt gtcttctctt gatatagata attttaaagc ttcacgttat   37560
ttatttattt actttaaagc ctcactttaa tgttaaaggt aaatgtaaat atagtataac   37620
aaggaagctc aaaatttgca taaagttta agataaaata ggagactcca aaaagtgtt    37680 actttcggca ggccctaggg atgctatggt gggaagtttg agtcatacct tagcattctt   37740
tctaaagcat tctgtcctaa tcctctgtat ggagaaaagc cagcttcctg gatgtacccc   37800
aaatcctggg aagtagggg caggagctgg actccctcca agcactaagg gcagggcatg    37860
gttgggaaca gggaggtgag ccagacagcc agaggcgaac gggctggcat gccaagcgtc   37920
ctagttaatg cccagctgag cctgggtgaa gaaggatggg ggtgtgggga agacaccccc   37980
caccaaccgc caaagacagg cgcacaccag ccagtctctc acttcccttt ttatttcctc   38040
taagacttgc aagcagcagc accagagagg gaacctgccc tcctggccct ggaaggggcc   38100
gacccccaac ccctaaccca ggacacagct ggcacctcag gccccttttcc ttctgaaagg   38160 agggctgtgt ctctctcaca ttcacacata cacagacaca tgcatgtgtg cacactcatg   38220
gcacatggga cctcagggt agcctgtttg ccgatccccc caagaggtac caggaggcag   38280
accgctagaa ggagataaga ggcaccctgg tctcctccaa cccaaggagg aagaaagctc   38340 aaccccctcta ggatagggac tgtcttcagt caatggagcg ttgacttagg gggcgttttt   38400
gaaggttttt tttcctcctt tttgcagtct ttacaaaaat agaacttctc ttggtattta   38460
taaatctacg gccatggctc tatgtgcatg ttacaggtag aaaagccata tggggcactc   38520
cttttggttg ctcaggcctt gattgcctgt catccaggtc ccttggtctg agaagtctat   38580
gcggtcacct cagagccgct aagcaccttc agtgggccca tcccattggc ggcgtactcc   38640
tgctggagcc gggcacggta atagaagagg taggaaggca acaggaatcc caggagtgag   38700
aatagcagga ggcccagatt caccttagg gcaaggagag agaaacagag tcaagtaggt   38760
agtcatctgc ccttagcctc ccacagggag gagaaggcgg ccatttttct ccaggtcctg   38820
agccagaata aatacagcta gtacttatta tgtgtagtca ttgttccacc agtatctcac   38880
ttaatgttca gcaattctgc aaagtggctg agatgagact tctcaggtat aacaagtggc   38940
agggcctggt gggtgcccac accatatggc actcactagg taggtatgag gaaggcacag   39000
cactgtagga gtctgggctg gtcaggctgc tcccgaaatg gggccttctg ggctcacccc   39060
```

```
tctgacctttt ggagatgtta accaatggga tcccgttcag ggtggcgaga ggaggctctc    39120
agacacagtt caaggaactg ggatgcacag cctggtggac agaaggcttg gaaggcccag    39180
gacacgcggg ctctgactcg gttcacatcc cactctgcat tactcactgt gtgactttgg    39240
gcaaataatg gcaattctta ctgagtgcct ccttctcagg gctgttgtgg cgaagatgta    39300
agttaaaaaa aagtatgcat catgcttagc acatagtgag tgcttggtaa atagaagcag    39360
ttatttcatc acaattcttt gggaggaggg tttacgtgtg ggtggcccca cagggcagat    39420
gaaagatcag cgtcagggag gcagatgagt tcaatgtaag gaaaagactt actaacagca    39480
gcagggctgc ctcgtgcagg agtgggtgcc ctaccactga gggtatctaa gctaagaggg    39540
aagggtcccc tttcaggggt gctggagaca ggatcccaca ctaggtagaa ctggattgga    39600
ccaatggtgc ctgaacacag gcccaagagt caggactggc cacttcacaa agcacctgga    39660
gtttactaaa aacagactcc taggaggtca ggcactgtgg ctcacgcctg taaccccagc    39720
actctgggag gccaaggtga aagatcatt tgaggccagg agtttaagac tagcctgtgc    39780
aacatggcaa gaccctgttt atctgtacaa aatttttttt taaaaaatta gccaggtatg    39840
gtagccatca cctgtggttg cagctactca gaaggctggg gccggaggat cgcttgagcc    39900
caggaatcag aggctgcagt gagctgtgat tttaccaccg cactccagac tgggcaacag    39960
aacaagacac cttctctaca aaaaaaaaaa aacaataggg ccgggcgcgg tggctaaggc    40020
atgtaatccc agcactttgg gaggctgagg agggcagatc acgaggtcgg gagatcgagg    40080
ccatcctggc tagcacggtg aaaccccgtc tctactaaaa atccaaaaaa aaaaaaaaa    40140 ttagctgggc gtggtggtgg gcgcctgtgg tcccagctac ttgagaggct gaggcaggag    40200
aatggcatga acccgggagg cggagcttgc agtgagccga gatcgcacca ctgcactcca    40260
gcctgggcaa cagaatgaga ctccgtctca aaaataaaa ataaaaataa ataaataaat    40320
aaaataacaa taaattaaaa acaaaaacag actcctacgg tcaggctgag atatcctgat    40380 tcagggggact ggggaatctg tattttaac actccgtgag gggttctaaa aggcagacaa    40440
cttggaaacc tgcagattag agacctctga ggtgcctctg gctgagatga gtgagggatg    40500
gcaccacata caaggcccta cccctgcccc caggagagtg gctcctgctc ccccacacc    40560 aaccctcgct ctcacccaga agggctctcc tttcaggggt cccaccatcc ccatgaaaag    40620
tggctgctga agcaaggcga acacagcact ggtgagggac tgcaggcctg tcagcgtccc    40680 aaaagggggtt ggatgggaac ctgtccccaa acgggagat caaagggtgg tgggggcctt    40740
tcagcccagg caagaacttt ttctttttcct tcccaacatg ggnnnnnnnn nnnnnnnnnn    40800
nnnnnnnnnn nnnnnnnnnn nnnnnnnnnn nnnnnnnnnn nnnnnnnnnn nnnnnnnnnn    40860
nnnnnnnnnn nnnnnnnnnn nncactccag cttgggtgac agagtgaaac cctgtctcaa    40920
aagaaaaaaa aatcttaaag aataaggata taaagaaaga aaatattttt gtgtagctgt    40980
tcaatgtttg tatttcaagc caagtgttat tacaaaacag tcaaaagttt ttaaaaattt    41040 aaagtttat aaagtaaaaa agctaagtaa gctagggtta atttttttat cgaacaaaga    41100
aaaatatctt tgtataaact tagtgtagtc taagtgtaca ttgtttttat ttatttatt    41160 tttttattttt ttgaaatgga gtttcactct tgttcccag gctggagtgc aatggcatga    41220
tcttggctca cggcaagctc tgtctcctgg gttcaagcga ttctcctgcc tcagcctccc    41280
aagtagctgg gattataggc acccgccacc atgcatggct agtttcttg cattttttt    41340 ttgaaatgga atttttgctct ttgacccagg ctggagtgca atggtgcaat ctgggctaaa    41400
tgcaacctcc acctcccagg ttcaagagat tctcctgcct cagcctcctg agtagctggg    41460
```

-continued

```
attacaggca tgcaccacca cactcggcta attttttgtat ttttagtaga gacagggttc    41520
tcaactaaag agaaccatgt tggccaggct ggtctagaat tcctgacctc aggtgatcca    41580
cccacctcgg cctcccaaag tgctgggatt gcaggcatga gccaccatgc ccagccagta    41640
tacagtgttt ataaagcctc cagtagtgta cagcaatgtc ctagaccttc acattcactt    41700
actactcact cactcactca cccagagcaa ctgccagtcc tgcaagctgc atgcatgata    41760
agtgccctat ataggtgaac cattttttaa tattttatac tatattttta ctgcacctttt   41820 tctatgatta gctacacaaa tgcttaccat tgtgttacaa ctgcctacag taatcagtac    41880
agtactatgt atgggtttgt agcctaggct ataccatgtt gcctacgtgt gtagtcgtct    41940
atactgtcta gtttgtacac tctatcatgt ttgcataaag ataaaatcac ctaatgacac    42000
atttctctga gtgtattcct gttgttaagc aacacatgta taaacattta caagaaatag    42060
ctcaaatttt ttttttcttt gatacagggg cttgctttgt cacccaggct ggagtgcagt    42120
ggcgcaatct cggcgcactg cgacatctac ctccccggtt caatcgattc tccggcctta    42180
gcctcctgag tagttaggac tacaggcacg caccaccacg cctggctaat tttttttgtat   42240 ttttattaag agatggggtt ttgccatgtt ggctaggctg gtctcgaact cctgacctca    42300
ggtgatctgc ccgccttggc ctcccaacat gctgggatta caggcatgag ccaccatgcc    42360
cagccattac gtttttttgg ttgtttaatt tttttttttt taagagacag attctcactc     42420
tgtcatcaag gctggagtgc aatggcacaa ccatagctca ctgcagcctc caactcctgg    42480
gctcaaggga ccctcctgcc tcagccttcc cagtaactga gactacaggt gtgagccacc    42540
atgctcagct aattattttt tatcttttat tttttgtaga gggggggtct ttctatgttg    42600
ctcaggtttg tctcaaactc ctgggctcaa tcaattctcc tgctttggcc tcccaaaggg    42660
ctgggattac aggtgtgagc ctgaaaacct tcagtgtgg aagtggaaga taggcccagg    42720
ccacttatgt tttcaagtta agcaaggttt aggtcactta tgaagcctga ctagttttgt    42780
ttgcttaagg gatctgcagg cctgacctcg gttttcattt gttttaacag tgtctatgtg    42840
tatgtgtgtg tttatgtacg tgcatgatgg ggggaaagct cagaaatcaa gtaagccaaa    42900
cacaaacatg taattataag cagggataaa ttctatgatg aagaagtatg ggccacggga    42960
gagtacttgt gccagtctgg tgatcaggaa caatgtcctt tgggaagtga catttgagcc    43020
atgccctgaa gtacggtagg agttggttag gggtgaggca gtaagaccca gagctggggc    43080
ttcctgcaca agctcagctg ggcactgagg acccagtgga ctctgctaca gggcagtgag    43140
gagcagaaag gctgaggaag gctgggtgtg gtggctcaca cttgtaatcc cagggctttg    43200
agaggctgat gggggaaaat cggtagagct caggagtttg agaccagcct gagcaacata    43260
gcaagactcc atccctgtaa aaagctttta aaaattagct gggtgtggtg gtatgcatct    43320
gcagtctcag ctactcaaga ggctggggta aggattgctt gagcctagga ggtggacgct    43380
gcagtgcgcc acgattgtgc cactgtactc caacctagga gacaaagcga gatcctgtct    43440
caaaactgaa tgaataggct gtgtgcggtg gctcactcct gtaatcccag cacttttgga    43500
ggctgaggtg ggtggatcac ctgtgattgg gagtttgaga ccagcctggc caatatggtg    43560
aaacccgata caaaaattaa ctgggcatgg tggctcacat ctgtaattcc agctactcgg    43620
gaggctgagg catgagaatg tcttgaaccc ggggggcaga gggtgcagtg agctgagatc    43680
gcaccactgc actccagcct gggagacagc gagactccat ctcaaaaaaa aaataataat    43740
aataacaatt aaaaaaaaat taaaaggcca gggagcactg gcagcctgtc caaggtttca    43800
```

-continued

```
ggtcacttta gtaaagggag aacaatggct cctcccagga cctctgggat ctcagcattg   43860
atacgacagt catggaaatg ctagggccca ggcagaccat ctcagggaaa acaagtggct   43920
ctgccctgcc ttggccactt cctgccctc tgcatgcccc agggtctcag caccaagctg    43980
ttctcagtga gtagctctca tttagtgcca gggctctcgg gcttacatcc tacgatgacg   44040
atggaatgca taaagatgg ggctgtgata gcccagagct aggggtttga atctcatgag    44100
atgttcatgg agccctggga gggagctcag tgcaagttca tttctctttt ttggttgaga   44160
tggggctcag aggaggaagg acttgttcaa agacacacag ggagtgtttc agtgtgggac   44220
ggaggtttat ggagaaaggg tgaccatcca aggcttggac aaagatcatg acttcgacca   44280
gcaagcctca actctgtaga cttggtgggg ccaggccct cccaaacaca cctgacaggt     44340
gtctgtggtc ttggggacat tgtcgctccc cttcctgctg atgctctgct gtccctctcc   44400
catgaagcgt atctcttcgc cgtccccat ccttgctgag agaggatggg ttctcttctg     44460
accaatactg aagatcttta gtaaagttct cttttttttc attttctgaa agtccctctc   44520
ttgagaaatc aggacaagtg agtcagggcc aggacaaaaa acagtgtggg acgagtgtgg   44580
tggctcacgc ctgtaatccc agcactttgg gaggccaagg tggcggatca cttgaggtca   44640
tgagtttgag actagcctgg ccaacatggt gaaacctcgt ctctacaaaa tacaaaaatt   44700
agccaggcgt ggtggtgcat gcctgtaatc ccagctattc ggggaggctga ggcaggagaa  44760
tcacatgaac ccaggaggcg gaggttgcag cgagctgaaa ttgggccact gcactctggc   44820
ctcttggcaa cagagccaga ctacctctca aaacaaaaac aaaaacaaac gacaaacagt   44880
gtagactttg tgtttttctc aaaagcactg tcaagccagt gcccgcagca gtgggcctag   44940
acacctccag tcttgcctca gggtcagttt ccagcctccc tggacacttc ccccaggtat   45000
gtgtactttt tgattgtcct aaatccagag tctgtggcct gacctggttt gtcacagctc   45060
tcagtccctc cccatcccga atcccaggga gccgcaggtg tgtgcagaag aggcacacca   45120
cactcaatac atcttgcatc ctcgctggac ccaatccatt ggcttggtga tgtacagact   45180
gagcctcatt atagccgttc gttcctgttg acctttccag atcaatctgc cagcttggct   45240
tctccgagtt tcgcttgtca gcatttctcc aatcccatca tgtactttgg acctctttgt   45300
tgggtggctt gctttatctg aaattttcag atttgacttc aggtctctcc tttgtccctt   45360
aatatggctt aatggtggac cctgtcaggg gtagagaaaa tattgaggag ccctgacttt   45420
gaggtgcaca agttagaggg ttagacaagt ccagccacaa ccagcccaag ctgcagtgta   45480
gggaggcctg tccagctgct ccacggttga gggtggagca tacaggaagg cttccttctt   45540
gctgcagccc aggtgttctg gctgccctag ctgcctggct ttggtagaag aaagaaaggc   45600
tctgtctctg acttgtcaac taatggcact atgagattgc acataattaa cctgggtctg   45660
ctcttccaaa agccttgggc ctctgactgc aacatggagt ctgggtatca ctccccatcc   45720
ctgcgccact cacctgctct ggcgctaggc gtgtgcctaa tcacttaatt tctctgtgct   45780
gcctcttagg tatcacttcc cctgatccca aatacttacc aggtgtggga tgacacctga   45840
ctagttactc cttggaggta tctgcttctc accgggact ccgaaaccaa acgaaaagca    45900
aggccaagcc cagcctaaag gacgcttcct acatgacttc aggcttgcgg gggctggagc   45960
gtgggggtgg caatggagtt ggggggggct cagggagggg atgtgaagt gctttgcttt    46020
gcaaactcta gagaaccgtg taaataggag tgattattct gtcccttccc tttctttcca   46080
acaggaatca gcatcccaca gcccatgttc agctatgaag aatggaaact gaggctccgg   46140
gagggtata gggaggagcc agcagggtct tgagttcata ttagtgccct ttcctccata    46200
```

```
ggcacatctg tgttttcttt tattttattt tgaatttaat tttttttttt tttggcagag   46260
tcttgctctg tcgcccaggc tggagtgcag tggcgcggtc tcagttcact gcaatctccg   46320
cctcctgggt tcaagtgatt ctcctgcctc agcctcccga gtagctggga ttacaggtgt   46380
acaccaccac acccagctga ttttttgcaat tttagtagag acagggtttc acagtgttgg   46440
ccaggcttgt cttgaaatcc tgacctcaag tgatctgcta gcctcggcct cccaaagtgc   46500
tggtattata ggtgtgagcc actgcgctcg gccacatctg tgttttaaat gagaggaaag   46560
gggataatgt gcattttgtg gaagcttggg ccgtttgtgt ctaggactct tatgatcttc   46620
ataagttttc ccccagggag gacactgttc cacttaggga gtcaggaccc ccagtcctta   46680
caagattcag cctctcaaaa tggagacagc agttccaggc ctgggctggg ttctgttcac   46740
actaggagag ggcaagtgag tggtgtttgg gatgtgggga agtattatga aaacagagat   46800
gctccaattc ctagtgatag gaaaccatta agctacttgg catcttaaaa ccaagagcgg   46860
ttcaagttct gagattgtta acacacctta caacaccgcc gccgttatta ggaagaagct   46920
ctgtttgatg acgtcccaca ctgtgggtac ctttatgaac aggaatttgc tttttcaaat   46980
cccagagaag taagattaaa gttggctgtt ctccatcctt gaaaaatttg gttttagggt   47040
gaattcaaga atgactgacc atacagaatg gggagcaaac ttgggaagaa agaaggcaca   47100
gttcagagct ctcccaatag tcacccctga actgcacccg gaccatcagt tatctctgtg   47160
ggtagagctc aggaatctaa aatccatttt aaaattaaag tatatcgggg ctgggcgcgg   47220
tggctcatgc ctgtaatccc agcactttgg gaggccgagg tgggaggatc acgaggtcag   47280
gagtttgaga ccagcctggc cacatggtga accccgtctc tactaacaa tacaaaaatt   47340 agccaggcat ggtggcagac acctgtagtc ccagctattc ggaaggctga gtcagaagaa   47400
ttgcttgaac ctgggaggca gaggttgcag taagccaaga ttgtgccact gcactccagc   47460
ctgggcaaca gagggagact ctgtctcaaa aaaaaaaaa aaaaaattaa agtatgtcat   47520
acatactgtt acaggcacag accttaagtg tacagcccaa tgaaatttta cacatctata   47580
cagctatata actaccacct atatcaagac acattccagg aactcagact ccatcatacc   47640
cctcctcagc agaggtaaca gacccacacc tctcctgctc cggtggtaat taaccactat   47700
tctaactttt ctatcaatta gttttgccca ttccttgagct tcacacagat atacattgtc   47760
aggcatgatg actcatgcct gtaatctcag cactttggga ggccgagacg ggagtatcac   47820
ttgagcccag gagttggaga ctactctgga caacatagtg agaccccccga ctctacaaaa   47880 aaaataaatt agctggtcat ggtggtgcgt gcctgtagtc ttagctattt gagacgctga   47940
gagaggagaa tctcttgagc ctgggaggtt gaggctgaag tgagccgtga ttgcaccact   48000
gcactgcagc ctaggtgaca gagtgagatt ctgcctcaaa aagaaaaaa tatggccggg   48060 cgcggtggct caagcctgta atcccagcac tttgggaggc caaggcgggc ggatcacgag   48120
gtcaggagat ggagaccatc ctggctaaca cggtgaaacc ctgtctctac taaaaataca   48180 aaaaagaaa gaaaaaaaaa ttagccaggc atggtggcgg gctcttgtag tcccagttac   48240
ttgggaggct gaggcaagag aatggtgtga acccgggagg cagagcttgc agtgagccga   48300
gatcgcacca ttgcactcca gcctgggcga cagagtaaga ctctgtctca aaaaaaaaaa   48360
ggaaaaagaa aaaatatata tacattgtgt acttttttggc atctggttta ttttgctcaa   48420
tatcacatct gcgaaattaa tctacactgt gtgtatgaaa ggttggttct ttttgttgtg   48480
atgcagtatt ccgtcgtgtg actacgggac aatttgctta tccgtattcc tatcggtggg   48540
```

```
catttgggct gttaccaggt tctggctgtt atgaataaag ttgctatgga tattcttgta   48600
cactacttct ggtgagcgta tgcactcatt tcgcttatgt aaatatcttg ggtggaatta   48660
cctgatcata aggtaggtgt gttggctttg taatgtgctg acttggttat gctgaattcc   48720
cttttttgtg tatttctggt tagagcggaa catgagggtg tctcttcagg gaatctggag   48780
ggtggaaggg aagcaggagt cggtttctgg ctcacacatg ttgtgactga actgctggta   48840
cacctggttg gcatggagct ggcttctcct ttggcgttgc ctactgttgg ggcaggtgtg   48900
tatgtggtta gctccatgca atgaacccgg gcttctgcaa aatacattaa caacgacaga   48960
gacaacaaaa gctgatgtgg atttaaaggc ttcagttcan nnnnnnnnnn nnnnnnnnnn   49020
nnnnnnnnnn nnnnnnnnnn nnnnnnnnnn nnnnnnnnnn nnnnnnnnnn nnnnnnnnnn   49080
nnnnnnnnnn nnnnnnnnnc cagcagtggt tctcaactga gcatagtttt gcctcagagg   49140
ggacatttgg taatgtctgc agacattttt tgattgtcac agcccagccg agaaggtact   49200
actagtatct ttttggtaga ggctagagag gctgctaaac atctaacaat gcacaggaca   49260
ggcctctgta acaaaaaagt atccagtcaa aaatgtccac agtgttgaga ggtttaggta   49320
agtaggcgct aaaacataag gagactgtgc ctgagagcaa aaggagtaa ttggaaagtg   49380 ctggtgtgat tagctctggg ttttagaaag ctcattttgg ctgcttgtag acagtgcatc   49440
agaggtggag gagggtggta agactggagg cagggaaagt aatttgggag ccactgaaat   49500
gatccaggtg aaaaacggtc agcaggtgac taggaaagtg gcagaggcaa tggggatggg   49560
tggctggatg agatggtgaa gaaagcacta taactaacta atgtgtggat gatgggcagg   49620 agggtgaag gatgaccaga gtcctgcctt gcaggtctag ttggaaggtg atggtttctc   49680
ctgagaaagt gaccacaaaa agtgaagcag gtttgtgcgt gtgtgtgtgt gtgtgtgtgt   49740
gtgtgtgttg agttcagtct gagatgtgtt ggactcacaa tgtccatggg acatccaagt   49800
ggagaagcat cttgggtgac catatgtgtg agtctgcagc tcagaaacag gcctggggct   49860
ggagatgaag acttgggaat gatctgcgta tatatttggt agcttgagcc acaagagtag   49920
atgacataac ccgtggtggg tgtgcagaat taggagagac gtgcaccaag aagccaggtg   49980
atccccaata tttaaccatc tggaagaata agaggagcct gccaacagaa atttgggaggg   50040 aatggccaca aaggctactg agaagggaag cagttcttaa gaaggggaa gtgaagaggt   50100 atcactactg cagaggtcaa gtaggataag aactgaagaa tgtctgttgg gtttggcaat   50160
ggggtagtca gtgggcacct gggcaaaagc agttttggtg gagcaatagg gataacagaa   50220
acaagactgc tatggtaaga ggaggaagag ggtgttgagg aagtggccag cgagtctaca   50280
ccacttgctg gaggagcttg gctttggtgc aaagcagaga agccagctca ctcattgact   50340
taacctccaa gaaacacaaa atcatccata tcctggctca aattccagca ctaccaggag   50400
atggttggcc cctagaaatg ccatcccact tctcctctgc ttatcctatc ctatctgtca   50460
gtctgttgag cccaggctaa gcgctacctc tcaagcaag ccttctctgc ctgccgtcac   50520
actttaagtg atcctgacaa cactgaaaat gtgtgtctct tccattcatg ttagttctac   50580
acttctgagt atctcctcaa tatattgcct tgttttacta atatgctcgt tctgtttgcc   50640
ttatttatca gctaccttaa acctccctgc aactagagat tctctttaag tatttgttga   50700
ataaatgaat gaatcaatcg atgatccaga gcctggtaga ggcttgtgtc catggtggat   50760
gaggctcaga aaatacctgt agaatcgaaa taaatgcatg tgtgctctga tctaaactca   50820
gctaaacttt ctccaggggg taagttcaa gttgattagt caattgatta attaattcat   50880
tatgtaatgg aaaaactcct tctatgacct gggcagagtt ataggcagtg aacaagacag   50940
```

```
acaaggtcct tgttgtcatg aagtttgctt tctgaaggag agagataata aacaagaaac   51000
cagtaagaaa gcaagattat atcattttgg taaatgttct tgtggaaata aatgtgatga   51060
tgtgtaacaa aagtaccaaa taggagagtg gggtgggtgg gcttctttta gaaagagttc   51120
tcggagaagg cttatctgag gaggtggcct tttaaccagt acaaatgctt tagcttggcc   51180
agtggagctg ggaccaggat gacaagggtc acttgtcatg ccagtgagtt tgagcttgta   51240
gacaagagcc tgatcatgaa agactttgca gatggtggta atgggtttgg gttaattgct   51300
actatgtggg aagactttga atgggaagca tggggacaat ggcctgtgat acatgttatc   51360
aaatatggtc gcaggggcta gtgaggtggc agcagagata gggagaagta gacggactgg   51420
ggaaggtaga gatggggca ggggaggcaa ttactgcaaa gacatattcc ttctaagctc   51480
actgagtgtt catggtctct gggagcagag gttcctggag gggaaagagg ataatgtcac   51540
ttcctgagga agcgggaaga acccatctga cgtgggga ctgtgctggt tcgtttctaa   51600
ggggccttcc agatctcaca tgccaatcgt cttggtctat gtcaattgtt ggggcatcca   51660
aatggggaac tgttgtccag gccgatttca cagaacaacc gcccagtcca tatctcccga   51720
gccattcacc cttgcagtgg cgttagctct ttcaccagct tttatctgcc ccgtggggat   51780
gttggccaag cccagttaac aagcagttga tcagccccag agatcaggtc cctggagtct   51840
gtcacttttc tgagggtggg gagagaatcc tggagcagaa catgtaacta gaagggccac   51900
ctggcttcct atggtctgag ggagagaatg gtgggatctc tggcctgaat caaacctccc   51960
tttctcagtg tccatcttac ctctctgctg taccttcgtt attttccagc agctcctcag   52020
cccgttcctg tgggacccct ctctgccaat ccctacaccc actgtaaatt tcaccgtggg   52080
agggagatgg gccttgaggg ctgtattagt cttctattct gcataacaaa ttgcctcaaa   52140
tttagcagct tcaaacaact catgtttatt agctcatcgt gagttcatca gcagtgtggg   52200
cccagcatgg ctaggttttc tgctcagggt ctcacaaggc taaaatcaag atgttgtctg   52260
ggctgtgtgc tcatctggag tttagggttc tcttccaggc tcacgtggtt gtggcagaat   52320
tctgttccct ggagttgcag ggctgaggtc ctgttttctt gctgactgtc agatgagggc   52380
tgctctcagg tcctcgaggc tgcccacatt gcttgccacg tgcgtggtct tttccatcct   52440
tgaagccagt gatggagaat ttcccttgga ttgaatcacc cacatggttg gactctctga   52500
cttcaggaag agagccctgt ctcttttatg ggatcacctg attagatcat acccatagag   52560
ggcagttcct tttccttaaa gtcaactgtg gcatgtaaca tcacacaacc acaggagtaa   52620
aatccatcat atttacagtc ccagggatta tgcacagtgc accagggac aactgaattc   52680 tgcctgtcaa aagggccaag caggacttta ttggtgaaga acagtggaat gtcattcttg   52740
gttcttccag aaaaaaatca ctcagtaaag ttagaggttc tcttgccttt tgggaagtca   52800
tcaaagaatc tcatggaggg tttggaccct caccctagaa acatcacacc atgttttcta   52860
taattgcagg gttcatggtc ccttgaagcc tattcatagt ttccaggttg aaaagctctg   52920
ctgcagggtg tggggaggga tgcaggtgga ggtgagggct gaatagtgtg agctgcatat   52980
ctggagctgt ggtggttttt ttagtcttta agctgtcatg tgttgggggt tgggcatggg   53040
aggggcatcc caagagctcc ttggtattga caccatctcc aaggtgatct ctgctctgcc   53100
tggtgcacac atgttttct cctgttgcaa cagcccactc ttgtagaaga gcagacccct   53160
cagtaccagg tctgaccctg gacagcttgt accaggagct acagcacact cccccacaag   53220
cctaaagttg ggatgagccc cccgagaatt agatcagaaa agattaaatg cagaggtgat   53280
```

```
ctgtcaggtc cccttttggaa gtgctggtat ggagaggatt gactgagtct gtttaggaac    53340
ctccaagctc tgtagtaact ttagggctag aaaggaggat gcctaagatt caggatcctg    53400
cagtgatgag tcaacatttc ttggggaagg aggcagggct gaggattaaa cggagatgat    53460
gggtatcgtt ctcttgctca aaggcactgg accccaaggc ctccagctct tcgctcccat    53520
ttgaaattca gtcctgagc acaccacagt tgtgatgcag ggaaagaatg tgcttatcag     53580
agagcctggg caagtgggcc ccttgtgagt accgttcaac ctcatttatg tcattggcac    53640
caaaagtaga catcagtctc ttgaaagttt gattaatgct ggtcacactc aaagaccctg    53700
ggtagcattc atttactaag caattactaa ataccagttt ctgtgctaaa tgctgcatca    53760
gtcagggctc ttaatggcag gcagcagaaa ctctccttgg ctgatctaag tagaaaaatc    53820
caggactgaa aggaaacgga gtagctcatg aaattgcagg aagggccgga aaaccagaca    53880
tggagccaaa gtcaggctgc agaacaggtc tagggaggat cccactgctg ctgagaccta    53940
gaccttgtgt ctggcaccca ggatgttgta gggctcagac cctggatcaa tgtatcctgc    54000
agtgcctctg tgggtactgc aactccagga actcaatctt gtcaacgcca ccgccagaga    54060
gaggccttct tggcctccat cttttttggtc actagctcca gattcaaaat cttgaataga    54120
tgcttcttct ctttgataga gcccagtcat atgcgttagc tgcaaaggaa gctgaaaatc    54180
tattaggaac ttttgtcttc aaaaatgaga ggcctgtcct ccaccaagat ccataggaaa    54240
tggaatccaa gaaaccacag gaaggggtga ggtgactggg cagctcacag catgcatgct    54300
acatgtgaat tatctcattc atttctcaca ctacccagtg aggtaggtat tgtcatccct    54360
acttcataaa tgatgatatg aggtacagaa agtttaagga acttgcccag gacacgacac    54420
gcagctatta agtgctagac ccagtcaatt tgagtctgac ttggactgtc tgactccaga    54480
agccaccctc tcagacactg ctgtatactt ccagtgaatg ttgatgaaat tttcagggtt    54540
gctaagctgt ggatttcaga tcctggattg tatgacctaa aagagagact tccctaggag    54600
tgagggtccc tgaacagtca actggttttcc aagaatgggc tccctctcat caccttatga    54660
cagtaatcct ctgtccaaca gccaaagagg tcctgtgggg agggcttgca gatgggagtg    54720
cgcagagccc agctcaaagc tcctgactag gctcttgttg agtattcctt tgattcctgc    54780
ttctgtcttt ttaaatcaat ggagacaggg gagggttatc tccatcctcg gctcaagatg    54840
aaatgcatcg ttcctcgttt ttctcattcc ttcccaatgt gtgtactgtt aactttagtt    54900
atgaaggaaa ttacagtgtc ctgtgcatat accaaggctg tccaacctcc acacctttgc    54960
tcaagctgtt ccttctactt gaaatgcctg tttccttccc ttctaattgc atctttccat    55020
ccaggtagga atcagctcct tggttcatgg agccttttct gctctgtttt actatgcatg    55080
gacttccttc tgaattagca gaggatgttt cctagcttgg tcttaaccct tctccttttg    55140
tttgacctca atttactcat cttacaaatt aggttgtaag ctaattgaat acaggatcta    55200
tgcttcactc tgatttttatc tccacctgga tagcatcatt tttgacacac aagcaggcat    55260
atgggagggg agagaagttt ggtgccagaa agaactggat ttgaattcta accctgttgt    55320
ttacgtgagt acgttactta accattaatt acttcaatgt atatttatta agtacctact    55380
atgtgccggg cactgtacta agcaccaagg atacaatggt gagtaaagag atgcagcctt    55440
caccatcacg aaggaagaca gatgttaatc cattaaccaa gtaatctcac aagaaaagta    55500
aaatgactaa ctgataagga caagcccctg gagctacaag agggtgtata cagggcatcg    55560
atccaataag ggcagtgttg cggggagatc aggagccaca cagagcctgg gttgtctcac    55620
ttggaaaatg gggtatcaac cacctacctc actaggtttt taaaatcagg ttaaatgagg    55680
```

```
taatacttgc catgaacagt attttgttga ttgatgattg attgaaacgg agtctcactc   55740
tctcgcccaa gctggagtgc agtggtgcaa tctcagctca ctgcaacctc tacttcctgg   55800
gttcaagtga ttctcctgcc tcagactccc aagtagctgg gattacaggc agccacccct   55860
atgcctgact aattttgta ttttagtag acacaaggct ttgcaatgtt gaccaggctg   55920
gtctcaacct cctgacctca aaagatccac ccacctcagc ctcccaaagt gctgggatca   55980
caggcatgag ccactgcatc cagccacttg ccatgcatgg catttaaaaa tgttcagtaa   56040
atgttaccat aatgaaggct ggtaggttgg ccaactgagt ggtctgattc agaaggaaag   56100
aagttagaca tacgtgaaca tttcctgtac ttgaagatcc tcaggacagt gactcctaga   56160
cccatcttcc atcacagtca gctgggaagc ttttaaaaaa atgcagacat ctgaccttca   56220
cgctagacct attagccaag cagaagtttc tgggcagggc atctgcatat ttttaaaaat   56280
ctttaataag gcagcctcaa aattacagat tcagcacgca tttaccataa ccactgaaga   56340
aatgcaaagt tataaaaaga agataaacaa caatctgtct cctgctttct tccctctcct   56400
cccctgcttc tggaggcaac aaggtcaact atttggtgtg attccttta gcattccctc   56460 catcaatggt cacataagga tgctcacaga taagcaccta tgcgggggtt ttttttttcc   56520
ttgtaaaact attcacatac taaatacttt cctcagtatc ttgcctttt tcacttcatg   56580 tcacagaaac atctcttcag gtttatagat acaggtccag ctcttctttt catagccata   56640
taacattctg tagaatagag aggacacatt ttactcagtg tccgattgat ggatatcaat   56700
attgttttca tttctacaaa tagtcaagga ataacataac tctgtaaaag ttttattact   56760
tataggcgca tttatgccta aaggatagtc tcaaaagagt gaaactgatc aaatgtgcat   56820
ttttttattt taataggtat ggacagattt gttctcaaaa tgtttgtggc agttcaaaac   56880
accagtaaaa caggggagat atgtattttg gaaaagcacc caaggcgatt ctgaagtgta   56940
gcccaggata agaaccattg cccagagctg ttccagatgg cccctgggtt cctgaagtgg   57000
gtatcgggag agaaatcttc actgaatgaa tgagtgggct ccccagggaa gtgatgaaat   57060
ggtccttatc agccttgcta tctccctctg acagaggcaa actctctctc cctggggaa   57120 gttcctccaa ggcctctata taagaagtct ttgtgagagg aagcaaagaa ggacctgggc   57180
tttgggaaga tctaaagacc caggaaggtc tctgggtggg tgagtgcttt ctctgctgtg   57240
gtggagctgg tgacagttta ttctcccagg aggtccctgg ctgtggctga cagtttctgg   57300
agggctggca ggcgtctacc tgtggctttc aggttatgag gatgtcagca ggggcagcct   57360
tcatcctctg ccttgcacat tccttctgcg ggatgtgaaa gtgctccttg ctggggaaa   57420 ggagatggtg gagacatgga ggagggtgtg ggtggcttct tgaactctga ggaggggaca   57480
taccttctaa gtcctatgtg ttcctaggaa agccaataat cattgcttct cccgcctttt   57540
ttatgtcata gactctgagg gacccattaa gtacaaacaa ataagcgtaa tagtcccttc   57600
tttacttccg ggcctgaagg aaagccagcc tcagccaccc ctcagggttt gctgcgttct   57660
gtttagaaag aggtccttgc gtcctggatc ctggagcatc aggagctggg cttggcatga   57720
gcttttctgg cccatcctga tttctattca ggccttcttt ttctccacct cactcccacg   57780
gtcccctaat ggtgtgattg tgatgtgtgt gcatgtgtgt ctgtgtgtgt caatgacaaa   57840
ctgtgttctc cgttgcagga taaagccaag atgaaactcc ccttacttct ggctcttcta   57900 tttgggcag tttctgctct tcatctaagt aagtgttttt tgccttcagt ctttcttcct   57960
ctgttttttc cctttctatg gtagatgggg tcagagttac acacccaccc ccttctttga   58020
```

```
tcgtcttcta tttctgaatt tctgtgtgct taaagggatg gggactctat ggccaggagt    58080
tgaaaggatt tctcaaggcg tctgttatgt ctgtggtctt ggttctactg tgacattccc    58140
aattttgtcc tttctccatt atgcttactt tgagcttact gagtgccttc tctcctttaa    58200
ctctcttagc atcgccatga agtaggtggt attgtatacc catttcacag aaatacagct    58260
ggtggatgat ggaaccagta cccaagccca tgactgcccg actctaagtc catgctctta    58320
accaccttga ccttgtcagg cagcttgggt tcccctcata gagactgggt tccaggttcc    58380
ccttcccagg cagagttgag cactctgatg cccagggcaa ggtgtgagct gtctgtggtt    58440
ctggggagga acaaggggag atgtgaagga aggacactta gctatcctcc ctgccagggt    58500
ctgagacttc cacctttgag acccctttgg gtgctaagac gctgcctgag gatgaggaga    58560
caccagagca ggagatggag gagacccctt gcagggagct ggaggaagag gaggagtggg    58620
gctctggaag tgaagatgcc tccaagaaag atgggctgt tgagtctatc tcagtgccag    58680
atatggtgga caaaaacctt acgtgtcctg aggaagagga cacagtaaaa gtggtgggca    58740
tccctgggtg ccagacctgc cgctacctcc tggtgagaag tcttcagacg tttagtcaag    58800
cttgggtgag tggcctatgg ctgaggctga ggtgggagca tggaacgggt gtgggatatg    58860
cccccagcat tgctatcact ggctctttt cccattgagg gccctggggg tgtcagtaga    58920
acctgagcct cagagaggtg ttggggtaag agggagggc cacctacaaa cagaagttgc    58980
attttggtct ccaaccttca aatggttgtg gcagggagg gagggaatga attgtgggga    59040
ctcaagaccc atgtgaattc atgtaggaag gatgctccat tctttgtctt ttatcctgcc    59100
ctgtagttta cttgccggag gtgctacagg ggcaacctgg tttccatcca caacttcaat    59160
attaattatc gaatccagtg ttctgtcagc gcgctcaacc agggtcaagt ctggattgga    59220
ggcaggatca caggctcggt aagagaagtg tgaacactaa atggggtgca cctgctgatc    59280
tcagccagca ctcagcttgc atcagatttg tctgtttttc tcctgtataa tctccagaag    59340
aaccagggat agatggacac ccacagacaa cactgagggg gctgcctggg cattcaggga    59400
agagctaagg atttagaatc aggaggtttg ggtccaagtt cctttccatc tctcactatc    59460
tatgtaactt aagttagctg ggcatggtgg tgcatgtctg taatcctagc tacttgggag    59520
gctgaggcag gagagtcact ggaacctggg agacagaggt tgcggtgagc cgagatggag    59580
ccattgcact ccagcctggg caacaagagc gaaactccgc ctcaaaaata aataaataaa    59640
taaataaaat aaaaaaaaaa ttaaaacaag accatgagtt tgtttcctca tctctaggat    59700
gagttggcaa cccttgttct acctttgtt agggctggaa ggcaagcct gtcactggga    59760 tgcatagaat ctgatggtga taattgccgt ggatcagcat ttcagatgac taggacagtt    59820
cccatcatgg tccagcaggg aagggcccat tgcccgtgg gcagcagaaa gagctggcag    59880
atacggggcc aggtctgctt ctctgccttc cctctgcccc atcccttctt cccctcttgc    59940
tttctccagg gtcgctgcag acgctttcag tgggttgacg gcagccgctg gaactttgca    60000
tactgggctg ctcaccagcc ctggtcccgc ggtggtcact gcgtggccct gtgtacccga    60060
ggtgaggtgg ggctggggat gaacgatgga aggtctggg agatgggaag tgccccaagg    60120
aggagatgct acaaagagcc tgacccttg tgggagaggc ttcctgggtc ttttatatac    60180
tctgactcca cagcagtgtg tgggtgggaa aagaggccct cctgtgggtt gagttgggat    60240
ggacaagagg ctgaaagtcc ctttctgttc tgccttcaca ggaggccact ggcgtcgagc    60300
ccactgcctc agaagacttc ctttcatctg ttcctactga gctggtccca gccagcagtt    60360
cagagctgcc ctctcctggg cagctgcctc ccctcctctg cttgccatcc ctccctccac    60420
```

```
ctccctgcaa taaaatgggt tttactgaaa tggatttatt ttctcctctg atcgcggatc    60480
cactctgctt agccctcatt gaaacttctt ccttatcatc tctccccaca ccacaacttt    60540
catagaagtg tcagaagcta ctactccttg aggaggagga tggagggtgg agttgggtct    60600
atggagcctt ttggagatgg aggaatgggc tcagctagtt ctcttcatag aacacctgat    60660
tactgggcac ctgcatagtg ctgccaggac ctttcaaggt tgtaggtaga ctcccaatgg    60720
cccagtttgc atctctgtaa ccaaaggcct tttctctctc tctctccaac cccagaactg    60780
tggttggttt tatatgtaag gaagttaaca tgtccctggg aacagtccac aacattcagg    60840
aatgaatgta taagtaccgc aatccccggc ccctcaagtg gaataaatct aacatgtatt    60900
gggcaccatt tcccagtggc ctgctgtggt agttggcctt attccatgca ttttttatggg   60960
ctgccttccc ttcctcaact gcattctctg ctccttccta ctctctgcaa ctcccaaata    61020
aacacttgta cgcaactccc tctctcagga tctccttctg gggaaacctg atataagaca    61080
gcttgccatg cgtcagactc tgaatgaggc ctgggaatac aagacatagt cctctggcac    61140
ttgggatata tggttatttg taacataggc acaaaaacat ctactagttg ttatcgctta    61200
ttgagcaccc acaacatacc ccctgctgtg gcaggcacct tgcctagatg acctcatgtg    61260
atcaataatt atgagcccta ttttacagaa ccaggctcag agaagttagg atctgtcaaa    61320
agacttgccc aagactgaac ctctaaatgc aactcatatt gaaattcaac tctgctccaa    61380
agcatgttac tttaaccctt gtgcttttac agctggctac tctcccctta tggtcacacg    61440
gggatgaagc acgggggag gaaagccaga ctgtctcact cttgggttca tcttgggaca    61500
caggacacca gcccagctgg aagtgaggga gctttaatca gagggagggg aggaaggcat    61560
tctcaaccc ttctgtacta gggaggtcag cagaagaaaa taattcaatg ttctaaagcc    61620
atttttttct ccagcattcc tccaattcat agatcttcat atgggattag gggctcagag    61680
aggggtgaaa caagaactct atttttttgg agtgtggtat agagaaggga tgctacttct    61740
ctaaggtcac atagtaagtt gagaaagaga gagaaatcaa actcaggttc atttcaacta    61800
ttgttccaca agaatctgtt gatttcaaag atggtggact atgggttcat ccctgtggtg    61860
agtgctgtga ggatgcagct gaggtggaac tttcactcct tgccctcttg gactttatat    61920
tctggtgtgg aaaggcattg cttcccttat ttcaatatta acaacaaagg gtaataatat    61980
ttcccattta ttaagcattt actaggtgtc aggtactgtg ctaaatgtta ggtgaacttt    62040
gtcttgttcc tcataaatct ctgccgctgt gggtgtgtac tttgacagaa gtttgacttc    62100
cagtccacag agatcttctt tgggggagta atatcaagaa ggggcacgaa ggaagctgca    62160
gggctcctag tccatcctg tatctcgacc taggcatgtt tacattggtg cattcactgt    62220
gaagtttccc tgagcagtcc actctatagt gtgctttata ggagcacatt gtacatccat    62280
tgaaaatttt tccttggccg ggcacggtgg ctcatgtctg taatcccagc actttgggag    62340
gccgagacag gcggatcacc tgaggtcggg agtttgagac ctgcctgacc aacatggaga    62400
aaccccgtct ctactaaaaa tacaaaaaaa ttagccgggt gtggtggcac atgcctgtaa    62460
tcccagctac tcaggaggtt gaggctggag aatcgcttga acctgggagg cgaaggttgc    62520
agtgagccga gatcgtgcca ttgcactcca gcctgggcaa caagagcgaa actccgtctc    62580
aaaagaaaga aagagatttt ttctttttct taaaagtaa aaatcatgaa ataagggac    62640
tgggctaata ttccaaaata tgggtttgtg tgtgaatttt cctctccagt aagatactaa    62700
ctaagctctg tgaaactgtt tatctatggt tctttatcat tgaatccttg gagttcctta    62760
```

-continued

```
cactgtgcag agcacagagt aggggctcaa tcaacagtgc actcattgct ttttcataga    62820
caagggccac cctcactcaa ctcatgtgcc aggcatagtt ctgagagctt tgcttaagct    62880
gatnnnnnnn nnnnnnnnnn nnnnnnnnnn nnnnnnnnnn nnnnnnnnnn nnnnnnnnnn    62940
nnnnnnnnnn nnnnnnnnnn nnnnnnnnnn nnnnnnnnnn nnnggtcact aatttggtat    63000
agagttatgt tcattgattt cattttattt tgtttctgat ttttaaagat tgttttactt    63060
gttttcttcc tattattatt ttattttatt tgtaaaacat ttacatatca gacatttaca    63120
ttttcccaaa ggtaaaactg tgaaacaaga tatattcaaa gaagtttact ttccctctct    63180
gtttcttgta cccctttttcc tcttctttag gtaaccattt ttatttttt aaatataaac    63240 attgtgtagg tgtatataca tgtattagtc tgttttcatg ctgctgataa agacctatct    63300
gagactggga agaaaaagag gtttaattgg acttacagtt ccacatggct ggcaaggcct    63360
cagaatcatg gcaggaggtg aaaggcactt cttacacggt ggtggcaaga gaaaaatgag    63420
gaagaatcaa aagtggaaac ccctgataaa cccatcagat ctcgtgagat ttattcacta    63480
tcacaagaat agcgtgggaa agactggccc ccatgattca gttaccctcc cccactgggt    63540
cccacccaca atacgtggga attctgggag atataattca acgtgagatt tgggtgggga    63600
cacagccaaa ccatatcaat acatttccct ctcttttaga taaaggtag tatactgtat    63660 acactattct gcagagtttt tttttttttt gatgtaactc tatcctgagg gtgctctgta    63720
gcagggacct ctcatgcctt ttaaccactg cctgggtctc cattacatgg ctgcagcata    63780
gttgccacag cattcctgta ctgatgacta tttggattgt ttccagtctt ttgctattac    63840
cagtagtgtt acaaagagga tctggctaca tgttcagggt ggggaggggc agatgtgtag    63900
cctgtcagga gggtattgca gtaatccatg actgagttaa tggtagttta aagctaggat    63960
gagtcagtgg ggttggagag aagtgggcac atttgaatga tatgtaggag gtgaatgatc    64020
agcattattg atgagtttga ggtgggggcat gtggggaaag gattcgagga tgactcccag    64080
gtttctgttg ggacagtgga tggatagtgg ctcctcccct ttttccaatc ttccttggcc    64140
cttcgctgac ttctgttggg ttggcctaca gagagcttct ttttcctctc tgttcgccca    64200
ggttcctcca cttttggcggt ggccctctgc tcgacggtgc cttcgctggc cctgacatcc    64260
ctgctgtgcc tgggcttcgc cctctgtgcc tcagtcccca tcctccctct ccagtacctc    64320
accttcatcc tgcaagtgat cagccgctcc ttcctctatg ggagcaacgc ggccttcctc    64380
acccttgcgt aagtggcctt ggggcgggct ctgtggagac ggacacactg gggcaaagag    64440
aagctggagg taaagaaatt gggaggcaag gcggggcctg gaggcagtca ggtgcgggag    64500
actgggtttg ggggcaggtg tggagggggt gagaccagag gtggtgggaa ggatagaaca    64560
ttcatgcact tgagccttta catctgcggt gccctctccc tctgttttct acctggtgaa    64620
ctcgtattca tcctctgagg cccacttctg tttcagttct ccagggaaga aatggaaaag    64680
tgtcttccct tctttgtgcc cttagtactc tagtcttact tcctttgcta gtgcgtgcat    64740
tgtctggcat gccatccatt tacatgcctg tcttttcttt cctggtgcag cctgcatgag    64800
ggtcctgtct gttttttccag ggccccgcat gtgccttctt ctgggttctg tgggtcaaat    64860
gtctgagcag agctgaagag ggaaaggcca gacaggtgtg gttggagggc aggcctagga    64920
caggggagct ggggacaagc ggccgacagc ccccagaggc caggcttctg cttgaggga    64980 gggtccctga agctcactgg aacccctctg gtttctctcc ccagtttccc ttcagagcac    65040
tttggcaagc tctttgggct ggtgatggcc ttgtcggctg tggtgtctct gctccagttc    65100
cccatcttca ccctcatcaa aggctccctt cagaatgacc catttacgt gagtactggg    65160
```

-continued

```
aggatgggga tccctggcag gaggcctggg ccttaggcct tggctgcccc aaatctggct    65220
gtgatggcct gggtatgtag catggtgcag cttcccaaag ggtctgtgtt attcaagtat    65280
ttggggcaaa agtatttgtg tgtgtgggga aacagacatt ctggagtagg gtggggaatt    65340
ctcacgaaac ttcaagcaaa atcctgagac ctcaaaggtg tttcctgctt gtggtgagtg    65400
caggcccacc ctggcctctc ccctaggccc acacaggggtt tccacagttg gccccaggga    65460
caggacctct gtgctttcac ctctgtgtcc ttacacctgg agggatgctc tgaggtcctg    65520
ctctaggagg tggtcgtgag tctcctgctc tttgcagaaa ctgaggctca aagaggttac    65580
ttacgtgttc agaggcacca gctaaggagc aaaagtcaac tttgaattct gtgttttgac    65640
tactgcacag ctctatttgc ctcattttt attttaaag cagcaaatct tagaatagga    65700
gtttaaatcc atcacttgga gaaagaaag actaaatgtt ttttgttttt gttttggaga    65760
cacgatcttg ctttgtcacc caggctggag tgcagtggca caatctcggc tcactgcagc    65820
ctcgatctcc tggactcaag cgatcctctc atctcagcct cctgagtagc tgacactaca    65880
ggcatgtgcc accatgccaa gcttatttta tttttatttt ttgatagaca ctggggttc    65940 gctatgttgc ctgggctggt tttgaattcc tggcctcaag cgatccaccc gtctctgcct    66000
tccaaaatgc tgtgattaca ggcgtgaacc actgtgcatg gccaaaagag taaacttgaa    66060
atctgaggcg aatgacttga ttgtgacatc aggtgaccta gtaatcagct gtgtattcta    66120
gctggtgcct ctaccagctt cccatgtgac cttgaacatg tcattgaatg ctcgctaggc    66180
ctctgtttct ttatctgtga aatgggcttg atattcctcc tctaccccaa ccgatagtgc    66240
agaatgaaaa gtaactgaaa gtccttcctc cagggcacca tagtgtctgg gtgaaaagta    66300
gaatataaac tcggtagact tctggtccct tcattggtca tggaatggac cagtgcttgc    66360
ttcattgagc aacagttctg ttgttcagaa ttcctggatt tcacctcact tctgctctcc    66420
ctgcaggtga atgtgatgtt catgcttgcc attcttctga cattcttcca cccctttctg    66480
gtatatcggg aatgccgtac ttggaaagaa agtccctctg caattgcata gttcagaagc    66540
cctcactttt cagccccgag gatggttttg ttcatcttcc accacctttg aggacctcgt    66600
gtcccaaaag actttgccta tcccagcaaa acacacacac acacacacac acacacaaaa    66660
taaagacaca caaggacgtc tgcgcagcaa gaaaagaatc tcagttgcca agcagattga    66720
tatcacacag actcaaagca aaggcatgtg gaacttcttt atttcaaaac agaagtgtct    66780
ccttgcactt agccttggca gacccttgac tccaggggag atgacctggg ggaggaagtg    66840
tgtcaactat ttctttaggc ctgtttggct ccgaagccta tatgtgcctg gatcctctgc    66900
cacgggttaa attttcaggt gaagagtgag gttgtcatgg cctcagctat gcttcctggc    66960
tctccctcaa gagtgcagcc ttggctagag aactcacagc tctgggaaaa agaggagcag    67020
acagggttcc ctgggcccag tctcagccca gccactgatg ctggatgacc ttggcctgac    67080
cctggtctgg tctcagaatc acttttccca tctgtaaaat tgagatgaat tttggtgttg    67140
aaagttcttc ctggagcaga tgtcctagaa ggttttagga atagtgacag agtcaggcca    67200
ccccaagggc catgggagcc agctgacctg cttgaccgaa ggatttctga cagactatct    67260
ttggggatgt tttcaagaag ggatataagt tatttacttt gggcatttaa aagaaaattt    67320
ctctcgggaa taattttata gaaaaataaa gcttctgtgt ctaaggcaac tactgtttcc    67380
atctctctag gctttgggcc ggggctgtgt gtgtgtgtgt gtgtgtgttt gtgtgtatgt    67440
gtatgtttct gaggaggccc taccctggca tgagagggta gggaatctgg ctacacatct    67500
```

-continued

```
agtgtggcag ctggacccag aggtggggca ggaaccctga ctatgattca ccccgctggt  67560
cctgggatgt gggcccagag acttcctccc ccaggaaccc ctctgcttcc tcttcctctc  67620
cacatcctta actaacttta gcagaaccct actcctcact acacaccccc agctagaagc  67680
gctggatgga atcagaaatt cctagtttga gtttcaattc tgcccctcag cagctgggca  67740
agccccttaa ccactctgag tcactagttc cccacctgca aagtgcagtt aatcatttct  67800
atctctgatg gcgattgtga gaatgtaaag tcattgcaac tgcctagcac atggtaggag  67860
cacatgaggg tttgctcctg tgtttactca tgacccttgg ggaggacggg ggcaaagagg  67920
gagaagttga gggtgcagga ggagagatgg caggtgggtg ggatgggaga atctgggca   67980
cacctgctgt ctcattccca ccttgctagg agagggacta ggaaagaaca gtgggaggca  68040
gggggatggg ggtggaaggc aggggtggc aggcaggttc atccatccat tcattcaaca   68100
aatgtttatt gagcacctgc cacgtgtcag gccctgtcct gggtgctggg gctataaaga  68160
tgcagaaggg tctgaaaccc agctcttcct tcttcctgtg gatgtcgggg tgtaatttcc  68220
aggggccagg agcctgggtc tgagggcgga caccaaagtt ctagtggtgt ctattagcag  68280
cgtttaaatc taatggatgg atttggtctt gttaccctgc tcaaaagctt tcagcagctc  68340
cccactgtcc acaggacaaa atccagatg ctagcctggc attcaaggct gtcactagtg   68400
tgatctcaac ctctcccctt ccctctttac ctcctaccaa cagcggggca gagcccaccc  68460
ctgtggacca agattcccag tctctgggtc tgtgtgtgca ccagttcctc tgcgtgggtg  68520
gctcaccctg cctcagcttg tgaaatccat ctggtctgct gggatcctgc tcaaaatgtc  68580
atcttctcca aaaatcatta ctcaggcttt ccagcatgtc tgagtccctg gcacttggtc  68640
acacccttcc tggtgactgg catttgcctc cacatcatga ccctcccacc ccttgcctgg  68700
gcagcatact ccaggaggca aggtctgttc tcgcctggct ctaattaatc tgtgcttacc  68760
atccacatgg taccagctaa ttcttgttga atgaatgatc gttgaatgag tggattcttg  68820
ttttggcctc agaaccaatt agaaggagcc agaaaaacac atgggggtgg gggaggtgca  68880
gtgtggtgca gtgaaaaaaa acccttctgg aaatctcagc tctgtcactt actttgtcag  68940
ctctgtgact ttggatggac cacttctttg tcagtatggt gggagaaata gacatgcctc  69000
tctgggctgt tgtaaggatt acaaattagg tcgagtgctt ggcatgtggt gggttgaaca  69060
gatcacagct agcattacag atgatatatt aaagccaaaa aaagatgcct aatgtccacc  69120
agttggtgaa cggacaaagg aaatgtacca tatttgggat attatttggc aatcaaaaaa  69180
agtactgaca cctgctacaa cacggatgaa tcttgaaaac attagactaa gtgaaagaag  69240
ccagacacaa gaaactgcta atgattccat ttaaatatga aatatcgggc cagggtgcag  69300
tggctcatgc ctgtaatccc agcactttgg gatgccaagg tgggcagatc acttgaggcc  69360
aggagttcgt gaccagcctg gccaacatgg cgaaacccg tctctactaa aaattagccg   69420
agtgtagtgg catgcacctg taatcccagc tacttggttg gctgaggcac aagaattggt  69480
tgagcctggc aggtggaggt tgcagtgagc caagatcgtg ccactgcact ccagcctgga  69540
tgacacagtg aggttccgtc tcaaaaaaaa aaaaaaaaa ggaaaagaa aaaagaaat    69600
ttccagaata ggccaatctg tagaggcaga aagtagattc atgattgggt aggcctggt   69660
gtggaggcca tgggtagtga tggctaatgg ggaaggggtt tcttttgggg tgatgaaaat  69720
gggtggactt atggtatgtt aattatacct caataaaact gttatttaaa ggaagaaaag  69780
atgcctggat tccccaggaa gtgtacagta gacttctgtg agaatcagaa atgatttctg  69840
gggaagatgg gcgagaggag agtaagtggg agaagtgacc acgtgcgcaa ctctcatcgt  69900
```

```
tctgccctga gagccttcct cctgcaactt tatttattta tttattttga aacaggttct    69960
cactctgtta ccctggctgg agtgcagtgg tgtgatctca gctcactgca gcctcgacct    70020
gccaggctca agcaatcctc ctgtttgagc tcctgagtag ctgggactac aggcgcatgc    70080
caccacatct ggctaatctt ttatttattt atttatttat ttatagagat gggggagtct    70140
cactctgttg ctcaggctgg tgtcaaacgc ctggactcaa gtgatcctcc cacccttggcc   70200
tcccaaagtg ttgggattat gggtgtgagc cactgtacct ggcacctcct gcaacttctt    70260
cctcaagtgg aaccaatgag gaagcaagca actcagagct ttcacaagtt ttgatttcaa    70320
tcagcaacgg gcttccaatg caaccttct ctcctgtaac cagcctcagt agagaggaac     70380
tggaggtgaa ttggccccca tcacaccccc acagtgccaa gctgggccct tccatcaggg    70440
ggagaacaca tgccgtgtaa gggacagcca acagcataaa ataggaattg tgtgatgatc    70500
cctttaagc ctattcagcc cagggaagtg catatgatca gccccatttc atagatgaag     70560
aaagtcaggt tcacccatta gcacattgtg gggctggtat ttaaaccagg tctgtctggc    70620
tcccaaggtc acattcattt agacattacc tttactttac atttcttctt cttttcttct    70680
tcttcttctt cttcttcttc ttcttcttct tcttcttctt cttcttcttc ttcttcttct    70740
tcttcttctt cttcttcttc ttcttcttct tcctcttctt cctcttcttc ctcttcttcc    70800
tcttcttcct cttcttttct tcttcctctt cttcctcttc ttcctcttct tcttcttctt    70860
cttcttcttc ttcttcctct tcttcttcct tcttcttctt ctttttttt tgaggtgggg     70920
tcttgctcta ttgcccaggt tgaatgcagc atcatcatac ctaaatgcag ccttgaactc    70980
ctggccttaa gcaatccccc tgcctcggcc tccaaaagtg ccaagatttc aggcatgagc    71040
caccatgccc agcctgcatt tattctcttg taagaaagat atcatttaaa acagacgaga    71100
aaataaagag ggacatgaaa aagacgcatc accattaatt ggaccactca gagataatca    71160
tggttaacat gttggtatgt tccctcccgt catttgactg gatgtatgtg ataatttaaa    71220
tgatctcata agcttttcct tatgtaatca aatagtagcc aaaaacatga ttttaaatgg    71280
ctgctcacaa ccccatctcg tggttctgcc acgccttgtt tatccccatc cacccccta    71340
tccctttccc cttccctgcc tgtgtgggg tcctagatga cggtgagcca gagggcagcc     71400
ttggtcagca gattggagag tgcaaataat aaaaacactc agaaggcgag ctgttgtcaa    71460
gtgggcttat cacaaaagag caccttggga tattccagag aatgacctca tacccgctaa    71520
tcactatcca taatctggtg ctaactgtac tttagctgaa ggtgctggca ggtcctgccc    71580
aggtgctgct aagaacactt ctattctgtg agaatcagag atgatttcta gggaaaatgg    71640
gcgagaggga gtaagcagga gaaacaaccc acaggcacag ctctcatctt tctgccctga    71700
gagccttcct cctgccacgt ggttttgttt gtttgtttgt ttgtttgttt cagatagggt    71760
ctcactctgt cacccaggct ggagtgtagt ggcaagatca tggctcactg aagcctcgac    71820
ctcccaggct caagcagtcc tccccaaatt caaagcttgg agtgatggtc ccagtggtta    71880
tgtctaggag ccctttttcc tgccagcccc tcagggatt tgatgactctc aaatgcttca    71940
ggtgtgacat gggcacagca gtgagtcatt cctctgacat tctttgggaa gaacattttc    72000
catccaggct tccaggcata agatccagtc tctggtgat aaggagttca cagacaggac     72060
aatgtctgag tgtatcttaa acccaggacc atggcttgtg ttcacaccag accctccagg    72120
gatttttgagg tgttttgttt gtttgttttgt tgtttgttt gttttttgag acagagtctc   72180
tctctgtcgc caggctggag tgcagtggca cgatctcagc tcactgcaac cttcgcctcc    72240
```

```
cggttcaagc gattctcctg tctcagcctc ctgagtagct gggactacag gtgtgcacca    72300
ccacacccgg ctaattttg tatttttaat agagactgtg tttcaccatg ttggacagga    72360
tggtcttgat ctcttgacct cgtgatcctc ccgcctcggc ctcccaaaat actgggatta   72420
caggcatgag ccaccgtggc ccgcccaatt ttgagttttt atgttctaat cccaaacatc   72480
tgctcacagg cccctcagca tattctttcc tgggtccagt gtcacctccc aggcctgcag   72540
gctggctaga gcagtagggt gtgtgggaaa gctctgggct ttgcaggcac tgatcagctg   72600 tgtgaccttga accaccctga acctcagttt cctcacctgt aatggaaata ggtaccacgg   72660
cagtttgttg caaggactag agagtaacct tgggaataaa aggtagcagc agcttgggct    72720
ctggagatgg actgtccaag accaacttcc agttcctccc cacacaagct ctggcactta   72780
gattcctggt acctccgctg cttcatctgt aaaatggagt aacaatagga atactttata   72840
gagttgtaag gattgagtgg ctggatgaac gtcaagcact tcaaagggga cctggcatgt   72900
agtgagtgat caatataaac cacctggctt gtagcaggtg tgctgtgtgt ggctgcaggt   72960
gttattagta acatctgtgt gcccttcaga gcgtgcacca cacttcacac cttgtggagt   73020
ctggaatgcc actattatag ttcaggatag aaaacctccc tgcaagcact cgctttagct    73080
tgtctccacc gaacaaaaca acacaagttc tttattactt ggaatgggaa aacttcaaag   73140
gcaaaaaaaa aaaagactt tcgagttacc ccaaatctta agccaaagtc aatgaaaaat    73200
atcaatcttc atattcaatt tttgcgatac ttttgtctcc ccagcagtca atggagagaa    73260
tccaagcaca cagaaatgtc aattaccagg ggcagggcta tgaattcctt tcagagccct   73320
gggctgggga agagtgcagg cagacagatc tgggtcctgt tatcacgttc ttagattggg    73380
tgtccttgta ggagtcatga agcatcttag tgcctttgtt tgctacctat aatgcctacc    73440
tcagagagta ataaggataa gtaaggctct acgtgaaaag tgctcggccc tggcacatag   73500
taggtccttc attaatggca gctactaatt tttattacat acgcaaaatc acattacagg    73560
tcaagtacgc tacatgacag tgaaacagtt ttttgtttg tttgttttga acagagtct    73620 cgctctgtca cccaggctgg agtgcagtgg cacgatcttg gctcaccgca acttctgcct   73680
tcaagcaatt ctcctgtctc agcctcccga gtagctggga ttacaggcat gtgccaccac   73740
gccagctaat ttttttggt attttagta gagacgggt ttcaccatat ggccagact      73800 ggtctcaaac tcctgaccttt gtgatctgcc caactcagac tcccaaagtg ctgggattac   73860
tggcatgagc caccgcacct ggctgtgaaa cagttttatt gtgtttctgt ggaatgtgtc   73920
ctacccaacc tatagctaac tcctatagtt ccctcagttc tcagctcaga tatcccttcc   73980
tttctgtact gttacctagt actggttttc atagcaccag gtacctctct ggcatagagc   74040
ttgtcacagt tgcagtttaa tgtaccatca taggatttta aaatattca gttgtgtctt   74100 ccattaggct ttcatttggg aactccacgc aggcagcagc tgtatatttt gtattgccta    74160
ctgtatcctg agaactttgt accctactta gcacagaatg gaggctcagt aaatactgga    74220
catgagagag agagagagag agagaggaga gggagagaga gagagagaga ttcaacctac    74280
aatcccagct ctgagcttct agttccctga tggtgaggac tgtgatgtgt ctcacacggt    74340
aatgagcact tatgcagaag aggctcagaa aatttctcct catggccaac ggaagactta    74400
gagttctttt ccaagctcca ccgtttgctg gcatgcaaaa tttggactat cacttaagtt    74460
ttccaagcct tgcttttct atccctaaca taggacaata ttcagcattg ttgtttgttt     74520
gttgggggca ccatgtttca ggcacttagt agatattgt accaccacat ttcaattggt    74580
cctcctcaag ccctgcaaca tctgtgaggt ggtcatcctt aacaactcac agatgagcaa   74640
```

-continued

```
caggagactg gggggatgag ggaactgcca aggaggtcca gcttatgggc agcagagcca    74700
agaatggaac cagggtcttt tatttttttta tttttttatt tttatttttt aaccagggtc    74760
ttttaacatc cgaggaccac attctttgtg ctttccaaat catcacctgc cccatgcaac    74820
ttacagggta agttacatta acaacgtat gtaaatggct tgtgctagt tattcaccac    74880
cacaggggaa gtgagtcacg gacaagagtg cagccgctcc attcggatcc tggctctgac    74940
acttacctgg aaaatgactt aaccattccc aggatcagct gttgtctgt aatttaggta    75000
gtttaatggc acttgtgtcc tagagttgtt tagaaggttg aataatatgg agcacttaac    75060
atacttagca cctagaaaca cttcctaaat attagttgct gctgttgtta tcgttattaa    75120
aatttctgcc taagatctca tttcaggag cccaactcaa tctttgacaa gcttaaacaa    75180
aaattgcttt tcttcattta ttcacttaca cagcaaacat gaattgagcc tgtactgtgt    75240
ttccagaact gtgcaggacc agagaggcac aggtgaagga agcaaggctc tggctctact    75300
ggggaaacag caagaagatt gctacaatga ggtgggaaga gggctggact agagagaagc    75360
cctgattagt gtccttgcta cctttctctg ggagagccaa ggcaggcttc ctggaagagg    75420
tgatccttgg ctgaaacttc gatgaagaaa aggaaagagc gcagtggtta gggaggaaag    75480
ggcattctgg gcagatgaaa tgacatgtga caaaatatgg gtgatcannn nnnnnnnnn    75540
nnnnnnnnn nnnnnnnnnn nnnnnnnnnn nnnnnnnnnn nnnnnnnnnn nnnnnnnnnn    75600
nnnnnnnnnn nnnnnnnnnn nnnnnngca ctccagcctg ggtcactgag tgagagaccc    75660
tgtctcaaaa aaattaaaaa aaaaagtcc agaagaacat ttgggtctca ctctgtggcc    75720
caggctggag tatagtggca caatcatagc tcactgcaca ttcaaactcc tggcctcaag    75780
tgatcctcct gccttagcct tgaaataagc ttggattaca gatgagccac cacacccagc    75840
cagaccatta ttcataatag ccaaaatgtg aaaacaaccc aaatctccat caactgacaa    75900
atggataaat agaatggtgg ttgatccata caatggagta tttactcagc aataaaaaga    75960
agtcctgata catgctacaa ggatgaacct cgaaaacatt atgctaagtg aaagcagcca    76020
atcacaaaag gctacatatt acaagattcc atttaaatga aatgttcaga ataggtaaat    76080
ctaacttttta tcacaggcaa agctatgaca ggaaatagat gagtggttgc ctagtgcttg    76140
ggggcagagg tgggggtgag gcgagtgagt actgctaatg gtacagagtt acttttgggg    76200
ataaagaaac tgttctgaaa tggactctgg tgatggttgc actactctga acatactaaa    76260
actgttaaat tatatacttg aaatgggtga cttgtgaggc atggaaatta tcttaaata    76320
aagctgtttt acatatttta catatttaaa aatgcaggtg gagggatgag ccctctaaag    76380
agaagcagga gtttgaggag gttctaaata ttgtgtggtg ggtactgagg catataaatt    76440
tgtcagacct catcaaaatg tatgatgtaa tcttcaagaa agttgatttt aaagaaacac    76500
caccagcacc aggtggagaa ggcaggaaga agttacacaa ggggtaggcc aagagtggtg    76560
gctcatgtct ataatcccag cactgcggga ggccgagctg ggtgggtgac ttgaggtcag    76620
gtgttcgaga ccagcctggc caacatggtg aaagcccgtc tctactaaaa atacaaaaat    76680
tagccagacg tgctcgcgtg aacccagggg gagaaggttg cagtgagcga agatcatgcc    76740
aatgcactcc agcctgggtg acagagtgag actctgtctc aaaaaaaaaa aaaaaagtta    76800
cataggggac agtggcaggt gtcaagggca ggcagggtct ctcctatctc caggataaac    76860
tcataggggga cttagatgcc atgtgggtcc ctaatagccc tccacttggt tcttgcagcc    76920
actcttatgt gtatcatttc atgtcaggcc tcttcttccc aacccaccca gccatcccag    76980
```

```
cctggctgcc aacccccacct cctccagccc ctgtcaccccc ataattgggg ccaggaggca    77040
tgggagagtc gccatctctc ggtgccatct gttgcatctt tacagataac catggctgga    77100
tgcggcagat cctggggtgg agcagccgct gttcagagca gtgatcaaga cctccccatc    77160 tccaccccctc aaggaatcgg ttttcttcca tagccacatc aggtgctgtg caggaaggag    77220
ttgaaacgag aagccaggag caacgagaag gacactaaca tttattaagc actgcagact    77280
ctcacagcac tcccacggaa tcgatattat tatccccatt ctgaagacca ggcaactgaa    77340
gctcaatgtt taaggaactc accgaagtca ccaactgata aaagtgatgg aagctgggat    77400
tcaaatccaa gctaaacttc cttccaagct tactccacaa cacagaggtt ggggaaaggg    77460
gataaaaaga gaggggagcc caattccatt tccacccagc tcctgaggcg gagcttgtca    77520
gcacagctct ctccttccca gaataggaag atacccatca gaggcaagtc ctagacacca    77580
gcagtggtaa ctccctgccc caaggcagct gcagacagcc tatggctgta gttactgctc    77640
ccaaagagtg ttagaattcc cactcccagc ttcggggcca ctcacacaag gtgattgaag    77700
tggaaaccag agactctcca caatgccctc ctagagtaaa tgaggctatg taactttgtc    77760
caaatgagta atttgaaaac ctgggggctc ccagctcctg aaaagggaag gatgtggggc    77820
cctttatatt catactccac tttgtgcagc tctcccttgt cttatgatag ccctattaag    77880
aaattcctct cccagcacgt ctccttcaaa gagctctaga cctgaggctg tcagaggctt    77940
aggactctgc ctattagtcc cagggtctgg atgaccagca ggacacctgg cattcagtga    78000
ccactggatt agataaatga aacagtgggc agagtgccac ccaatctccc cctgaagttt    78060
gaagaggtcg agaagtgagg ctgtccaact gctgaccctg ctttctgtcc acctggccac    78120 ctaaccttt ctggcttcca cctgcccctt tgccatccct ccccccagcc cacccagccc    78180
attttcaggc atacctgggc acgtgctgga atagaagccc tcgttcttca gaatgatcaa    78240
cagggagccc cagcccagga gtacagcaga gaagaagagg ttctccagca cagccgtgca    78300
ggccatccac cagcgcctcc ggtacgcctg ttgcagcgtg ggggccatgc tggccccgag    78360
cctgcacaga aacagagcgc tgggtgaagg gcccccagt ggccccaggg aagggtcctg    78420
catcatggtg gcacccgaga cctctcgggc cagcccgcga ggagcccctc atggaggccc    78480
catagagccc tgggcttccc agccggtgcc aaggagctgg ctccgcgcgc actagcagtg    78540
ccagaggtgc acgcggcacg gggctcccgc tgagccacta tcggaaacaa ggaaggtcct    78600
gtctgcgcgc tgcagcttcc tagcaggctg ccgggttctc tcaccaggc cagggcgctc    78660 agggccgggc tgctggggag aaagtccgca tctgcccagg tccccagagg acagcaaggg    78720
gcagagcgcg ctctgaagca ccgcgggccc atgtccggac tctcgcgcca ggaaagaccc    78780
ctagaagctg gcaggaagaa gggcaagttc aaggctaccc tacgacccca tcttccagtt    78840
gcccctccaa gacctctcct tccctctggg gccgggcgac agcaagccct ccccctttcc    78900
gtatcaggtg acccacgacc ctacagtctc tcgggccaag ccaacagctg ccacgtggag    78960
ggagacccag gacgggctct cctcggttcc ctcctccccc gcgcgcccct cactcactcc    79020
gcagggctcg gggcaccagg cttttgcacct cggaacccgc ttgcccccct ccagccccgg    79080 gaggggctc ggacttcggc aggaagtctg gcggctgctg actttataag ggcagcggtg    79140
gcggatgggc tggcgggcgg gtgtgtttac caaaggaggg gaaagagccc cagctccccc    79200
cgccgcggcc gctgcagcct cggcgggagg agagggaacg cgggcagcgc ggggcgggg    79260 agcgacaact gggatgagac cgaggaaagc ggagaggaga aggcaagaa agacccgag    79320 agagggagg aagtaccagt cacttcttcc aggggggactc ggtattctca tctgtgaaac    79380
```

-continued

```
ggggctttgg gttcaagcgc tccaggaggt ccgctggaac tctggcaaac gcgcagctct   79440
aagcagagga agtgcagcga gcggggaccc gggaggaaga gaagagtcgg aggggtcaga   79500
gaaaagaaaa gggaaggacg cgcttggcga gatgggacac tgtgccgcgg gaccgcgggc   79560
gcaagtaacg gtctttcctt gggaagcctg gcagtgtcgg cgggagccgg cctcggtgtc   79620
tctcagccga cgcatagccg gagaccctac gcgcgccccc tccccgccca cgctgctcac   79680
ctccggtcac cggcaaatga gcagccagca gctgcggacg cctccgggag cgcaacgctt   79740
tcgcggcgcg tccggagtcc cgtgggccca gccctgagcc gcgccggcgc tggggtcttc   79800
tctgcgtgca ggacccggcc gccacggagc ttcagcctga cagcccggtg gcctcgcctc   79860
cgctgtctcc tcggaagaag cggggggaact gggaacccgc cgggcgccag aggtctgcga   79920
agctgggctt ggatgaagtg gatctgcgga gttgatagtt gtatttacac gcgtccggag   79980 ctgcgcccg aggtgggggc gggggctccc ttcttttccc ctccccttag gtcgagtttc   80040
acgcgcacgt gactcgcccg ctggtcccgg acactctccc tctggcacag ccccagcacc   80100
tacatttcca ccctgacccc ccatcttctc ccccaagccc ccagactaac atcaggcagc   80160
gccctctgta tccttgttca aaacaaagtg cgattcggct gaagccgact gaccgcgatt   80220
cagggccgcc ttgggtgggg ttttgaactg tgcagctgga agcagtgttt ccgagaggc   80280 agagtggcac gggtttcttt ggagttagtc agatcgaggt ctgagtcttg acttttaac   80340 tgactaccct gggttaccta gggcaagtta cctctctgag cctcagcttc ctcctcttta   80400
aattcggtta aaatggaacc tacctaactg cccaaaggaa tcgcgattgt gatgcaggta   80460
aaatgctaag catagcattt ggcatagtaa gcataatgtt aattgttgct gctgtcatta   80520
tttcagaaga cctggtgatc ggatgcttcc agatcaacaa ttgattgact ccaggtaaat   80580
ctctcagcct ccctgagcct cagtatcctc atctgtaaaa tagactacta tggtgtggag   80640
taatgagaag taatctcatt acatgtgagt ttaattgtgt gttaagagtg ctgctaatgc   80700
atgctgagct taatacctag gtgatgggtt ataggtgca ataaaccacc atggcataca   80760
tttacctacg taacaaacct gcacattctg cacatgtacc ccagaactta aaataaaaat   80820
aaaatttttt taaaaaaga gtgatactgg tggccaggtg tggtggttca tgcctgtaat   80880
cccagaactt gggaggcca aggcaggagg atcgcttgag ctcaggagtt cgagaccaac   80940
ctggacaaca tggtgaaacc ccgtctctac aaaaaagaaa aaaaatagc caggcatggt   81000 ggtgtgcacc tgcagtctca gctacccagc aggctgaagt gggaggatca ctgagctgga   81060
gagatggagg ctgcagtgag ccaagatcat gccactacac tccagcctgg gtgacagagt   81120
aagactctgt ctcaaaaaca aaacaagaat gactacagaa agctccaaga aggcctcaga   81180
taaaagggaa ccctgaaca gatgagccac caagccaaga gaggaactaa tggctaccat   81240
agacagggca ctttccaaaa taaaaatact gttattaatt cctcaagaca tcatggtccc   81300
atttaaacct catagctttt cacagaggga gaaactgcag gcttgaagct ggagcaaggt   81360
tagaggtagg atgcagagtc aggtcggcct ggcatttaag tacggctcct tccattcctc   81420
ccagaaggag aatggcaaga gcaaaggctt agctgtggga atggcacaag gagttctcgg   81480
tggccaaagc acatgtcagg ctctgatggt ttaacttctt aaaatgcaat actgcctccc   81540
agaacttcca gatcaaggtc aaactcctca gctctacaca gggggaccta gagtcaactt   81600
tctaagctag gagagtcatg gatccctttg agaatacaaa agacagtggg gcgcggtggca   81660 gtggctcatg cctgtaatcc caacattttg ggaggctgag gcaggaggat cacttgagcc   81720
```

```
caggagttca agacctgctt ggtcaacata gtgagacccc tatttctaca aaaaattcag    81780
ctgagcatgg tggcatgtgc ctgtagtctc agttactggg gaggctgaag taggatgatc    81840
cctgagcctg ggaggtccag gaagctggag tgagccgaca tctcgccact gcactccagc    81900
ctgggtgaca gagaccctgt ctcaaaaaaa aaaaaaaaa gaagaaatat gttattgatc    81960
tactcttgac aaaaatgctt gtgtgaacat ggacacacac actcatcaac attcacattt    82020
caaggttttc atggacccctt tccatgaggc tctagtggtc catggacccc catggctgga    82080
acacttgctc ttcctcatct caacccacat ttccatggag ttggactgtc tgctgcatga    82140
ggacacaggc ctcatttggt gtgttcattc actgctgtgt atcccagcac ccagaacagc    82200
acctcaccta aggggcactc agcacatgtg cagtgaagag tcagtcagct ggtttcacac    82260
ctcccagtct ttgcacctgc tattccttct tgtgggaatg acagatttcc ttcatttctt    82320
tttttttttt ttttgacaga ttccagctct gttgcccgag ttggagtaca gtggcacgat    82380
ctcagctcac tgcaacctct gcctcccagg ttcaagcaat tctcatgcct cagcctccca    82440
agtagctggg attacaggtg cacaccacca cctgtgagct gatatttttt tcttttcttt    82500
tcttttttcc tgagacagag tctcactctg ttgcccaggc tggagtgcag tggcgtgatc    82560
tcggctcact gcaagctcca cctcccgggt tcaagtgatt ctcctgcctc agcctcccaa    82620
gtagctgaga ctacaggcgc gcaccaccat gcctggctaa ttttttgtatt ttttagtaga    82680
ggcggggttt caccatattg gacaggctgg tctcgaactc ctgacctcgt gatccgccca    82740
cgttggcctc ccaaggtgct gagattacag gtgtgagcca ctgcactcgg ccatttttg    82800
tatttttta gtagagatgg ggtttcacca tgttggccag gctggtcttg aactcttggc    82860
ctcacgtgat ccacccacct tggccaccca aagtgttggg attacaggca tgaaccactg    82920
cgctcagcct ccttcttcat ttctaatgta ctcatccttc acaactcagc tcaagtttca    82980
cttctctctg gaagctctac tctaggctgg attcagggcc ttgtccacat acccaccaaa    83040
tactctgctt acctctatgg aagtccccac actgatctag aataatcagc ttagttttct    83100
gcccccatcc cgccccatga gatgtacatc ttgtgggggc aggaaccacc acgtggtagg    83160
tgatttgtgt gcctgctgcc tatcacaggg cctggcgcct aataagcttg cggccaacat    83220
ttgttgaata aatgaaaagg gaatggtggg aaaggaagct gaaaaggtag gctaaaatca    83280
gtttggaatt acctctggga ggccaaggac tttcagtctt gcagggtagg taacaggaaa    83340
ctcctggatt ttgttttctt ttggttttgt ttgtttttaa tgaagggtag cgttatcgtc    83400
aggttttgt gtttaattaa tggagcatat attggaaagg acagagacct taaagcagtt    83460
aggagaccac cataatagtt cactttttgc agccataaaa aggaatgagg ccaggcatgg    83520
tggctcactc ctgtaatctt atcacttcgg gaggttgagg caggcggatc acctgaggtc    83580
aggagtttga gaccagcctc accaacatgg agaaacccca tctctactaa aaatacaaaa    83640
ttatccaggc gtggtggtac atgcctgtaa tcccagctac tcaggaggct gaggcaggag    83700
aatagcttga atctgggagg cagaggttgc ggtgagccga gatcgtgcca ttgcattgca    83760
ggtacatgga tgaagctgga agccatcatc ctcagcaaac taacacagga acagaaaacc    83820
aaacaccgca tgttctcact cataagtagg agctgaacat tgaaaacaca tggacacaga    83880
ggggaacatc acacactagg gcccgttggg gagtggggggt tgggggtaa ggggagggaa    83940
cttagaggac gggacaatag gtgcagcaaa ccaccatgac acacgtatac atatgtgaca    84000
aacctgcaca ttctgcacat ggatcctgtt ttgttttaag aagaaataaa gaaaaaacca    84060
agaagaaaca aacaaacaaa aataattccc atttaaaaca ataaaaaata ggccaggcat    84120
```

```
ggtgactcag gtctataatc ccaacacttt gggaggccaa cgcgggcaga tctcttgagc    84180
ccaggagttc aaggccagcc tgggcaacat ggcaaaaccc tgtctctaca aaaatataa     84240 aacaaacaaa caaaatagcc aggagtggtg gtgcatgcct gtcatcccag ctactcaggt    84300
ggctgaggtg ggagaatcac ttaagcctgg gaggcggagg tagcagtgag ctgagatcgt    84360
gccactgcac tccacctgga gcaacagagc aagattttgt ctctaaataa ataaataaaa    84420
taataaaaaa cagagaagag gaaagacacc tgagatatat ttccatatct gaatcaatag    84480
gatttatcaa cgttctcctc tacccccaaa actaattcct tcctaaactc tgttctcctg    84540
acactactca taggttaagt ataacagcat tatcacattg gctgtcatgt gggctcctgg    84600
ctagaggctg cttcacagct taatggacaa gagcactgag acagggtggg tctaaatcct    84660
ggctctgcag ctgattattt gtgtgatttt gtccaaatca ctccatctca tgagcctcac    84720
tcttctagtc tgttaagtgc tgaaaataaa agtatccaat tcaattcatt atttaatgaa    84780
ttatttagcc taacaaatag ctattataaa tatttaggct gggcacagtg gctcacgcct    84840
gtaatcccag cactttggga ggccaaggtg ggcagatcac ctgagtcagg agtttgagac    84900
cagcctgacc aacatggtga acccccgtct ctactaaaaa tacaaaaatt agctgggtgt    84960
ggtggcatgt gcctgtaatc ccagctactc aggaggctga ggcaggagaa cgcttgaacc    85020
caggagacag aggctgcagt gagccaagat cgtgccactg cactctagcc tgagcaacag    85080
agcaagactc tgtctcaaaa aaaaaaaaaa aatctctgca tgaagaatgt acataaaatg    85140
gtgcagccat ttcggaaaac agtttggcag gtcctcaaat agttaaacat agagttacca    85200
ctatagccca gcaattccac tcctaaatat actcacccca agagaattga gaatatttgt    85260
taacacaaaa atgtgtatac aagtatttat agctgtatta ttcattacag ctaaaaagtg    85320
caaacatccc agcagtccat cagctgatga acggagaaac aaaatgtggt atacccatac    85380
aatgtcatat tatttggcca taaaaaggaa gtactgatac atgctacaac atggatgaac    85440
cttgataatg ttattctaag tgaaagaaac cagacacaaa agaccacata ttgtatgact    85500
gcatttatat gaagtgccca gaataggcaa atccacagag acagaaagta gattagtggt    85560
tgccagagac tggagggagg agataatggg aaatgtggaa tgactgctaa tggtatgggg    85620
tttcttcttg gggtaatgaa aatgttgtac aattagataa tggtgatcat tgtaaaactt    85680
tgtgaatata caacatgctg aattttatac tttattatat tttattttttt ttgagacaag    85740 gtctcgctct gtcacccagg ctggagtgca gtggcacgat ctcagctcac tgcaatctct    85800
ctgcctccca ggctcaagca atcctcctgc ctcagcctcc tgagtacctg acactacagc    85860
atgtgctacc atgcctggac aattttttgca tttttagtag agacagggtt tcgctatgtt    85920
gcccaggctg attttgaact cctggactca agtgctccgc ccacctcagc ctcccaaagt    85980
gctaggatta caggtgtaag ccaccactcc cggcctaaat tgtattcttt aaaagactga    86040
attgtatggt gtgcgaatta tatctcaatt taaaaaaaac aaaacaaaac aaaaaaaaaa    86100
cctttgcgtg tgtcaggcac tagggattcg atgctgaata agacacagac cctaccctca    86160
gagaacacag agcccagcag gagagagtca cagatgaatc aagtgttaca tcatctatag    86220
gaagcgccat ggaagaaaga catggtgcca tgagaacata cgcttagaga agggaatttc    86280
atctagactg gggctcaggg aggaatcttt cagggtgatg cttgtgctca gagttttcca    86340
tgtcagaatc agtagaattt atcaatcctc cagaggagga aacagcaaat gaaaaatctt    86400
acaacaggag gatgcggaga cattccgaga gctgatcaag ggctggtgtg aacaaagcac    86460
```

```
ataggatgca gagcctgtgg tgtgaggttg cagctggaaa ggtaaaacac taattacatt    86520
ggatcttctg agacaataaa gagtatgcaa taatctcaaa cgaccgaaac tgaccttcct    86580
cctccctaac ttgcttgctt ccactgttgc ccgtatcata aaagcaccac cctcttctac    86640
ccagtggctt aagacacgaa actcaagtca tcccaggctt tctccccacc tcactctcca    86700
catccagcct atcagcgagc ttgtgggtct taccacgtaa agacttctca tctccagcta    86760
ctaccatccc ccaagcccag atcaccatca gctcaggcct ggactcctgc aacctttcta    86820
accgggtctt cccaatccta cccccgcaac atgaccccaa tagccccatca gaatggacta   86880 atcgagatgt agatttgatc aggccacatc ccttgaaagg cttcctgtga ccctcgggga    86940
aatgcacaaa ctcccaatga tggcccctga gtcctgtgcc atctgggtct gccctctgcc    87000
ctctgtgtct ttgccatggt aacctccttc acacccatta atactccatg ctctctccta    87060
cctcaagttc ttcctgggct ggaacattct ctgcactagc ctagccaact aacccttag    87120 atcttttgtt tgtttgtttg tttgtttgtt tgttttgag acagtcttgc tctgttgcca    87180
ggctggagtg caatggtgca atctatctcg gctcactgca acctctgcct gccgggttca    87240
agcaattctt ctgccttagc gtcctgagta gctgagacta taggcaccta ccatcacgcc    87300
cggctaattt ttgtattttc agtggaggtg ggttttcacc atgttggcca ggctggtctc    87360
gaactcctgg cctcaaatga ccaccctcct cggcctccta aagtgctggg attacaagca    87420
tgagccactg tgcccaggca acacttcaga tcttaatgat catttccttt aagtgcctga    87480
cctcttgtag taactagcct gactccagca atgaatcctt ttgcaatgta acctatataa    87540
catctgagtt tcccttttgat aaaactcatc atatatttgt tcctctgaca gttcagaggg   87600
caagggcctt tgcccacctt cctcaccact atcctctcac cacttaacac agaactcacc    87660
acccaccatg cctcctgcct gacaaattcc taaccatcct tcaaatctca ctcacctatt    87720
accttctggg aggcagtctt ccctgagcac caagacaatg ggacacattc ctttatacac    87780
cctgctgaac atctctttt tgaggggcgg gtagagatga gtgtctcact atgctgccca    87840
ggctgacctc aaactcctgg cctcaagcga tcctcctgcc ttggcctccc aaaatgctgg    87900
gattacaggc atgagccact gtacctgacc gcaactgggt tagnnnnnnn nnnnnnnnnn    87960
nnnnnnnnnn nnnnnnnnnn nnnnnnnnnn nnnnnnnnnn nnnnnnnnnn nnnnnnnnnn    88020
nnnnnnnnnn nnnnnnnnnn nnncctgggc aacaaagacc cttcctctac aaaaaaaaaa    88080
aaaaaaaaaa aaaaaaaaaa aaattatttt aaattagcca gacatggtag tgcatgcctg    88140
tagtccaagc tacttgggag gctgaaggga gaggatcact tgagcccagg aggttgaggc    88200
tgcagtgagc cgtgatcgta ccactgtact ccagcttggg caacagagtg agacctcatc    88260
cctaaaaata aagaagaaaa tatggcaatt tgactgtaca tctctaatgg gatatatcct    88320
aaggatgaga aaggaataag gaaggacaga aaaaaggaaa caagaagta gcaacagtat     88380 ttagcaattg tattgttatc aagtaacatc aatattggta aaaccagtaa ttatatttaa    88440
aatactatat atgtgtatgt acatttacat atgcatatgt taggaaccaa gtttatcaga    88500
ggaagagaaa gggctacaaa tgtaaaatca aggaaataaa aatttgaata aaaatatcag    88560
tattaagtat ttatgatatt tttcttataa aaaattata tatatgttaa ctctatccaa    88620
aacccaaaag cagtgacaac ccaggagcaa taaaaaacct cagcatccag actgtagtct    88680
ctaccatttc caattaaaga aacccagggc tagttgggaa aaatgacaat ttcatgtcta    88740
gggcaagaaa cacacctagt gaaatggacc tgaacattta attgtgttag aaagtaagga    88800
aactctctag aaataatgtg atttcatcta aaagacacag attctgggct ggtaaagttt    88860
```

-continued

```
tcaatggcca aaggtgagac aatttgagca tcaagaagaa tcatgacaga acagattaaa    88920
acatgtcaaa tatattttaa aatgaaatat tataaaagaa acaattagta gccatccctg    88980
aaggtcacta gggcaccaac tcatatttca aactggtaaa taaatgtgta agccaagcat    89040
ttatttctgg gtaacaaaat agtaaggaat gttttttcttt ctagaagaat tctagtgatt   89100
aaaagtagaa gatagaaata gaaaatcatc cttttggcca ggggcagtgg ctgtaatccc    89160
agaactttgg gaggccaagg caggtggatc actggagatc aggagtttga gaccagcctg    89220
gccaacatgt gaaacccca tctctactaa aaatacaaaa attagccagg tagtgggtgc     89280
ctgtaatgcc agctactcgg gatgctgagg caggagaatc gcttgaacct gggaggcgga    89340
ggtcgcagta ggctgagatt acgccactgc actccagcct aggcaacaca gtgagactct    89400
gtctcaaaaa aaaaaaaga aagaaaagaa aatcatcctt ttgcgatcct aatgaaataa     89460
tgggcctagg cattgatcat taatggctcc taaaatcact aagtatatgg ttgatgggaa    89520
actttatagt ggatggatca gactcgcaat gtctaaacca gttgatcaat cttaacatcg    89580
taacaagaca acagacacca ggggctgctg acaggagaac agaggaaacc catagctcta    89640
ccactgagtt attcacggca aaaaaaaaa aaaaaaaatt aaactgcgtt tcctccaagc     89700
ttctaatcct gttgtttaca ggaaatacc aaggaaagga atacttttaa atgacacatt     89760
aaaacaacgc caaatccaaa atatggggaa atgacccagt ttcttcaaca aataaacaag    89820
aaaaggtagg ggggaggact gttctagatt ttaaaagcta tagaagacac agcaaccaaa    89880
tacactgcat ggaccaggca tggatcctaa ttggaacaaa ccaactgtaa aaggatgtat    89940
ttgaaatgat tggaggaatt tgaacagtga ctgcacagta gatgatatga agaaattatt    90000
gttattttt aggtgtgatc atgatttat ggtgatgttt aagtaaaaga ggccttattt      90060
gttagagata catgtacggg tatagagaaa tatttacgga tgaaatgata cgatgtctga    90120
gatttgcttt gaaaactcta gcaggtgtgg gagaagcagg tgcatgggtg ggggaaggga   90180
tagatgaaat aagtatgcaa aatgttagtc tactttttgtc cctcctgacc cagcaggtta  90240
aaatacctca gcatacctct actcctccaa ccaggtccaa ggatcaggcc aaaactccct   90300
gatgtggtaa acagcctgac cccttcttac ctctctctct ccagccactt ccctaagatt   90360
ccccagtgct ctgtgcccta gccagcccga ctcatctgcc cagattcctc aatgtttcac   90420
tctctcattc accattttga ccccactgtg ctcctgggcc actctccaag gccccgcctc   90480
ttcatctcct ccctccttac tcatccttca ggtcttggct taggtgccat tccctccagg   90540
aagccttccc tgacaccaat cccatcctca cctagaacag attatgtgcg cttctttgtg   90600
ccccccatgg cccccctgtgg gtttgcttca cggattataa ctgcctgact acctgccttt  90660
ctccacccct tagactgaga acaccttgag aaaaagaaca catctatctt gtctgtcatt   90720
gaatccctgg tgtctggcac catggctgac acataactat cactcagtga ctagtgtttt  90780
aatgaatgaa tgagtgcaac tagacagggt taagaacaaa agagaagacc aggcatggtg   90840
cttcacgcct gttatcccag cattttggga ggctgaggcg gcagatcac ccaggtcag    90900
gagttcaaga ccagcctgac atggtgaaac cccgtctcta ctaaaaagac aaaaattagt   90960
gggggatggt ggcacacgcc tgtaatccca gctacttggg aggctgaggc aggagaatct  91020
cttgaaccca ggaggtgcag gctgcaatga tctgagatca caccactgca ctccagcctg   91080
ggcaacagag taagactcta tcacaaaaaa aaaaaaaaa aaaaaaaaa gagcgagaga     91140
agatgtcatg gggtaaatga agacctccct tcctggttcc ctgaccagcc cctgccctcc  91200
```

```
cccgcatctc acctgtctttt cttgcttcct tctggtactt ctgtttaagc cggtccatga   91260
gcaggccatt ccagggggca cacagcactc cgaactgagt gaaggcaaag gcatttgtgt   91320
aggtgctgac tgcagaagga agagagaggt tggttgatga gaagtttcca aaactccctt   91380
ccagcagggg actctcccac cttacccttg tctgcatgtc cctcctcccc acaccatcag   91440
accctcctct ggtgtgtaca gccctgctgg gaggctctgt gttccagct gggacatgca    91500
gatgggctac ctcccagccc taccacatac ctcgtgccat gtccccaccg gccatgttgg   91560
tcagcaagga gttgagagtg ccaatgaaga ggtagtgcca caactgtatc acagacagcc   91620
acaccaggtg ccaggcaaag cgccgagaga agcgtagct ccagaaggag cggagttcct    91680
gcttctgccc tgcccctggg gtctctaatg gggagaggag gatctgggcg tgaattacga   91740
ggaaagtgga caggtaggat ggggagtgtg gaggcttcaa tggaacattt cagatccggg   91800
cccaccttct acccttggct cccagaactc acccggcgtg ctctgcacct gcctcggact   91860
cacacatccc cacctccctg ctttgtcatg ctggccctac caccttggat gaccctctgt   91920
gttcttctct attgaaatcc gatctgtctc tcacagcctg gtcaatgaca cttcttgcag   91980
taataccttc ctgatctttc tcagcgagaa aggtgaaagg aacgacaagg agaggagaaa   92040
gtcagaaggg agaggagaat gagtgtggat actctgttct aacctgctcc tcagcacctc   92100
cctttctttt gataccagta tcctgagttt ctttgggaaa tcttcctcta ccctaatctt   92160
catggtccag atgggaccat gaattcagtg ttctgttcct ctctcaaggt taaccaatga   92220
gatggttcct cctaacaagg cagaccggcc atgagtttag attaggatgg acttaatcta   92280
aaataggtcc tacaccctgg caagttcaat gtcctccctt gattttggaa gcttcccaga   92340
accctattct tctttctttta aaataaataa ataaatacat gttttggatc caattgtcag   92400
atggtaaaaa taaaacaaa aaaatcaatt ttattctgta tatttaagat atacaatatg    92460
aggtcatagg atacatatag ctactaagat ggttactaca gttaagcaaa ttaacatatc   92520
catcatctca catttctacc tgttttgtga caagagcagt taaaatctac ttgtttagga   92580
aagtcccaaa cacaatgcag tttgatgacc tacagtcttc gtgctgtgca ttagatctct   92640
aggcctgttc atcctgctca tctgctcctt tttgtccttc gacctgcatc tcccatctcc   92700
tctcccaccc cgttcttatt tctactgtag ctagctgcgg tttgtgatgt gtgtaaccaa   92760
agacgcagaa cagagaggaa ggaaaggaag cagtgataga gttgggacaa taagagaggg   92820
cggacccagg agacctggag aaatgggggc actgtaccag acttagtgca atggcatcac   92880
agaagagggc agaaccgagg agtgggggga agggaaggca acccatggca ggcgggcttc   92940
aagggtgggg gaagtgatag gatgcgaaat agagaaaaga gggacagaaa agagacgaaa   93000
gccctggacc ctccattaag tgagagggtt gggaagatgc ctaaggccct ttttctgtcc   93060
tgcctttcct gattctgggt ccctggggga gctctggagg tgaggggcca ggaaaggcac   93120
aaggagaggc ttgggtctgg aggagagatg ggttagccag cagggctcac cttccttcgc   93180
tgaaaggaac tcctttgact gtagctccct gttttcatgc tcagctgttt ccttctcttc   93240
ctttgtggtg ccattcccag ggcacaggct atggaaacaa agccccacc agcaaggcca    93300
aggactgtga gccgaacctg agactcagac tgagggaat agcatggtga atcccacatt    93360
ccaccgcact ttggaatcac cttttagcca ctctgatgcc caggttgcag accagaccag   93420
ttaaatcaga atgtctggag gtgagagcca ggcttccttt tctaagatct ctatgtgaat   93480
ctagtgattc taataagcag caaagtttag gaagcatgaa aagagtaggg caggcccagg   93540
ttcaaatccc agctctgcct cttcctagca acagaaagat ggctcagact taaccctct    93600
```

```
gagcctcatt ttttgcattt agaaaatgga gataaggata tctcagagga ttattgtgag    93660
gatgaaatca gagagcacat ggggtctgac aattagtaag tgagcagcaa aggaatgccc    93720
ttcctctact ccttgtggca aatgactgca aaaatgatca catttcttca cctcctctgt    93780
atttccccca atttgaatga gactgcagct ctatttcccc atgccctgaa tctgggccag    93840
ccttgtgaac tgcttcagcc aaaagaatgc agcagaagtg gctgtgccaa ttccaagctt    93900
aaatctcaag aacgcttgtg catttctgca ctctttcaga accctgaaat cacggtgtga    93960
atgagcccac gctggcttgc tggaggatga cagccacgtg acccaggcat ccctgtcact    94020
ccaaacctat gtgagtgagg ccatcctagc atagccagcc cccatgtaat cctccaaatg    94080
atcagatgta tgaatgagcc ctgtcaaaat catctacatc tggccctgat cagcggaact    94140
agccagctac ccacagactt gtgaaaaata ataaatgctt aacattttag gctgctgagt    94200
tttgagatag tttgttatgc agcaatagct aacagatgca ctgctccagt cctcctcctc    94260
tcctgtgata ggtttgcttt accctgtcca tcccacccta gggccaatga ggggctctgg    94320
cccacaatca ccagatagtc cttacccata gctgtagttg gggggcagtg ggtatgggat    94380 gtgccccgg ggcatcagga ggaaagtgcg tgctacatgc caggtactgc agacagagat    94440
gaagatgaag gaggccctga ggctgatgcc tttttcataa agaagctgca gaaggagaag    94500 gaaaagtca gtgtcacacc cacgttcata gcagcactat tcacaatagc caaaggatgg    94560
aagcaaacta agggtccatc agcagatgaa cagctaaaca taatgtgatc tatacacaca    94620
atggaatatt attcagcctt aaaaaggaa agaggcaacc atgctggctc acacctacaa    94680
tcccagcact ttgggacgca cgaggatcac ctgagcccag ttcaagacca gccttgacaa    94740
catagtgaga ccctcacccc ttctctagaa aattttatt taattagctg ggtgtggtgg    94800
catacacctg tagtgccagc tactcaggag gctgagtggg aggatttctt gagcccagaa    94860
gtttgaggct gcagtgagtc atgactgggc cactgcaccc cagcctggac aatgaaacat    94920
gaccttgcct ccaaataaaa aaaaaaagg aaaggaaaga aattctgaca catgctgcaa    94980
catggatgaa cttaagagc actatgcagg gccaagctca gtggttcctg cctgtaattc    95040
tagtgcttta gaagaccaag acaggaggat tgcttgagtc caggagcttg agaccagcct    95100
gggaaacagc aagacctcat ctctactaaa aataaataaa taaatcagct gggcgtgatg    95160
gtgcacgcct gtaattccag ctacttggga ggctgaggtg agaggatatg attacatgat    95220
tacatgcctg taatcccagt actttgggag gctgaggcaa gcagatcacc tgaggccagg    95280
agttccagac cagcctggcc aacatggtga accccgtct ctactgaaaa tacaaaaatt    95340 agtgggcat ggtggcacgc acctgtaatc ccagctactc gggtggttaa ggcaggagaa    95400
tcgcttgaac ccgggaggcg gaggttgcag tgagccaaga tcctgccacc gcactccagc    95460
ctgggcaaca gagcgagact ctgtctcaaa aaaaaaaaa ggttaagata gtaaatttta    95520
tgttatgtat attttattgc atacaaaaac atcagcagaa gaggcagggg ctggaaccct    95580
gttttctaag gagtcctagt acaagccatc acctactatc ctgtaagctg attagggaca    95640
cctggtacac acatgccccc acccacccca agacacaccc ggcagtagag gagtcctcat    95700
acgacccatc cccacagccg gtggagcctc ctcgtgtggc tccccagaga tcttctagcc    95760
cagtgccttt ttcccccaa cgacagcaaa ggcctttgt tcaaagaaaa ttttacacaa    95820
aaattcatct tacaaaacac accaatgggg agcttgccag tcatctccct ctttattctc    95880
cttggtgact ggtatgacat caaagagaat ccctaagttc ctcaacagct cagttttgaaa    95940
```

```
accaccgacc tagcccaacc tcctcccatt ttacagagag tgacgttgag gtccagagag    96000
gtgcagtgaa ttgctcaata aattgacaga gtaagcagca gcaaagtcag attaaactaa    96060
gaattcctgt tcctgctccc tttcccttc caactctaga gagacaggag agaggctggg     96120
catggtggct catgcctgta atttcagcac tttgggaggt caaggaaggc ggattacttg    96180
aggtcaagag ttcaagacca gcctggccaa catggcgaaa ccccatctct actaaaaata    96240
caaaaataag ctgactgtgg tggcacgcct atagtcccag ctactcagga ggctgaggca    96300
ggagaattgc ttaaacccac taggcagaga ttgcagtgag ccaagatccc accaatgcac    96360
tccagcctgg gagacaaagt gagactccaa ctcaataata aaaaaaaaa aaaagagag      96420 aggaaagaaa gatgaggcag ccatctgggt tctccagggg aaggagggag aacccagaaa    96480
gtgactctta tgccaggagt agaaaggctt gagtgcctca ggggctcagt ctctgcataa    96540
ccctccaaac ctccaaagct tatgggacta agctagactc atgtctgggt ggtgactgcc    96600
agagatcctc ttctctgccc ccataacctg caggcagtgc caactgcctg tgacctaaca    96660
ctaagcccag agagaagtcc caggttggat ggcttgagat ccacactctt cccttccttt    96720
cactcagcca tctgtggtgt gctggcttta gtcctccagc ttgctgcctc ataattgaag    96780
catggttgcc acaactccag ctatcacatc ctcacaccac aacattcaat gaggaagact    96840
ttgtttttac tctgctttca ccttgcgtca gggaagaaaa gtcccctttga atcttccact   96900 atatacactc cctttatctc attaaaaagg actggatcat atgctgacct ccacctatca    96960
ctagcaacgg gtaaatggat tgccatggtt ggctttaatc aatcaggatt catccctggg    97020
gctaagcggg tcactgccca gataaaactg ttcgcaatga ataagacaga atggttgttg    97080
attgacctct aatagccttg gcaacagttc atccctgat accccaacat cagccactgg     97140
gacagctgga caagcctctg tgtctgcccc tgctgtaccc actagccact tgccaccttc    97200
ttgtccaaac tagaagctca cagcagcaaa cgcccactc taaaggtccc ccagcctcta     97260
cccaacactg gcccaagcac attatgacca ctgccacaaa agcttgggca agtctgaaga    97320
aggggcttag cggttacaag ctcaggctct agaaccgaca agcctgggtt caagttccag    97380
tatcatggct actagctgca gaaccttcaa caagcttttt aacctcagag actcaaatgc    97440
ttcatctgta aaatgggggt aacacagtac ctacctcacc gagttgatgg agacaaataa    97500
tgcaggttca caagacaagt gtctggcata tacaagtgcc cagtgaatgt aggctgttgc    97560
tatatttacc ttaataataa ggaagactgc cgaggaagag tcaaatgctc cattgtacag    97620
agtgatgatg gtcgaacggt gttggccaaa taggttccca atctggggat gataggacta    97680
gcctggatca cttatttatt catgaaacag atacttcctg agcacccagc atgtggcaga    97740
ccctccttat acccaaactc accctccacc gctagagctc ccacctcagc ttgggccaac    97800
cccatctgag gcagccaatt atagaaaagg gtctctcctt ccctccacct tcccgccacc    97860
ctgccgagtg cctgggatta gggaaggctc ccacctgcag gttggtgatg agaaacagga    97920
ttcccccaat ggtgagcatt ggcatggcca ggaagagcag cacggctgag cctggaccat    97980
caaagtcaga ggtagggtgg tgtcatagtg caacccaaac atggagcccc aaactctgct    98040
cccacctgct ccaaattccc aacaatcctg gtatccaggc cccaattcta gccagcgttc    98100
cagcgtcctt caagggtttt taggataccg gccaaggctt cccagatat ctctgtgaa      98160 gtcttctgag ccaccttctt cccaaccaaa gttggtcctc agtctgtggc aggccaggaa    98220
gtctacagac agaggcagag ctctaagtga agccacctct ctcttccctc agtaaaccac    98280
aagctgcctc tcccttcat ccttgacact cctggaaaag aagaccctgg actcaggtcc     98340
```

```
ctggctcaac cctctagccc attccctaat tcatggtatt ggccttgagc ttcaatcatc    98400
tgtttaatgg gaacaacagt tcctgctctt cctgtctcag gtgctatgag aactgagtga    98460
gaaaaggacc atggtctttt ctttgttcac taaactctga gcacttcttt ggtgccaggc    98520
attgtgcttg gcactggaaa tgcaagatga atcagatagt ccttgccctt aaatagactg    98580
acatgcaaac aaatggttat aacaggtctg gtaagtgtga gaccacagca aaaaagctca    98640
agagctgggc tagggaacc cttgacaaat tcttcctccc caaaccagac ttctgcccac    98700
cattattctg gccacaacct atgcctgtcc tattatttgc taaaatgttt taagttgact    98760
cacttttatc caaaaagtat ctatttttaa aggacacttt atatcactac tgtagatgaa    98820
aacactggca ttacttgtca tgaatagaaa gtaactgtca aaataaatac aatgaaagga    98880
aaacaatgtt attcaattgt agctggatgc atttgacctt agaatgttca aagcctaaga    98940
cctgctcttc ccatcagtgt taaaatcaca ctggccccac atgaagacat tctttcatga    99000
aatcagaagg actgaaagag aaataaaaag ggaatagctg ttctaccagg tgatttgatg    99060
tttgttagtg tagttcacgt agtatgcgtg tgccectaac atcctcttaa ctaccgtgct    99120
ataccttaag aagcactgcc aagagctaat tttagagtat tcacacagtt taccattcaa    99180
tttctgtctt tataaaatgt acatctctcc tactactaaa ggttggagac tcctttcaca    99240
atagagtcct tatgggctca atgctttttt caaaactgaa aagccctata ttatggagga    99300
agaggaggat tgttgctcag acgatttgca ggcacgagtc aaacattacc cagccaccac    99360
ctccacattc agttgcttaa aaatcattta caggctttta gagtagatga tgctggtttg    99420
ataaggagag tggtttgaaa taattggttt gaggtgctgg gccatctcat gagatctgtg    99480
tgaacaaaga cactcagcct ctgtgtttgc ccagcatgag tgcagacaat ctcatgatgc    99540
tgtcagcttt agcatagctt acacacacaa gagtaatgta ctttctttcc taaaccaaaa    99600
attgagccac gggtctaaca ctaggaagga atattgggag gcatctcgtg gccaccataa    99660
ccaaggcaat gacagaaaga agagtgaggg atcaggaggc ctgcacatca ggcccacctc    99720
ccacttgctt tctctgtggc catggacatg tcttttgcaag gggtcctgct gtggcttcag    99780
tttctcctct gtgtaatggg tggaagggtg gtggaaaata aaccagattg gagttccaga    99840
cttaacagac tggtgaaatt ttaaaacaaa gattttgagt acaataggt tgtcaacttt    99900 taccctgcta agtaaggata tttgcaaaat ggtcattcat ataatcattt cattaaaaag    99960
agaaagagaa cattttaaca cataggaaa ggatgtaaag gttttttgtt gttgttttgt   100020
tttttagggt tttttgtttg tttttttggta gagtctcact ttgtcaccca ggctggagtg   100080
caatggtgtg atcttggctc actgcaacct ctgcctcctg ggttcaggca attctcctgc   100140
ctcagcctcc tgagtggctg ggattacagg cgcgcaccac catccagcta atttttgtat   100200 ttttttagt agagaaggga tttcaccatg ttggccaggc tggtcttgaa ctcctgacct   100260
cagatgatcc acccgcctca gcctcccaaa gtgctgggat tacaggagtg agccactgca   100320
cctggccaga tgtaaagttt tgaataaatt ctactctctg aagtaatccc tctccatcat   100380
ccttgctttt cacattttct caataaactg ttttcacaga ccagcaatag ctcaagatcc   100440
ttccaggatt ctttcaagct gcagatctct gaataaccat gtggtctgta tatcttgcct   100500
atagccctct gctcacacct gccccagcca ccaggtgcct ctgagcttgc atccctccca   100560
cccacctgac agcactcacc tgcagaggt aaggctatga tgagtgtggc ggtggtgtag   100620
aaaaatctga aacacataac aggaaaagca gaatattgtc aaggaggag aaacctggga   100680
```

-continued

```
gaaaaaacat gattctgctc agccagccca caagtgtagg acttgaccgc accctcagcc 100740
tgggatgcaa cgggcactga tgcctctgag ccccaggctc aaaaccaggc gcaagaagcc 100800
gcgatgagat tgagatgtgg tcctgacctc atggacagtg cattttgctc attctgaggc 100860
ccaaggctag catggaaagt cttggacaat gagctcagct gacgatgtga ttggcttggg 100920
acttagccag gacagaatgg gcaaagcgaa ggtcctccca cctggaagcc caacagccc 100980 aaccccttgg agaagggggt tagtgcctgg tctgcaaatc aaggccttga gttctaactc 101040
ctcctcactc tgtgaccttg ggcaaggcgc tgtccttctc tgggcctcag gagccttttc 101100 tataaaaga aatgatcgga ctgatctagc tcagagtgct atgatttcag gactacagtc 101160
ccaaggttat caggctccct tagcatttgg gggtcttgta aggcatggag taaaaaaaaa 101220
aaagcaatat cctaaggctg gagaagaggg aggggacaaa ggaaggggag gaaaggggag 101280
gtagcaggga gccaaggacc aagaaggact gaggtacagt cattctgcat ccaaaggctt 101340
aaattgtaag ggactggctt tactctggct gtttccggaa aggcaggccc agccagccct 101400
cccgtctctc tctctgacag ccaatctcac atgtgcctcc ctgggagcac ctgctctgag 101460
ctgtatcagc ccccagcagg ccgctgatta ccactgagcc tggccacaga gcacgagatt 101520
aggatgcagc aacacactgt gtgtgagatc acgtcccgaa ccttctgact catctgcaca 101580
ggaaaccccc ccagtctccc ctccagtcag aagggacctg aaattccacc agtggcaata 101640
ccaaagaaac ttcctattag ctaagcccct agggagtgat tggctgttgg ggcggggagg 101700
gggggcggtg aggaggatga ggatgaagcc tgggcaacct ggatgtgagg ctgtgcaggg 101760
gatgaggaca aggatccttg gggtgaagga agagaagagc aattttaggt tttgctaatt 101820
ttgtaaccct ggctccaagc cagcccttac aggaagtcac cctggcctcc ggctcaattc 101880
agcacgtgat agggaagcca catttatgca gagcaggaa cgaggtaagg aaatggaagt 101940
ggggctgtgg tgaagtgggc aagtctagag agagtcccgc tgcctgggc tgttcctaac 102000 agctgctggg agcgagctgc aggtgtggtg cctggcaggg tggccgggct gtctgactct 102060
ggatttcact ccaagctagg ctgctgcctg aaggattcct cttacccacc tttgcctggg 102120
ctggcctttg ggacttacat ggctatgagg cgtgccacgg tggtcttgaa ccggtcaaag 102180
atgtagccag tggggaatgt catgaagttg ttcatgaagg accccagggt gaagatgagt 102240
gagaacctct catcctgggc tttgcagtct ggagtagaaa aaaggtctcc catgcatccc 102300
agccttcctg ccaaatgagc acacaggctg ggctcccctc cacctcagac agcttgtcgg 102360
tcgcaaactt gtcccttaag ctgagttgaa atgtggctgc ccctaattac ccctcaggag 102420
ctggtgcctc cctcccaggc acttcccaga tcaagtgggg tgagagctgc tgacccttcc 102480
tctcatcata gaaagagggg tgggcagggg gcagagtcct tcctgctcct tgccaccacg 102540
tgggagccag acttaacttc cttagaaaag tcatccctgc ccttaccagc ctgccctgtg 102600
gcattgccaa tcggcccagc atctggtcca cacagatcct taaagtaatc ttcattcttg 102660
aagacaaaca ctagtgaagg ccagccaaag aggacgccag caaagcccag gcattccagc 102720
agcccagtca gcagtgtggc cacgtgcagg ggcaggccct ggcccgccat gagcagaagt 102780
ggagtggatc ttcaaatccc actttgtcct cctggacgga tcacaggcgc cgtaagcctg 102840
gcgtttgagc acttggaaaa ttcctctggc aagccaagcc cttcctttcc cgtagctctc 102900
tggttgtttc aggcctgggc aaaaaccatc agcgggtgat tctctggatc ctgtagaata 102960
aagatagagc ctgctggaag aggaggcctg cgggaaaggg aaaggtagac tagagttatt 103020
tgtgaggtgc attaagaggc aggatgatca tggccgctgg cagcaaatgt ggggaataaa 103080
```

```
tactccaata catcatctta ggcactgcat ttgagtaacc acgtggcaag tagagaggca 103140
ggtcttgatg gccacctgga gtcacaggtg agataaacga cttacccaat agctccccgg 103200
gagcaggtgg agaagcggag ctcctgcgct cgaattctga ataccgtccc ctaaaataat 103260
gacagcaact caaccaggtg cagaggcagg gagatttcat acagaagaca caaactcccg 103320
ctgccaagtt ggtgttatct tcagtttact gacaatgaaa caaaagctcc catggatttc 103380
aggaacttgc ccaaggtcac agggctagtt tagtcacgac gcaggccatt ctactgccag 103440 aaatacccccc aactcccatg accctcgcct aggactcgca aacctggtcc ccgccgccct 103500
tcctcgcatc aacttctacc aggaaagcct ccggggggccg ctccccgcca gcctccgcac 103560
cccgctccag cctgcggcct gccctccccg cagaggagcc cgaggggcca ggccgcgctc 103620 ggcgcccccat ggcgcccgaa aggggaccct tcgccctacc cgcctgctcc gcgccggggc 103680
tctccgcgcc ctttccgcac gggccaggtt cgcattcgcg cctctcgcag cccctcccag 103740 tccccctgctc gcctccgccc cctcctgccc gcccggaagg ggctggggca gacctcccac 103800
tctccatcac ttccttcttc ttttcccttg ctcacagcct cccgcgccct ttttaccctct 103860 ccctcttgaa acttctccct ctagaacccc ctagaacccc agcggtgtct ttccctccct 103920
cctcgctgcc tttcagcctc ccagccccct tgcctctgcc tcccctaacc aagttagttg 103980
aatgctgtta ctcgctcagg cccacctagg gaaaatgtca cacccagcac ccagaggaca 104040
cacagacagc acatgagggc ataggggacac acacactcta tttgtgcatt ttgccttgac 104100 cgctggggttg gcagggaaca tatttttcct atttgctcac cagcttaacc gtctctccca 104160
gtttcacact cccagagctg ccaaaaaaat cccaaccaca gaatcaggaa gccaagaacc 104220
aggactgagg gcttttcaga aaccatcccc tggaggactg ccccatattt tcactcccaa 104280
aaacccctta gatgactccc tgcctcaccc ccgcccccca ggttctgaaa gagccttccc 104340
gccagactgc attgattaac cattcattgc cccatttttt attaatcaaa gacatatata 104400
attgctcatc ggagcttgtg atcagcgtga ggccttacta agcagctgcc ttactatcct 104460
tccagcccag agcacgtgag ctgacgtctt ctttggcctg tgtggccgtt tccttgccaa 104520
aagctcagtt tggggagagc ttcttgcgta ttagatgcag tctgcagact cccaaccccca 104580 gctacctgga tcccctgagg gcccaggaac tccagctatt ccaagcccac tcctctttttt 104640 tttaagagga agaaatagag gttacgatag gggacagcca gaactgagga ttttccagct 104700
caccaccaaa gcacaaaaga taaaagtctg caaccaccct agtgacttga ctgaatggag 104760
gaagggtggc tggggtcctg taccccaagc tactcactag ttatacaacc tgaggcaagc 104820
tctttggctg ccccacctgt aagacgagga caatagtacc ttaattatag gaattgtcat 104880
aaaagaagta taagatgggt gtatgaggtc cctgcatggc gcaggtgcta taggcagatt 104940
gtagggtagt agattttcta gtctgcagtt atgtagacag agccagagaa gcagctctgg 105000
ggaggaattt caaggaaact tgcccacggt cattctacaa agctgcagta ccttcccaac 105060
tctgaaacgt atgctctcat caccccgtct taacaaacat ttggacatta gagaaaacaa 105120
gtcttttctt aaaataacat tatttatggg agaaaatcca caaaaatata gcatcccagg 105180
acaaacaggg cttaagatgc aagatttcct attttactgc aagacacaaa gactctgaaa 105240
ttaatgcatg ccctatcttc tgctctggca tacatttag tctcctgggg ggatcagtaa 105300
gtgtggaagt agcaagggag aaacagaaaa aagtcaaagt aaagagacag attttagaat 105360
gttaatctgc aggagcctgc cagaaagatc tagctcatgg gctatctgta catccaggac 105420
```

```
tgaagcacgg gacacggggc aggtcgtcca gggttctgtc caccttatct tgttacctct   105480
cttgactctt agagcctcca ctccacatct cccatcaatg tctgcagaag acgtggcctc   105540
cactaacaca agtcttactg aactgatggg acaggaaatt agaatatcct ctgaaccatt   105600
cccatgttct ttggttcgaa ttccagcagc tagaaaaggc agatgctatt ctgatcactc   105660
tcctgcgtgg ctccaatgag gattaatgag taacatcaga gagagaagtg attataataa   105720
ggtctgacgg tgcacccgat gtcttcatcc ttttctcttc gcctccttcc tcatcatctc   105780 acacctttt  tttttaatt  gactgattgg ttcaacaaat acatgtggta cctcaggctc   105840
tgtgccaagt gccgggattc gtagagaaga gattcagtgc ctgctctcaa ggggctcatt   105900
ctcttgtggg agagacagac aaagaaaccc aagatttctg gagtgtggga atggtcttcc   105960
aggcagatgc tagcacagca cattgaaagg cacggaacct caacaaaaca ataacattta   106020
ggaaccagct agagcacagg gtggtgaaga aagtggaaag atttgaggcc agcgtcgcca   106080
tctaagtgag ggcattaaga attcagccca catcaatcaa tcatgtccta ttgatttcac   106140
cccttaatat ctctcctatc tatccgtggc cactgctcta tgcagacact catcatctct   106200
cacagaggca tcatctgctt ccaagccatc gccattctcc tgcaagagtt tatttccatg   106260
gttcccactg gatggcttca cttaactgct caaaacccett ctgaggtcca gtcaactggc   106320
tggtaaggac cagtccaggg tctgggatg  ccagccatga gacattgctt tgaggggaag   106380
agggagcata gaactggatc tcctgcatcc tactgcccaa gtaccaatgc tggaggtggt   106440
tttccttccc atcatcagca agtctggata tccaggatcc accctatgga tgttttatg   106500 gacagagtgg gaagatggat atgtttaggt tagggaaaga gggtttgcca aagagggcag   106560
tataagtgag ctgcactcca tcattcccct ggcacaaaca atggctagta tcctctagtc   106620
ctcaagagca ccaccttcca atgcagtccc tgcctgtcca cagacctctc tcctcaaact   106680
tcctctgaac aacctcagcg agggcaattg ccactctctg ggcagagtcc agatattctc   106740 tcctacccctc tgacatcact ttctaaattt gtatatgtag ataaactctg agccattcac   106800
ataaagggct ttgatttcgg atacgccaaa cacataaaca aacaaacata agcttcctt   106860 tcacaatggg ctcatgtaaa ttaaaatgtt tggttttcca cctacggtct tgaaaggggt   106920
ttctacagcc tgttttggaa gtcagaaagc aaaaggtaaa tgcaaacatc atttcacctg   106980
cagagaaaat tctaatcctc ttgaggcagt gccaaaaata atacaagcac actgctatcg   107040
agccaattac tggtatctct gagcttccgt ctcctcatct ataaaattgg aatcgagctg   107100 tatgattaa agataatgta tgaaaactgc ccaattagta cactattaat aaatagcagc   107160
tactgttgtt aacaaatatt attgacttac tggaaaacaa agaggaaata aagtcacatt   107220
tagggagaat ttcaaagtgt tcctaaccta aaaagaaat  aaattagggg gaaaccact   107280 aagtaatggg tgagctcagt ttaccttgct taagaagtcc caccctagag aactgatctc   107340
tagatgacac ccaaatgcac tcagtacaac cccccaagac tgtctgggct taaggcaggg   107400
gcttggattg tcctgtaagc tgtgggaagt ctgttcatga gccacagtag acaggaaggg   107460
gatggagtct tagagctggc tcttcagggt atctcctagt gtgttcaaag cagttctcag   107520
gagggtgggg aactactaca tagccaagta aatatgaggc ctccttgctc tggggagacc   107580 tttctctta  acagaggtga atctgaaagg atacccaaag aggcactgga gggtggggc    107640 cactctggcc cctcagagca gccagctcag cttcagtgga tgctagaggc agcagaggat   107700
cagcctggat cagcctccct ttcaccatgc agaaaacaga gctcccccac cagaccagat   107760
actggaagca ctgggccagg cctaagagaa agcagagccc caagccccac cacaccaggg   107820
```

```
cttatgaggc tactgctacc caccctccca agccccagct ccacttctat gttcatcaag 107880
caactgttta ctggtaactg cacttcccga tagactttgc tagaaaggaa tgcctcagtg 107940
cactgacaat atctaaacct gcaactctaa ggactaggct ggggaacact gtgtcaacat 108000
ggaggcacgt cctacccctg agaagaaaaa taaggaatat caataatacc tgctgggcac 108060
tgagcactga ctatgtatct gattcgaagc gcttttgct taatctgtca ctgaatctca 108120
cgataggtgt tgttattagc atctattatc tgggccaact gaggcctaga gggacgaagc 108180
aactccccca acatcaccag gtagcagtgt caggactggg atagaaacct gatgctctga 108240
ctgaaactaa tgcttttttt tttttttttt tttttttttt tgagacagca tctcactctg 108300
tcaccaaggc tggagtgaaa tggtgtgatc tcagttcact gcagcctcca cttcccaggt 108360
tcaagtgatt ctcctgcctc agcctcccga gtagctggga ttacaggcgt gcaccaccat 108420
gcccagctaa ttttttttgca ttttttgtag agatgggggtt tcgccatgtt ggccagactg 108480
gtctcaaact cctgggctca agtgttctgc ctgccttggc cccacaaagt gctaggatta 108540
caggcgtgag ccaccatgcc cagccagctg atgctcttaa tctgtgccct acccagcctt 108600
cctgggaggc ttcccaagag ctacacagag catgagttct ggaatcgggt tgatggggt 108660 accagttatt actaatagga atgaagatgg gtaattcttt cagacagcac ccttgattaa 108720
aacaagagag tagtgctgcc tctctgtgat tctgtgtctc cctgccctgc tcacacagac 108780
accacaccca cccacacgca tgatcatgaa agaggaaat ggatccagga gaaggagacg 108840
actcctgagt gaaacaacg gggttttttca cattgagagc tttgcccaac accccaaaga 108900 tgaaagagc aggaaactgc tggggccgat tgaacactgg acttttgttg tggaaaaagg 108960
caaagggaag ccggaagaga ctggaacagt ttccatggtg ctggaggatg gggaagtggg 109020
tagggattag ctggagggag aaggagaagc tgggtgga ggaaccctc cacttgccag 109080 gagagcacat gtaggatggg aaccccagat gatactcaag gcatggcatt agaccagaag 109140
caagtctgtg gtgaaattag ggaaggctcc actgcggact gtagacagag cactggacaa 109200
ggaagtggga gacccagggt ccagtcctgg ctctggagcc ccctgggtgg gctgccccgg 109260
gcacctttct ctcttgggggc ctccattcct acctctgtga agcgagtgct gaacctctct 109320
tagccctgac ttgctgaaat gctgggactc tgtacagagg ctgacattaa gcagggatct 109380
gtcgtggggt gctgcaatgt tcctccagat gctgcacggg agagggcaga aaaggcctat 109440
atggtgagtc cgcccctggga gcctctgctt ggaagctgaa gtggcctgag agtgactcag 109500
aaaccacgga agttcccggg gctgatgggt tcttatagat tgtacatgca gctctcctcg 109560
tgggctgcaa aaccgcaaga tgggctgtga ccactctcaa ggaaagagcc ctatctgcaa 109620
aaagcattct gccctccagg tcttaaagca aacacagact caatccttat tccttttaag 109680
acaaaattgc ctcagggggca tcagggaggc agcaggcctc aaatgtgtgc ctttctagaa 109740
ttctcaatga aagcacccctt ttggggtatta ataatgacaa cagtaatgac agtcatttac 109800
tgagtgctgc ttttgggaca ggcattgggc taagagctat atgtaatata tattattatt 109860
tgatgcccac agccacccca taaggaggcg gaggtactat cattatgcca actttaaaga 109920
tgaagaaact gaggcctcaa gagatgaagt aacttggcca agtcactcag ccagtaaatg 109980
ggaagagata gacttcccag tatccagagc ccatgttttc accattatgc tgaagtacct 110040
cttttcctgt gccaatgtga tctgcctcca ggaatcctgt cttgatgttc ccttccccat 110100
acagaagtcc tctctgtgtc ctcttcagcc tgatagtata tcttttcata ccattctttg 110160
```

```
gacatctctg ttatactact ccaatggtgt tccctcccct accccctccct gggagcttag   110220 ttgttgtgat taagtatagg ggaaatgacc cacactaaac aaaactcataa gagactgatt   110280 gataaacctg aaatgcaatt tattaattaa cactgagaaa tgaaaccacc cagcagatgg   110340
gaatcctaag gctgactggt cagcacaatc tctttcagga aggacaggct tttgggaaag   110400
gaaatcaata ccagaaggtt ctttgttgag tacaaagtca gagggaaggg agttgatgga   110460
ttgacacata ggtgaagctt gacataccctc tataaagcct ccatcctgcc aaggatcaga   110520
atatccaagg cagggagcca tctgggtgtc ctctcctttg acagtgctg gattttctg     110580 gatcctatga agatcttacc tttctggctg catttatcat gattgtggaa ggcttttgt    110640 ttccttgttt gcttagatta atttctgcgt atttaataga actgaaaggc aatttcccat   110700
tgagacccac tgaagaggaa taatcaatac atactagttg tgttgcccctt tgcagagaat  110760 tcacttctgt gttgtcactg tatcctcatg cttccttata atggagggac agagatggta   110820
aaaacatgga cttggaagcc agaccgtctg ggtttgaatc ctggctctgt tacttataag   110880
ctctgcaacc tcgggcagat tacctaagtc agtttccccct tctctgaatt ggggatataa  110940
tagcacccac ctcaacatct gtcaagagga ttcaatgagg gaatacacat aaagtgctca   111000
gaacagtgtc tgccatctgg taagcagtcn nnnnnnnnn nnnnnnnnnn nnnnnnnnn     111060 nnnnnnnnnn nnnnnnnnnn nnnnnnnnnn nnnnnnnnnn nnnnnnnnnn nnnnnnnnn   111120 nnnnnnnnnc taattttgt attttggta gagacagggt tttgccatgt tggccaagct    111180
ggtctcaaac tccgacctc aggtgatcca cccgcctcgg cctcccaaag tgctgggatt    111240
acaggcatga gccaccacgc caggccccac acaccttttta aacaaccaga tttcattcat  111300
cgggaagtgc ctgtggggct ggtgtggaca tgtgggtgaa ggtggcactg ggagaagtta   111360
ggattctcca tgacctctgt tactcatatt cccacactcc tcaaattagc ctgagtctcg   111420
aggacagtct gatggctggg caaaccctgc ggcaaaccat tccccagccc tgccctctca   111480
accagagtcc ttccgataca tgattctggg cagctgttgt tacccgtgtc ctccatgttc   111540
ttccagagat atccatgcat gcatcggcat atgtgtataa ttattatatc tatatttcat   111600
cccacaagct tttgacatca atagtagcat attattaaat tgttctgtac attatttat    111660 taacttggta tctctggtac tgctcaatat aagaacatat agacctggcc aggcacagtg   111720
gctcacatct gtaatcccag catttggga ggctgagatg ggtggatcac ttgaggtcag    111780
gagttcgaaa ccagcctggc catcatggtg aaaccccccat ttctactaaa aatacaaaaa  111840
ttagccaggt gtggtggcag gcgcctgtaa tcccagctac ttgggaggct gaggcaggag   111900
aattgcttga acctgggagg cagatgttgc agtaagccga gatcacgcca ctgcactcca   111960
gggtaggcaa caaagcgaga ctctgtctca ataaaaaaaa aaaaggaatg tatagacctt   112020
ctttattctt tttgatggct gtaggtggat gttctaaaat ttgtgtaacc aatctcctat   112080
tgataatatt taagttatgt cttcagcatc atatgaaact tacaaacaag gttgcattga   112140
ctatccatct gtaaatgtct ttttgaacat ttctagaata attgcaggat aaactcctaa   112200
aatgagaatt tctgggtcaa agaggatatg cattttacat ttaatagata tttgtcaaat   112260
tgtcttccaa agtggtcgta ccaattaaca ccccgacctg taatgaatga gagtgccttt   112320 tttcccccaca ccctgagag atgaaaaatt tatgggccca ctttggagtg catggtggag   112380
gaagctgttg gccgttatat aaccctcgtc attaataagc ctgggggtgg ggggggagaa   112440
agagaggtta gttagtgggt gcaaacatac aattagatag aagtaataag ttctaatgtt   112500
cgatagcaga ggagggtgac tatagttaac aacaatgtat tgtatatttc aaaatagcta   112560
```

```
gaatggagga cttaaaatat tccaacacat agaaataata aatgcttgtc tgcggccatg    112620
ccaccctgaa tgtgccagat cttgtttgtt cttggaagct aagcagggtt gaacctggtt    112680
agtatttgga tgggagaaat gataaatgct tgaggtgata gatatcctaa atacccttgtc   112740 gaacattata cattctatat atgtaacaaa atatcacacg tatcccataa atatgtacaa    112800
atataatgta tcagtaaaga gagggctggg cacggtggct cacatctgta atcccagcaa    112860
tttggcaggc cagggtggga ggatagcttg aggccaggag ttcaagatca gcctgggcaa    112920
catagcgaga ctctgtctcc acaaaaaata aaaataaaaa cgaattagcc aggcgtggtg    112980
atgcatgctt atagtcccag ctacttggga ggctgatgca ggaggattgc ttgagcccag    113040
gagtttgagg ctgcagtgag cctacgactg caccactgca ctctccagcc taggcaacag    113100
aggaagacca tgtttctaaa agaaataaat taaataaaat aaataaaaat aaaaagactg    113160
aaaagcagag tggtaagaga aaggactttg gggctcaaca gtactagcct tgaaccctgg    113220
ctgttactta cccatcgtgt gataagcaaa tgccttaacc cctgtgtgcc tcactttctt    113280
aacatataaa atagaagtaa aaatcatacc cacttcaagg gtcattataa aaagccaata    113340
gagataatgt atataaagct tctggaataa tgcctggcac acagtaggag tttaataact    113400
ggaaattcat tgttgtagtg ggcagccttc tgaatctgtg tcctctttgt ccactaatgg    113460 cttttgatctg gatttggctc aggcaagacc tggggaaggg cagagactga gggcaactgg    113520
aggtataggg tggtctgagc ttccccagca gagtgaggct gggaaaggtc tgggagacag    113580
accaggcagg tgctgataag accggaatgg gaggctggag cataaggcag ttcagttttt    113640
cccaaagggg ggtgtacaaa acgatctcgt atgactcctt tatactgtta atgttttcat    113700
tttatcgcgc actgaaaaac aaaaccaaca tatttaatga atgattccaa ggggattctt    113760
gcttttacaa aaaatgctaa agtaggcatt cacatgttta aaaattgagt tgatttaaat    113820
tttaaaatta ctaagtcata gtacataatg tgtgagccac agctatcccc aaaatcatga    113880
tagcgataca ttaatgactg aagttcttta aacatcaaca tacaatgcca attccagaat    113940
tcagctcaaa ttctgcaatt acacaggctg gggttgaaac ccagcttttt tgctaactgt    114000
gtaaaattag gcaggagggc taacctcgct gaatctcaga tgtctagtct gtaaattgaa    114060
gataatgttt gttttttatct cacagagttg ttgtgaagat tcaataaaat cacaacatgt    114120
gaggatgatc tggctgtgac acctgtcacc ccactgatct ccagagttga ttcggctgat    114180
caggctggct gggcaggtgt ccccttttctc cctcaccact ccgcatgcat tcctcccgaa    114240
actgcacact tggtcaaaga ggaagacctt tcctgataga ggaggaccat tcttcagtca    114300
agggtatatg agcacctgtt ctgtcctgcc agaatctccg aaggagctct cagtaaaatc    114360
acaagatttt attgtgcatg gtagcatgag cctgtaatcc cagctactca ggaggccgag    114420
ctaggaggac tgcttgagcc caggagtttg agaccagcct gcgcaacata gtgagaccct    114480
gtctcaaaaa aaagaaagaa agaaagaaaa gaataataat agtaataaat cacctgtgca    114540
acgtgctcac ttctctcttt ggaatgtagt aagtgtacct aataaatgtg atcattgtaa    114600
tcatcacagt gagcacaggc taaagcatct tgactttatt ctataagcaa taaaagagga    114660
tttgttttta cagaactcat tatgttgtga aaataatttt ccaacattaa caaagaacat    114720
tcttcaagta aaaggaaaac cacccatcat tctcccaacc ttcaataatt ttcaattttg    114780
catattctcc agactttgtc aacatgaata cttactttac atggtcgcaa tcagtgttca    114840
tgcaaattct tttatcctga cttttataaa caaatatgat gttataaacc ggtctccatg    114900
```

```
tttctgcata ttctttataa ttatcatttt gtggctgcat aatattgcat tgactatgtt  114960
aactgcagtt ttcttaacca tttcactgtc tggggaaatg gaggataatg ccagggtcat  115020
gcctggagct ttttttttgtc tattgcatta tattcttaag atcaaatccc agcagtgaga  115080
ttagtcagtc aaaaagtaat aatattttca aggctcttgt tatattttac tagattgttt  115140
tccagagttt tgcacactgc tcccagagat gtaggaacac agacgtcatc caaccttgcc  115200
agtgctgggt gatggtgttt ataaacttct gctaatttaa taagtatgaa atgctatcct  115260
cacacggctt tcatttctat ctctttgatc attaacaggt tgaactattt tccaagtatt  115320
tgtttactct ctgcataccc tcttgggtga agtagtcatc cacttccttc acctgtttat  115380
ctgttgaagt cttgaggctt gttttataaa tgtgagcgag cacttcagag tcaatagaca  115440
ttaattgctt ccagccagat ttggccactg aggctcctga gcaggggaat gcatgatcaa  115500
aactacaccc tggacagatt aaattaattg gagaaaatgg gctgagaggc agagatatgt  115560
gtcactggcc tactgtgttt gatcctatag tggggcctg aactgggca acggcctgag  115620
tcccccacta ccagtagcag gaggctccat gtgtccccca tattagagct gcggcactt  115680
ccatttgccc cacctcctac aatacccac atacatgtac tcactctccc ttgcaaatct  115740
agtggcttca acccacagaa tttaagggga aaggaattgt tctgtcctgt tcacttactg  115800
cagaaatgag aaaagcgttg ttcacatggg atcacctaat gaaggatgc catccccaac  115860
ggtgcctata aggaaatggg ggagggttgg agagttgtgc aaaatgcaac agggaatcat  115920
cagagtctct tgccccatga tagagggttc tcaaattaag agagtctaca gcaactaatc  115980
tcacggccac tctaggcagg gcttcccaat gcttccccaa ccccacctcc atcctagact  116040
ttacccactc tgctgaacac agatgttacc catagcacct tgcaccatga ttgtttgatt  116100
agcacctccc acagtagact gtgtttctga taggtcagca acatttgctg agcacctact  116160
ctgcagggct gtgccaggtg cacaaaataa acaaagccaa agacaacatg gaccctgaac  116220
tcagcaagtt cagagtcaag tgggatagg aggctctctt cactggaagg taactccaag  116280
aaacaatggg actcaacttt ctaaccaaga gaactccagg gagctaaaat tctgacttct  116340
ggttaagact ggtgtggagc ttcattaaag aagaaaagat tcacccagac ttgagttcat  116400
agcctggctt tgcagctttt aagtcatgta acctttgatg aagttatgtg acctctccac  116460
ccagctgccc ctaacacctt gcaggggcag ggctggagtg caaagggagg cactggtacc  116520
acagcctggg aggcaccacc ccactagtgc aagccgggca acctctgccc caaggcatc  116580
cctagcctcc caactgcaag catcaatctt gcacttggaa aggaacctca cctttgaaat  116640
ctaggttcaa atttagaatg atccagctcc ttgaagttct atacagaaat acagccagca  116700
gccaggcccg gtggctcacg cctgtaatcc cagcactttg ggaggctgag gtgggtggat  116760
cacttgagga cagaagttcg agaccagcct gaccaacatg gtgaaacccc gtttctacta  116820
aaaatacaaa attagccagg catggtggta cacgcctgta atcccagcta cttgggaggc  116880
tgaggcagga gaattgcttg aacccaggag gcagaggttg aagtgagcca agatcgtgcc  116940
attgcactcc agcctgggca acaagagcga aactccatct caaaaaaaaa caaacacac  117000
gcagcttccc tccacttccc aaccacagct ccatctcaga caacaagggg cctcatgtcc  117060
atgcacatga atatccaacc aacatgtcta aggcccaacc acaccctctc caaacatctg  117120
cccccttggcc accctttggc catgggttca tgcactggca gaaaggtagt tcagagaaga  117180
agcccacaaa gggccgggaa gtccacttgg gcttttgag attccagggt ccaggataac  117240
ctaagtgtgg tctagaagag agatgcagct tctgggaggc acattccttg gtcttaggga  117300
```

```
cttcttgccc ccatggaggg aaactggcta gatgagggcc aaagcagagc cctctaaagc  117360
acagggctca gggaaggact cttttttgacc agatctaaga gcagcactac ctctctgagc  117420
ctgtttctcc atctgtaaga aggggacatt aatagactct ccccgctaga gttactctac  117480
atcagccagc acacgtaagt tcatgacatg aagcaagggc ttaatatata cccgttgtac  117540
tataaataat aggccaggcg tggtggctca cacttgtaac cccagcactt tgggaggccg  117600
aggaggatgg atcacaaggt caggagtttg agatcagcct ggtgaaacct catctctacc  117660
aaaaatacaa aaattggccg ggtgtggtgg cgtgcacctg tagtcccagc tacttgggag  117720
gctgaggcag gagaattgct tgaacccggg aggcagagtt gcagtgagc  caagatctca  117780 ccattgcatt ccagcctggg tgacagagca agactgcatc tcaaaataaa taaatacaca  117840
catacataca tacatacata catacataca tacatacata catacaatac atggacaggg  117900
accctaaaaa tgagacaggg aaagagaaaa acatgttctg acaaccttgc cctttatact  117960
aatttaggtt ttcttgcctg ttttagaaag ggcctggaca ggagccctgt tcccctcagg  118020 ccagcagaa  caaggtgtgg aactcactgt ggaagggttc tgggtgacaa gtgcagcccc  118080
gtccctccac ctcccagcac agtaggcagc acgtgtctcc attgactggc tcaggagcag  118140
gcctggtgac cagtgggaga gctgaggagc ccagggtggg gtctgaagga atccctagaa  118200
aatctgattt tcccccaggg cccacatcac gtgcccagag ctgggaaagt ggaggcagca  118260
tgggatctag ctgagaggct ccattttttgg tagcttctag tttgggagtc acagagacac  118320
ctggatgata cgaagatgta gctttgcagg actctctaga acatggagtc caagatattc  118380
ccttcaatga tgggacactg aagcccacag aggagaggtc tgtcccagtt actcagccat  118440
tcggaggcag agaccaggct agaactcagg acttttaatt tggaccagga ttcctttttac  118500 cacagtgggc agccctagca agtgccaggt agggtggaac tgtgaaggtc atccgagggg  118560
tagtacacgt gggtaggaag tcatatctaa gaactgaccc ccagacctgg ctctgccact  118620
cactccttat gagaccacag gtgctgggtg cagtggttca cacctgcaat cccagcactt  118680
tgggaggcca aggcaggcag attgcttgat tccaggagtt cgagaccagc ctgggaaaca  118740
tagtgagacc cccacctcta ccaaaattag ccaggcgtgg tggtgtctgc ctgtagtccc  118800
agctacttgg gaggctgagg tgggaggact gcttgagcct gggaggcgga ggttgcggtg  118860
agccaggatc atgccactgc acaccagcct ggatgacaga gtgagacaga atgacacact  118920
gtctcaaaat aaataaataa atgacagcag atcatcattt ttctttctgc ctctagactg  118980
caatgcctat ttctccaggt agtcactagg ataaaagtaa aaataatatt atcagcattt  119040
accaaataca gggtcagcta ctctgttatg ttctttcatg ctttgtttct tttaagcctc  119100
aaacaactct atgagctggg aacaagtatc gtccttcttc ctcccatctt atttatttat  119160
ttatctatgt atttatctat ctattcattt atttatttat tttgagacaa ggtccttcta  119220
agtcaccagg gatggcctca aacttgagct aggaactagt gtcaccaccc cccaatttct  119280
tttattgatt gattgattga ttgattgact ggttaatttt gaggcagggg tctcgctaag  119340
tcgacagggc tggtcttgaa ctcctagtct taagcaatcc gcccgcctca gcctcccaaa  119400
ttgctgggat taccaacacg agccaccatg cccagcccct cccatcttct gaataggaaa  119460
actggggttt gaaaaggtaa gcgacttgcc caaggtcccc tccctagcta gagagcttca  119520
gagccagggc acaaacccat caaagcctgt gctctcgccc attgagccac cggacctcgt  119580
acactaaccg ccaagtgttc tacacagtga aggtgacaaa gaggtgaagg gaagagccag  119640
```

```
ggaggttctg tggactcact cggtgggtat gcccagaggg aagggggatc ttgggtggca   119700
cattgagagt agctgcgctg ttagtaagtg agaactcgga agtccagact catccagtct   119760
gtgccaataa accctccctt ctacctggtc tcctttccaa agccagctgt tctccagaca   119820
atgggtggg  cggggcggg  tgtcctcctc cttctcaggg aaaatccgac gctgagccca   119880
tctccagaga tcttggcttc ccgtggggct gcagatccac ctagagccac cagagggcgg   119940
gccagcactg cggccaaggc ttgaagaccc agcacaccaa agcccggcca agcctccagc   120000
ccagtgtcca agagtccagc cagaggccga gtcctcgatc tcaaaatgtc taactgcaga   120060
agcccaactc atgttcaggc atgatgtgtc tgattctact gggacaatca ttgccaccaa   120120
agaattactg ccaaaatagt aacgacatta gctacctacc ccctccac acaccaacac   120180
acctcatttt accaagcact ttctcatgcc tggggtgcct ggagacttaa tgcagcctcg   120240
cgatgaccgg gtagcctcac cgtacagatg aggaaactga ggcacaagga aggggagtac   120300
attgtctagg gtcacctgga gaactctgat ctccagactc aaatttccaa ttcgtccccc   120360
ctccccccaa ccctaaccgg agctaggtgg ggtggggaca gcaaatgtgg atgggggag   120420
gtaagagggg tcagagtgct ctacagagaa gaccaaatgc attgtggcac ctactgtaaa   120480
atgagaccag ccagccaccc acccaccagc cagccaccta aaagtcttca gtgggcacct   120540
gctgaaaaca cgacaatgga tgacacgagt tccctgccct caaaaagctg gtagtctagt   120600
tgggggtgga ggggtgagt  cagcagataa ttatgggaaa ccgtgacacc tgtataaggg   120660
gcggggatga gcagagggc  tgcgactgcc tggagccagg gattcccgga cggggcttcc   120720
cttttcctcgc agctcgtccc aggaggagga gctccccccc agcttcgggg ttccgcctgc   120780
cttgggggcc cggggtcccc tcccacccct ccccgaagag cgcgggcccc gggaaccgat   120840
gacagcacac ctgagtcagc ccgccgccca cccgcccctc agcgtctgtc tccgcatctt   120900
gtgatatttc gctcccgggg agccagcccc actgcgctcc ggaggcagct cggcaaacaa   120960
acccagcgac agattgtgcc gcggctcatt ccggggaagg acgccaaacc ccaccctgct   121020
accccccaaca ctccctcccc gccgccgcct ccaggccctc cccccaggcg caggccctag   121080
tcggggtggg tcctggggaa acgcagggtc ctgtcctgcc tcctggaaat aggggggagcc   121140
ctgggtgagg gaagacggga gccccagaga cttttctttc tgtttctacc tgatccgaaa   121200
acgagagggg cgggaaagga aatttagggg cacagagagg agctgggggg ccgagaaggt   121260
ccgaaaatgg aaccagcagg gggcacccga gagccgaggt gcccacgggc cgggagcctg   121320
ggaatgaaac tggggaagag gggagagaa  agggaggcag agacaccgag acacacagag   121380
acgagagaca gagacgcagg gagccccgcg gggaggagga gagagacgaa gacacagaga   121440
gacagtgaga aagacagaag accgggcagg gaaacagacg agtagagaca gaaaaggtcc   121500
gagagagagt gagggaggga gggaacagag agacagagac cacgaaatat gagtaagagt   121560
cggggggagaa aaccagagaa atcgaatgag aacgcgagaa gaacgagaga ccgtggaggg   121620
agcagagaat gaatgggaag aataagacca acatttatca agagccgact gtatgccagg   121680
cactgcattg gaccctggca cggataggaa aggaggagcc gcggcgcggg cagcggggcg   121740
aggggcttct gtgctcgcgg gagcggcagc ccagggggct cagcagcccc ggcaccgccg   121800
cacctgcggc tccagcagcc ccaaccccgc cagcgctgcc tggccaccgt acccgaagcg   121860
gctcccccga gggccccgag cctatcctac gccggggcgg ctccgcggac gcgccgggcc   121920
gagtcaagac ctgggtcaac cgccctgcag ccttttgtagg gaagtgccta ggtgatgggt   121980
ctgctgatac cgcctgtgac caggccatga agggccagag gggctccagt gagaccataa   122040
```

```
tccgcccctc tttaaaaggg ggtagaggaa gttcacgcga agccaacagt cttctcccca 122100
gctttgggtc ctctcctgca ccccgcggg agataaggtc tcccctcccg gacacatcat 122160
acatacacaa aaaaacgcac acactcgcac gcgcgcccat ctcgcacccg cttgtaaatg 122220
cactaagggg catacacaca ccgggcacat atttctttcc acccatcccc aagatcgcaa 122280
gcgcaaaacc tcgcacagcc tcacgtttcc caccagctca gacatgcacg ctggcggact 122340
ttcagcggct cacccgtgtg cacactcacg tgccccccc cccgcttccc caagcccgta 122400
caaagggtaa cgggcaagca tcctgagtca cacctgcaca agcatccttg cgcgcacgtg 122460
cacgctcata tgcactcgat cttgcacgca caaactcttg catatactat tcttatagtc 122520
gcacactggg cttgaggtct gggagtggaa ggaaaagtgg aatcttggag ctgtcccagg 122580
ggacagaaat gctggaggct gggacactgg cgcgagggac gcggctgggg gcggggagg 122640 gggtgaccca gaagctcatc ttctcctgga aagttgggag gggggaacag gacaagtcca 122700
cggcgttcct ctaaactacc gcattccccc aagaagggat ttctctagaa gagtggcgcc 122760
gcgaggacga tcgaacacag tcctccgggt cgcttaagcg ggggggaggg gggcggggtg 122820
gagggggtta gaaagccgct cccgcctcct agtggtcgag aaagggttaa gtcggcaagc 122880
cagcaaacga gggaggagcc agcgagtgcg ggaaggagtg ggggtggttg ggaagagctt 122940
cctcgctgtc cccactctcc ctcggctagc agcctgggca cacggacaga cggactgacg 123000
gactctcgag cggacagcgc agctagcggg gcgcgggcgc tgggcgtcga cggccagccc 123060
cagccttccc cgccccgtcg cgccccgccc cgtcccgtcg gggccgatgg ctcctcccga 123120
ggcccgcagc ccgggcggcg cagggtagag cgccgcggcc cggccacgca gcccggggac 123180
tcccgggccc tccggagcc ccgcggggtc ccgccgtgc atccggcggg ctcagggagc 123240
gagtgggagc gccctccccc cgctgccccc tccccgagc atcgagacaa gatgctgccc 123300
gggctcaggc gcctgctgca aggtaagaac gccagcggcg ggagagcgga gggcatcctg 123360
gggagagaag cagggcgtcc cctctttcag ggattgaggg tggggcagtt ggggaggtgg 123420
ggtaacctgg ggaagggaa aagctcagcg ctggggccgc gccccgccg ccagggctgt 123480 tctcagcagg agggcacttg gctgggagcc cgcgggcgcg tgcgaggagc tcgtgaccga 123540
ggtgggacgc aggggcagg tggacccggc ccggagcggg gagggaggct caggttccgc 123600
tgtccccgct ccacctgctc cggggacgc tgaggactcg ggccggctgg ggaagcgccg 123660
actcagcaac tcctcctgcc cggtgcctca gcactttctg gccacctggg aagacaggag 123720
atgtgggtag ggggctgtct ggggaggtag gaggcgcaga gggaaatcca agtggccctc 123780
tctggtagga gagatggagg gcgctagaaa gaggatagtt ctactgattg agtgacagat 123840
aagggtgtgg gccagagact gggggtgggg tggggagggg tcaggggag agggatagga 123900 aggagaactc aaagatggag aaagtggtga ggaagctca aaggaggagg gagatggagc 123960
gggggagggg gagaaggaat aaaggttaga tgggaaaagc gtggagggaa gtgggaccca 124020
ggtgaagacc aaggaagagg gaaggagagg aaagaccaga tcaggggagg gatgggaaga 124080
agactatgga cagggaccca gaatcctggg atggaggtag cgggaaagag aatcaggact 124140
gggaccctgg ggactggaat ggaaaaggag aatggaaaga tcagaaacca gagaaggatg 124200
gggatggtga ctagagaagg ggtatcagga accggcgaag agggttggag acagggaacc 124260
atggatggga gaggggctgg agaggaggga agaggaggag gaagagaaag gctgagagag 124320
agggactggg gattgggggt gctgcccagg gatgagacaa agaggcttct ggtaaccact 124380
```

-continued

```
tccacgtggg aagccctcca ttcccaaagc gcctgcctgc cacatttctt ctctcaggga 124440
gtggctggtg ggccagatgg ggggtgcttt gagctcaggg ccctgggggt ggctgtgagg 124500
gacagagggt gaggactttg aagggggagt gacagcctcc gagggtgggc aaacaggctg 124560
gctcctgtgc tgccatttat ttatccggcc cggacgttgg attctgcagc cgctgccgcc 124620
accacggtgg ctgcttattt tggggtgtta cattctggca gagtgagaag ctgtttgcag 124680
cagctctaaa cctccgtcac ccgcgtcagt gcctcccccag gccctgcgt cactggcatc 124740
accaccacct ccatcccact cctcagctcc cacctcctca gccctgccc cctcagcatc 124800
tgcccgcagg ccccagccct tccctgaagc agcccgttgg gtgtggagcc cttgcttctc 124860
gtctgggacc ctgtgcccct ccttccagag cgagaggcct ctgctgcctt tccagggagc 124920
atcctttcct gggaccactc tgcaccgcg actctgccct gtgggtgggt agcctggatc 124980
ctgcccccta ctttgggtcc agttttcttc tcctcaagtt ccttcttcta cagggcctc 125040
cggcccaaag agtggcctgt gggctgagaa ctttgtttct gagccttggt actccaaggt 125100
ttgatagcca gagtcctgga cagtggtccc tcagtgaaca gatacttttg gctctggaca 125160
cttcagcctt ccgggatcaa taccatgttc tggcctctct tggctccctc ccctggtcag 125220
ttctggccat atattctgga cagggtcat ctcttcttga ctcccacatg taatcactac 125280
tctagaacaa ccgcaactgg aagcctagga ggtgaaagtt gcagagagag ctggagtccc 125340
ttccttgcct tgaccctgaa tagccaaaca gactcagcat tgtggctggc ccagccctag 125400
gcacctgggt gcaatttctc tcctgtcttt acctcaaggg cagtgtctca cacattcagg 125460
cgtggtttct gcggaggatg tggccacctc ttaaagaaag atcagagtgt ctctctgaca 125520
tgggcttgat gtccctcttt tccaatctgg gttccacctt gtactagctg catgacctga 125580
ggccactgtg tcatgtttct ggggctccct tccttcatct gcaaattggg ggccacaata 125640
ttgacctcca ggggattatg tgtgttgtgt tcaatgtata aagaagttaa cctgtacaaa 125700
tgcagtgcct aggacaaaat aggtgcttct tggtttcctc ctaccctgct gtactctccc 125760
ctgcagctct agccatcccc tgctgacttt agaggagggg gtgagcagag agggtggggg 125820
aggctgctac aaagggcttt cctctgtcca tgaagtagtg gagggatgaa atgaaggctt 125880
ctgagaaaga caatgaaggc gagctgtaga gacctggtca ggaggcctgg ggtgctcaga 125940
aactcacact tcccctcccc agccctcaat ggtgttacct atgatgtgag gggtcggctc 126000
taggtggcca ccgaggtatc ccccttttcca gctctgatac tctgtgcatc ttgccccagt 126060
ctccaccggg aattcacaaa atgaaggcca ggagtggagc cgtggtcctc gggagagaca 126120
ggaggcctgg gcctgagggg aaggagtggt ggtgctgagg aggagtgaga acaggggtg 126180
gggaagggac gtggcaagaa agaaaagggc acacactggg cagggcaggg actgagggcg 126240
ggggagagag ggaaaggcac agctctctag tcccccaacc ccccagtccc accacctctg 126300
ccctggagtg ctcgctccag ccccagcagg cctggggcag tgaagcccag agccccctcc 126360
cctcccctcc tccttgcctc cagtgagagc cgctgcgtga attatggatg agctccttgg 126420
gttacagctg ctttgcacgg cagtggcaag ggccagaaat ggcaacagag tcactgttat 126480
gcagcagctg ttatggagga gccccagca ccgggtcgct cttcagagag cctgcaggga 126540
ccactatcat gggctggggg aggtgagccc tggttggggg agacatggga acaagatgga 126600
aggagagtgg ggaaagagaa gagaagtagt ctaatgtggg caggtgggga gcaggagagt 126660
ctagggagag aaagaggagt aggcacccct gccagctcct gcagagttta ccctcaaggc 126720
cggaaggaac cctgatgcca gggaatgggc ccttgcctct gagattgcac atccttccct 126780
```

```
ctgtctctcc tggggcagcg gtcagtccgg aggctggggg aaagctctgt aatcctccag   126840
gggctagcgg ccatcagggc tcacactctg gtgagcttgt ggataagggg taggattaag   126900
ggatcagaga aggatttggc ttcttttggt gtcaagtcct tagggaagtg gagatcagag   126960
ggtgactctg acaggaaggg aagtgccctg gctgggcatc aagagacttt tctggcccTT   127020
tccctgccaa cactttgctg tgtgaccttg ggtaagtcgc ttgctctctc tgagctccag   127080
tcatcacctc agtagaactg atgcttgaac cagaggaatc gagggaccct ttgcggcttt   127140
gaaatctcca gttctaagcc ccaaacctca accctcatga aacccactca gggtccccac   127200
tgtgcttcca cactccacct ctgcctggtt cagatgaggg gtaagagaca ttgctcctcc   127260
accccacgtg ggtctaagaa actcgggagg agaaagtaat cgtgaaacgc cgcacggggg   127320
aggggtgaga agggccgaga acgcggagg tggtgtgaac gaatggaaca gcagccgctg   127380
tgtcactgag tattcatca cacccagcct acacacgcac ggggcccggc gctcacacac   127440
acgcggagga cagccagcac gcaccgacgc agcaccgacg cagcgccagg aggggccggg   127500
gacactcacg gtgggcccca aaagcgagga gcagcacact gggagtgtgg atcttccacc   127560
ccgcacctgt gtgctccccc ctctggagga ggaacaccag ggcagctggg atgccagcgc   127620
cacactcggg gcctgtcagt cccatgcgtg cacacctggc tgagcagcac tgcatttggt   127680
gagcacctgg ctcacgccac tacccaaaat cacagataca tacacacatt cacgcacacg   127740
gcaacctcag gagcgtgaca caacacacac aaaaccacca ctaagcaagt gcaatttgca   127800
gccttggaga ccccacactc aaaatcacca accctcagt ctctcccagg gtctctgaac   127860
cccaaggagc cccaggatgt cagagtgcag aaacaagtct tcctcccctc tgccttcaaa   127920
agcctaggac gttgcttgaa gcagaaggtg ttcagtcact gtgtgcccag ggaatgactg   127980
cctggctttg ggggtgcagg ctcccttttt cccaggcaa aactgccaga agaaaatccc   128040
aggagtcacc tggaaatcat aagaaagtgt agaggtcaag ctagttccgg cctagaactt   128100
tatcagctat agtgacggca aaggccaggg atgatgggag gccctgcacc cctattaaaa   128160
tatgagtaca gacacctgca ctccactctc tagcccccag gctctctggg cctgcttttc   128220
catcagtatc ataataagga tggatcatat ccaaccttca aaagttactt tgggggaaaa   128280
aaaaaaaaaa gctttggctg gatgcggtag cttatgcctg aaatcccaac actttggag   128340 gccaaggtgg gaggattgtt tgaggccagg agtttgagac cagactgagc aacatagcaa   128400
gaccccatgc ctacaatttt ttttttttt ttttttttt tttgatacag agtctcgctg   128460
tgtcacccag gctggagtgc agtggtgcga tctcggctca ctgcaagctc cgcctcccgg   128520
gttcacacca ttatcgtgtc tcagcctccc aagtagctgg gactacaggc gcccgccacc   128580
atgcccggct aaattttttt tttgtatttt tagtagagac ggggtttcac cgtgttagcc   128640
aggatggtct cgatctcctg acctcgtgat ccacccgcct cagactccca aagtgctggg   128700
attacaggcg tgagccaccg cgcccggcca aaatttta aaaattagc tgggtgcagt   128760 ggcacgggcc tgtggtccca gctcctcagg aagctgaggc aggaggattg cttgagccca   128820
agtgatccaa gctgcaataa gctgtgatcg taccactgca ctccagcctg ggcgatggag   128880
caagaccctg tctccaaaag aaaaaaagaa agaagttttt aagtaactgc gaatgaggag   128940 agcctgggt gtaaaatgca gattcccagg ctgtcccccc aggaattctg catagttcct   129000
aggactggct ggtggcctca cttagagacc cgacccttaa ggcccctccc ggcacaaaga   129060
ggctctgact ctgcaagggc gaaagtaca ggaaagtaag ggcactgggc accagtgggc   129120
```

-continued

```
tggcaagacc agaccccaga gtgagtccat ttcacacggg cctcagatct ccaaagggtc 129180
ccaagttact tccagtcatt ctccaatggg gtgactttgc cccccagggg acatttggca 129240
atgtctggag acattttggt tgtcacaact ggaggcaggg tgctgctggc atctagtggg 129300
tagaagacag agatgctgct aaatgcctta tatagggctg cccccacaac gaggaactat 129360
ccggcccaac tgtcaatact gaggcagaga aaccctgacg ttagtctttt gacattaatc 129420
tctagacaag gtcaaacatg caatagtgaa acaggaatg aagagatgat cattcttcaa 129480
ccaatttgca gtgctttcta caatggcctt ttggcattat tttttaatat atgagaagcc 129540
tcagaaagtg gaagtggcca ggccacttga ggctataacg ttgtcccctg agccccagaa 129600
catgggagca ccaggggctct aggcctttat ttttatttc tatttttttcc cctgaaacag 129660
ggtcttgttg tgttgcccag gctggagtgc aagggtgtga tcgttgctca ctacagcctc 129720
aaactcctgg gttcaagcga tcctcctgcc tcagcctccc aagtagttgg gactacaggc 129780
acatgccacc atgcctggct aatttttttt ttttttcttgt aaagacaggg atctccctta 129840
tgttgcccag gatagtctca aactcctggc tcaagcaat cctcctgcct tggcctccca 129900
aagtgctggg attacaggtg tgagccacca tattcagccg ggtctaggcc ttttaccaag 129960
ttgggggget ggccccccagc tggcactcct gccctggaag cccacctagt aagttctgct 130020
tccccctcccc acagctcccg cctcggcctg cctcctgctg atgctcctgg ccctgcccct 130080
ggcggcccc agctgcccca tgtctgcac ctgctactca tccccgccca ccgtgagctg 130140
ccaggccaac aacttctcct ctgtgccgct gtccctgcca cccagcactc agcgactctt 130200
cctgcagaac aacctcatcc gcacgctgcg gccaggcacc tttgggtcca acctgctcac 130260
cctgtggctc ttctccaaca acctctccac catctacccg ggcactttcc gccacttgca 130320
agccctggag gagctggacc tcggtgacaa ccggcacctg cgctcgctgg agcccgacac 130380
cttccagggc ctggagcggc tgcagtcgct gcatttgtac cgctgccagc tcagcagcct 130440
gcccggcaac atcttccgag gcctggtcag cctgcagtac ctctacctcc aggagaacag 130500
cctgctccac ctacaggtga gcctgccctg cccccaccct cagcccctt ctggttctcct 130560
ctctctgtgg gcccctctgc tccccgaccc tggcgtgcgt ccctcctctc tccccaggcc 130620
acccttcctg cctcagcatc tccatttctc tctgtctatg tctctttcct ctcttacatt 130680
ctccagggc tttactttt cccttctgcc tctctacctg tttaggtccc ttgctgttcc 130740
tctctctctc tctccctcta actccacaac cttcacctct ctgcctctgc ctgtctgtct 130800
gtctatccct ttccatccat cactgcctct ctcactaact tgcctccccc atctgtcttc 130860
tgcctcttct gtctgtctcc cttcacacac ccactccgca tacacccca tgtctgtctg 130920
cgtgtgtgta tctgtctctt tctgtgatct cacgtgtttg ccttcagggc actctgcctt 130980
cccccagggt ccctgcccca aaggcctttg cagctgtttt tctcacccac cctcaagtct 131040
gcccacatca cggtgaagta gagagagaag gcagagccac agccactggc atcccacaga 131100
aagttgcgct tctctccaat tcactgggca atgggacggg agaagcccac acccttcta 131160
gattcccatt ttccaaacct gtcatctcaa tgcaggggaa gaaagaaag ggtaaatctc 131220
tgttatgcag ctggagaatg gatgctctga aaatggaagg aataccagta attgttattc 131280
attgttatta ttattgatct aattattgtt tattgttgtt atgctgactg tttgacacgc 131340
aaatcatccc actccatttc cccaggaagc aataacacac cctccaaacc accctgagag 131400
aaaatcttcc cttggctaca gagcctccgg ctggaagggg gtgaaaatat ccaaattctg 131460
ccctctccct acttgaacct ggaacgtgct tcctctgcct catccaggc tagtgcctaa 131520
```

```
ctagttatca atctgctagt tggaaaatca ggtcagtgct gatgatgcta atgataataa    131580
caatagccat aacaacctaa caaacatact gagcacccac tacgagctag atgctaagaa    131640
tacagtagtg aacagaacag accaaacccc ctgccttcac agagatacca ttcccatgag    131700
gagggaaaga agtaaaatgc acggtatatt ggaaaaatat gtcttatatt attcttattg    131760
ttgcctaaat agtgacagta atagcagtag ccgccaccac ttagtgggta cacagggtca    131820
gccacagtgc caagcacttt ataggtatcc actctgccat ttacaagcgt gtgacatttt    131880 tttttttac ctcctcagac ctcagttttc tcatctgtac aatggggtag caagagcacc    131940
catctcctag ggattttgaa agcattaaat gcatgaataa tttgtaaagc acttagaata    132000
gtgcttggca tacggtaagt gctatataaa tgcttgttaa aatactattt taaaaaaga    132060 aacgagcctt atttaacatt ggtttcagtg aagtggccca acttggactc catcctgaag    132120
atgtgggtca acttcaagga ttatactaag gtcatgagtg agtcccagaa attgcacctc    132180
acagtttatg aagtgcactc agccacctca tctcatttct acagcccagt tgggagatta    132240
ttttcacctc cttgttaaca atggagaagc tgaggctggg ggccctgaag accctataga    132300
gatatagtca cctccaatca taaatctttt caaccattgt cggtgtgacc ggaggcttat    132360
gtcttctcac catcatgttg agcctcacaa caacctggtg ataggacag ttaggggcac     132420 tagggacatg gaatgaatgt tcctgaggcc acacacccag gaagagctgg cgcttgaacc    132480
tcatggtctg gctacaaggg gacagtactc tggagtacaa ttgagcaggc tcattttga    132540 aagcacacag tttggactca gcaagaccta ggttcaaatc ctggctccta tatatatgac    132600
tttggacaaa ttacttaacc tctctcagtc tccatttcct catctctaaa atggcaatca    132660
ggatagtact taataataat cttttttttt tgagacgacg tcccactcta cgcccaggc    132720 tggagtgcag tagtgcgatc tcggctcact gcaacctctg cctcccaggc tcaagtgatt    132780
ttcctgcctc agcctcctga gtaactaaga ttacaggcat gtgtcactac acccagctat    132840
tttttgtatt tttagtagag aagggttttca ccatgttggc caggctggtc ttgaactcct    132900
gacctcaggt gatccactca cctcggcctc ccaaagtgct gggattacag gtgtgagcca    132960
ccatgcccag ccaataataa tccttattta agaagttttg taaggattaa aatgtaaggc    133020
atttagcaca aggattaaaa tgtaaggcat ttagcacata tgggcactat aataataatt    133080
actactacta ctactactaa tactgagatc aaatactact acaaattgat catgcattta    133140
atgctttcaa aatctcctta tcaatatata ttagttattt aggaggaatt tggagtcaga    133200
gggcctgagc ttgaatcccc gatctactat tttctgactt atttaacttt aagcaggttg    133260
ctaaccctct ctgaacctca cttactttat ctgcaaactg ggaataatga aaataatacc    133320
ttccaccaag aatggctgta aataggaaac gagttagtgt atagaaagcc catagttcag    133380
gctggtgtgg tggcccatgt ctgcaatccc agcacttcgg gaggccaagg tgggtggatc    133440
acttgaagtc aggagttcga gaccagcctg gccaatatgg tgaaaccctg tctctactaa    133500
aaatacaaaa attaggcagg cggggtggca ggtgtctgta atcccagcca ctagggaggc    133560
taaggcagga gaatcacttg aacctgggag gtggaggttg cagtgagctg agatcgtgct    133620
actatactcc agcctgggtg acagagcaag actctgtctc aaaaaaggaa aaaaaaaaa    133680 aaaagcccat agttcagtgc tgaagaaatc atgttattat gaccccatcc tccattgact    133740
ctcaggccaa caacagcaat caggacctga ggtcagcaaa ggcttgggca gaggggacct    133800
caggtggaca ttggggtctt ctgaaatggg aagtgtttgt tctctacgcc cctggcatga    133860
```

-continued

```
atggtaccag gcatcatggg aaggaagcaa cttcacacct ggccttttat agaggagatg   133920
gaaaacacag cctctgcctg tgaactgcct ggtagggctg ggctgggaga tgccacaggc   133980
aggtgaggaa acatgggctg gggtgagatc cgcagggtgc aggtgtgacc caagatggag   134040
ccaggcctgc cccaaagggg agctttggag gaaactccac cagaggacca cagcttttca   134100
gaatggggaa gggccaggca ctgtgccagg tgagttcatt catcaacaga tatttactga   134160
gtatctacca catgccaggc aatgttccag gtgccaggga ttcaggagag aacagaaaca   134220
gtggccctgt tctcccagag catattccct actcaagtgt agccagatga taaagacact   134280
tgttttcttt cttttttttt tttgagacga agtctcgctc tcttgctcag gctggagtgc   134340
agtggcacga tctcggctca ctgcaacctc tgcctcccag gttcaagcga ttctcctgcc   134400
tcagcctccc aagtagctgg gattacaggc atgtgctacc atgcctggct aattttgta   134460
tttttagtag agacggggtt tcaccatgtc ggccaggctg gtcttgaact cctgaccaca   134520
ggtgatctgc ccaccttggc ctcccaaagt gttggattac aggtgtgagc caccgcaccc   134580
gccgacactt gttttctctt tcagtcatta cagtggcctg catggttttt gtttgttttg   134640
ttttgttttg ttttgtttt tgagacagtc tcactatgtc acccagctgg agtgcagtgg   134700
cgcaatcttg gctcactgca gcctcacctc ctgggtcaa acaattcccc catcttagcc   134760
tccccagtag ctggaactac agacatgtgc caccatgtcc agctaatttt tctattttat   134820
agagacgggg tttcaccatg ttgcccaggc tggtctcaaa ctcctgaact taagcaatcc   134880
acccgcctcg gcctcccaaa gtgctgggat tacaggcatg agccaccgta cacagctggc   134940
ctgaatggtt taaaatagt ctttatgctc aagcagatca gatctcagtt tgaattccag   135000
ccacacctct aatttgctct atggctttgt gcaagttatt taaccactct gagcctcgat   135060
ggacccatct gtgaaatggg gataacctgt accttggcga gcagggggttg tgaggattaa   135120
aggagatact actgagctca cagcccaatg tctggtacaa agtgagtatc caatgaatgg   135180
tagctatcca ttaacaccag ggaggacacc aactgaagct cagcaaaata aaagcacagt   135240
ccaaggtcac ccagctagta aggaacatga cctagaattg cccaggtct gtctgactcc   135300
agagtgcagt tgttcagagg tctctggagt tggaagccac gttccactgc atattagctg   135360
ttggaccccta gccgagtcac ttcacttctc tgaggctcca tctcgtaatc tctgaaatgg   135420
agataataat agtatccacc tcataggggtt gtgacaatta agttactata taggatctgt   135480
gtagcacaga gcttggcaca tggtaagagc tcaatcagtt acctgcttga caatgctgac   135540
gccgatgatg acgatgatac ccatcctaga ctgatgagct ctgtaagcgg gggtgcctgg   135600
cacagagtag acactcggta cagctctgtg gaatgaatga ggcacatccc agaactcacc   135660
aattcataaa aatcagatgc agatgggatc ttaaagatca cctatcctaa gtcccttgtt   135720
tcacagatga aaagacccag gcccagagag gtgcttggag ctgcgcaagg tcacacagcc   135780
aagcagctca tttgattagt gtcagagcca agagctggga gtttggaggg aggcaaggtt   135840
aagaacagga tgctgtcagg gaagcaggca gggatgctgt gttaagattc caaatggatg   135900
cagagagctg tgaaccggcc agtggggagg caagggaaat gtggtttttg aaatggaaga   135960
ggatgacttt agcagaggct ctcagcccag agggagggga gataggagg ggagataggg   136020
agggcgggg ggagggctag ggctgtgaaa gtcaagagct tattaatgca tagagaacgg   136080
ttttaacagt ggagagagga aggaccggat ttgaaagcta cattcaagga agtggcaacg   136140
ggatttggca acagcttgga tgggggggagg aggcaatgga ccccaaggca gaggctcaga   136200
gaagggaggg gcaggacttt ttgcagagaa acaaaaggag aggagaggag gttagaatca   136260
```

```
agaaattctg tgggccaaaa cctggggctg tgggtcaaag gcacctgaat tccctaggat  136320
ctctggaact ttggtctact cttctgacct cccgaggtcc cccaaaatgt ggattacccc  136380
tgctcactct cccccaaccc ccggccccctt atcgatcctc tgaccataca tctctgggtg  136440
tgtcctactc ttgctgacac ttcataaaaa gaggaacccc atttaggtgt tttgagtggc  136500
agggattcca agcctacccc ctggatgggc ctggaagaga acaagagcac caggccatgg  136560
tgagtcaggc tgaggccagg gaggtgcaag gagccagctg gaggcctgag ccaggatttg  136620
gggtggtggc agcaggggc ggagaatggt ggtgtcagag gcagccgaga aggttgaggg  136680
ggacggatct caatgtggcc aagaggaggg ctcttggcac gctcagttcc tgtagcgaag  136740
agggcggaag ccagatggga gggggcgaga acaggcagga gcacaggaag gtggaggctg  136800
tgggtgtagg ctgggagtca atgccctccc ccaacctgag gcctccgacc aggctcctgg  136860
gtggcaggca tggggaggaa agcgtctccc caggcagtga gggagggaga gccacagtca  136920
gggaacaggc ccctggggtg aactggcctg agcagagtgg atgctcctgt tctgagaccc  136980
agacctcctg gaacctgctg accacagtga tgccctgcac aagaggggag gacctcaagg  137040
cagtgaggtc agggagctga agtcctgctt ccctctctgg caagcccctta tctctttgag  137100
ccccagtgct ctcctctaaa aaagtgagct gggctgatgg gtgccaaggc attagctccc  137160
aagtcagctg atcatcagaa tccctggtg agctggttat aatgcagagt ccaggaatcc  137220
ccactggccg tgggccacac acaccgccg cccccgctg ttaattctga accatagttc  137280
caaggtcctt tctgcactaa tgtggcctga ttaggtgact ccctagcacc aggcaggtgg  137340
gacagcgcct ctaaggggag tagtaatgca atgtggcttc cttcctctcc tcccctgccg  137400
cctctggggg tggagctgat gcccctcacc ccaatacccca gcctagtagc agtactttgg  137460
ttcccccagg gagctcctct tttaaagaaa agggacagga cccaattgtt actgagcccc  137520
tattgtcata gtagccacca tttattgatg gttgactatg cacctgccag atactgtacc  137580
cttaacagca tttatcatcc aaccctcctt tagcctgctg aggggggttat acataataag  137640
gaatattgta catactgagg aacctgagac tccatgaggt taaaacttgc ctaaaataac  137700
acagctaggg aaaaggcaag ctggattttg aactagggct ctaagtgctg agcctgtggg  137760
cttcataatt ggaccaaatc cctgtgtgct gggcacgtgt ccagcacttc cctcatatga  137820
tctttatgtg aaccatcctc tggaatcctc agaacaaacc caggaagtag gtatactcat  137880
ccccattttta cagatgagga acaggcaca gagagatgac tggcttggcc aagttaagaa  137940
taatggctaa caaacaaaaa caaaaacaaa aattaaaaaa aaaaaagaa taatggctaa  138000
ctcatggaac tcatagaact ccacaaggaa aggtgttcta agcaccttca tacatgctgc  138060
ttcatttaat ctctacatta tacagatgag gaaactgagt cacagatatc ctgagtgact  138120
tgcccacggt ggcatcagtt aatgacagat ccaagatttg aaatcagaaa ggctggctcc  138180
ccagtctcca tacttcacca aaccagaagt tctgaaactc aaactgtggt cctgccaatg  138240
gccacactgg cttccctggg gaacctgtag acatggggat tcccaggctc caccccaaac  138300
ctcctgaatt agaaactctg cccccgccc caccccgctc agagatccgc agggatcct  138360
aatacacccg aaagtttagg aaccactgac ctcaccaata ccactttttc cacagcaaat  138420
aggttagagg aggcagaatc caaatccagg atgctatgaa tcaaaggtc aacccttttct  138480
cttctgccac ggtgcacccc cttccctccc ccggccaagg cccagcgggg tctgcaccc  138540
tgcctcaggc ccattctctt cttctgtgcc ccactccacc ccacccagga tgacttgttc  138600
```

-continued

```
gcggacctgg ccaacctgag ccacctcttc ctccacggga accgcctgcg gctgctcaca    138660
gagcacgtgt ttcgcggcct gggcagcctg gaccggctgc tgctgcacgg gaaccggctg    138720
cagggcgtgc accgcgcggc cttccgcggc ctcagccgcc tcaccatcct ctacctgttc    138780
aacaacagcc tggcctcgct gcccggcgag gcgctcgccg acctgccctc gctcgagttc    138840
ctgcggctca acgctaaccc ctgggcgtgc gactgccgcg cgcggccgct ctgggcctgg    138900
ttccagcgcg cgcgcgtgtc cagctccgac gtgacctgcg ccaccccccc ggagcgccag    138960
ggccgagacc tgcgcgcgct ccgcgaggcc gacttccagg cgtgtccgcc cgcggcaccc    139020
acgcggccgg gcagccgcgc ccgcggcaac agctcctcca accacctgta cggggtggcc    139080
gaggccgggg cgcccccagc cgatccctcc accctctacc gagatctgcc tgccgaagac    139140
tcgcgggggc gccagggcgg ggacgcgcct actgaggacg actactgggg gggctacggg    139200
ggtgaggacc agcgagggga gcagatgtgc cccggcgctg cctgccaggc gcccccggac    139260
tcccgaggcc ctgcgctctc ggccgggctc cccagccctc tgctttgcct cctgctcctg    139320
gtgccccacc acctctgact gcggtgctga gatcgaagag gccagtgtcc gatcccgct    139380
tcccgtccac ccggggctgc ggctccggcc ccagtcgccc caccttccct ggccttgctg    139440
cctccctttc ccctcccagc tcctctcctc cccggggagc aggccgcctc tccttgcctg    139500
cccccctgggc tgtcctgact tgtgcagcc caagagggc gtgtgtggtg gctcagccct    139560
gccctcccca gttctggcca ttaactcttc cccatcccaa ggctggggtg gggcccccca    139620
ggcagccgct gacccgcact cctaaggcc cacagcggac accagagggg cttttgtctg    139680
cagagcgtct tccaccagca gagcctttgg aagctccccc agggagcccc acccaggacc    139740
ctttggggga tgcctcagtc agggccaggc tgaccctgac ccctgcttac cctagtcccc    139800
tcaacctcct gacactggag gaatactttt ctcctaagtc taccctggac acttttttagg    139860
gcacctggag agaactttcc tctccactgt ggccctgcg tggtgaagat caaagaagt    139920
tgtttgggaa aaaaaattta ttaaaaaatt ctattatttt atctactgta agatttgttg    139980
acttgggacc ccgaaagcgg gatgaggtct cagaatgtaa ggattgcagg gccaggaggg    140040
ttggagaagg ggagccgtcc cccgccatca aagagcttcc tggtggctgg aggtggtgtg    140100
cgctcccccg ccatgaggag gagctgaagc cctgcattct aggtgaggcg cagtgtggca    140160
gccaagagtg ggtgctggtg gcacctcttc tcttcatttg tccaggggaa gagctgcagc    140220
caaccctgag tggtctggcg cctgaggaac taagcctggg gaagacctgc tgtctggtta    140280
acagccctct tccagaccct gttccttcag gaaacaagag cagttctcct gcaaggagga    140340
gtcacataca cactcctggt cacagacagc cccaacatgg ctttgggtaa atgtgaacaa    140400
ggcactgctc cctcagggaa acacagcccc atgccagagc aaacaccta gcaaacagag    140460
accaaggctg ggtttccgcg tacattgcc tccttggcta agtgcccttg tgcagtgcac    140520
agcgtacaca cctgcacaca gcaaccctgt gggtatgtgg tctctctctc agctcctgtg    140580
aggtagaagc catcagggat gaaccaggtc agagaagcag gtttccaaac aggctagaag    140640
agggaccgag gaactcgggt gatcagaggg acaggaatcc caaattggga tgcattactg    140700
gcttgaggta caatcagaac cttcatcttt ctggtgtgtg aagagaggc tggggactgg    140760
gaagagctca ggctaagaag gacttgggtt gggatttagg ggtgagtctc atcagactga    140820
gcacttggag agaagtttgg tagtttgaat ttggagctaa gaatctagct tgggcagggt    140880
gtggtcgctt gcacctgtaa tcccagctaa ttgggaggct gacgtgggag gatcacttga    140940
ggccaagaat ttgagactag cctggacaac atatcgagac tgagtctctt aaaaatgttt    141000
```

```
ttttaagaat ctagtttgga gtggggtgtg atgtctcaac gtctgtaatc ccagcactct 141060
gggaggctga ggtggacaga tcacttgagg tcaggagttc aagaccagcc tggccaacat 141120
ggcagaaacc ccgtctctac taaaaattca aaaaaattag ccaggcgtga cggcgggtgc 141180
ctatagtccc aggtactcag gaggctgagg cacaagaatc actccagcct gggtgacaga 141240
gactctgtct aaaaaaaaaa aaaatctagc ttgggaggtg ggaatagaaa gatagagggg 141300
gcctagatgc tagggcttga ggaagcaggc tgaggttctg tgattctggc tagggaggtc 141360
aaatgatctt gagaagaaga gaagaaagga gaagaaatca gcatctaagc ctgaggcagg 141420
tagactccgg ttaagggtgt ggggtgggct gggggagagt gagagcagct ggtcagaaac 141480
ccagggagct cggagtctgg ggtcttgcag gggcttgtgt caggctggct gtgaggaggt 141540
taatggggtg gattggaggg acagccagac aagagctctg gtggaggagg ggctgctggg 141600
gcctgggcag ggggagggga gctgctggta aattagaggc aggctgtcca ggtcatagaa 141660
ttatcattgt gaaatattca tgggccatcg gtccagatgc tatttcagaa cagtgaaagc 141720
aagaggagtg tgtgagcctc aggaagaagc ctgaagcaaa gccactctcc accaacccc 141780 accccctccca ccaccagccc agacagaccc acggacgccc atcacgtgca cacccacact 141840
cccgagctct cacacacact cgcaccaagc agagccatgt agcacgtgca agcacaccaa 141900
ccacccacgg gtcccacaaa caggcaggtg tccctaaat tctgacatgc acactgacat 141960
gcacacccac tcaatcagga cccagcagag atcacctcca gcgatctcac atgcgcagac 142020
ccccaaactc tccaaacaac ccagattcac caccttgacc cacacaccct gagataggag 142080
ggatgttcaa ggccatccag cccaaccccc accaatgctc tgatggggaa actgaggcca 142140
tagaaaggaa gggatttgtc tgagattcct ctatcccctg aaaaaagcaa aattcattca 142200
cctcccacat tctgagtgta cccccattct gcattttcgt ctgccagaca cccagcctag 142260
ttgtaattaa ctcctcccctt tctctaattt cctgcatcta ttcagttacc cagtccccca 142320
cccagccaca gtctatccct tccttcccat tctccccacc acctccctgc tccagctact 142380
cattacctca tgcctggaat ataaaagaaa actgcgataa cctcctcgct ggtttcctac 142440
atggaatctc tccctccctc ccacccagcc ataccgtggt gaccagattc atctgatcaa 142500
aatttgcata tgttatgatg tcactcagga gcctgtaatg gcttcctaat gcctataggg 142560
taaaggtaaa acaccttagc agagcatcaa agatccctca gagtctggta ccaactgctt 142620
ttctagcctt ttctctcaca atctcatccc aaaccttcac tccagctaga acgtttgtat 142680
catactggcc accagttatc atgtatgtga aacccaccaa ccgactttga gtgcccccct 142740
aaaatttctc agtctctcct gaagtaggaa acctcttccc cctcctcaga tctcagactc 142800
cagagccctt tcccaaggcc aagactgcac ctctctgacc atatacaggg gttcttcaaa 142860
gcagcagaca gaggctcagg ctctggctcc ctccaagcag acggctgccc ccgactggcc 142920
accttgggaa gcacagccag gtttcagtcg tctagaacag agaatgagca tctaaccgcc 142980
tggggagagg actaggacac cagatgataa ggtttataag ccccttaagcc tctaaggttc 143040 ttacacccag agtaggggggg ggacggttct cagccctgtt tccctagctg cgggctccca 143100
attttcgatc cctaatccga gaggaactcc tctccaatga aatacagact tgggactctc 143160
aggacactgt ggaagggaaa tttcccaaca gactctgaga gtccaggagg ccaggggatag 143220 accaggtggc aggcccaagg tccagctggg gtcaggtttc tatatgaatt tttaatgctt 143280
ccagatagac ttgtcagatg ttctgaaaac tgagcatctc ctttcacctc tgtacatgat 143340
```

-continued

```
gcccttctcc aacccccattg cccctgcagg agggcaggcc tgggacagat attcagtggc    143400
ctctggagaa acggttttgg gacagtagaa gggtaaatga cctagttatg ttcccactag    143460
taagctgtgt gaccttgggc aagttactta acctctctga acattagagt tctgtgggtt    143520 tgttttttgtt ttgtaagctg gggacaatag tgccagccta aatcaatttg ttgtggggac   143580
tcagtgcaat agcccatggc aaagtgacct acatgcttgc tgttattatt ctctttcctc    143640
aagttctgcc tccctcttcc agcttttctt ccaaccccaa agatgtctct ggctattgct    143700
tcgaaggtag gaactttggt tggttctccc ctttctcttc aggcccaaac tccccacctc    143760
aagatccttt ggcctttgta gaaacttcag gtgaggaggt ggcagagaaa taagaaagtg    143820
tgcaaggctg gtggagtgag agaggaggat agatggcgaa gccctagcag aggggaggga    143880
agtgggcagt ggagagagg                                                 143899
```

```
<210> SEQ ID NO 16
<211> LENGTH: 215980
<212> TYPE: DNA
<213> ORGANISM: Mus sp.
<220> FEATURE:
<221> NAME/KEY: modified_base
<222> LOCATION: (1001)..(1100)
<223> OTHER INFORMATION: a, t, c, g, other or unknown
<220> FEATURE:
<221> NAME/KEY: modified_base
<222> LOCATION: (2123)..(2222)
<223> OTHER INFORMATION: a, t, c, g, other or unknown
<220> FEATURE:
<221> NAME/KEY: modified_base
<222> LOCATION: (3728)..(3827)
<223> OTHER INFORMATION: a, t, c, g, other or unknown
<220> FEATURE:
<221> NAME/KEY: modified_base
<222> LOCATION: (5168)..(5267)
<223> OTHER INFORMATION: a, t, c, g, other or unknown
<220> FEATURE:
<221> NAME/KEY: modified_base
<222> LOCATION: (7481)..(7580)
<223> OTHER INFORMATION: a, t, c, g, other or unknown
<220> FEATURE:
<221> NAME/KEY: modified_base
<222> LOCATION: (8849)..(8948)
<223> OTHER INFORMATION: a, t, c, g, other or unknown
<220> FEATURE:
<221> NAME/KEY: modified_base
<222> LOCATION: (10375)..(10474)
<223> OTHER INFORMATION: a, t, c, g, other or unknown
<220> FEATURE:
<221> NAME/KEY: modified_base
<222> LOCATION: (12270)..(12369)
<223> OTHER INFORMATION: a, t, c, g, other or unknown
<220> FEATURE:
<221> NAME/KEY: modified_base
<222> LOCATION: (13438)..(13537)
<223> OTHER INFORMATION: a, t, c, g, other or unknown
<220> FEATURE:
<221> NAME/KEY: modified_base
<222> LOCATION: (15902)
<223> OTHER INFORMATION: a, t, c, g, other or unknown
<220> FEATURE:
<221> NAME/KEY: modified_base
<222> LOCATION: (15939)..(16038)
<223> OTHER INFORMATION: a, t, c, g, other or unknown
<220> FEATURE:
<221> NAME/KEY: modified_base
<222> LOCATION: (18223)..(18322)
<223> OTHER INFORMATION: a, t, c, g, other or unknown
<220> FEATURE:
<221> NAME/KEY: modified_base
<222> LOCATION: (20974)..(21073)
<223> OTHER INFORMATION: a, t, c, g, other or unknown
<220> FEATURE:
<221> NAME/KEY: modified_base
```

-continued

```
<222> LOCATION: (24403)..(24502)
<223> OTHER INFORMATION: a, t, c, g, other or unknown
<220> FEATURE:
<221> NAME/KEY: modified_base
<222> LOCATION: (27574)..(27673)
<223> OTHER INFORMATION: a, t, c, g, other or unknown
<220> FEATURE:
<221> NAME/KEY: modified_base
<222> LOCATION: (30892)
<223> OTHER INFORMATION: a, t, c, g, other or unknown
<220> FEATURE:
<221> NAME/KEY: modified_base
<222> LOCATION: (30901)..(31000)
<223> OTHER INFORMATION: a, t, c, g, other or unknown
<220> FEATURE:
<221> NAME/KEY: modified_base
<222> LOCATION: (34443)..(34542)
<223> OTHER INFORMATION: a, t, c, g, other or unknown
<220> FEATURE:
<221> NAME/KEY: modified_base
<222> LOCATION: (38205)..(38304)
<223> OTHER INFORMATION: a, t, c, g, other or unknown
<220> FEATURE:
<221> NAME/KEY: modified_base
<222> LOCATION: (42373)
<223> OTHER INFORMATION: a, t, c, g, other or unknown
<220> FEATURE:
<221> NAME/KEY: modified_base
<222> LOCATION: (42386)
<223> OTHER INFORMATION: a, t, c, g, other or unknown
<220> FEATURE:
<221> NAME/KEY: modified_base
<222> LOCATION: (42393)
<223> OTHER INFORMATION: a, t, c, g, other or unknown
<220> FEATURE:
<221> NAME/KEY: modified_base
<222> LOCATION: (42461)
<223> OTHER INFORMATION: a, t, c, g, other or unknown
<220> FEATURE:
<221> NAME/KEY: modified_base
<222> LOCATION: (44809)..(44908)
<223> OTHER INFORMATION: a, t, c, g, other or unknown
<220> FEATURE:
<221> NAME/KEY: modified_base
<222> LOCATION: (51380)..(51479)
<223> OTHER INFORMATION: a, t, c, g, other or unknown
<220> FEATURE:
<221> NAME/KEY: modified_base
<222> LOCATION: (56740)
<223> OTHER INFORMATION: a, t, c, g, other or unknown
<220> FEATURE:
<221> NAME/KEY: modified_base
<222> LOCATION: (56765)..(56864)
<223> OTHER INFORMATION: a, t, c, g, other or unknown
<220> FEATURE:
<221> NAME/KEY: modified_base
<222> LOCATION: (62818)..(62917)
<223> OTHER INFORMATION: a, t, c, g, other or unknown
<220> FEATURE:
<221> NAME/KEY: modified_base
<222> LOCATION: (68518)
<223> OTHER INFORMATION: a, t, c, g, other or unknown
<220> FEATURE:
<221> NAME/KEY: modified_base
<222> LOCATION: (68534)..(68633)
<223> OTHER INFORMATION: a, t, c, g, other or unknown
<220> FEATURE:
<221> NAME/KEY: modified_base
<222> LOCATION: (74552)..(74651)
<223> OTHER INFORMATION: a, t, c, g, other or unknown
<220> FEATURE:
<221> NAME/KEY: modified_base
<222> LOCATION: (81446)..(81545)
<223> OTHER INFORMATION: a, t, c, g, other or unknown
<220> FEATURE:
<221> NAME/KEY: modified_base
<222> LOCATION: (88519)..(88618)
<223> OTHER INFORMATION: a, t, c, g, other or unknown
<220> FEATURE:
```

-continued

```
<221> NAME/KEY: modified_base
<222> LOCATION: (93791)
<223> OTHER INFORMATION: a, t, c, g, other or unknown
<220> FEATURE:
<221> NAME/KEY: modified_base
<222> LOCATION: (93794)
<223> OTHER INFORMATION: a, t, c, g, other or unknown
<220> FEATURE:
<221> NAME/KEY: modified_base
<222> LOCATION: (96565)
<223> OTHER INFORMATION: a, t, c, g, other or unknown
<220> FEATURE:
<221> NAME/KEY: modified_base
<222> LOCATION: (96570)..(96573)
<223> OTHER INFORMATION: a, t, c, g, other or unknown
<220> FEATURE:
<221> NAME/KEY: modified_base
<222> LOCATION: (96579)
<223> OTHER INFORMATION: a, t, c, g, other or unknown
<220> FEATURE:
<221> NAME/KEY: modified_base
<222> LOCATION: (96590)
<223> OTHER INFORMATION: a, t, c, g, other or unknown
<220> FEATURE:
<221> NAME/KEY: modified_base
<222> LOCATION: (96596)
<223> OTHER INFORMATION: a, t, c, g, other or unknown
<220> FEATURE:
<221> NAME/KEY: modified_base
<222> LOCATION: (96602)
<223> OTHER INFORMATION: a, t, c, g, other or unknown
<220> FEATURE:
<221> NAME/KEY: modified_base
<222> LOCATION: (96616)
<223> OTHER INFORMATION: a, t, c, g, other or unknown
<220> FEATURE:
<221> NAME/KEY: modified_base
<222> LOCATION: (96629)
<223> OTHER INFORMATION: a, t, c, g, other or unknown
<220> FEATURE:
<221> NAME/KEY: modified_base
<222> LOCATION: (96633)
<223> OTHER INFORMATION: a, t, c, g, other or unknown
<220> FEATURE:
<221> NAME/KEY: modified_base
<222> LOCATION: (96668)
<223> OTHER INFORMATION: a, t, c, g, other or unknown
<220> FEATURE:
<221> NAME/KEY: modified_base
<222> LOCATION: (96715)..(96814)
<223> OTHER INFORMATION: a, t, c, g, other or unknown
<220> FEATURE:
<221> NAME/KEY: modified_base
<222> LOCATION: (104447)..(104546)
<223> OTHER INFORMATION: a, t, c, g, other or unknown
<220> FEATURE:
<221> NAME/KEY: modified_base
<222> LOCATION: (114521)
<223> OTHER INFORMATION: a, t, c, g, other or unknown
<220> FEATURE:
<221> NAME/KEY: modified_base
<222> LOCATION: (114527)..(114626)
<223> OTHER INFORMATION: a, t, c, g, other or unknown
<220> FEATURE:
<221> NAME/KEY: modified_base
<222> LOCATION: (127063)..(127162)
<223> OTHER INFORMATION: a, t, c, g, other or unknown
<220> FEATURE:
<221> NAME/KEY: modified_base
<222> LOCATION: (139133)..(139232)
<223> OTHER INFORMATION: a, t, c, g, other or unknown
<220> FEATURE:
<221> NAME/KEY: modified_base
<222> LOCATION: (151051)
<223> OTHER INFORMATION: a, t, c, g, other or unknown
<220> FEATURE:
<221> NAME/KEY: modified_base
<222> LOCATION: (153242)..(153341)
<223> OTHER INFORMATION: a, t, c, g, other or unknown
```

```
<220> FEATURE:
<221> NAME/KEY: modified_base
<222> LOCATION: (164706)
<223> OTHER INFORMATION: a, t, c, g, other or unknown
<220> FEATURE:
<221> NAME/KEY: modified_base
<222> LOCATION: (164708)
<223> OTHER INFORMATION: a, t, c, g, other or unknown
<220> FEATURE:
<221> NAME/KEY: modified_base
<222> LOCATION: (164710)..(164809)
<223> OTHER INFORMATION: a, t, c, g, other or unknown
<220> FEATURE:
<221> NAME/KEY: modified_base
<222> LOCATION: (182242)..(182341)
<223> OTHER INFORMATION: a, t, c, g, other or unknown
<220> FEATURE:
<221> NAME/KEY: modified_base
<222> LOCATION: (192158)
<223> OTHER INFORMATION: a, t, c, g, other or unknown
<220> FEATURE:
<221> NAME/KEY: modified_base
<222> LOCATION: (192192)
<223> OTHER INFORMATION: a, t, c, g, other or unknown
<220> FEATURE:
<221> NAME/KEY: modified_base
<222> LOCATION: (198842)..(198941)
<223> OTHER INFORMATION: a, t, c, g, other or unknown
<220> FEATURE:
<221> NAME/KEY: modified_base
<222> LOCATION: (199437)..(199438)
<223> OTHER INFORMATION: a, t, c, g, other or unknown
<220> FEATURE:
<221> NAME/KEY: modified_base
<222> LOCATION: (208276)
<223> OTHER INFORMATION: a, t, c, g, other or unknown
<220> FEATURE:
<221> NAME/KEY: modified_base
<222> LOCATION: (215974)
<223> OTHER INFORMATION: a, t, c, g, other or unknown
<220> FEATURE:
<221> NAME/KEY: modified_base
<222> LOCATION: (215976)..(215977)
<223> OTHER INFORMATION: a, t, c, g, other or unknown
<220> FEATURE:
<221> NAME/KEY: modified_base
<222> LOCATION: (215979)
<223> OTHER INFORMATION: a, t, c, g, other or unknown

<400> SEQUENCE: 16
ttgggggtat aaacccagaa gtgggattac tgcaccatac aataatcctc taacttcaag      60 caattttcc acaatggttg tatcatttta cattcccact ggctacgaga agggttccca     120
cttctacaca tcttcaccac catttctgtt tttgttttg agtaacagct gcctaatgac     180
tgtgaagtgg tatcttatct cagtgttgat ttgcatttct ctgatcatta atgtgggaag    240
gcatcgtttc atatgtttat tggctgtttg tgtatcatct tctttggcga tgttgattca    300
agttatttgc ttgttttttt aattggagtt ttaaaaaatt gttgttgagt tgtgggagtt    360
cttcattagc tctgcatatt aataccctga tgaaaatgat taacaagtat ttgcttccat    420
tttgggggct tccattctgg gctgttttta ttcttttgat actcttttga ttctcaacag    480
tttaatctga ctaaaattca gtttatttct tcttttaatg gccatgctat tgacacatcc    540
cgtaatcact gccaaatcca gtcatgaaga gtttctttca agagatttat agttttagct    600
ctttaagttt gtcatgtctg tttcacttaa ttttgtatag tgtacaaaag tctaacttca    660
ttcttttcta tatggcttgc tactagtata cgaagagcta aatttctctt tccttgagtc    720
tcaacctctg atgtgtagca atttcttcag aggaaaacat ggtgggaagt tccttaaaca    780
taggatgctc catggaggtg aaatagttca tcctacaggg aagcttgtta aacacaggaa    840
```

-continued

```
gtacatactc agcagctcta gtaagtgagt gaaactgact ggaggcacta ggtccctcct    900
tccctacgca tatagaagct gtaaggattg ggaagagata ctgtcaggtc agctcagctg    960
ctgcccggaa gaagctcaga cccactggcc tggctccaag nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn atcactcttt actcaggcca cctacacgct gtttatagcc   1140
tgcctttgtc tctttggcta tacttcctgt ttatgtctat gcctcccctc tttcttttc    1200 tttctcttct cttctcatct catctcatct ttcttcaggg gggagcctgg tctagaactc   1260
acaaagattt gactgtctct gtctccttgc actaattaaa aaatcttta caagcatctt    1320 ttagcaattc ttacagggaa attttggaat gttaaactct gattgttagc gggctgaaga   1380
taacaatagc tctgatgata aattgcttgc caggcaagtg tgaaaatctg agtttgatcc   1440
aaaaagccgg gtacagaggc caaagagtcc ataatcctag taggggcagg aatcagggat   1500
gggtgggtcc ctggggtttc ctggtttgtc agcgtagccc aattgggaat agccaggttt   1560
cagtgaacga tgctttctgc aagctgagag aggtccttgt tcaatctctg tgacccaact   1620
ggagggagaa gagagccagc tctccagaag tggtcctctc aactttgtgc atgcatgtcc   1680
atgttcacac agggaatgga taatgcttaa aaggaagacc ggcaggggt tggtaatgca    1740 cctcctttgg tgacatgctt tcctcttgtt catgctgctc caggtgtggt cggcagcacc   1800
aaaaaccagg tgtatgtttg taatcccagt attctctggt cgtcagtagg aaatgaaaag   1860
cgaggtcatc ttcgtataga gttagcaaac tctaagccag cctcggctac atgagacttt   1920
gtctcaaaac aaaggaaaaa tcaaggagga cggctcccga gcactgtcac ctgaagctga   1980
cctctggcct ccacatgcat gtgcgcaaac acatgtcctg cacaaacaca cagacacccg   2040
catctgctcc ccgacaaaag aacctgaaac cagtatactt tgagaatttc ccattcatag   2100
ttaccattgt gtgttccttg tgnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnggtggtgc ctttctctta cccagtctag aagggctgga ggcagggtgg atggggcact   2280
ttgaactccc acctaggcaa aaacccagt gatctctggg ccagtgtgtt gtttgcaagg    2340
gaataaggta gagagccgcg gaggaagaca ttgggggttc tatgagtatg tgaaggggtg   2400
cacacaccac acacacacat ttttttttgtt ttaaatttac aaacattaaa ataggctgta   2460
atgtggctca gtgggtagaa aaacctgctg tctaagcctg gtacgagttc aatccctgac   2520
aagctggaag gagacaacca accacaactg ctagcagcca gaagcactgc ttgctaacac   2580
tcaagagagc ctggagtgga agacactgga tccccagcag gcaagcctgc aagaagatgt   2640
gccttgccta gacaacggca gaacaaacat caaggctggc agagctgtcc aggactgttc   2700
atattaatca tgtatagata agagggaatg gcacagacag aacaattcaa cacacggggt   2760
atgaaaggaa aggaacaagg cacacaaagg acaaagaacc tagcatacaa gaaagcctaa   2820
gcagagagtg gcacttccca gaagggagtc ataaaataga ctgaattcat taaaacaaga   2880
gccaaagata aacggctcaa aaaactcacg gaaaacaggt caaaataacg tcacccatct   2940
gacagttgat actgtcaact taaccgtatc tagaactcca gcaggcacat ctccaggcat   3000
gcccctgaag gggtctttgg actaggttaa ctgacgtggg agtgacacca tctatggacc   3060
gaagcctcag acagaataaa aaggagccag tgagctgagc gtcagtgctc attgcttctg   3120
gcttcctgtc tgtggctgca gcgagacacg gtgcttcctg ctttagctgc catgacagac   3180 cacacccctca aaccgtgaac caaaataacc tcctctctac attgctttta ccaggcattt   3240
```

```
ggtcacacca atgagaaagg ttaactaata cagcactcaa tacttaaaaa cataaacacc    3300
aaccttgttt gcatgtgtga gactttgaag ctcacgggcc agttatgccc aatgccaggt    3360
ctgctggcta agggtgagag tgcacaccta taatcccagc tgctgtggaa tcagcaaaag    3420
cgctacagat ggaaggcagc cagggcagct gagactgact caaactgata gaggtgggag    3480
gcatagagaa aaccagatta atagagtgtt ccccactatg caagaagccc tgggtttcag    3540
gacgagagaa ctaagaatac agaagtctac tgtgtagaag cactgctagg tcacacagaa    3600
acatcactca agtgtctctg gatgctacac ggagggcgtg tgaagtattg cttcctgatg    3660
atctgtatct actacagcac tgctgtttta gtatgcgctc ctccactaca gctcctcacc    3720
acaccaannn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnaat taatcaaaga    3840 aaacacacac caccagttag agaaagttaa tcaggccgaa tggcggcttt ccctgtatc    3900 caggctaccg tcaggacggc tcactgccac tggcaactct gcctgaacaa agcccgcagc    3960
caacgtgggc ttcaggggct ctaaacactg caatcaaagg ttgtgtgtgg gggtgggggt    4020
gctgctgcta ttcaaggatt cccaaagctt agatgtattc atcatactca caggaaagcg    4080
tgttcaaccc atcactcatg agcagtcggt accggggtga cctattccct gtagaaatgg    4140
gacggatgtt ctggaaaagt tgacagaaaa gttgattcat taggcaggct ctttgcccaa    4200
gccctgaggg taagcaaagc taactggcag gagactaggt ttgccattaa tctgagacaa    4260
gatgaaccac ttgcccatcc tcctgacacc taaatactaa tgaaagaaca atggattgag    4320
ctggcattat taaaaacgat agaaacagaa gtatcaatag tcatgtgttc tttctcccat    4380
atgtcaaaac aatgtgtaag atggcatcga acacatgcag aaactgttta gggaacatgc    4440
tgaaaatatg aagtaaaatt aaaattggaa agaaagacaa tttgcctaaa gcagctcaga    4500
gctggagaag ggaccgaggc agagataaca gcaacgtgtg gacatacgga tctggggcag    4560
agcagtcacg gactcagccg gaaagggtgg ggcagcctct gaaggaagtt aaggtaaata    4620
gagccacaag gtgattggcc caggagtggt gccaccttca cctcctgcct caaagtctga    4680
aggaatgatc ctggagtctc ccatctattg atatatgaaa ttcacagtat gttttagaac    4740
ccactgaatg atgggtagat taactaaaag aaatttaagc ggggtggtgc aggtcttttta    4800 atcccagcac ttgggaggca gaggcaggtg gatctctgtg agttcgaggc cagcctggtt    4860
ccaggacagc cagagataca tagagaaacc ctgactcgaa aaacaaaat taaaagctca    4920 tcaaaacaac aacaacaaca aaaaaaacaa aaaaacaaaa caaaacaaca aaacaccta    4980 tagtacctgt tggtgagttt gagtgagtga gtgagtgtgt gttagagaga ggggcgggga    5040
aagtgtgttc tggaaatggg agaaagagaa tgtgcatgtg tgtttctggg atgtagacaa    5100
aactacatgt cttccatcaa atgcaatgtt taattatcta tgagttgaac catcttcatt    5160
ctgctaannn nnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnaac aaaaataaac    5280 caaaccagta acaaaatcc tgtaagataa agcctaagac aagacacttc ctggggctgg    5340
ggagttgctt agaccataag gagttcataa tccaggcgtg agagcccgag ttcaggtccc    5400
tgggcttcca agtcaggagg agaccaagga atcaacaagt ctcgactttg gtctctagtc    5460
ccatgcacac acacgcgtgt aaatacgtag atgttcactc acacacagaa gactgcacct    5520
ggctctctca catctcagcc aacatataaa gcctgcatta tcagaacatt ctaggttcta    5580
```

```
gtttcagtca actcttacac agaatggcca tcatactccg tctacaactt ctcctgatct    5640
acccacgtgt cattgcttca gtattaacaa acccagaat aaccagctgc gtagatcctc     5700
cctgatgccc cagtcattgt cttactgaga ctactaagtc acaaggtagc actctggatc    5760
caaaaagcaa tatccaattg agagttacaa cctataagga ggagtttacc ttcattatag    5820
ggcactggat tcccaatctt taatccaacg tcttcagcag atttcataac ttccaagtcc    5880
atcaaaacaa ctactttcct acaaagacag acacaagtta gaattaagaa ctctgcagcc    5940
tttcagatga gttactaaga agcttacttt agtagttgtc tggctaaaac tgtatccttt    6000
accaaccttt tctcattctg gactaacttg agaagtatta attcctaagt aaatacttca    6060
cttattcttt ccccacatct ccaatgtttt tgtctttaat ttattatagg gcaattcatt    6120
tcctatctag ttccctgatt aaaacagtag accttgctgc atgccattat cctcatggag    6180
gcactgatac aatttagatt attaaataca aaaccctaaa acacaaaaag atgattttt    6240
tttaaaacaa gattttaaaa aaagcatgtg ctacgcttcc ttctgccact aagcctacac    6300
atggtcctct gactgaattt ttcccctcat tctgcttcat ctaatatgtg cttttcaaac    6360
ctggaattga accagggact tattcatgct aggcaaatgc tctaccatag agctataccc    6420
ctccaactcc catctcaaat atcatttcca aagacatttt cttggtctct tatttagatc    6480
aggtttcttt gtcctcctgc agctatgact tcattccttc agaacactcg tcttagcttt    6540
aagttctgta ttaattagtg attgttttca ttctctctgc tagaatgcac tttcaataaa    6600
ggcaggtagc cagccacagt gcttaattaa gcaacagccc aacgatgtca ttcactacat    6660
actgggacaa gatgcctaac atcatctgca gataaagacg aactactggt gtcaggagac    6720
agctaagggg tccagggctt gggcacgctg agtgtgagca ctggagtccg ggtgcccaga    6780
aacgcacata aatgcaatat ggatgtggca atctacctct aattccttct ttaagacagt    6840
ggctctccag agcaagctgg ctagcaagac aagccatatc agtgagctct gggcttgacc    6900
aagaccctgc ctccaggtgt aactcccaag caaaaggatg atggctcaca aatctcaggc    6960
tatcatgttc atgtacaaaa tgtcaaccgg catacacaca tgcacacaca tgaaaactgg    7020
gagaaaataa gaagaattgc aaccaaaaaa tgtaatttga ggacacataa ttgcaggcgg    7080
ggagtggggg gatgacagaa ggtgaactga gtggaccgag ggaaagctgt gctagcggca    7140
atgagaagaa gggtggggca gtctgagcaa gggttcagca atcaccacgc tttactgtct    7200
gcacagcctg gctgtagaat gctgggcttt atcacacaga attattcagt atgtgctatc    7260
tttacagtaa agttattcta tcaggctatg ctacttcaat agaacaagcc tgaaaaagtg    7320
gtctgctgct gagaacctga caaagatgac ctgttagaac tgtctgccaa gtgtggaatt    7380
ccagcactgg ggaccaggag ctcgagggtc accccagatg cagggagtta gaggccagtc    7440
ttggcaacat aacatcatgc ttcagaaatt aaaaacaaaa nnnnnnnnnn nnnnnnnnnn    7500
nnnnnnnnnn nnnnnnnnnn nnnnnnnnnn nnnnnnnnnn nnnnnnnnnn nnnnnnnnnn    7560
nnnnnnnnnn nnnnnnnnnn catgagatag ttaataaact gaagaaagcc atacaaggag    7620
taaagtagat agttgcaagc atgaagaaag acaaaccact tgagcttttc ttttgtcgta    7680
aggaggaaac cagacaggtc cagagagatg gctcagagat taagagcact gactgctctt    7740
ccgaaggtcc tgagttcaaa tcccagtaac cacatggtgg ctcacaacca tctgtacagc    7800
tacggtgtac tcatatacat taaataaata aataaataaa taaataaata aatcttaaaa    7860
gaaaaaaaaa aaaacctaa ccaatcagcc aggcgatggt gacacatgtc tttaatccca    7920
gcacttggga ggcagagaca ggtggatttc tgagttcgag gccagcctgt tcttcagagt    7980
```

```
gagttccagg acagccaggg tgatacagag aaaccctgtc tcaaaaaaca aacaaacaaa    8040
caaacaaaca aacaaaaaag gaggaagcca gacaggatgc actttatacg tgaatggaat    8100
tgacaaaaga caagttctat aagtgttagg gaaaggggga ggacaacggg ggttcatgtc    8160
tgtggtggaa cacgtattag aaggctctgg gtatcctgtt tccgacaaac aggcactccc    8220
aatcacacag gccactggat gtctcaggca gagaaagatg tgatagattg acttttttaac    8280
aatcacagac tgtgtggaaa atatttgtaa ggttgtcatt gtcacccagg atagagctga    8340
tggttattca aacgaggatg ggacaacaga aatgggagag agggatgtga gaaccatttt    8400
gaaccagggt gatttactgc gcacgtgtat agggtctaca gggagtggga tatgtagagg    8460
aggcctatgt tcctaacttt ggtaatgagc ttattacagt tactatgcac agcctggaag    8520
atactggaaa aggtgcaggc taggctagaa aggtactaac tgagggtttg acagcccctt    8580
ggatgtcagg atgcagcaag cctacctctg tatgtagtca atcccttctc aggctatggg    8640
tcctgcagat catccgtctc tgtatccatt attcccagtc catcctctga gtggctccct    8700
cttatccagt ttaacaaaat gctgactgca agctcccaag cccagggctc tggctccttt    8760
actccttgtt attgtacttt accctgtttg cttgggatag agtgtgccct ttataaacat    8820
ttgtgaaagg gggaatgaag aagaataann nnnnnnnnnn nnnnnnnnnn nnnnnnnnnn    8880
nnnnnnnnnn nnnnnnnnnn nnnnnnnnnn nnnnnnnnnn nnnnnnnnnn nnnnnnnnnn    8940
nnnnnnnnag agagctcaat ggttaggagc actggatgct cttccaaagg tctccagttc    9000
aattcccagc atcaccatgg cagctcacaa ctgtctgcaa ttccagttcc aggggattca    9060
acactcagaa acataagtgt aggcaatcta cgtaacataa aaataaataa atgagctgga    9120
aaagaaaaca tgtttcaaaa tatacaagta atggggctgg aggagatgtc tcaatgggta    9180
agatcattgg ctgctctttt ggaggttctg ggttcaattc ccaccaccca catgacagct    9240
cacaactgtc tgtaactttg gtcctgtggg agctgatgcc ctcttctggt gtgcagacat    9300
acatgtagac aaaacacctg catacataaa ataagttttt aaaaaagtta cacatacacc    9360
cgtgtgtaat ataacacaca ctggcttaac ttcctcagca ctgactgttc accatacgga    9420
ttcccatgag gttttggttg cattctatca ccgaaaaaaa aaaaaaaaaa ttagaagaaa    9480
gtatatacat ataaacctct ccctaaaata aagttttctt ttctaaaagt acatccttat    9540
tttttattt ttttttttt ttaagaaatg ggaacaacag ttctgctcac actgtatttc    9600
tagcatgtaa catcttgcaa gtacttaacc gtattctata tcagctcaac acacttacta    9660
ccgaagactc aagatcacaa aaaaaaaaaa aggacccaga ctggataatt aaacgtttct    9720
tttgttgtag taagcgacct cttccttaga agatactaca gtaatgctga agaaatgaca    9780
catctactgt aatctgttct ctgggattcc aacttgtttc ctctgctact cctcccttgg    9840
cggcaatgtt cgtctgcatc cggctgagct cctcgctgcc ttgttaaacc tccttcctga    9900
acttccgacc tgtagttccc gctctacagt gcaagcgagt ggataaggaa gcgcatacct    9960
gccgtctttc agggtgttga cgatgaactt gtggacctgg cagacacagt tgctggccag   10020
ctgccctccc tcgaccaggg tgttcagctg cgtggccagc atgaacgctg caaaagcaga   10080
gagagagggg ctcagtctcc aagcctttcc ttaacccgaa agctcatcac aaggagaacc   10140
attaaataca gctgtttaaa actcctccgc cctgcagaga ggaaagcagc atcaatccgc   10200
cccatgtaaa agtctgaggc tcttcctaaa tggtatctgt ttctcacagt ctccaaatca   10260
tttttactgt aattctagtt tctggggaaa gacctttctc ggtctttagc cccgtgacta   10320
```

```
gagacaacag gcaaatattc cagaaaggcc cccattttct ttttaaagct tctannnnnn    10380
nnnnnnnnnn nnnnnnnnnn nnnnnnnnnn nnnnnnnnnn nnnnnnnnnn nnnnnnnnnn    10440
nnnnnnnnnn nnnnnnnnnn nnnnnnnnnn nnnngcacat cttgtgaagt gtccacatct    10500
ttcggtccct cgaatttggg tttcttctgg gacgtggtag catgtgactg tcactccagt    10560
gcttggagca gcagaggggt caggaactcc aggctggcat tagctgcaga gctggagcag    10620
gtcctggaga acagaaactt tggttgcagc attaatgaac tagaagaatt tttttgtctt    10680
ctgttaaata taaataccct cattatcttc tcataaacag tgttgccttt ttatttaagt    10740
ttttaaggat caggcacaga gactccatgc cagactacca ctcaaccact gagctacacc    10800
cccaacttgc ctttctgcta ttttttaaat tgtatcagtg gccaccaaac atggggagag    10860
gtcagggggc tacgtggagg aattgtttct ctcctaccaa gtgggcccca ggtttcaaat    10920
tcaggtgacc tggcttggca gcaagcacct ttacccctaa gccatctcat tggcttcatc    10980
ttttaatggc cccttcccct gctctgaggc aggctctccc tatatagccc tggctggcct    11040
caggctcgca ggtccaccag tgagcaccag gtttctgctt gtccttacct ccccagcact    11100
gtggttataa gcatgtgcca ctgtgtcaaa ctcagtcact aagctttgcc aagccatagc    11160
ccagcccttg agtttactgt ttgtctgtgt ggtgatttgt caaaccactt ttgttccact    11220 gaggtattt gtcaagtttg acaaaattag ttgagtatgt aggtctttt ttctggaatc    11280 ttctgttata gcttagtctg gtcttgaact catgatcttg cctcaacctc acgattattg    11340
aggattattg agatggacag gctgtgtgac catgctcggc tgtgtgtttt agcatgcatt    11400
agtcatttga aaaacgttgg ctcatgacac tttacaggtc ttccatgttt gatatgtttt    11460
atttaatcca aagtaattcc agcaccagag gctgagacag gaggatctca aggtcaacct    11520
agagatgcat agcaggcggg gccccactcg gttaggttaa tatcatcact gacttcagga    11580
gaaaagtctt aagtattggg gactaaaagc aggaggatct gaagttcaag gtcatctta    11640 ggaacttagc agacttgagg ccagcttggg cgctgtggga ccctgtttt aaaccagaaa    11700 acaaattgaa aggaaaaaaa aaaaaagctg gaggaagtga atgtgagtgt tcacatagtc    11760
ctgtttccac aagaaaacag ggttactttt ggcaacaaat aggtgctttc tttgaaggct    11820
ggcatttttg tgacttgtca ttggagaaat gatttaatta agacttttct actgagtgcc    11880
tctgaagagg ctcttttaaa tttagtttaa ttttatctca ttgttagtgt ggtgtgcttg    11940
tgcacacaga aggcagcttt ctagagtctt ttcactctct cctccacagc tcctggagtc    12000
aaactcaggc cctggctagg caagctctta ggacagtgtt agctgtagct tattaagttt    12060
ttaagaattt ttataagact ctgttttct ttctcaggtc atgatacagc aggaaaatac    12120
atccataaag cccatcctgc aggtcattgt aagtaccggc atgtgtgttt agcataatga    12180
agatggttca cttatagtta attaaacatt ggattggatg aagacatgt agttttggtt    12240 acttcccaga aacacaaatg cacattcttn nnnnnnnnn nnnnnnnnnn nnnnnnnnnn    12300
nnnnnnnnnn nnnnnnnnnn nnnnnnnnnn nnnnnnnnnn nnnnnnnnnn nnnnnnnnnn    12360
nnnnnnnnng aattcagagc tgatatgtag tactaactcc tactcaatga atccttttgtt    12420 cttctattcc ttcattacat tactgttaat agtggtaact atgtaccaaa gagtcaaata    12480
actcttggac catccaaggc agaaggaagg ctggcaaaaa tgtatgatga tctgggatgg    12540
gaatgtactt cagtttgtac aggaggccct tggttcattc catttctggc aatgcataga    12600
cctgtaggat ctcagcactg gtgggggtg ggggtgagg gtgaagggc gggaggttaa    12660 aggcagaata gtcataaatt caaagtctgg gtcctggaaa gaggactaaa cgattaagag    12720
```

```
ctttagctgt tcttctagag aacctggtgt gatccccagc acatggtgcc tcacgactgt    12780
ccgaaactct gattctaggg ggatctgaaa accctcttct gccctctgta gatacagaac    12840
acacatggtg cacatacata catgcaaccc aaacaaccca tatacataaa atattttttt    12900
ttcaaaaaga cattcaaatt cttcctcggc tatatagtgt ttaccaaacc tcaaaaacaa    12960
aacaaaacaa aacaaaacaa agaatcatta atgttttgcc ttcatgtatg tctgcccacc    13020
acggacatgc ctggtaccca gggagattaa agaagacat tagctcccct ggaatggaga     13080
taggtatgat ctaccacttg ggtgctggga acctgggtcc cctgcaaaag cagtaaatct    13140
ttttaacccc taagctgtct ctcccaacgc ctaaagattc ttgtaacaca gcatgatgag    13200
cactggcaag catagcatgg taatctgact tcagggcgcc agattttgag cttaatgctt    13260
gattattaga agtaacgtac tagatttaat gcctggagct tcaagcaaca aaattaactg    13320
aagaataaaa ataaaaaccc tgccagccat gatggtaatc ccagaacttg agaggcagag    13380
gcaggtgatc tctgtgtttt gcaaggccag ccacaatcta catagcacgt tgcagtannn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnncga ataaatctac acatgtaaaa    13560
agaaattcaa agaaacaaat gccaaataaa tacacatatt gtaataaaga gataattgtc    13620
taaaaaactc aaggctttaa atggtaagat atcatattct tggatgaaaa gatctaatgt    13680
caaaatatat caatttaatg caattatgta tattcaggag atctctggtt ggcttttgaa    13740
cttgatagca ctcttataat tcacatagaa gaaaaaaaac catgaaaact gccaaacatt    13800
attagaatac tccacagatg gtattttggc agcacataca tcgaagggct gtgaaagatg    13860
tgtagatcat ccacgccttg ctagggagag ggcgggtgtg tgtgggggt atagctgttt     13920 gggaaaataa cctggtaatt cctcattagt taaatcatag tcagaacctg gactagcaac    13980
ttctctctaa aatacattca ccctcagcat ctgcattgcc aggaaaccac tcctagcagg    14040
atctgtacgt ggatcaaggt agtagcatct gcatttaatt gacattctcc taaatgcttt    14100
aaattatctc tagattactt atagtagcca agatgatgca aattatgtta cactgtatta    14160 tctgggcgt aacaagaaaa tgtctctact caggttcatt caggtgcagt acttcccctg     14220
aatacttctg aatacacgga tcaagaagcc acagaaagag ggctaaccat atacaagcat    14280
atagtacact aataaccatg tacaaccata tagtacacta atattcagtg cattactcaa    14340
aatgcaaaca gatggaaaca atccaacagc ctgtaagctg aaaaacaaga taagcaaaat    14400
gtgctgggcc tagaggccca ggtctataat tccaactaag gtcgaggcag gaggatctca    14460
agttcaaggc cagcctagac aacttagcaa gaccttgtct caaaacaaaa agtaaagagg    14520
ctgaggatat agctcagtat agagcatctg cttagcatgt gcactgacag ccgtatcaca    14580
gaggaaaaaa aaaataagc aaaatgtgat ctgtctgcac aacaggatat cacagccccc     14640
taccacaggg gaacgacaca gtaacacaac aaaaacttag ccctgaaaat actatggtaa    14700
ataaagaagt gtcactgagg atcaggaaat gcatgactcc atttacatta tatagaaatg    14760
agaagatcag tgagcctcta ggactcaaga gatttgggat tggcagctaa agggtactgg    14820
gtttctttat gggggtaaga aaacattcta aacttaactg tgagaatgac tactcaacaa    14880
tgtcaagtgt tcaaaaatca tacttttttt tttttttggt ttttcaagac agggtttctc    14940
tgtgcagtcc tggaactcac tctgtagacc aggctggcct cgaattcaga gattcacctg    15000
cctctgcctc ccaagtgctg ggattacagg catgcgccac cattgtccgg ctcaaaatca    15060
```

```
tacttttaaa aattgcccag tgactcatga atacaatcag aggcgggaga ggacagtggc    15120
aaactcagga taccagtgtc ttttatgtct gctgcccaac tatcaatttc ccatagttac    15180
cagagaactt tttggtttgt ttcatcttat ttgttgcttt tggtagaatc tcaatatagt    15240
aagatacaag gctggcctca tactatatag ctgaggacga ctttgaactt ctaatcctcc    15300
tgcttccatc tcccaagtgg tgggattaca ggggtgtacc gctatgccca gcaagcacaa    15360
agccatttga accacacccc agccttttca gagaaacctg tacaagcctt agtgccttag    15420
catattaagg caacaaaaga cataatgcgt ggctaccata gagtgtttgc ctaccatgtg    15480
tgaggctcta ggctaaatgt ccagcactta taaaaaagag ttaaaaacac tcatgactca    15540
aggatgacta tgcagtcttg tgtacaaagc cccgcattca atccccagca ccgtgcacat    15600
caggcaggct ctgtagagga cccagcttaa ggtcatcctt aggtaagtta gaggccttag    15660
atggctacat tagatgagac cctttctcat aaacagaata ataatttaa agctcctgat     15720 caaacactat gccttcccat cacactcaga ataaagcact ctactggccc tttaaggact    15780
gcccatctgg aagagaaacc taagttacat tccttgcttg tgtcatatgt gataacaaac    15840
tcactggaaa tacgaaaata cagtcttaag cttggtcaga aagcttcccc agcaacatga    15900
tntcagagga cataatgcag aaagtggaca aatgcaaann nnnnnnnnnn nnnnnnnnnn    15960
nnnnnnnnnn nnnnnnnnnn nnnnnnnnnn nnnnnnnnnn nnnnnnnnnn nnnnnnnnnn    16020
nnnnnnnnnn nnnnnnnnaa tcagaggaca tctttcagga gttagttctt cctccctct     16080 atagctttca gggatcaaac tcaagtgtgt actgagcgct tatgcccagt gcgccatcgc    16140
accaggcctg cttctttgtt ttttatgggt ctgaatcaat tagcaccatt acaacaatgt    16200
tgacaatcag caagtacctt tctctacctg gctagtaaga gaagtaagtg cctttggtgt    16260
gtgaacgcag tttctcttgt gaagtgcatg gacttgatct ttgctcacaa cgttttttag    16320
gtccttaagt tgcttgggtt ttatgggaaa ggctcttggg tttttttgaaa agatttttact  16380 acaacttgat ataatcatta ttttttaatcc tttaaatagt atgacttatt ttaacagatt   16440
aatattgaac tgttctttca ttcttacata ataaatcctg ccttaaaaaa taatcctctt    16500
agcttccttt ctctattttc aaatttgttt tatattttg catgattttg aacatttata     16560
aaagtaggca gacaacacag tagaaccaag tccccatata gctgtgcaca tagcttcaga    16620
ttattgcctg ataataggtc ctgttttgtc tctgttttct cacagggatg tgttattgtg    16680
tgtgtgtaca catacataca tatatgtatg tatgtatgta tgtatgtatg taatgaactc    16740
cctttaacaa aacaagtact gggctgggaa gacagcacag ttagttatgt gtttaaccgc    16800
acaagcatga caaccagagt tgagatcccc accaaccgca taaaaagctg gcatagtgg     16860 cattgacctg tagccctggt gctggatgaa agctggggag gcaggtagat cggcagagct    16920
tactggcaac aaatctgccc agtaggtaag ctctgggctc agacatccta tataggaaaa    16980
agatgaaggg cgaggcgcag cggcacacac ctttcgtggt agtgcttgag aggcaggggc    17040
aggccagtct ctgtgaccag cagcctggcc tacatgtcaa gttgcaggac agccagagcc    17100
accacctact gagactgtct cagaaataag tttttttaaaa aattgagatg aaggagctgg    17160
taagatggct tagaaggtaa aggcacttat cactaagcct gaagccccga gtttgaccct    17220
ggaccccaca ctgtagaacc aactcctcca agttcttctc agacctccag cagagcacaa    17280
gtgtatgcag acacacacac taagtaagtg aatgtaaaaa acatgacgta gtggcactgg    17340
cctttaaacc cagcattggg aggaagaagc gggtggatcc cttgagtttg agaccagctt    17400
agcctacata aggaatttca aggcagccag ggctacctag aaagtagctg tttatgaatg    17460
```

```
aatgaataga aggaaggaag aaagagagac agacttaaaa aatatatgct ggagagtaac   17520
agaagaggac accggcttgc tggtgtcttg acctctggct tgtacacata cacatgtgta   17580
gtgcatacac ccacatacaa ttgtactcag acacacacaa acatgtactc attcatatac   17640
tgcacacctc aacactcaga aaatgaaaaa acaggtacca tttacacctc cgtgttcggt   17700
ttccaaccac tcatatgtat gggttgtaaa tgcttatatc tgtatgtgtc tgtatatttg   17760
tgtatacatt caaagttgag tcaggatcca acgtaaactt ggatagtagt gggttgatgg   17820
tctggaagcc tgctcgcagc tgtctttttc tcctcgtacc ttttcccctg tttgtttcta   17880
cgacagcagg tcatttgtct ctaagtgtta gtttcccatc ctctctcttt tgctgatggt   17940
agccttgtag tagtcacctg tgttctctgt aaaatggctt tgccgtgtta tttcaatatg   18000
ctatcatcct catcttgcta tatttcattc aatatatgta tatattacaa gatagattaa   18060
aattatttta attttatgct tatgaatgtt ttgcctaagt atattgcacc ttgtgtgtct   18120
agtgtccaca gaactcagaa gaaagtgtca catattctgg aactggaatt gcaggtggtt   18180
gtaagccacc atgtgggacc tggaaaccaa atccaggcgc cannnnnnnn nnnnnnnnnn   18240
nnnnnnnnnn nnnnnnnnnn nnnnnnnnnn nnnnnnnnnn nnnnnnnnnn nnnnnnnnnn   18300
nnnnnnnnnn nnnnnnnnnn nncctttggt caaagatcct cagtttcgac tttgattacc   18360
cagacttcct gtttctctca tggaacagtt tcccctgag atttactagt ggaagaaagg    18420
cactcaaaaa gcagggagcc ctcgtacaaa tgagacttcc tagctatata attaggccga   18480
gatgcacaca tccacagtca ttacccttct tcagagcctt tgtcatgtca agtgtatttc   18540
gcccatgtga actttagaac tggcttgttg tgtttcataa aaagtgtagt tgggctcttg   18600
attgggattg tgttaaattt atagattcat ttagggagag ctgacaactt tacagtatta   18660
aatgttttca tccgcggaaa aggttgtctt gccacttact tgggctttct tttatgccct   18720
taagtaaagg tttatagttt tctttatatc agtcttgcac atttcctgtt agatttattt   18780
ttgcttgtaa ggtttccttg gttggtattg tgtataaaca ttttctccca attcatacc   18840 ataattgatg gttaggagta taaataaaag gtagaatttt aaaattgctg tatgaatgac   18900
tgctttgcta taattcaaca tcttttcatt tttatgccaa tctacttgac atgtttaggt   18960
taaatgatga tatctgtaca gagtaatcct ctgatccagt atttgcacat cttactttct   19020
aacgtccata gcatagatac acatcttata ctgttgagta catatatatt taaggtattt   19080
accatagtct tataatatgc agcgtgcttt ggttcaagac agttgccctg tgttcctcaa   19140
cattaacatt tttttcatca caaatacaca ttgaccttta tcaaattttt aaaactatct   19200
tgagagaaat gaccattttt cttaatctgt taatgtaaaa ttttttataaa aatagttata  19260 aataatatta gcctacatat ttcttctgtt ctcttttca actcttagaa tcagagtatg    19320
gtagtctcag actaaaccag gagcttccta tctgtttctc tgttcttaag tcacttatat   19380
aatgtaagga tgctgtgtat atctgccagc taggccttat atacaaaagg cacccatcac   19440
aaccttctaa aacagtctta ccacttagag accatgttca acatatggg cctttgaggt    19500 aattgccaca ttcaagctat aatattgtta tctaagggaa tatcttcact tctagcagat   19560
gcctaaaaat atctaaaggt aaacactggt aattgctgtg tttgttgatg ctgctcttcc   19620
tcctcctcct cctcctcttc ctcctcttct tcctcctcct cttcttcctc ctcctgcttc   19680
tccttttctt catcctcctt tcttttctta tttttgaggc atgatttcac catgtagccc   19740
taggtaaccc gtaacttact atgtatgtag accaggctag cctctgtctc ctgagtgctc   19800
```

```
atattaaagg tgtgtatcac catatccagc aacacttgct ttgagatggt tagaggaaaa   19860
aaaaatatac gtaaataaag atggatgcca attactaaat tgttacttcc agtcaaactt   19920
tgtacctagt ctaaggccaa ataggggatt tttttctac tttgcaagtt ggctccatta   19980
agaggctttt cttctcttgg tctcactaga taggaaggag agagaggagg gaaggagaga   20040
aagcggttga ggagtgggag gtagtgtgac cgagaatacc cagtaggctc atatatttaa   20100
atatttggtc cctagttgat agaactgttt agaaagatta ggaagcatgt cttaggggct   20160
ttgaggtttc aaaatttaat gctagaccca gtctttcaag ggaggggggcg gtctgtctct   20220
ctctgcctgc tgcatgcaga gctctcagct actactctag tgtcaagcct gtgtgcttcc   20280
tgcctcaatg atcataaatt aactgtaagc aagcctccaa ttaaatgctt tcttttatag   20340
ttaccgtgat catggtgtct cttcacagaa atagtaacct gtggtgattt taatatgcct   20400
ggaccaggga gtggcacttt taggaggaat ggccttgtta agaggaagtg tgtctctgtg   20460
ggggtgggca atgagaccct cgtcctaacc atgtgagaac cactcttctc ctattggcct   20520
tcagatgaag atgtagaact ctcagatcca cctgcaccat gtctgcctgg aagctgcctt   20580
tgttcccacc ttgctgcccc aattaaatgt tgtacttata agaattgttt ttgggggggct   20640
ggagagatgg ctcagcagtt aagagtactg actgctcttc cagaggtcct gagttcaatt   20700
cccagcaacc acatggtggc tcacaaccat ctgtaatggg atctgatgcc accttctggt   20760
gtgtcagaag acaggacagt atcccacat acattaaata aataataaa taataaaata   20820
aattcttttt aaaaagaat tgctttggtc atggtgtctg ttcacagcag taaaacccta   20880
acataaccct gactaagaca acaagtgagg aaaggtgttg tgtgacactc tggatctctg   20940
gaagctcacc tcagcatgaa gcttgtcgaa gcgnnnnnnn nnnnnnnnnn nnnnnnnnnn   21000
nnnnnnnnnn nnnnnnnnnn nnnnnnnnnn nnnnnnnnnn nnnnnnnnnn nnnnnnnnnn   21060
nnnnnnnnnn nnnatctaag tacactgtac tgtcttcaga cacaccagaa gagggtgtca   21120
gatctcatga cagaggttgt gaactcagac ctttggaaga gcaatcagtg ctcttaactg   21180
ctgagcatct ctccagccca aaataattct tactagtaac atggaacaat caagttttat   21240
tatatgatac atattaatca acttataagt acatgattat gcacatttat catatcgtgc   21300
aaccatcact gctgtcgttt tgttttgttt tgttcttttg aggcccggtt tctgtgttgt   21360
tctggaactc actctgtaga ccaggctggt cttgaactca atgatctgcc tgcctctgcc   21420
tcccaagtgc tgaaaacaaa tgtgtgcacc accacctctg gctatcactg ctgtctttt   21480
ttttttttta acagttattt atttcgtgca tgcatgtgtg tataagcatg taacgtatgc   21540
catggtatgc atgtggaggt cagaggacaa ctttcaggag ttagttcttt cctcccactg   21600
tgggttctag gaaccaagct caggttgtta gacttgcatg gcaagtgcct ttaccacaga   21660
gccatcctgc tggccctact ataggtcctt atataaaaag atcatatgcc gggcaaaaac   21720
caaacaaaaa ataaacctca aaaacaaaa ggaccatata atattgtggg ggagtggatg   21780
aagtcctgaa cgaatgtgtt ctgttgacat gtctgtactt cagacccatg ggaattggca   21840
aagccttcct ctggtcctgt gaggatgctg atagtctgtc taaaactag agatcacagc   21900
tttctcctct ggatgactgt aaccccagat tgttcctctt cagagactgt ccaccaagct   21960
accctgccta cttaagctgt acacaatgaa tgagctgagt tccaggtta cagcacagta   22020
gacactgtcc atcagtgaga gcacagccta gcctaacagt acacatgtct gctttcttca   22080
cgtttccaga accaagcctt gctggataga gcatatttgt ctgtttggct tatttcactt   22140
gataaaaagt tttcaaggag ggccaggtgt ggtggcacac gcctttagtc ccagcactcg   22200
```

```
ggaggcagag gcaggcaaat ttctgagttc gatgccagcc tggtctacaa agtgagttcc    22260
aggacagcca gggctataca gagaaaccct gtctcaaaaa accaaaaaaa accaaaacaa    22320
aacaaacaaa caaacaaaca aaaagccaaa aatccaaccc cccccaaaaa aaaaaccaaa    22380
ccaaaaacca aaaaacaaca acaacaaaaa gttttttgagg tttaatttat tgcatgtcac    22440
agaatttcac tgtttaaaaa aatggctgaa taatatttca ctatccattc acgtatttgt    22500
aggcattcat gtgtgtagtg gtttaaataa aaatagcccc cataggcttc tacagttgaa    22560
tgcttagtca ttgagtagca gtactagaga gggaattgaa ggtgtggcct tattggagta    22620
ggagtggcct tgttgcagga attgtgtcac tttgaggtcc cagcaacaag gttgctctga    22680
tcacatccaa agacattcta ggtctatgtg atctggctgg aattcagaca tgcccttaat    22740
acacacctt taatcccaaac aatgaaggta aagttagttt ataaaagaa gcacccatgt    22800
ttgaaagtga cgtttaatta agagtgatga attagagaaa gatctgctgt cacagagcag    22860
agaggaaaga gaggcagcat aagagggagc atggcagagg gagagggagg aggggttttc    22920
accagggcat ttgtacagag acaggttgca gagctagaac aggtgaagac agaacaagcc    22980
agagaatgag aaggagccag gagattagga cagattgcca atgttaatag gctaagcaga    23040
gcattttagt cagaaactga gagaagtcaa attgaatcag ttagcttgga aaggagtttg    23100
agcagcaaca gctgagttaa actagccaac agaatccaga aagaactaga aaagatgagc    23160
ttactcagca gcaaatctca gaggctaaaa acatcttaga cctagattag actgcatgga    23220
ggctagacgc ttccagggct aggcctaggt tagcagacgg agagagtaat aagccttgga    23280
gacaacagtt aatacagaag actatgtaca gacatggata tgaacctctc agccacttct    23340
ccagcgtcat gcctgtctgc attgttagga gtcatctagg aaaggctaag ggcaggcaag    23400
caacttttcc agagatggtc cactgttttt tgcatggctt ttgagaggcg agctctgaga    23460
gggaaggttc caagagactt catcccagga ttgctgctta attacgacat gccttttctt    23520
gtcactgtta tttagtataa tgactcctga gctttagccc atcctattgg gcatatttcc    23580
tgcagatcaa cataaagatg aactttcaca aattaatgct gtttagatga ataaatgatt    23640
ttataaaatt cctgatttga tttaaataat tttaggaaga aagctttagg agatagttta    23700
gttggttttgc cagaaagatg taataacgtc agaatcaaga atagaatgtg gctgggcagt    23760
ggtggcagat gcctttaatc ctagcacttc ggaggcagag ataggcggat ttctgagttc    23820
gaggacagcc tggtctacag agtgagttcc aggacagcca gggctacaca gagaaaccct    23880
gtcttgaaaa acaaaacaaa aagaaaagta agtaaaggct gcataataaa gaatacaatg    23940
agctttcaca actacaccaa aaagagacat gcttgggaca aatttgtgat caaggaaaaa    24000
tattcattct agatcaggtc caaggatgaa gccacaagtg tgtgatatga tgaacaagac    24060
catggataaa ctgttgtttt gagcttaaag aataaaacac tgctttgaaa ttaactatca    24120
acattctact gtaactttcc ttttttataaa ttttatctat gagataattt tctaaagaac    24180
ttgtgtctat aaaggtatag aaggacagag agaaagaaat aaggtgtggc atctgggctc    24240
tgctccatcc acccaaataa atatgtgtgt gtgtgtatgt atgtatgtat gtttatctat    24300
atgtatgtat atacatacat gtgtaggtag gtatatgtgt atgtatataa gtatgcatga    24360
acacttggga agttgatgag acaagtgaga ggttgggccc ccnnnnnnnn nnnnnnnnnn    24420
nnnnnnnnnn nnnnnnnnnn nnnnnnnnnn nnnnnnnnnn nnnnnnnnnn nnnnnnnnnn    24480
nnnnnnnnnn nnnnnnnnnn nngaattcac tctgtaaacc atgctggcct tgaactcaga    24540
```

```
gaaccgtgtg cctctgcctc taaagtgctg ggattaaagc atgtaccacc acaacccagc    24600
tagtttaaat gtttcttatt ttttttgttta tgggtctttt acctgtatgt atgtgtgtgc    24660
accatgtgga tgcatggtgc ccttagagtc cagaagaggg tatcagatcc cctggaactg    24720
gagtgacaga gggttgtgag ctgggacttg aacctaggac ttctaaaaga gcagcaggtg    24780
ctcttaatag ctgagcctta tctccaggcc gtcccatgga tttgggggc tttgtttcat     24840 tttattttgt tttgagacag ggtgtgtagc tcatgcttga atttactatg aagccctgac    24900
tcccctcaaa gtaaagatcc tcctgcctct gtctacagct gctaggattc gaggtcttgt    24960
accacatgct cagcacagcc atgattcata acaataaaaa agaaagaga gacctaaatg      25020 gccttagaga taaataaatt attttttttt taaagattta tttatttatt tattacatgt    25080
aatgcacact gtagctgtct tcagaccccc cagaagaggg agtcagatct cattacagat    25140
ggttgtgagc caccatgtgg ttgctgggat ttgaacttcg gaccttcgga agagcagtcg    25200
ggtgctctta cccactgagc catctcacca gccccgagat aaataaatta taatgtatgc     25260
gtaaggtggg atcatctcag tctccgggaa tcttgcctgt tactccttcg ctctcccttc    25320
tattcatgct tgggtaactg gccctggctg attgatgaga gctgatttcc ccactgccct    25380
gtggcaggga ccactgcgcc cacagggctc cctcaggatc ctcagtacag agctgcacag    25440
ctgggtggaa gtagagggct gcatatataa cacgatctca actttatttc tttaaataaa    25500
aattttattt aaattttata cagctctata taaacgaagg aactattgaa ggttcagcaa    25560
ggacctgcca acggttgtca agggtaatgg cgatgtagtg attttttttc ccccttccat    25620
tttacttcca tactttctac attaccccac aactggcaag tattatttta aaatgaaagt    25680 aaaatagtgac agatgacttt gaaggaaaat tgaatcggta aaaagaaagc tgagagacca    25740
cccgggaagc ccaggctaaa tgtaatctgg gtcaggcctc ccaggcctgg ggtctcaaga    25800
tggtcagctg agggaccctg gtgaccctct tgggccagca gggacgggga ggagccggaa    25860
gctgagtacc caaagtgctc ctctgggctc caagggcctg cacagagact gtgtgggaat    25920
caaaggatac aggcatgagg actgaggcct gacgaaccca gctatcattc gtcctagaac    25980
aggaggcaga gctccaagag tccaaccaag aggcaggaag ctttgggacc cgagatgggc    26040
gatgggatta gaaaggcatg tttgcaaata ctttcaaatt tacgatgcac actcactgga    26100
aaccccaccc ctgggtgtcc cttccctgcc tcttgccaca cccaatagct gacatcactg    26160
gagaaagtcc caagaccagg ctggctggag ctcctgatag gttccaccct cctgcagagg    26220
gccctcgaag actagcttgc tcgcccacac cgccagatgt ctgtgtcttt ctctcttttg    26280
cctcccaccc tcgtctcttc ctccaacctc agtggagggt cccctgcttc ctggggaaag    26340
tagaacttgc cagtgctcac tgtaatgtcg tccctgtagg tgtcatggtc ccccattact    26400
gggagcaggt atgcctcaga tctccctcta ttcgctgccc tttcaggctg tctcagtttc    26460
tctctgacag ttcctctcct cctgaatcct gcttgttggc atgcgaacag gctcaatatc    26520
ttccatctca aaaacaaac actgggaagg tgttgagaga cagagagcat gggtaatggg     26580
tgccccagct tggctgggaa ggggtaactt acaatgctct actgcccagt agggtagctg    26640
cagttgtcaa ttaattgtaa atttcaaaat agctagtaga gaggatttta gatgttccca    26700
atcccaacac aaagaaatga taaacattca aggcgatggg tatgctaatt gctctgatct    26760
gatcaccgca cattgtatac atgttttga aatgtcaggc tgtaccccat aaatatgtac      26820
aattaccgtg cagtgattca agataaaaac tataatttta aaaagctaaa acagaagga     26880 aatagctgcc cttgaccccc ccaccccac aagtgtcttc ctgtttgtcc agccacttaa      26940
```

```
tgtcagagct tcctgtggga gggtggtttt ggtgtacaca gacactcctt cctccctcct    27000
tccccataag aggagtcacc cctgtcccac gatgccatgc agggccacat gcgtgatatt    27060
aaccagtaag atgtgagcag ggatgatacc tgtctcttat aacaaacgga aaaaaaacca    27120
caccaaacca aaacaaaca aacaaacaaa caaacaaaaa cagggttggt ctgtccctgt    27180
gtcttttccc acataaagtt aagcacacaa agtagccacc atttatttat ttgtcccctc    27240
ccccacccct ccccgagaca atgtttctct gtataacagc cctagctgtc ttggaactca    27300
ttttgtagac caggctggcc tggaactcac agagacacag agattcacct gcctctgcct    27360
cccaaatgca gggattaaaa gcatgagcca cgaactaacc agtacccag agctcttgac     27420 tctagctgca tacgtatcaa aagatgacct agttggccat cactggaaag agaggcccat    27480
tggacacgca aactgtatat gcctcagtac aggggaacgc cagggccaaa aaaatgggaa    27540
tgggtgggta gggaagtggg ggggagggta tggnnnnnnn nnnnnnnnn nnnnnnnnn      27600 nnnnnnnnnn nnnnnnnnnn nnnnnnnnnn nnnnnnnnnn nnnnnnnnnn nnnnnnnnnn    27660
nnnnnnnnnn nnnggcagga tcctgtgttc atgtgcaaca ctcgatgcaa gctgtgtagt    27720
gtttggttct gagcacctga aggggaccaa gcaggctgat gcccaggcca cgggttcttt    27780
ctggccccac tgcccactcc caccctctgg catccccatg atgaacatgg ccacagatca    27840
cactactctg ctcctctccc agatccacgg agccataggg tccccagatt catctctgca    27900
gctaacaagc tgggcagtgt cacctccctc aaggttcctt tcctgctctg agcagcagtg    27960
tctcccacag tgagacactc atgtccactg aagatattg tagccattaa attcctgtgc     28020
taaaataact aggggacttt gtcaatcact acactcttag ccccggactt ctgactcata    28080
gagggtggtg acagctcagg gacctgcatt ctaccaaata gccatgtgtc cctgatggag    28140
gaactgcccc tggacaacct ctgcagcaac tgaaccctct gtggtctcct agttcttctg    28200
gacaggtgtg accccagtac ctagtgccag gtgagagagt gctagggcca cactaagggg    28260
tgacaggaca aggttggagc tggtagatgt ttgggccacc aaagagaaca ggtcagtagt    28320
aaaagccatc atggcctgag ccagcctgcg agtctcctct gcagttggga cactcttgca    28380
gtgtcctggg gacctcttga gggtagcatg gtcaccaaaa tcctacaagg acagatcaga    28440
agtcagtgag gtcaagggaa cagctctagg ttctctgtgt ccctcacgga cctttttttt    28500
tttttttttt ttttttaagat ttatttattt attatatgta agtacactgt agctgtcttc    28560
agacagctcc agaagagggc atcagatttc gttacggatg gttgtgagcc accatgtggt    28620
tgctgggatt tgaactcagg accttcggaa gagcagtcgg tgctcttaac cactgagcca    28680
tctctccagc cccctctcag tcctgatgcg acagggcagc aaaggccttg tcccagatct    28740
gaggagagtc atgctgaagt ccttcctacc ccacccctc cgaaccctg aacatcagcc      28800 ccataactac tgactccccc accccattc ccttgcttcc actgatccgg tcctcctctt     28860
ccctctggcc ccacccattc ttccccagcc ccacctgatt gtacctggtt gtccaacttg    28920
aagagggcag gcaggggcag cttctgctgg gcctgctcac tcactggctg tagaaatgag    28980
aaaggagatg aagaaaaggc ccttcccatg ggtccccatc ttgccaagac ataggtgagt    29040
ccctttggct cttccccta aacctctcac ttttgagtac ctgctggccc gggagatcca     29100
cggcgctcac cggagagaac tgttgagaaa agggagaaca gagaactcag cgttcctccc    29160
tctccaccct tctggcctct cccagatttg ccccgcccc ccagcatctc cttcagcctg     29220
actgaccact tcccactcag acctcagctc tgcctcaccg tgaaacaggg accttgcagg    29280
```

```
caggacaagc tgagtacgag gagcccccgg agcagtgcca tgttcctgta tccagaacag   29340
ggagtgttag ttcctacctc acgctcgaag gccaagcagt agactgctat ccatgggttc   29400
cttgaccgca ccaggctgcg gaacctggac tcaaaacata gcagctgtgg acctcactca   29460
ctctgagagg tgggatttcc ataagctttt tttttcacct gtacatttag tcttcattct   29520
tttcgtctta cactgtggat cagtcctggg ttcaaattta aagccctcat cttgcaagag   29580
gaccttgcgc atctcccttc atgcctttgg ctttaccctg tcttggtaat tcatggcaga   29640
agttcttcct gctcccatgt agatgttgag gacccaaata agaatctctg taaatactga   29700
gcatgatgcc tggcccccac cctagcaaag ccacctgacc tgttgttcat ttcatccagc   29760 cttttctcagg ctgccctggt cctacccaaa ggctctgaga gctaatctgg gctggcaggg   29820
cagccagaaa cttctttgtt gaccaatgaa tgactggccc agacaccttt ggacttacgg   29880
gaactacaag cctcatccca cttctgctcc aagttctgat ccagggtgct cggggaagc   29940 ccagctggcg gaagggggga ggctctcagc ctagagagcc ttccttttcca tcctcagccc   30000 cctacccagg ccttatttca ggaccagct cttctaaaag gtccttctgt tatccctaga   30060
cctccacaac tgtgttcaag aaccttcagc cagggcctca tctccaatct ggatatatga   30120 ttttttctcgc caagagtagg cctccaggtt ttggagttct agaggtttct cctggagctg   30180
cctggaccct tgctcctcac caccccagga cgctgtgaag ctgcaggctc cctgaataaa   30240
ttcatccaga ccccttgcca aggtgccagc tgtctacttc ctctgctgcc caagcagcag   30300
gctgcaccac ccctccatcc tacctcttca ggcttcttag cgcagcacac gcagcacacg   30360
gtgttctcct ggaccagctt gctccccacg ctcccccagt gcagccagca gggcctagct   30420
ctctcctccc acaggacctt tgctctcagc caaccccgt tcagcttgtg ttcagtgctg   30480
gtaaatattg acctgtacat ccggttaaac attgatatgg gggccagaag acccttttccc   30540 atcaaggcta cccagaaccc tgcctgagcc tggagaaggg gtttacagga gcagataagt   30600
gaggaggttg ggcctggcaa gccttctaat gatccctcaa cataggggat tatccacagt   30660
cagtgaggct cagagaggct gtgtggcctg tgtaagggcg cagagtgggc tccagagtca   30720
cagccaaagt cccaccacca ccaccaccac caccaccacc accaccacca ctaccaccac   30780
caccaccacc accaccacca ccaccaccac caccaccact accaccacca ccaccaccac   30840
caccaccacc accaccacca ccaccaccac cacctcatct acccatacta anttgaggct   30900
nnnnnnnnnn nnnnnnnnnn nnnnnnnnnn nnnnnnnnnn nnnnnnnnnn nnnnnnnnnn   30960
nnnnnnnnnn nnnnnnnnnn nnnnnnnnnn nnnnnnnnnn tctatgaggg ttacatttta   31020
gaacatctct ccttttttcc tttttgagac aatcttacta tatttaggct ccccttgaac   31080
gtgtgatcct tctgcctctg cctcccaagt gctgaggtta caggcatgca cagtcacatc   31140
tgcctacaca atgtcttagc agcccttagc agcaccaggg gtcaggaagc cctcaactgt   31200 cccctttagct ggcttctctt gtgaagggct atgtcttctt cccttccta gcatggagac   31260 ggctcttagc cccagagcct tccttccttc aggttaaaca gcaccagttt tggtgggac   31320 ctcccattttc cctctatctc cctaagcaac gacctttttct gctctgactc tcatctggca   31380
cttggaccac aagacaaaac tgcagcctgg gctgtgtgtc ctcgcacatc attcctgtgc   31440 cccccctggag tcagtctcag gggaggaaga cagggttcac gactcagaaa agaccactgg   31500
ctgtcctagt gtgccctcac ccatcctata gcacgcacat gctgatgtgc cccctccgct   31560
ccatcaccat cctctcatgt acacgtgccc tccctcgcca gacacatgca tcactaactt   31620
ttctgacttc ccagaaaaat atctgatctg agaagttagg agtctgccat catcagctat   31680
```

```
ggtccttaaa attaagtcag acaatccatg ggacatgaag ggcaacaacg agaagactcc   31740
tcgttccttg ttcactctgc ttttggcagc accaccagca ggaaccaacc tggctctccc   31800
taatccctca tctatagcag gtctcccggt gggaatttta gggacctctg tgttctcatc   31860
caggggcact gccactcagc tgctcaggga gagacccctt agaacaacaa agaaatcaat   31920
gcagatttag gcttcttgtt tcccttccca gcccctccca tcacaggcaa cagcctccct   31980
tggctgagcc tcaggaggct gatttatcag agaggtgctc agagaggcac ctctggtccc   32040
tctgggtagg tagcaactga gacaggagga gatggtcacc ctgggcatcc tctaccagga   32100
agtaaatgag ataccctggc agatgggacc cctgaagttc ctcccggggg cgggggtggt   32160
ggtggtggga gtctaagtca cagatctttg ttaccacgtg gttagactga ggactgaatc   32220
tgaggtggga aatctgatgt gcatgggaaa acacagaggt ccaatgctgg ccaagagcta   32280
caagcaggga caggtgctag ggggatgtct gaatgttcca ccccaagcca caggaataac   32340
ggaaatggag actctaaagg gcagaaagtg agggtgtgca gcaggggctg cacaggacac   32400
atgcaaggcc ctggctgcaa taactgggtt ggggaggcag tcattggcta gccaggggca   32460
ccaggacagt gatgccatcc tgtccaaagg gcagtgtcca agccagattt ctaggctcca   32520
gggggaggag ggtccgggga gaggggtcaa gattctcccc ctctgagtca aggttggcct   32580
tcccatgtgc cccaaatcag gaggcacaga aactgggatg ttgtggtctc acatccaagc   32640
tgagaagaca agtgggagcc agtacatgtg tttcagatta aacccagtcg gagacaaaca   32700
tgttgctcct cctcctccca gagccaagct gccttcaagc cacatggcag tgaatatgcg   32760
gacagtgcag gggaggacac ctctctctcc actggctcaa ggacagtttc aagggggttca   32820 ggctggctgg ctcatggcta cgccgctcac cccctggaca gtttgggggtt tttccctcct   32880 gaaatcttgg aatctgaatc agcctgagat accccataat tgtacctccc aacaccccca   32940
gaaaggtcag ccctgcagaa cagaactctt tggtccccac ccatcccccct cagccctgga   33000 ggctgaactg atgggcagct aaggtccaga cagtggctgg ctcttggaaa gcctgtctct   33060
ttcctttgac tcagaccact ccctgccgtg gcttacatca ggaggtgcaa gggctgcagg   33120
agggcagcca gaccccacaa accagctagg ctaaatggtg cttattgttc gcaagaggcc   33180
atgacctcat ttgtctccca gctcttttgg taagagagaa tgagaggaag ctggacagag   33240
aacctagcag gcctcaggca gcccactgct ccttgctgta agggaaccag caccgatggt   33300
tctgaaaagc agcgatccga atggagtcag gctgagctgc aggaagctca ccttccttgc   33360
tcactgctgg tggaagcaac ttcaggaaga gcccagccta tgggactata gctcctccgg   33420
ggtactgctg agtccagccc cagagcttag ctccctgctt cccaccaccc accaccacat   33480
cctttcccaa caccattcaa aacccagtc cagcctctcc tactggtcta cagtgagcgg   33540
ctaatagagt cctgggcctc tgtcccccca attctctctc ccctctcatc tgttcacctt   33600
ggttcctaaa ctgcagggc tactataacc ctacctccac ttccttgcac ccctcttttc   33660
tgctctctgg ggtgccctg ccactcccag tccctctagc cagggagcct cttccatatc   33720
tgtcttcccc aggctagacc aggcgctgcc ttacctgtgg ttgcggcagc ttctctcaca   33780
gcctgcactc tgagggctc caggaagcag tgaggggagt agctgcctct caaccagcgt   33840
ccagcaggct tcagattaca gctactcttt tcttaaagtg acctgactcc atttggaatc   33900
tgtgattgca tcattgtctg gtgttaactt taacccactg ctgccttcc gccatgtggc   33960 tccaagacca cacgttggcc accctcctct cccaccacat ctcccttgga tctttatctc   34020
```

```
tcttcattgg gaccttcatt gggacatgat ggctaacttc aggggcactt gggccagcct   34080
ggggtaggtc atgagtctga acttgaacat ctgaaaggat tggctgagag gcaggctgca   34140
tggagagact gtgagccagc cggtatggag atgctggtt cttccaggcg cttggctctg    34200
gctcactgca ggtgggagca aggtgattct tctcccctcc tcacctggaa aatgaaggaa   34260
tgggactgta cctgacagct ctgaaggttc caaaggacag tggggtgggg actagagagt   34320
tggcccagtg cttatgagca ctggctgctc tcgcagagga cctgagttct gttcccagct   34380
cacatagcaa ggactcgaaa ctgcttggaa ctccagctcc agagaatctg acgctatctg   34440
ctnnnnnnnn nnnnnnnnnn nnnnnnnnnn nnnnnnnnnn nnnnnnnnnn nnnnnnnnnn   34500
nnnnnnnnnn nnnnnnnnnn nnnnnnnnnn nnnnnnnnnn nnatgtcagg catggtggtg   34560
catgccttta atcctagaac tcaggaggca aagcagatgg acatctgaat ttgaggcccg   34620
cattgtctac atagcaagtt ctaggctagc caggtacatc ataagaacct ttctcaaaaa   34680
ataaataggg ccagttggca aaatttagct tgccctccta acacaagaac ccaaagtcaa   34740
ccccagcaac catgtaaaaa gaagcaaggt gtggtggcac ttgcttgtga tccagcattg   34800
tcaaggtgga gacagacgga tccatggggc tcactggcca gccagctagc tggtctactt   34860
agtatgctcc cagccagtga gagactgaaa aataaataaa taaataaggg gttaggaaga   34920
ggtaacatgg tggctcagtg agaaaagata cttgtcatac aagcctagca accctcaatt   34980
ttcagtggcc actaaaggtg gaaggagaga accaactcca aagaattgtc tcctgacagt   35040
tttatgctgt ggtacacaca cacgcacaca cacacttgtt acatgcatat gcatacaatt   35100
aataatttaa aatgttatgt gtatgggtgt tttgcctaca tgcatatctt tctgtgcacc   35160
acatgtgtgc aatgcctgtg aaggctagaa gaggacatca gatcccctcg gagttacaca   35220
gggttgttag ctaccatgtg gattctggga acaaaaccat gggttttcca aaagaggctc   35280
ttaatcactg agccatctct ccatcccctc aatagtatat atttctgggg ctggagagat   35340
ggctcagagg ttaagagtat tgactgctct tccagaggtt ctgagttcaa ttcccagcaa   35400
ccacatggtg gctcacaacc atctgtaatg gaatctgatg ccctcttctg ctgtgtctga   35460
agacagctgc agtgtactca tatacataaa gtaaataaat aaacctttt tttttttgtt    35520 ttgtttttt tgtttttcga acagggaga cagggtttct ctgtatagcc ctggctgtcc    35580
tgaaactcgc tctgtagacc aggctggcct tgaactcaga aatccgcctg cctctgcctc   35640
ccaagtgctg ggattcaggg tttgcgccac cgccaccacc tccaaggctg ctgctgcggc   35700
caccaccacc ccaccaccac actacctgac tatttaactt ttaaaggcag ccatctcatg   35760
gaaaatgaca cctagcattg tcctctggtc cctacatgac cccatgtgca aacacatacc   35820
tgcataaaca cacataaata cataagtaaa cttagtctgg ttgttttgga aatgtgctat   35880
ggtttggatt gtgtccccc aagggaaaaa ttgggtccca gagtagtact attggaagag    35940
agtagaactg ttagggttta ggcctggtgg gaagtggcca tggctagaga gacatgccaa   36000
ccaaggggaa tctctggctt catcttttcc ctttgctttc aggtcctaag acagtcacaa   36060
ggctgcttca ccacatgccc agaagcaagg ggagcagtca tggctgggac cgctaatgca   36120
gctgttgatt tccccagata tttgtagtag taagagacag gtgaggaacc ccacagcaag   36180
tgttagtaat tgtgtgtgga ggtgcccctcc ggggacgggg gccctcctgg ggcaggacgt   36240
tcctcttcct catccaccctg cactccgaga acaggaaatg gtgactttgg cagagcttaa   36300
gcagagcccg ttcatgttac aagtatgtaa attcataagg accagtttct ctccatatga   36360
aacagcttca aacaggagaa ggaagaagca aacattaagg aaaagctctt ttattgcaga   36420
```

```
ggctacactg aagctaccgg ccgccttcct ggaatgtata atcagcttcc ctctggggt    36480
tctgtagagc actgagacat taagtactac tggggtccag gattctgcct atgaagagga   36540
gggccccgt gtccgtgtcc ctcagaacaa agaggaaagg ttggttaagg tgatagtcta    36600
gcgggaaggt gaggcggacg ggctggaggc ctgggctggg gctgcttcct gccccctctt   36660
cattccactc gaaagcagcc ctgtgttcca cttgggtgag cttcacgggt ttgccagtaa   36720
tcttgctgaa gtcgggtgat tcaaacaacg actgtagctc tgtggagatt cagagattcc   36780
attaacacca cacacacaca cacacacaca cacacacaca cactccctgt ttgtgtaggc   36840
tgattttcaa gaaagcaagc tagaagtgga gtacctcaca gtgacttgtg agctatgagg   36900
cactctgtga caggctcagt gacctacctg agaacttata gccaagatgg ctgaagccag   36960
acctggcctg agagaatgtt ttgggctgtt ataggacaca tagagataca cacacacaca   37020
acacacacac acaccaagga ctgagtctaa tgggaggtgg ttcttcattc ccctcccctg   37080
taatggtgtc acatgttccc tgagccaccc tacaaagaaa gccacaggac tcagttctgt   37140
cagcaaggtg gcaggctcca agactcagcc ccgagcgcaa agtggccttg caaacatact   37200
catgtcctgc agagacttgg taagttcgcc ttcgaagctc agcttcagct tggggacagt   37260
cagcacagct tggatagtct tcagttctcg gtcgatgtca tgaatgaact cagaggtgag   37320
gctctcttct atcatggtca agttctgggt cacggtcagg ggcaggaaga agatgatgct   37380
catacttcct gtcaagggca gctgggcaat ctaacccaac agagatgcgc acaggttagt   37440
tgtgagccag aaaaaacaaa acaaacaaac aaaaaaacac caacagctgc cttcccctct   37500
gctgtaacgg ggccccagcc ttgtgctccc cagcctcagc ctgggctgta ggctactggt   37560
tactggcagt ccttccatga gtagggagtt ttcttctcag cctaaaaccc acagaagttt   37620
aatgaacaca cgtttgtttg tggttccgct acggtttcta ttgtgataaa acatgactga   37680
aagcaacttg gagaggaaag ggtttatttc atctgacaat tcgcagggtg tcttctcatc   37740
actaagggga ctcagggcag gaactgaagc ggaagccgtg gaggaacgct gctttctggc   37800
ttgctccccg tggcttctta gcctgctttt ttatgctatc cagaaccact tgcccaggag   37860
tgacactgcc cattgtgggc tgggccccc cacatcaatc actaatctag aaaatgaccc    37920
acgggtttgc ccagaggcca gtctggtggg ggcattttat caattgagtt tcacccttcc   37980
aaatgactct aacttgtgtc aagttgacca cacgaatcag ggcctggttc ttaggagctg   38040
aagtggaatg tcccccagag actgcctgcc agcactgctg accatttgct ttgtatagag   38100
cattgaacca gaaatgaaca ataaaatgga tcctttgaac agatgtgttg atcctagggc   38160
ctgtggacac agcgactggg cttcccagag ccccatgga atcannnnnn nnnnnnnnnn    38220
nnnnnnnnnn nnnnnnnnnn nnnnnnnnnn nnnnnnnnnn nnnnnnnnnn nnnnnnnnnn   38280
nnnnnnnnnn nnnnnnnnnn nnnntggcct catcaggtat cagagagaga gagagagaga   38340
gagagagaga gagagagaga ggataaaagg ttagcccagt ggtggtggca catacccttta  38400
attccaacac ttgagaggca gaggcagggg gagctctgtg ggccagtttg gtttacagag   38460
taagtttcag aatagccagg gctacacaga gaaaccctgt cttgaagaga aacacacaca   38520
cacacacaca cacacacaca cacacacaaa taagatcttt aagaagaaaa gaaaggatag   38580
tggggaaaca tctgagcaga ggaagaaatg gggtgcgcag acacccacc ctcagaggag    38640
gccctcactg gaggtgtctg cacaggagaa cacttgcact cagcttgccc tagggcgtca   38700
gaactcagaa ttcagtttca aagcactgac aggagcagtg actggggacc ccaggttgaa   38760
```

```
tcccccttt  atctaaaatg  agtaagaacc  aaaaaaacaa  aagtgtttgg  gatttggaat   38820
ctgggttatt  tgcatctaca  aaagaggtct  tggggaggaa  acccagttct  acccctggaa   38880
ttcatcagtt  tcctataccg  ctgactacac  aggggctgaa  ggtaatctca  atgttttcat   38940
aactggtgtg  gtgctacttg  ctcatgatcc  caacacttgg  aaggtaggtc  agaagttcaa   39000
gagcagtctt  gactactcag  tgaatttgag  gctagcctgg  gctacatgaa  aactcataaa   39060
acaataaaag  aaaagaaaag  gtggcgagtg  aggtggccca  tcaggtaaaa  gtgccaacca   39120
cctcgcctga  aagcctccac  acggaagggg  aaagccagct  tctacatgtg  gtcctctgcc   39180
ctccgcatgc  accatggctc  gtgcacccccc  acacccaccc  acccaccac  ccacatgaca   39240
taaatacttg  taatgattag  tttctgaaga  acaatatttt  cgttgatctt  gtttagggaa   39300
caaagttcgt  gcacattgac  ctgtcgaccg  tgtagtacgg  gatccgctcc  aggaagctaa   39360
agattttggg  atgcttcatg  ttgcagctac  tctgatgaac  agtgttgctt  tctgggccag   39420
gtaatggtgg  catataccctt  tgatcccagc  acttgggagg  cagaagcatg  tagatctctg   39480
tgagttcgag  atcagcctgg  tctacagagt  gagttccagg  atatccaagg  ctatacagaa   39540
aaaccctgt  ctctaaaaat  cactaattta  aaaaaaatt  cctttctaaa  cctatataac   39600
aaatgttttg  taggctgcct  taacaaagcc  caatggccat  tcagagaagg  ctcaaaagag   39660
aaagtttagg  ggactctaca  agcatcctca  ggaaggccac  agaaagcaga  gcctgggcca   39720
gtgagacttt  gcagtgggca  aggttcagct  ctttatgtag  gaagaagaga  gtcaacagtc   39780
agagtccagc  tttccataaa  acctgtgcag  ggcctctagg  caaagccctg  tgttaggggc   39840
aaaggcatt  gcagtctaag  cccggtgaca  tgagctcaat  ccttggaacc  caggtggaag   39900
gagtgtgctg  actccacaaa  tttgtcctct  gatctataca  tgtatgcacg  tgcacgcaca   39960
ctcacataca  tgtccacatg  cacacatgca  tatacatgcg  catgcgtgca  cccacacaca   40020
gggtcaaaag  cagcaagaga  tgccctgtga  aaaacgtctc  attcagtctc  ccatcatcca   40080
gtgccacact  ctgagcacag  gtggtactga  tatcgttcct  gattgatcga  tcagttgatt   40140
tgagaccccg  cctcactatg  tagcccaggc  tggcctggaa  ctcacagtga  tcctcttgct   40200
tctgcaagat  gagcccatca  tgcccaccat  gttattgaag  caataccatg  ctctataaag   40260
caaacctagg  caggcaggat  ggtggactcc  tgtaatctca  ggacttgaaa  agtagaaggg   40320
agatgaggag  ttcacatcaa  tctcccgtat  gcgttggagg  ctggagtggc  tgttccctgg   40380
gcgcttctgc  cagcacctga  ccaatgcaga  tgcagatgct  cacagccaac  catcagactg   40440
agctcgggac  cccagtgagg  gtgctggggg  gaggactgga  ggagctgaga  cgggattgca   40500
agcccatagg  aagaacaatg  tcagctggcc  aaaccaccca  gagctcccag  ggactagacc   40560
acgaaccgag  gactgcacat  gaaggatcc  atggctccag  atgcatatgc  agcagaggac   40620
agccttgtct  gacagcatgg  gaggggaggc  cattggtcct  gtggaggttt  gatgccccag   40680
tgttggagga  tgctggagcg  gtggggcagg  agtgggtggg  taggtgggga  gcaccttcat   40740
agaggcaaaa  gggatggggg  agaaggcaga  tgggatgggg  gggttgtgga  gggtaagaa   40800
agaaaaaga  tgtctctgaa  agtaaaaagt  acttgtcact  aagcatgagg  atatgagtca   40860
accccaagc  cccacagggt  ggaaggagag  aaatgagtcc  cacaagttat  tttctgatct   40920
atacgtgcaa  tccatggcat  acgcagaaac  gcaaagacag  acaatgagtt  gggtgtggtg   40980
gtgcacatgt  aattccatca  ttcaggagac  agaagcagca  gagttgttgg  aaatctaagg   41040
ccaacctaaa  gacctacacc  caagaaggaa  caaactataa  ggaaaaggt  ggtcgaccaa   41100
tgtaacatta  aagttagaaa  tctctcttca  cactgtgtag  atactgtaca  aggaagagaa   41160
```

-continued

```
aaggcagcca catcaaaaca gtgtaaatca acgagaaaac cagaaacaac tcaagagaag   41220
gctgcagggg cctgaattct gttctcagaa cctgcatcaa gccaagagaa tcaaaactgt   41280
ctgtaactcc agctccctgg gatccaacac ccatttctgg cctccatcag catcactcac   41340
aggtgtgcac acatacacat caataaaaat caaaaccagg gatgaagggg tagggaggtg   41400
catgtggatc tgggaggagc tgagaggcac tgggtgaata caataaaaaa tttggtgcat   41460
ggtggtgcac gcctttaatc ccagcacttg ggaggcagag gcaggcgaat tctgagttc   41520 aagaccagcc tggtctacag agttagttcc aggacagcca ggtctacaca gagaaaccct   41580
gtctcaaaaa aacaaaacag ccgggcggtg gtggcacacg cctttaatcc cagcacttgg   41640
gaggcagagg caggtggatt tctgagttcg aggccagcct ggtctacaaa gtgagttcca   41700
ggacagccag ggctacacag agaaaccctg tcttgaaata aataagcatt tgttgctgtt   41760
acagaaaact ccagcccagt ttccagcaca cacagggtga ctcacaacat cataactcca   41820
cttccagggg atccaatgcc ttcttctgac ctctgtgggc accaggattg catacagtgc   41880
acagacatgc acataggcaa aacactcaca aaataaaata aatctagcaa aaaaaatttt   41940
aactaataat ttaaagaaaa aaataaggaa gccgggggtg gtgtcgcacg cctttaatcc   42000
tagcacttgg gagacagagg caggcggatt tctgagttcg aggccagcct ggtctacaaa   42060
agtgagttcc aggacagcca gggctacaca gagaaaccct gtcttgaaat aaataaataa   42120
ataaaaaata aggccaagta attcttggaa gaatcccaag gggacactaa gtgtatataa   42180
aggcgttcca tagggctagg aatgaggctt agcgagagca acttcgctgg tgtatgaaag   42240
tccctcagct gcatgtggta cctttaatct aggctctccc gaagcagagg cagaaggatt   42300
tctgtgagtt caaggccagc ctggtgtaca tagctagttc caggacagaa agggcgatat   42360
aatagaaaca tcntacctag agcccngcca aanaaggggg agacctgaga ccagagagat   42420
gactcagtgg ctaagagcat tgactgctct tccagaagtc ntgagttcaa ttcccagcta   42480
aaaatttatt taaatgttta ttacttgtat tattatttaa atttaaataa ataagtaaat   42540
gggagcctag gtttgagtcc ccaaatcacc aagaaaaaat gttatcattg ctaataatca   42600
aattaagagc ataagaactt cttttttaaag aattcttatt tatttttatgt atgtaagaac   42660 actgtagctg tcttcagaca caccagaaga gggcattgga tcccattaca gatggttgtg   42720
agccaccatg tagttgctgg gaattgacct caggacctct agaagagcag tctgtgctct   42780
taagtactga gccatctcta cagctcttat caggttgata aaatttaatc tcgtggagcg   42840
ctgagaccaa gaactaaagc tgggagattg aaaaatgcag accaccaagg ccctgctcat   42900
ttctccagtt ctgatcagct cccgtaccag gggtctaacc aggcctgtgt ctgcttccct   42960
gagtagacca gaggccccat ctaaacagcc tgcctgcagc agctcctctc tctaggtgga   43020
cagatgggaa tttcagacca atgtcatttc ccaggacatc aacacagcag ccaaatttat   43080
tggtgctgtg gctgccacag ttggtgtggc aggatcaggg gctggcattg gcacagtgct   43140
tgattattgg ctatgccagg aaccagtctc tcaagcagca gctcttctcc tatgccatgc   43200
tggggtttgc cctgtctgag gccatgggac tcttctgttt gatggtcgcc ttcctcatcc   43260
tcttcgccat gtgaggctcc ctggggtcac ccagccgtcc ctgctgcctt gactccatgc   43320
cagtcctggt gctggagtct actgagattt accattaaac agcaacgttt ctctaaaata   43380
ctattaatta attaattaat cacgtgacaa ccccagcgtc catatgggtg tggaaaatga   43440
ggaactctac ccatcataca tggcgactat gaagaacaat gtgacagaaa atgctaacat   43500
```

```
catgtgtgac cgcatgcatc agccctgact gctaaaagtg acaagcccg aagcgaaagc    43560
ccaatgttct acttctaaat gcatgcacca aacgcctccc acaggaccag aggtgcagct   43620
ctgatagggt ccttgcctgg catgcatgaa gctgtggaca cgaggcatta ttcgcaagaa   43680
cattctagct gtctggaggg ccctcaatcc actgtgttcg cgctgttcca gcaccagtgc   43740
ctcctggggc tgcacctgaa aaaggggact gcttaagagg gctcctacca agcctactgc   43800
cacagatgca tgatgggaaa gccttctgga agcaactggc tgccaaaggc tctggacaag   43860
agatcaccct ctactggaaa ggtggtttca gtctaggttc tgtgggattc caggaaatta   43920
gacaacactg gcagtccaac agacagacga tctaaacttc caaggcacag ctggtagaac   43980
ttgctgcgga accagacaac aaggtacgag ctactcccat acaacataca aaaagcaga   44040
gagagagtca gagacagaga cacacagaga gagacagaga gagagtctaa agagagtcag   44100
ggtctcagga ctgagggtat agtctactgt agagcatttc cccagcatat acaagaccct   44160
ggattcaatc tgaacacagg aaaaaagggg gggggggact tcgattatct caaattctcc   44220
tttttgtgac acacccctaa agtcactgcc tacttccctc accgccatga agtaaagagc   44280
tgtttgcgct tatgtctaca cagtctcggc tcccacttcc tcctcccctc tgcttctgtg   44340
ctcatctcct ctgaaaccac tgcagcaagt gacttgtgtt gactgccaca cggaaactct   44400
cctcagtagc aggcagcaga gcagagctct gtcttctcgg agcttcttct ctcttgtcgc   44460
cattttctcc caccctttaag taccctatct tctctgtctc tgcttgttga tccttggacc   44520
cttttccttt ctatgaacaa aatatctcct taaaggatct cttctagttc agggtccccc   44580
cgcccccact gtggagaaaa cccagggcct tgcacatgct cagcaggagc tccatccagt   44640
ctctagctcc atgacttaaa gcatctctgt gctgtcaaat atacacttcc agcccttacc   44700
aaaatattca gtcaactcct tgccattcaa aatggatgac ctcaaagcca gagtcagcgg   44760
tgctatgact cccagatcca tccacttggt agcccaggaa tgaactcann nnnnnnnnnn   44820
nnnnnnnnnn nnnnnnnnnn nnnnnnnnnn nnnnnnnnnn nnnnnnnnnn nnnnnnnnnn   44880
nnnnnnnnnn nnnnnnnnnn nnnnnnnngg ttactgggat ttgaactcag gacctttgga   44940
agagcagcca gtgttcttaa ctgctgagcc atctctccag ccaccaccac caccaccacc   45000
accaccacca ccaccaccac caccccacca ccaccccgcc ccacctgctc attcctgatt   45060
ggttggttag tttagtctgt gagacaggag ctgtcccttt tctatagtgg aaggtgaata   45120
agaaactcct gaaagtgaag gcctacaaaa cagccacact tatttgttgg aaaatactgt   45180
aaatgtgaca tgtaaatcaa tgctaaaata attcgttaag tcagtgaaca accttaaaac   45240
acagtctgta gcctgaatta cagacacgac acgagccatg acagaggctg aaataagacg   45300
cctttgcaag gagaagggca gaagcttcca tccttgctag caaatctttg ttccaagctt   45360
tatcagattt tattgctttc tcttttctgtt tttctttatc atatttgttt atttgttggg   45420
ggaaagccta atcttcatag cccatgtatg tgagcacttc agcatatgtg tgtgaacacc   45480
aacagcacac gtgtatgagc accacagcat aggtgtgtga gtaccacagc acatgtgtgt   45540
gagtacgata gcacgtgtat agagttcaga ggagaactga gagagtccgt cttttcctcc   45600
tactgtgtag gtctcagggg tggaacttgg gctcagcctt ggtggcaagc tcctttatcc   45660
acagagtcat cctgccagcc cagctttctc tttttctctc tgttatgtct atccactctg   45720
ttcaaggcta actcactgac tctgagttat cagaactgct tgtgagagca ggagtaactt   45780
tggacatctg tgctggtagg aacaccatcc ccactcggct tggatgacga agggggaaaaa 45840
aagcatcacc aaggagttcc accacctcaa ccagcaaata tttacctcct atacatggat  45900
```

```
aggtggggtg ggtgagcctt gtgatttatc gttaggatct catgggagtg attacagctg   45960
gtctactcca tgaccaaaat ggtgacggtg gctgaccaaa aagaaacagc tacacctggc   46020
tctagttttc tttctttctt ttttcttttt cttttacccc acggtactaa ggattgaacc   46080
caggaatgca agagctctgc caagtgagct acattcccag atctgttttt ccatttcttt   46140
ctttcctttt agattttatt tcgatttatt tgtctatgtt tgtgtgtatg tgtgtatgct   46200
tatgtgtacg tatcagtatg ccatgggtat acagaaacct gagaaggcca gaagagagtg   46260 tctggttac aggagtttcg agctgtcctg tgggttctca aatgcagcag caccaccacc   46320
aatcaccccc accccacccc agccttcgag ttcaattctc atcatcacaa aaacacacac   46380
acagacaagg gcctgcaaga tggctcagca ggtaacgaag ctcgtgtcat aagcctgaga   46440
acctgagttc actgtctgga acccgcgtaa aggggggaagg gaagaatcaa ctctatgatg   46500
ttgtcctctg ctctcccccat gtgtgccatg gaatgaacag ccctcccaaa cacacatcaa   46560
gaataaataa aactaaaatt agcttagtaa cttttatgtt gaaagtggtt tttacatgcg   46620
tgggcaacaa taacaccgag agtagaaagg caagcatgta tgtcactgaa cagcattgaa   46680
gaaaaaacaa acacatttcc tgtacatcgt tctgggagtc tgagttaggg tttctatgct   46740
gggataaaaa caccctgaca aaaattaacc tggggaggaa gctgtttatt tcagctttta   46800
tgtctacaac atgacctgtc acccagggaa gtcagggcag aaattcaaac aggtcagaag   46860
cctggaggta gaagctgata cagaagccat ggagctgctt ctggcttgct ctagcacaca   46920
ggagtactag cctaggggct gtactgccca cagtgggcta ggctctccca cagcaatcat   46980
aaatttagaa aatgcactac aggttttgcac acaggccaat ctggtagggc cattttctca   47040
attgaggttc cttcttccaa aaggacttta gcttgcatta tgttgacata aaaactagcc   47100
agcatattgg gattatagat attctcataa aaaaagaca tttagattcc cacataacac   47160
catattcaga aattaactca atgtgaacca gaagctctga aagtaagagt taaaactatg   47220
aaaaattctt acaaccatcc ataacaaaaa tctgatgccc tcttctggag tgtctgaaga   47280
cagctacagt gtacacacat ataaataaat aataaatat ttaaaaaat atatgaaaaa   47340 tcaggctggt gagatggctc agtgggtaag agcacccgac tgctctttcg aaagtccaga   47400
gttcaaatcc cagcaaccac atggtggctc agaaccatcc gtaataagat ctgactccct   47460
cttctggagt gtctgaagac agctacagtg tacttacata aataaataa ataaatctta   47520 aaaaaaaaa aaactatgaa gaactatgaa ctacaagaag tcaggaatag ggctgggggt   47580
gtaacccaac agaaaaacac ttgcctggcc tgcgtttggt ctctagcacc accaacgtag   47640
aaagagaaca gcagaggatg agggcatcct gacttgagtc aagtgacaag tgataatcct   47700
cgagacacca aaatcacaat gataaaagag atcaacaagt tgggctttat ctgaataaag   47760
agctgtgtcg ttaaatacca cgcaggaagt gaagaggagc tgagtctggt aacacaggcc   47820
tgaaatccaa gctactgggt ggactgaggg aggacaacag ctagctcaag gcccacctgg   47880
acgccagagt taactcagag agcagcttgg gtagctttaa tgagactctg cccaggccag   47940
tgcacaggag agatggctca gtggttaaga gcattactcc tcttgcaaag gacctgagtt   48000
caattcccag cacccacgtg ggcacttaca atcatcccata actttagttt caggggatcc   48060
aatgcccttt tcacagtacc aggcatgtac acagtgcaat tacatacata catgcatgca   48120
tgcatacata cacaggcaaa acttacataa aatactaagc agataaatct taaaagaagc   48180
cgggcgtggt ggcgcatgct tttaatccca gcacttggga ggcagaggca ggtgtatttc   48240
```

```
tgagttcgag gtcagcatgg tctacagagt gagttccagg acagccagga ctacacagag    48300
aaaccctgtc ttgaagaaaa taaaaaaaaa aaagaaaaaa atcttaaaag aaaaggagag    48360
gactggagag atggctccac agttaagaac acttgttctg aggtctacag agtgagttcc    48420
aggacagcca ggactataca gagaaaccct gtttcgaaaa accaaaacca aaacaacaac    48480
aacaacaaca acaaaaccac ttgttcttac agaggacttt ggtttgattc tcagaatcca    48540
catgatggtt cacaaccatc agttgcaggg atccaaggtc ctgtcttctg tgggcaccag    48600
gcatatatgt ggtgtacata catgtataca ctcatataca taaaataaaa agttttaaaa    48660
aggaggctgg gtttgtagcg cagaggtaga ggtaaaaaga ctctagcttg tttaatgttg    48720
acatgaaaaa aaaagacat ttagattcct gcatcacacc atatccaaaa attaactcaa     48780
tgtgaatcat aagctctgaa agtaagaata agcctagtat gcactgtaag gctctgggtt    48840
cactccccag cactgcaaaa gatcatgaaa ccagaaatgc agatcctctg aaccacagca    48900
tgggaatgta actcagccga tgcagtgctc acctgtcgta tacagagcac aggataaatt    48960
gattgtggtg gtgcatacct ataagctcac tacgtggaaa gtagaggcag gacgaccaaa    49020
ggttcagtga catccttggt cacatagaga atttgaggcc agtctggtct gctggtctat    49080
ttggaatgct gtctcaataa ataaaagaaa gaaagaaaaa gaaagaagaa agtcctatga    49140
ttgtcttaac ctctgacctc tgtgttcatc aagtctcctc ctcaggaact cactggtcat    49200
cttgtgaaaa cctaccccag agtctctgtt cagaggaccc aggctccagc tgtggttacc    49260
acataggatt tttatactag aaaaataaaa tgaataagta tgtatttttt aaaaaggtgc    49320
agagctggat atggtggtgt ctagttatag catccagaac tgagacagga tagccatgag    49380
gttgagaaca gctagactat acggtctcaa caaacaaaag taagggatct gagtagatga    49440
ggttttaatt ttttctttg tgtttgttac ctaacgtgta tggttgtttt gaatacatgc      49500
atgtctgtgt atcacttgtg tgcctgaaac ccaaggaagc cagaggaggg catcgggtcc    49560
cccggaagta ttattacaga aggttgtgag cagccatgtg ggtgctggga atcaaatctg    49620
aaagagccac ctcgggctgg agagatggct cagtggttaa gagcactcaa tggctgctct    49680
tccagaggtt tggagatcaa atcccagcaa ctacatggtg gctcacaacc atatgtaatg    49740
ggatccgatg ccctcttctg gtgtgtctga agacagctaa agtgtactca aataaataga    49800
tcaaaaaaga aaaagaaac agccacctct ccactctccc tttttaaaat cctcttgcct     49860
ctgtccctta atgttaataa cacaggtata tgatactatg ccttgtttat gaatagaaaa    49920
tacacgtgct aaagcaagtg tgaaccttaa atacattatg ctgagtaaaa ggagtgagtt    49980
gcacacaaga ctttctgct caagagtatc tgtatgaagt attgaacatg tgaactctga     50040
aatcgggagc tgaggaagat atggggagtt ctaatggcta caacatttct ttttggaatg    50100
atgaggatgt tctagaactc aaaaatggtg ataactcagc atatatacta aaactcattg    50160
aattgtacac tttaaatgaa tgcaataaaa cttgtctcag taatgtggtt tagaagatgt    50220
acagacatgt gtgtgtgtgt gttaaaacat tcttggcat ggcaataaaa atacagtttt     50280
agccaggtgg ttgtggctca aaaaataatg ataataacaa taataaaaat aatgaaaaca    50340
gaggctggag agatggctca gcggttaaga cactgactg ctcttccaga ggtcctgagt      50400
tcagttccca gtaaccacat ggtggttcac agacatctgt aatgggatct gatgccctct    50460
tctgatgtgt gtctggaaac agctacagtg aaagtcattg caaggacttt acaatagtga    50520
ccatgataac attgaagcta gacttgctac tactgctgag tgtgtctgct ggctcttttct   50580
aaggagtaat gttagctttt tgtcctaaat ttgtttcctt cctttcctct ctccctctgc    50640
```

```
tgttttttct tacccctctt ttactttgct ttccctctc  atctcctctc ttaacagagt  50700
tgtcctatgc agcccaaatg ccatcttcct gcctcagcct ccccagtgtt gaaaaatact  50760
cttccacag  gttatgttag gagactggag tctgctcagt cggggaggga gcctgggtca  50820
agttctgagc tcaattcctt ttcttcttt  cttctctct  ttcttcttt  cttctctct   50880
ttcttctttt ctttcttct  ttcttcttt  ctttcttct  ttcttctttt taagacaggg  50940
tttctttgta taccctggct gtcctggaac tcactttgta gctggcctgg aattcagaaa  51000
tctgcctgcc tctgcctccc aagtgctggg attaaaggtg tgcaccacca ctgcccagcc  51060
ctgggctcaa ttcttaacat tgtggagaga aagtattgt  agctgttctg gccacctgga  51120
attactttgt ttctgatctt ttgctgcagt caaatccttc tcatccatct ttcctcgtca  51180
ggctataata tagactctcc ttgcaatact tggaaatgct ctacagtcag ctacatcctc  51240
agtcctgctc ctatatttt  tcctaagctt ccttctaagg tctttattgg tttatgattt  51300
acacagaaca ttttttttc  ttgtctatag catgcgttag agtgatcgtt gccagataga  51360
ggaaagagaa atgagagaan nnnnnnnnn  nnnnnnnnnn nnnnnnnnnn nnnnnnnnnn  51420
nnnnnnnnnn nnnnnnnnnn nnnnnnnnnn nnnnnnnnnn nnnnnnnnnn nnnnnnnnnt  51480
cagctactga ttcctcctcc tccctcctcc ttcctccctc ctcccagcc  tcatgctctg  51540
ctcatcttgg acttctgcgc atgtcctcag cccagacctt ctgctcttgc ttctcctctc  51600
cccagcagcc ccccagttct cttcctgaaa cttctgaggt actctccatc acctcctttg  51660
gctcctgctc tgattggtgt cacctgctgg ataggcttgc tcctgactcc actgttcgtg  51720
tctcaattag ggaccctcac cctctgatat accacacatt tccctagtgt ctccacctcc  51780
cacccccacc ctatacgcac atacacactt agctgcatca ggatcctaca ccagggactt  51840
cttaccttc  taatcctccc caccggacac tgcccaggga cactgggct  ccagagggct  51900
attgccacac ggacacacag gagatctcat caaggagatg tgcctacccc agagggtagc  51960
tctcaccatt cacaagcaca ccacttctgc ctccagcttc tactctctcg caggaagtag  52020
ccagcccggt gccaagtatc cccaactaca tccccaaaat tctcagacac tgccagcctc  52080
cagctgtcag cctggccccg gctggcgggc gcctgctcct ggcatagcga ctagggtgta  52140
attagaaacc cgctagctcc ctaattgcca gttctgagct gtccttgtta ccggctgccc  52200
gaggcacaca tagaggaaaa ggctgagagc tgagccaggc tggcatggag gtagccctag  52260
tagacctaga gaggactggc atgtggccag ggaccaaacg tggcacagag agggctcagt  52320
gcaatctgcc ccgtgggtgc ctcccagcca catccatttg cccagaactg tgacgtcaaa  52380
ccagcccggc ccattcattc tttattcagg tggcataaaa atcactacaa aactttaca   52440
aaagagtctt gggagctaaa gggtcccttc cttgcctcag tccccaagat tcctggcagg  52500
ggaggacaag agagagaaga aggaggaaga ctcctggcag tgttggcatc tccaaatacc  52560
agagggtga  cttgggtgac aggacacagg ttggggacct gaatgtcttc agcaagggac  52620
actcttgtag ggtaggtcag cctccaacca tgaagtataa caccaaggcc agtctaagct  52680
tgggagacca acacttgtct ctcctttcc  cacccagggt gtctggaata tgtctaaaga  52740
tggcctctcc agcctctgct tacaaatgtg gagggaccct aagttaggga cttgcctaac  52800
ctacctctag ccaaaactgt gtccacaagt gccagcccac aaaagatcac ccctgagcc   52860
ccttgggaag aaatgaagat tccccatgcc tgccttcctc caggccccac cccacctgct  52920
gcaagagaac agcttctaca ctggtgatgg tccttccggt cccaccctat cccacaaagc  52980
```

-continued

```
tggttagaaa gagtcacagg agctgagagg ctgatccagg tggggactca ggatgctgct   53040
gcccagggcc cctcctcact tgggggagct gaactggggg tagtcttcct ccatgcgggg   53100
tgcaagtttc aagtcaggac caaaggtctt gcctccatgg aagtcagctt tgtcattctg   53160
gcctatgagc ctgttgtcag gggaatctcg ctgttcctgg agctggggca gcgcgctggg   53220
gttagggttc ctcacactgc ccacaaagag gggcacgcct atggtgtcct ccatgatgaa   53280
gaagaggaag ggtcggttca cagtgaagga ggagagggac attcgattca tggctacgct   53340
ggtagctgcg gctgcctcca caccagcctc gctgagctcc atggtagact gatgttgcac   53400
gctagacacc accagattct gctcagagat cccacgaagg tctgggccct ggaacaattc   53460
ctgcaggcct gcccagaaca gcagatgact ggtcagtgct gccccaaggc tatgtggatc   53520
tgtctagcat cctggctaaa gggaacactt gaacccagcg gttgattgga atctgttaga   53580
cctcagtcta gacaacactt ctagaaacct tttttttttt tttttttttt ttttaaatca   53640
ggatctgcgc taggtacagg acagaaagtc tagaggagca tatcaaatgc tcccatccag   53700
gaagcagggc cacctctggc tcaggcacac tggcagctcc cgtactctgc ccagaccacc   53760
taggggcacc ctatccccaa gctccttacc cagttggctg agggtggcca ccaggtccag   53820
ctgctgttgc agatggagtt taggcagcca caccttggtg ggcctctcct gcagcgaggg   53880
atggtacaga gtatcccagg tcaggttggc tagtacctcg acacgttcc  actcaaaata   53940 agtgggcatc acgaccacaa agctcatgtt gttcttaaag gggaaatgag ccacctacag   54000
ataagaaaag gagagaacat gaggaccaga cagcacctgg acctgtctgg agtctgggcc   54060
aaaattactt ctgtactttt gagacaagag ccagaaaattc agggttagca tgctttcact   54120
taactggtga agtggaataa taccacttac ccctttgcaa ggtgacatgg gaccaaatga   54180
gataatgctt ttacacctct ctgtgtgcac acataagcat atatgtttgt atcggtgtga   54240
gtgtgtttgc tcatgggtat atggagtcag aagtaggtaa acatcagtcg tcttcctaca   54300
ttgctctcca ctttttttttt tttttttttg gtgttgccat cttttgttg ttgttatttc   54360 aagacaggct ttctctgtgt agccctggct gtcctggaac tcactctgta atcaggctg   54420 gcctcgaact tgcagagacc cacctgcctc tgcctcctga gtgctgggat ctaagatgtg   54480
tgtaactaca catagctccc tcttttttgg acacagggtc tcatggatcc caagctggct   54540
ttgaaatgac tgtttggggc tggagagatg gctcagcggc taagaacact gactgctctt   54600
ccaaaggtcc tgagttcaaa tcccagcaac cacatggtgg ctcacaacca tccgtaacaa   54660
gatctgactc cctcttctgg agtgtctgaa gacagctaga gtgtacttac atgtaataaa   54720
taaattaatc ttttttaaaa agagaaagaa atgatggcta catacttctc tctcgtctct   54780
ctgccccaag tgctgggatt acagagctgt acaacaagcc caagtttgtt gtgttttaga   54840
catgctaatg tatcccaggc tgtcctcaga ctctctatgt aattcagaac gaccttgaac   54900
ttcttttaag gtttattttt atcttatgtg tatgggtatt ttgcctgagc atttgtctgt   54960
gtaccgtgtc cttgcagtac cctcacagtc cagaggaggg caccatttcc ccctgaactg   55020
gttgtgagct gcatggtggg tgctgggaat caaaccctgg tcctctgcaa gagaagccag   55080
taagtactct taactgctga gccacttctc caccttgagc ttttcttcct cctatctcga   55140
tctaaaagta ctagggatgg cggatgtgcg ttcatgtgcc tggtttatgt gttgctaagg   55200
gttgaacaaa gggctttgtg catgccaggc aagcactcaa caactgagct acacatcccg   55260
acagactttg actcttctag tagtagtgtc tccactacag cctgagttct ctatctgctg   55320
tcagcaagct gtacaaacaa gctatgggcc ttcctgtcct tgcctctcag ttctctccgc   55380
```

```
aggtggggct actggctttc aaaatgaccc atagaggagc cacagcaaac agtaggaagc    55440
ttgcccctcg tctttcaccc tctcccagag agtcagctat aattcgagtt ttttttttcct   55500 ctctctctct ttaaacagga tctggttatg tggccctaac tatcttcaac ttcagtcttc    55560
ctgcttcaac cttctgagtg ctgggattat ggtgtaagcc accacactca gctcacacaa    55620
cctttttttt tttttttttt tttaaagaat ccatgcagtt aggacagcat ggaaatgacc    55680
aggctcaggc ctccctgggt accagcataa tgcctgcagg cgggtcctct gccagtgggg    55740
ggatggaaag atgagccag aggatctttc ctctctgaac ctcaatgtcc cacagtgaga     55800
cactcatgtc cactgggaga tactgtagta ttcaaggaag aagcaacagg aaggtgagag    55860
ctaagtggag ctgagcaggc tcgtatcctc tcaccacggg ctacagagaa gtctggctgc    55920
cccctccaca tggctcctcc ctgcagaact ggcaatgctg ggcccggctt gcccagtcaa    55980
actaaccaac agaatggatg agcatgtgtg gtgccacaca cctgggaccc cagcactcag    56040
acagctgggg cagaagggtc atgagtccaa agcgaacttg tgtaacattg tcagaccctc    56100
gaacaaacaa aactagcccg tcctgttatc tcagccacag atgatgggcc caaggatcag    56160
tactctagcc aaggagtcac ggttaggcta gaagcaaggg aagccttagc tgagacagct    56220
tggcacggag cttcatccaa tcagaatgtt cagagcaata agctttgaaa cccgacttcc    56280
atctatgaag cactgtgtgg gaactcctct cttcccttac gagcagggcc ctggtcctct    56340
tgggctccgc taaaacccca gcacagagaa cagttacctg gcacgtgaca aaaactcaat    56400
atattttctt tgaggagatg aacctcaaag aagctgtgtc ctggatagac acagcataat    56460
aaacccttca ggagctacct acccagggac cagactttac ctcccagtac caggcctcgt    56520
ttgccagcca aaggcaaagt ccagactgac ctgtatctca ggttgctcca gcaggaacca    56580
tcgaagagga tatgacaccg cgtgcatcat gtccaccgac actgtgaacc gctcatccag    56640
gtggaagaaa tctttctggg tgaggctcgg gtcaaacttg gtcctccaga aacctgcagc    56700
caggcagagg gcaggagcca tgtaacataa aatcagcctn ctgcctgtct tgcctagaac    56760
ctatnnnnnn nnnnnnnnnn nnnnnnnnnn nnnnnnnnnn nnnnnnnnnn nnnnnnnnnn    56820
nnnnnnnnnn nnnnnnnnnn nnnnnnnnnn nnnnnnnnnn nnnnaaccaa ggcaggtctt    56880
ggaaaaagga atcttaaatt agaagatgcc ttgataagat tggcatgtag gtatgtctca    56940
ctaatgattg atgtggaaag tcacgaggga tggtgtcacc ctgggcagat ggcctggggt    57000
atataaaaac acaggctgaa caaaccacaa agcagtagtc ctcaatggct tctgctttag    57060
tttctgtctc aggttcctac cttgacttcc ctcagtgaag gcatgtcaca tgagagttgt    57120
aagaggaaat aaacccttc ctcccacat agttttggt tatgatgtta tatgtcaaca      57180
acagaaacta taactaatat agttggtttt ctttttttgt ttgttttgtt ttgttttgag    57240
acagggtttc tctgtatggc cctggctgtc ctggaactca cttttagac caggctggcc     57300 tcgaactcag aaatccacct gcctctgcct ctgcctccca agtggtggga ttaaaggcat    57360
gcgccaccat tgcctggctg gttttcttt tttttaata catttataat gcatttaga      57420 tttaaaaaaa aaaatggcca tggcatataa tataaaaga agtgcttaca aatcaccatg     57480
tgcccttgcc ataaattatg taaaaatttc catatggaca tcagtctcaa gcttacaatc    57540
tcagcactca tgagcctgag gcagaggcag gaggatggtg agctcaaggc cagcttagtc    57600
tacataacaa gatcctgtcc aaataataac aacagtaata atttcataca tagaactaga    57660 agggggccact gcaaagacag tatgacaaaa ccactggccc tgcctaattg tatttttaaat  57720
```

```
aactgtcctc ctctctgtaa ttttcagttt ctaattttta cataactacc atgtattctt    57780
tttgtaattt taattagttt tttaataata gaaacaagct aagtgctaag aatattttca    57840
tatgaacatt ttcaaggcac ttgatacata cctcagattt gccctccagg tgagcagtac    57900
caattacgtg ccaccagcaa tgttagcttc cttttttccc taccatctga ttctgtttca    57960
gtctattcgt agttctgatc ttgttatatc ccttttatt gtttccctgg gttccaacac     58020
ctcccagttg agtgttctca ttgaatttca ttagcagctg tttcattaat ggcacagaag    58080
aaggattaca gtgttaacta ggatagactt tgacaaagaa ctatgagaac atatcttatt    58140
atctttgcat aaattctttt taatcaaagt tcctcaaaag cctctctctg ttcccatctc    58200
agggagtagg tctggccact gatgagtgtc caggccacag tacaggtgtg cgtggttctg    58260
tccctgtggg aagggcacat ctgtgttgta acaggattcc tgtcttaaca agccttgctc    58320
aggctctaag tggtcctgag ctagctaact gcccttggct ttcccttgat taccagataa    58380
ctattcactc ttctcatttt gcagagcact taccaggtag ctatgtcctg gaagtacgaa    58440
tgagtccttc tattgttttt cttttactta aatcccattt gaaatgcgcc agggacactt    58500
caatccaagg tacactttg ctaaagaatc actcattttt atatgcaaaa tgtcacctat     58560
taactgcagc tgatatggta catacatatt ctctcttcct attatccact aataggtgac    58620
taatgcgaaa tattgagtaa tttttaaaaa tcaatactca atttttaga aataattaga    58680 gagacattca actctgacac cagcacccta ctcagttcct gagccttcct ctgccggagg    58740
agaatctata aataactcac gaagctgaca ttactcactg tgttgcagtc atttttttct    58800
gagaaaattt tagcaactgt tctaatagag cctgccagtt atcagtagtt gagaatgcaa    58860
gtcaactttt aattatgcag acgctgatta ttcagacgac aaattgttgg tgcctgcacg    58920
gctccttcct gctgcctacc tttaaccgtt ctcagtgctc attagcacat gttccagaag    58980
gtaggctttg gaggggcgga caggcactca aaccagctaa gcacttagag aagctctgat    59040
gaaagatgtt aatgcagttt gtagaattat tgactaaaat tgagtcattt ggattccctg    59100
tgaattgtat ttacatgccc tgtccctgtc ccccatagca acagataata ggattgtctg    59160
cagagagaca acatagttct tatatttaat ttttttccttt gtcgaacatt ttcacatgat   59220
ggttcgtggt gtttccttg ttcattacat ttgtatccag actagttact tctgataagc     59280
ggttagttag gattcctggc acgcggacag tgacaccaca gttgtctgat cgtttcccac    59340
ttttttacaa aaccgtttgc ctttaagagt cagtgttttg cacatttcac ccagattatt    59400
ggaaatatta tttccctcct gcttaaaccg aagctgtgat cataatttaa gcctttctag    59460
gtagccgatc ttacatgtat catacctatt tctggcatat gtttgtctat tacaaagacc    59520
tcgtaggtat gcagttagaa gcctctagtt aaatgaaatg ttgcgtgtgt gatgaacctg    59580 gagtgggat ggccttttgt gtgccccaag gctgttgtgt ttcacacagt tgttttctgc     59640
ctcctctggt ctatcactat cctgccactg ccagaaaacc ctgctgtgtg ttcccgcgt     59700 ggaggatctc tgcttctgaa cttctttggc ctgagaaact ccataaccaa atcagttagc    59760
attttgttta aagagcaggt aggctgttag agcttgggtc ttacatgtct cccaggtcca    59820
cttgccagcg ccttgaccac tgttaacttt tgttaaccaa ctcatctttt gctgcctgtt    59880
ttttgggggg ttttttttggt tttgtttaag ccaagatcag ttatatggcc caggctgagc   59940
ctctcttccc agcctctcaa atgttagaat tacaagcatg catccctcag catacctttc    60000 cttttgctttt tttaaaatag agttttgcca tagcaacaga aatctaacct aactaagcat   60060
agccgtgcac atggtatgag gaactcacat atgtgtgaat ggaagttcat agagaccggc    60120
```

-continued

```
atcactgcct agaggcccct ttcttccttc cttgcagttg tcgtgctagc tgactgtact    60180
acaaaagagg ttgtctgagg cataagacta ccttcaataa acatgcaca gacagtttgc    60240
ttctctgaga tttcagagca gtgactacct tcaataaaac atggacagac ggtttgctta    60300
cctgagactg cagagcagtt tccaaaaatt ttagacaaag ggtaggatga agaaggctgc    60360
ggggttttgc acacacttaa ggtgcgtaag taaatgaaact gagctacact gacaggatgc    60420
tcgttctagt agccaaccaa agagcagttg aaccaaagca cctagacttc aaacatcgtg    60480
gggagataat cttaggagtg ctatgcttct gcgtcctaca agtattatga aactgtctag    60540
aaagcacccc actggtaatc ccttttttgat tattttttttt ataaattcta gtcttgggt    60600
tttgagtggc acacagacat aatggttagg cttcggtgtg tgctcattca ctttgcttcc    60660
tggggaccag agtttgcgat gagtcatgtt ccatctgatt tctgtcggat ccggctgcag    60720
agccatgact cagatgggct tcaggcccag ctgctcagtt catcttctgg ggaatagatg    60780
acaaggacgg gacaaatgtc ctgacgcaca tttccttctg ttcttgcact tccagggtct    60840
aacgagagca tcattaccaa cagcaggcag atacgcctgg ccacaggcat cttccctgtt    60900
gtcagcctcc tgaaccactc ctgcaggccc aacaccagtg tgtccttcac tggcactgtc    60960
gccaccgtcc gggcagcaca gaggatcgca aaaggacagg agattctgca ctgctatggt    61020
gagccagcct ttctttccac taccctgctg tgcctcacac ctcacatgaa aaggataagg    61080
ggacaggaat cagcagatat gggcccagtg cctctactca tcctctgagt ctttcctgga    61140
aagggcaatg catccttggg ccaataaaaa aggtcttctg gctgtaataa aaaagcccgt    61200
tgagggcagt gagccatatc cctccatgcc ttgtagacag cctatcctga aaatgagcga    61260
ggagcacttt cttggcttct ttcttcctgc cccagcagct tggaaacgta tccactttca    61320
cccgtgtttt gttgtttttt ctgagatgat agggcagagt acccaacctc atataggcta    61380
ggctagtgtc tatcactgag ccaggacccc aacccagcac caccatgcca gtcacgtgat    61440
gactaggcca gccctcggt agagtaggca ttgactctct tggtgtgact aggaactgtg    61500
ggtaatctct ctccagggcc tcacgagagc cggatgggcg ttgctgagag gcagcagagg    61560
ctgagttctc agtacttctt tgactgccgc tgtgggcct gtcacgctga gacactgaga    61620
gcagctgcag ctcccagatg ggaagccttc tgttgtaaga cttgcagagc gctcatgcag    61680
gtaaatctct gctgttccca ggggcagggc tccagctaaa ggttgtcagt cgccaggaga    61740
accattcctg cttcccttct tgtaactcct ccctacatgt cgcccggtcc tgcagaaaac    61800
acaggttgta tttcctaata ttttccctat aagtgacaca aaatcttaaa ttacacaaag    61860
ggaccaaaaa aaaaaaaaaa aaaaaagccc tagaaattta cttgctcaaa taagtcatca    61920
aaagttgtgc atcaggccta gcacttgggt actggtaacc ctagcactca ggaggctgag    61980
gaagaaggat ctcaagtcgg aggccagtct caagtgacac cccatctaag agatcaccat    62040
tccaaggagc tatttcagag atggtttaat ctggggaccc agattgtgga ttttctgtct    62100
gttcaattcc atctctctgt gctggcctca tcagacacac tctgtagtaa ctgtgggaaa    62160
atccgaccca catagttttc cctcagcctt tgacccagag ggaagagcca cagtggagag    62220
catgagagca gacccttggg tgctactgcc aggtaatggt gtagacactg gagtcttcaa    62280
cattcatgcc ccaatgcaaa atggtctcca caccagagca tggcattctc attagaaata    62340
agtaaatgga attggctgtg ttgaaaattg taaagccaag ggtcaagaat gaagccttcc    62400
ccagcatgtt ttgtttttgtt tgtgttttta ggcagcgtct ctctgtgtag ccttggctcc    62460
```

```
tgccctctgc tacctctccc aggtgtgcca ccatgctggg cctaagcgcc ctgtgcatta    62520
gtgctccctc gatcctgctc actcttgaga cagtcttcct tctactctgt atccccagat    62580
aacctagagt tcacttcaga gcccaggctg gcctcaaact tgagatcctc gtgtcccagc    62640
ttctcaaatg cagtgatatt tacaggccta cacctggctt tccctgatag attcctagta    62700
agatgattat cctttgagcc atatctctct tctgcttctt cctctcttcc tgcagggttg    62760
atctagaatt tattctaaag ctgactggcc tcagaattgc catccttctg cctttagnnn    62820
nnnnnnnnnn nnnnnnnnnn nnnnnnnnnn nnnnnnnnnn nnnnnnnnnn nnnnnnnnnn    62880
nnnnnnnnnn nnnnnnnnnn nnnnnnnnnn nnnnnnnaca tagtgtcaac tttcaaattc    62940
tgccttaaga gttctttgtt tatgggaatt tatgggaatg ttccacagaa cccatccagc    63000
ggagttctgg ctgttgtttt ttaatcttta ttcatcttgc gtgtgtgtgt gtgtgtgtgt    63060
gtgtgtatgc gcgcgtgctc aacttgcaaa attgcaaaat tcagtctcct ctttccaccc    63120
tgtaggtcct ggggatcaga ctctgttagg cttggtggta ggtgctttac tgagccatct    63180
tacaggcccc ccatggacaa cttttttcttt gaaaacctgt ttctggcttg ggtgtgatag    63240
ctcacacctg tgaccctacc accactcatg aggaagaggg aggaggacta acagaattgg    63300
aagccagcct ggactacaca gtgagtaaag gctatctata tactcaccac atggcaagac    63360
cccgttttaa aacactgggc aaggtgaaac aaaagtcaat taatttcaca taaagtcaat    63420
agcttcatta acggcctagt tatctttaaa actgtatgca ggttagtact tggtttcaat    63480
tttattactt tttctctgga acatttaaaa gtacttttagg ggctggagag tcagttaaga    63540
acagtggctg ctgccaaagg actggagttc actcccaagc acccaggtgg caatcacaac    63600
tgtctgtcat ctaattctag gggatctgac cccctcacag actcacaggc agtggaacac    63660
caatgtacat aaaataataa ttaaaaaaat gaaataaaat accaggcaag gtggcacacg    63720
cctttaaccc cagcactcag gaggcagagg caggcagatt tctgaattcg aaggcagcct    63780
ggtctacaga gtgagttcca ggacagccag ggctatacag agaaaccctg tctcaaaaaa    63840
aaaaaaaaaa aaggacttta aattgggctg gagagatgga ttaaaagcat tggctgctct    63900
tcccagaggt cctgggttca attcccagca ctcaaatggt ggctcacaac tgtctatatc    63960
aacgcaatct aacaccctct tcaggcatgc aggttacatg tagacaaaac atccatatgc    64020
ataaaataca taagtaaatg agtctttttaa tgtatactag aagctgggtg gtggtgcatg    64080
cctttaatcc cagcacttgg gaggcagagg caggtggatc tctgagttgg aggccagcct    64140
ggtctgagta aatagagcct tgtacttcta cttatcacta cagttacatt ttataacttt    64200
gggccctagt gcttccattt tccactgttt gcttaaccac tggggcctga agcttttgtg    64260
ctgacacttt tgttcgctaa tcatcaggca accaatggtc tctacactcc atcaccatca    64320
acacaaacaa aacaaaacac aacactacgg atcctggcat ggtggaacat ctttagcccc    64380
agtacgtggg cttgagttca aggccggcct ggtctacata gcaagttcta ggatagtagg    64440
gatagtcttt aaaacaaaac actattttat ttatgaacaa acatgtaaa gaaagaaaaa    64500 aaactgcaaa tttatctatg aatgaagtct aagtaatact tcaatattgg aaatagcttt    64560 ctaaatatt tttatttaaa gaaaactcag caaattattc aaacaacctt ataaacgttc    64620
gttataaaag taaagaatta tttgcaattg ccttaagggt ccaaggtggc agcctcttaa    64680
aattcagaac aatccaagct tcacattcca gttcaacatt tctacagccc taacgtattc    64740
aaatacctcc attctgacaa ctgtttcccc tcttcttttc ttctaagctg cttagatgtc    64800
tgtcccaggc ttttcatgat tttagtcatt cacacaacta gcaaacatta tctagggact    64860
```

```
aaaacttgcc agatactggg atatcaccct aaagggggac tgaaagtagc tgcaggctac   64920
agtctctaca atctcctgaa tgaaatacaa agtagctaat atttaccaaa taaacatgta   64980
cacctgtgat gattgctagc tgtactagca gaagctaaac actaaatcta gaaactcagt   65040
cctccaacta gccccttgct cggcttcagc ctcattttta caaacaaggg aaagagtttg   65100
gaatgttgcc caaagccata cataagtgaa caaaaaggag ttggagtctc caaatgcatg   65160
gatttgggct agttactttg ccaaccaact cagtaacaac tgagctgaac aggaacactg   65220
tggtagcaaa agaaactgga actatcaatg gcctctagag caaaaatata tttaaaaga    65280 aaaaaacaaa caaggcctgg caaggagact gtgagaagag tgtgctgact gaaattgact   65340
agttcagcca acaaaagact attccagggc tggtgagatg ctcagtggga taagagcacc   65400
cgactgctct tccgaaggtc aggagttcaa atcccagcaa ccacatggtg gctcacaacc   65460
atccgtaaca agatctgact ccctcttctg gagtgtatga agacagctac agtgtactta   65520
catataatca ataaataaat ctttaaaaaa aaaaaagact attccagtgg ggatggaaaa   65580
gttaagtgtg gagttaaaat atacttcaac tggtgatgga ctaggtgtcc agagtcgggc   65640
aaaaggatgc tctgtggtag aggtgcctgc tgtgtaagcc cagctacctg agctcaatcc   65700
acagaatcca cagcggagtg ggaagagaaa caacgtccca gagttgtcct ctggcatccg   65760
acgcacattc gccatcccca agatgtcata catatgtgta catactacac actggcgcac   65820
gcgcacacac actctttttt aaaattcaga cttagaggga cataaaggat ttgctctgat   65880
atatgttcaa ttgaaaatga ctttgaagat agagggcaga tcgaaggaag ctcagcagga   65940
aagaattaat aacatgcagg tgaagggcta taaactagtc tgcagagggc cttggctcga   66000
caaaaaaatc tatggggttt gccggtaaaa taaggaaaaa gttgtcaaca tgaaacacag   66060
aacactagca agagaggagt gttagcagaa agaagccaac aagctcaaac aattaggtcg   66120
gctgaaaaat tttaaaatgt cttctgattt ggctactggg aagccactgg tgacttcggt   66180
cagcgttttc tctctcgtga ccagagagat gtctagtagc aataatgagt taggaggatg   66240
taaaagaagt aaaacagccg aaaacaagtc caaaagtttt ggggtgatgg agaaaggag    66300 gaaacagagg ccgccgaaga tagacagcgg catgtttatt tgtcttgttt tcttagatgt   66360
aaacaaacta aaaaaactcg tgagttcttc tgccagtacc gggttgcctc cagcatcctc   66420
tgatggtctt agagaccccg ggatgctccc ccgcggccgt ataatttcct ccctgacgct   66480 ctccgatcg acacggctc cctcccgg tcctcttgc accgctccaa ggccgcgctg   66540
ctagggccat cgagcccgct cagggtcgtc tccttacctc gatggcccc tcgctcaggt   66600 gtccaccat ggctgcaccg ctaactcccg cgctcgcgct cttgcaccgc ctgagcttct   66660
ctgccggggt cccgcgggct gctcaacgat tggctagagc aactgtgcgt gccgatccgc   66720
ccccagcgtg agcgcggtgc gaggggcggg cctagacgcc gatagccacc gcattggcta   66780
ccgcgcggca ggcagagcac gtgactcttc cgaggccggg ttcgaggcct agtggcggga   66840
tggcgggacg tgagggcggg gcgctgggtc gcagtgcgcc tgtgtcagcg cggtgctact   66900
gagttgttcc cccgccagct gtcggaactt tgcccgccca gtcctttggc ggacagacag   66960
aatggcaacc cagggaacag tcggagctct cccctggtaa ctgctgctaa atatagtcaa   67020
agcagtgacc tgggtacttc ttcacgcagt gcgtgcccgg cgccggtgcc aggcccagag   67080
cttggcactg tgggataaac aaggtaaatc agactcagtc tccgccctct tgagttccac   67140
ctgagagttg tggccgcaag gaacccagcc tcaaggatgg tagacgcgat atgggccaca   67200
```

```
catgtggagc tccagagtgg gggtcaaaaa tcaatcaggc tttcgagagg cgatgcggtt    67260
tgaactgagt taaagtgtgt gtagaaattt gtcaggtgga ttccagtgag gatagtgatg    67320
ttcctaaaag cccaaatggc ctatgcaaaa gtattggaga gcctggcgtg ctggctggct    67380
ctgatctgtt tgtaatccca gcctttggga tgtagaagca gcaaaagttc aaggtcaccc    67440
ttaacaccgt tgagttcgag gtcaacctga actaaatgag accctgaaaa atcaaaattt    67500
gggacccagg cgtggtggca ttcgaggtaa aagcaggcag atctctgagt tcgaagccag    67560
ccaggctaac ataagatccg gtctcaaaaa aaaaaagtaa taaaaataaa aaggagagag    67620
ggctatatga actgaaagaa agacctggag atcaaaacag aaaactgagc cgtctaagaa    67680
atgaaaatat ttaacttcat agttgctgga gtaagaagtc tggaaaactt tgggcaacta    67740
aggtaaacag gtctagaaag actggaatag tagccatcta ctggtatttt gatctctgtt    67800
tgtacaacca caacctacta tagttttctca aacagttcca aagaatatgt ctgggtgaat    67860
tggtaccaca ccacagatta actctccttc agcatatcaa cagctataga aaacccagaa    67920
agaaatgatt ttggttgcgt gtcacttggt aggatgaaat ctcgattttc tagaactatg    67980
cattaataga aagctgaatc ttcatgttct gactttacag agctgcggca gcatggatct    68040
accggtggat gaatggaagt cctacctact taagaagtgg gcttcactcc cgaagtctgt    68100
gcaggacaca atttctacag cagagacttt gagcgacatc ttccttcctt cttcttccct    68160
tcttcagtaa gtgaatggaa acttcaggga aattttggtc tggaaaatgt tctgccttgt    68220
catttggtct gaatatctct tttttatagg agagagtagc tttatattct ttatagtatg    68280
gggcatttag cagttactgt tggttttcac gtttctccct agtctgtgat tactagaatg    68340
ggtaggcact aactgctttc ctcttttggc atgtgtttata cttaaggaat gtagtatctt    68400
gctgtcgtcc cagtgctgtc actcatagga tctggtgcag gttgtgtagc tgcccctaga    68460
agctcattca gtcctaatgg ggagaaagaa ccctggcact tggttagttg agacccanaa    68520
cttctcaagt tctnnnnnnn nnnnnnnnnn nnnnnnnnnn nnnnnnnnnn nnnnnnnnnn    68580
nnnnnnnnnn nnnnnnnnnn nnnnnnnnnn nnnnnnnnnn nnnnnnnnnn nnntttagtt    68640
tccaagtgcc actttactgc aatgtgtcac cacatccaga gttctgtgtt tgtttatttg    68700
tctgtttttg agacagggtt tctctgtgta gccctggctg tcctggaact cactctgtag    68760
accaggctac cctcaaattc actgagatct gcctgcctct gcctccagag tgctgctgta    68820
cactaccacc acccatccag ctttctatat tggttttcct atggcgtttt aaaatagcca    68880
ttatacgtgt gtttatcatc taaagtcctg gtcccaaaag gagatgagag gggctgctaa    68940
ggtgaaaagg attacaaacg cttatcaatt ctgttcaaaa attaaacctc agagtgggat    69000
tagctgcttc tttcattaga attgctatca gaattcactc aggccttgtt tgcgtgtgtt    69060
attgaagaag tctcttcctc atcaggtcag tgactcctta gctcaagtac atgcaatatg    69120
cagtattgat aactgttctc gcttaggaat aaaaatagaa ctgacttcca cagggaaatg    69180
atgtgctgag ctgtagcaac gaatcttgca caaactctgt cagcagggac cagctagtct    69240
ctcgcctgca ggaccttcag caacaggtct gcatggccca gaagcttctc cgaaccggta    69300
aaccaggtga gattggctcc ctcgccctag gcctcagccc ttcccttgtt tattttggta    69360
tcaccttgcc ttactgagca gtcctcaata aatgactgag gacttgaatt taattatccc    69420
agcaccagcc acaagatggc tatgtaggcc agtgagacca gactgtgacc agctgttact    69480
ctggtgccct tgaaagtctt cctgatggtt taagctgtgt ctgctgcgcc agatagttct    69540
agcagctcga gcaccagaaa ggctgtctga cttccatggg cttttgtgtgg ctccagaggt    69600
```

```
ccaatgccat catctgattc ccagcttaag gacctaagct ccgagaaggt tgctctgccc    69660
tcagcagcag cagcaagtcc tgagtgctgc ctgggctcgt ggtgtgactc aggagtagag    69720
ctcggtagct agcctgagct gagagctgag agaaagaaag gactcctctc ttttcagaaa    69780
gggatttgca gaactcgatg ttagaccctg acatggtagg aatctgtttt gactattcta    69840
gcctagattc tgaagttgac ctttagccta gagtcaagaa aactaatgat tacaggagga    69900
atgtagagtt ggttgttaaa tgttggttgg aaaatggatg ttagaagccc agggtaaatg    69960
tgaggaagcc tcatctaaca cctcttttac tgaaagagaa aacataagca accaacagct    70020
tccctggaat gcccggctgt tgactccgtg agataaagag gcattttcac tttgacctaa    70080
ccgatagaga ccttgcaacg tggtctctcg tgtccaggac tagatctgta tctgttgtga    70140 ggcattttc ctttgaatcc atagagcaag ccattcagca gttgttgcgg tgccgggagg    70200
ctgctgagag cttcttgtca gcagagcaca ccgtactggg ggaaattgaa gatggcctgg    70260
cccaggccca tgctacctta ggtatgctac cttaggtata gccggagttc tccttccctg    70320
ccgtgtgttc agtgcggccc ttgccttgtc tgtttggttc tctcttgcca tctgaattga    70380
cgctcttctc cctcccattc tgcattcctt gcccccagag ccttaggcta atggtgtttc    70440
ttttccggaa tgagacattt ctcttctcac agggaactgg ctaaagtctg ctcccatgt     70500 acagaagagt ctccaggtgg ttgaaactcg ccatgggcca tccagtgttg aaattggcca    70560
tgagctcttc aaactggccc aagtcctatt caatgggtag gccttttcttt ttcctagtgt    70620 ttggccaggg cacacagtgc tctgtgtttt cctaggtgct tctgtgtatg gcttttgct     70680 acagtgcttt aaagcatgtt gaaactcttt tatttcctct ttaggacaga tatttgccct    70740
ctgcttcact gatagacttt aagctttgaa ttccttcctg aggatgtgga gaaagccatt    70800
aggtctgcat ggagcttccc agggaggatt tggaggcagc ctcacccgcc tctagcattc    70860
ctgtctgctt aatcacacct cccttggctg cctcagtccc tgctctctca actccagggc    70920
tcggcccttt ccctggtttg cctcttattc cttttaaagc agtggttttc aactagaagg    70980
gattgcaaat ggcatttggc agtgtttaga gacagttttg attgttatgg ctgccagcat    71040
ctagtaaagg ctaaacctac agtgcacagg accgcctcca cagtggagag acccaagtta    71100
gctatgtgaa ggctgagaat ccctgctttg gagattaaaa aaggaagctg agggaaccac    71160
tcagttggaa gcaccttgg tggcatgcac aaggccctgg ttctgtccct agctctgcac     71220
aaaaaataga atacaaggaa gagtaaccct aatgagctgg tccctcaccc agtgtgccac    71280
tgaggtcact tgaagggaag tctagcccca atttagtatt ttttgtggct gccataccte    71340 cagccttgat caaatctcat ggtatacatt ggtaagaaaa agggtttgaa acatagacct    71400
gatactcgga catggaaaca gtatgtttgg tcagagagag cgaaggacct gatagacgag    71460
ggcaatatca gagagagggc atcagtcggg ttagacacga gcattccaca gtgagcagct    71520
ctggataagc tttttataaat gctggttaag gttttgaatt tgcccaattt tgtcaggatc    71580
ccagagtcta tcacaaacat acacagtttt ctcaaatctg ctttgcagta tgcccgtgaa    71640
tgtctcttat ctatactttc agatggtaag accctgaggg cagaggaact cagacccttt    71700 gtgcccctg taagccctg ggggatgcag tggacccgac tttgtgttct ctgcacagaa      71760
aggagtccac tttcgttgag actaaggaag ggaactgaca agcttccctt tctggcttca    71820
ggttggcagt gcctgaagct ctgagtgcca tctggaaggc agaaaggatc ctgttggtgc    71880
actgtggccc tgagagtgag gaggtccggg agctccggga aatgaggtcc tgcttactgg    71940
```

-continued

```
actcgtcatt cgtccctgtg gggcccttgg tgtagagcaa tcatcctcac cctcaagaag    72000
gagctctggt gatgactgag atgttctgtt ggcttggagc tctcatcaga gaggacggga    72060
ccttcccacc tgacctgagc ctagtgtctg cacagagag cacttgaaaa cagattgaga     72120
cactcacctg ccatgctggc tgctgcttgc aagagctaac tgccctctga tggaaacccc    72180
atgcccagaa aagactaaat ccagtatcta aaggctgctt taaagggttg tcactgcagc    72240
cgggcttggt ggcacacgcc tttaatccca gcactcggga ggcaggcgga tttctgagtt    72300
caaggccagc ctggtctaca aagtgagttc taggacagcc agggctacag agaaaccctg    72360
tcttgaaaaa ccaaaaaaat aaaaaataaa aataagtaaa aaataaataa ataaataaat    72420
aaagggttgt cactgatctg caggcagctc atgctagcct aggcttttgg ctcgatttca    72480
tctcactaaa cgatgaatct gtttccctgg aacattccta tggtttctag tagtaatgaa    72540
gtgctgtgtt ccactccagt gagaacttca attcttagtc ttgtattata attgaaaaat    72600
aatatatagc aagaaatcag tatgactgct tacctcaaga gacatacaat tccacttaca    72660
atatcctgct tccttaaatt tttcattaag actggtgata tataatttgt gaatggagaa    72720
ataaatacgt cttactgttg gcagtttctt cctgggatgg caactctgta ttggtttcct    72780
accagtgtcc taattcttac tcagtggctt tcattgagtg ttcttggcac tcactgtcca    72840
agcactgatg caaggcaacc ctgtagcatg acttcatagc acaggcctcc ttgttagcac    72900
acctgaaagc agaccactct ggctgtttca cttgcagaca gaatcttact ctgtaagcca    72960
gtctagcctc aaacaacatc ctcctgcctc agccttccaa gttctaggtt tataggaaaa    73020
ggccaccttg cccagcttga gactgcttct tactgccatg tctcttcagg ctcacacatg    73080
aagtccaggg cactccagga ggagccgtga gtctgtctgc agggcactcc aggggagcc    73140
atgagtctgt ctgcagggca ctccaggagg agccgtgagt ctgtctgcag ggcactccag    73200
gggaagccgt gagtctgtct gcagggcact ccaggggag ccatgagtct gtctgcaggg    73260
cactccaggg ggagccatga gtctgtctgc aaggcattcc aagagcagcc atgggcgtca    73320
ctcattggta gactgtgagg ctacatctcc agatgccccg agtgctgtgg ttgtgagcac    73380
tgctgctcat ggtttccaac tgagacagag ggaaggactt tgccccttc cctaaggatg     73440
ggtagtaata gtccagacca caagggacag atagctatgg ggttttctga ctcatcctta    73500
gtacattatt gctgatgacc agtttgtttg gatgagttag tgggaaagaa gacccaagtc    73560
catacactct gcttttttaga acttgctcat cctagccatg cccaaggagc agccgttgac    73620
tgtcatggca ttacagtgag gaaataaaca gtcctgaagg tgcctggcag cagcttttca    73680
agaagctggt gttaaaagac agtattcaaa catctgcgga ctgggaactg ggcagcattt    73740
gagtctcctg ctgtctgtta atttaccctg acaaggaggt gacttgaaag gtttgttttg    73800
tttggggtag agcttttttca ggaaaaaagt ttagtcctac agacaactct atagttattc    73860
tagtccaaac tcatgccttg tgttttattc ctaaaagccc tgtcacactt tgtaaaatag    73920
gtgctcttcc tcaaaggata tatttaacgt tttatatatc aggccttatt ctgtgcatgg    73980
aagctttttt tagatgcttt gtaagatggc tcagtggtta agagcatgta ctgctcttct    74040
ggaagtcctg ggtttgattc tcagcagcta acaccagctg ttattccagt tcctgggatc    74100
tgatgccctc ttctggccta tgtgagcact gcatgtgcgt agtgcacaga caaatgcagg    74160
caaagcactc atacataaaa ctaaattcaa aaaactcttt cattgtctca tgtgacctag    74220
cttgagaata cctgtgctta tattataatc tagtatgagc cagccacggt agcaacacac    74280
ctattatctc agcactcaga agattgagac tagatggtca agagctagag tctgggttac    74340
```

```
aaaacacctg tctcaaaagt aaagggctg aaaaagtgtc tcagcagcta agagcacaca    74400
ctgcttctcc agagggcctc atttcagttc ctaatacccca caccgagtga ctcaaccacc   74460
tgtaactcca ggtccatgag atccaacacc tctggtcgtc tgcataagct cctacactca    74520
attatacaga gagagagaga gagagagaga gnnnnnnnnn nnnnnnnnnn nnnnnnnnnn   74580
nnnnnnnnnn nnnnnnnnnn nnnnnnnnnn nnnnnnnnnn nnnnnnnnnn nnnnnnnnnn   74640
nnnnnnnnnn ntctagagtg tttcaggttt tttttgtttt ttttttttttt gagacaaggt   74700 ctctctatta tgctgcctgg aactttctat gtagaccagg ctggactcaa acttatagtg    74760
atccactact tctgcctctc agtactggta ttgaaggcat gtgtcaccac accccactac    74820
ttcaagatct tagatttcca agaagccgt agcctagaaa aggttaataa gtactgattt     74880
aaaacagaaa gaaatcaggt acacttagag ctgtagaatg tcagcatgtg acatttgtga    74940
caagttgtca aaactttgct cttaattcta aagagagaag ctgtcaaaag acttgaactg    75000
gggctgtagc caacttggtc gagcccttgc atgaagctgt gtgtttactc cccagcactg    75060
tggggtttga attgatttga acccagtaga ttcgtatatt tgaatgttta cctcatgggg    75120
aatgacatat tacaaggtgt ggccttgttg gaggaattgt caatttgggg gtgagctttg    75180
aggtctctct gctcaagctc tgcccagggt agaaagggag cctcctcctg gctgtctaca    75240
gaggacatag tctcctggct gccttcagat caagatgtag aactcttggc tcctccagca    75300
ccaagtctgc ctgcacaatg ccatgcttcc taccatgatg ataatgaact gaacctctga    75360
aactgtaagc cagcccccaat taaatgtttg tctttataag agttgccttg gtcatggtgt    75420
ctcttcataa caataaaagc ctaactaaaa cacattcctg ctgggcagtg gtggtgcacg    75480
cctttaatcc cagcacttgg gaggcagagg caggaggatt tctgagttcg aggccagcct    75540
ggtctacaga gtgagttcca gaacagccag ggctacacag agaaaccctg tctcaaaaaa    75600
aaaacaaaaa caaacaagca aacaaatgcc agcatttggg aggtagagtt aagaagattg    75660
ggagtacaaa gtcgtctcag ctagtatgtt tgaggccagc atggaccaca tgagacgttc    75720
tcaaaacgaa agaaacgaat gaatagataa acatttgagt gtccagtttt ttcctttctt    75780
tcttgctttg ttttttggcgg tgctgaggat taaacccagg accttgttca tactaggcaa    75840
gcattctcca ctgaggaaca ccctggcgag tgcctagtct gtctgtctgc ctgcctgcct    75900
gcctgcctgc ctgcttgtta tgtgtatgag tggtaacctg catgtctgtc tgtataccac    75960
agacatgcct ggtatctgca gaggccagaa gaggatgttg gatcgcctgg aactgggatt    76020
acaaatggtt gtaagctgcc atgtaggtat tcagaattga acctggtgct ctgaaagagc    76080
agccagtgct cttgttgttg gttttattgg gggcaggagg tagttatttg gttggttggt    76140
tggttggttg gttggttggt tttcttgaga cagggtttct ctatgtagcc ttggctgtcc    76200
tggaacttgc tctgtaggct caaactcaga gatctgcctg ccctgcctc ccgagtgctg     76260 ggataaagtc atgtgccacc aactccagac aagcagccag tactcttaac cactgagcca    76320
tcattccagc cctttctttgt gttttgagat ggtcacaaag tacaactcag actgagctct    76380
tgatcaccct ccctcagcct cctgactgct gggggttaca ggtgtgtcac tgtcctcaat    76440
tctgagtgtc agatcttgaa aacccattct cgtgaccttg atccttaaaa caaaccctgg    76500
gagaatgagt tctgataact atttctcact cctcttcaag aaaaggaaag ccagagaaag    76560
gggggggggc aagccccaga aacattgata acttgcccaa agttacacag caaaattcag    76620
acagcctgca catctcagtg gccatctgtg ccatatccac cctgcccttc tctgacctcc    76680
```

```
ccacctccat ccctacagac cttgcagttg agatcagagt ccaagccgta tcgtaagatg   76740
gccttaggat ctgacatcat ggggactctc acggtcctgt cctcgtccaa atgaaaatcc   76800
tggagggtcg tctttctcga gtcaaacttg gttacccact gccctggaag gaaacagatg   76860
gagcatcctg agccactgtc cccagaaagg ccacaggtcc acgctgtgcg tccactggcc   76920
aaagcaacct gagctgtcag cagcaagaac acaggagccg ctgggtccca gcatgtgtgg   76980
cacagaccat aggctccatg caccacgggt tctggctatc ctcctgtagt aaactcagaa   77040
ataagtgggt gttctctctc tgacttggat caccacgctc cttctgttta aagtggcctt   77100
taatatgctg gtgtgtggta cgtgcctgct ctcctgtccc ctgggacttg ggagtaggaa   77160
gccccagggc tttcctctaa gttaggatcc actcttgcta ctactccata agatggtcac   77220
aaagcaacgt aaaatggaaa ttaatcaaac cattcctgcc acaagaataa aacagatctc   77280
aggggaggcc tgtggaaggg tctcctgagg ccttaccact gtctagaagg aagttgacag   77340
cagttcttga gcagggtgc gactccagga gttgggggct gctctgagag caggacagca   77400
tgtattgtag agtgtctggg agggagctgt gttatcctta ccgtgaagat gaggacacgg   77460
gctcatgggg gcagagccag gattaaacct ggtctgattc aaaaagccag agatctgtgc   77520
ccagccccac gcagccattt cactggtcaa ctaattcaga aacacttggt ctgatatgct   77580
catatgctac aagcactgtg gccttcagat ctccctctgg cctggtacct gcattcaggt   77640
tcaccaccat caccacacac acacacacac acacacacac acactcggcc agagacaagt   77700
ggggaagccc tcacccttga agtaagccac gccaaggaga aggatgctga gggcactggg   77760
catttccctc gtggaccggg caatcttccc tttcatctgg gcctgcaccc agttgttaat   77820
ctcctgaagg tctactcgag ggttgcccgt gaggatccgg ggcctggtcc cataggactt   77880
ctccagaggg gcaacaaagc tggatttgac tcgaagttct tgagaggaaa cagatcaaag   77940
atgagagctg aatcagcacc ctcactttga aagcatgcca gacccagct tcctgctcag   78000 catcttcctt tgacttgctg gggcatctgc cggcttgccc agaccctggc tagggaacag   78060
tggattccac cgtttgcatt ccccgtccca ggccctcctg ctgtctccca gagcccactt   78120
cctctttctg ttcctctgtg gtctcactgg ctctttcctg cccaccagtg ccaggcctcg   78180
cctgagcaca cacagcctat tgtttagaca tcatggaagc atacagacaa cccaggccaa   78240
tgaagcaact tcacgccagg cataatgggg cgtgcctgcc cttcagaagc agaggcagct   78300
ttatgagttg ggggaccagc tgagactcta tagactttga gaggtggggt ggggtgggg    78360 ctactgactc ctctcaaaca caattctgga agcactcttg aggttcttct cagggcagt    78420 aacagaggca aggagctcct tgtaggtgct gtggatgtca gggttggtga tcaggtcgta   78480
gtagagagcc cggtgaatga cagactctgt tcgatgttca gctcctgcca gagagaaaag   78540
gatgccaagc ttcataactg cccgtgaggc ccgcatcagg ataggacgt tagacatcaa    78600 tccttttgtc ctctgagagc ccgaggaggc cgatattgca gatgtttag ctggacaaga    78660 tcttcagggc gtggaaagaa ataatgaccg ccttgctagg aagagctcta agacagggca   78720
aggttatcag agctacagag agaagagtgg gatgtggtcc tgaagttctc ccatcgtaac   78780
ctaccctgtt ctgaggagga gccagctctg ctcacggcag ctgtacccct agaacctggt   78840
taaatgacta aaacacgata ggaggccact taaggaacca aggtcgagtg ccacttacaa   78900
agtggtaggg attgtgtgtg tggcccccac cgccccttc ctgttcctct gacggcggca   78960
gcatggaaac tctgagtggg ggaaattcag gtccacctgc agccttcttc agttgacact   79020
cacccagaga aagggcagag agggccgtgg ccacgctgag tggagacagc aggacgttgc   79080
```

```
                                                       -continued ccgttgggct ggcactggat ctcaggcggt acagatcgta gccgaagttg gagacagctg   79140
ctgccagctt gttcacaggg accttgaaga aggggtcctc ctcctccacg ggctcgcccg   79200
tgctgtccgg gactggggag ccctgggtta gaatacaagg accagtaggg aggcacagtg   79260
agtacatcac ctcctggttg ggttggtcct ctagtccctg gggccatgag tctgaggtca   79320
gaatgagtgt gtgctctctg actccacaac ctgtgtgctg ggaggtgggg agtgggaagg   79380
gcaacacaaa agggcttgcc agacctgaac tgtggtctga aacctgaag cctggcccac    79440 tttaaaataa aacttgtagg gctggggaga tagcacagta gataaagtac cagcatgcaa   79500
gttcaaggac ctgggttcag tccccagagc tgggcacggg ggtgcatgct tataatccca   79560
acactgggga ggcagagatg ggcaggtcct ggggctcatt ggccaatcag cctgaactaa   79620
tcagcgtatt ccatctcagt gagggtcct gtttcagagg gcctgaggaa tgactctggg    79680
ttgactacta gcctactctg tgtctgtttc tgtctgtctg tctgtctgtc tgtctgtctc   79740 caccctctc tgtccccttc cctctgcagg gaacttcctc accaccacca accccaaag    79800 aaacccaccc tcagaccagt cttccctatt cagcttgctg gctggtccta gtctgcctag   79860
gttctgctgt gacgccctcc ctgtctttcc tgacaagcca tccctctga ctagacccga    79920 gaggaatttg tcgttttctg acctgttttc agtgtcagcc tcttccttat gagactttct   79980 gctttttgt tttgttccca gggctttgga tcaaagctgg gctcttacat acgttaggca    80040
aatgcttggc cacccagctg tacctcccgt ccctgttgct tttcggtttg gaggactttt   80100 ttttagttt tctgtttggt ttttggtttt gattttttgt tgtttgtttg tttgttttga    80160
gacaggattt cgctatgtga ctctagctgt cctgggactc actatgtaga ccaggctggc   80220
cttagattca gagatccacc tgcctctgcc tcctaagtgc tgggattttt agattttaat   80280
ctgtacctac caacctcaaa ggaagtgtcc atggatagag ttcagtacta catcatgtgt   80340
gtaacatgtg tgagggcctg ggcttcaccc ccaacagaga agggggagtt agtaggtgag   80400
gaataagtga ctggctagtg gcaagacagt attgtctaag gtcactaagc cttaagccac   80460
acttaaagcc cacaatccag gtctaatatg cccatctgcc ttgtccttgt gtgacatgac   80520 cccacccta cttcctccgt atagtggcag ctcctctgga tcctgaaagg agagggaaga    80580
tattcttgtc tcgatgttaa agtaaccaag gcctagaaga gtgaaggcca aagcccaccc   80640
tggatccagg gctgcctccc tgcactgtct cttctgctgt cccacctacc caccctactg   80700
acctcagagc tgctggggac gttctggctg ctgccgtgcc cgagcagggc tccagtccag   80760
aggagtagca ccagggcctg catcccggaa ctacaagaga aacaagagag caaacgactc   80820
ccctcaccca caccctcccc tgccactgca cattgcacac tgcacaggga caagagtcag   80880
gcagagtgag ccccttcccct ccctccagct ctcagcccca agtggaccct tgacttgagg  80940
tcttccgtcc ctgacctgcc cctgcacttc tccttgagct gtgcccccat gttggttcct   81000
atcaggagac ccaccttccc atctaagctc cagcacaggg aagacccagc agcaggctct   81060
tcaggcccca agacaatgct ctagcacaaa cacacaccaa ggcttttccg tggaggcaca   81120
cggccagctc ctttggtagg atttggaacc ctgtctcagg atgggagcag agcccaggtc   81180
atagacttac agaacatctg gtctggtcct gctatccacc aatagttctc tgaccaaagc   81240
ctatgttaaa gacacacaca cactttcttc taggtaggtt cttgtgtatg tagcccaggc   81300
tagccttgaa gttgcagcta ccctacttca tttgcctcct gagtactaca atgccaggtg   81360
tgagccatca tgcctgactt gactcccttc ttctatttca agagcaattc ttagttaaga   81420
```

-continued

```
gggtatgaac cagggccaca ctgccnnnnn nnnnnnnnnn nnnnnnnnnn nnnnnnnnnn    81480
nnnnnnnnnn nnnnnnnnnn nnnnnnnnnn nnnnnnnnnn nnnnnnnnnn nnnnnnnnnn    81540
nnnnntctta tttttagctt gtttgttttt cttacttgag acctgggag ggggaggtgta    81600
tgtgtcttcc atttgcttct tctacctaat aaagtttctt ggtgatgttt ggggggggg     81660
gaggggtag  gactcaagaa gggattctcc cataagctgt tccgtttggg tagtactatg    81720
taaggaagtt acaggtgggc agagctcggc tctgcctgac tggcgtgctc tgaggtaaag    81780
gtgagatggt gcaagatttg ggccctcagg agttggctct gttggccctg taccttctgg    81840
tctgtgggta aggatgacca gtaggtgaga gatgagggaa ccagaacaga aggtgaaagt    81900
tagtggggcg gagccccaga ctagtcaggt gggggtaaac tagatgactt tctggaaccc    81960
caagggctc  ggagactagt ggtgttggag aagacctcta atgtgttgta aggcctctga    82020
actcagtagc cgaacttgat gccagaaagc cccaaactgc taaacccaag caggagcggg    82080
acgccatccg ttccatggct tcacccgagg tggccccatg gctgcgccaa tcaatgagca    82140
gccgagagat aggggcgtgg acaagccagg aaaagttaca gcacgctgga agataatac    82200
aggccaggaa gccccaggca cagcagggtg gaaaagctag atcccgattc tgccggaggg    82260
gggccccttc gaggtcccgg gcaccgggtg ccaggatcag agaaactgac tgaaacctag    82320
ctgacctgcc cagaccatgg catcctgggg actccttgtg gctggcgctt ccttcacggc    82380
gtttcgggga ctgcactggg ggctgcagct gctgcccacc ccgaaatctg ttcgggaccg    82440
ctggatgtgg cggaacattt tcgtttcgct gatacacagc ctactctctg gagtaggggc    82500
gctggtcggg tgcggaactt ggggactgac aaagcactga ggggcggggg tggaaaagag    82560
ggcctggaag actgaagttg gaacctttg gaatggaact ggtttgggtt gtggatgggt    82620
gggagtaccc agtgggagaa tggatctagg tctgggagaa attgaccta  gctctttgtc    82680
ttctccaggc tgtggcagtt tcctcaaatg gtcaccgacc caattaatga tcacccaccg    82740
tgggcacggg tcctagtagc agtgtcagtg ggtgagtgta cagaaaaggc tgaatcggga    82800
aaggccttgt tggaccggga attctaggtt cctcccccat cttttggaatg gagcagatgt    82860
tgctggaggt ttgctgtgag gaattaagga cctgagaaaa gtgggacttg agatatctag    82920
gctgtgcatc agctctgagc gaggagcctc atagtcttct ccggtgcctt caggttattt    82980
cgctgcagat ggagttgata tgctgtggaa ccagacattg gcccaggcct gggaccttct    83040
ctgtcaccat ttggcggtaa gactctgaag ggagaggcca ggtagtaagg gagcatgtcc    83100
aactcaaggg cccaacctct ctcttcagtg ttctgtcctc tgacttttcc acaaagcccc    83160
ctgaaaacct atcctctcag acttggattg agttggaggg aggttttgac tggctagcca    83220
ctcctgggca ctgcccaagg agtttggttc tccccacaaa cctccagctg atcataaaaa    83280
aaaaaaaaa  aaagccagga atgaaagcta gggtatgcta tgcaaatagt gtggcttggg    83340
gtaagagaac ctctggtcca gggctgctca tgcccctag  ataagggtca gcagaaaggt    83400
caggattgga ggcagtccta aaaaatgctt gggtaatata aagtgaataa ataaaaaata    83460
aataaatact aattttaaa  aagctgatac ctggaaggat gaggcagaga gtagaaaaaa    83520
catgcgtggg tgtccctagg ataaggagct gggacttgtt gggcacaggt catgcaaagc    83580
ctgaaccttg aaccttgcct gcaggtagtg agctgcctca gcaccgctgt tgtgtctggc    83640
cactatgtgg gcttctctat ggtatccctg cttctggagc tgaactccat ctgtttgcat    83700
ctacggaagc tactgctgct ctcccataag gccccatcct tggccttcag agtaagcagt    83760
tgggccagcc tggccaccct ggtcctcttc cgccttctgc ctctgggatg gatgagtctg    83820
```

```
tggttgtccc ggcagcacta ccagctgtct cttgctctgg ttctgctttg tgtggctggg    83880
ctggtcaccg tgggcagcat aagcatctcc acagggatcc gaattctgac caaggatatc    83940
ttgcagtctc agccctaccc gtttatcctc atgcacaagg aaaccaagac acgtgagcct    84000
gttgccagga acacttccac tctcagtctg aaaggtgtgg aagttttctc ttctgtcagc    84060
ccccagggag gtggggctgg gaagaggaga tggtagccca ctgcatagtc tactatgtag    84120
caaggactag actgtatcat cagagagaga gagagagaga gagagagaga gagagagaga    84180
gagagagaga gaacattgta tgagatctcc attacagtca ggaaatcagg agatctaaat    84240
aactttaaaa gtcccacagt ctttacatat tcttaaaatt tcaatctctt taaaatatcc    84300
atctctttta aaattcaaag tcttttttaca attaaaagtc tcaactgtgg gctccactaa    84360
aacagtttct tccttcaaga gggaaaatat cagggcacag tcacaatcaa agcaaaagt     84420 caatctccaa ccgtccaatg tctgggatac aactcacgat cttctgggct cctccaaggg    84480
cttgggtcac ttctccagcc aggccctttg tagcacacgc gtcatcctct aggctccaga    84540
tacctgtact ccactgctgc tgctgctctt ggtggtcatc tcatggtact ggcatctcca    84600
aaacgctgca tgaccccttc agtcctgggc cttcaagaga aagactaga gcctggcaaa     84660 gtggcacatg ctgataatgc tagcacttgg gaatgacaag cagaaggatc agaagttcaa    84720
ggccagcctg ggctacaaga gactctgttt caacaaacaa acaaacaaac aaaccaaga     84780 agagaaagaa aaaactggac atgacagccg gaacattatc tgacattcat aaggtcctga    84840
gttcaatgcc aagttggcag tgcctagttt gataagggtc tagccactct ggtaatacca    84900
tggctgactg aacaccttac ccagcaactt gctgatagac tctgccttcc agcaaagg     84960 aggagcttcg ctgaggagag aacattgaac cctattgtat atgaataaat tgctgtgcaa    85020
atgatttcat cagtctcttg tgaatgtgat tgctttgagt cattttttctt ggctccagtg    85080 ttatcctggt ctgcagtgtg gtgtggagtt gtggaagctt tgagttggga gggtttcctg    85140
ttaaggtttc tctggctctt ttcttttcctc ccggttttttg ttttgtttgc ctggtggggt    85200
tctctggtgt gtgtgtgtgt gtgtgtgtgt gtgtgtgtgt gtgtgtgtgt tagaagttgg    85260
cggggggtgg aggggctgg agagatggct cagcggttaa gagcgccaac tgctcttcca     85320
aaggtcctga gttcaaatcc caacaaccac atggtggctc acaaccatcc gtaacaaaa     85380 aatctgatgc cctcttctgg agtgtctgaa acagctaca gtgtgcttac atataataaa     85440
taaataaata ttaaaaaaaa aagaagttgg catggatgat gtagtgaaga ctggcattag    85500
atatctctgg atcccctgc ctctacctct tagacactgt gagtatggaa gtgtaccacc     85560
gcaccaggcc aggctagaac attctctgat ctacaaatac ctagagtatt attcctctat    85620
gatcagaaaa cagacccagg gggccacaga aatgtcttag taggtaaaaa cacttgcttt    85680
caggcctgat aacctgcggt tttttgtttg ttctgggggg cgggagaggc tggctggctg    85740
gctggcctgg aattcacaga gatccacctg cctctgcctc ctgagtgtca ggtaccagga    85800
tcacaggtgt gtgccaccac acttggccta actgcctgag tttgagcatc agtactcaca    85860
tggtactgag gatagaatag actctcacca gctcttctga cttccacatg tgccctgcag    85920
catgggctct ccttccccaa aggaaaaata aatgtaagaa ttaaaaaaaa aaaaaaaag     85980 caaacccagg tcttgtgtga tggctcagca tcaaagctac ctcccgccac agctgaccac    86040
ctggtgataa cttatagcct tgttatgctc cctttgacc tccacgggca tgctgtacac     86100
gtatgtgtgc ccacacaaac acacaatcaa gaaataaatg cagccaggcg aggtggcaca    86160
```

```
cccctttaat cccagcactt gggaggcaga ggcaggtgga attctgagtt cgaggccaac    86220
ctggtctaca aagtgagttc caggacagcc agagctacac agagaaaccc tgtttcgaaa    86280
taaccaaaaa aaaaccactt taaatattat ttttattttg ttttgtttat cctggaactt    86340
ggtctgcaga ccaggctggc cttgaactca cagagatcca actgcttctg cttcccaagc    86400
acattaaagg atgtcccacc actgcctggc taaagattta ttttttcttt cttttttgttt   86460 tgttttgttt tgtttttttct aaaaaatttt tttaaaaaga accatccctc ctagcactca   86520
ggagactctg aagtcagggc cagccaggtc tactgagtga gctctagggc agccagggct    86580
ccacaaagaa accctctctc aacaaacaaa caaaagagaa cagacccaac cagacctgag    86640
gacacacact tgtaatctaa gcccttgaga ggctgagaag ttcaaggcta gccacaagtg    86700
tgtggtgcat tcaagagcag cctgggtggg ctacagaaaa agaaagaggg agagagagaa    86760
tggttaatga agatgactct ggaaaagtga aactcaagag aaagcccctc agatttgctt    86820
aagacgagtt gagggtggag aaccgccaaa gcggacgagc cagacagaga ctgccaacaa    86880
agttcaatcg gttcaggtac attacttcca aaacgccatt gccacatcag gatgcttcaa    86940
tcagccaaac caacgcagcg actattgact tctgcatttc agagacttcc gtctctgtcc    87000
agggcaatgt cactttagct ttcctttgca gaaaggaaaa gtccctgcct ctgatgtggt    87060
agatcctcac acaccttctg ccagatccag acactggtat gactcagcct cggggagctc    87120
tatctacaga gataagggta caaggcgtgt gtgtttaaag tatgtgttta aaagtacaaa    87180
gtgagagtcc ctggaaaggg ctccctgccc tcaccatcac cgaaagcaca aaccttaggg    87240
taatatctga cattcctgga aatgtatgta tgtattcatt atgtagccct gactgtcctg    87300
gaatggggta taaccagga tggcttcaca tctcagagac ccatttgcct ctgcctccca    87360
agaactaaga ttagaggcat gcactaccat acttggctca tgatttactt aacttttattt    87420 tatgttcacg aatgttagcc tgcatgtatg tgtgtgcacc atgtgcatgc ctggtgcccc    87480
agaggccaga agaaggtgtt ggttggattt cctggagatg aagtcccaaa caactgtaag    87540
cagtccaatg tgtgtgctgg agatgaaact tggttcatcc acaagagcag tatgtgctct    87600
taactgtgga ggcatatctc cagcctcaga tttcccagtt aatgtttgct ttcgcaccca    87660
ggcccatctg cgcatgcgct ggagacctcc tttaccgcct tgagcctcat ggccaattg    87720 tggctgggag acttgcagat cccaagtggt acaagagaag aataaactgg tgtgctatga    87780
actcacctct tctctgtagc cattggctga gcatactttg cctcaaccta ccgcccttcc    87840
ttcccctaat cctaaatctt tgccctctcc aaatgtgctc ctccccgca gtaatccagt    87900 ggtcgctggg gctctagaga gatggggggg ggggagcaa cgggtacagc ttaaggcagc    87960
tgcagcagaa cttttttgct gtatattgag tcttaaaaat tcatataaac tttgtgttct    88020
gtttctaaat ataacccat ctgtttcaac acaaaatgca acaacaaaat gtttcaaatt    88080
gctatttgga ataattaaaa aatttcaata cttgatttaa aaatgcttta acttttttaaa   88140 taaattttaa atgttattat ttttaaaaag ttacaagttt aaaaaaaaga aagatagaaa    88200
tcacataatg aaattaacca tacgcaagtg aggctcggtg cactggtaca cagttacagt    88260
agccatttgg agtggaggcc atggcgcttc acattgaatt ttatactttc tttatagaat    88320
attttttatg cacctatcta ctactgataa caaaacaccc atgagagagt tagaattaga    88380
catcaattag ctttgatcct ctgtcataac tcgtgtccac tccctgcctt agtcctacct    88440
catccctgtc ctctttttcta catccttatac tgaatccaca cactcagttg tttacacaaa    88500
cacatacatc actgtccann nnnnnnnnnn nnnnnnnnnn nnnnnnnnnn nnnnnnnnnn    88560
```

```
nnnnnnnnnn nnnnnnnnnn nnnnnnnnnn nnnnnnnnnn nnnnnnnnnn nnnnnnnnag    88620
tgcctggctc tgttttgctg ttgttgtttt tgtttgtgtg tgtgtttaga tttggtttgg    88680
tttggtttga ttttgttttt ttttagagaa tcttactatg tagctcaggc tgtccttgaa    88740
ctcacagaga tctcttgtct ctgccttcca agtgctgaga ttaaaggtat acaccacctt    88800
acctggcccc tttcatctat ctatctatct atctatctat ctatctatct atctatcatc    88860
tatctatcta tctaaaattt atctgtgtgt gtctgtgtgt acattcccca gagcctgtgt    88920
ggtagtcaat aagtaaccct cagaagttgg cttctctaa tccttggatc aaacttgaat     88980
tgttaggctt ggtagcaagc atgtttaccc actgagccat ttatgacccc atggcccagc    89040
atcttccatg ggtctggggg acacaaatgt gtactttgat gtttacagga caagcgctta    89100
accaaccaag tcattttccc agccccatcc tgactcccat taagtgttct ttcccccaac    89160
ccaggaccaa atctagagga gtgtccatgc caacaaaca ctctgccaag cctctcccct     89220
tactgctctt ctcccttccc ttccttcatt tcttcgttcc ttcttttctt tcttttgaa     89280 acaggtcttt tctctgcatc ccaagctagc cttgaacttg tgatgtagct caggctggct    89340
ttgaactcac agctgtcctc ctacttcagc ttcccaaaca ctgggattat agacctatgc    89400
taccacacct ggctcatttt tcaaataaat aaaagaaaa tcaaaagtt cctagaacag      89460 tcacaggatt cacaaaaact ttggaaggag actaaaaatg gattttaaa aaatgcttga     89520 agcacaaaga gttgttgaaa gaagagagaa gaggaaagt tagcttagta ggtagaagtc     89580
aatcaagcct cacaccctga gttcaattcc tgaccctatg gtagaaggag aagagcaatg    89640
ccggaaacat tatcctctga cctccagacc cgctgtggca cgtgcatgca cacacacaag    89700
caggagccct tggagggaag tcctagaaat gaatcttact gaagcaggtc tgccaggccc    89760
tgtgctcagc catttatt ttcctttgtg tacccgacac gcttccattc tcaaagttgt      89820
gagtctgaga ggaagtactc actgtgtccc cagtgagctt ctgtcttacc ctgggtcact    89880
tagatggggt cacttagtgg tagccttggt gtggagaaag agaacacagg tccgagtagc    89940
cagtagacct gagtctttat atctgcaaag ggtgttgggg cataatcaaa tctccccccc    90000
tccccggggt cctgatacca ggttgtatta agtgtatgtg catggtcctt ccaagtcttg    90060
acacatcatc caactccaag tggctttctc attttttcctt gccagtagcc tcttggtgag   90120
gaaatggctg aggaaaacag agttgcagaa agacagggcc atggcctggc tgcaggcttt    90180
ctctgagtct gaagagggtc agcgactctg agaaatgaag ctatttctga gtgagagggg    90240
ccaaagaagg aacacggcag agggagagcc cccgaggaga tggagacaga agccggagag    90300
ggaccctgtg cgaggctgga ggggaggaag aggggggagg agtgagaccc actgtcatct    90360
gttgggcaga gagggctac attcatctgc agtatggtgt agagggggaca gagagtgatg    90420 gtaacaggaa aaatttgggg ttgaggggg cagcctgtag ggctgggccc cagcagtgta    90480
cagctaggta gagtacacag taactcccag aattctctgg ctccactaaa tccctgttcc    90540
gctccgtgca gagtaaaacc cacacagggt ggatttcagt ctcctttgca ccccctcca    90600 ccccccctcc accccagct ctggtcacag ccagtcagag ttggggtgg ggcagatctt     90660 gtaaaagagg ctggtgagga catcggaaag tctgtaccct ccactagcaa agtgccagac    90720
gctccgtgac actttaaatg cctcagataa aacagtgaga gactctcctg gtggcaggca    90780
agatgatggg tcaggacct cagcgcctct gaggctcaga caccaggata aagaataaaa     90840
acaccacgga gacccctgtg acccctcgt gcagagggag aatgccaatg tggcccagct    90900
```

-continued

```
agctgctgga gcgcaagcct caaggcctgt gctagttatg agtctactgc tgctgccttg    90960
tcccaataaa cccctttccg cccaggatta gtggacacgc cttgctcaag ccgagtccct    91020
gatctgccac cttatcacac acatacaaaa atcccttgag gatggttacc atcctgggac    91080
aaagcctcat tctctgctta acccaagtga cacctatatg gcagatccct gtgtccttct    91140
cctgatgata acaacccttg caatccaata gagggaact cgggtttctg tcagcttcct    91200
ttatgctgat agaaatgtac tctgcatgtg gggagcctgc cttgctcacc ctgagacccc    91260
atggggctgg ctgggctttt gcacatcatt gggactcaga gatgttgact acatgaacgt    91320
cccacacttg gttgcacaag gcagaatgac aggatgttat gcctggtgtg tgagtgtgtg    91380
tgtgtctctg tgtgtgtaaa acgcctctct ctggagccct cctgtctgtc tgcctcttgt    91440
tcaatggctg cacaattgtc ctttctcttt ccaaggacct ctgtatgggt gtgtccttca    91500
ttcagtgcct ttcctctgtg ggtttgtcct gctagccccc tgtcactgag aaagtcttct    91560
gtctgtcctt gggttgtctg gctagaacac agacatcatt gtcttttttt ttttttttt    91620
tttttttaa agatttattt atatgtaagt acactgtagc tgtcttcaga cactccagaa    91680
gagggagtca gatctcgtta ggatggttgt gagccaccat gtggttgctg ggatttgaac    91740
tccagacctt cggaagagca gtcgggtgct cttactcact gagccatctc accagccccg    91800
acatcattgt cttgcccacg actgctctcc agaatggtgg gcaggaggat gtgaccccc     91860
accccaggc accgggacac aacatcttct acacgtgtag gtcttgtgca ctggctttgc     91920
tttcttcttc caagcaggtc tcccaggaaa tggcacttac agagattgaa gagtttaata    91980
catgtctcgc tgcctctctt tcgggaacc cccagaggg agcagcagaa accagggctg       92040
gcaggggctc taagctgcct gggcaaagga gcaggggta gcatggagcc ttagccaatt     92100
tggaaagcac tgtgacccaa gcacattttg cagcagtaat gtcaaattct gccgttcagg    92160
catgccattg atgtgcacgc tgccacacag aaaccagtga cacaaaggca cagccttctc    92220
caccctcctg gtgcttagga actaacggct ctaatgagaa atgagagctg aaaggagaga    92280
gacgggggcg ggccacagca gcgcaggctg gcactgcgtg ttggaggagg ctgacccact    92340
tctcgtagag gtaaggggcc cactgaaatg tcacttaaat tagccaccac tcccaacact    92400
agatctcctt tgtccccata cctcagcccc acgcttcttt ctttttttct tcttttttctt   92460
ctcctctggg gcagcctcaa gcccagcacc cacttttttag agctgtaaac caccctggtc   92520
ctagaagccc tcttacgtta ggggatgaca ggaggtagag atcaggaagg agggagggag    92580
gggaggagga aaggaaaagg gaggggagag agggaaagag atcgagagag catgcattca    92640
tcacaaagag ccctcttttc tggcttttttg actgcactgt gagttattta gccaacaata   92700
gatgtttatg tatttttttta gaacccgtat ttattaacag cctgaaagga gagagacgga   92760
gatttatata ggaagtgcag tgagttaagg ggggcaatta agagagcaga aagagatacg    92820
gaacacagac ttgtaaaggg ttttgtaaca tccaatcaaa ggtgcttcag gtattttcca    92880
aggaagcaga aggtaaaaaa aaaaaaaaat tgtcccatta gaagctgaca ctggatggag    92940
caatggccca ggcggaactc ctgcttgaaa gaaggtgaga agggagggac acagaccagg    93000
atccgatgag ccagagtgtg gccatagctg ggtcatgagg cccagggttg gaaggacccc    93060
actaaagtgt gcactggcct ttccttgaca aaggatgcac ctatagctag gcgtggtggc    93120
aagtggttgt tattctagta cttaggaggc tgaggcagga ggatcaccat gagtgtatgc    93180
ccagcctgga ctgcatagca acacccagtt tcaaaataac aacaaaagga agtgggggtg    93240
gggagggcaa catttggaat gtaaataaat aaaacatttt ttttaaaaaa agaaagggc     93300
```

```
tagtgagtta gttcagcggt taagagcgct gactgctctt ccgaaggttc tgagttcaaa   93360
tcccaacaac cacatggtgg ctcacaacca tccataagga gatctacgcc ctcttctggt   93420
gtgtttaaag tcagctacaa tgtacttaca tataataata aataaattct ggagtgaggg   93480
ggccagagca agtagaggtc ctgagtttaa ttcccagcaa ccacatgatg gctcacaacc   93540
atctgtacaa ttacagtgca ctcatataca taaaataaat aaataaatct ttaaaaaaag   93600
aagaaagagg gtgggcaggg ggagggaaga agaagaaagg taagaagcta aataaaaggc   93660
acagagatga gcttcatgtg gaaacacagg cctgtagtcc tggcactcag gtggggttgg   93720 gggggggctac agtgagagta tcatgagttc aaggtcaact tgggtgagac cttgtctcaa   93780
aaaatacata ngcnaaaaaa aaaaaaaaaa acatagccag gcatgatggt atacattttat  93840 agtcccagca cttagaggac tgaggcaggg cagaaagaaa aggaattcaa gatcaggctg   93900
agctgtatgc agtcctgatc ctatcccctc cccccccccc ccagagacag acagacagac   93960
agacagacag agagaaacac aaagaaaggg gccttcagat ggctcagcaa ttaaaggcgc   94020
ttgctattca gacccatga cctgagctca aagcctggga cccaaggtag aaggcaagag    94080
ccaactccac agagctgttc tatgatctct atatgaatgc tgggcatgt gcctacacta    94140 tgttgtgcac acatgcacag attagaaaaa gaggaggaag aaaaacataa gattgtttca   94200
agaaaagaaa ggctggcttc ttccacgtca gtgtgagagg agggtctggc ccctttgtag   94260
ccaggtcctt cccagtccag tgggggctga actgaggcag cggaggaggc aataacggag   94320 cttttcccaac gcagtgtcca gcaaactcaa ctctacagcc tgtcctgatc cacagagaag   94380
ccttcctggc tccctcacca atgcgggggc attggctccc aggctcctgg gcccccccccc  94440 acacctgtgg agtgctaggt gatttgctaa tgttgggcaa catttgccca cgtgggggttc  94500 ttggctcttt ggtaatagac atgcctagca ggagggcgga gcttggaggg gggagtcctg   94560
gggttgcccg tggctccctg cagctggggt gtctggccag ctgaagaagg agccatggca   94620
cgcaaatggg agagcatgga acagaggctg tggatgctaa gcaatatggg aggcagtcta   94680
agcttggaag cagcaggtgt ctgggaacgg gcctgtggcc caggcagatt tccagtgagc   94740
actccagttt tttggcacaa ggaacaagct ggctgagccc aagaggcaag tggtgataat   94800
gaaacccgca gttgaggaac agcgggtaag ggtgccatgg gagcccatgt gctcatgaag   94860 aggctgggt gtgaagaaga gccatgcag ggaagccaca catcccctcg agttccaggc    94920
agaggcagag tccctgagtg gggctccctg ggtctcccct tacctaacca gtctcccggc   94980
accccagcaa acaaaatccc atccataatt tgaggtttat agagacctca aaggctgagc   95040
tactgtgtgc cactaaccat cagcctaacc ctcccccact gtcttctcta gctgcccctc   95100
tttcttctga gactgtgata gtggcgggga cgggttggga gtgtgtgtga agccctctcc   95160
gactctccaa ccccagctga gccccttgtt ctgcagctca gtaacacagt aacacaggct   95220
cagttctaca ctggttgaga acactcacgg ctctctcagc tccttagaga gcctgttttc   95280
tcattttcct gtccccaaag cctagacaat ggctggtcca tttgtaagct tatctgagga   95340
tgccaggggc cacccccatgt ctccactagg ctggcaatgt tctctgtcac tgtagtacag  95400
aagactgcct ggtgggaggt gagataagga aagggatggt ctcccctggg gttcccacac   95460
agtgctgagc ggaaaatggc agaatgggct gggaggtaac tctgttgcta gagtacttgc   95520
ctagcatgtg caaggaaggg cctgggttcc atccccagca ctacagaacc caggcgtggt   95580
ggttcatgct ggtattctca acattcagga ggtacagtca ggaagagcag aagttcaagg   95640
```

-continued

```
ccatcctcag ctacatagct agcttgagac cagcctgggc tatgtgagac tttgtctcca   95700
acaaacaaca acaaagcagc agaaggccaa ctggcaagag gagtattacg taaagtaaat   95760
ccatctcaaa aagcaagtag catgtatctt ctttcatttt tttttacatt ctataaaggc   95820
ctatcaagtc atgtatatat gcatgtatgt ttgtatgata tgaaagtagg gggctggata   95880
gatggctcag cagttgagag cacttggatg ctctttcaaa gaacctgggt tcaattccta   95940
gcacccacat ggcagctcac aactgtctgt aattccagtc tcaggggatc tggcaccctc   96000
acacagatat ccacgcacat aaacaccaat gcacataaaa taataatttt ttaaaaaaag   96060
aaattggaag taaaactctc taaggagaca aaagggactg aggggaagtg ggaggggcat   96120
gaaggggggag ggcataggtg tgtggtgtgt ttaacatgca gaatacactt ctataaaagc   96180
tttgggggttc attatgcaat gtatacatgt gtgggtgcaa gatgtaagct gtgcatatgt   96240
gtgggggcca aaggtctcct cctcaatccc tctctgcctt attttcattt aaattataat   96300
tattactatt agtgtgtggt gtgatgtgtg tgggtgtgtt aagccctcac ggcaatcaga   96360
ggatgtctgt ggtctgagga tgctctctta ccatgttcgt gtgggttctg tggatggaac   96420
tctggtagtc aggtttgcaa agctagtgtc tttatctgcc gagccacctt gctggccttc   96480
aaccttattt tttgcattga acatggaact tcctgagttg cctggacagc aagtccccaa   96540
gaccctcctg ttcctgcctc ccccntgtcn nnntcacang aggacacacn gcttantggg   96600
tntccggatt gctgcncacc tccccgccnc ccnagcctcc tgcctccccg cccctcgccc   96660
ccgctggncc ctcccccccc cccccccccc cccccccccc cttccccccc cccnnnnnn   96720
nnnnnnnnnn nnnnnnnnnn nnnnnnnnnn nnnnnnnnnn nnnnnnnnnn nnnnnnnnnn   96780
nnnnnnnnnn nnnnnnnnnn nnnnnnnnnn nnncagaca cacacactca aattaaatat   96840
agctctaact gctgttaaat tcacactcct tcacatcccc acgctaggac tctaaggagg   96900
caccagcaag gcccaggtcc agcttgactt agagcaaagc atcctccccc ctccacacaa   96960
tggaaacgga cggaaagggg catggaagca gaaccagaca acagcagcct agccaagccc   97020
aggactctgc tccttccccc catgcctgcc gtgcaactgg ggaggcaaag ccccagccgg   97080
tgctttctga ccgcttagcg gaagacaagg ggagcctgtg attatgattt ctgctgattt   97140
gcaatgaaac actaatgcag tgggcttttc attaagccag atttattcaa tctaaagatt   97200
ttatttcctt tatgtagaaa gtgcatcttt atatgttgtt ggaggagcag agatgtgata   97260
aaaagaaatt tctcttatga actaatagca ctgatacata gtggtagcta tgcctaggcc   97320
tctctctctc tctctctctc tgtctcctgt gcatgtgtgt gtgtgtgtgt gtgtgtgtgt   97380
atgaatgcac acaaagtagc ccccccccat attatttctt ctgtgggatc tccagactca   97440
gcaaatggtg gtgactggga agtctggcca tgcaattctt gccttttctc ttgccagccc   97500
aatcccttttg cattcaaacc cgggctgctt gctgtggcca gcccttttcac ctggagtcct   97560
tcctcctcct tacctgtctt cccatccttt gcagacaatt atcctcaata actagccaat   97620
tacccttaag gacaattata ctcttccatc agcaaacacg ggtgttcttt ccttgagtct   97680
tttgatgaag tcgatattaa agagatgctt tatttacata aagtcaaata gctcccttt   97740
agaagggttt gggttcgatg tcaaagtttt aaaatcttaa ctagaggatg ggtgtagagg   97800
gcttttggct agggtagaaa agagatggag atacttattc tgatgttgct ttaaaaggta   97860
ggatgcccag agaaggtgga aggatggggg agggagggtc cctcctcaag ctaatgaatc   97920
taaaagcagg gatgagctgg gcgctaggag tggaaccagt cagaagtgtc tgcctttgac   97980
tgaccacagc tcctgccctc ccctccccca gtctctctgt gaaccgccag cattaggagc   98040
```

```
taatcgcttc agaaagccag attggaatgt gttgctcacc ctccactgct cagaaaacct   98100
ttattccagg caaggactga cccaaaccga tcatggcatc tgccaatcag gaggccaaag   98160
gtgccggcag ggcgggacct agctgtgcag aaacagctcc gttatggcgc gcagaaaaag   98220 ctgggggaa aggctaccgt tttatctctt ggcagatggc ttctctcttt gatgctttgg    98280
gccttacctg ttactgcctg cacttgactt gacctaggca aaaatagcag cgagatacag   98340
gttctcgaag ttagaaggaa aaaaaaaag ccccaaacca caacacaacc cggaagtgtg    98400
cccccgctgt gtttctaaag agctgttttc ttcccaagct ctacagcgtg gtggctctaa   98460
tcggaaattt cttttaatc atagcaggag tcccaattag cgtgttgggt aatctttcaa    98520
gtagagtggg agttccgtgg ccacagagag cagaggcaat attcagcata aagccctaga   98580
gaaagaggtg ttgtgggcct gtgcacacat gtgtgtcaac gcacatgtgg cttgtggagg   98640
ctggcttccc actctcaaga tgaggtgtgt gcaccccagg ccttttgatt ctcaaagctt   98700
tattaggacc agagggactg tgtgtgtgga ggggtgttgc tcacagtgca gaaacccaaa   98760
cctggcttct ccaggagccc acatgccaac aaacaggctg cacactcttg ctagtacatc   98820
ccctaaaggt atggggatga gggaccaagt gctttgcaag acagcaggca cagagttctg   98880
ggacgctcct gtaccccaga ctcagccgcc acccagggcc agctctgatc tggcttgacc   98940
tactttcttc tgttgttgtt tttggaagtg ctgatgtcaa tgcagaattc agcagagtgg   99000
ctgagtgaga aaaagagga gaggaggaa aaggggggg ggacgggacg ggccgaggcc      99060
aacaggaaag ggcaggcaac aagacaatga ccacaaggtc cctgtaacta cactaactgc   99120
ttacctttcc tgaccccag ggcttagcca atatagctga gacccagtct tggtgctgtg    99180
gcttcaggct aagtaaacag ggaagagttg gacatgggtc tccattctct ctcctcatcc   99240
aacaagggga ggaggcagtg gccaggcagc catgcccacc gatgccatcc ttctgggagg   99300
agccagacat ttcaggcacc tctccttccc tgggtgccta gaggtgctgt gtctgcatcc   99360
atctgccatg cctgccatct gagagaggcc actgggactt ggtagagagg ttctccacac   99420
atgctggcct ggaggaaatt ggtctttagg gacactgaag gcagtttcct ctgttcagtg   99480
gctccttgga aacccacgtg acagagctcg catgacaact tgccggctct caactcccat   99540
tcttagctgc ctcaagcact gtaaggttta ggagagcccc agatgtaagt atggatggga   99600
agaccctcca gggagtcatt gcctacccct ctgaactcta acatggtcca gcttttccat   99660
tccacaattg aggagacgcc agacctggca ggggagcaag cctttgtttc tgacccattt   99720
gcaaacccca gccactgagg aacttgcata caagaaactg cctctgggcc tctcctggac   99780
tgagccctgc ctcccagggg acaactgggc aacagatcct tccaggtggc tgcagtgaca   99840
gatccatgct tttatgacat agaaaggcct cagtctcagg atttcacaca ctgtatttcc   99900
ctcatcctgg ggaccaggga aggcgagcat cttctgctcc ccccaaacaa gtgtgggaat   99960
gattaaaatc attttttttt tctgctccat gaactcatac agttttcaga taccgaggag  100020
acaaagccct cctgtgctga aattagaccc cgaaaaatag gttagctgac aattacttgt  100080
ttctaagtgg agtgtgatgt agtggcagga gcgcaggatg ggctgccagg gctgcagtct  100140
cccccccccc aaacttactg tctcttaacc tctcgagtcc ctgggtttct tgccgggatg  100200
ataattctcc ccatctccct cctctggtgg gctggtggaa agcgtaatga atcaacgctt  100260
gaagcacgct gaagaggcca gactcgggat gccatgtaag tacacagcat cgccagccac  100320
ctctcaagtc tacacggagc tgatttattt acctcccgtg aaagagacaa caatcatcat  100380
```

```
atttacactt catgccgcag cttcctgcgt ggcacggcag cacccctcc ctctccgctg    100440
ctgaggactc catcaagcac gctgccttgc caggatgaca gcagcccact ctcagcctct    100500
ccctggcctc cttacagatc atgacctcct gccccgtgag gtctgtcacc cgaaaaccac    100560
ggtacaccgg gggctgcagc ctctctatgg gggaggctga ggaaatgaat tccgtaggta    100620
aaaggcttcc taggaaatca gacgctgcta gtaattaagg agcgaagcat aggtgcgtga    100680
aaggtaaatg gatgttattt aaatgttgcg tcatttaaag agtgtcctgg tgcttcagtt    100740
ccttgttacc atgcagggct gtggacgggt ggcaattagg ctggcacggg tagagctcac    100800
ctgctgagct gagggagggt ggggacacac cttccggtaa ttgctgctgg gcagctctgg    100860
gtctccccac ccccgccccc gccctcactc cccaccccccc acttctttcc tgacagctct    100920
ttcatttgca gcagcttaca gggcttgttg cccttaccca gaaaatcacg ttggaagaaa    100980
tataagaaaa agaggaatga aagagaaagc cagaaaagtt catattaggt tcggatctgc    101040
ggccaaacct ggccgagaga atccatgacg gtccgcgcgc atataaccct gtggcaacag    101100
ggcccggcac aacagggccc gccacaagag cttcttgagt tgccacctgc caggagacag    101160
gatgaatgaa tggatcatct gtccttagag cacaagccag gcctgattct ccaatattga    101220
tgtgtgaggg agatgtcaac agaggttccc taaagaatga tgcttctatt tccatgctaa    101280
tcctggggcg tcagcttcag tcggaacagc cggaccgtta ccttagctct gctgttctcc    101340
tgtctgtaac ccgcagaggg aagggcgggg tcacccagca ttgccactcc ccccaccctc    101400
acgtggtcca gacccctctt gggttgatct gctcctgaaa aacagtgttg gctcaagttt    101460
gcctctgaag gtatgtcacc gctggctcag ccagcttatc tccccggtgc tttcaagatc    101520
aaaacaccca aacgaaagaa aaactttgtt tcaagagcag agtgtggtgc caactctgat    101580
caaagtgttt ttcagcatga caactcactg cccgtgacaa ccagtacttg gctgttgtgg    101640
ctcagagtga gatgcggagg gaagtggatg acaacagctg tatccaggtc caaacagagt    101700
agattcacgg ctggcagaaa atggctgaga gccttgggct gcatccctcc tccctcctg    101760
cctctctctc ttttcaaggt ggttttttgga aatgtccttc ctgtgggttg tgtgccttt    101820
ccatgtagga cctgggggcct gtgcagatgg ccctgtgttc ctggtgctgc tgttgagatg    101880
tgaacgagtg ataggaaccc aggcactaaa cacacaatgt ggttgtatct gactagaagc    101940
aaggcaagag caggaggcat ttgagggtaa aggagtgtaa ggactgtgta aagagatgag    102000
ggttctatct gggaggcagg agtcccaatg ccagcaaata caatggactc tcctggtcga    102060
cccaaccaga gagaattcaa gatggcagag ggacaggctg tctgagtttc ctatggctgc    102120
accgataaat ggtcataagc agagtagagg aaaaccacag acagaaattc atgccattga    102180
gactagaaat ctagctcaag gttgtgtgtg gcagggttgg ttcctgggtg ttcaaccttt    102240
tcacactgtg acatgatgct gtggtctgca gatgtgttgg gctgcatcca tagctaccct    102300
gggacacatt catggaccgc aggttacaca tgctatttaa aaactccaag ggaagggcta    102360
gagaaatggc ctggtagtta agtatgcttg ctgatcttcc agaagacctg agctctgttc    102420
ctagcagcca tgttgggcag cttacaacta actatgactt ctgagctcca aagctctctt    102480
ctaatacata catacataca tacatacata catacataca tacatacata cgtacacaca    102540
cacacacaca cacacacaca cacacacact ttaaagaaaa aaattctggg ttggagaggt    102600
ggctcagcaa ttaagagcac tgactgctct tacagaggtg ctgagttcaa ctctcaacca    102660
catggtggct cacaaccatc tgtaatggga tctgatgccc tcttctggtg tgcgctgaag    102720
acagatacaa tgtactcata tacattaaat aaataaaata gaaagaaaga aagaaagaaa    102780
```

```
gaaagaaaga aagaaagtgt aaacgaggaa aattcctaat taaaaaagaa agaaagaaag    102840
aaagaaagaa agaaagaaag aaggaaagga attctgaggg agaatctgcc ccttttccta    102900
acttccaggg ctataggcaa cctgtggcct ggggaagctg tagacaacct gtggcctggg    102960
gaagctgtag acaacctgtg gcctggggaa gctgtagaca acctgtggcc tggggaagct    103020
gtagacaacc tgtggcctgg ggaagctgta gacaacctgt ggcctgtggc agcatcatgt    103080
caacgcctca ccctctgtgc ccaatttcct gttctctaag gacacatgcc atcaaatgca    103140
taggacactc tacatcaaga tgatcttgtc tcaagatgtt taacaaaatt acatctgcaa    103200
agacctatct ttacatgtga ggtcactcca caggttctag acatattttt gaggagccac    103260
catccaactc actatgtgac agagtcatct agagatttgt gtccaggaca gactggctgt    103320
atctgctctg agagtcccct gcctgcccgt gggaactccc cagtggtcct taagggccct    103380
gaggactttg gatctgcaaa gccacatctt ccaaaaccat tttcctcttt tggagagcta    103440
ctctaccctg aaacccttttt ctctgaggtg gcttttagag aggcaggtct cagcagggca    103500
ctgtgcccac aagaagtccc ggggagaagg gacccaaggg ccagtgctga actatcgctg    103560
agactgagaa cattgtgtct cacctaaaat cggtggtcgc aaggaccaag caggctctat    103620
aaatgtctta ctgcctttat ccttttcct ccgctccatc ttactcctca ttttttgtttg    103680 tttgtgtgtt tgtttgtttt cttctgagat gtagcccagg ctggccttca gctcactatg    103740
taactaagga tgactttaaa cttctgatcc tttcttccct ccacttccag agtcctgggg    103800
caggtgtgtg ccaccgtacc ccagctttat ttgagactat gattcaggct ccatacttca    103860
tgcatattag gtaagcatgc taccaacttg gctatattcc cagcctttct ttctttcttc    103920
tttgagacaa tgtcttttttt tttttaatta tatgagtaca ctgtatctgt tttcagacac    103980
accagaagaa ggcattggat cctattagag atggttgtga gccaccatgt ggttgttggg    104040
atttgaactc aggacctctg gaagagcagt cagtgctttt aaccgctgag ccatctcgcc    104100
agtccttgag acaatgtctt gctatatggc acatattggc ctcaaactca gaatccttcc    104160
gcttcagcct cctaaatact gggattacat gtgagccatg tgtttggct tctagccttt    104220 cttccttccc tttcccttcc cttttcctt ccctttccct tttcctttc cttttccttcc    104280 cttcccttcc cttcccttcc cttccctcc cctcccttcc cttcccttcc cttcccttcc    104340
cttcctttcc ctctctctct ctctccccct cttctttttc tttcagagag tttctctgtg    104400
taatcctggc tgtcttggaa cttgctctgt agaccaggct ggcttgnnnn nnnnnnnnn    104460 nnnnnnnnnn nnnnnnnnnn nnnnnnnnnn nnnnnnnnnn nnnnnnnnnn nnnnnnnnnn    104520
nnnnnnnnnn nnnnnnnnnn nnnnnaaga agaagaagaa gaagaagaag acaacaacga    104580
cgacaacacc ggcgccgctg cctccactgc catccacctg agacaggact caaatccaga    104640
ccaattttta aaaccagtgt ttcaagccgg tacactgaag tagtagtccc acttgggatt    104700
atagctcctt actttgttttt gctttgacgt tttgtgacat ggtgtgatgt agtcttggct    104760
gtcctagaac tcaatgtgta aattaggctg gccttgaact tgcttctgcc tcctgctggg    104820
atgatagact gatggtgtaa aactccactt aggaggcaga ggtgggagga tcagaaattc    104880
aaagtcatcc ttggctatgt tgtgagtttg aggaccaacc ttggctacat gatatcctat    104940
ctcaaaaaga aataaatgta ttgccgggca tggtggcaca cgcctttaat cccagcactt    105000 ggggaggcaga ggcaggcaga ttttctgagt tcgaagccag cctggtctac agagtgagtt    105060
ccaggacagc cagggctaca cagagaaacc ctgtctccaa aaacaaaaaa caaacaaaaa    105120
```

-continued

```
agtgaacccc aacagtactg ccggacagtc tggtgtcttt cctaagtctc ctttcaactc 105180
tgtttaccca ggtgtaccca caaggtgtgt gagcagctct atacccagag gtgatacggt 105240
tgtttgaatg agagaaaagt ttcccatcag ctcgggtgtg tgaatactcg gtccccagtt 105300
ggcagtattg gctggagagg tgatggggag gtgtagcctt ccggtggaga tgggctttgg 105360
gagtttaaag cttcctccac gaagaccact gggctgatct tgttaccaac agaattggat 105420
tggcctgctc ttggctccgg cctcagttta tctaaaattt acatgttacc tgatcaaaaa 105480
ctgtttcctc ccccacccct ctccctgtct gtattccctg ccctctagtg gtgctggctg 105540
tatactacac tggtgatctt gactgtattt cagtttacct cttgttctct ctctgctgac 105600
tctagagatg tcctttcatg gctgggacct ggctcagaaa tttctaaggc actgagcctt 105660
cctccatctg aactttagga aacttcttgg cttaaaggtg tatttctgac ttagtatgca 105720
atgagacctt ggagcctgca ctttgttaag caccctgggt ggtggtggtg gtggtggtgg 105780
tggtggtggc agtagtagaa ctctgatgaa cagttagtta ttcaaggccc atctagaaaa 105840
agaaaggctt tgggtgcaca tggctataac tcagtggcga gagacgtgct tcccatgaat 105900
aataatgatg acgatgaaaa taattctctg tgactgttct ccccacttcc ctctctctca 105960
ccctagctct tatctaccga atccctgcac aagcacccat ggggtttaca gaatctgggg 106020
cggaacgtta gtcacttccc ttcgcctact tcagtattgt gtttccagaa gtacccattt 106080
tggctagtca ctgaggaaaa cggcagctgc ctgtgggcca ccagcccatg ccaagtgagg 106140
tcagcaagaa agaagctgac agcaaatgtg ccaactgtgg gtctgctgga tttctactgt 106200
gctaagtggt ttcaagaagt ttcttcttaa cccctacaa gaaaccacaa attttattat 106260
ctacactgtt ttgtagatga agaaaacacc attccgaagc tcactgccag tcagcactgg 106320
aactggaatt tgtttggcta attcagtggt tctcaaccag ggtggatttg gactccccag 106380
gggatatttg gggacacttc tggtcgtcat aattgggatc atgtgctact ggcacctagg 106440
gtagaggcca gggtggtact gaccttccta ctatgaacag ggcagccatg tacataaatt 106500
ctctcgatca aaacatcaac agtgctaagg ttgagaaatc tcaggctgaa accctgtcat 106560
ttggccttga ggtgggtggg aggaggttag agagtggaat aaaatcagaa gggccaccac 106620
agaggcctcg agtgaggagg gaacagggct cctatgctag ggataatgga gaatagggca 106680
gcttgttgaa acttttcttt cttccaagct tggctagagc cctgctcaat ttcccccaac 106740
tctgccaagt cagtcccggg acttcgcact aagtttgtcc tggagtgacc ctgactccag 106800
cttggagctg gggcaacaca tttacctggg tcttcccagg agtgggttaa aagtcaaaga 106860
taagtggcat ctgagaagtt aaaagtgggg tgagtgggta aaggcaggag gaccccatca 106920
atcagctgac ctaggaagga agagagcaac tgaagcagca aagagctggt ccaggagact 106980
ggattctgac ccactaggct tatcttccac agcctttctt gtttaggctt gggctcagtt 107040
tccctgcatc atccgcagga gccctggag caccacatt cagccggccg ccaggacagg 107100
ctccccagca gtggcctccc cactaactga cagtggtgac aggaaatatc tccattcca 107160
atctcctcag aagtctgaat aagtaaggga cagatgttgg ggagaggcgt cactcttggg 107220
ttgatgaaga aaagatcatg agaagcatac attttacccg ctatggttgg ggttccatta 107280
ccacccatgg cggggttgag ggggaaggc agaaaaaagg agatgagaa ggacagacac 107340
gtaagaagga ggatgtggtt agggctgatt cgtcccctgg ggtcgaacaa tcagctgtta 107400
ctggggcgga aggcaggaag tctccttaaa gacacaatat tctgaacgtt gaactcagga 107460
tttgaagcaa gcccagcagt caccttagtg gagcccatac ttaatttaac acagaagcgg 107520
```

```
ctatctcagg cttccctctc atttctttgt ctcagatgct ctcacttaga aagcttagat 107580
gctcttagaa atgactcaaa agtcaagaac cccaggccac aagtttctct ttgggggtgg 107640
ggagggagtg aagaggtggt cccagtcttg tccctttaaa taagcaattc agcagctttt 107700
gccaagtcat tgggttcatt tcggttttg cccatcccc gcctttcaga ctctgattgg 107760 ccctaggga aggagccgcc tcttcattgg tctccacctt tgaaatcact tccctaagta 107820
ggcctgagtc agagaagcgt ttcggagggc gggactgaat gggtgttaat cttagaaccg 107880
ggtttctggt tgatactact ttggtaaaga tcttcccta attttaaaa agacgcttcc 107940 tctctaaaag tgagggcgaa tcctttgtta agaacgtgcc ccttgagaag ccgtgggctc 108000
ttcagcgact aagacgagac attcactaga aaagatttca ctaaacccac gagggataga 108060
ctagacctcc agtgaagatt gggcctgtgc gggtgacatt tgtccctata ccccgaagac 108120
ctcgagctag ctctccagtg aagactgggg ccgtgcgagt gacagtggtc cctatacccc 108180 gaaaaaaaa aagtcctatt tgtggaaaaa aaaaagact tcgggtgttc tgctgcatcg 108240
gtggctggct tccatcttta gttctactca ctcctgttgc ttcgcgtgct ccaccttcgc 108300
ttagctcagg cctcctgtga atcagttttg aggctaaaag aagttccaag aaggaggggc 108360
tgtagccctt taaggacttc cccgcgaccg agtcagagat cagtttaaaa atgccaactc 108420
acagagcgcg ctgcattctg ggaagctgag tgtcaccgta agaacttcat tgaccggaat 108480
gcactgcaaa aatacacgcc tatacttcct tctgctcttt aaactgtagt ttgacgtaaa 108540
gctggtctaa gcaagtcgcc taggccgagg gttagccaca cctttcagc cattggccag 108600 ttggttagtt ggtaggcgtg gcttagagaa gctcctccag gcaaggggt ggcctccttg 108660 ccaatcagag cccagacgcc tgaatgggcg ggagtaagca gaggtgctgg cgccccgag 108720 tgggtgtggt cacgttgccc agcaatgggc ggtgattggc cctgggtggt tcattcgcag 108780
ctcgtgcgtc acgacgccgc cagctgatcg gagactggag ccggtgtgtg ctgggcgctg 108840
ggaagagaca gagcggtcgg ccgtgcggac aggtcgcagt gattttgctc ctctgtccac 108900
agcaaccccc gcacccagca tcaggtgggt gtgatctggg gacccggtca tcccgggggg 108960
aaccgcggta accgggtgat gggggaaagta gggtcctgac ggccacaccc tgcccttctg 109020
ggggagggga gaggggcggg cggggacagg ggcgctcttg ggagaggagc ctggactctc 109080
ccgagtagtg tgtctggacg tttaaagaga gagtcccgga caggagtcgt ggcagaaggt 109140
ttggagaagt aactggggag gaatatgaga ggccagaggg ccggggcgt ctaaccccga 109200 cgcccttgg tttgaggatg cccgagctga ccatttagcc tagggaggat ctggacgagc 109260
gaggggtgcg gaggtgcatt gcctctaccg gcgctgactg ggtcagggcc agttcaagtc 109320 cctgcaggg aaggggtcgc tgggcggtcc ggcccctcct ctcgttccct cccggggatg 109380
ttatgtaagg ggggagggga aaggagtagg ggcggcggt gcggaggcct tatgcaaccc 109440
aaaggttagg gtttcaccgc gggttgggcg gaggttgggg ggggcggaca ggaggagtgc 109500
ctggaaactc tacccgcacc cccctccca gcctaactgg ctgtcttgga cagagagaag 109560
gtcacctttg cactccccc ctagtatgtc cggtagagag gccctagcc cgggcttggc 109620 ctgactgcct gggaagccgg ctggctgggt ggggcgcctg ggttagtcat cgctgggctc 109680
cctctctccc cacctcctgg ccaactcttg gcccctccc acggcctccg gttaggctaa 109740
cgttcccacc tccctctggc cctagtttca gtctccaact catttggcct gtcaccctgg 109800
ctgttagagt aggctagaag ctgtcatggt gccagagagt tgatggagca gctggtcaga 109860
```

```
gggtcagtgc cctgggccca ccccgccccg cagccaaggg cacctgcttg gcacaaactc  109920
tcagcagcca gtgaaccctg tggcctgaac agagctatcc tgggcagaga gaagtggaca  109980
gagactgatc acctaggaga aggaagatcc gacaaagttt atacttccca agaggctttt  110040
ggaatttgaa agttgcccac cctagtgtaa tctttccact ctctgaaaat agaaatccca  110100
aggcaaagtc tccttggccc ttctatctgg cagtggccat gtccttggac tgactgtgca  110160
gaaccaccct ctcgggctcc cagccctcta gcctgccacg cccccagccc ctccctgag   110220 ccatgctgta gggccccggc ttttactgct gattcatgcg ttggaactgt ggggcgggg   110280 cttggaactt ggaacaaagt tcagacgtgg aggggccggc agacagcctg gaattcatac  110340
cagatgtacc cggaatgtgc aagcggaatg cctggcatct ctagtcctga ggaagctgcc  110400
cagccaccct acccatacct ccctcccctc ctgcctttgg tcagctgtcc tccctcagac  110460
tcctgagagc ccctgctgac cttccaactc tagtgcccct cccatttcta accctacaca  110520
aaccctcctt gctgctgaat tccctaagaa caagtcattt gagttgatca cagagctcat  110580
atttctgaag tacatttttt tttttaactt gggacttggg ttctacaccc tgccctttga  110640
atgccgaaga tgctgggctc cttagcaggt tgccaagagt tgccagctcc tagtctgtaa  110700
aggggcacaa agcaagtgca tttagaagcc tcttgcttct tattcaagaa cccctcatta  110760
gaaggtactg aaagtcagct agagccaggt ttggatggcc tctgggtcgc tggccctgtc  110820
acccagcttt cctgtttttt ttttttcctcc ccttccttttt aggaacctgt gcctcccaca  110880
ccctcacctg gctgagccgc agtagttctt cagtggcaag ctttatgtcc tgacccagct  110940
aaagctgcca gttgaagaac tgttgccctc tgcccctggc ttcgtggagg aagaggagaa  111000
gcagcagctt tgcctatcat ccggaaggtg acagaactgg ggtgggaagg tctggacagc  111060
tggggtgatg gctttatggg agggaaaccc tggtcctctg gggagccctt accccactg   111120 gcccagtgaa agatttaggt taaaggcact gtctataaat tggggaatag gtgactccac  111180
ctccccaaga ttagttgatg tctgtgtggc agtgggaaga aatagaagga aaagtctgtc  111240
tgtttactga gacttccttg taggcctgcc tttcttatct tcatcatcac catgccaaca  111300
cacacacaca cacacacaca cacacacaca catacacaca catacacaca cacacacaca  111360
cacacacttt cctttccatg aggtccaaaa gtaaatgtac tcaggaaggg ggacattgaa  111420
actccgttct aagtagtcat ttgtgtattt actttttttg tttatttgtt tgattgactt  111480
tcgagacagg gtttctctgt atagccctgg ctgtcctgga actcactttg tagactaggc  111540
tggcctcgaa ctcagaaatc tgcctgcctc tgcctcccaa gtgctgggat taaaggcgtg  111600
tgccaccacc gcccggctgt atttacattt ctttatttat ttttagtctg gcccagattt  111660
tgggtttagg ggtacttacc cttacacctg tggattttttc cacctgtata atggggaatc  111720
ccatagataa gtaggcagga gggcattaaa agtccaccag tggtgactca gagcctgggc  111780
tcttcttctt ctcgtggatg gaaacgaaac agctcttcac atgaactgtt gtccttcccc  111840
caccccctga ctactcaccc agctcagggg gattaggatg gaaggaaagg ctatggttaa  111900
gtcccaggca agctcgtggg aggctagtcc tctactggct tctcaccatg catgggtggt  111960
ccaaggcttt ccctccacct aaagcaaaac tgtagctctt ggttgggttc tagcaaccac  112020
tgccatttat tttctgcctt tgcttttcag gatagtgaga ctctgctcaa tactgtgcag  112080
gcaagaaatt gtcaggggag atgggttgta tgatatgagt cccttctgct gcctctagct  112140
cctgattcat tctcacgtat gggcttggtc tctgattgtg gttcaccttt ggcccagtct  112200
tcctaacaga agatgggttc aggggtaca ggaggctgtt tgttgtattt gacaggagga  112260
```

```
ggagttctag cctgttcccc atttgtgaga aactgaaagt catagggggag actagatcat   112320
ctaatccagc cccactgcag tctaagctga gggataggat gtgtaaggga ctgtagcaga   112380
cgggctgggg aggctgagtc ggctcacaca ttgcgacaaa gattgccctt ccctcgacct   112440
cgcttgcttt ctttcctcct cccttccctg gccacagtgt gtccctccag cactgggtac   112500
atggctctgc tgtcctcatc caacatggag cctcagaggt gagaaagggc agcctggaag   112560
caacagaggc aggcacaaga cagtggagga cctggcctgg aaccacaagg gcctatccgg   112620
acattggtca gagaggcacg tagaagcctg gagaacacca ggaaagagag cagccagcca   112680
gcctcagtga aagacacgtg cttccagcca tctcctctca ggacctgcct tcctgggaga   112740
tgaagggcct ccaggaagta tggtcccatc tctaccctgc agtttctata acagcctca   112800
aggagcatga gccacctctg aaaggaaata cacagcaaat tcaaaagag attcaaatgt   112860
gtaacactgt gggaaaacat atctatgact ggggttgtag ctcagttggt aggtttgctt   112920
aacatgcacc aagccctggt tctgtcttct gcattgcata aaactgaaca ggttggccca   112980
ggtctgcaat cccggcactc tggaggtggt ggcaaaggag cctacattca aggtaatcct   113040
ctgctataca atgagttctg agccagcctg ggctatatga gactgtctca aaaataaaa   113100
caaaataaaa taagcattg gttagtaatt caaagaaagc agatgtggct gaaaccgttt   113160
tccctgatca taatacaaca agcaaatgaa agccagaaga aggctcctgt gccttgtgtg   113220
tggcagtacc aaccattgtg agagatgcct ttggacctgg tagtttgctg tcttagaaat   113280
gtatcctaaa ataaggattt ggttataaaa tgttcatctc agggttgtaa tagagaaaaa   113340
tggaacgcag ctgtttgttt ggaagtccat tccttttctg ctgtcatgaa aatgtatagc   113400
tagggcttgc ctaagtaaat tatattcatc tgatggtggt gttctgtgca gccatccaaa   113460
gtcttacaga agaaaaattg agtggaaata taaatattga atactaaaaa gattataaaa   113520
gtatgagttt gtgactgttt ttaaaatatg aacacatact tgtaatatat tttttaaaa   113580
accatccaat tgagtggaaa tataaatact gaatactaaa aagattatga aaagtatgag   113640
tttgtgactt tttttaaaat atgaatgcat acttgtaata tattttttaa aaaaacactg   113700
aaagtggatt caaaatgtta agaatggttg ttttttgtatg gtgggatagt acaattgtga   113760
attttccct tgttttttct gtctttctaa tttttaaata ttgtgcattg ctttcatatg   113820
ttaaataaaa tacaaaagac aaataaatgt tttaaaattt ttactctttt atgagtgttt   113880
tgcctgtgag tggcaggaat ccaacattgt cttctgaaag cagctagcgc taacttctga   113940
gccgtctctt cactccctct gtaattttta aaaatatat ttgtatgtta tattatgtgt   114000
ctttgtgcac cagagtgtgg gtgcacattc tgcagaggcc agaagagggc atcagattcc   114060
ctggagctgc acgctgtttg gatcttctga tgtggatgct cagaatcgca ctcaggtcct   114120
ctagaagagc agcaaatgct cctagccact aaagccatct ctccctctag tcctcattgt   114180
catgtttaga ttttggagaa tttgcttgta ggaggatggg ctacaccaag tgccaggtga   114240
aagaaaatgt ttgcttggga tacctattgc ttcttgagtg tgtgtgtgca tgcttgtgtg   114300
tgtgtgtgta tgtgtgtgtg tacactggag ctaggaatca tatccagggg ccttttcaag   114360
ctccaccaca ctaaagtcaa ttctatgaac ttcattaatt gtctgaatcc acctactctc   114420
tacacacagg aagcattcct ctgactttct gactgtcagc cagctaagga ggtgtggctt   114480
agaataagaa agaagggaaa tgctcaaaac ctgtcactct ntggggnnnn nnnnnnnnnn   114540
nnnnnnnnnn nnnnnnnnnn nnnnnnnnnn nnnnnnnnnn nnnnnnnnnn nnnnnnnnnn   114600
```

```
nnnnnnnnnn nnnnnnnnnn nnnnnncccc tattttacca agcattgcag gataaataag  114660
aacatagctt aaagaattct agagaaaaaa aaaaaagtcc actaatgttc aatgttttaa  114720 ttaatttta atgggaaaaa gtaatatcaa agaaatccat gtctacggca tattaatgtg  114780
gttaatgcaa acaggacaga ttatcttggc caaattaaac cacagtaaca cgttttgaac  114840
taaaagtcat ctatttatac gagatgaaat gtgaattagc gtgcgcgcgc aggtgcacac  114900
atgcacacat acaaacagag tcttttatt cttaagccta ccaaataact ctttaagcag   114960
taaataattt taagctctaa aatttaaaaa atagtgaaac cccttcaggc tatgacagaa  115020
tgctgctttt gccattcttt ctgataaaag tcccaaaggg tgtcataatc tgtatccttc  115080
ttagaaaagt aaggagcaca tcctatgagc tggtgacctg agttttacac ccaagtcaca  115140
cgtcagcaca cagcaatgtc ctggaccatt tgtgaggagc cccacgctgg tcctgagcaa  115200
caactcactt ggactggtac ggggtgaggc tggcgatggg caccactttg gactgtgtcc  115260
cacctgaagg ctgcagcagg ccagttccgg caggttttcc aaatggcttt gaggcaccat  115320
aagccttagc tgcagtggaa cctatgcaaa cacacaggaa aagggcagtc attcccgttt  115380
tatttctcga agtgaatgta caggcaccat ggcacgcatc tggaggtcag atgataatct  115440
caaaaaaatc caacttttgt gagacaggct cccttcattg tcttcccacc acacttgcca  115500 ggttagggc acaagctccc aaggagtatc tgctctccta agggcactgc catcagagac  115560
actctgacta ctacacctgg cttttaggtg ggttctgagg atttgaacgc agatcatcat  115620
ggttgtatag caaattttta ttcaccaagc cagacaaccg tttttaact tttttaaaa   115680 aaagatttat ttttatgagt acagtgtggc tgtcttcaga cacaccagaa gaagacatca  115740
gatcccatta cagatggttg tgagccacca tgtggttgct gggaattgaa ctcaggacct  115800
ttggaagagc agtcagtgct cttaaccgct gagccatctc tccagccctt atttaacttt  115860
taaaagttta aaattaattc tcattatgca cgtgccacag ggaagtgtaa cataagcaca  115920
tgtgtttgaa gtatatatgg ggatgtagtt atgtgacggc cagaggacaa ctctgtgaag  115980
ttgattcttt cctttcactg tgggtcctcg gagcgtcaat agggtcagca ggcatttac   116040 cagctgagct atcttgtggg ccaccaaact tattttaaa aagctagaag ttggttaaag   116100
agaaggaatt catgtaattg aaatagaaaa gcagagttga agaggagga gaggaggtga   116160 gtatgatatg gtaagaaaaa ccaagaaaaa acctctacaa gtaaatctag tcgtgttcca  116220
cagatcacta tgttcaagga tggtgtccca gaaaagggtc ctaaaacaaa gcccaggaag  116280
taatcaaaat gatcccatcc agacctgcta cagagaagct ggggggaagg agggagaggc  116340
cctgtaacct caagtccccg ggcagcacag cagagctgtg cccaatgatc tccgtgatac  116400
aggacaacag gatatctgag aaggagtccc agtgagcgtg tagcagaagc cagaggcctc  116460
gaacaaaacc aacaacttca ccatgatgaa catcatgaag atgtgtggac aaaagggtgc  116520
actctgggac acagtgtcac acactacagc ttccacctgg gacaaaaagt cacacactac  116580
agcttccacc tgggacacaa tgtcacacac tacagcttcc acagtcagat tatttttctt  116640
ctagcggaga ggctgcaagg gtggagggca ggtacaaggg aacaggggtg agtgggatcg  116700
gggtgcatga tgtgaaactt acaaagaacc aataagttag gaaagagaga tgaagacata  116760
gaagccatgg ccaacaaccc cagcactctg gaggcaggca ggagggtctc catgccaaag  116820
gtaatgaatg ctatgtctaa agagatgata aagtcccatg agagttacaa agtcagagga  116880
gaaacttgga cagaaaagcc aaatgtaaca aatgcatggt aggtggggaa aggtggggat  116940
ttaaaagaaa tttcacaaaa aggcacagaa tgtaaggtga aagcgagcga ctaccagata  117000
```

-continued

```
aagcatcaac taagaggagt caggaacagt gtattttaac tacctttata aaaaaaatac 117060
tcgggctggt gagatggctc agcggttaag agcaccgact gctcttccaa tggtcctgag 117120
ttcaaatccc aacaaccaca tggtggctca caaccatcca taacaaaatc tgatacggtc 117180
ttctggagtg tctgaaggca gctacaagtg tacttacata taataagtaa ataaataaat 117240
aagtattaaa aaatatgcaa taattggaat tattctttgc aattctacta tgaatggagt 117300
ttttgttcct gttgtttgtt ttccgagcct gtttcatgta atccaaactg gcctggaacc 117360
tgctaaatag tggaagatga ccttgaactt ctgattcccc tgtctccacc tcccaagtgc 117420
tggcctaggc tactctgcct gactcaggct cagtgaattt caaacactg cttcaaccttt 117480
gaccccctaac ttccatctct tgggtcccat cttacccatt cccagactcc cattctgtgg 117540
ctggggcttg ctggctggtg gtgtcgctgc agaggctggg gaagggactg cttgctgctg 117600
ctgctgctgc tgctgctgct gctgctgccc atatcctgga gatcaaaaca ggccaattca 117660
gtgcaaaccc agtcaagaga tttcaacacc agcagtaaat accttaggaa aacccacctt 117720
tggctcttag aggagcagac tgcaccacgc tgcacaccct gtgtctgcaa agggctcact 117780
tttttgtctg cgcatagtaa agactggttc catttccctt tcaactgttt agaattgaca 117840
gctttcagtt ttaatgaggt tctccctgaa gccttgccca tttctccttc aagaacctgc 117900
agtaaagtca ctgggctcaa tctgtgatac taccactatt tccatagcaa caaatcgatg 117960
tcatcaacag gacggtgtgt tcgtggcagg atccattaga agagaaagca gggtggtaag 118020
gaaaacctaa aagcagttca attgtctctc aagtgctttg gcttcaaagg aaaaggagac 118080
gtttacaaag ggttctaccc tttcccccaa acaaagcaac cttattttgc aactgacagc 118140
tggtggaaaa tatgagttga aagagtctca ggtaccgtga agtgctagtg aactgtcaca 118200
gcagggagag atgagaacag agttcagaag cagccgtgtc aaggcaacag ggagataaaa 118260
aggaggggga ccgagcacgc ttctaaagca gcaaataaga cgcgccaccc tgtcggagtg 118320
tgtatttgcc cttcacccett tatacaaatg tttaccaagt tgaagaatgt taacattgta 118380
aattgcctac cactatttct aaaataacga gtttatgggg tttgatttta cttctgtgat 118440
tggctctgaa ggctgaagcc agcctcgttt aggctgctca cctggagtgc ttgtagatga 118500
caaaggcagc taaaaaaaaa aaatgtccc agagctcctg aaacactaaa actggtgcgc 118560
acaggcagga agtctcccct tgccactgagg ctctcccttc tccaactgta agttctaact 118620
cctgctgggc ctcctgaggt cccaactcac cgggcatgct acatgcccat ggaattcatt 118680
tttggcaaaa ttactcttaa gtagctcaag gaatgagacg taattgtgtt gctggagaca 118740
aatacattca gcacaaagtt gagaagatta aatagaattg attatgcttt agttcatcct 118800
acagagagaa aaagtgagac acctatttac ataggagagg ggcccaggct actgacaatg 118860
agcccttcct ttacagctca gccttcccat tatcactcaa ctcagacacc agcccagtt 118920
cagtctatgt gaagcatttt taaaatcagc aagagaaagg tgagttgctc agtagtacac 118980
tgaaggaaag tagaaatgag cacacagtga cctgctgcat aagacacagt ttaaaaggtg 119040
acctatcttc cagcgaagtt cttgccttct ttaaaaagaa tgtggtattt gctggtatgt 119100
gcacctcacg aaggtgcttg cagctatgtg gagggcagag accatcctga gggaatcggg 119160
tctccttcca ccagagtcct agggatggca caaaggcacc gggcttgaca gatgccttta 119220
cctgctgagc cctttcccca gcctctcctt ttctacagtc tccaaattac ctgaggtagg 119280
agcctcattc tcagaaccat ttctgctgcg catgtctgac tgaactggat atggtcactc 119340
```

-continued

```
gactcaattt ctataaaaag ataactgagg agccggcttg gttggtagag aaaacataaa 119400
gacccgagtt ttgttcccac atggggcgtg cgtgctagag aggtgaggac ggactaggca 119460
gggagcagag gtaggcagat cccaggcctc aatagccagg cagcccaacc tgagctctaa 119520
gttcagtaag ggagcctgta accacagaag acactgtgcc gtgtaaccac ggcaagcggc 119580
ccgctgcagt ggcatctgct catagccaca gctacccagg aggctgagcc acaagactca 119640
ttgaagctgg aggtcaaggc cagcataggt accataggta gaccccatc tcaaagttga 119700 acagtaaaca tatattttac tacaattaaa aaaacaaggc cgggtgtggt ggcgcatacc 119760
tttaatccca gcactcggga ggcagaggca ggcggatttc tgagttcgag gccagcctgg 119820
tctacaaagt gagttccagg acagccaggg ctacacagag aaaccctgtc tcgaaaaacc 119880
aaaaaaaaaa aaaaaaaaaa aaaaaccaa aacccaaca catgtaccta ttctaacata 119940
aaattttcat tttttataaa aattacagtt ataatttta gttgaacata atacaatgat 120000
aagtctccaa cttgataatc tgaggctggg ggtgtagctc atttagtaga gtacctgcct 120060
agcagtcgct aagtccgggt agtcccttgc ctgtatccca gtgcttgggg aacaggcaga 120120
aagaggacca gaagttcaag gtgctcctcc tcttcaggta atgaggagtc tgagccagcc 120180
tgggatgcgt gagacacacc agtaacagca actactgcct ggagtgctca ctctggacca 120240
ggaacaagag ttaagtgcgt tactcccgta actgtctgca caatgatgga gacagtacgt 120300
catctttaac atctttggct gagaagagaa aacctggtat tcctcagctc gttctggcta 120360
agttcatgta cttcatcatc atgcagttaa tttgtaaaca accaatcctg gcagcaataa 120420
ctctaattat atagaacata agatgtggta attaggaaaa gctactaatc cacttaatag 120480 agtaacctt atctcttgca aatctggtac aagagacagt cccaaatcaa atgatggcaa 120540
gaattccaga gcattgtaaa tagcagcaat tgcccttcaa ttaacgcatt gtaacgcagc 120600
agctgcccac aagacctcaa atcaatcagt ctatagctaa ggaaaaatct ttctaaagcc 120660
aaaaccattc tacaaagcag taacgtaggc tccgttata ataacctgtt ttgggccacc 120720
tgcaaatcaa gctatcccag gaagccagat cgtaattctt aggctctgct ggctacacac 120780
tggtcccaag ccatgaggga actagattac agcaggctcc gccctcggtg acctgctcat 120840
agctatcatt cttacagtct attatggcaa gtgagctctg ggcagagaaa aattcacaaa 120900
caaacccacc aacttcccaa gcaagcattt tcttaacaaa cacaaagaat aaataaatag 120960
agcctgccat ggtagtgcac acctgtaatc tcagcatgtg ggaggcagag gcaggcagat 121020
ctctgccagg agttccatgc cagcctggtc tagacagttg caagatcaac aacgctatat 121080
ggtgaggccc tgtctcaact cccaaaccac tgaaaacaag taagacgata tggatcaatg 121140
caatatttct cagttcctac tgacagaaaa tggacacaat taggctgggt ataattccaa 121200
tatgaataat aagtatatta tacagtacct agtttaagtc tgagcaagat attatcgcca 121260
acagcacaga tacaggacac acacacagct gcaagcgtga aggatttaaa ggcacccatc 121320
cctacagtat atgcagcatt gactgtctag ttttatttcg cacactttga atcatccatc 121380 cattttgct caatatggca gcagtaataa aatgtatatt tgcattttga tgcatggtgg 121440
aattcttact agcctgggct gtgtttgctc actaactcca gtggacttct gacgtaagag 121500
gcgctggact agcttccaga ggatgtaaat ctaactttgg ttctcggcct ccctgaagc 121560 ctttgctgtg gtgaaaggtg ctgtttctga agccacgaca gtcccatggt ggtttgagta 121620
acaatactcc tggcttggta acaatgccaa aaaataccaa aaaaaccaaa accaaaacca 121680
aaaaaagcac agagctcaca tctgagccaa aaaaaccgac actccctatt ttttgaagaa 121740
```

```
ctcacagaaa tcaagaagaa aaacaagcaa acaaacagca cataacaggc taacaacaac    121800
aacaagtcca cttcagaggc caaaaaccaa aaggcaaagg ggctcttaaa catttacaag    121860
gacagacctc actcagaaca caagctatag ccatgatact gctcttcatc catcaattct    121920
taaagacaca gaagatgggc tgctggcatg actgggaaga gaccagtgtg ctcactcatt    121980 gctgggtac gctgtaacaa gcagaggaga atgtctaact gtgtctgcca atcacaggca     122040
cattcccagt taacccagca atcacttctg gcaaaaaaag cccactctgc ccgcacactg    122100
gtgtacccag gaggtaattc actgcggctt ctggtggatc ttttttcctt cttgcagtgc    122160
ttgggttcaa attaggatca agcacacttt tatagtcaga gcacggagac aaaaggatct    122220
aaccacagag ttggttaaat aaacaacaga acagccacac cagaactgct gggggcggg     122280 gggagggggg ggagggaagg gggagaagct agaatcccag cattcaggat gcagaggttg    122340
gtaaacaagt ttcaggctca gtcggggtat aaggtaagac tttatttcac aaaaataaat    122400 aatttttta aagaggacag aaaaaagaca gcgtagagaa ctagctatct tttatgtaaa     122460
ccatgtgggg tacaggagca gcatttgcat ttggttactt ggcgaatagc cctggtagga    122520
taaagaaacc ttaaactgtg ttatctataa agggcagcag tgggtgcaca atgcagtggg    122580
taggagccca cccattgcac gccatagttt tgattacaaa gtcacgcagc tctactcaaa    122640
aattaaaaca aacattaatg cttgttaaag aaacagggct gcagagatga tggctcagtg    122700
gttaagagca cagcgcccat atggaggctc tcagccatct gcttctccaa ttccagggga    122760
agctaacgcc ctcttttggc cttcaagagc actgcatgca catggtacgc ttacctacat    122820
gcccgcaaac attcaaagaa aaatacaaac tgctataaaa cccatatatg accatcttaa    122880
gattctttca tttttttgag acagggtttc tctgtgtagc cctggctgtt ccagaacttg    122940
ctctgcagac caggctggcc tccaacccag agatctgcct gcctctgcct ccacagtgct    123000
ggaattaaag gtatttaaca cacacattat acatatcttc cttcttcttc ttctttttt     123060 aaagcgtttt gttgttttt gttaagtttc aattaaaaaa ctacatagtt ttataggcaa     123120
acataattaa aaatgccaat gtgaaataaa taatatatac atatataaca ttctgtaata    123180
gattcactca cacaacttat atacttaaat acaattttca caataatgaa agctttgaa     123240 atgaagactt ctggatacat tagaaacgta ccctgaaaat cgcaaatgac ggttttcatt    123300
tctttgtgtc agacattagt gtgagtgtct aaacttgcat aaaggctctc ttctctatca    123360
cttcctacct attgcagtgg ttctcgctaa acctggaacc tggggctcct gttccttggc    123420
tggactacaa ggcagcaagt cccagcaatc ctcctgtctc acctttcttg gaaccaatgt    123480
tataagtgtg tgtgggcact agccttgtta catggctgct gggactagaa ctctggtctt    123540
caatattagg catcaagagc tcttaactgc taagccatct ttctaccctg attagaattt    123600
cttgaagcaa agaaaactca cagatggtca gagtttacac acacacacac acacacacac    123660
acatacacac acacacacac tcacacacca aggcttagtg accactgtga aaagggaagt    123720
gcggtgagga actgtaaaaa taaggtgtca ggaaagctct gcacaaaatg gtgtcctctg    123780
gacaagccag ggcctctgcc ctcatcagct cttagtaact atggttgcct acagcaaacc    123840
atgccaggga ccactctaac atggagctgg gatgggctcg agaggccctg ttattaaagg    123900
agaagctgta gagagttgat ttgatggatt ctaaagtagg gggaatcgat ttccttatc     123960 gatatgggtc agccatgctc tagtgagtgg ccccacaccc acccatgagt atgtgtggac    124020
agcacacacc ggacctggca agtcaataaa acaaaaacaa aaacaaacaa ataaacgttc    124080
```

-continued

```
tggtccacca tagtggctgc tcgtggttgg gagctgtccc gcacttatgg caggaagaca    124140
gtggctgcaa agaggacaaa agtctctgga actgatcaac tctagagtct gcttgttatg    124200
agaactggga agtacccgct gggacagaag cagactctga aggtgatcag gacagagatc    124260
acagaaggag agactggtta tcggaggaaa tctgaaacat aactcgacgc atactggtcc    124320
aaactggtgc ccatcactac aacagcagta attgaattgg gcacaacatt cagaaaacag    124380
aaaaagacta cagagtacgc accctggcta tcatcaaccc aggcgattct ggcactattg    124440
gaagcaagcc agactggaga aaaggaaaca aaaagttatt taacaaaact tcccagagca    124500
tgttaaaaaa aaaaaaaaga aagccagaca tgggggtgca cgtttttaac cctagcactc    124560
aggaggcaga ggcaggtgag gcaggaggat ccatgagttc gaggccagcc tggtctgtac    124620
agtgggttcc aggaaagcca ggcaacaaag aaaccctgtc tcaaaaatca ctgactgggg    124680
agagaggaag tggatccaag agcaagagag agagagcaga gagagtgggg gtttggatgt    124740
cagcgttatt aaatgacagc agaaaagatg gcccgaccaa atgacatccc agaaatggca    124800
aagatgaaaa aataaacaca agttctaaat atcattttaa taatgctgt gtgtctgctg      124860
gctcattctt gttatccaaa caaactaaag caggggtggc cgggatttac ggccagccag    124920
gactagagtg agacactgct ttaaaaaagc aatagatgca cgctaaccat taatcagcgt    124980
aactggagtt tgagggaggg agtgggcccg ggaagcctgt gcctataaac ccaacctgcg    125040
aggcctgaag cccgaaggtt gaactgagaa catctcaaga caaagcacag gcacaatctc    125100
ttacaaacag tttaaacaca ataccagcaa taaattgtca gctttatgac agataggctg    125160
acaggcatac cacaaagatc gggaagaaga aacgggattc ttgcacaaca tttttacaaat   125220
cgacacagct gagcctagtg acaggccgtg ataagctcaa acatgcaca ctgcaaacac      125280
cacagcatgg ccagagtgac aggtcacag caatacagca acagagacag taagaaacat      125340
tggaaaaggg aagaaggcaa agagcaccac gagagaaaag ttaacccgcg attccatatg    125400
agggcccagc atccctctcc cacctgacag agaaaaccag gaggacgcag ctgaaacact    125460
gtacaactat aaatactcct tcctagtgta gacagagttt accaaagggt atcgtaatct    125520
gaagcacaaa cataacactg taagttacca gaagtttaga cacgttgaga atttaataga    125580
agttgagaca tcaaacacac gtttgatcct agggggaatta aattattggt aacagaaaag    125640
ctctttacaa agtctccaca tttataaacc aaatacactt gtatcagaat tgttgtctga    125700
gccagaggcg gcggcacaat ggtggctgag gcagcaggat caagtctgga gaagcccctg    125760
ggtccaggga gcactagtga attcaagtaa acattaaaca ttaaataaga aagacggatt    125820
ctacaggagc ctagacaccc tgtaaggtca gtactactaa gataccaaaa ccaaactgac    125880
tcaggggct gatgagatgg ctcagtggct aagggcatgc actgctcttg cagaggacct      125940
gagttcagtt cccagaaccc gtatcaggca gttcgcccac ctgtaatgta ccagagaccc    126000
taaacatttc tatcctccaa gcacagacac acataaacat aattaaaaat aaatcttaaa    126060
aaaaaatctc tcgtggacag acagcaaaaa atactgaacg aaatctaatc aggtagactc    126120
agcaaagcaa atccaaatat gcgaaaagga taatacaatg caaatccaga cttatcccag    126180
aaaccccagg tcgctttagc atccaaaaaa ttcaatcatc ataattcacc gtattagcta    126240
accgaaacag aaaaggcatt tgattattaa taaatacagg gaaagcattt gacaacattg    126300
accattcact cttaataaaa atgttaccaa acaggagaaa gaagtaaaat ctcctcaacc    126360
cgatgaacag gaacacaaac tggctgggca cagtggcaca tcctgaaacc ccagcaccca    126420
gatagctgcc agactgggct ggcatgagaa ccaagggtaa gaggcaccca aacacttaat    126480
```

```
gatccaaggt gctgcctccc ccccccccct gtgtcactta aatccgtaat taaatttctg  126540
ggaggagggg tttgacacag ggtctcactc tgtggcacag gctagcctga atggagtcaa  126600
tgctggcctc aaaactcttc tgcctcagtt ccagagtgag gggaaacaat catgagccac  126660
ctcacccagt tttaatgcca tttaacagta caaggttaaa cgctgcctga aagaacaag   126720 acaaagaaag atcacacaga caaacatcac acaggtgctg tttgagacta ggtctctagt  126780
gatgtaggct ggtctcaaac ttgcacaaga aaagaatact tttgccatca agatcaaggt  126840
tgctatcacc catggtggca tttcggaagc agaggcagga agatcagtag tacaaggtca  126900
tcctcagcta ccatgggtgt gaggccagcc aaggcagcac gtgagccagc tgtggaagca  126960
cacatctgta accccaccac tcaggaggct gaagcaggaa gttcaagcca cacaagagcc  127020
acttaaaaat aaataaaaac ataaataagg ttggagagag ggnnnnnnnn nnnnnnnnn   127080 nnnnnnnnnn nnnnnnnnnn nnnnnnnnnn nnnnnnnnnn nnnnnnnnnn nnnnnnnnnn  127140
nnnnnnnnnn nnnnnnnnnn nnggaaaaca cccattagac tgctgaagag actgagaaat  127200
tgtcatcttg aagggttgaa atcactgagg aatggctaat gacaaaactg cttaaggaga  127260
attttattaa aaacaaaac tccttctgga ggagtactgt gctcccttca gcattaacta  127320
ctgtgccagg gaacccactg ccagcagaca cccaacttca aggataatca agcttgctac  127380
gtaacatggc tgcttacgca gacaccacac acacttcctg tatgctgggc atcacctcta  127440
gcttacttat aatatcaaac ataagtacca tgtgagcgct acagggcctg gccaatgaac  127500
agcgatggga aaaataacct gcacatggtc agtaatgggc aatccactcc ccagacactt  127560
ctaacctcag ctgcagactt gtgggtactg agaacggacg tgactaagtc aattcacaga  127620
agcagagccc tgtgcctgtg ccaggaacg gaggacgctc tcaatgggc agagcttcag   127680 ggcgggaaga gatggaaagt ggagctaggg cccgatgacg tgaatatggc taatgccata  127740
ttgtgtgtgt gtgtgtgtgt gtgtgtgtat gtatgtgtat gtggtgtgta tgtatgtgtg  127800
tgcatgtgtg tgtgtgtgta tgtatgtatg tgtgtgtatc caaaatggtt ataaaaatcc  127860
catacaatgg ctatgcttat gtgtctttta ccacaagtaa aaaattttaa gtaatcttag  127920
gaacacattt ctaaatttg gaatacttgt tggggaagct atctgagccc cagcatgaat  127980
caggaaatgg gtaggagagg caggagagat ggcttagtgg ttaacacaca catggtggcc  128040
ctttcctggc accaactagg tcactcacaa ccaggatctg acagcctctc ctggcctcct  128100
caggcaccag gcaggaaagc ggccccacat ccctgcaggt aaaacatttg tactgaaact  128160
aaataaaaac ggagcagaag ctgggcctgg aagtccttta cctccagcac cgggaagcag  128220
gtggatattt tgtgagttcc gggtctacat agtaaaaact tgtcgccaag taaaacaaaa  128280
caaaaactgg gggctggtga gatggctcag tgggtaagag cacccgactg ctcttccaaa  128340
ggtccaaagt tcaaatccca gcaaccacat ggtggctcac aaccatccgc aacaagatcc  128400
tcttctggag tgtctgaaga cagcaacagt gtacttacat atattaataa ataaatcttt  128460
aaaaaaaata cctttaaaaa aacaaaacaa aaactcccac taaaataatt ggaaaagtcc  128520
agggaaagcc acactcgatg gcgcaagcgt gtgatcacag tattctgtag gtaaggcaag  128580
aggatcacag cgggacggag gccagcctca gctacacagg ccggtctggg ctacagtgtg  128640
agaccccggt ctcaaaacaa aacaaaacaa aaaagcgtt cacattatca tatactcaag   128700
gccacaaaac accttcttct tcccaatcct tgaatgctat cgaatttggt tactttttt   128760 tggtaatttt ttgtttgctt ttcaaggcag ggtttctctg tgtagccctg gctatcctgg  128820
```

```
aactcactct gtagaccagg ctggcctcta actcacagag atgtaattct ttttcaaagc   128880
tggattttga tttgggggtg tgtgggtgat accacaggga cacttgggcc ccaaaccaaa   128940
ccaaagaaaa aacacccccc ccccaaagta tgaacatcaa ctgtatataa aactaacagt   129000
tcatataagc taagtagcct gcaggtacat ggttatggaa acagctttat catacagact   129060
tctttcagta gatgccattt gagaaaaaaa aaaaaacaaa acattctttg gattttcaac   129120
atgtaaacga aaatatgtta aatcttaaaa aaccttaaag cagacgccac tgctctttgg   129180
ggtcagggaa gcacggctgc aggcccccag agcagcacat tccctgaggg aagccttgtg   129240
cgtcctcacc agcaccaaga acagccaact ataataagct cataaaaaat cctgaaaggc   129300
tgcccaagcc tgaaaatctg atatgaaaac agagggcaag acagataaaa ggcaaactat   129360
actttaaaag tcaattccag ctatctgtgt ggaaggactt ctcgggacgg actatctgct   129420
aagaccttgt gggtgattta acagcgtgg agggcagaaa aagaaaggaa agtgcaggaa   129480
acaatggcaa aagctcctcc tccgtggcct ctacacgcat ccaagcgata tggagggagg   129540
agggaaggac actatacaca ggtaccaatc cccacgaact agaaaacaca gcttttacta   129600
actagtctat tttttttttt accttagcta gtgtctttct tatgtttggc ataatttctg   129660
ctctgcatta aataaaccta gtgtataaga aggcaaatga gtaaaggtaa agtcagttaa   129720
tgttcatttg ttttgactgt gtggtgtgca tgccaggcgc attcgtggag gtcagaggac   129780
aaccgcatgg agcaggtctt ctccttccac caccccaggg gtcgcagggg tcccagggat   129840
ggaactcggg tggtcagatt tgcttggcaa gggcttcact cactgaggcc ccccaagggg   129900
cccaattcac ctgtttactc taatgtatat attttggaga cagggtcttg ctatgtagtc   129960
caggctagct ttgaactcac tgtggacact agctggcctg gaggtctgag tgaacctcct   130020
gtttccaccc aagtgctggg acaacagaca gcaaccatca aggcaaaatg aagtcttccc   130080
ttcacaccaa agtggcttcc tatgaccttc tcctgacaac cccaaacagc aagtgcccgg   130140
atatgcactt gcgtttctct ttttttactt caagctttga ctccactttc ctaaaaggtg   130200
tttactaggc tgaagcacac ttcaggagac accctgtagc tctggagtga ccggaaacac   130260
accagctctg atgcaaaaac aaaaaacagc gatggggatg gggcaaaggt ggcttgtgct   130320
tctgtgcaat ggcattccct gacgcattac ctcacaccag atacatacag aaaagacaaa   130380
ggtaagtcct cactcagtgc gcgcatccac cacacccaaa gcaagcattc aacagctcag   130440
tggcataagg ccagcattat cacagcgcgg acaaacacaa agccaaacct ctctttgagt   130500
tccccaaggt acatagtgtt ctgtccaagg atggcctctg cagactcctg gaaacacgtc   130560
acccactggt tctcttgaaa atctgcaata tttgcctaaa aaacacaact ctattatttc   130620
agcgaataaa taacaaaagg aagacacccc aaggacgagg gaagattatc ttttcctact   130680
taaagtaact tccaagggag aaatgacatt gccgccacac acagccccg actctttggt   130740 taacggttcc cccttatgag gaagtattca cttctggtca ccccgtgttt cacttttagt   130800
acagtatcta atgaattaca ggagccactc aatacccttta tcataaagtg ggctttgtgt   130860
taggtgattc tgaccaagcg taggctatgc aaatgctctg agcacactta ggggaggctg   130920
ggccgtgcta gccctgctac atgcaggtaa tgctacgcca gtcttacgcc acaggaagaa   130980
gcttaaaatg tggtcgaact caatctgcta gaggtgtgag tttagacctc gggagacggg   131040
ccaagtaaac ttccgcagat gtcggagcat cagacagagc tgtcccctcc tgatgcaaaa   131100
ggcttcgcac ggcaagtttt taatgagcct ccatggtaat agtgggttcc tctctctcct   131160
cctcccttat caatatgctt gacatctttt agtttttga dacagcaaat aacgtagccc   131220
```

-continued

```
aatctgcccg catacttact gggcagccac agctggccct gaactcctcc tgcgtctcct 131280
ttaccccgta acaagtgctg gggttacaga catatgccgc catgttcagt gtaagtgacc 131340
gctgcccagc agggcaaagt cttccttatt tacaaagcag cagccaagcc ctgcagccca 131400
ggcctatctg atttcctcag cacaccccca agggtctcac cgatggcagt cagtccatga 131460
acaccgtagg cttctcacaa tccacactac tcaccgataa gatcatgcgg tatttgaaat 131520
tgggaaattc ccggtcacac ttctcacagc ggtacaaccc attctgctgg tcaatcactt 131580
tcttattgca gtcctgggtt gggcaggcct ggtacataca gttctctttg cggagaaaca 131640
ccaccgctgc cacagtgctg aaatagtccg cctgcaggcg aaaggaagac cgccatcagc 131700
aagcaacaca ggtctggaac aggcaactca aagctgctct tccttgcaag tggtgagcgc 131760
gtgtacatcc tagctcccac gctcacgagc gatatgcaga atcactaact ctggtttcag 131820
aaatcacacg tgctacacgc agaacccaaa gaagtaacaa accggcactc acgcacctca 131880
cttttttccat tttggagacg gcggctcact agctagcctt gaactcagag tttggtctgc 131940
ctctgtctct atagagtgcc tggctaccac acctgggcac tttgttttcg agacagggtt 132000
tctccggaac tcactctgta gaccaggctg gcctcaaact cagaaatcca cctgcctctg 132060
cctcccaagc gctaggatta aaggcatgtg ccatcagcgc ctgacccaat tcttttttatt 132120
tatagttatt atttgttaca tatgtgtatc agtgtgtatg acgtccatat gtatatgact 132180
gtgtgcagtg tgcacatgtg tgcaggtcag aggacaactc tcaggagtca gttctctcct 132240
cctactgtgg cgtttgggga actcaggttc caagatagca ggaaaagtgc ctttaacagc 132300
tgagttatct cgacactgac atgtaatgat tcagtgtgca cacagtggtt ttgcatgtag 132360
tcatataaac cacagcgtgc atgtgcaggc taggaaacaa cctgtgggag ttggtgatct 132420
cccctcacca tgtgagtgag ggagaggaac tcaggctgtc aggctcggtg gcagtgcctt 132480
tactcactga gttcccttgc tggccaagca ttatttataa gatggtgatg tctacccctta 132540
tctttaggga tcagtaagtt tttccccaag acaagccaga aaaccttttt aggcccaatg 132600
agccattcag tcagtctcta ctgccactcc tcaacctgtc tgtggggcag acaagccac 132660
agacaacctg aagacggaag gtgagccaat aaaatcttac tgacagtaac agccagccag 132720
ctcacaggct tgacaggcaa ttcttggact gaatgcgttt aagagaatgc agaattaccc 132780
atgactaaga tcttctaaat ggaaaaatgt ctggttaagt aacccagcaa ggagctaagt 132840
cacgcaagcg gtggatacct gctttgcctc tgaaccctgc acaggttttg gtttatgttc 132900
aatcatgtca agtacctaca aaatccagat ctagcctgaa ttcaaagata ggctacctac 132960
cctgcccccg gacccccacc cggggtctca ctgtgtagtc ctggctgtcg tagcgctctc 133020
tatacagacc agctgttatc aaattcagag acccacttgc ctcccaagtg ttgggattaa 133080
aggcatttgc cactatgcct ggctctcact ggttgtacca gaggagcaaa acaatgtggc 133140
catttaaaga gacgaagcta gaaaccagtt tagacagctt tggggctgtg ggtgtagctc 133200
agtggaagag cttgcttagc atgcacaagc tgttggtttt aaccctcagc gtgacagaac 133260
cgaatacata agaaggctta gaggaggggg tggtggtgga gagatgggtt agaggttaag 133320
agctggttgc ttaatttccc agtccccaca tggtggctca caacatccat aactgcagtt 133380
ccaggggatc tgatgtcctc ttctgacctc cttggggaca tgcgactcat ttggctcaca 133440
tgcaggatgc ctcgggccac tatgctggct caggggtgaa ggtgcttgct gccaagctgg 133500
gtggatttga gtttggtccc tgggacccac aaggaagagt ttgacttcta tacactgagg 133560
```

```
tggaacatgc atgctctacc cgcaaattaa aaacttaaaa tttaaagagg aagctgtaga 133620
gaaatagctt ttaggaggat gcctaaggaa cttctctgcg ttttcaggtg agattcagac 133680
tcaaagccca atttaaaagt ttgagtgctg tcacgtgttc tgtatgccca gttctggctg 133740
tccgttgtct gtctttagtt taagagagca actgggtgag aagtaactga gagtctagcc 133800
gatgtttaat tctcaagatg tcctgtgata gcattataag ttgctgtgga tgacagtgat 133860
ggatcgagca cacagtgaaa tgagacagtg aggaagaaaa cctatattgt atacgaggac 133920
aataatggag cagtggcgag cgatattttg ggaatacaat agaaataaat gattcaaata 133980
tccaagagaa cgcaggttag accaaggtag gaagaggatc actgggctgg agagatggct 134040
cagtggttaa gagcactgac tgctcttctg aaggtcatga gttcaaatcc cagcaaccac 134100
gtggtggctc acaaccatcc gtaataatat ctgatgccct cttctggagt gtctgaagac 134160
ggctacagtg tacttacata taataaataa ataaatcttt aattaaaaaa aaaaaaaaaa 134220
aggaagagga ccactgagca cacattgaaa tggaagatgc aactgaaatg caataccaga 134280
gccagtctgt ggcatggcag caggaattac agtctgttca aaacccagca cggacctgag 134340
gctacattat gtccctctac actggccgtg actgaaaagc agcaacgtgg taccctggag 134400
caggcctgag gtcccaggta aggacacagc cctgacctgg cactaggaaa caggtgtaaa 134460
aactcaagcc cctgccgttc tctgggtgtc tggagcgagg ggtgcgaggt accttgtctc 134520
cctggcccag gttctcagat ttagcctcat gcaaagtttt ccagttggtg ttgccccctc 134580
cggcccctcc actcctgtgg tcagagatgg aaacaccatc taaggcttgt ccttctgagt 134640
caaacctagg ggagaaagaa acaaacgtac tgctgacagg aacttcacat ccttctcaaa 134700
tgtgctgtga atgcaccagc cccgagctgc gccccctcgg ctctcaccta ggtctcagca 134760
cacctagtcc actcaagaaa tgcaatgccg ttgctccttc catctcgtgt ccttcaatgc 134820
ccctcctcct ccacccgcaa ggtcagacaa actgccaaag taccacagac cctttcccta 134880
aactgggctc acattgacag cagccatgaa caaaggcagc aacagcaagc cacactggca 134940
cccctccccc caccctcggc ctcaagcctt caccccaatc accaaaatga accagatgaa 135000
aagggacatt tttgtttcat gagtctgcca aaaatgtttt catgggagaa atcttttaa 135060
gcccaatcag ttatagaact caatcagaag gcattatctg ctgtgttaga gatttgcatt 135120
ctcagtgaga atttgtttat ggaaatatca aggttaaatt catttatatg aaattattat 135180
taaaattgac tatacttctt gaccatctat tggctaatct gaaggaaaag aggccaggga 135240
gaaggtagca aggacaggct agtggcagag gacagtgagc ctgagatgaa aacacctcaa 135300
ctacacgatt ggtggtaact aaagctgccc ccacacagga ctgactccct aaggagactc 135360
ccaacagagt agcggtggcc caaggcaagc agtcacatcc gtcagaggac aaggtccata 135420
aatccgtctc accactacta gccgctcaag tttaacttca cacaggcatc ggcaaccaaa 135480
gacggctcat caggagtgaa cagagccagg agacaggcag cctctcttat agtaaaaggt 135540
ccactcttag agccaagatc taaagatcgc taatccttgc ctgggtaggg gggtatact 135600
gaacttgtag atcaatgaca gtattttgtt cggggggacag acatgcctgt ttgtgatttc 135660
tgtgatcaca gttactgaca gtgaaatatg aacaccttaa tgtagacaca caattaacct 135720
ggggttgtgc tcagagtctg ggagaaaaac caaccaacaa accagaccaa tgccatggct 135780
gtctctggtc agacttctgt cctacaatgc aacgctagct atcagcacag ttacacagcc 135840
agacccacac cactgaggat gccttaagtg acagacaccc cagatggatg ctctaagtag 135900
taaatattgt tattggttta catcagactc aaaacaaaaa tgaggagcgt gaaatatgag 135960
```

```
ctgtttttct tgagtctctt aaattctacg acacagctgg aaaccacaca tgcccaccct  136020
ggtactacag ctattcaatt tccttaagct tgggctaggt aaagtatttt ctttgaccac  136080
ctcaatcctt ctacacaaca ccctcaggat gaagtgctct tccaaggcag agtttaatgc  136140
cttaaaaagc tagatatggt gtggaggttc taacaagctc tcctcatctc ctgagtgctt  136200
tgggaatgac aatgtacagg caacaaagag tccattgttc tcactgtact ttaccgagtc  136260
cagtgacaac acaacagaag atgtgaccag ctccagagac tcagcagagt aagaaagtac  136320
attctacccc cacatcagct gcccacagtg caaactgaag atgctctcag cactgttctt  136380
cagcgcgcag ctgttaaagc cttgccgtac ctggcgggat caaggtcagc acttagattc  136440
taattgcttt ctctggctct ctatgttcat caggggatcg tgggtttgtt ggtttaagag  136500
ggctttcagg ccaccatctc agaagacata atgcctcgaa gaagtatagg aaccactcca  136560
ctcaatagca aaggcttggc aaaacagctt ggcagcagtc cacatgctga cagtgtccag  136620
ctctggttta ccagagcccg agcacagata acccctgagc tgagttgcac aaaacctacc  136680
agccacgaag cttataggcc tctgggatgt caggattcac aatgacagtg ctggatgaga  136740
ggaccgagag gctccgtcca ccgaagtcag agactcgggc tcctttgatg gccatcacgg  136800
gctgccgaga gccgtcaaac ttgtcagcct gcaaatcaaa cgcacgcaca catcactgac  136860
aagaagaatg tacaggatgg ttttatggag aagagtcagt caatgtctgt ggactctaag  136920
acagacctcc cactcgggaa ggagcattgc actacaagaa gctgcaataa ccgatcatct  136980
cacacagcga aggtcttcaa atacttactg gatagcacaa ctccctgagc taaagcccca  137040
ccctcaggac tcggctcagt gcaaggactc acatcttctc cccacagagt tgtggtcacc  137100
accttccctg acatgtccat caaatagata tttctcttag caacttctct gttgttcgac  137160
ttcactgtga ttttaatcga atcttcatag ctcttgcaga ttccaatgat gtctgaaaca  137220
aagaacactt tgtaagagct cccatcaagg ctcctcttta aaacacggca gggacgaaag  137280
gcaagcacgc tagtcacgca tcaccccaaa cactggagac aaaaatcacc actctttgcc  137340
ctcaaccctg gacgcaccta ctagtgcgtc tttagccttg ctctctaggt caccgatccc  137400
tgtgaaatca aactgaactg tgggtaagtg atggccatct tcacagggaa ggacagaagt  137460
ctcattattg aaggtcatct catagtcatt tttaacagcg gagaactgtt tgttagcgat  137520
cttcagggcg ccctttgaga agtaatacac ctgcaaaaga ggccaagtca gggcaagcta  137580
ctcagtccat caaagcccgc cccacaatgc agccttccaa actgtgctca tggctctcac  137640
agttcagcct gtcagctctg actcaacacc gtcttcttac cttgttcact tcaataaggg  137700
gaaagaactt gtccacttgc tcattgaaag cagtagctct gatttcaccc tgcagaagca  137760
agggagagca cattagaact gcgctgctag gccctcgctc tcaacagcga gagcaggcca  137820
ttttgacagt tagacaccat cctcggagca acagtccaag tgtaaagaga ccctcacagg  137880
gctgcagaca ttgcagaatc ccacatatac agttacattt tcaagctatc agctctggta  137940
aaacaaaagc agctcagcca cccgagccta cagttgtaag ttaacacata aaacgaggga  138000
gcctcgagat gatctggaag acaaaggtgt ttcctgtgcc aacctggcca ccctagttta  138060
atcccggaac cctcgggatg gagaagacaa tcgccccacc aagttattct ccagcctttg  138120
cacacgtgtg catgcataca cacgaaaata attcttacat cttatcaaaa cattttaga   138180
aggaatagct taatattccg ataatgaaac ctaatattct gggtcccgag tgatgggctg  138240
gaagcccaca ggaaggcgtg ctgaactcca atgattcagc actcttcctc acgcccgcaa  138300
```

```
cctaagtgac ggcttacttc acagtcagga gctggtgcca aaaatgttcc aacaagtcat 138360
gctttcaagc tgactgcact gttacttttc tgtcaggcaa tatgttacag atggataaga 138420
aacttaacta aatggctaaa accttaccca gacaagctgc aggaaattag tttctgatac 138480
tgaatctgcc atcacagtta agatatctgc tgtgctacac cgtgacaaga ggaagaagag 138540
ggggagagag ccccaaagct ttgcccttcc cggtatcatg gcttatttta cgtgtgtggg 138600
tgttttacca gcatgtatgt gtgagcatca ctgagtgtct gatgcctgag gtgaccagga 138660
gaggtactgg atcactgaca cgggagtcac agatggttat gtgctactct gttggtgctg 138720
agaattgagc ccaagtcctc tcaaagaaca gcgagtgctc ttaaatgctg agcagtctct 138780
ctggcccctg cattttgctt taagtaaagc ctagtgagta taaatgatca gaagccctcc 138840
ccgcagacta gttaaagctg agtagctgct gctccttctg ctggaggcaa acccgccctg 138900
ctcggcaggt atcaccccag ggcttcaact gtgcccctag caatgtaatt agagcgctgc 138960
agtctctgca gacggagact atttacagtc caccaatctg tattgctaca gacgcgtccc 139020
tttaggagca ctttatctca tgtctgaccc tgtgccccag atagcatcaa aggtctccaa 139080
cagaaggaaa gccacaatga ccgccatgtt cctcggagct gagccccacc cgnnnnnnnn 139140
nnnnnnnnnn nnnnnnnnnn nnnnnnnnnn nnnnnnnnnn nnnnnnnnnn nnnnnnnnnn 139200
nnnnnnnnnn nnnnnnnnnn nnnnnnnnnn nnttttttatt aattatgtat agatatagat 139260
atctctatat atgaatgagt atcctgtagt tatcttcaga cacaccagaa gagggcatca 139320
aatcccattt acaggtggtg gtgagccatc atgtaattgc tgggaattaa actcaggacc 139380
tctagaagag caatcagtgc tcttaacccc tgagccccct cccttttttt tttttttttt 139440
ggcagcttat ttttaattgt tttaaatcac gtatatgttt ctgtatgtag ctatgttcac 139500
ataagcgcag gcactcatag aggtcagaga tgtaagatgc ctttggagct ggacttaaac 139560
atggttgtga gccatctgat atgagcacca agtggacttg ggtcctctgg accgccttgc 139620
tgccttccac ctagaattac agtatatgca attagctgct cagccacccc ctcagtcctc 139680
cttagtactt tcaacatagt gtaaatcgga gagcactcct tggtgcaaag attctgtgtg 139740
ttctatcatt ctctacaccc aggcttcatt gggacgtgtg atgccagcga tgattcattg 139800
gcgtgaagta tgagttagag tcagacaatc agtgctctct gctctgagtg ggtctccctg 139860 ccccctgtgtc tctgagacag gggaggattc tcctgttgga tcacatagtg catagagccc 139920
tgtgtgcaca gcgctctcaa ccatttgttg ccatttcaaa tacagtgact tcagagtctt 139980
ccttgaaata acagatttct ccattttgtt tgttcccttc tttcgtcaca aagacctgag 140040
gatgagatgt ttttgaagga actttctagt agttactcgg tggaaaagga caatgatgct 140100
cccctcttct acagagaaga aggaaacagg aaattccaag aaaaggagta cacagatgct 140160
gcagtgctgt actctaaggt aacgtgcgtc caaccagcag ttgaacaagg cggaagatag 140220
aggcaaagtg cagactcata accagtccat tgttttgctt tggttagttg ggttggttgg 140280
tttgtttgtt tgtttgtttc ttcttcttta ttagtcggat tggatttggg aaaaatgtag 140340
tagaattcta ttgttgatta tattcacaaa caaaagactg tttatatgtc ctgaattttg 140400
gcaagattct tcccatattc cttcagaccc atagcagcag caagcttagt ggccctttgc 140460
caggtattct cactgagctg tacagcattt gtctgaagaa ctgatgaaca ttttagctta 140520
tgctcctatg ttagtaaaata gctaggtttt tagctagcca ccttgctagc ttacaactag 140580
aatgcctctg gctgagtttg gtggcacttg ccttttagttc cagcactcag gaggcagaag 140640
caggtgaatc tctgagttca aggcagcctg gtctacataa caagttccag cctggccagg 140700
```

-continued

```
gatatgtagt aagactctgt ctcaataaag taaacagcca gaatgactta aatattgcta 140760
aaaaagaaag aaagaaagaa agaaagaaag aaagaaagaa agaaagaaag aaagaaagaa 140820
agaaagaaga aaatgagtgg atttgccata gcctagtcaa actagatttt cttggttata 140880
tgttaacata ctactattaa caacaacaaa tactttacac taaccatgac aagctatatt 140940
tttaaattat tattttatat gtatggtgtg ggaagctgtt gcagagtggc agttggctac 141000
tgctggccac cacacataca taggcagtga aggttctttt gccaagacaa gttaaccaat 141060
cagatgtgag acacgcctct cctaggccta tgtaagcagc accagttctg ggctcagggt 141120
ctcttcgcct ctacaatcaa gctctcccaa taaacgtgtg cagaaggatc ctgttgcagc 141180
gtcgttcttc ctggccagtt gagcgcgcac aagagtatgg gttttcacct acatttatgt 141240
gaactgcatg tgcacttggt acccagggag cccagaagag ggcatcatat cccctggaac 141300
tagagtcaca ggttatgtat gggttctagg aatcaaaccc atgtcctctg gaagaacagc 141360
cagtgttctg gatttaactg ctgagtcatc tctccagccc caccatgatg gatttaactg 141420
ctgagtcatc tctccagccc caccaagctg gatttaactg ctgagtcatc tctccagccc 141480
caccacgctg gatttaactg ctgagtcatc tctccagccc caccacgctg gatttaactg 141540
ctgagtcatc tctccagccc caccacgctg gatttggaag cagaactgag gctttgaaca 141600
ctgtgttatt ctaactcttg cttccttgga accctgagaa aattccttct attggctttt 141660
cagagatctg tatgggctta aaacaagaat atgtccaact cttgatctct gattttatat 141720
attaaaagaa tagagtgagc ctaggagttt ggcacactcc tatgttccaa gcttcaggaa 141780
gggaagaagg tcaggagttg aaggctagtc agtcttagct ttgtgacaag tttgaggcta 141840
acgtgagctc tatgagaccc tgtctaggag aggagaaaga aagggtaaa gtgaggtgtg 141900 gctccacgct accacttgcc taacacgcat gacgcccaag gtttccgttc ccagccctgg 141960
ggttcagagt attgtgcaca ccctgtatct ttaaaagtca atagtcaacc cttggaatta 142020
actttccgaa aaatattaaa gctacatcat ccactctaca aacttgtaaa agcccttctt 142080
tgtaatggtg taagaaagta tttggcttca gttttatggc ctttgcatcc taatgttac 142140 cccatggaaa gttgcttaat gaaacaggt aaaataaga caggagggac tgcaaagatg 142200
ctcaggctca cgagtgctta ctgcccttgc agagaccatg gcaggcagtg ggtctcccta 142260
ctgcagggaa tccaaaaccc tcttttggcc tctgcaggca accacattaa cacatgcaca 142320
catacacata atttaaaaa taaataaat ctttaaaat gagctctaga acgagtttga 142380
catcagtcta ggctacacaa gaccttgtct caagaagaaa gaaatgaagg tttgctgtgg 142440
atggagaggg agatgcactt cctattccat gaagctgcta ttttggtgat tatggtactt 142500
tgcaatttta tagagagctg ctattttctt tcttttaaag taatgcttgt tgttttgact 142560
gtaaaagtaa taaatgttac tttggaaaat atagagaagt ataaagagta aaaaaaaag 142620 tcataaccag tgaagtaccg ttaacatttc tgcttctatc cggccagcca gagttttcc 142680 tgtgagaatg tgttttcttt ttacaaaatt gggataatgc tgcacttact gttttgtagc 142740
ccactctttc ccttcacgat ttattgtacc cattttctca cagtattaaa ttttcagctc 142800
caagtaattt tccatagcta actctgtgtt ctgttacaga gaagaaatgt acttaattta 142860
agatctaata ttggcataat atttggcatt atgatgctat aataagcatc tttctgtata 142920 aatatttta tgtacagcca gtgttttgtt tgggatgaat tagcacaaga gtaaagtgtg 142980
gggtcaagcc tctgagtgac gctgaattgt tctcaggaaa ggactagtta acatccattc 143040
```

-continued

```
tgaaagaatg tgggaatgct catttcttaa gcaacactgg ttattattac atactattat    143100
tttgttagta ttatacattt atttaggggg ataggaaata tgctcatata gttcaatttc    143160
aagagttgca aaaatatatg gtgtggtttc ttttcctgtc ccctagttta gtctcacttc    143220
cagccccata atctaccttg ttaaatatac tgtatataag gcatatgtag gtgaataaaa    143280
aacagcctag tatggtggcg ttaacctcgg gttacttgag aactgctctt gcagagaaca    143340
tgactttggc tccgaaagcc ttcctggaat tccagctcca agggatgcag tgcctctggc    143400
atccttgggt acgtcactca tgtgcacaca tacacatttg gtttttaatc ttaggaactc    143460
caagtgggcc aatgagatgg ctccatgtat aaaggcagtt atgcaaaggt ctggatgaca    143520
tgagttcagt cttcagattc tgcaagataa caggagagga ccaacccctg cgagttgtcc    143580
tctgacctca gtacacatgt catggtacgt gtgtagtatg cacatgcaca gaagtcccag    143640
cactcgggag gcagaggcag gaggatctct gagttttagg ccagcctggt ctacaaaacg    143700
atttacagtt atataaagaa actctgtttt gaaaaacaaa acaggggttg gggatttagc    143760
tcagtggtag agcgcttgcc tagcaagcgc aaggccctgg gttcagtcct caactctgga    143820
agagagagag agagagggag agggaaaggg agagggagag ggaggagagg gaaaggaagg    143880
aaggaaggaa ggaaggaagg aaggaaggaa gaaagaaaga aagaaagaaa gggaaagaaa    143940
gaaagaaaga aagagagaaa gaaagaaagg gaaagaaaga aaggggaagg aagaaagaaa    144000
gaaagacaaa gcaaagcaaa actaaataaa atacatacaa tatattaaat tttaagactt    144060
gagggcatag atcagtgtta taatgcttac ctagcatgcg taaaactctt ggcttctaaa    144120
cctagcaccc taccgcaaaa tatttgctct gtcttgctaa attatattgc tagttgtcag    144180
actactgtgt actttcacta gcaacataat gagaatgttc actatcccac tcctctgtca    144240
agtaatctgt tcttggtttt attttctttt gccaaattga tgggtgaaca agtatttcag    144300
ctagcctaga acacacagag aactctcttt atgaactcaa gtttcttatc cttttatgat    144360
ctccagaggt ttgtttttgt gggtttatta gtgttttttg tttggttggt tgtttgtttg    144420
tttggttggt tggttggttt tgctttactt tttcttattc attttttat ttctttattt    144480
ttttgttttt aatttaatgg actggttcca tgtggccaag gatagcctca actttgtagc    144540
agaaactggc tttgaacttc tggtcttcct tcatctacct cccaagtgat gggattaagg    144600
cacgtgccac cacatctaac aatatctggg tttctttatt ggagtttgaa agggattcct    144660
ccagcattac tttgactctt catagtttct tccagagtta ttacactttc atttgttaca    144720
ttaagagttt gatccagggc tggagagatg gctcagtggc taagagcacc aactgctctt    144780
ccagaggtcc tgagttcaat tcccagcaac cacatggtgg ctcacaatcg tctgtaatgg    144840
gatctgatgc cctcttctgg tgtgtctgaa gacagctaca gtgtaatcat ataaataaaa    144900
taaataattc tttaaaaaaa aagagtttga tccatttaca ctggacttct tgaggcagca    144960
ggatcataaa ttcaaggtga gcctgggtga actggcagaa gtggcagaag ctgtgtctca    145020
cactgctgta ttcatttcct cattgatctt cagaggtttg ctaacgggaa gtaagtggaa    145080
cagaaggttc agtattcttt ttttcccaat tctattcagt ctttagtagt agatccctca    145140
ttatctgaga tgcagagtcc cctttattcc tgtgaccatc tcgttgtttt tcagggagtg    145200
tctcattcaa ggcctaacac tgaggacatt tcactgtgct atgccaatcg ctctgcagcg    145260
ctcttccatc tgggtcagta tgaagtgagt attgaagaac ctggtgtcct gcctgtggct    145320
gcagtgaaaa atgagctcct ctctgttctt ctgcacacat tgaaatcaac tagcttgcaa    145380
acactgacat ccacccagac ccattctctc ttctgactca tgtcacctct cataggtgac    145440
```

```
cacaaacaat atgtagttga caagaagtag ctatgtcatt gtccacagtg catggatttg    145500
ttccaatagg ccagcacttc tgtgtccata tcagctagat gtgctgctga tagtatttta    145560
gattccaaaa tgtgtccaga tattacctcc ttcgtttgtt tcttctaaat aagccaggca    145620
caaagacttg aaagatggct tgatggctct tccagaggct gggtttgatt cccagcccca    145680
acatagcagc tcacaatagg ctataacgtc atttccaagg ggtctgactt cctgttctgg    145740
cctctacagg cagaaagcac agacatacat gcaggcaaaa cacataaaca taattgaaag    145800
aagatattaa ataatagccc acgcttgagc ttattcctct gatgatacag ctctcctgaa    145860
gtcatcatgg gcagtgtaaa agtaaaggtg ccccgccctg cccagggggca tcagtgaggt    145920
agctgactgt gagtggcttt cttctcatcc cctaactgct gcaacatcat caactgtgga    145980
gcattatatc cgtggatttt aagttaggaa atgacaaaga ttagatctat ggccaggcac    146040
tagtgcacgc ctttaatccc agcactcagg aagcagaagt aggtggatct ctgtcagttt    146100
gagtttacag agagtgtcta ggcagccagg gctatataga gaaattctat ctggaaagaa    146160
taaacaaatc agatctgtat ttcaggaaga tgcctatgag ctgtttgaca tgtgtgatag    146220
aggtccttaa ggacaggaaa gtattccaca tgtgtgcatt ttacagaaat tggttataca    146280
ctggagttaa ggactgttgg aatagttgaa tgttcacact cagtgttctt caaatcaaat    146340
agaagaacaa gaatctatct gggcatggtg atgcacaact gtattcctaa catgtagaag    146400
actgaggcat gctatgtgtt tgtggctaac ctgggctaca tagtcaatat tggacagtca    146460
gagctgctac taaaacctaa aaaacaaaaa tctaataatc tgggatttta tattttcctt    146520
ttttttaaaaa aagagtgggc agaatgtctc tgattttgtt cagatggcca cagaacctag    146580
aaaaactgct gctgctgctg ctgctgcata gcacacagct aatatttgac tatacgtata    146640
taaattttgt tgtatacttt agctgtgctg tcaactttgg aaaaaaagta cccagtttta    146700
tcattttaaa ttggcactgt acagaaatta acagccatat tagtctagac acattaaact    146760
tcatttttcc atttatacag aagcaatgta ctgtattaaa tattcagtct tatctacagg    146820
ggtttgatta cagaaactat caaagtattc tctaaatgat gaaaaagat tcaagaatct    146880
gactgtagat ccaaaggaca agtggagaaa aacttaggaa gaattttccc tttatcccct    146940
ccctatattg atcatctctt ttacttctaa taatagtggc catttattga acatacccag    147000
gagttccttt catcactta gatatataat ttatctcatc ctaaaatgac ctgttgatga    147060
gtcatctctc tttcagatga gaaacaaaga cattgaaaaa tctaacttgc ctgcataaga    147120
tcacacctag cctcttactc actccatgaa tattccttt tttttttttcc tttgagacag    147180
aatctcacta tgtagttctg gttgtcctag aactcaatat atagaccagg ctagcctcaa    147240
actcacagag atctgatagc ctctgcctgc cgagtgctag ggttaaatgg atgtgtcacc    147300
aagcccagca aaatttacct tcttaatttt ctaagacgtt tctcctctta aaaaatggaa    147360
ctattgagcc agtcatggtg agacaggctt aatctttaat ctcagcactt aggaggcaaa    147420
gacaggccta tgggttcggg gcagcctgat ctatagagag agttctatgg gttaaagttt    147480
agggttaaag ttttgagaca aactttgtg tcaaaaacaa acaaacaaag ccagactgct    147540
taataagaca aatcagacat aatattataa acaagtatta gtgtcactca attaaaagt    147600
cactcaggag gtgagatcaa tccccagcat aatgagggga ggaggggaga gaaggaaatg    147660
aatgggaggg gaggaggaag gaagagagaa aaaggaaaga tctcaaagca gaacacagga    147720
tgtaattttaa ggcctaagct ctcgactgaa gttgtccact tttaatgacc cttttcatgc    147780
```

-continued

```
tcatggtttt ctgtcttcgg tacatagtga agagtggaaa ccaagggtca tcctggaatt 147840 tcctttgtt ttcaggcatg tcttaaagac atagtggaag caggtatgca tgggtatcct 147900
gaaagactgc agcccaagat gatggtgcgt aagacagaat gcctggtgaa cctggggaga 147960
ctccaggagg caagacagac catcagtgat ctcgaaagca gcctcactgc caagccaacc 148020
ctggtgcttt cctcttacca gattctgcaa aggaatgtcc agcatctgaa ataaagatc 148080 caagaaaagg agactctccc agaacccatc cctgcagctc tcaccaatgc cttcgaggat 148140
atagccctgg gggaagagaa cacacagatt tctgggcct ccctctctgt cagcttatgc 148200 acacacctt tgaaaggccg ccatctagtt gccacaaaag acattctccc aggagaactg 148260
ctggtgaagg aagatgcttt tgtaagtgtc cttatcccag agaaatgcc acgacctcat 148320 cattgccttg agaacaagtg ggataccaga gttaccagtg gagacctcta ctgtcaccga 148380
tgtctgaagc cactttggc cacagtacct tgtggcagct gcagctatgc caagtattgc 148440
agccaggaat gtatgcagca ggcatgggac ctctaccata gcacagagtg ttctcttggg 148500
gggctgctcc tcacactcgg ggtcttctgc catgttgccc tgagaatgac tcttttagcc 148560
agatttgaag atgttgatag agttgtaagg atgctttgtg acgaggttgg tagcacagac 148620
acctgtttac ctgaaagcaa gaatctggtc aaggcatttg attacacaag tcagggagag 148680
agtgaagaga agagcaagat aggtgaaccc ccaattcctg gatgcaatgt caatggaaag 148740
tatggaagta attataatgc tatcttcagc cttttgcccc atactgaaaa gcatagccca 148800
gaacacagat tcatctgtgc catcagtgtc tccgcactgt gcagacaact caaagctgac 148860
agcgtgcagg cccaaacctt aaagtcccct aagctgaaag cagtgacccc agggctgtgt 148920
gcagatttga ctgtttgggg agcagccatg ctgcgacaca tgctacagct gcagtgtaat 148980
gcccaggcaa taacatccat atgtcacaca ggtaagtcag aaatggtttt tacttacatt 149040
attggtattt caagagctaa tgtttaagga gaaaaacact ataaaggaag cctggcatca 149100
aataaatcag tgacctaaaa ggaaaacaca gccgtcttat atatcattat gctattgaga 149160
agctttgagc acatttctgt gaacccgag cttgggaggt ggagatagga tgattaggag 149220
tctaagacag ctttagctat acagcacgtt tgaggtcagc ctgaactaca tgagaacttg 149280
tctcttaaaa acttgagcca gagccaggtg gtggtggcac atgcatttaa ttctagtact 149340
caagaggcaa aggcaggcag atccctgaat ccagcctcgt ctatatagtg agatccccac 149400
caggctacat agtaagatcc tgtttcaaat aaataaatat aacaaaaaca gcaataataa 149460
caatagcaac aaattaattt tttagatgta tttatttatt ttatgtatga gtacaccatt 149520
gcttttttca gacacaccag aagagggcat tggatcccat tacagatggt tgtgagccac 149580
catgtatgtg gttgctggga attgaactca acacctctgg aagagcagtc ggtgctctta 149640
gccactgagc catctctcca gtccattaat taaaaattta aaactagagt atttttaaac 149700
atttattcat tttgtgtgtg gtatacatac tataatacag gttcataagt caattctctt 149760
ctaccatgtg tgtcttggag atcaaactca ggttcttagg catgggagca agtatttact 149820
tcctgaacca tctccctagc catttctagt attcttttct tttgtcttga agatttatt 149880 tattatatgt aagtacactg tagctgcctt caaataccgg aaagggaat caggtcttgt 149940 tagagatgat tgtgagtcac catgtggttg ctgggatttg aactcaggcc tccagaaga 150000 gcagtcagtg ctcttaactg ctgagctatc tccagcccca ttttagtat tcttattaag 150060 tggtttccat tttatccaaa gatgccttta agggcctggg aagatggctc agtgggcatt 150120
gaacttggtg tgtgagcatg aagaccagag ttcagatccc tagcacccag gcagatgctg 150180
```

```
aatgatggtg gcctgcctga gattccagga caacggagac agacagggc  cctagctaac 150240
catactacac actagctgag ctgtgtgctc aagagagcag ccctggctta ctgtgcagga 150300
tggagagtga tcatctccac aggcaagcac acacctgagc acacagacat gcacaaagga 150360
aagaaaagtc cttttaaggt ggtggtggtg ttgttgtttg ggggtctttt gttttgtttt 150420
tttctccccc tccctcattg tgatggcaca ttcctttaat ctcacatctg gacaaagag  150480
gccggaggat ctttgtgaac tggaggtcag cctgttctac atagcaagcc catttcagcc 150540
aggacgacat agatataccc tgtctcaaac agacaaaaat tatttatttt atatatttga 150600
atgttttgcc tgcatgtatg tctatgcaca ttatgtctgg tgcccatgaa agccagaaga 150660
gggcatcaga tctctcagaa ctggaatttc agacacttat caagtactgc ctgagtgcta 150720
ggaatcaaac caaggtcttc tggaagagca gcaagtagtc tttttttttt ttaatatttt 150780
tttattacat attttcctca attacatttc caatgctatc ccaaaagtcc cccatacccT 150840
cccccccccc ccccgagcag caagtattct tcattgctgg gccatctccc catctccttt 150900
tctagttaat taagctgaaa gggagggagg tagatgttgc ccaaacttag gatttattga 150960
cagattaata ctctgttagc ctaactacac tatagaagct tattctttag actttcacat 151020
tacactgtcc agattttgcc atccttttg  ngtgtatatg tctacagatc ttaattcagc 151080
tgccaattta tacagtgttt ataggtattc tttgtgacgt ggatctttta cccatcttaa 151140
agcagtagga tttgaaagct gacatttatg tggcctatgg tcctgttaaa tcacatttca 151200
agttagtctc tgtggtacac attttggggt ctatctgcgg ttccgcatct cacacttttc 151260
cctctcaggg tgtccagaag ctgctgcaca ctgggctgga aggatgaagt ggagtccaga 151320
gtgagtggaa ttctgcagca tcccggtcca gctgggagtg aatgctgggg tcaggaggag 151380
atgggtgaga gggccttctc caagggcctt cttagtgtta cagctctagg caaaggcctt 151440
ctctgacaat cttagcctgt gcatagtttt ttattcgaga tgagcttgta tgcatacact 151500
ttattggcag taaatcagag gttatccact cttagggaag gagataggaa tacccaaggt 151560
ggacagaggt cattggctga aggataacgt actgagatgc tcattagcac ggggaggcat 151620
cccaggaatc tcaggtgctt gctgactggg tttcttaggg ggttgagagg gtagcagtga 151680
tttcaccaag gttatgtatg gcagagggta taggggtttc aggctcccca gacaaagaag 151740
gagaaggaga agccctgctg ataagggaag tccccatttt tgagccactt cagaaggcta 151800
tcaagacact gatagacttt gtccttaatt agcagggccc aacaagtgtc tgttttcttt 151860
tctgccttca ttggctcttt gagccactgc tacaaaatat ccaaatctgg gccaggaagc 151920
tggctcggct agtaaaggtg tttgcctcta agcctgaagg cctgagtttt cacttgattt 151980
ggtttggttt ttgttttttt gagacaaggt ttctcagcat agccctgggt attctggaac 152040
tcactctgta gatcaggctc aacttgaatt cagagatctg cctgcttcta catcccgagt 152100
gcttagatta aagttgtgcg ccaacactgc ccacctaaaa aaaatatgag gggctggtga 152160
gatggctcag tggtaagag  cacccgactg ctcttccgaa ggtccgaagt tcaaatccca 152220
gcaaccacat ggtggctcac aaccacctgt gatgagatct gatgccctct tctggtgcat 152280
ctgaagacac ctacgggtgt acttacatat aataataaat aaatcttaaa aaaaaaaaa  152340
aagaacacta ttcacaaggt acaacaacag tgtactagga aactttaaaa tagcccatca 152400
ttcattctag gggaaaaatc ttttttaaact ttagtgtgta agaaagagag aggggctgta 152460
gaaaggccac agcacgtgta tccaggttag gagtcaactt ttcagaagcg gagtctcccc 152520
```

```
ttctacctgt ttttgaggca gtctcttgtt tctgccctac actttgtaca tgaacttcaa    152580
gatggttgtt ctatttctgc ctctcatgtt gccctatgca tgctgagctt actgatgcca    152640
gccaccacat aagcatggca ccagcactga gccaagggca ggcatctggc tcacatggag    152700
agttacccat caagccatct tgctagcccc agaaaatgta tttttgacag gtgtggtggt    152760
gcacatattt aatcccagca ctcaggaggc agaggcaggc agatctctgt gtctgaagcc    152820
agcccagttt acaaatcaag tcccagaata gccaaggcta catagagaaa ccctgttttg    152880
aaaaacaaac atccttctgt gttccagtca caatgactgc tgtaacaata atatgaggat    152940
ttgggcgtgt caaaaatcac aagtagcaag gtgtaatggg caggccttta gtctcagcac    153000
ttgggaggca gaggcaggag gatctctgtg agtttagcac agccagggct gttacacaga    153060
gaaaccctgt ctcaaaaaaa ccaagcaaaa atagaattac aagttaacca gggtattggt    153120
gttaatatga aatagcagaa ctcaagatag ctaatgaaac aaaggattct attttataaa    153180
ggagacattc catactgaaa tatatgcaga gcctgatgct tgcctagcaa ctgaactaca    153240
cnnnnnnnnn nnnnnnnnnn nnnnnnnnnn nnnnnnnnnn nnnnnnnnnn nnnnnnnnnn    153300
nnnnnnnnnn nnnnnnnnnn nnnnnnnnnn nnnnnnnnnn ngcctgggca agagtaagca    153360
aaccgtcagg ctcagaggca ggatggcagt gatgtgtttt ggggcacaag gccccctttc    153420
attaaagcac caaatcttgt actaaaaaca gccctctgct ctcgatctgc agagatacga    153480
gagaggcaca catagcttcc gggcccttgc cctctgctct cccggtcagt tcctggactc    153540
ctgggagaag cttgaagctc aagaactggc cgctgttgcc tttgtgctga cgccagaacc    153600
agcagctatt cagcagctgc ggctcttggg caagcttgga agtagctcgt tccttctcct    153660
tctgcagggg aaagacaagg agatggcact gagctgggta gccaggatgt gggaagtaaa    153720
ttgtgtctat gtgggtgagg gaagtgccgt gtgtgtgtgt gtgtgtgtgt gtgtgtgtgt    153780
gtgtgtgtgt gtgtgacaga gacagaaagg gagagtgcat gttcttgtgt gttcctgtga    153840
gtcagtgctc cctttggctc ctcctgccaa aaagcatgct gtgttctcag agtcaagctt    153900
ggccaggctc gcccacccca ccaaagccca ggatctgcca ccccattaag aatgcgggt    153960 taggaaataa aaaacagggt tcttgtccaa gagaatttttt attattattt tttctctctt    154020
aattggattc agcatttctt actcctcagt atcctctctg gtagggaatt caggtctgtc    154080
tatgcagagc acaagagact gtgcttgcca gaaaaccttg ggccaacagc cctattccct    154140
gactgggctt gcctgcaggc tgccttctgg gctgacccct gagtctggcc ctctgacctc    154200
tgcccgtcct ggggtcatcc aggaggagca ggaccactgt gatacagggt tcctgagatg    154260
gctactgaaa caccctcatc tgctaaggcc actagatttt tttcccactg ccagactact    154320
cagggccctc agtaggtcac tggccaaaga gcctagatgt taaaactgca gctaaagcct    154380
ctcctgaggc cagagctcag agcctccctg gcctgcacaa agtgctaaga aggacattgt    154440
ccatccaacc cattggacta acactgtaga cgctgccttg tctgccagct tgaaaacccc    154500
agaaacctct tccccagctc cgcctagctt gcctccagca ccctgacatc cacttctctc    154560
gctaatgtct gcagcttcta cagtagggt gacggggtgc tccggggtgc cagacaggcg    154620
tgtgttgcat ataaaaacga ggtgatgttc taagtatcta agaatgttgg tccctgaag    154680 tgattcttgc tgcttctctt ccttcccgac tcttcccact gacacctttg cccccagcaa    154740
gcccagggac tattgttgct ggctgggtt ctgaacaaaa ttgccgcagt tttttgtttt    154800
tttttttctt gctagaagtt accgatacag tccttaattg agcaaatata ggttcccgta    154860
tagtttataa acatgataag acatacagtt tggtaaggag tgggttgggg gacctgtgca    154920
```

```
tttatatatt tatatatata tatatattat gtgggtgtgt gggcagagtg aggatatata 154980
taagtggaca taggtataaa actgcacctt ctgtgtgact ctcattgcga gtacagttct 155040
aaatgtcatc cactggcgat ctctcctttg gtgattggtt cttggacccc agcaggtctg 155100
ccggggctg cctgagacgt caggaatgag aggcattacc cccatggata gggactgagg 155160
gtggcatagg gttggacagg gcaggttaac taagtgatct cagacaagag ccaagagtgc 155220
tctgagattg ctggttgccc cagctggctc tgggagagcc ttgttctgag tcctgctcct 155280
tccaaaacca gcaggtcct tcagcccttc tctccaaatg accaggcttc cgcagagccc 155340
agcttcttca agggcgcat gtcccgacac cactaatgac tcactttgcg tgcctttgac 155400
cactgtgctg gagtggatac ggtccagagg cgctcggtca ggacagccga gtgagacgtg 155460
ataccccttcc cgtctacggc tgtacatttt gggcttataa tccaccagga agggtccaga 155520
cggtggctga aggcttcagc agcctttttcc tgaaacccag cagatcttcc acttaggaaa 155580
aaaaaaagaa agaaagaaag aaaagaagaa aaaaattctg ttccttgctg gacatgtggc 155640
agtgctgggt gacggagccc tgggtcctca gcggagagtg actgccagcc ccagtatcca 155700
ggccaggagt ggggcccaa gggccgtgcc tgaggatgcc tgctgcaccc cactggggc 155760
acggatgggg gtcctgcgag cacacttgcc cttcctcttg ggtcgtgcgg tgggcatgat 155820
gtcaaagctg aacttgtgct gatagtcggg ggcatagtcc tgcagttcgg taagctcttt 155880
cccagagctc accttagaga tctggttccg gttcctgtgg ctggtgcagt tcttgcctgc 155940
cttcttgtaa cctgacctgg agccaggcgg atggccatgt gggtggcctt tgtccctgga 156000
ggccccatgg gacggatggt gctccttgcg ggcagccctg tcagaggtgg taagcgtgtg 156060
agacttgatc tggtgaggag acactggtcc tgtgcagttc cggaagtcct ccaccctcag 156120
cagcttcaga tcctggcctt gccgcagctc ggggtcgcg caggggacag cagagctaga 156180
gccacggaac cttcgcagcc attcccacag ggaacgtgcc cggcagccac agtcccaagc 156240
attcccattg aggcgaagga actccaaggc caccaggggg gccagacagt caccctgcag 156300
ctcagtgagg ctgttgttga agagaaagag ggtggttagc ctgtggaggt catggaaagc 156360
cttgtggtga acccactgta gctggttctc atgcagcagc aaccggtcca ggttcaccag 156420
gccccggaag atgccttggc ccaggctcca tagcttgtta ccatggagaa acaagtgact 156480
gagattgacc aggtccacaa agatgtcatc ttggaggtac tcgatatggt tgtcctgcaa 156540
gtagagatac tgcaggctgt gcaggccacc aaagatgcct gcgggcaggg cgctcagtcc 156600
acacttatag aggtagaggg cgtgaagctt caccaggcct tggaaggtct cgggtgccag 156660
cgttcgcagc tgtcggttgt ctccaaggtc tagctcctcc agatgcacaa agccctcgaa 156720
ggtgttggga gcaatgaaag tgatgttgtt ggagtagatc cagagggtga ccatggcggg 156780
gctgaagtgg ccctgctgga ggaaggtgat gcgattgttc tgcaggaaga tgcgctcact 156840
gtcctctggg atgccctccg ggatggcagc aaagttgtgt gcctggcagc tgacagtcat 156900
gggcgcaggg tagcacacac agtctcgagg acaaccacca cccagaggta gctctccagc 156960
gagcagcaac agcagcaatt ccacacagca cctggtggg gagagacaga acagcagtga 157020
ggggctgccc agaggaggtg gagatagatg gggaacagag ggtggaatgg gggactggca 157080
aatgactctg ttggctcaca gaggttctgt cctctgtatt gtatgcaggg gtcccttgga 157140
cagggcattt ggggccaagg cccacattat ctccctcacct ctttagctct gtccctaaag 157200
tctctaattc catccgaaca cttcttcaga ctgtcagccc caccgcaggg tggaacacac 157260
```

-continued

```
ttgtgaacac aggcgagtcg gcctccggct ctgggtccgg ctctgccact cgctcactgt 157320
tagctgcctt agcaaggaat gactctaaca aagcaaatct ggagtcctga atgatcactt 157380
tatttaaata attcctcaaa ataaagaaag cattgagtcc atggtaccaa agcatgcctc 157440
aataagcgcc tctttcacac tgtggtacaa aaacttcaaa cctacaactc ctccatggct 157500
gtttcctcat gagttaaaca cagttcacag ggctgtgtgt acagacaagg cacatttctg 157560
tgagggctg tgagtgacac cagggctgac gcacgaggct tcccttgggg ttcacagtac 157620
tgccagatcg aggctgcatg ctcctctccc ccattcacac ccccccctcc tgtgctggag 157680
attgccaggc tgtggctgta aaaccgggcc ttgcctcttg actgtccaga gcatttcctc 157740
tgtagcttcc ctctaattgg gcattaatta ggcattcgtt aatggatcct taaaataatt 157800
attttcggat gtgtccagcc tgtggtcggg taataggcct atgctcatta tggaagccgc 157860
ctcattatgg acgattgtca ttacctgcct ttttccaggg tcacagctgc cccaagtggc 157920
ccagcaggcg cgtcaggaag atggggacag gctccaggcc tacgggcgcc cacctgaag 157980
ggccaggcag ccacgaccta tgtcgcctca gttggcctct tgccccttct tttccagctt 158040
gttcagctgg gactcttggg agagccaggg cccctggggg aatatgagct gagctgaatc 158100
ttcttgctgc tagctgtgct cagagcaagt ggaaggagca gggaccttct gaccaggctt 158160
cccacttggg gtcccaggcc cagggactgc ccaggccccg gcagagtagg ttgccacctt 158220
gacttctgac gccccccccc cattcccaac agaaacagca tcgtaagttg acagctccca 158280
gctgttggga gttatgggct cccagagagt ggcagctgct tctcgtccct gtaatcaccc 158340
ggcttcagct agaatgtttc tagcacataa aaatcatcgc atataattta gttttgcat 158400
aattgggttc agttgtgatt tcagagcaat tatgacctca gcagcagggg tggcacagca 158460
taggacccct ttctgggccg ggccatgccc tgcaggccct ctgcagtgct ttctgcccac 158520
cggcccttag acagcatgca ggctataacc atctctgcct caatttcctg ctccaaaacg 158580
tgtctagatg ttactctgtc gatcttcctc ctcagcatcc tgggtgtggc ctccagcctg 158640
ccagcctctg tcctagggat cctgtgctgc agagggaggc acagtcggag ggaggggagc 158700
ctgccctgtg ccaccagcac tcacactggc tgcacagtcc acagacccac agctccaacc 158760
tccctgcttg gcttgcaccc tctcttccag gaaggccatt cttgccagaa cctttcccaa 158820
cggtcccctg ggaaagcctg gactctaggt tcaaggacat tcatgatgct tgccccacat 158880
tttatgctgg atgagacaca gcagagcctt cttcactggg gggtcctgtg aaaatgaaag 158940
cttttcttcc ccggcctgca gctgcaggca ggtaggggtt gcagtgggct tatcactaat 159000
accattcgac atttgtacag ctcatcggag tttacagagg gcttttgttg taccctcaac 159060
ttcccctgtg ttctcccacc tactgtggct gctctgtctc tgtgcacccc aaaagaatct 159120
ggaagtccct tggggagatt acccccctta catagggcc tccaaggaat acaggctaca 159180
gctctattta ggaaaaaaaa aatcaaactg aaccaaacct caggtgtgga cttagtaacc 159240
agtttataaa cataccgtgg caagtggagg aggcaggcgg cagaacggca tgaaggtagg 159300
actgggtttt tccctctaaa agggcaatgg ggggacaaag ggactctagc caagacctga 159360
tgcagaacca ggctcagttc ccctgttatc tcaaggctat catcactagg aggcctaagg 159420
caatggacca caaggacctt gtccttgtag gacagtcact tcctgcagtg aagtgctctt 159480
ctggaagcat actaatagga tgtaggctca ggacagctgg tctctgtcct ttagtatttt 159540
tccacatgcc agggatgtta accttccaag cctccatctc ttctaatggg ggggggtgt 159600
tgagggcctc agccactctg catccatgtc tttgaaagcc agtggtatta ctccaggacc 159660
```

```
ctgagcaagc tgtcctagtc agccctggcc acttctggac tccttgcctg agtcagtagg 159720
tgccaatcct aggattgtca ccagcaggtt tcttcctagg gaggcaagca ctgtatcacc 159780
atggcgcctt ctatgccccc tctatgaggc ccttgggagc cccgcccac tgattgcctg  159840
attaatgtac caacaatgag gatggagcct ttgccatgca tttttaacatt gcaaattagc 159900
aggaatccaa gtctctgtgg aggggccctg cacctcttct gccagactca tcaagcgcct 159960
cttgggcagg gctgccttct acttgagggg gcggaaggga gaagacccag ttccactctc 160020
cttcccctcc aggaggtgcc cttcatcgtg ttctgcttcg ttactctcaa gcctccggcc 160080
tcccacgcac gtgagctccc aaggggctct acagcctccg tcattccttc ttccattcat 160140
acttgccccc tagtctagga gagccatgga agacagtgtg ggaagggctt gacaatgagc 160200
atcatgcccc atttgcatat gcggtggcaa taccctggtg ggtaccagga gagtataggg 160260
gaaattaaga gaggggccta aggaaagcct ctgctatccc tgggctacca gtcagcattg 160320
cttggtcact gatcccctct gtaacaccag cccttctgca acctgccaga gtttttgacc 160380
tttgaactag ggctgagaag ggtctgctct gttcagctgc cttggctggg agggggaatct 160440
gctcagacct cagcacacac tcaacagaag gcatgcaagc aagggagcta gcagtggcct 160500
tgggtcagct ggcaagcccc aaactcttcc tgccaagctg agcatgaaaa gccacctcac 160560
catggtccca tgggaccaga cctggtagga taggtggcaa ggctaaggca gcggaatagc 160620
atgtgcaaag gcactggggt gggaaagggc ctgtgcttct caccccctct aatggtgcag 160680
agcctccaag gaatactgta acctcagctc agctgggctc gggtggccag agagcttggc 160740
accagaacca gcatcaacag ggcctgtctg ctaaacccag acctcacaag ccagtttagt 160800
aggggccctg tagcaccctg gccaccagaa ctaacgagga gatctgacg ctgggaatat  160860
gtctttaatg aaaagccctt ccggaagcca catttgcaca gaagaaaatg aggtgcccag 160920
agcatcagtg ggctggttgc agctggagaa cacagcaggg ggacaggtcc taccaagcta 160980
ccctgccttc aggctggggc tctagccagc tccctgatgc ctggagtagg taaagcagcc 161040
tcgaaatggg ctgggtcagc tttttcaggc tccaaagggt caggacagct gctgcagctt 161100
agcacccaag ggggctgccc ctctaccccct aagtagaggc atccccatgg cccctgggca 161160
ggtcagtggg tctctctgaa gctttgtagg ctgcttcttg gccatgtagc caatctctct 161220
ggccttcagt cctccctccc tgcccccagc ctggccagct gctcttctct gagcaatcga 161280
tgttaaccga atgctctctt gctgtgggga tggcggcctc aggccaggcc agctgcactc 161340
ctggggctgc tggcgcctca ggccacttgg cacttgtgcc acttgtgttc taaacacagg 161400
ctccttcctg gctcggccct gaagacaaga aagctggcca gggaacagct gggctccat  161460
ctcagcctcc actgctgtgc agagcggccg gcagcctcct atccatggct gtgagtagaa 161520
cagggctgtg gagccagagg cctaagttga atcctggctg ctccttttaa tgcttgcagg 161580
agcctcgttt tcctcacctg caaaatgggg cagtcattgg aagctcagcc agtcctccag 161640
cccacagata ctggtaccca cctgcccttc ccacatctcc atctgtctaa ctgaaaccat 161700
ccaaaccaag ctcttctctt cctctccggc ctcctccgtt cacaacttct ccatcttggg 161760
taaagatggt ccctttacat cagctgcctg ggaggaacac ctcagaatca ccgtggctca 161820
ctctggggaa attctgctgg ctagatttta gaatgtatcc agtatctatc cacttatcat 161880
actcgctatt gctaccattc acccagtagc ctcctggatg cctctccccc cccccgcaa 161940
gccctgcctc ctcacccccta cacctccttc aacaggaact agggtagtcc agggaaagtg 162000
```

-continued

```
agtcaggaag ggctgctcct tagtctgcat cctccagagt gcccatctaa ctagaagctg 162060
ccccaggtct ttctcccagc ccagaggccc tgcctctccc tggctacaca gaccttgctg 162120
ccgtccctcc cacatgccag ccctcagcct ccctcctgcc tttgtccatg ctgttccatc 162180
tacctggacc ggttcccagt gtgtctgcag ggctgcttcc cagagaagcc actcttgagc 162240
agcgatttgc aaggagcttc tttcctggga cattttactc tacagcacgc gacctcttgg 162300
acagcacgac ataagtcact tgtttccttt atgtccgctg ccactttgtt ctgatgagtg 162360
tgctccctgc acacagtagg tgctcattaa cagttctggg ggagggaatt accttctcaa 162420
gtctctggag aattgaatga tgacactcag gaagccctag gctcaagcct ggggcctgga 162480
tcatagtagg tgctcgataa atgttggttg taattagtcc tgggagactc agagccttca 162540
ggagaacaga cacctgaact tggctcacat caagactcct taggcccatc aaggaagtga 162600
ccgtttgttg gatgagcact ctgagaagga cccaatacca gtcctttcct gggcaagggg 162660
aaatagactg ggactgggga gtttcccaag gtatgggatt ttcagcacta aactggaata 162720
atgctaaaga aaaaaaaaag ttagtcactc taaaagggggc caggaccaaa acctttcaaa 162780
cagaaatgtc tgggtttatg aagagaggaa gccagatatg gtgggcaca tctttaatcc 162840
aggtgcttgg gaggcaaaga cagatggagc tctgtgagtt tgaggccagc ctattctaca 162900
aagtgagttc taggacagcc aaggctacat agagaaaccc acttgacttg ccacccaaat 162960
taaaaatctt agtgggggag cagtcaagga ggaaacacac acacacacac acacacacac 163020
acacacacac acgttagtat aatatcatac tatggctctg tgcctgcagt ccaggaatga 163080
gggctgaact cagagtgtta gtgtgtgcta gtggatattt gagctctgta tttatgtgca 163140
tgtctgtgta gatgtgtacc tgaggtgttt atgtgtacac aggtgttggc ctgttgcata 163200
tggatggaga catggttgtg tttgctaggc atttgcatgt gtctgagttc atgcacataa 163260
actcacatct acctctggag actgagagtg acaacccagg gcccttttat cctgcagcac 163320
cccaggccca gcaccccgac ccagcatccc aggcccagca ctccagaccc agcacccag 163380
gcccagcatc ccacgcccag catcccaggc ccagcacccc agaccagca tcccaggccc 163440
agcacccag acccagcacc ccaggcccag catcccaggc ccagcacccc gacccagcat 163500
cccaggccca gcaccccagg tccaagcact caatgcccag caccccgacc cagcatccca 163560
ggcccagcac cccaggccca gcatccaagg cccagcatcc cagggacagc acccaggcc 163620
cagcatccca ggcccagcat cccagggaca gcacccagg cccagcatcc caggtccagc 163680
atcccaggga cagcaccca ggcccagtat cccagggaca gcacccagg cccagtatcc 163740
cagggacagc acccaggcc cagtatccca gggacagcac cccaggcaca gtatcccaca 163800
tggaggcagc acatactgaa gatagggaat gtctctgagg cctcttatct tggtccttac 163860
cctcattgct ttcagcacct gctctcctca cactcggaat caaacaccct gtgcaggttc 163920
tcccagtacc aggattcccc tcagctgagg aatgggtagc taccattttg gcttttgtct 163980
gtctggggtt ggcagcccca tgctaattgg actgacagtt tctcctgaga gcaatttggg 164040
cagcacatcc tgcccattag gcctaacctt gcctgcaggg gtgtgctgta ggggcaggga 164100
tggagcctac cctgtatagc tctgtattga ggcactcccc caagctatga cccatgccag 164160
tgggagtcat ttcacctagg caactccaga tgggcacaaa aatctctcca ataagggtag 164220
gtatgggaat aggtaaggag agcatagtga gcctggctgg gcacctgaga cctgagcagc 164280
ctgcacggga gattgtgtca ctgtggttcc agactgccaa gacatcttgg cttttcacccc 164340
aactcaggat ggtccagaat ccagagctct taagagagca gatgctgaga ggcacttaac 164400
```

-continued

```
ccagggctaa gacccttcct tggacggttt cttggctttc tactctgtcc tctgtcccag 164460
tctgtcatcc ccatctgtgc ctaacagctc tctgtggaaa acatgaggcg tatgagctct 164520
ctacttctcc cagcatccca tgcccgcacc ccagctcact gtgtgccctc atgttactca 164580
aatcttctgc taggtttgag ggccccaggt tgaggctgtg ggtttccctc catctgtccc 164640
tcccttttac caccaccact aatcctcttc ctcctcttcc tcctcttcct cctcctcctc 164700
tttctncncn nnnnnnnnnn nnnnnnnnnn nnnnnnnnnn nnnnnnnnnn nnnnnnnnnn 164760
nnnnnnnnnn nnnnnnnnnn nnnnnnnnnn nnnnnnnnnn nnnnnnnna caaaggacgc 164820
aaattgaact tacagaggaa acacaaatga gctgtaatga cagaaaagga atactatttc 164880
ccttgtgatc agaaagctat agattaaacc ccagcccttt ttgcctttgt ttttcatatt 164940
tagtggttct ggggactgaa cccaaggaag gacagctgct tggaatgttg gagacctctc 165000
aggcattgct tatgctaagc tgacaaaggc tttctgaatg catatggtag tatctattca 165060
tcttaagatg cctataacca tgggtggagc aattctctaa gagtctgtct gaacttctta 165120
agcatgtgct caaaaacaca cataaagatt gtttactgaa gcagtatttg caacagtgaa 165180
acaaaaccaa acaacaacaa aaagtactta atagctcatc agtaggaaaa agaacaacaa 165240
attgggacac atttatacta ttctcgttct atcacacgac tattaagaag attaaggtgt 165300
gaggatgaaa agcccctgca gaacaacgca cacaatgaaa ttgaatagag aataaagaaa 165360
aaaatatata gtgtatttat gtaaaacata cataaacaca taaaaagaat agaaaactct 165420
ttgactgtat atctttgaaa agaaccagca gagtgctatg gtttataaat gaaaagttcc 165480
cccaaaattc ctgagttgga ggttcaatgc agagttcata ctcttaggaa gtaactaaat 165540
caggaatgct ctgatctaat caatggattg accaactgat agattaataa tctgaaggca 165600
acacttccag gaggcagaaa caaggtgagg cctaactgga ggaagtttgt caccagaggc 165660
atgtccttgg agaggctacc tcatccttga tccttcctt tctccgcttc ctggctgtaa 165720
aagtatttat ttgactgatg taactgtcat cttggaggct tactggctcc atcagctaac 165780
ctaggcctag ccctggaagc ttctagcttc catacaatct aatccaagcc tagaatgttc 165840
cagcctttag gacttgctgc tgagatcacc gtttcctgtt cttttctgaac tctagctggc 165900
tgattcagtc cccctgttcc gggctcaaac tcctctcccc gatgatttta ttcacaatct 165960
gtctttttctc ttggcctctg aattgctctg cttggtctca aactaactct agcaatcttt 166020
tctaatctct tgtctccttc acactctctt gcttgttctg tctttactgt gtctagtttg 166080
ttctctcttc catccttctc tgtaaagctc tcccggtaaa cctgcctcct cctcccctc 166140
tgtgccgctc tactctccct ctcagctcta ctgcactgct ctccacagct ctcctgtatc 166200
ctgtgctgca ctctcttctc cggtaccacc tgtgtctccc ttacgtagct tcccttttcct 166260
ctctcttctc ctgagggttg ggcagatcct atcctgtcaa acctttctct gattcttcac 166320
tttgtctgcc actcaattag acatcacttt caagcaggag tgcctcctct acaaaccaac 166380
tttaccttca ttgttccaaa ttaaaggtga gtactaaggg tgtgtctctt tttcagccag 166440
tgagagtaaa gatgtgtgct aataaggctg agccaactct agctagaaat agtttctttt 166500
tctccataaa taacgaatc ttagggttca caatacgatc aaatatcctg agacagctgg 166560
ctgccatgtg gtgaagagaa tgcagagagt taaggatgtg ctcttgaggt ttcagatggg 166620
aataagcatt ttcttgggag ttggattaga gtcattcctg tgacactgtg acaaaggact 166680
cgactacatt ttgccatgcc ttgagactgt ggagggctga gcgatggatt aatacactgg 166740
```

```
agtgaatttt aaggcagcca aggctgtggt tggactgtta ctagctacgt ttagctggat  166800
ttatattaag aattgggaac aaaaaagcag agtagaaagg acagttttgg cagaaggagg  166860
tttcttcata tacaacttag tttttatagt tagctttta tgttgctatg accaaaatac   166920
cttatggaaa ctgaagaata aaatttta ctgaactctt cttcacccca gaacccgacc    166980
cctcccatct agagattgtt cccggaacac tcctgaactc ttcacccag aatgctttcc    167040 tgaactcctc accctagagt tcgaaccctc ccaactaaaa actgttccaa gaacatttt    167100 gagataaggg cctcctaaaa caacctcaaa atgaaccggg tacattgcca ataatagga    167160 catgacccct tagttacgta gattcccttg gcagaacccc ttgtcccttg acagaacccc   167220
ctagtgatgt aaacttgtac tttccctgcc cagctctccc cccttgagtt ttactatata   167280
agcctatgaa aaatttggct ggtcgtcgat tctcctctac accactaggt gcatgagttt   167340
cgacccagga gctctggtct atgttccatg tgctttcttg ctgttgttct attaaatctt   167400
gccttctaca ttttgagtac ggtctcagtg tcttcttggg tccgcggctg tcccggggct   167460
tgagtgcttg agtgagggtc tcccttcggg ggtctttcat tttggtgcat tggccgggaa   167520
acagcgcgac cacccagagg tcctagaccc acttagaggt aaggttcttt gttctgtttt   167580
ggtctgatgt ttgtgttctg tttctaagtt tggtgcgatc gcagtttcgg ttttgcggat   167640
gctcagtgag accgcgctcc gagagggaac gcggggtgga taaggataga cgtgtccagg   167700
tgtccaccgt ccgttcaccc tgggagacgt cccaggaaaa acagggagg accagggacg    167760 cctggtggac ccctttggag gccaagagac catttgggt tgcgagatcg tgggtttgag    167820
tcccacctcg tgcccagttg cgagatcgtg ggttcgagtc ccacctcgcg ttttgttgcg   167880
agaccgtggg ttcaagtccc acctcgcgtt tggtcacgag atcgtgggtt cgagtcccac   167940
ctcgtgcaga gggtctcaat cggccggcct tagaaaggcc atctgattct ttgagttgct   168000
tgtggtcgac gcagagtcgc cgccgttct ggtttctttt ttgtcttagt ctcgtgtccg    168060
ctcttgttgt gtctactgtt tttctagaaa tgggacaatc tgtgtccact ccctttctc    168120 tgactctgga gcattggaag gaggtgcggg tcagagccca caaccagtcg gtggaagtca   168180
gaaagggtcc gtggcagacc ttttgcgcct ccgagtggcc aacgtttaga gtaggctggc   168240
cacctgaggg tgcttttgac ttgtcactaa tcgctgccgt caggcgaatt gttttcagg    168300 aggaagggg tcaccctgat cagatcccct acattgtgac ctggcagaat ctcgtccaat    168360
tcccacctcc gtgggtcaag ccttggaccc caaactcttc gaaactgacg gtcgcggttg   168420
cccagtctga tgcagccgga aagtctggcc catcagcacc ccccaagatc tatccagaga   168480
ttgacgacct cctctggata gactcccaac ctccccctta cccctgccc caacagccac     168540 ctgcagctgc cccaccacag ggaccaatag cgagaggggc tcaggaccg gcgggggaga    168600 ctcggagtcg ccgaggccga agccccgggg aggaaggggg gccagactca acagttgcct   168660
tgccactcag agcacatgtg agagggccag caccaggacc taatgatctc attcctttac   168720
agtactggcc ttttcctct tctgatttat ataattgaaa aactaaccac cctcccttct   168780
cagagaaccc ctctggactt actgggctcc ttgagtcact tatgttctcc catcaaccca   168840
cttgggatga ttgtcagcag cttttgcagg ttctttttac aacagaagaa agaaaaagaa  168900
tcctcataga ggcgagaaaa aatgttctgg gagaggacgg cacacccact gccctcccta  168960
acctcgtgga cgaggctttc cccttgaacc gccccaactg ggactacaac accgcggaag  169020
gtaggggacg cctccttgtc tatcgccgga ctctagtggc aggtctcaga ggagccgcta  169080
gacggcccac caatttggct aaggtaagag aggtcttgca ggggcagact gaaccaccct  169140
```

```
cagtcttcct tgagcgtcta atggaggcat ataggagata cacccctttt gaccccttgt    169200
cagaggggca gagagccgct gtagccatgg ccttcattgg tcagtccgct cccgacatta    169260
agaaaaagct gcaaaggctg gagggctcc aagatcatac gctccaagat ttagtaaaag     169320
aagcagaaaa agtctatcat aagagggaaa cagaagaaga gaggcaggag agagagaaga    169380
aagaaataga ggagagggaa aatagacggg atcgccgtca ggagagaaat ctgagtaaaa    169440
ttttggccgc agttgtgaat gatagacagt caggaaaagg taaaataggg ctcctgggca    169500
acagggcagt gaaaccgcaa ggtggcaaaa agataccact ggaaaaagac caatgcgcct    169560
attgcaaaga gaaaggacac tgggctagag attgccctaa aaagcgggag cgatccaagg    169620
tcctaaccct agaagatgat tagggaagtc ggggctcaga ccccctccct gagcctaggg    169680
taactttgtc cgtggagggg actcccgtca acttcctgat agacaccgga gcagaacatt    169740
cagtactcac taacccccta ggcaagctag gctccaaaaa gaccatggta attggagcca    169800
ctggtagtaa attttacccc tggacgacca aacgagctct tcagatagac aaaaatatag    169860
tgacccactc ctttctggtg atacctgagt gccctgctcc cctcttgggg cgcgatctgc    169920
taaccaaact aaaggctcaa gtccaattta cttcagaagg cccacaagta agctggggaa    169980
aggcccctgt tgcctgcctt gtcctcaaca cagaaaaaga gtaccggttg catgaagaac    170040
aacccaaaaa tgcagtctct tcaggttggc taactgcgtt ccccaatgtc tgggcagaac    170100
aagcaggaat ggggttggct aaacaagtgc ctccggttgt ggtagaactt aaagctgatg    170160
ccacccccat ttcggtaaaa caataccca tgagcaagga agctagaaaa ggcatccggc      170220
ctcatatcca gaggttgctg ggccaaggag ttttagtggc ctgtcagtcc cctggaata    170280 caccacttct gccggttcaa aaaccaggga ccaatgacta tcgcccggta caagacctcc    170340
gggaggttaa caaagggtc ctggacattc accccacagt cccgaacccg tacaatttat     170400
taagctctct cccaccctgag agaacatggt atacagtcct agacttaaaa gatgccttct    170460
tttgcctgcg tttgcaccct aagagtcagc tcctgtttgc ttttaaatgg agggacccag    170520
agggcggaca gactggtcaa ctaacttgga ctaggctacc acaggggttc aaaaattccc    170580
ccaccctgtt tgacgaggcc ctccatcggg atcttgcgcc ttttcgcgct cgaaaccctc    170640
agcttaccct actacagtat gtagatgatc tcttggtcgc ggcggcctcg aaggagctgt    170700
gtcaccaggg aactgagagg ctcctcacag aactgagtga cttggggtat cgagtttcgg    170760
ctaaaaaggc acaaatctgt caaactgagg taaccttcct ggggtatacc ctccgagggg    170820
gcaaaagatg gctcacagag gcccggaaaa agactgttat gatgatccca tcgccaacta    170880
ccccacggca ggtacgtgag tttctgggga ctgctggctt ttgtagactc tggattccag    170940
gctttgcaac cctagcagca cctctatatc ctttgactaa ggaagggtt cctttcaagt      171000 ggaaagaaga acaccaaaga gcttttgagg ctatcaagtc gtctctaatg actgccccca    171060
cgctagcatt accagacttg actaagcctt tcgtcctata tgtggacgag agagcgggtg    171120
tagccagggg agtattgaca caagcactgg gaccctgaaa aagacctgta gcctatttgt    171180
caaaaaaatt agatcctgtt gctagtggat ggcccacatg tctgaaagct attgcagcag    171240
tagccctgct gatcaaagat gctgacaaac tgacaatggg acagcaggtg accgttgtag    171300 ccctcatgc cttagaaagt atcgtgcgac agccacctga cagataagat gacaaatgcc      171360
cgaatgacac actatcagag cctgctgcta aatgagcgtg taacctttgc gccccctgcc    171420
atcctcaacc cagctaccct tctccctcta acaaatgatt ccgtcccagt acatcaatgt    171480
```

```
atggacatcc tcgctgaaga aactgggacc agaagtgacc tgactgacca accctggcct  171540
agagctccca gttggtacac ggacggcagc agtttcctga tagaggggaa gcaaaaggct  171600
ggagctgcgg tggtagacgg gaaaaaggta atttgggcaa gcgctttgcc tgaaggaaca  171660
tcggcacaaa aggctgaact tatagcgctt atacaagccc tccgagaggc taaaggtaag  171720
atcgttaata tctacactga cagccgatat gcttttgcta ccgcacacat ccatggggcc  171780
atctacaggc agcgagggct attgacctcg gctggtaaag acattaaaaa caagaaaaa   171840
attctggccc tgttagaagc catacatgca cctaaaaagg tagccatcat ccactgcccc  171900
ggccacccaa aaaggagaaa acttggtggc caagggcaac cgaatggcag acttagtggc  171960
aaaacaagtt gctcaagggg ccatgatctt aactgaaaaa ggtgatccgc ccaaaagccc  172020
tgaggatggg aggtataaca taaaagagct atggtagacc agtgatcccc tcccatactt  172080
tttttgaaag aaaaatagaa ttaactcccg aagaaggaat aaaatttgta aaaggactac  172140
accaattcac ccacctggga gttgaaaaaa tgatgagact aattaaaaat tcccgatacc  172200
aagtccccaa cctgaagtca gtggctcaaa agattataga ctcctgcaaa ccatgtgcat  172260
tcactaatgc aactaaagcc tacagagaac ctggaaagag acaacgggga gaccatcctg  172320
gagtgtattg ggaggtagac tttactgaag ttaaacctga aatgtatggt aacaagtatc  172380
tgttagtatt tgtagacacc ttttcaggat gggttgaggc atttcccact aaaacagaga  172440
ctgcccagat tgtggccaag aagatccttg aagaaatcct gccaagattt gaaatcccta  172500
aggtaatcgg gtccgacaat ggaccagcct ttgttgccca ggtaagtcag ggcttggcca  172560
ctcagttggg catcgattgg aaattacact gtgcttaccg ccctcaaagc tcaggacagg  172620
tagagaagat aaataggacc ttaaaagaga ccttgactaa attagccatt gagaccggca  172680
gaaaagactg ggtggctctc cttcctcttg cgctcaaaca cccctggtcg tttcgggctc  172740
actccttttg aagttctgta tggaggacct cccccttaa tggaagctgg tggaacatta   172800
gtttccgact ctgaccctgt cttaccctcc tctttgctta ttcatttaaa ggccctaaaa  172860
gtgattagga cccagatttg ggaccaactg aaagcagcct ataccccagg gaccaccgca  172920
gtaccccacg ggttccgagt tggagacaaa gtcttggtca gacggcatcg aaccggtagc  172980
cttgagccac ggtggaaggg accctatttg tgttactga caaccctac tgcggtaaaa    173040
gttgacggaa tcgcctcctg gatccacgcc tcccacgtca agagggccgc cagtcaagat  173100
gaagaaaacc acgacgacaa ttggacagtg gcagtcactg acaatcctct taagcttcgt  173160
ctgcgccgca ggcgccactc tagacctagg gaaccttaac cctcatgctc caattcaaca  173220
gtcctgggag gtgcttaatg aaaaggaaaa cattgtatgg gcaaccactg cagtccatcc  173280
cctctggatt tggtggcctg atctcacgcc tgacatctgt aagttagcgg caggatcccc  173340
caattgggac ctctcagatc atactgatct tagcaaccca cccctgagg agcggtgtgt    173400
cccaaatggg atagggagca catatgggtg ttcggggcag ttctaccgag ctaatcttag  173460
agctgcacat ttttatgttt gccctggtca gggtcagagc aaaaggcttc aacaaaaatg  173520
cggggggca tcagattact tttgtggtaa atggacatgt gaaacgacag gagatgctta    173580
ctggaagccc tcctctaaat gggacctaat cacggtaaaa cgaggtagtg ctatgataa    173640
gtcaaacgaa ggagaaagaa acccctataa atatcaagag agtgggtgcg cttttaaaaa  173700
cagagcaccc tcaggaccat gcaaagataa atactgtaac cccctacgta taaggttcac  173760
cgagaacgga aaacaacacc gtctaagttg gcttaaagga aataggtggg gttggcgagt  173820
atacattcca ctaagagatc ctgggttcat tttcacgatc agattgacag tgagagaccc  173880
```

```
ggcagtgaca ctcgtagggc ccaacaaggt ccttataaaa caggggcccc ccagtcgtac   173940
tggctccccc aaaggtcccg actgtaccag ctccaccaac tccacagccc aacacagtgg   174000
taccctccct aggaactaat actctcctca taaagcctac cttggcttcc ccaccgcccc   174060
taggaacaga ggaccgtctg gtcagtctag tccaaggagc ttttttagtt ctaaatagaa   174120
ctaaccctaa tatgactcaa tcatgctggt tatgctatgc ctctagcccc ccttattata   174180
aaggaatagc tcagatcagg acttataata ctacttcaga tcattctcaa tgcctttggg   174240
gaaaaaacag aaagttgact ctagcagcag tttcaggaag agggctttgt ctgggccggg   174300
tacctcagga taaagggcac ctctgtaatc agacccagaa catccagtct agcaaaagcg   174360
gtcagtatct ggtgcctccc ctagacacag tgtgggcttg caataccggt ctcactcctt   174420
gtgtgtctat gtctgttttt aatagttcca aagatttctg catttggtt cagcttattc   174480
ccagactctt gtatcatgat aatagttctt ttttagataa atttgaacat cgggtccgct   174540
gaaaagaga acccgttacc ttaactttgg cagttctatt aggattggga gtagcagctg   174600
gagtaggtac aggaaccgct gccttaatta agaccccccc aatactatga gaactacgt   174660
gcagttatgg atattgatct tagaactata gaacagtcta taaccaaatt agaagaatct   174720
ttaacttccc tgtccgaagt ggtgctgcaa aatagaaggg aattagactt attattcctt   174780
aaaaaagag gactctgtgc tgccttaaaa gaagaatgtt gtttttatgt tgaccattca   174840
ggagtaatca aagattctat ggctaaactt agagaacgcc tagatatacg taaaagagaa   174900
agaaaaagcc aacaaagatg gtttgaaagc tggtttaata agtccccttg gctcaccact   174960
ctcctctcca ctatagcagg acctttaatt acactatgc ttttgcttac ttttgggccc   175020
tgcatcctta ataagttagt agcttttatt agaaaaagga taaacgcagt ccaggttatg   175080
gtactaaggc aacaatatcg ggtccttcag gaggttgaaa actcgctcta agattagagc   175140
tatctcctaa aagaagtggg gaatgaagaa taaaaatttt tactgaactc ttcttcaccc   175200
cagaacccga cccctcccat ctagagattg ttcccggaac actcctgaac tcttcacccc   175260
agaatgcatt cctgaactcc tcaccctaga gttcgaaccc tcccaactaa aaactgttcc   175320
tagaacattt ttgagataag ggcctcctaa aacaaccgca aaatgaaccg ggtacattgc   175380
caaataatag gacatgaccc cttagttacg tagattccct tggcagaacc ccttgtcccc   175440
tgacagaacc ccctagtgat gtaaacttgt actttccctg cccagctctc cccccttgag   175500
ttttactata taagcctgta aaaaatttgg ctggtcgtcg attctcctct acaccactag   175560
gtgcatgagt ttcgacccca gagctctggt ctatgttcca tgtgctttct tgctgttgtt   175620
ctattaaatc ttgccttcta cattttgagt acggtctcag tgtcttcttg ggtccgcggc   175680
tgtcccgggg cttgagtgct tgagtgaggg tctcccttcg ggggtctttc aaaactactt   175740
cagaggaaaa atgtattctg cctcatgggt tcagggggtt tccctcagca aattcaggga   175800
agacaagatg gaacagctca acctgctggc aggagggtgt gggaaaggac aagtgttcat   175860
tgtgtggtgg acaggaaaca gagagctgcc tacagtctta caggcctacc accactgacc   175920
tacctctgtc cgtcaggccc tacatcttaa aggatctaca gttattaaa agaacactac   175980
cagataggaa ccaagtatca aaccaccagt ttgtagggga taaaaataca aggaacacat   176040
ctcaatagga gtgtgttcca ggatgtggac aaggagaaca cagttgttta aaagcttaac   176100
gctggccagg agagctgcac acctttaatt ccatcactcg taagagggaa gcaggttcat   176160
ctctgtgagt tcaaggcaag cctgggctat acaattctag attagccaga gctacatcgt   176220
```

-continued

```
aggagcctgt tcaaaacaa acaaaaccaa accataaaaa agcatttctg aggctttggg   176280
tttaatcccc atgacctcaa atagccaaac agctctcctc agtccaaacc aaactgcaaa   176340
attggagcta gtgagatggc tcaacatatg aaagtccttc ccaaaaatat tgacaactgt   176400
agcttatctc tggggacaca cataatggga gaggaccaat ttctacaagt taccctctga   176460
cctccacaca tatgcctccc acaaataaga aaatatatat aataaaaaga aagaagtcta   176520
cagctgcaca tggtcatgca tgcctataat ccagcactcc agaggctgag gcaggaggat   176580
tattagtttg agatcgcata gcaagcagta ggctagacag ggctacatag tgtaaacctg   176640
ccttaaaaca caaaaatcaa ttaagcaaca ataacagtaa caaccacaac aaaaacccaa   176700
aagagtactt tgtagtaagg acaataccaa aaatgttcct ttaaggacag ttctggaatc   176760
agcaatagcc ttccgagtgc tcagggatgt ataaatactt agaaaacttc ccctggagaa   176820
atgagcacca gggtacactg ctctcagagc tgcccagaaa gttgtttatc ctggattcat   176880
ttcagccttc ctaactgctc aggcattcag aggtcacttc tgtagtagcc aatgtctaaa   176940
aaggctaaac tactgctcag catggctgtg gtacttggca ttatcatttt gtgactggtt   177000
ttgtagttat gcagaattca agagttatag catcatgaaa gtttccacca agttcctgat   177060
ccagtcacct cttaaaggtt ggatgcacca agtgcctttg gggtgataaa ttatattcaa   177120
ataatggtat tccaccctaa tccccaaaga cttctggcca tctcataatg taaaatgctg   177180
agccatcgca ccagcccatg gccttgaact cttgatggtc ctgtctcagc ctgtgtttgg   177240
attataaatc tgttggtgag gtattccttt gctgataata caagcaaatt cttcaagctt   177300
ccatcctaga ctgaagacca gcagctctcc aggagtcctc aatgcagact ggcccagctg   177360
ggacattgag cctcatggac tcagccgcta ctagattcgc aacctattca gacaagccac   177420
tgttggacta cccagacaat actatgtaag ccaatcccat tttaatacac atattcatct   177480
gggtgtgtgg cacacacctc tactcccagc acgcaagagg cagaggcagg cagatctctg   177540
atttcgaggc ctggtctata gagtgaattc caggccagcc agggctacac agagaaaacc   177600
tgtttcaaca aaaccaaaac cgtaaattca ttctatcagc tctatttcct tagagaattc   177660
taatacatgt gggtaccagg ggttgaactc aaagtcttca tgtttacgta gcaagtttcc   177720
ttctgctagc ctagtgaagc tgaggcaggt acagccggtt cttactgct ccttgcaaat   177780 ggtcctcctg agctttcctt tgagagccta caaagaactc tttttttctt taggtctcca   177840
ggttttggtc ttaagaggtt ctggacttgg atctgtagct gtcatatcac agacattcaa   177900
catctggcaa atgtcttgac aaaggagatc acttgtgttt gctgcagtgt cccttctggc   177960
tgtgagattt tgctcctcac cactgcagga ctgcagatct attctgcctt tttagttgac   178020
ttttcattcc tgagaactgg ggaaaactga cttttgtattt gggctttgaa tttgtccatt   178080
tgtcaatcca tcacaccaga cctaaccaac tgccaagagt tctgctgact tttgttttct   178140
ctagggtggt cactttgctg ggctcatcct catccttggc ctgcagttta tcccaggaa   178200 agaaaatggc taacgactgc taagaagcag tctttccttc cagaaatttt agtctatcta   178260
gaccttgctg cagtctgaag tctttaaaat gtgtttgtta tggtagaata ttttgagttg   178320
ccttaggagt attgcttgct gtcacctatc atattctatc aggaagcaga cgtcccattt   178380
accaaatgtg aagaaatatg gcatcaatac ccactgcaaa aagtgtaaat aaataataaa   178440
aaaatagatt tattacagag tgcaagggaa aagaaaaaaa tcagccagtt tcagaattgt   178500
aactggacaa atgttggtac agttcatgaa gaggttctac aaaatggctg gggtgggaa   178560 cataatgagt tagtttgctt ttttttttct ctttccttcc cttttccttt cttacaaggt   178620
```

-continued

```
ctcatgtagt ctatggtctc aaactcacca ctgtaaatca ccttgaactt ctgatccttc 178680
tgcacgctgg caatgtaagc atgtgccacc aggcctggct cacacatttg gtttttcaat 178740
acagaatagc tctgtgatga ttaacttcaa tcatcaactt gacataacca agaatcgtct 178800
gaggaagagt ctcagtgact gggtgggcta agggcatgct cataagggat tatcctgatt 178860
gttaattgac atggaaagat caagtccatt gtgagcagca cacgccctg aacagaagtc 178920
ttctgaagta taagaggaga aagcttgatg agagcaagca ggcaagcaag ccaggatcca 178980
cgtgtttatt ctctgtctgt tcttgaccgt agatgtgatg gctgtcttgg cttcctggga 179040
aacatgaact gcaccctgga attgcaaggc aaacaaacct tttcctcttc caagttgctt 179100
tatgctaaga tattttatcg cagcaataga aatgaaactt agaacaggcc cataactgcc 179160
agctttggaa ctgaacctaa ggctgttata attcactagg atagggacca ctggaagtga 179220
atctgatttt gatggtaaaa tcatgtgttt gtttctggat atgatagatt tatcaatttg 179280
agactcagaa aagaagttag gacttgaatt ccgttttaga gacattccag agaaaactga 179340
tgtcattgtt ctgaatgtaa gtgcctcagc tgaaaataca aagagtacag gaagaaagc 179400
ccaggctaga atctgaagga actcctctat tttttgtttg cttgtttgtt tggttggttt 179460
tttgagacag ggtttctctg tgtagccctg actgtcctgg aactcacttt gtagaccagg 179520
ctggcctcga actaagaaat ctgcctgcct ctgcttccca agtgctggga ttaaaggcgt 179580
gtgccaccac accaggctag gaactcgtct attacacatt aacaccctc tttaattaac 179640
tgttcctgcc aatgtaccaa atagtcaatt gattcctgtt tatttaccac atgtttctgt 179700
tagtaaacca gaataactta tctagccaaa gtctgcctat tagccatatt ttcatcagtt 179760
cccaaccatt tttggaattc tgtgagggga atccacagat gctgtagacc gctttagaca 179820
ttttcagct tttttcaagt tgcaggtcat gattcagtgg gtcatgaaat taatttagtg 179880
ggttctgatt agcatttcaa aatgaggcaa gcagagggca tattgtcaca gcacagcaca 179940
tgcggtaagc agccacacac tcttgcttgg aggcttagtc agtttctggc tctaaacgcc 180000
ccaggtttgt ttctctatcc taggcctctc tcttaaattc caaacatagt tagacattac 180060
cattggggca cgtgcaactc aaacacggag tgtgactcct ttccccatct gcggttccca 180120
gatttggcaa tgtcaccctc ctcccttctc cctagggtca gttttacctc tcacactcca 180180
caacacaaca cctctcatct caagaattgc cattagggct ggtgagatgg ctcagaggtt 180240
aagagcaccg actgctcttc tgaaggttct gagttcaaat cccagcaacc acatggtggc 180300
tcacaaccat ctgtaatggg atctgattac ctcttctggt gtgtctgaag acagctacag 180360
tgtactcaca tatattaaat aaataaatct aaaaaaaaaa aaaaaagaa ttgccattaa 180420
atgtacctca gagtccaaat gcttcttcct cccctgacta cactcacgct ggcctgagtc 180480
cattttctta ttgaggttac tgcttctctg cttctaccct ggctccttct gctgcctatc 180540
cttgacacag cagacaagca gttctttaaa gcagggctca ggaccagtga gactgatcgg 180600
ctctggtggc acttcctgcc atgactgatg atctaaggtt aagcctagaa cccacgaggt 180660
agaagcaaag gacctactct ccaaagccgt cctctgacca ccatgtgtaa actgcacatg 180720
tacatgcatg cacatggtac acacacatac acagaagtaa aaagagattt aaattgaaaa 180780
tcattaaaaa gaaaaatcag ggctcagcaa actttccgtg tagaaaacta gagtacttag 180840
gctttgaaag ccaagaagtg gatattaatt atagttattc attatagcag agatttctaa 180900
aacctttga caaaactaaa aaatataaca gagtgtattt tttttgtaat gtaagtttac 180960
```

-continued

```
taatggcagc agtgggatta gtttcttttt tagattattg ttattatttt tattaattat 181020
tagtgttttt gtgtttattc atattccaca gcatgtgtgt ggaattggat ttctgcttcc 181080
acctttgtgt gggtcctaga gattgaactc aagtcatcaa gcttgcacag taggtggtca 181140
ggcttacaca gtaggtggtc aggcttgtat ctttggaagg caagcatttt acttcctgtg 181200
ccagctcact ggccttcttt gtttaaaaaa agaaaaaaaa agtccttttt tgtttaatta 181260
gggttcatgg ccagtgctct ttatcttaaa atcaactgca aacttttatc tggtaaaaag 181320
ccatccttag ctgtggtcct aggagaaaaa catacagttg gatggcttta tcctgcaggc 181380
ttagtttgat catctctctt tgaagatata atcagctcac atcacactca agcctctgcc 181440
aacgagtttt ctacttctgt tcaacaaact acccaagctg agcagctcca acaacagcc 181500
agttatgatc ctcacagtcc ggtgggtcag aagcctaagc gggcgtggct acctcgctgc 181560
tattgcctga ccctgctcgg tgcatccaca ttcacatcct ttcctggtga gtgtggttct 181620
ttgactggtt ttgttccaat ttttagtata tgtgctgctg aaacaatctt tttgcctctg 181680
cctccagact gcagggatta atgttcttga ctgccacaga gcactaatat ttactgaaca 181740
tgtgatcatg tggtgctcag cactcttgca cccaaggctc ggggaacatg gaggaagagg 181800
gggtggaaag attccaagaa ccagaggaag aagaaagtca gaggtgagac tgcatctcct 181860
agaaatgtca gggacatttc tagacctctg aagtctcaag aacaaggcct gaaagtctta 181920
tttatatagg ttaacctgaa aggggaaaaa attcttacag gggtccaacg ttagacaaag 181980
aactctaagc aactaaggaa tgttgggggg gggtagtct tccccaggga acactcctct 182040
acccttcaag ccccacccaa gctggttatc caaaacaaac tggtcagtcc tgaagccata 182100
tacgcacaag taacatcata tggatgggca gattgcattt aggaatacac acatacacac 182160
acacaactta aaagagagg ccatgaattt aagagagagc aaagcaaagt gggaaggggt 182220
acatgggaag gttggaggca gnnnnnnnnn nnnnnnnnnn nnnnnnnnnn nnnnnnnnnn 182280
nnnnnnnnnn nnnnnnnnnn nnnnnnnnnn nnnnnnnnnn nnnnnnnnnn nnnnnnnnnn 182340
nagagagaga gcctattatg tcgttggttg cttctaatca ttagaaaacc actctcttag 182400
gctgagtcag aactagccta gctgagacac tgtccaccca ctgtcccaga gcaaggccat 182460
cgctgtccca gatttgcctt tggggccct tgaaatgaaa gtcaccagca ggctccggaa 182520
gctgcctcat gctaatcagt tgaggttgtg aaaatagccc tgcagtggtt cctgggcctg 182580
cagctgggcc agagccacta aggggagtct ggtcctttgg agcagagtta acagtcatca 182640
gtgcttttt ttttttttta aatgttccct gctttaggct cagtgctgtg cgctacttct 182700
aatccttgca ataggctgca agacaggcaa gaatatcatc cctgttttgc cctcaggcaa 182760
attctgaagt ctggcaaatg aaagatgtgg gatttgaaca cagacttgtt tggccaaaga 182820
attctcactc tacttctgcc tgtgccacct tcctctcatg cacggggagg ggagggagc 182880
ccacctccca tgctcagggg ctaggaagtg gggagaagat ggatgtcctc aaagcagggt 182940
gagaatgaag tagaagccag cttcaaatct aaactaagca atgtttttatt tccatttccc 183000
tgaacataaa gttcagttac atttggttta aaaaaaaaaa tccctacaca actggttctt 183060
gagaaatgtc aagtgctaca attcagtgga tgtggatgaa acaatcaaaa tgttgaacac 183120
ccccaaacag atacaaacct tcatcaaagt ctcttccaaa ggctgggtct gaaaagagcg 183180
actcatgttc cagcccagtt ggctccttct catgtgagct ccgacttcca aagactgctt 183240
gcaccaggag gaaatataat agatgtcctt tttaagggg gtggggtctg tctgacaacc 183300
tcccacagtg actgtggata cagcccagtt agtagagttc tcgcctagca agcgtgcggc 183360
```

-continued

```
cctgggcttg agatctagca ccctaaggca tagtggtaca tgcccatgac cacagcactt 183420
gggacgtaga ggcagaagga tcagttcaag gtcagatgag gggtggggag gcattccttt 183480
aatgccagca tttgagaggc agaaacagat gaatttgtga gttcaaggcc agcctggtct 183540
acagactgag ttccaagaca gccaaggcta cacagagaaa ccctgtcttg tcaggaaaaa 183600
agatagtggg agagaattca aggttatctt ggactgcata agactttgat tccaaaataa 183660
acaaaaatgg agcatgaatg cttgcaactg tggacaatat tgggttcata catattctgt 183720
tttgtcacct acataccaat tatacaaatc agattcagct gggcccactg gtgcatgttt 183780
gttcccagca tctgggaggt agagatgggc agagctctat gactttaagg ctagcctggt 183840
ctacaaagta agttctagga cagccaaccc tacagagaga tacactactt ctaaatcaat 183900
caatcaatcc atcagtcaat catgggctgg agagatagct cagtgatcaa tagtgccatt 183960
cttccagagg acctgggttt gattcccagc acccacatgg cagctcacag atgtctgtaa 184020
ctccaatccc aagggacatg acaacttcta ctggtctctt tggtcaacag gcatgcacgc 184080
agcatacaat atatatatgg gtaaaatgct atatatataa aaatcagatt cacaaatcaa 184140
gtacagaaag agatcaacta taatgaaaca accataacac atactgtttt aaaagctacc 184200
ttcctgtcct gacatctgac ttcttgcgtg acccagtgcc tccacaatga gacaagcaga 184260
tggtgtagtc cctgtgaccc aggattaggc aaccactgcc cctgggaagc cattcctagt 184320
aacaggatca aatcccacag tgctccactg tacccccgcca gaggacgtga agcctccctt 184380
ccccggctgt ctgtgcagca ccgcccagat gcttggtgtc actgagtgac catcggagcc 184440
caactgagga gtgcctcagt gctcctcagg gcagtgtgca attgaaactt gcatgtgatt 184500
tctggaattt gtcatttgat atttccagac tccagctgac cttggataac agcacagagg 184560
gcagaactgc agaggaaaag gggcactact gtgactgtta tcccctgcat gattatagaa 184620
gggtctgtgc tttctcttac aaatcattgc ggcctctctt cacttccctc ctttgaagtc 184680
gaaaaaaata gatgcatcct cacagtacag gatggcaggt acgaggcggg ttccgggact 184740
gaggcaggac tcatcatgca gcctctttcc ctcaactaca ccgccgcccc tgcagagttc 184800
cctctgatca aatcagtttc aggcctggaa agaaacggcc actcaggctg gggatgtggt 184860
tccattagag gcctgcatgc acgaagctct ggatttgatc ttcagcacgg gcataagccc 184920
agtatggtag tatctgttta gcatggtgtg gaggtatacc tatctctgca cagggagacc 184980
agaagttcag agttatcctt gcacttacag taagttcaaa gctagcttgg gcaacatgaa 185040
gttttgtctt aacaaaacga aacaagaggg gccggggaga tgcttcgctg tgctgagtca 185100
tttgctgcca gtttgatga cctgagtttg gtcccttgag cttatggtgg aaggagagaa 185160
atgacgcttg aactccacgc acatgccaca gcccacgcat gaatgtgtat acacacacac 185220
actaagtgga taaatgttaa aaataaataa atcaaaggaa tggccactca aaatctacca 185280
tcgttgggaa gggagggggaa aaggcaggcg agggagatag ataaccctga tatgaacacg 185340
gaaagagcca gtgtgccacc aaagctgccc agtgtgccac caaagctgcc cagtgtgcca 185400
ccaaagctgc ccagtgtgcc accaaagctg cccagacttg attacagatt tggccaggga 185460
cacaggaggc cagcaggagc agccaggttc cacctcagag gtggagccac aaacctggaa 185520
atgaaacgtc tttccctttc ttcagaccac agcagtgaca gctgtcctgc agagtctgga 185580
gggctggcag ggctcatcca ctctagtgtg cctgtggcca aacaggcct cagtcacagg 185640
tgcttttcca aggtcttagt gtctaattaa ggttagcagc caaattggag agagaagggt 185700
```

```
gctggacttt actctgctgt aaggactttg ggcattgttc cattccgtga tcaaatacca  185760
ctggctctgc caaccaccat gtcagtgggt cttcagaggg agaagaactc atccttttt   185820 gagaggtttg gtctggtcct tgtctaatgc aaaatgcctg gggcaccagg ttaatgtcaa  185880
ctcaaaggca agtgctggtc cagcatgtgt ggaatcctaa gttcaatacc catcagagcc  185940
ccaagcccta gaggacagac atgctttaaa aaaagtcat gctttaaaaa aattctgttg   186000 aggggctgg agaaatagct cagcagttaa gagcactagc tgctctttca gaggacccag   186060
attccgttcc taacatttc atggtggctc aaagctgtct ataattcaag tcctagaggg   186120
gaatctgttg ccctctctgg ttttctcagg caccaagaac acatgtggtg caaacataca   186180
cgcaggcaaa acactcatac atatgaaaca tttttataa acctgctcgg atgtggtggc   186240
tcatgccagc gatgctctca gcactcagat ggcagaggca gggggatttt tgttgagcc    186300 cagcctgagc tatagaatga gatgctgtct caaaagaaaa aaaaaacaa aaaaaaacaa   186360 aaacaaaaa caaatctgtg ggcttaatca ttcctagcca aaggagctg gctccagcaa    186420 caatggatcc ctagagctct gctttgcccc ctggtctgga gagcttgctc tagaaaggaa   186480
ttctccatag accacatttc tattttgggg accactctgg gcctgcacat ggaaaaatgg   186540
agagttgagg tttacatggt cattttttt gttgttacag taatgagagc tttgaaatga    186600
tcacaaaagg aaaataggaa aatatgcctc ctaaaaagag ccgagcaaa ttattatagc    186660 aaccgaatcc taaaggaat gttcaagtaa aaaaaaaaaa atatggctca tgcgaagttg    186720
ttatggcaac tgacatttaa aagtaacagg atttgggcaa gtttcttct ccaccctctc     186780 tgcaaagtct tgcaggaact tcatgctaaa attatgcttt aattttaatt agccaaatag   186840
gtcataaata tagcttattc ccaaatcctt agaatttcta ccctgcaagg agctgaacta   186900
ctaatgagga aatatttcca caaaaaccca cttaccatta agaaccccca tccgatattt   186960
ttctaatata atttatcaat ttaaacacat tgcataatgt gccactctgt agcattccat   187020
taaaatgata aatagcaata gtggtgaggg gtgggggca aaaaccagga gattaaacat    187080
atccaaagca gtgtagctat atttaaatac ctcaatccat tgtagaggaa aacacactgt   187140
tctcatccgc agatacagtc tagactcaga gcagcatatc cttgactgta agggtattaa   187200
taggacagac gaaggggggc aataagaaat gacaggaaac ttcagaagaa ataaaatttc   187260
tattaggctt tgttataaga ttacatcaaa gcagttcata tgttttaatc tggggaggaa   187320
aaaaagcaac tacttggggt ttgcgcctgg gggctgcctc tgtgtactga accagacagt   187380
ttgcataatg aacaattttc attcaatcag gatctcagca gagatagctc ctactcaaag   187440
gaacccggca caggctcata gtttttatct cccagctcca cctgctggag aaaccttgta   187500
ttgcagggag agaaagcagt cgggaggcat tgtcctagtg gctgtgtacc taaagttaca   187560
gacctgactt taaacagttt ctctctggag gttgaaaggg gctctgtaag ataccagagt   187620
ggattgctct caaagactct cggactcctg ttacaggcaa gtaaggtcct agcagatggt  187680
agcatggatc tccggcccttc ctcactgctt tcttgaatca gggatttaga aattgctatt  187740
tgcataccag gaggactgaa gtttggctcc cggtgaccag aggacaaggt cattgtttaa    187800
aaccacccaa actcatttcc gacttggttg gtcaaatttt caagtttccc agcagtctaa   187860
ggattcataa aataaggcag aggcagagaa acggagggtg tgtgtgtgtg tgtgtgtgtg    187920
tacccaaaat ggaactgcat tttcatgcac aatagaaaac ttaaagactg aaccaatcat   187980
tttggaaaac tggcacagct gacattggct agaggaagga acggccaggg cgagccagct   188040
gcaccaagac ccagggctga ggcctaatcc gcctttatcc gagggtttag tgaggctccc   188100
```

-continued

```
gccgctcacc aatcccggct ggagccgcag aagagctctc ttcacttggc tcagtcccag 188160
cacagtcgca ctatgctctc ccgtggggag gccgctccgg gagggggagc gacatcaagc 188220
tttgtgaaac tgttttcgaa aacctgggat gatcatttaa atgtttaaaa tatgcacatg 188280
gtaattcaaa actaattacc ctgagcacat tgaaacatt tatgccatca tcttggatcc 188340
tgcctactga ttgtgcgctg cagctcactc tggtgtttct ataaactgct tcagcgattt 188400
taacttccag gctaaatcag gcagccacag gcgctgcctc cagccctggg ttggtggaga 188460
gaccccatc cctgacttcc aggcgaggag gcggcccgtt tctccagaga gccgtttgtc 188520
agggtcttgt agttctggct gccgaattat tgctcttatc cgtgttcata attctcatct 188580
gcattattta atttaggcta gaatgacctc tttccctccc gagtcttcct ccctcattcc 188640
catttcctct tcttcaattc gtggccccca ttttctgatt ggtccaaata tatagacaaa 188700
tatccttgat cgtcccaccc cacttggcta catcttcatc tgggagccaa tgtggtgagt 188760
tttctgggtt tgcaaggtgg tcaggtccac cagtcatcct aaggtgtgtg agagaggtag 188820
accaacatga gcggcgcaca gccgccatca ctgagagagc acgtgccctg cagctcaggg 188880
acaggcatgc acacaccggc agacatgtgc acatgcgctt tccccagcaa accctgcttg 188940
cagagtaatt aggcctaggc agttcctgaa gcaaattcat ttccccctttt tccagaataa 189000
aatgagttct cttcctttgg gggtgctaaa ccagcatgcc agtggctaga agcctgagat 189060
gggtgatgtg gctgaaacca tttctgcagc caagcctgtg ggcagaagct aaccttgggc 189120
tggggagctg cagtcggaag aggcacaatt ctgggatcaa gaaatgagca ctggtttata 189180
ggtacactcc cagaaataga cagatgaggg ctgcctcctt attagcgctt tgaagatgcc 189240
catggcgggt ttttagacat ttaggaatat aaaagtaggt tggattccca cagtcagctg 189300
aagtttgaca gagtgatatt accgggttta actagagcca ttaagagact cttcattatc 189360
ccacaccacc gccacccaag ttatcacatg agccataatg caagagaatt ttcattccat 189420
caacaagaga gggagccggt ctatctttgt ccaaaggaaa tgagcagccc agcgtgaagc 189480
ttgtgaggaa ttgagtgtac aacactccaa taacatcccc tgcaggattg cctctgcgat 189540
ttagtcggtg aagcaggggt aactgcgctc gagcagtctg cctgtgtacc tggcttgcaa 189600
gaacaccagc tcgaggaaca ccaaaaaggc cgattaatga caaaggacac tcatagaggc 189660
ccgaattcca cagggcttaa gtattaagcc ccaaagaaat caaggtctag gccattctcc 189720
tggcgctcag caatctcatt tattatttct ctacaaagat ccaacactca atttcccagg 189780
tatcccctgt atctgactca cattctcctg ctcagtaagc catcctggtt tgaaacgggc 189840
ctcccctcct cctgcctatg catgcttttgc gtcttcacaa cgacagctgg taatttgcaa 189900
gaccccctcc actggactct ctcaccccac atacttggaa ctactccttg gaactacttg 189960
tttatcaagt gttctgttgg tgagccttct cttgcattaa agctgtgaga aggaaccaca 190020
gtttctatttt cctttacatt tcttgtagcg tctcacatgg gagacaccca ggttagatat 190080
actgagggtc ctggtagttt tagagttgga gttagatgac ccagcaacat gccttccccc 190140
accacgcacc aagcaaaaat tgcacccacc cttccctcag atgttcctgg catcttataa 190200
ctcgcccaaa gccagattta ttgctcctgc tgtaaagtgt atcttctcta agcctcactt 190260
aaaagctacc acttggcaga agatcaagtc agaagtgcag gctagcaggt gacggtgagg 190320
acagggcggg atggggcggg tagggtggag cgaataattg aagctccaag agttaccagc 190380
tcaatatttta acctaactgg taatttgctg tgacaattac gccatgaagg gaacgctgcg 190440
```

```
actatgcaag aatgttgctc tctaattaag agggctctgc atttcctagt cacccgcact   190500
ttaataacac acagaatgag ccttggctcc gggagctaaa ggttccatta ggagcacggg   190560
cagcatatgg ctgtgcacat aggccgtgag tgatgcagcc cagttaagcc cgctaacacc   190620
ttcaattcgt cctcagatag agcccagaga gcgcggctca ggccctcacg ccacgagccc   190680
catttgactg acaggcatct tcccggaaag cctgcgcgtg cctacactgc aaatggacct   190740
gcttcccaca gcccggcttt caaccaggaa ggcttggcgt gggtctgatc cttcaagagt   190800
aactttaata aggattttct cacagaaaga aaagtccatg gaacaaatc  ctcctcttaa   190860 gagcgtgaga caggaatggg gacacaagcc aacaccccaa ttgctaggct aactctgata   190920
tgagacaaaa gaatattaat atcttggcta tgaaggagga tggtgccatc ttctgaattg   190980
atgggagttt tgaggcatgg ctaagctggg caaaccattt tcttttttt  ctcttcttaa   191040 ttagtggttc atttatggag ggcttgctgc ccggagagcc catcagaaga gagctcgctt   191100 tatgagatg  tagcttataa aactactcag attttaaaca aacagtgcag gaggccagag   191160
gtagaagtgg tggggtggg  gtgggcaag  agaacaattg catctgcaga aggctagccc   191220
tgcaccccaa gccatgtttt agggttgatc agcttcccga ggcaagccca gaagcctcta   191280
aaattttagg ccaatagaaa tgacctctgc accacggctg actgaagcta taaataagcc   191340
tcgagttgag cagtggtgtc aacgagagag cagaggaaa  gtccaatcag agcttcattt   191400 tttttttta  aagtccactt gcttgggact cacctgaagg cagggcattg agtagagcct   191460
tggctccctg cagcgagagg ctccagtttt cccaggcacc agcccatcgg ttggttacct   191520
aaccaccgaa agggaactgc acagcacaca agttaaatat aggctgggtt atctgcattt   191580
tacaagctct gagcaagcta tctgaagaag ctgtcatttt taatgacggc acaaacttcc   191640
aattaccgac tgggtaatcc actagggagc aggtagtttt ggaagaacag ttcaccatta   191700
ttaaaagttt acacaatcac ttttgagttg actataagta tttcacacga ggcaggtggg   191760
attagggact ttttggtgg  tttactcgag gctgcaacca acaatgagtg ttttctcaag   191820
aattatacat tgagatttgt caactgctgg ggagtagtgg agggtcctgg taatgcagaa   191880
aggttatgaa atggccaggt aaggttgggt gcttccaagt ctcaaatata ctcctaaggc   191940
cagctccaag tcataagctc aaacaagtct tcaaggggcc tggagagtta agacaaataa   192000
ggatcactta ggctacccac ggacaagcac ttctcataca aggaccggct acctccaaca   192060
ccatcttccc aacatggctt ctatgttgct tcaacaacca gggcagggtg aattaggggt   192120
gggtctctcc aatgtggact caaatcatga ctacagcntg gggttttttt ttttttttt   192180 tttttttt  tntttggttt ttcgagacag ggtttctcca tatagccctg gctgtcctgg   192240
aactcacttt gtagaccagg ctggcctcgg actcagaaac ccgcctgcct ctgcctctgc   192300
ctcctgagtg ctggaattaa aggtgtatgc taccacgccc ggccgagtcc gtcttgataa   192360
tgaagttccc agtgacctgg atgtcaactg aagttggatt ttactgtgat gactactgag   192420
tccggctcag aattttgggg ggacaaggta ccttgattta actgggcact acacgactgt   192480 aaccccccaca ttgggagagg cagaggcaga ggcagaggca gaagttggt  tggaggctag   192540 gcaaggctac acagcaagaa gctgtctcaa aaccaaagac atctttcttg atccaaatcc   192600
tgtcggaggt gtgaggcct  tggggccag  aacaaggtgg tcaaggaaga ccactgactc   192660
tgtcctttgc tccattactt aatcagaatc gccatcacag atatagctag gagattttaa   192720
gccttggtgg ctgcaatctg catttaagag ctaagtggga taaactcagg ggtgggccca   192780
atgcctccct ccccacccct cctgcatccc tccatttacc tgtttccagg gatctgctta   192840
```

-continued

```
atttacctgc cagcctttgg tgggacacag gcttagtggc ttagcgctgc tcggggcacc 192900
agagaccctc acagaagcac ctgaatgtac tttcagcgct gcagagcacg cacggctcag 192960
gcccatcaga agaacccagg cttatgctaa ggagccagaa agtagaagca gctggcaaga 193020
gtgattcagc cccataaatt tacacatccg tacagccaaa cccacttgaa gtgatccaga 193080
gccactttta ttgaaataga aaagatgcct attctggagt gctaagtggt acaggagggt 193140
gggtatataa gagataatcc catgttgtct ttgatgtggt gctagggaga taacccagga 193200
cctcacgcct gcctgcaagg tagccaccaa gccacaccca caacctctat ttatacacac 193260
actaagtgtg gaggtatgga taaaaaaaaa tgtcccaaga cctcacgaat ctgcaaacat 193320
ggtgcctggt tggtggcacc gtttggggag gcagtggacc atttggtctt gcaggaggaa 193380
gttatgtcac tgggtatggg ctttgagagt ttgtagcttt gctccccttc cagttaactc 193440
tgctctcgta aggttcctgc caccatgttt cctctgccat tatggacacc tggtcctcta 193500
gaactgtaag ccacttactc tcaggtctct ttcagtcctg gagtcttatc atagcaatga 193560
aaagtaactt gtgtggcagc cagctaagca agggctgtgg ccgactgctt gggattatgg 193620
ttgtgtctgt ctgtctgtct gtcattccat ttatatagtc ctgagaattg aaccacttta 193680
ccactgacat gtctcagtcc tcttggtatc atatattcac ttaagacaag atctcattaa 193740
gtcattcaga ctggttttga gcttgcaatc ctcctgcctc tgcctcaagg cgataggatc 193800
cctagggtac tcgaccagac tgggagtagc aggttctgtt ctcttagctt tctacagtga 193860
ttgtggatta tttgtgtata aagatctgat ggcccgaccg actcccttcc ctttaagtga 193920
acatcaacag tatttagcat caacttaata aactcatttg gtaaagccat ctccccacct 193980
cttgaacaaa tgaaaatcaa acagcagtac ctgttctcct agagcagcgg ctctcagcct 194040
tccggccttt taatacagtt cctcgtgttg cggtgacccc ccccccccc agccgtagaa 194100
ttatttcatt gcttaaccag agttaactgg aagggttaat aataaaacca gtctgggaga 194160
ctaaggttac ccaaccacgc taggaaggag aggaaagggc cactcgcaca aacctgtctt 194220
tgagatgaag aacaatcaac ataacaggga cagagcagtc cttgtaacaa gtgcaaagga 194280
gagagagagg ctgagtttct acttctataa ataaaccctt ggcaggcgga tcactaaagg 194340
aacacaagtc aatataaacc tttagacatg gggctgccaa acttcacttt tcgacagtat 194400
attaattatg tagtcaatag ccatgggttt cattagcgta ttaaatacca cgatcaatat 194460
tatttatact tttcgaagac aagccactca gggaaaaaat ggtgggggga ggaggaggaa 194520
caatttgacc ctgtagttca aaaaagtca gaacagcaca ctagagatta gcaagggttt 194580
aatggaaggc ataaaacact ggaaatatgg acagaaatca gatccctgcc ttcattttc 194640
tgccttttac aaagagactg gagggaattc agaaactatt taaaataaag gcaaatgat 194700
tagagcccct ccctcccctc agctgcttaa cactggggtt gtggtggacg caaataagc 194760
attgagctct aagtgataga tgagaatcag aacaggaaca gtgttttga ggcaaaatat 194820
gtccaagaga attcaaagaa ctgtgggcca gaatctactt aggcagtcct ctgggacccg 194880
aatccctcac aggcgttaac agtggaacca atttccaagg cagccctgct ggtgatctga 194940
tttttgagta gggaaatctg ttaaacatcg tcccacgagg gagcccagct ctttcactcc 195000
ccacgggttt ctacatgcag ctgtgctaga tctgctgaag tggccggtga ggaggtgtgg 195060
ggattggttc agcgacctca gaggacattc ttgttcacta gccctcgtgc actggggcga 195120
tgaccgaatg ctgtgagcag gagatatcaa aggccggcta ctggactgaa aactagatca 195180
```

```
ccatctctaa cctgcaattt gtcaatctca gacagcaatg aagactgtga ttttctagtc    195240
aacgctttgt aagcaaggtc agatagaggc tccataaaaa ttgttcaggg ttcaggcaga    195300
gaatcaagtg taactcaatc cctatctcct gagattaggg aagggaagga aggctgtgtc    195360
tactaaacca gtgagcctca agcaaagcct gtctgttctc agcaaggtga gccacccacc    195420
aaagatgcca acagctaagg gccagggatg tagtgcaggg tgctgtgata tcaacagctg    195480
ggagacagaa acaggaggat caggacttca aggtagtttg ggctataaaa tataagcttg    195540
aagctaccca cttgaagact gtccccaaca aaacaaacaa gctgggtatg gtggtcgatg    195600
cttgtatttc tagtgtatga gacgaaggaa gaaagctcaa gcccgagacc tgcttgggtt    195660
acatagggaa gatggtgcct caaaaacagg acagccgagg agcagacaga cagggcagac    195720
agggtgcatc gatctaaatc cacatacctg gatttaaagt aatatctggg agactggtct    195780
gtgagggccg ttccagagat ttaataaaga cccaccctga ctgagtatgg gcaacaccca    195840
tgggtggccc aggggtccag actgaataaa gggaaaatgg gaggaagttc agctggtagt    195900
gtttccaagt attaggacca cagcctggcc cctggcatgt gctggccagc tagtctagct    195960
ccagtatcaa gcttcaggcc agcggcaggg cactggacag ttcccacaca cgacacacac    196020
acacacagag cactagcatt cacctcctgg tctcttcttg acaacagata aaatgtaact    196080
ggctgccaca gtgagagtcc cctaccttcc tcaccgttaa ggatggtaca aactgtgagc    196140
cagcagcagc catttctcca gtaacttgct ttccacagat actgttatag cactaagaaa    196200
agcaactgaa acatggggtg ctgtgacccc ttggcaccac aaagccatgg caagctgaag    196260
tgcacacatc acaggccagg cctgaagatg ctgggggact gcaatgctgc ctggattctg    196320
gcagagatgt gcagcagatg ccaagaggtg ggctgcagca accagagata attaatatga    196380
ttaggaacac actgagcagg catgctcttg ccgaatgaaa agcctcgcag tgtaatgact    196440
gttttcttcc tcgatcacgg tctccacgtt tcagagttgg cttggtgtta ggctgccgcg    196500
taaacatcaa tccaaccccg aggggccaga tcatcggtgt tcctgggctc aatcgccttt    196560
cctttttgtgt tttcattcat ttaaagatgc attccagggt tgcaaacatt agtgagaatc    196620
atctccaggc ctcagtctaa tctctgagtc tgtaatgagt taacatcttt ccctagtgaa    196680
tatttattat gaaggctaat taattgcttt ccagttacaa gaatccttta cagtcaaaga    196740
aagtaggatc cacaaagata tactgtttat tcaaacaaag caaaggaaac aaagcttctt    196800
tcttaaattc tatttaacat agctttaata aaggtacaca ggtccgcctg caaccgaac    196860
ggtaactgat gcaaactgaa gccatgctct gtagcagcct ggatgtccca gtgccacctc    196920
tgtctgcagg ctttgtcgga tttactaaga ttctgttatc ttcaaacagg gattgtgtct    196980
caagtaactg accccactat gtggataatg aagtaaatta tgcaatttgg gggtttgctt    197040
ttccccaagg ggacagcaag ccagtgctta tcagccgtcc tcagaggaga caattctgat    197100
taatatcaga gtcatctgac tcagtctatt aaacctatca aaccctgaag gaaggatatt    197160
cagatattaa cgataggcct ttgattaata attctacctt gttgccattc taagcattaa    197220
caaccatgca gtaactctgc aaaacagacc ctttgattcc aggcagacgc accctctgaa    197280
cacctgggtt ctcccctact cttctccccc caggaggaac tcaagacaaa aaggtgccac    197340
cactggaaaa gcacactcca ggttacataa tttgcctcat tatccagagt gggggttaatg    197400
acttgtgaca taatttctgt ttgaagataa caaaatttca tgaaatccga caaagccgga    197460
aggcaggagg aggggactgc tgccacacta ccggtggctg agaactggag cggaaggttc    197520
acacacagcc ctctgagctc actgtctttg cttatcagtg agtcccaaga ggggcccaga    197580
```

```
tgggttgcca gcctccccta gaggatcttc attgtggagc tgtcccatgg ggcgggaagg 197640
aagccattct atttctgttc ttctctcttc cgttctggcc accagtggta cttgctccca 197700
tcacatgttc ttcctgatgt tcgcgatcag ccgtctgcca tagtctctga agtccacggg 197760
cttcacgtcc atcacagtgg ccttaattcg agattcatcc tttagaaaag agagaagctg 197820
tttgtgagtg gcagagcctg gcgtgcagcg gaagagagaa cttctttgc ttcagtggct 197880
tcaatgagtc cagcaggaag aaggaaagtt tacaagtctc agagagaaag tgctgtgact 197940
tcctggagtt gggccagatc tcttccaca gacccttttcc ccatcctagg tgccctgtgc 198000
tcagacctag catcctcccg gagaagcctc tgtctttcta tgggtgcagt gggggcccag 198060
agcagacagg taactcaccc taaagcatca ctttcatcta gaggagctct gtggtagtag 198120
ggactgaggc ttctgctcca gctctgggca aggttacttc tctgctcttc accattcctg 198180
tccatcccag gaagacagaa aatccctaca ctctcccttg atctacccga ctttctgaca 198240
ccagcctacc tatgttcatt aatacaaca actaaaatat ctattcacag gcactaagct 198300
ggtgataacg cagaatgcac aaactctgcg gctgcagggg agacggcaga gttcctcctc 198360
cacttgtctc cttgaactaa acagtgtctt tgaggcagaa cagggtgaca cctagggaca 198420
cacaagtcta gctgggggcc ttcatgcttc catgtgctta gtaattaatt actacatgca 198480
ccgctgttta caagtatggt taggagcccg actgcctggg ttggcctctc gcctctgcca 198540
ctccatggct ttaggttcag agtcattctc tgcatgcctc tgcctgtctc tccgttggta 198600
aagcttgcaa caacagctcc aacacagaaa gtgctgtgag ggtcgacagt ggatagatgg 198660
ctagatagat ggggcaggac ggactgtcca gtaagcaggg ttcatcatgg ctatgcagct 198720
ctggacatca ggattagttt aaacacttgt caggtggggc acttttacca gcacgtgcta 198780
tttgtttaat attctgagtt ttagaaccta aactgtggga acaagagtc cacacataac 198840
annnnnnnnn nnnnnnnnnn nnnnnnnnnn nnnnnnnnnn nnnnnnnnnn nnnnnnnnnn 198900
nnnnnnnnnn nnnnnnnnnn nnnnnnnnnn nnnnnnnnnn ngccttgaac ttgcttctgc 198960
ctcctgctgg ggttacaggc ttgagccacc atgacagctt tagcaatagc tttgtaaatc 199020
cacagtgtca agctggatat gatggcacat gcttgcaata ctaacctcca aagattccct 199080
gaactcgagt tggtgaaata gtccaccagg taaaagagct tgctgcccaa gcctgaatct 199140
gattccctgg tcacatgctt taaggaaaga acttgccgaa gatgtcctct gagtgccacg 199200
tgtaccgatg catgcttgca gccacccaca cacccacaca agtgcactgt ctcacacagt 199260
gagaacagca agtgaacaaa caaacaagcc ggggggggg ggattgtgac cagaataatt 199320
gagggggggt gtaaagctct tggcaggtgg ctggctcctg gtaacactcc ataagtgggg 199380
aagttccaca tgtaaggtca tgtgatcgag tacatctggg cctccaacag tccttgnnga 199440
agaaacagat gcagtctgtc atatctaaac cattgttgtc gtatctctgg gtagtctttc 199500
ttttctcctt cctttctttt ttctctccct ttctctttta aaaattatt tatttattat 199560
tatatctaag tacactgtag ctgtcttcaa acacaccaga agagggtgtc tgtcagatct 199620
cattatggat ggttgtgagc catcatgtgg ttgctgggat ttgaactcag gaccttcaga 199680
agaacagtca gtgctcttaa ccgctgagcc atctctccat ccccccaaccc ctttctcttt 199740
tgagttaggt tttgtgtagc cctgggtggc gttaccttaa ctacactggc tttgaacttg 199800
caatgatact ctgcctgatc tgtcttaatc attttgagat agggactcac tacatagcct 199860
ttgctggtct ggaactaaca gagatctgcc tgtttctgcc ttgcaaatgc tgggaataaa 199920
```

-continued

```
gttatgtacc accacacctg gagtttaagg gttttttgtt tgtttgtttt tcgagacagg   199980
gtttctctgg gtagtcctgg ctgtcctgga actcgctctg tagaccaggc tggccttgaa   200040
ctcagaaatc cgcctgcctc tgcctcccaa gtgctgggat taaaggcgtg tgccaccacg   200100
cccagtttaa gggttttttt ttgtttgttt tttcctgaga cagggtttct ctgtgtagct   200160
ctggatgttc tggaactcac tctgtagagc aggttagcct tgaactcaga aatctgactg   200220
cctctgcctc ccaagtgctg ggattaaagg cgtgtgccat cactgcccag tgattttttt   200280
ttttttaatg tgtgtatttg tatgggtgtg tgggtgcttg tggaagccag gtgtcagatc   200340
cccagagcgg aagtgttctt aaccgctgaa ccatctctct tccctcttcc ctaactctga   200400
ttttaaaggc accaaactct taggtaggag actatacaca cacacacaca cacacacaca   200460
cacacccgta cacacccgta cacaccacat gaccatgcct gagcacacaa gtggttttat   200520
tgctggtctg gcctgtgtat gagctggaac caaaaccttt gtcgggagat ccgcagtctg   200580
cagtttgagc acaggctctc tggtttctgt tctctgtcct gtgtcgcatc ttgactagag   200640
gcagagaagc atctgcaagg ctgtgaccac gctggctggt gctctgccat ctacattttc   200700
aacaggaaat ctcaggagag tatttccttt taagaacgcc agacttttgt gcctgggcca   200760
cttctctact tcccagaaca ttgtgtgcca agtggcaagt tattaaccaa gtgctttgga   200820
aaattaaact ccttggtttg cagagtagca tgggagcatt gagagggtgt atgcctaaag   200880
gcctggttct gctgctggca gagctgacac ttggctaaag ggctggcatt tctgagatga   200940
gcctcactag atccgcgtct cagagtctgc aggagaaatc agagagggga gaaggtccag   201000
tggcctgttc aggatgatct tcctctgcat ttaagggcgg ctggtttgcc cacgtagccc   201060
cagaaccaaa cgagcctcgg acgaagcccc ctaaaggcag taggagagac tgagccttgg   201120
ctcttcagca ggggtgggga caagagcaag aggcgggatc tcgcccggcc ctttagagac   201180
acgtgcggtt gtttccgtgt ctgggagatc acatgacccg catcagctga cccgtcacgg   201240
tggagctcag cgctggtgct tcgcgctccc cgccctgctg cgccccggag cgcaggaccc   201300
tgcggagggg taagaaaacc cccaggcttt ctttcctttg tcgctggttc gcgcagtcac   201360
ctgcacccta ccccccgctc ctcgttcatc ccagtcttcc cggcctggca ccccggaagc   201420
cactgcgagg agggccgtgg ccaggctcag ccttgcgctg cccccaggcg gccaggacca   201480
aatggcccag gggagcagaa ggcggaaagt ggttcttaca gcagggtccg agggctggtc   201540
cccttcctca ggacctgaca tggaggagct gctccggagc gtggagagag atctgaacat   201600
tgatgcccgg cagctggccc tggcgccggg gggcactcat gtagtggccc tagtgtccac   201660
gcgttggctg gctagtctcc gggagcgccg actgggaccc tgtccccggg ctgagggcct   201720
gggtgaagca gaagtcagga ctttactgca acgttcggta cagaggctgc ccccaggctg   201780
gactcgagtg gaggtgcatg ggctgcggaa acggagactg tcctacccgc tgggtggagg   201840
cgtgcccttt gaggagggt cctgtagccc tgaaactctc actcggttca tgcaggaggt   201900
ggctgcccag aattaccgga acctgtggcg ccatgcatac cacacttatg acagcctta   201960 cagccacagc actgcccct cagctctacc tgccctagac tctatacgac aagctctcca   202020
gagggtgtat ggatgcacct tcttgccagt gggtgaatcc atcccatgtc tatcaaatgt   202080
cagggatggg ccctgcccct ctcggggcag ccctgcctgc cccagccttt tgcgagctga   202140
ggctttgctg gagtcgcccg agatgctcta tgtggtacac ccttatgtgc aattctccct   202200
gcatgatgta gttaccttca gccctgccaa gctgaccaac agccaagcca aggtgctctt   202260
tcttctcttc cgtgttctga gggccatgga tgcctgtcac cgccaggggc tggcctgtgg   202320
```

```
ggctctgtct ttgcaccaca ttgctgtaga cgagaagcta tgcagtgagc tccggctgga 202380
cctgagcgct tacgagatgc cttccgagga tgaaaaccag gagggctctg aagagaaaaa 202440
tgggacaggc attaagtctg aaaagaggg ggaagggaga actgagtgtc ccacctgcca 202500
gaaagaactt cggggccttg tgctagactg gtccatggc cgaatcagca acttccacta 202560
cctcatgcag ctgaatcggt tggcaggtcg acggcagggg gatcccaact atcacccagt 202620
gctgccctgg gtggtggact ttaccacacc ttatggcgc ttccgagacc ttcgtaaatc 202680
caagttccga ctcaacaagg gagataagca attggacttc acctatgaga tgacccggca 202740
ggcatttgtt gcaggtggtg caggaagtgg ggagccaccc catgttcctc accacatctc 202800
tgacgtgctc tctgacatca cgtactatgt atacaaggcc cgtcgcacac cgcgctcggt 202860
gctctgtgga catgtccgag cgcagtggga accccacgag tatcctgcca ccatggagcg 202920
gatgcagacc tggacaccgg atgagtgcat acccgagttc tacacggacc cctctatctt 202980
ttgctctatc caccctgaca tgcccgacct ggatgtgccg gcctggtgca gttctaacca 203040
ggaatttgtg gctgcccatc gagccctcct ggagagctgg gaggtgtccc aagacctgca 203100
tcactggatt gatcttacct ttggctacaa actccagggc aaagaagctg tgaaggagaa 203160
gaatgtgtgt ctgcacctgg tggacgctca cacccatctg accagctatg gcgtggtaca 203220
gctatttgat cagccacacc cccaacgcct ggctggatct cctgccctgg cccctgaacc 203280
tccactcatc ccccggctgt tggtccagcc tattcgggag gccacaggcc aggaggacat 203340
ttcaggacaa cttataaatg gtgcgggcag gcttgtcgta gaggccactc catgtgagac 203400
tggctggact agagataggc ctgggacagg agaagatgat ttagaacagg ctacagaagc 203460
tctggattcc atctccctcc ccgggaaagc aggtgaccag ccaggctctt cctccagtca 203520
agcatcacct ggcctgttgt ctttttctgc accctcgggg tctcgaccag gccgtaggag 203580
caaagctgcc gggttggacc ctggggaggg tgaagagggc aagattgtcc ttccagaggg 203640
cttcagtccc atacaggcct tggaagagct ggagaaagtg ggtaacttcc tggccaaagg 203700
cctagggagc cagttggagg agcctgaaaa gcctcacgcc cagccacctg tgcacctgca 203760
gagcctcttc catcgagaca tgcaggtcct gggtgtcctg ttggctgaga tggtgtttgc 203820
caccagggtc cggatactgc agcctgatgc acctttgtgg gtacgctttg aggctgttcg 203880
gggtctctgc atacgccact ccaaggacat ccccgtgtct ctgcagcctg tgctagacac 203940
actcctacag ctgagcggac ccaaaagtcc catggtgtcg aagaagggca agctagaccc 204000
actgtttgag tataggccgg tttcccaggg attaccccca cccagcccag cccagctcct 204060 cagcccttc agctccgtgg tccccttccc tccatacttc ccagcactgc acaagttcat 204120
tcttttatat caggcccggc gtgtggagga tgaggtccag ggtcgggagc tggcgtttgc 204180
tctgtggcag cagctgggtg cggtgttaaa tgacatcact cccgagggct tagagatcct 204240
cctgcctttc gtgctgtcgc tcatgtctga ggagcacacg gctgtgtaca cagcctggta 204300
cctatttgaa cccgttgcca aggccctggg ccccaaaaat gccaacaagt acctcctgaa 204360
gcctctcatc ggtgcctatg agagccctg ccgcctgcat ggccgcttct acctgtacac 204420
cgactgtttt gtggcccagt tggtggtgcg gctgggcttg caggccttcc tcacccacct 204480 gctgcccat gtcctccagg tactggctgg ggtggaggct tccaggagg agggcaaagg 204540 cctggtcggg accactgagg atgaggaaag tgagctcccg gtgtccggc ctggctcctg 204600 tgcctttggg gaagagattc agatggatgg gcagccggct gcttcctcag gactggggct 204660
```

```
cccagactac aggtcgggcg tcagcttcca tgaccaggcc gacctgccgg acacggagga    204720
cttccaagct ggactctacg tggctgaatc tccacagccc caggaggctg aggccgtgag    204780
cctgggccag ctgagtgata agagcagtac cagcgaagcc tcccaggcg aggagagggg    204840 tggggatgat ggcggtgccc ctgcggacaa gaacagcgtc aagtcagggg acagcagcca    204900
ggacttgaag cagagcgaag gctctgagga gaggaggag gaggaaggct gtgtggtgtt    204960
ggaggaggac caggaggatg aagtcacggg aacatccgag ctcactctgt ctgacacgat    205020
gctgtccatg gagacggtgg tggctcctgg tgatgggaga cagagaag aggaagagga    205080 gccgctgaca gagcagacag aaggcaaaga acaaaagatc ctccttggtg agcccgtggg    205140 ctgaggggc atgggtcagg tgcttttcct tcaggctctc atatgctggg tgtgggtcca    205200
accagatcca ctgtagcacg cacagccaca gtcagacaca gtgcatggaa tgtggaagtg    205260
ctgtgtgtga gtggaaagtg gggcttagat ttagctttca ggagacagaa agctcctta    205320 aaagccatac cttgggctga ggctgggagt ggagttgagt ggtagagcac ttgtctggta    205380
tactcgaggg ccctgggtgt cttatctcta gccccagaag aagtattaag aaataaaagc    205440
aagtggtggt tgagatgtga atggagccag aactggccgg aacagtcggg tggaagtggg    205500
aagagtgttc cagacaggga acagtgtgtg tgtacctctg aggctctcat ggttccatca    205560
gagaggcagg gaaaggctaa aatggttttc ttaagagagt ccagaagggc tgggcttggt    205620
ggtgcaggcc tttaatccca gcactcagga ggcagaggca ggcggatttt tgagttcgag    205680
gccagcctgg tctacaaagt gagttccagg acagccaggg ctatacagag aaaccctgtc    205740
tcgaaaaaaa aaaaaaaaa aaagagtgta gaagggtgga agccagggac aagtctgtac    205800
aagaaggaac ttgggagcat tgccgaaagg atgacctctc tgcaggtcct gcccgaggag    205860
ccagtttctg gggaccttga ccatggctag gtgaatggac ccaggatggg atggtcaggc    205920
ttgctagcag agccacagcc gagttggctg ggtggggtgg ggtggggtgg gaagggtgag    205980
ttatctgatg agctcaggac cttttcctgc cctgcagata cagcctgcaa gatggtccgc    206040
tggctgtctg ccaagcttgg ccccacagta gcctctcgcc atgtggcccg gaacctgctg    206100
cgcctgctga catcttgtta tgttggtaag gtctgtggtt agtgctggag accaggttcc    206160
ccagccaggc ttctgcccat ccttagccct ctctaggcga ctccttccct aacttcccag    206220
cactccctga gcagggcctg ggtctcaccc attaagctgg gttttcttgg gtaagtgggg    206280
aagagcccag tattgaatga atagaagcca ccccacagtc tcagaaggcc ggcttccctc    206340 ctgcccctcca ctggcttctc aacgctgctg cccttccttg gtagggccca ctcgacagca    206400
gttcaccgtc agcagtgatg acacccctcc actgaatgcc ggcaacatct accagaagag    206460
gccagtccta ggtgacatcg tgtcggggcc tgtgctcagc tgcctcctcc acattgccta    206520
cctgtatgga gaacccgttc tcacctacca gtacctgccc tacatcagct acctggtcag    206580
tccctggttc gtcaaacccc ggcttggggg tgggggcaag gatccaagga ccagcccag    206640 gtcttggggg ttccaggagg tctgtggggt gacctgtccc tccctcatct attctgtggt    206700
tctaggtagc cccagggagc aactcaaacc ccagccgact gaacagccgc aaggaggccg    206760
ggctgctggc agcggtgaca ctgacgcaga aaatcatcgt ataccctctct gacacgaccc    206820 tcatggacat tctgccccgc attagccacg aggtcttgct gcctgtgctt ggcttcctca    206880
cctccttcgt cacagggtag gcccctgctg cttgggagag ccacctggct gagggggccc    206940
ccaggaaggg ctaggaagct caggagaag cagataccgg cctgagtcat ggttctgatg    207000 ttggggtag tggcacaggt cttttcattcc agcacccaga ggagggcaag tttctgtgag    207060
```

```
tctgagacta gcctggtcta cagagagagc tccaggctat ctaaggctcc atagtaagac  207120
tctgacttaa gaaaagagtc gtggttcatt ctgggttgtg ggtgtggctt ggtgatggga  207180
cactttccca gcatgcagga ggagctatgc ttgagttcca gcccttcaga aaacaaaaa   207240 tgggggctgg aaagaatagc tcagggttta agagcactgg ttgctcttcc agaggatcca  207300
ggttagattc ccagctgcca catggtagct cataaccatc cggcagttct atggaacctg  207360
ccaccctcct tcggtctctg tgggcactgc aaacatgtgc acagacatac atgcaggcag  207420
aaaaaacacc catacacata aaattagacc aaaaaagttc atgttctctc ctacctgtag  207480
ctctgactaa gctacactgc ttccctgtgc ctcagtttcc tccctggtc tggactgatc    207540 agccttacat gcagctcctg ttatttgaag ttcctggtaa attggtcaag tccttcaggg  207600
aagggctggg aactcttgca ctttgattct aggttcccca gtggggccca ggcccggact  207660
gtcctatgcg tgaaaccat cagtctcatc gccctcatct gcttgcgcat cgggcaggag    207720
atggtccagc agcacctgag tgagccagtg gccaccttct tccaagtctt ctctcatctg  207780
catgagcttc ggcagcaggt aggcaggcag cttctgggct gggtgggcca ggccaggcca  207840
ggccaggcca gggcagtgga cccactgaat ctgtggtctt cctacccgca ggatctgcca  207900
ctggatccta agggctgtac tgagggccag ctgccagagg cgaccttctc tgatgggcag  207960
cgacgaccag tggaccccac cctgctggaa gagctgcaga aggtgttcac cctggaaatg  208020
gcgtacacaa tctacgtacc tttctcctgc ctgttgggta ttgcccatca cgttcctttg  208080
cacagagttg gtgactacat ctcttccctg ggtgtgggccc cgatgctttc acctccagag  208140
tcagcaatgg aatctttta ttttatttt gacatgggt ctcatttagc ccaggctgac      208200
ctttaactcc agctccttcc agcttccacc gtctcctgtt ggcattgtag tcatgtggca  208260
ttgctcaggc ttcttncatg ttcttatttt taaatgacct gtgtgtgtgt gtgatatctg  208320
tgtgagtgtg gaggtgacag aataacagtt ggggggtcag cagatgcctt gcctgatgag  208380
catctctcta gatccagttt ttggttttgt gggcttttat gtgtgtgttt gtttgtctgt  208440
ttttgtagac agggtctctc tgtgtagcct ggccatcctg gaactcattc agtagaccaa  208500
gctggccttg agctcacaga gattcacctg cctctgcctc ccagtgctgg gattaaaggc  208560
gtgtaccact cctgcctggc tttgtttttg ttaaccacca tcctcctgcc tcagcatctg  208620
cctcccctgt gctgggatta caggtgtgtg ctatcacacc cagctaacag tggatttaaa  208680
cgtaggaatt ttaggatcag agtgaccaga tttggtccta gggcccaatt tccacagtga  208740
ttatctatct tagttaggat ctctgttgaa aatcatggtg gaacatcatt accaaatgca  208800
acttggggag gaaaaggttt attttgtctg acaactctca ggtcaccaag ggaagtcagg  208860
gcaggaactc gaggcagaag ctgaagcaaa agccatggaa gaactctggc ttgttcctca  208920
tggcttgctc agtctggtgt accccctccc cacccacctc cccacaatgg tttctctgct  208980
tatgcctggc tgtcctagaa ctcactctgt agactaggct ggcctcaaac tcaagagatc  209040
cccctgcctc tgcatctcaa gtgctaagat taaaggcggg tgccatcacc cctgccccag  209100
gggtggcact acccactgta aattggtccc ttcccatatc agttgttaaa taagaaaact  209160
cctccatagg ccaatctggt gggggaattt tctcagttga gggtttctct tctcaaatga  209220
ctgtagctga tgccaaattg ataaaacaaa tctcaaacca ccaccaccaa caacaataaa  209280
accaaacaaa ccaaacaact aaccaagaca gtgacttata aagagaatct gaacattttc  209340
cagcaggaaa ggctcaggag ctggccattc aagtctgggg aacagaatgt agggaatat   209400
```

```
gatggtctcc agaagctacc tgcaaaggaa tgaacagctt gctgggtttt gtggcttccc 209460
ttatgggatg ggcgctgtac tgggcttctc tctgagtagg atgggccacc ctgtagttgg 209520
gaatattttg ctcctacaga attgtaagtt cccagaggca ggacacatct gtcttattct 209580
tcattgtgtg tctgatgcta aatggtgcc tggcatacac gtgtgtgtct ctatagagac 209640
agcactcatg tctacgtatc gataaaggaa gctgttttgg ggggaggaaa caggcttaca 209700
gacgagaact taataaccca gagtagccca gtcagtacct tgccttggct tctgttgttt 209760
ctaagctctg ggtagatagc taccttgcca tcttccctga tcttagaact ttccccactc 209820
ccctgtaggt gacatcatcc ggaaaatcat ccccaaccat gagttggtcg gggagctggc 209880
agggctctat ctggaaagca tgagcccgag ctctcgaaac ccagccagca tggaacccac 209940
catggctagt gccggccctg aatgggaccc tcagagtggg agctgtctcc aggacgatgg 210000
ccactcaggg acctttggga gtgtcctggt tggaaatcgc atccagatcc ctgactctca 210060
gccccagagt cctgggccac tgggctccct ctctggagtg ggtagtagcg gaggcctcag 210120
caacaggaat gaagacaacg ccctgaagcg ggagctgcct cggagtgccc atgggctgag 210180
cgggaactgg ctggcgtact ggcagtacga gatcggtgtg agccagcagg atgcccactt 210240
ccacttccac cagatccgcc tgcagagctt cccagggcac acgggggccg tcaaatgcgt 210300
ggccgccctg agcagtgaag acttctttct gagtggcagc aaggaccgga ctgtgcgcct 210360
ctggccgctg tacaactatg gggacgggac caatgagacg gcttcccgcc tcatctatgc 210420
ccagcaccgc aaaagcgtct ctacgtgggg ccagcttgag gccccgcagt atgtggtgag 210480
ctgtgatggg gcagtgcacg tctgggaccc cttcacaggt gagcgggccc aggtgaggcc 210540
tgttcgacgc tgctttact gtgccttagc caggcctctg gaacgggac ctagtgcgaa 210600
acgtacaatg gcgtattttg acggggaaga ttcagtgagg caggaagaga agaagagtca 210660
ggacttagaa tctgtgggac ccaagtttga atccactccc ccaacttacc agcaatcggc 210720
tcagttgctg caggcgtctg ccttctacct gtaagaacca aaaatttaga agattccacg 210780
agtatggctt tggcttcttg tacgacgtca cctgtcgtcg ttgtaaagag aagtatcgag 210840
tggaggaggg tcagggcaga cggaggtcgc agctagttag agcatgctat gtgaagagag 210900
cagactgttc tggggctgga cccttgactt cactgtggaa gcagcaagat gagaaagccc 210960
tgagattgtg ttttctgagg gtcactgggg aatgggatgc aggtgtgggg tgagttggag 211020
tttgaagtag ccagggctct tgatagcca ctaagtcccc agatgtgtcc ttttcagga 211080
aagacccttc gcacagtgga tccttcagac agccgggtgc ccctgacggc tgtggctgtc 211140
atgcctgccc cacacaccag catcaccatg gccagctccg actccactct gcgctttgtg 211200
gactgcagga agccaggctt gcaggtcagg agggtgcag ttcctgggct actggggtc 211260
tctaggtacc agtcaggaaa gacactcagg ggactccacc aggaacgctg cagtgacagg 211320
cagccctgtg tgggtggggc gctggcacgg atggggcttt tctcttccgg ggatggagtg 211380
ggagggtcag gcctactggt ttcgtgggcc tgaatggggt gagctgcagt agggtgggtg 211440
gcagtgatgg atggcgacgg gcacttgaac acaatctcct cctatagcat gagttccgac 211500
tgggtggagg gctgaaccct gggcttgttc gctcgttggc cgtcagcccc agtggccgga 211560
gtgttgtggc tggcttctcc tcgggcttca tggtgctcct agatacccgc acgggcctgg 211620
ttctacgagg ctggccagcc catgaagggg acattctaca gatcaaggtg actgactgcc 211680
tgaggtccta tcctttcatt tctacttagg gcctggtctg ggagaggaca ggtttatgct 211740
ggtgtccctt ataactactc ggggacattc agtgggtgg gaaaatggcc ctcgtaggcc 211800
```

```
agctcaggaa ccagctgcac aggaggcagg ctaggggcag gaatcagggc tagaactgac 211860
cctgatgctc cacagcgatg ttctaatgag taacccttgt ccatatttgt cttgcttgga 211920
ggatcagggg tcacgccctg tccgtgaccc agttcaggtt aaataaagcc aggaggctgt 211980
ttactgcctg gagaccactg agcagagtcc atgcccctg ctgggctgtc ctgatggggg 212040
gcaggaacag gcgcaggcct gcgcatcgtg ttcctgcctc ctatattcaa tcatagacct 212100
cagagctcag caggttctgg gagggagaa ataggctgc ttgtgggagg atttctccct 212160
gcagtgggaa ctctcctccc ccgccgtcca gatggaggtg aaagacaggc actgttgctt 212220
acagggaagg caggctgccc ccagctctat ccaggacccc aggggaccct gggtctcagt 212280
gtctctaaat cccaacattc taagaaagtg tcaggatggc tctggggtca tcctgggtgt 212340
tagtcccagc tctcggagtc ttctctgagc accagttctt ttcctatggg aagtaaggac 212400
atgccaggtg ttctttgaga ggacctgagt ttggttctca gcactgtcta gctctggctc 212460 caggggttc aacacccttt atggcttctg tggacacata ttcttatgtg gcctgcacgc 212520
acacacacga acacaaataa aaataaatgt taaaagaaga cagcggcacc ttgtacctca 212580
catgttagta cgattggatg tggcagtgcc tcacagaatc tgtgggactt tatttattta 212640
tttatttttt ggtcttaaaa ttttaaaaga ttggtttagg agtggtggta cacaccatta 212700
atcgcaacac tcaggagcag aggcaggtgg atctctatgg gtttgaggcc agcctggtct 212760
acagagcaag tttcagggca gccaaggtta cacagagaaa ctctttctca aaaaataaaa 212820
acaaaatatt taaaagattt acttacttct tatttgagct aggatctccc tattagccct 212880
ggctgtcctg gaactcactg tatagaccag gctggcacct taaactcacg aagatcctcc 212940
tgcttctgcc tcctaagtgc tgagattaaa gtagtgttat accatgcccc actatttct 213000 ttatagattt ggtgttttgc ctgcttgtgt atatatgcac taccttcatg cagtgctaat 213060
aggggtcaga ggcgagtatc agctcttcct ggaactagag ttatggaagg ttgggagtca 213120
ccatgctggg actgggtcat ttgcaagagt tacaagtact tctgagccat ctccagcccc 213180
ctagagtttt tttccccct ggctgtcctg aagtagaatc tgttcttgtt ttgttttgtt 213240
tttcgagaca gggtttctct acataggcct ggctgtcctg gaactcactc tgtagaccag 213300
gctggcctcg aactcagaaa tccgcctgcc tctggctctc agaatactgg aattaaaggt 213360
gtgcgccacc acgcctggct cagaatctgt ttttaaatga gagtaatagt tacaggtttt 213420 ttgtttgtt tttttttt ctttttgt tttgttttt tggctcattt gtttttattg 213480
ttttgagaca ggtctcactc tgaacccta gtggcctgg agcttgctat gtagaacaca 213540
ctgactttaa acttgtttc tgagtgctgg atttatgggc ttgtgctatt ttgcccagcc 213600
tctgatggtt gttaataaca atattattta gcttttcttt tggagatagg ctctcactgt 213660
atatcaccca gacagtggct ggtctggaaa tcactgtgta ggccaggctg accttgaatt 213720
cacagagatc tgcctcccga gttcagaaat taaaagcact ctgggatggt tttggagttt 213780
ggtgagtacc caagcctcca ttgatgctat ctgtccctcc cgctctctgc aggctgtaga 213840
gggcagcgtg ctcatcagct cctcttccga ccattccttg actgtttgga aggagctgga 213900
acagaagccc acgcaccact acaagtcagc gtccgaccca atccacacct ttgacctgta 213960
cggcagcgag gtggtcaccg gcactgtagc caacaagatt ggtgtctgtt ccctgcttga 214020 gccacccctct caggccacca caaagctcag ttccgagaac ttccgtggca cgctcactag 214080
tctggctttg ctgcccacga aacgccacct cctgctgggc tcggacaatg gcatcatccg 214140
```

-continued

```
cctcctggca tagggccagc caggagttgg ctgagggcag ggcgagatga catctctcag 214200
ggcccgctcc tcattcttga tctcgaagcc gattcttcta ggcaagcccc aggctctggc 214260
tacccacatg gcctgctgtc tgggattgca cagctcctga atctccaaag ccttgaagtg 214320
gcttcatgaa actcgggaga tactgttcct aaccagcaag aattgggggca aggaaagcac 214380
tgtgatcccc attgctcccc agttctgcct tctggattca catggggaca gggcagctcc 214440
aggaaatgaa aggagttggg cctttgctca gccagcttcc tctagccacg ctctccttag 214500
ctctgttcct cccttgggta ggaaactgct cctgtctagg gttctgatgg tactgggact 214560
ccaggctcag gagggctggc caggacctac gactttcagg gcttggtctg ggtttttagc 214620
attcattcag ccaggtcttc agtatggac cagaaaaaag gggatgtgag aacagggcta 214680
gggaaggggt tatatgggcc cagctggtcc aggaatgaat ccatgccttg ccttggtacc 214740
cctaaccaca gcgtttgtgc cttcagccgg ggaggcagcc cttgggacca gcatccctag 214800
ggacaggagg cagcgggaat catctctgta tctcgggttc tgcccagggg atgggcagac 214860
tctgccatct cttgagtgtt cgtttggaga agcctgagat gtggcccctg ctgccttctc 214920
actagttgca gtctatgtaa ataaggtcaa taaattcttt ggaagagcca cggagctgag 214980
tgaggctgtg ttgtgttttg ctttgcctag gctgggctca ggcagctctg cctcagcctc 215040
ccaaggagct ggggaactgg tatatgtcac tgtatatgtc actgtgcctg gcttatggct 215100
tggcttggct tttttcaga tggtctcaag tgcctcaggt tggccttgat cttgggatga 215160
ccttcctgct tgaaacagag tagtgggctt ataggcatga cccaccaggt ccaattttta 215220
tttttaaag gcattgattt ttatacgtgt atggttgttt tgcccacttg tacatatgca 215280
caccatactt gtgtctggtc cctgcggagg tcagaagagg gcatcgggat cacctggaac 215340
cgaagttaat gaatggttat gagccacatc tcgatgctga agattgaacc tggatccttt 215400
gcaagagcag ccagtgttct tacccactga gccatctcta agcccacac ccagcttctt 215460
ttgatacaag gtctggtagc tcaaacttga tatgcagccg aggaggttga cctggtattc 215520
cctacctacc ctcttctctc taccttccaa gtgctgatat tatacatagg catggatagt 215580
catgcccacc agtttgcctt gatggcacca gagtcaggaa agtccaaacc tggtagttgc 215640
aaacacagca agagggtaga ggcagccatt gtcctctggc tgccttggat acagagcttc 215700
tgggttgggt ggccttgggt cagttttccg aatggttcac ccttggggaa agggaacact 215760
gctgaagagg tgggaccctg ggagggccgg cctccagctg gtctctcca gccctcgcct 215820
tggaacctag gctggaggga gccaaccagg atcctggact tgctacagtt aggtgaacag 215880
gctcctgcag cctcccttc ccttgggtag ctgtggtggt ggtggtgtgt gtggtggtgg 215940
tggtggtggt ggtggtggtg gtggggggg gggngnngnt                        215980
```

<210> SEQ ID NO 17
<211> LENGTH: 473
<212> TYPE: PRT
<213> ORGANISM: Mus sp.

<400> SEQUENCE: 17

Met Lys Arg Ala Ser Ser Gly Gly Ser Arg Leu Leu Ala Trp Val Leu
 1               5                  10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

-continued

```
Gln Ala Val Pro Thr Gly Ile Pro Ala Ser Ser Gln Arg Ile Phe Leu
     50                  55                  60
His Gly Asn Arg Ile Ser His Val Pro Ala Ala Ser Phe Gln Ser Cys
 65                  70                  75                  80
Arg Asn Leu Thr Ile Leu Trp Leu His Ser Asn Ala Leu Ala Arg Ile
                 85                  90                  95
Asp Ala Ala Phe Thr Gly Leu Thr Leu Leu Glu Gln Leu Asp Leu
                100                 105                 110
Ser Asp Asn Ala Gln Leu His Val Val Asp Pro Thr Thr Phe His Gly
                115                 120                 125
Leu Gly His Leu His Thr Leu His Leu Asp Arg Cys Gly Leu Arg Glu
                130                 135                 140
Leu Gly Pro Gly Leu Phe Arg Gly Leu Ala Ala Leu Gln Tyr Leu Tyr
145                 150                 155                 160
Leu Gln Asp Asn Asn Leu Gln Ala Leu Pro Asp Asn Thr Phe Arg Asp
                165                 170                 175
Leu Gly Asn Leu Thr His Leu Phe Leu His Gly Asn Arg Ile Pro Ser
                180                 185                 190
Val Pro Glu His Ala Phe Arg Gly Leu His Ser Leu Asp Arg Leu Leu
                195                 200                 205
Leu His Gln Asn His Val Ala Arg Val His Pro His Ala Phe Arg Asp
                210                 215                 220
Leu Gly Arg Leu Met Thr Leu Tyr Leu Phe Ala Asn Asn Leu Ser Met
225                 230                 235                 240
Leu Pro Ala Glu Val Leu Met Pro Leu Arg Ser Leu Gln Tyr Leu Arg
                245                 250                 255
Leu Asn Asp Asn Pro Trp Val Cys Asp Cys Arg Ala Arg Pro Leu Trp
                260                 265                 270
Ala Trp Leu Gln Lys Phe Arg Gly Ser Ser Ser Glu Val Pro Cys Asn
                275                 280                 285
Leu Pro Gln Arg Leu Ala Asp Arg Asp Leu Lys Arg Leu Ala Ala Ser
                290                 295                 300
Asp Leu Glu Gly Cys Ala Val Ala Ser Gly Pro Phe Arg Pro Ile Gln
305                 310                 315                 320
Thr Ser Gln Leu Thr Asp Glu Glu Leu Leu Ser Leu Pro Lys Cys Cys
                325                 330                 335
Gln Pro Asp Ala Ala Asp Lys Ala Ser Val Leu Glu Pro Gly Arg Pro
                340                 345                 350
Ala Ser Ala Gly Asn Ala Leu Lys Gly Arg Val Pro Pro Gly Asp Thr
                355                 360                 365
Pro Pro Gly Asn Gly Ser Gly Pro Arg His Ile Asn Asp Ser Pro Phe
                370                 375                 380
Gly Thr Leu Pro Ser Ser Ala Glu Pro Pro Leu Thr Ala Leu Arg Pro
385                 390                 395                 400
Gly Gly Ser Glu Pro Pro Gly Leu Pro Thr Thr Gly Pro Arg Arg Arg
                405                 410                 415
Pro Gly Cys Ser Arg Lys Asn Arg Thr Arg Ser His Cys Arg Leu Gly
                420                 425                 430
Gln Ala Gly Ser Gly Ala Ser Gly Thr Gly Asp Ala Glu Gly Ser Gly
                435                 440                 445
Ala Leu Pro Ala Leu Ala Cys Ser Leu Ala Pro Leu Gly Leu Ala Leu
450                 455                 460
Val Leu Trp Thr Val Leu Gly Pro Cys
```

465                 470

<210> SEQ ID NO 18
<211> LENGTH: 283
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (3)..(4)
<223> OTHER INFORMATION: Variable amino acid or not present
<220> FEATURE:
<221> NAME/KEY: MOD_RES
<222> LOCATION: (6)
<223> OTHER INFORMATION: Variable amino acid or not present
<220> FEATURE:
<221> NAME/KEY: MOD_RES
<222> LOCATION: (9)..(10)
<223> OTHER INFORMATION: Variable amino acid or not present
<220> FEATURE:
<221> NAME/KEY: MOD_RES
<222> LOCATION: (12)..(13)
<223> OTHER INFORMATION: Variable amino acid or not present
<220> FEATURE:
<221> NAME/KEY: MOD_RES
<222> LOCATION: (15)
<223> OTHER INFORMATION: Variable amino acid or not present
<220> FEATURE:
<221> NAME/KEY: MOD_RES
<222> LOCATION: (18)..(25)
<223> OTHER INFORMATION: Variable amino acid or not present
<220> FEATURE:
<221> NAME/KEY: MOD_RES
<222> LOCATION: (27)..(29)
<223> OTHER INFORMATION: Variable amino acid or not present
<220> FEATURE:
<221> NAME/KEY: MOD_RES
<222> LOCATION: (31)..(34)
<223> OTHER INFORMATION: Variable amino acid or not present
<220> FEATURE:
<221> NAME/KEY: MOD_RES
<222> LOCATION: (36)
<223> OTHER INFORMATION: Variable amino acid or not present
<220> FEATURE:
<221> NAME/KEY: MOD_RES
<222> LOCATION: (39)..(40)
<223> OTHER INFORMATION: Variable amino acid or not present
<220> FEATURE:
<221> NAME/KEY: MOD_RES
<222> LOCATION: (42)
<223> OTHER INFORMATION: Variable amino acid or not present
<220> FEATURE:
<221> NAME/KEY: MOD_RES
<222> LOCATION: (44)..(50)
<223> OTHER INFORMATION: Variable amino acid or not present
<220> FEATURE:
<221> NAME/KEY: MOD_RES
<222> LOCATION: (52)..(59)
<223> OTHER INFORMATION: Variable amino acid or not present
<220> FEATURE:
<221> NAME/KEY: MOD_RES
<222> LOCATION: (62)..(63)
<223> OTHER INFORMATION: Variable amino acid or not present
<220> FEATURE:
<221> NAME/KEY: MOD_RES
<222> LOCATION: (66)..(69)
<223> OTHER INFORMATION: Variable amino acidor not present
<220> FEATURE:
<221> NAME/KEY: MOD_RES
<222> LOCATION: (71)..(74)
<223> OTHER INFORMATION: Variable amino acid or not present
<220> FEATURE:
<221> NAME/KEY: MOD_RES
<222> LOCATION: (76)..(80)
<223> OTHER INFORMATION: Variable amino acid or not present
<220> FEATURE:

-continued

```
<221> NAME/KEY: MOD_RES
<222> LOCATION: (83)
<223> OTHER INFORMATION: Variable amino acid or not present
<220> FEATURE:
<221> NAME/KEY: MOD_RES
<222> LOCATION: (87)
<223> OTHER INFORMATION: Variable amino acid or not present
<220> FEATURE:
<221> NAME/KEY: MOD_RES
<222> LOCATION: (90)..(91)
<223> OTHER INFORMATION: Variable amino acid or not present
<220> FEATURE:
<221> NAME/KEY: MOD_RES
<222> LOCATION: (93)..(96)
<223> OTHER INFORMATION: Variable amino acid or not present
<220> FEATURE:
<221> NAME/KEY: MOD_RES
<222> LOCATION: (98)
<223> OTHER INFORMATION: Variable amino acid or not present
<220> FEATURE:
<221> NAME/KEY: MOD_RES
<222> LOCATION: (101)
<223> OTHER INFORMATION: Variable amino acid or not present
<220> FEATURE:
<221> NAME/KEY: MOD_RES
<222> LOCATION: (104)..(105)
<223> OTHER INFORMATION: Variable amino acid or not present
<220> FEATURE:
<221> NAME/KEY: MOD_RES
<222> LOCATION: (107)..(108)
<223> OTHER INFORMATION: Variable amino acid or not present
<220> FEATURE:
<221> NAME/KEY: MOD_RES
<222> LOCATION: (110)
<223> OTHER INFORMATION: Variable amino acid or not present
<220> FEATURE:
<221> NAME/KEY: MOD_RES
<222> LOCATION: (112)..(113)
<223> OTHER INFORMATION: Variable amino acid or not present
<220> FEATURE:
<221> NAME/KEY: MOD_RES
<222> LOCATION: (115)
<223> OTHER INFORMATION: Variable amino acid or not present
<220> FEATURE:
<221> NAME/KEY: MOD_RES
<222> LOCATION: (117)..(118)
<223> OTHER INFORMATION: Variable amino acid or not present
<220> FEATURE:
<221> NAME/KEY: MOD_RES
<222> LOCATION: (120)..(123)
<223> OTHER INFORMATION: Variable amino acid or not present
<220> FEATURE:
<221> NAME/KEY: MOD_RES
<222> LOCATION: (125)
<223> OTHER INFORMATION: Variable amino acid or not present
<220> FEATURE:
<221> NAME/KEY: MOD_RES
<222> LOCATION: (128)..(129)
<223> OTHER INFORMATION: Variable amino acid or not present
<220> FEATURE:
<221> NAME/KEY: MOD_RES
<222> LOCATION: (137)
<223> OTHER INFORMATION: Variable amino acid or not present
<220> FEATURE:
<221> NAME/KEY: MOD_RES
<222> LOCATION: (139)..(142)
<223> OTHER INFORMATION: Variable amino acid or not present
<220> FEATURE:
<221> NAME/KEY: MOD_RES
<222> LOCATION: (144)
<223> OTHER INFORMATION: Variable amino acid or not present
<220> FEATURE:
<221> NAME/KEY: MOD_RES
<222> LOCATION: (146)..(147)
<223> OTHER INFORMATION: Variable amino acid or not present
<220> FEATURE:
<221> NAME/KEY: MOD_RES
<222> LOCATION: (149)
<223> OTHER INFORMATION: Variable amino acid or not present
```

```
<220> FEATURE:
<221> NAME/KEY: MOD_RES
<222> LOCATION: (152)
<223> OTHER INFORMATION: Variable amino acid or not present
<220> FEATURE:
<221> NAME/KEY: MOD_RES
<222> LOCATION: (155)
<223> OTHER INFORMATION: Variable amino acid or not present
<220> FEATURE:
<221> NAME/KEY: MOD_RES
<222> LOCATION: (163)..(171)
<223> OTHER INFORMATION: Variable amino acid or not present
<220> FEATURE:
<221> NAME/KEY: MOD_RES
<222> LOCATION: (176)..(177)
<223> OTHER INFORMATION: Variable amino acid or not present
<220> FEATURE:
<221> NAME/KEY: MOD_RES
<222> LOCATION: (185)
<223> OTHER INFORMATION: Variable amino acid or not present
<220> FEATURE:
<221> NAME/KEY: MOD_RES
<222> LOCATION: (187)..(190)
<223> OTHER INFORMATION: Variable amino acid or not present
<220> FEATURE:
<221> NAME/KEY: MOD_RES
<222> LOCATION: (193)..(194)
<223> OTHER INFORMATION: Variable amino acid or not present
<220> FEATURE:
<221> NAME/KEY: MOD_RES
<222> LOCATION: (197)..(198)
<223> OTHER INFORMATION: Variable amino acid or not present
<220> FEATURE:
<221> NAME/KEY: MOD_RES
<222> LOCATION: (200)
<223> OTHER INFORMATION: Variable amino acid or not present
<220> FEATURE:
<221> NAME/KEY: MOD_RES
<222> LOCATION: (203)..(204)
<223> OTHER INFORMATION: Variable amino acid or not present
<220> FEATURE:
<221> NAME/KEY: MOD_RES
<222> LOCATION: (206)
<223> OTHER INFORMATION: Variable amino acid or not present
<220> FEATURE:
<221> NAME/KEY: MOD_RES
<222> LOCATION: (209)
<223> OTHER INFORMATION: Variable amino acid or not present
<220> FEATURE:
<221> NAME/KEY: MOD_RES
<222> LOCATION: (211)
<223> OTHER INFORMATION: Variable amino acid or not present
<220> FEATURE:
<221> NAME/KEY: MOD_RES
<222> LOCATION: (213)..(214)
<223> OTHER INFORMATION: Variable amino acid or not present
<220> FEATURE:
<221> NAME/KEY: MOD_RES
<222> LOCATION: (216)..(219)
<223> OTHER INFORMATION: Variable amino acid or not present
<220> FEATURE:
<221> NAME/KEY: MOD_RES
<222> LOCATION: (221)..(222)
<223> OTHER INFORMATION: Variable amino acid or not present
<220> FEATURE:
<221> NAME/KEY: MOD_RES
<222> LOCATION: (224)..(225)
<223> OTHER INFORMATION: Variable amino acid or not present
<220> FEATURE:
<221> NAME/KEY: MOD_RES
<222> LOCATION: (227)..(228)
<223> OTHER INFORMATION: Variable amino acid or not present
<220> FEATURE:
<221> NAME/KEY: MOD_RES
<222> LOCATION: (233)
<223> OTHER INFORMATION: Variable amino acid or not present
<220> FEATURE:
<221> NAME/KEY: MOD_RES
<222> LOCATION: (235)
```

```
<223> OTHER INFORMATION: Variable amino acid or not present
<220> FEATURE:
<221> NAME/KEY: MOD_RES
<222> LOCATION: (237)
<223> OTHER INFORMATION: Variable amino acid or not present
<220> FEATURE:
<221> NAME/KEY: MOD_RES
<222> LOCATION: (239)
<223> OTHER INFORMATION: Variable amino acid or not present
<220> FEATURE:
<221> NAME/KEY: MOD_RES
<222> LOCATION: (242)
<223> OTHER INFORMATION: Variable amino acid or not present
<220> FEATURE:
<221> NAME/KEY: MOD_RES
<222> LOCATION: (244)
<223> OTHER INFORMATION: Variable amino acid or not present
<220> FEATURE:
<221> NAME/KEY: MOD_RES
<222> LOCATION: (247)
<223> OTHER INFORMATION: Variable amino acid or not present
<220> FEATURE:
<221> NAME/KEY: MOD_RES
<222> LOCATION: (249)..(252)
<223> OTHER INFORMATION: Variable amino acid or not present
<220> FEATURE:
<221> NAME/KEY: MOD_RES
<222> LOCATION: (254)
<223> OTHER INFORMATION: Variable amino acid or not present
<220> FEATURE:
<221> NAME/KEY: MOD_RES
<222> LOCATION: (258)
<223> OTHER INFORMATION: Variable amino acid or not present
<220> FEATURE:
<221> NAME/KEY: MOD_RES
<222> LOCATION: (260)
<223> OTHER INFORMATION: Variable amino acid or not present
<220> FEATURE:
<221> NAME/KEY: MOD_RES
<222> LOCATION: (262)..(263)
<223> OTHER INFORMATION: Variable amino acid or not present
<220> FEATURE:
<221> NAME/KEY: MOD_RES
<222> LOCATION: (265)..(270)
<223> OTHER INFORMATION: Variable amino acid or not present
<220> FEATURE:
<221> NAME/KEY: MOD_RES
<222> LOCATION: (273)..(274)
<223> OTHER INFORMATION: Variable amino acid or not present
<220> FEATURE:
<221> NAME/KEY: MOD_RES
<222> LOCATION: (276)..(278)
<223> OTHER INFORMATION: Variable amino acid or not present
<220> FEATURE:
<221> NAME/KEY: MOD_RES
<222> LOCATION: (280)..(282)
<223> OTHER INFORMATION: Variable amino acid or not present

<400> SEQUENCE: 18

Cys Pro Xaa Xaa Cys Xaa Cys Tyr Xaa Xaa Pro Xaa Xaa Thr Xaa Ser
 1               5                  10                  15

Cys Xaa Xaa Xaa Xaa Xaa Xaa Xaa Xaa Pro Xaa Xaa Pro Xaa Xaa
            20                  25                  30

Xaa Xaa Arg Xaa Phe Leu Xaa Xaa Asn Xaa Ile Xaa Xaa Xaa Xaa
        35                  40                  45

Xaa Xaa Phe Xaa Xaa Xaa Xaa Xaa Xaa Xaa Leu Trp Xaa Xaa Ser
    50                  55                  60

Asn Xaa Xaa Xaa Xaa Ile Xaa Xaa Xaa Xaa Phe Xaa Xaa Xaa Xaa
 65                  70                  75                  80

Leu Glu Xaa Leu Asp Leu Xaa Asp Asn Xaa Xaa Leu Xaa Xaa Xaa Xaa
                85                  90                  95

Pro Xaa Thr Phe Xaa Gly Leu Xaa Xaa Leu Xaa Xaa Leu Xaa Leu Xaa
```

```
                100                 105                 110
Xaa Cys Xaa Leu Xaa Xaa Leu Xaa Xaa Xaa Phe Xaa Gly Leu Xaa
            115                 120                 125

Xaa Leu Gln Tyr Leu Tyr Leu Gln Xaa Asn Xaa Xaa Xaa Leu Xaa
            130                 135                 140

Asp Xaa Xaa Phe Xaa Asp Leu Xaa Asn Leu Xaa His Leu Phe Leu His
145                 150                 155                 160

Gly Asn Xaa Xaa Xaa Xaa Xaa Xaa Xaa Xaa Phe Arg Gly Leu Xaa
            165                 170                 175

Xaa Leu Asp Arg Leu Leu Leu His Xaa Asn Xaa Xaa Xaa Val His
            180                 185                 190

Xaa Xaa Ala Phe Xaa Xaa Leu Xaa Arg Leu Xaa Xaa Leu Xaa Leu Phe
            195                 200                 205

Xaa Asn Xaa Leu Xaa Xaa Leu Xaa Xaa Xaa Xaa Leu Xaa Xaa Leu Xaa
210                 215                 220

Xaa Leu Xaa Xaa Leu Arg Leu Asn Xaa Asn Xaa Trp Xaa Cys Xaa Cys
225                 230                 235                 240

Arg Xaa Arg Xaa Leu Trp Xaa Trp Xaa Xaa Xaa Arg Xaa Ser Ser
            245                 250                 255

Ser Xaa Val Xaa Cys Xaa Xaa Pro Xaa Xaa Xaa Xaa Xaa Asp Leu
            260                 265                 270

Xaa Xaa Leu Xaa Xaa Xaa Asp Xaa Xaa Xaa Cys
            275                 280

<210> SEQ ID NO 19
<211> LENGTH: 50
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid or not present
<220> FEATURE:
<221> NAME/KEY: MOD_RES
<222> LOCATION: (4)
<223> OTHER INFORMATION: Variable amino acid or not present
<220> FEATURE:
<221> NAME/KEY: MOD_RES
<222> LOCATION: (6)
<223> OTHER INFORMATION: Variable amino acid or not present
<220> FEATURE:
<221> NAME/KEY: MOD_RES
<222> LOCATION: (11)
<223> OTHER INFORMATION: Variable amino acid or not present
<220> FEATURE:
<221> NAME/KEY: MOD_RES
<222> LOCATION: (14)
<223> OTHER INFORMATION: Variable amino acid or not present
<220> FEATURE:
<221> NAME/KEY: MOD_RES
<222> LOCATION: (16)..(19)
<223> OTHER INFORMATION: Variable amino acid or not present
<220> FEATURE:
<221> NAME/KEY: MOD_RES
<222> LOCATION: (21)
<223> OTHER INFORMATION: Variable amino acid or not present
<220> FEATURE:
<221> NAME/KEY: MOD_RES
<222> LOCATION: (25)
<223> OTHER INFORMATION: Variable amino acid or not present
<220> FEATURE:
<221> NAME/KEY: MOD_RES
<222> LOCATION: (27)
<223> OTHER INFORMATION: Variable amino acid or not present
```

```
<220> FEATURE:
<221> NAME/KEY: MOD_RES
<222> LOCATION: (29)..(30)
<223> OTHER INFORMATION: Variable amino acid or not present
<220> FEATURE:
<221> NAME/KEY: MOD_RES
<222> LOCATION: (32)..(37)
<223> OTHER INFORMATION: Variable amino acid or not present
<220> FEATURE:
<221> NAME/KEY: MOD_RES
<222> LOCATION: (40)..(41)
<223> OTHER INFORMATION: Variable amino acid or not present
<220> FEATURE:
<221> NAME/KEY: MOD_RES
<222> LOCATION: (43)..(45)
<223> OTHER INFORMATION: Variable amino acid or not present
<220> FEATURE:
<221> NAME/KEY: MOD_RES
<222> LOCATION: (47)..(49)
<223> OTHER INFORMATION: Variable amino acid or not present

<400> SEQUENCE: 19

Asn Xaa Trp Xaa Cys Xaa Cys Arg Ala Arg Xaa Leu Trp Xaa Trp Xaa
 1               5                  10                  15

Xaa Xaa Xaa Arg Xaa Ser Ser Ser Xaa Val Xaa Cys Xaa Xaa Pro Xaa
            20                  25                  30

Xaa Xaa Xaa Xaa Xaa Asp Leu Xaa Xaa Leu Xaa Xaa Xaa Asp Xaa Xaa
            35                  40                  45

Xaa Cys
    50
```